US009689880B2

(12) United States Patent
Urdea et al.

(10) Patent No.: US 9,689,880 B2
(45) Date of Patent: Jun. 27, 2017

(54) MARKERS ASSOCIATED WITH ARTERIOVASCULAR EVENTS AND METHODS OF USE THEREOF

(71) Applicant: True Health Diagnostics, LLC, Frisco, TX (US)

(72) Inventors: Mickey S. Urdea, Alamo, CA (US); Michael P. McKenna, Oakland, CA (US); Patrick A. Arensdorf, Palo Alto, CA (US)

(73) Assignee: TRUE HEALTH IP LLC, Frisco, TX (US)

( * ) Notice: Subject to any disclaimer, the term of this patent is extended or adjusted under 35 U.S.C. 154(b) by 0 days.

(21) Appl. No.: 14/704,286

(22) Filed: May 5, 2015

(65) Prior Publication Data

US 2015/0346218 A1    Dec. 3, 2015

Related U.S. Application Data

(63) Continuation of application No. 12/755,146, filed on Apr. 6, 2010, now Pat. No. 9,057,736, which is a continuation of application No. 11/811,441, filed on Jun. 7, 2007, now abandoned.

(60) Provisional application No. 60/811,996, filed on Jun. 7, 2006.

(51) Int. Cl.
*G01N 33/68* (2006.01)
*G06F 19/00* (2011.01)
*G01N 33/74* (2006.01)

(52) U.S. Cl.
CPC ..... *G01N 33/6893* (2013.01); *G01N 33/6845* (2013.01); *G01N 33/74* (2013.01); *G06F 19/3431* (2013.01); *G01N 2800/32* (2013.01); *G01N 2800/324* (2013.01); *G01N 2800/325* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| 4,208,479 | A | * | 6/1980 | Zuk et al. ............. 435/7.9 |
| 4,230,767 | A | | 10/1980 | Isaka et al. |
| 4,231,938 | A | | 11/1980 | Monaghan et al. |
| 4,233,402 | A | | 11/1980 | Maggio et al. |
| 4,275,149 | A | | 6/1981 | Litman et al. |
| 4,302,386 | A | | 11/1981 | Stevens |
| 4,316,906 | A | | 2/1982 | Ondetti et al. |
| 4,337,201 | A | | 6/1982 | Petrillo, Jr. |
| 4,344,949 | A | | 8/1982 | Hoefle et al. |
| 4,346,227 | A | | 8/1982 | Terahara et al. |
| 4,374,829 | A | | 2/1983 | Harris et al. |
| 4,376,110 | A | | 3/1983 | David et al. |
| 4,410,520 | A | | 10/1983 | Watthey |
| 4,444,784 | A | | 4/1984 | Hoffman et al. |
| 4,508,729 | A | | 4/1985 | Vincent et al. |
| 4,512,924 | A | | 4/1985 | Attwood et al. |
| 4,587,258 | A | | 5/1986 | Gold et al. |
| 4,659,678 | A | | 4/1987 | Forrest et al. |
| 4,727,022 | A | | 2/1988 | Skold et al. |
| 4,739,073 | A | | 4/1988 | Kathawala |
| 4,772,684 | A | | 9/1988 | Brunck et al. |
| 4,780,401 | A | | 10/1988 | Heusser et al. |
| 4,816,463 | A | | 3/1989 | Blankley et al. |
| 4,845,079 | A | | 7/1989 | Luly et al. |
| 4,885,292 | A | | 12/1989 | Ryono et al. |
| 4,894,437 | A | | 1/1990 | TenBrink |
| 4,897,402 | A | | 1/1990 | Duggan et al. |
| 4,904,646 | A | | 2/1990 | Karanewsky et al. |
| 4,906,624 | A | | 3/1990 | Chucholowski et al. |
| 4,906,657 | A | | 3/1990 | Roth |
| 4,920,109 | A | | 4/1990 | Onishi et al. |
| 4,923,861 | A | | 5/1990 | Picard et al. |
| 4,929,620 | A | | 5/1990 | Chucholowski et al. |
| 4,939,143 | A | | 7/1990 | Regan et al. |
| 4,940,727 | A | | 7/1990 | Inamine et al. |
| 4,940,800 | A | | 7/1990 | Bertolini et al. |
| 4,946,860 | A | | 8/1990 | Morris et al. |
| 4,946,864 | A | | 8/1990 | Prugh et al. |
| 4,950,675 | A | | 8/1990 | Chucholowski |

(Continued)

FOREIGN PATENT DOCUMENTS

| EP | 253310 | 1/1988 |
| JP | 2004105145 | 4/2004 |

(Continued)

OTHER PUBLICATIONS

Zoccali et al., "Adiponectin, Metabolic Risk Factors, and Cardiovascular Events among Patients with End-Stage Renal Disease", J Am Soc Nephrol 13: 134-141, 2002, 134-141.*
Choi et al., "Serum adiponectin concentrations predict the developments of type 2 diabetes and the metabolic syndrome in elderly Koreans," Clinical Endocrinology 61(1)75-80 (2004).
Cote M. et al., "Low levels of adiponectin, metabolic risk profile, and risk of new CVD events in men in VA-HIT," American Diabetes Association (Jun. 2005) Retrieved from the Internet: URL:http://professional.diabetes.org/Abstracts_Display.aspx?TYP=1 &CID=50668 [retrieved on Jul. 22, 2015] Abstract.
Ingelsson et al., "Adiponectin and risk of congestive heart failure," Journal of the American Medical Association, 295(15):1772-1774 (Apr. 19, 2006) Abstract.

(Continued)

*Primary Examiner* — Jacob Cheu
(74) *Attorney, Agent, or Firm* — Perkins Coie LLP

(57) ABSTRACT

Disclosed are methods of identifying subjects with arteriovascular disease, subjects at risk for developing arteriovascular disease, methods of differentially diagnosing diseases associated with arteriovascular disease from other diseases or within sub-classifications of arteriovascular disease, methods of evaluating the risk of arteriovascular events in patients with arteriovascular disease, methods of evaluating the effectiveness of treatments in subjects with arteriovascular disease, and methods of selecting therapies for treating arteriovascular disease.

14 Claims, 252 Drawing Sheets

(56) References Cited

U.S. PATENT DOCUMENTS

| | | |
|---|---|---|
| 4,957,940 A | 9/1990 | Roth |
| 4,963,538 A | 10/1990 | Duggan et al. |
| 4,968,693 A | 11/1990 | Joshua et al. |
| 4,970,231 A | 11/1990 | Lee et al. |
| 4,980,283 A | 12/1990 | Huang et al. |
| 4,992,429 A | 2/1991 | Ullrich et al. |
| 4,994,494 A | 2/1991 | Regan et al. |
| 4,996,234 A | 2/1991 | Regan et al. |
| 4,997,837 A | 3/1991 | Chucholowski et al. |
| 5,001,128 A | 3/1991 | Neuenschwander et al. |
| 5,001,144 A | 3/1991 | Regan et al. |
| 5,017,716 A | 5/1991 | Karanewsky et al. |
| 5,018,067 A | 5/1991 | Mohlenbrock et al. |
| 5,021,453 A | 6/1991 | Joshua et al. |
| 5,025,000 A | 6/1991 | Karanewsky |
| 5,034,512 A | 7/1991 | Hudspeth et al. |
| 5,036,053 A | 7/1991 | Himmelsbach et al. |
| 5,036,054 A | 7/1991 | Kaltenbronn et al. |
| 5,055,466 A | 10/1991 | Weller, III et al. |
| 5,063,207 A | 11/1991 | Doherty et al. |
| 5,063,208 A | 11/1991 | Rosenberg et al. |
| 5,064,825 A | 11/1991 | Chakravarty et al. |
| 5,064,965 A | 11/1991 | Ocain et al. |
| 5,066,643 A | 11/1991 | Abeles et al. |
| 5,071,837 A | 12/1991 | Doherty et al. |
| 5,073,566 A | 12/1991 | Lifer et al. |
| 5,075,451 A | 12/1991 | Ocain et al. |
| 5,081,127 A | 1/1992 | Carini et al. |
| 5,081,136 A | 1/1992 | Bertolini et al. |
| 5,085,992 A | 2/1992 | Chen et al. |
| 5,087,634 A | 2/1992 | Reitz et al. |
| 5,089,471 A | 2/1992 | Hanson et al. |
| 5,091,378 A | 2/1992 | Karanewsky et al. |
| 5,091,386 A | 2/1992 | Kesseler et al. |
| 5,095,006 A | 3/1992 | Bender et al. |
| 5,095,119 A | 3/1992 | Ocain et al. |
| 5,098,924 A | 3/1992 | Poss |
| 5,098,931 A | 3/1992 | Duggan et al. |
| 5,102,911 A | 4/1992 | Lee et al. |
| 5,104,869 A | 4/1992 | Albright et al. |
| 5,106,835 A | 4/1992 | Albright et al. |
| 5,112,857 A | 5/1992 | Vickers |
| 5,114,937 A | 5/1992 | Hamby et al. |
| 5,116,870 A | 5/1992 | Smith et al. |
| 5,130,306 A | 7/1992 | Duggan et al. |
| 5,132,312 A | 7/1992 | Regan et al. |
| 5,135,935 A | 8/1992 | Alberts et al. |
| 5,166,171 A | 11/1992 | Jendralla et al. |
| 5,182,298 A | 1/1993 | Helms et al. |
| 5,196,440 A | 3/1993 | Bertolini et al. |
| 5,202,327 A | 4/1993 | Robl |
| 5,250,435 A | 10/1993 | Cover et al. |
| 5,256,689 A | 10/1993 | Chiang |
| 5,260,332 A | 11/1993 | Dufresne |
| 5,262,435 A | 11/1993 | Joshua et al. |
| 5,273,995 A | 12/1993 | Roth |
| 5,276,021 A | 1/1994 | Karanewsky et al. |
| 5,283,256 A | 2/1994 | Dufresne et al. |
| 5,286,895 A | 2/1994 | Harris et al. |
| 5,302,604 A | 4/1994 | Byrne et al. |
| 5,317,031 A | 5/1994 | Macconnell et al. |
| 5,356,896 A | 10/1994 | Kabadi et al. |
| 5,369,125 A | 11/1994 | Berger et al. |
| 5,385,932 A | 1/1995 | Vickers |
| 5,474,995 A | 12/1995 | Ducharme et al. |
| 5,521,213 A | 5/1996 | Prasit et al. |
| 5,536,752 A | 7/1996 | Ducharme et al. |
| 5,543,297 A | 8/1996 | Cromlish et al. |
| 5,550,142 A | 8/1996 | Ducharme et al. |
| 5,552,422 A | 9/1996 | Gauthier et al. |
| 5,604,253 A | 2/1997 | Lau et al. |
| 5,604,260 A | 2/1997 | Guay et al. |
| 5,622,985 A | 4/1997 | Olukotun et al. |
| 5,639,780 A | 6/1997 | Lau et al. |
| 5,677,318 A | 10/1997 | Lau et al. |
| 5,691,374 A | 11/1997 | Black et al. |
| 5,698,584 A | 12/1997 | Black et al. |
| 5,710,140 A | 1/1998 | Ducharme et al. |
| 5,733,909 A | 3/1998 | Black et al. |
| 5,789,413 A | 8/1998 | Black et al. |
| 5,817,700 A | 10/1998 | Dube et al. |
| 5,849,943 A | 12/1998 | Atkinson et al. |
| 5,861,419 A | 1/1999 | Dube et al. |
| 5,922,742 A | 7/1999 | Black et al. |
| 5,925,631 A | 7/1999 | Black et al. |
| 6,040,147 A | 3/2000 | Ridker et al. |
| 7,189,518 B2 | 3/2007 | Schonbeck et al. |
| 2002/0038227 A1 | 3/2002 | Fey et al. |
| 2004/0122296 A1 | 6/2004 | Hatlestad et al. |
| 2004/0122297 A1 | 6/2004 | Stahmann et al. |
| 2004/0137538 A1 | 7/2004 | Bradford et al. |
| 2005/0054005 A1 | 3/2005 | Ellis et al. |
| 2005/0136429 A1 | 6/2005 | Guarente et al. |
| 2006/0078998 A1 | 4/2006 | Puskas et al. |
| 2006/0094693 A1* | 5/2006 | Aziz ................... A61K 31/69 514/64 |
| 2006/0099608 A1 | 5/2006 | Epstein et al. |
| 2006/0264780 A1* | 11/2006 | Holmes et al. ............ 600/583 |
| 2007/0099239 A1 | 5/2007 | Tabibiazar et al. |
| 2007/0137538 A1 | 6/2007 | Sterr |
| 2007/0218519 A1 | 9/2007 | Urdea et al. |
| 2007/0259377 A1 | 11/2007 | Urdea et al. |
| 2008/0070926 A1 | 3/2008 | Fogari et al. |
| 2009/0068207 A1 | 3/2009 | Breitbart et al. |
| 2009/0118133 A1* | 5/2009 | Melrose ............. G06F 19/704 506/8 |
| 2010/0143958 A1* | 6/2010 | Pugia ............................ 435/29 |

FOREIGN PATENT DOCUMENTS

| | | |
|---|---|---|
| WO | WO95/00501 | 1/1995 |
| WO | WO95/18799 | 7/1995 |
| WO | WO02/070742 | 9/2002 |
| WO | WO2004/056456 | 7/2004 |
| WO | WO2004/085996 | 10/2004 |
| WO | WO2004/088309 | 10/2004 |
| WO | WO2005/093083 | 10/2005 |
| WO | WO2007/002677 | 1/2007 |

OTHER PUBLICATIONS

Koenig W. et al., "Low serum concentrations of adiponectin are a risk factor for coronary events in apparently healthy middle-aged men. Results from the 14 year follow-up of the Monica-Augsburg Cohort 1984-1998," European Heart Journal 26(Suppl. 1, 2792)445-446 (Sep. 3-7, 2005).

Krentz, Andrew J. et al., "Low adiponectin levels predict the metabolic syndrome in older men and women: The Rancho Bernardo study," American Diabetes Association Jun. 14, 2005 Retrieved from the Internet: URL:jtt[://professional.diabetes.org/Abstracts_Display.aspx?TYP=1&CID=51539 [retrieved on Jul. 22, 2015] Abstract.

Liu et al., "Lifestyle Variables, Non-traditional Cardiovascular Risk Factors, and the Metabolic Syndrome in an Aboriginal Canadian Population," Obesity Research 14(3):500-508 (Mar. 1, 2006).

Matsudaira et al., "2293-PO: Correlation between cardiovascular risk factors and adipocytokine in Japanese children," Diabetes 55(Suppl. 1):A530 (Jun. 1, 2006) (Abstract).

Pischon T. et al., "Plasma Adiponectin Levels and Risk of Myocardial Infraction in Men," 291(14):1730-1737 (2004).

Pucilowska B. et al., "Leptin and adiponectin plasma concentrations in patients with metabolic syndrome," Journal of Hypertension 23(Suppl. 2)S337 (Jun. 2005).

Satoh et al., "Leptin-to-Adiponectin Ratio as a Potential Atherogenic Index in Obese Type 2 Diabetic Patients," Diabetes Care 27(10):2488-2490 (2004).

Schulze et al., "Adiponectin and Future Coronary Heart Disease Events Among Men with Type 2 Diabetes," Diabetes 54(2):534-539 (Feb. 1, 2005).

(56) References Cited

OTHER PUBLICATIONS

Soderberg, S. et al., "Leptin, but not adiponectin, predicts stroke in males," Journal of Internal Medicine, 256:128-136 (2004).
Spranger J. et al., "Metabolic syndrome: Role of cytokines as endocrine and metabolic molecules," Aktuelle Ernahrungsmedizin 28(3):143-150 (Jun. 2003) Abstract.
Trujillo et al., "Adiponectin-journey from an adipocyte secretory protein to biomarker of the metabolic syndrome," Journal of Internal Medicine 257(2)167-175 (Feb. 2, 2005).
Anderson, Candidate-based proteomics in the search for biomarkers of cardiovascular disease. J. Phvsiol. Soc. 563.1: 23-60 (2004).
Blankenberg et al., Circulating Cell Adhesion Molecules and Death in Patients with Coronary Artery Disease. Circulation. 104:1336-1342 (2001).
Cook, Use and misuse of the receiver operating characteristic curve in risk prediction. Circulation, 115: 928-35 (2007).
D'Agostino et al, Validation of the Framingham coronary heart disease prediction scores. JAMA, 286:180-7 (2001).
Fleckenstein, Calcium channel-blocking drugs: A novel interaction for the treatment of cardiac disease. Cir. Res.. 52(Sunnl. 1): 13-6 (1983).
Folsom et al., An assessment of incremental coronary risk prediction using C-reactive protein and other novel risk markers. Arch. Intern. Med. 166:1368-73 (2006).
Folsom et al., C-Reactive protein and incident coronary heart disease in the Atherosclerosis Risk in Communities (ARIC) study. Am. Heart J. 144:233-238 (2002).
Grundy, Primary prevention of coronary heart disease: Integrating risk assessment with intervention. Circulation, 100:988-98 (1999).
International Search Report and Written Opinion of the International Searching Authority issued in connection with International Application No. PCT/US2007/013688, European Patent Office, dated Dec. 6, 2007.
Jousilahti et al. Sex, Age, Cardiovascular Risk Factors, and Coronary Heart Disease: A Prospective Follow-Up Study of 14 786 Middle-Aged Men and Women in Finland. Circulation 99:1165-1172 (1999).
Koening et al., C-Reactive Protein, a Sensitive Marker of Inflammation Predicts Future Risk of Coronary Heart Disease in Initially Healthy Middle-Aged Men. Circulation, 99:237-242 (1999).
Luc et al., Circulating soluble adhesion molecules ICAM-1 and VCAM-1 and incident coronary heart disease: The PRIME Study. Atherosclerosis. 170:169-176 (2003).
McCall et al., Calcium entry blocking drugs: Mechanisms of action, experimental studies and clinical uses. Curr. Probl. Cardiol. 1O:1-11 <1985).
O'Marca Igh et al., Estimating the predictive value of a diagnostic test: How to prevent misleading or confusing results. Clin. Ped. 32(8): 485-91 (1993).
Pasterkamp et al., Paradoxical arterial wall shrinkage may contribute to luminal narrowing of human atherosclerotic femoral arteries. Circulation, 91:1444-9 (1995).
Pasternack et al., Task force #1—Identification of coronary heart disease risk: Is there a detection qap. J. Am. College Cardiol. 41(11):1855-1917 (2003).
Pepe et al, Limitations of the odds ratio in gauging the performance of a diagnostic, prognostic, or screening marker. Am. J. Epidemiol. 159(9): 882-90 (2004).
Potoczna et al., Gene variants and binge eating as predictors of comorbidity and outcome of treatment in severe obesity. Soc. Surg. Aliment. Tract, 8(8) :971-81 (2004).
Springer. Traffic signals for lymphocyte recirculation and leukocyte emigration: The multisteo paradiom. Cell, 76:301-14 (1994).
Vasan, Biomarkers of cardiovascular disease: molecular basis and practical considerations, Circulation. 113: 2335-62 (2006).
Wang et al., Multiple biomarkers for prediction of first major cardiovascular events and death. N. Eng. J. Med. 355:2631-9 (2006).
Wasserma N et al., Atherothrombos is in acute coronary syndromes: Mechanisms, markers, and mediators of vulnerability. Mt. Sinai J. Med., 73L: 431-9 (2006).
Wilson et al.. Predication of coronary heart disease using risk factor categories. Circulation, 97:1837-47 (1998).
Wirth et al. Post-translation modification detection using metastable ions in reflector matrix-assisted laser desorption/ionization-time of flight mass spectrometry. Proteomics, 2(10): 1445-51 (2002).
Wong et al., Nonpeptide angiotensin II receptor antagonista. I. Pharmacological characterizat ion of 2-n-butyl-4-chloro-1-(2-chlorobenzyl)imidazole-5-acetic acid, sodium salt (S08307). J. Pharmacol. Exp. Ther. 247(1): 1-7 (1988).
Yamaoka-Tojo et al. Central neurotranspeptide, alpha-melanocyte-stimulating hormone (alpha-MSH) is upregulated in patients with congestive heart failure. Intern. Med. 45: 429-33 (2006).
Zweig et al., ROC curve analysis: An example showing the relationships among serum lipid and apolipoprotein concentrations in identifying subjects with coronary artery disease. Clin. Chem., 38(8):1425-8 (1992).

\* cited by examiner

FIG. 1

| Clinical Parameters | Traditional Laboratory Risk Factors | Core Markers I | Core Markers II | Supplemental Markers I | Supplemental Markers II | Additional Markers I | Additional Markers II |
|---|---|---|---|---|---|---|---|
| Age | CHOL (Cholesterol) | ANG | CCL2 | APOA1 | APOB | ACE | ANGPT2 |
| BMI | CRP | CD40 | IGF1 | CDK5 | APOE | ADIPOQ | CCL11 |
| Diabetes | FGA | DPP4 | LEP | EGF | BAX | AGER | CCL13 |
| DBP (Diastolic BP) | Glucose | IL6ST | VEGF | FTH1 | C3 | AHSG | CCL7 |
| FamHX (Family Hist) | HBA1C | POMC | | IGFBP1 | CD14 | ICAM1 | CCL8 |
| Hip (Circumference) | HDLC (HDL) | VCAM1 | | IL18 | ENG | IGFBP3 | CSF1 |
| HT (Height) | INS (Insulin, SCp) | | | IL2RA | HGF | INHBA | CXCL10 |
| RACE (Ethnicity) | LDL (LDL) | | | IL6R | HP | PLAT | IFNG |
| SBP (Systolic BP) | LPA | | | IL8 | | SELP | IL3 |
| Sex | TRIG (Triglycerides) | | | SELE | | SHBG | IL5 |
| Smoking | | | | TNFRSF1B | | VWF | IL7 |
| Waist (Circumference) | | | | | | | |
| WT (Weight) | | | | | | APOA2 | MMP9 |
| | | | | | | FAS | NGFB |
| | | | | | | FASLG | TNF |
| | | | | | | IL6 | |
| | | | | | | MMP2 | |
| | | | | | | RETN | |
| | | | | | | TGFB1 | |
| | | | | | | TNFRSF1A | |

Notes:
Glucose includes fasting plasma glucose (Glucose), or glucose levels during and after oral glucose tolerance (Gluc120) or other challenge testing.
INS includes fasting insulin (Insulin), or insulin levels during and after oral glucose tolerance (Ins120) or other challenge testing. It includes its precursor pro-insulin, and cleavage product soluble C-peptide (SCp).

FIG. 2J-2
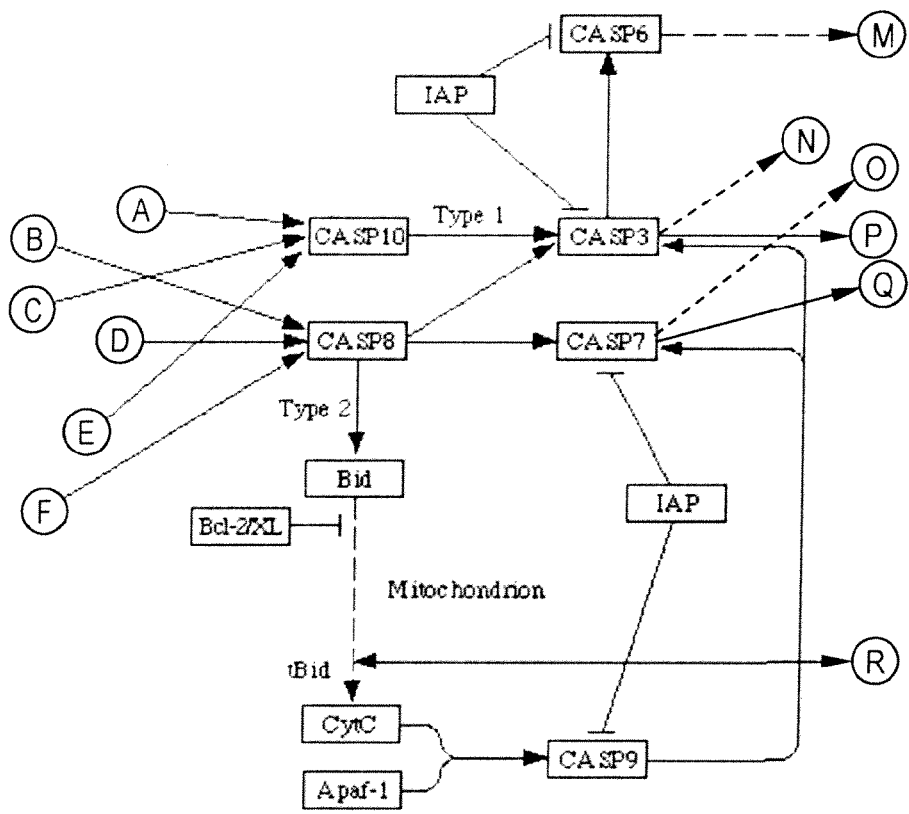
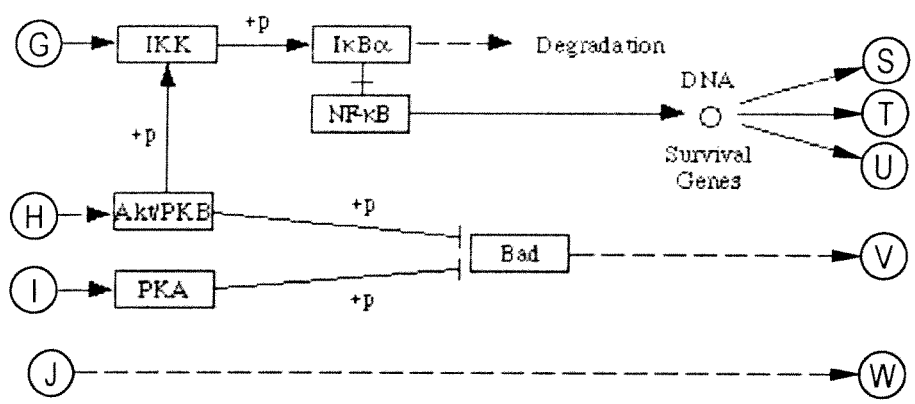
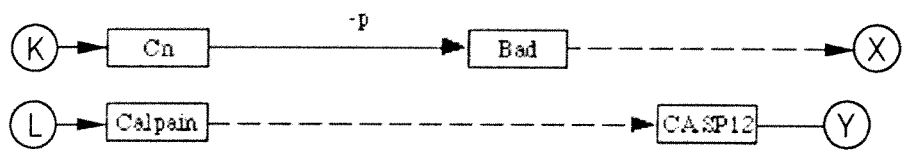

FIG. 3

| Excluding Stroke | | | | Including Stroke | | | |
|---|---|---|---|---|---|---|---|
| | | Cases (n=26) | Controls (n=724) | | | Cases (n=33) | Controls (n=724) |
| Age | Mean (sd) | 54 (4.7) | 49 (6.4) | Age | Mean (sd) | 53 (5) | 49 (6.4) |
| Sex | Male | 21 | 441 | Sex | Male | 28 | 441 |
| | Female | 5 | 283 | | Female | 5 | 283 |
| Family Hist. (Cardiac) | No | 24 | 656 | Family Hist. (Cardiac) | No | 30 | 656 |
| | Yes | 2 | 68 | | Yes | 3 | 68 |
| Hyper-lipidemia | No | 8 | 212 | Hyper-lipidemia | No | 11 | 212 |
| | Yes | 18 | 512 | | Yes | 22 | 512 |
| Diabetes | No | 26 | 717 | Diabetes | No | 33 | 717 |
| | Yes | 0 | 7 | | Yes | 0 | 7 |
| Smoking | No | 18 | 517 | Smoking | No | 22 | 517 |
| | Yes | 8 | 207 | | Yes | 11 | 207 |
| Dyslipidemia | No | 5 | 151 | Dyslipidemia | No | 6 | 151 |
| | Yes | 21 | 573 | | Yes | 27 | 573 |
| Hypertension | No | 12 | 338 | Hypertension | No | 12 | 338 |
| | Yes | 14 | 386 | | Yes | 21 | 386 |
| High HDL | No | 23 | 548 | High HDL | No | 29 | 548 |
| | Yes | 3 | 176 | | Yes | 4 | 176 |
| Risk Factor Score* | -1 | 0 | 12 | Risk Factor Score* | -1 | 0 | 12 |
| | 0 | 2 | 90 | | 0 | 2 | 90 |
| | 1 | 3 | 134 | | 1 | 3 | 134 |
| | 2 | 5 | 167 | | 2 | 7 | 167 |
| | 3 | 5 | 178 | | 3 | 6 | 178 |
| | 4 | 8 | 103 | | 4 | 11 | 103 |
| | 5 | 3 | 36 | | 5 | 4 | 36 |
| | 6 | 0 | 4 | | 6 | 0 | 4 |

*Definition of Risk Factor Score
One point for each risk factor as below:
LDL > 160 HDL< 40 (IF HDL>=60 then Score is -1) CHOL > 200 BP: SBP >= 140 OR DP >= 90 AGE >=45 (MEN) or AGE >=55 (WOMEN) Baseline Diabetes: Present

FIG. 4A

| Variable | Units | Transform | Converters (n=33) | | | Non Converters (n=724) | | | pvals |
|---|---|---|---|---|---|---|---|---|---|
| | | | Mean | SD | BT (Raw Mean) | Mean | SD | BT (Raw Mean) | |
| ACE | ng/ml | Log 10 | 2.31 | 0.17 | 203.02 | 2.28 | 0.21 | 190.40 | 0.4412 |
| ADIPOQ | ng/ml | Log 10 | 4.38 | 0.67 | 24,066.37 | 4.32 | 0.46 | 21,110.76 | 0.5024 |
| Age | years | Raw | 53.03 | 5.00 | 53.03 | 49.12 | 6.39 | 49.12 | 0.0004 |
| AGER | ng/ml | Log 10 | (1.10) | 0.34 | 0.08 | (1.09) | 0.34 | 0.08 | 0.8085 |
| AHSG | ng/ml | Log 10 | 5.87 | 0.47 | 738,897.20 | 5.83 | 0.48 | 669,465.10 | 6147 |
| ANG | ng/ml | Log 10 | 2.84 | 0.37 | 696.26 | 2.67 | 0.38 | 472.25 | 0128 |
| APOA1 | ng/ml | Log 10 | 6.64 | 0.27 | 348,517.95 | 6.58 | 0.28 | 3,810,433.95 | 0.2176 |
| APOE | ng/ml | Log 10 | 4.77 | 0.31 | 8,333.28 | 4.68 | 0.33 | 8,007.17 | 1479 |
| BAX | ng/ml | Log 10 | (0.22) | 0.42 | 0.60 | (0.18) | 0.40 | 0.67 | 0.5171 |
| BMI | kg/m2 | Log 10 | 1.46 | 0.08 | 28.69 | 1.46 | 0.06 | 28.90 | 0.7722 |
| C3 | ng/ml | Log 10 | 6.62 | 0.57 | 4,128,173.26 | 6.60 | 0.61 | 4,026,147.53 | 0.9207 |
| CCL2 | ng/ml | Log 10 | (0.79) | 0.59 | 0.16 | (0.86) | 0.29 | 0.14 | 0.2644 |
| CD14 | ng/ml | Log 10 | 3.67 | 0.34 | 4,662.24 | 3.54 | 0.35 | 3,480.68 | 0.0420 |
| CD40 | ng/ml | Log 10 | (1.17) | 0.24 | 0.07 | (1.03) | 0.32 | 0.09 | 0.0061 |
| CDK5 | ng/ml | Log 10 | 1.73 | 0.26 | 53.28 | 1.72 | 0.30 | 52.71 | 0.9302 |
| CHOL | mmol/L | Log 10 | 0.75 | 0.09 | 5.60 | 0.76 | 0.08 | 5.70 | 0.5631 |
| CRP | ng/ml | Log 10 | 3.65 | 0.48 | 4,432.83 | 3.37 | 0.61 | 2,357.79 | 0.0114 |
| DBP | mm Hg | Log 10 | 1.95 | 0.05 | 88.47 | 1.93 | 0.06 | 85.40 | 0.1316 |
| DPP4 | ng/ml | Log 10 | 2.73 | 0.18 | 539.59 | 2.67 | 0.22 | 469.63 | 0.1184 |
| EGF | ng/ml | Log 10 | (0.39) | 0.34 | 0.40 | (0.40) | 0.29 | 0.40 | 0.8624 |
| ENG | ng/ml | Log 10 | 0.20 | 0.23 | 1.60 | 0.17 | 0.27 | 1.47 | 0.4236 |
| FGA | ng/ml | Log 10 | 6.33 | 0.27 | 2,143,376.06 | 6.23 | 0.31 | 1,714,914.83 | 0.0781 |
| FTH1 | ng/ml | Log 10 | 2.80 | 0.54 | 628.70 | 2.72 | 0.56 | 524.23 | 0.4255 |
| Gluc120 | nmol/L | Log 10 | 0.85 | 0.12 | 7.12 | 0.84 | 0.15 | 6.90 | 0.6184 |
| Glucose | nmol/L | Log 10 | 0.78 | 0.10 | 6.08 | 0.78 | 0.09 | 6.00 | 0.6953 |
| HBA1C | percent | Raw | 6.29 | 0.93 | 6.29 | 6.11 | 0.91 | 6.11 | 0.3065 |
| HDLC | mmol/L | Log 10 | 0.05 | 0.12 | 1.12 | 0.11 | 0.12 | 1.28 | 0.0055 |
| HGF | ng/ml | Log 10 | (0.03) | 0.18 | 0.94 | (0.06) | 0.24 | 0.88 | 0.4692 |
| Hip | cm | Log 10 | 2.02 | 0.05 | 104.25 | 2.02 | 0.04 | 105.27 | 0.5297 |
| HP | ng/ml | Log 10 | 5.92 | 0.73 | 822,889.65 | 5.64 | 0.73 | 436,944.40 | 0.0401 |

FIG. 4B

| Variable | Units | Transform | Converters (n=33) | | | Non Converters (n=724) | | | pvals |
|---|---|---|---|---|---|---|---|---|---|
| | | | Mean | SD | BT (Raw Mean) | Mean | SD | BT (Raw Mean) | |
| HT | cm | Raw | 173.94 | 8.45 | 173.94 | 172.33 | 9.42 | 172.33 | 0.3350 |
| ICAM1 | ng/ml | Log 10 | 2.93 | 0.22 | 856.43 | 2.94 | 0.25 | 863.50 | 0.9363 |
| IGF1 | ng/ml | Log 10 | 0.88 | 0.37 | 7.54 | 1.04 | 0.40 | 10.89 | 0.0238 |
| IGFBP1 | ng/ml | Log 10 | 0.80 | 0.52 | 6.38 | 0.79 | 0.47 | 6.11 | 0.8250 |
| IGFBP3 | ng/ml | Log 10 | 1.84 | 0.18 | 68.65 | 1.84 | 0.17 | 69.09 | 0.9286 |
| IL18 | ng/ml | Log 10 | (0.55) | 0.24 | 0.28 | (0.55) | 0.22 | 0.28 | 0.9901 |
| IL2RA | ng/ml | Log 10 | (0.53) | 0.14 | 0.29 | (0.57) | 0.21 | 0.27 | 0.3540 |
| IL6R | ng/ml | Log 10 | 1.31 | 0.19 | 20.56 | 1.31 | 0.21 | 20.20 | 0.8361 |
| IL6ST | ng/ml | Log 10 | 2.52 | 0.18 | 329.98 | 2.43 | 0.20 | 272.11 | 0.0189 |
| IL8 | ng/ml | Log 10 | (2.13) | 0.21 | 0.01 | (2.09) | 0.37 | 0.01 | 0.5072 |
| INHBA | ng/ml | Log 10 | 0.50 | 0.33 | 3.17 | 0.52 | 0.31 | 3.32 | 0.7308 |
| Ins120 | uIU/ml | Log 10 | 2.38 | 0.31 | 239.37 | 2.31 | 0.35 | 205.48 | 0.2721 |
| Insulin | uIU/ml | Log 10 | 1.63 | 0.24 | 43.07 | 1.66 | 0.26 | 45.40 | 0.6186 |
| LDL | mmol/L | Sqrt | 1.91 | 0.28 | 3.66 | 1.92 | 0.24 | 3.68 | 0.9061 |
| LEP | ng/ml | Log 10 | 1.06 | 0.40 | 11.51 | 1.20 | 0.43 | 15.75 | 0.0765 |
| PLAT | ng/ml | Log 10 | 0.70 | 0.19 | 5.00 | 0.70 | 0.28 | 5.03 | 0.9546 |
| POMC | ng/ml | Log 10 | 1.07 | 0.37 | 11.88 | 1.29 | 0.35 | 19.58 | 0.0006 |
| SBP | mm Hg | Log 10 | 2.15 | 0.06 | 140.74 | 2.13 | 0.06 | 134.88 | 0.0720 |
| SCp | pg/ml | Raw | 640.16 | 152.91 | 640.16 | 627.29 | 178.12 | 627.29 | 0.6825 |
| SELE | ng/ml | Log 10 | 1.87 | 0.25 | 74.35 | 1.91 | 0.28 | 81.02 | 0.4580 |
| SELP | ng/ml | Log 10 | 2.71 | 0.31 | 508.23 | 2.67 | 0.30 | 469.55 | 0.5153 |
| SHBG | ng/ml | Log 10 | 3.77 | 0.27 | 5,863.42 | 3.74 | 0.30 | 5,509.25 | 0.6148 |
| TNFRSF1B | ng/ml | Log 10 | 0.61 | 0.15 | 4.04 | 0.61 | 0.17 | 4.09 | 0.8612 |
| TRIG | mmol/L | Log 10 | 0.19 | 0.22 | 1.57 | 0.16 | 0.24 | 1.45 | 0.4238 |
| VCAM1 | ng/ml | Log 10 | 2.65 | 0.20 | 446.59 | 2.60 | 0.18 | 393.90 | 0.0853 |
| VEGF | ng/ml | Log 10 | (0.46) | 0.27 | 0.35 | (0.59) | 0.31 | 0.26 | 0.0168 |
| VWF | ng/ml | Log 10 | 4.23 | 0.30 | 17,060.56 | 4.15 | 0.27 | 14,130.36 | 0.0879 |
| Waist | cm | Log 10 | 1.99 | 0.08 | 97.85 | 1.97 | 0.05 | 94.11 | 0.0840 |
| WT | kg | Log 10 | 1.94 | 0.10 | 86.61 | 1.93 | 0.07 | 85.58 | 0.6930 |

FIG. 5A

| Variable | Units | Transform | Prior Event (n=3) | | | Event LT 3 Yrs (n=13) | | | Event GT 3 Yrs (n=10) | | |
|---|---|---|---|---|---|---|---|---|---|---|---|
| | | | MN | SD | BT | MN | SD | BT | MN | SD | BT |
| ACE | ng/ml | Log10 | 2.31 | 0.20 | 205.82 | 2.28 | 0.18 | 189.97 | 2.33 | 0.18 | 214.15 |
| ADIPOQ | ng/ml | Log10 | 4.27 | 1.37 | 18,410.64 | 4.31 | 0.77 | 20,210.31 | 4.33 | 0.41 | 21,144.34 |
| Age | years | Raw | 50.20 | 8.83 | 50.20 | 54.26 | 4.46 | 54.26 | 54.44 | 3.67 | 54.44 |
| AGER | ng/ml | Log10 | (1.13) | 0.14 | 0.07 | (1.05) | 0.27 | 0.09 | (1.04) | 0.47 | 0.09 |
| AHSG | ng/ml | Log10 | 5.67 | 0.89 | 469,585.24 | 5.92 | 0.51 | 839,072.68 | 5.78 | 0.42 | 608,306.37 |
| ANG | ng/ml | Log10 | 2.90 | 0.56 | 799.05 | 2.83 | 0.39 | 675.76 | 2.86 | 0.31 | 723.47 |
| APOA1 | ng/ml | Log10 | 6.66 | 0.15 | 4,603,249.52 | 6.72 | 0.27 | 5,274,464.54 | 6.57 | 0.27 | 3,674,590.74 |
| APOE | ng/ml | Log10 | 4.50 | 0.33 | 31,758.22 | 4.85 | 0.27 | 71,467.64 | 4.70 | 0.24 | 50,197.43 |
| BAX | ng/ml | Log10 | (0.28) | 0.38 | 0.53 | (0.17) | 0.54 | 0.68 | (0.24) | 0.23 | 0.58 |
| BMI | kg/m2 | Log10 | 1.46 | 0.05 | 28.98 | 1.43 | 0.05 | 26.94 | 1.44 | 0.05 | 27.73 |
| C3 | ng/ml | Log10 | 6.62 | 0.82 | 4,172,971.76 | 6.58 | 0.53 | 3,797,827.87 | 6.63 | 0.54 | 4,252,904.06 |
| CCL2 | ng/ml | Log10 | 0.18 | 1.88 | 1.51 | (0.89) | 0.20 | 0.13 | (0.91) | 0.20 | 0.12 |
| CD14 | ng/ml | Log10 | 3.75 | 0.52 | 5,573.93 | 3.73 | 0.28 | 5,359.24 | 3.54 | 0.30 | 3,487.02 |
| CD40 | ng/ml | Log10 | (1.09) | 0.45 | 0.08 | (1.16) | 0.29 | 0.07 | (1.13) | 0.18 | 0.07 |
| CDK5 | ng/ml | Log10 | 1.76 | 0.19 | 57.27 | 1.68 | 0.28 | 48.37 | 1.83 | 0.29 | 68.19 |
| CHOL | mmol/L | Log10 | 0.69 | 0.04 | 4.92 | 0.78 | 0.09 | 5.98 | 0.74 | 0.08 | 5.47 |
| CRP | ng/ml | Log10 | 3.79 | 0.85 | 6,207.66 | 3.70 | 0.47 | 5,061.94 | 3.41 | 0.32 | 2,566.84 |
| DBP | mm Hg | Log10 | 1.91 | 0.09 | 80.82 | 1.93 | 0.04 | 85.00 | 1.96 | 0.05 | 90.87 |
| DPP4 | ng/ml | Log10 | 2.56 | 0.20 | 364.66 | 2.75 | 0.16 | 556.32 | 2.76 | 0.22 | 573.85 |
| EGF | ng/ml | Log10 | (0.46) | 0.36 | 0.35 | (0.42) | 0.34 | 0.38 | (0.42) | 0.34 | 0.38 |

FIG. 5B

| Variable | Units | Transform | Prior Event (n=3) | | | Event LT 3 Yrs (n=13) | | | Event GT 3 Yrs (n=10) | | |
| --- | --- | --- | --- | --- | --- | --- | --- | --- | --- | --- | --- |
| | | | MN | SD | BT | MN | SD | BT | MN | SD | BT |
| ENG | ng/ml | Log10 | 0.23 | 0.13 | 1.70 | 0.11 | 0.20 | 1.30 | 0.25 | 0.24 | 1.78 |
| FGA | ng/ml | Log10 | 6.11 | 0.13 | 1,278,503.85 | 6.28 | 0.33 | 1,899,190.33 | 6.42 | 0.24 | 2,640,224.68 |
| FTH1 | ng/ml | Log10 | 2.31 | 0.97 | 203.02 | 2.81 | 0.40 | 638.62 | 2.80 | 0.54 | 632.54 |
| Gluc120 | nmol/L | Log10 | 0.89 | 0.13 | 7.80 | 0.83 | 0.14 | 6.81 | 0.89 | 0.07 | 7.68 |
| Glucose | nmol/L | Log10 | 0.75 | 0.07 | 5.58 | 0.77 | 0.03 | 5.88 | 0.77 | 0.08 | 5.85 |
| HBA1C | percent | Raw | 5.53 | 0.38 | 5.53 | 6.08 | 0.35 | 6.08 | 6.29 | 0.67 | 6.29 |
| HDLC | mmol/L | Log10 | 0.01 | 0.12 | 1.03 | 0.07 | 0.14 | 1.18 | 0.06 | 0.11 | 1.15 |
| HGF | ng/ml | Log10 | (0.03) | 0.21 | 0.93 | (0.03) | 0.22 | 0.92 | (0.04) | 0.15 | 0.92 |
| Hip | cm | Log10 | 2.03 | 0.03 | 106.82 | 2.00 | 0.03 | 99.26 | 2.03 | 0.03 | 105.96 |
| HP | ng/ml | Log10 | 6.87 | 0.05 | 7,493,177.83 | 5.80 | 0.73 | 631,642.59 | 5.56 | 0.64 | 364,649.76 |
| HT | cm | Raw | 167.83 | 11.36 | 167.83 | 174.92 | 8.10 | 174.92 | 173.65 | 8.66 | 173.65 |
| ICAM1 | ng/ml | Log10 | 2.89 | 0.43 | 784.91 | 2.97 | 0.22 | 931.35 | 2.90 | 0.19 | 794.83 |
| IGF1 | ng/ml | Log10 | 1.31 | 0.52 | 20.35 | 0.81 | 0.37 | 6.51 | 0.81 | 0.35 | 6.41 |
| IGFBP1 | ng/ml | Log10 | 0.76 | 1.03 | 5.80 | 0.90 | 0.45 | 7.90 | 0.73 | 0.55 | 5.37 |
| IGFBP3 | ng/ml | Log10 | 1.79 | 0.19 | 61.78 | 1.80 | 0.18 | 63.37 | 1.91 | 0.19 | 80.37 |
| IL18 | ng/ml | Log10 | (0.76) | 0.18 | 0.17 | (0.56) | 0.14 | 0.27 | (0.54) | 0.31 | 0.29 |
| IL2RA | ng/ml | Log10 | (0.64) | 0.18 | 0.23 | (0.53) | 0.11 | 0.29 | (0.48) | 0.16 | 0.33 |
| IL6R | ng/ml | Log10 | 1.17 | 0.06 | 14.64 | 1.32 | 0.18 | 21.10 | 1.33 | 0.23 | 21.19 |
| IL6ST | ng/ml | Log10 | 2.40 | 0.18 | 252.36 | 2.53 | 0.19 | 340.19 | 2.52 | 0.18 | 331.25 |
| IL8 | ng/ml | Log10 | (2.18) | 0.08 | 0.01 | (2.09) | 0.21 | 0.01 | (2.16) | 0.24 | 0.01 |

FIG. 5C

| Variable | Units | Transform | Prior Event (n=3) MN | SD | BT | Event LT 3 Yrs (n=13) MN | SD | BT | Event GT 3 Yrs (n=10) MN | SD | BT |
|---|---|---|---|---|---|---|---|---|---|---|---|
| INHBA | ng/ml | Log10 | 0.30 | 0.19 | 1.98 | 0.53 | 0.39 | 3.42 | 0.59 | 0.31 | 3.88 |
| Ins120 | uIU/ml | Log10 | 2.51 | 0.19 | 326.99 | 2.33 | 0.36 | 215.56 | 2.42 | 0.20 | 264.81 |
| Insulin | uIU/ml | Log10 | 1.56 | 0.23 | 35.95 | 1.61 | 0.26 | 40.77 | 1.58 | 0.18 | 38.18 |
| LDL | mmol/L | Sqrt | 1.78 | 0.16 | 3.18 | 2.01 | 0.26 | 4.04 | 1.88 | 0.25 | 3.55 |
| LEP | ng/ml | Log10 | 1.03 | 0.76 | 10.77 | 0.97 | 0.31 | 9.30 | 1.05 | 0.39 | 11.32 |
| PLAT | ng/ml | Log10 | 0.53 | 0.44 | 3.40 | 0.68 | 0.17 | 4.80 | 0.75 | 0.13 | 5.59 |
| POMC | ng/ml | Log10 | 0.86 | 0.29 | 7.19 | 1.03 | 0.42 | 10.63 | 1.13 | 0.33 | 13.52 |
| SBP | mm Hg | Log10 | 2.12 | 0.05 | 131.39 | 2.12 | 0.04 | 131.79 | 2.18 | 0.08 | 149.77 |
| SCp | pg/ml | Raw | 581.67 | 313.29 | 581.67 | 634.75 | 127.69 | 634.75 | 654.03 | 152.03 | 654.03 |
| SELE | ng/ml | Log10 | 1.64 | 0.18 | 43.28 | 1.95 | 0.24 | 90.15 | 1.94 | 0.16 | 87.15 |
| SELP | ng/ml | Log10 | 2.69 | 0.33 | 489.47 | 2.63 | 0.27 | 425.58 | 2.69 | 0.26 | 487.02 |
| SHBG | ng/ml | Log10 | 3.62 | 0.07 | 4,194.21 | 3.74 | 0.29 | 5,434.43 | 3.79 | 0.24 | 6,201.29 |
| TNFRSF1B | ng/ml | Log10 | 0.48 | 0.09 | 2.99 | 0.61 | 0.15 | 4.07 | 0.62 | 0.20 | 4.17 |
| TRIG | mmol/L | Log10 | 0.15 | 0.15 | 1.41 | 0.17 | 0.19 | 1.49 | 0.17 | 0.26 | 1.48 |
| VCAM1 | ng/ml | Log10 | 2.62 | 0.23 | 419.22 | 2.64 | 0.17 | 432.10 | 2.70 | 0.26 | 498.24 |
| VEGF | ng/ml | Log10 | (0.36) | 0.24 | 0.43 | (0.50) | 0.31 | 0.32 | (0.42) | 0.23 | 0.38 |
| VWF | ng/ml | Log10 | 4.13 | 0.09 | 13,571.77 | 4.25 | 0.28 | 17,617.24 | 4.20 | 0.36 | 15,997.41 |
| Waist | cm | Log10 | 1.97 | 0.05 | 93.57 | 1.97 | 0.06 | 94.10 | 1.97 | 0.07 | 94.07 |
| WT | kg | Log10 | 1.91 | 0.06 | 81.42 | 1.92 | 0.07 | 82.28 | 1.92 | 0.09 | 83.38 |

FIG. 5D

| Variable | Units | Transform | Stroke (n=7) MN | SD | BT | Control (n=724) MN | SD | BT | p values ANOVA | KW |
|---|---|---|---|---|---|---|---|---|---|---|
| ACE | ng/ml | Log10 | 2.33 | 0.17 | 211.58 | 2.28 | 0.21 | 190.40 | 0.9088 | 0.8835 |
| ADIPOQ | ng/ml | Log10 | 4.65 | 0.43 | 44,918.13 | 4.32 | 0.46 | 21,110.76 | 0.4964 | 0.4460 |
| Age | years | Raw | 49.96 | 5.05 | 49.96 | 49.12 | 6.39 | 49.12 | 0.0044 | 0.0035 |
| AGER | ng/ml | Log10 | (1.28) | 0.27 | 0.05 | (1.09) | 0.34 | 0.08 | 0.6280 | 0.4603 |
| AHSG | ng/ml | Log10 | 5.97 | 0.25 | 935,562.99 | 5.83 | 0.48 | 669,465.10 | 0.8216 | 0.7499 |
| ANG | ng/ml | Log10 | 2.82 | 0.43 | 656.83 | 2.67 | 0.38 | 472.25 | 0.1661 | 0.1813 |
| APOA1 | ng/ml | Log10 | 6.58 | 0.34 | 3,771,575.45 | 6.58 | 0.28 | 3,810,433.95 | 0.4641 | 0.4423 |
| APOE | ng/ml | Log10 | 4.81 | 0.43 | 64,341.45 | 4.68 | 0.33 | 48,007.17 | 0.2584 | 0.2607 |
| BAX | ng/ml | Log10 | (0.27) | 0.46 | 0.54 | (0.18) | 0.40 | 0.67 | 0.9411 | 0.8660 |
| BMI | kg/m2 | Log10 | 1.53 | 0.12 | 33.72 | 1.46 | 0.06 | 28.90 | 0.0150 | 0.3512 |
| C3 | ng/ml | Log10 | 6.66 | 0.72 | 4,597,815.00 | 6.60 | 0.61 | 4,026,147.53 | 0.9988 | 0.9282 |
| CCL2 | ng/ml | Log10 | (0.85) | 0.20 | 0.14 | (0.86) | 0.29 | 0.14 | 0.8399 | 0.8399 |
| CD14 | ng/ml | Log10 | 3.70 | 0.46 | 5,048.68 | 3.54 | 0.35 | 3,480.68 | 0.0000 | 0.2222 |
| CD40 | ng/ml | Log10 | (1.25) | 0.13 | 0.06 | (1.03) | 0.32 | 0.09 | 0.2047 | 0.0377 |
| CDK5 | ng/ml | Log10 | 1.64 | 0.14 | 43.44 | 1.72 | 0.30 | 52.71 | 0.1752 | 0.5440 |
| CHOL | mmol/L | Log10 | 0.73 | 0.10 | 5.39 | 0.76 | 0.08 | 5.70 | 0.6937 | 0.2602 |
| CRP | ng/ml | Log10 | 3.82 | 0.52 | 6,545.47 | 3.37 | 0.61 | 2,357.79 | 0.4169 | 0.0709 |
| DBP | mm Hg | Log10 | 1.98 | 0.04 | 95.33 | 1.93 | 0.06 | 85.40 | 0.0688 | 0.0972 |
| DPP4 | ng/ml | Log10 | 2.74 | 0.15 | 552.31 | 2.67 | 0.22 | 469.63 | 0.1093 | 0.2388 |
| EGF | ng/ml | Log10 | (0.28) | 0.35 | 0.52 | (0.40) | 0.29 | 0.40 | 0.3465 | 0.9678 |

FIG. 5E

| Variable | Units | Transform | Stroke (n=7) | | | Control (n=724) | | | p values | |
|---|---|---|---|---|---|---|---|---|---|---|
| | | | MN | SD | BT | MN | SD | BT | ANOVA | KW |
| ENG | ng/ml | Log10 | 0.30 | 0.28 | 1.98 | 0.17 | 0.27 | 1.47 | 0.5292 | 0.5568 |
| FGA | ng/ml | Log10 | 6.40 | 0.22 | 2,485,863.61 | 6.23 | 0.31 | 1,714,914.83 | 0.1814 | 0.1028 |
| FTH1 | ng/ml | Log10 | 2.99 | 0.58 | 982.70 | 2.72 | 0.56 | 524.23 | 0.4407 | 0.5611 |
| Gluc120 | nmol/L | Log10 | 0.83 | 0.15 | 6.69 | 0.84 | 0.15 | 6.90 | 0.8562 | 0.6011 |
| Glucose | nmol/L | Log10 | 0.85 | 0.18 | 7.13 | 0.78 | 0.09 | 6.00 | 0.2086 | 0.3990 |
| HBA1C | percent | Raw | 7.01 | 1.64 | 7.01 | 6.11 | 0.91 | 6.11 | 0.0771 | 0.0417 |
| HDLC | mmol/L | Log10 | 0.01 | 0.11 | 1.03 | 0.11 | 0.12 | 1.28 | 0.0582 | 0.0525 |
| HGF | ng/ml | Log10 | 0.01 | 0.16 | 1.03 | (0.06) | 0.24 | 0.88 | 0.9383 | 0.7432 |
| Hip | cm | Log10 | 2.04 | 0.09 | 110.40 | 2.02 | 0.04 | 105.27 | 0.0966 | 0.1389 |
| HP | ng/ml | Log10 | 6.22 | 0.60 | 1,669,105.82 | 5.64 | 0.73 | 436,944.40 | 0.0090 | 0.0248 |
| HT | cm | Raw | 175.14 | 8.45 | 175.14 | 172.33 | 9.42 | 172.33 | 0.6518 | 0.6775 |
| ICAM1 | ng/ml | Log10 | 2.93 | 0.20 | 846.44 | 2.94 | 0.25 | 863.50 | 0.9721 | 0.9006 |
| IGF1 | ng/ml | Log10 | 0.91 | 0.28 | 8.16 | 1.04 | 0.40 | 10.89 | 0.0590 | 0.1030 |
| IGFBP1 | ng/ml | Log10 | 0.76 | 0.46 | 5.72 | 0.79 | 0.47 | 6.11 | 0.9250 | 0.9018 |
| IGFBP3 | ng/ml | Log10 | 1.82 | 0.15 | 66.55 | 1.84 | 0.17 | 69.09 | 0.6766 | 0.5866 |
| IL18 | ng/ml | Log10 | (0.45) | 0.27 | 0.36 | (0.55) | 0.22 | 0.28 | 0.3408 | 0.2760 |
| IL2RA | ng/ml | Log10 | (0.55) | 0.13 | 0.28 | (0.57) | 0.21 | 0.27 | 0.6879 | 0.5626 |
| IL6R | ng/ml | Log10 | 1.34 | 0.17 | 21.72 | 1.31 | 0.21 | 20.20 | 0.7890 | 0.5001 |
| IL6ST | ng/ml | Log10 | 2.54 | 0.20 | 347.90 | 2.43 | 0.20 | 272.11 | 0.1542 | 0.1361 |
| IL8 | ng/ml | Log10 | (2.15) | 0.20 | 0.01 | (2.09) | 0.37 | 0.01 | 0.9427 | 0.9460 |

FIG. 5F

| Variable | Units | Transform | Stroke (n=7) MN | SD | BT | Control (n=724) MN | SD | BT | p values ANOVA | KW |
|---|---|---|---|---|---|---|---|---|---|---|
| INHBA | ng/ml | Log10 | 0.41 | 0.26 | 2.54 | 0.52 | 0.31 | 3.32 | 0.5601 | 0.5416 |
| Ins120 | uIU/ml | Log10 | 2.34 | 0.42 | 220.21 | 2.31 | 0.35 | 205.48 | 0.7183 | 0.6404 |
| Insulin | uIU/ml | Log10 | 1.79 | 0.27 | 61.22 | 1.66 | 0.26 | 45.40 | 0.4820 | 0.4595 |
| LDL | mmol/L | Sqrt | 1.83 | 0.37 | 3.34 | 1.92 | 0.24 | 3.68 | 0.4111 | 0.4099 |
| LEP | ng/ml | Log10 | 1.26 | 0.41 | 18.03 | 1.20 | 0.43 | 15.75 | 0.2636 | 0.2388 |
| PLAT | ng/ml | Log10 | 0.73 | 0.19 | 5.41 | 0.70 | 0.28 | 5.03 | 0.8226 | 0.8190 |
| POMC | ng/ml | Log10 | 1.18 | 0.36 | 15.08 | 1.29 | 0.35 | 19.58 | 0.0061 | 0.0185 |
| SBP | mm Hg | Log10 | 2.18 | 0.04 | 149.85 | 2.13 | 0.06 | 134.88 | 0.0251 | 0.0658 |
| SCp | pg/ml | Raw | 655.44 | 149.49 | 655.44 | 627.29 | 178.12 | 627.29 | 0.9611 | 0.9507 |
| SELE | ng/ml | Log10 | 1.72 | 0.31 | 52.25 | 1.91 | 0.28 | 81.02 | 0.1661 | 0.1516 |
| SELP | ng/ml | Log10 | 2.88 | 0.41 | 763.19 | 2.67 | 0.30 | 469.55 | 0.4286 | 0.4504 |
| SHBG | ng/ml | Log10 | 3.86 | 0.31 | 7,195.00 | 3.74 | 0.30 | 5,509.25 | 0.7680 | 0.7791 |
| TNFRSF1B | ng/ml | Log10 | 0.64 | 0.06 | 4.33 | 0.61 | 0.17 | 4.09 | 0.7351 | 0.5808 |
| TRIG | mmol/L | Log10 | 0.29 | 0.24 | 1.94 | 0.16 | 0.24 | 1.45 | 0.7314 | 0.6938 |
| VCAM1 | ng/ml | Log10 | 2.62 | 0.14 | 417.24 | 2.60 | 0.18 | 393.90 | 0.4096 | 0.7610 |
| VEGF | ng/ml | Log10 | (0.48) | 0.30 | 0.33 | (0.59) | 0.31 | 0.26 | 0.1792 | 0.1508 |
| vWF | ng/ml | Log10 | 4.29 | 0.35 | 19,435.55 | 4.15 | 0.27 | 14,130.36 | 0.4487 | 0.6690 |
| Waist | cm | Log10 | 2.05 | 0.10 | 113.45 | 1.97 | 0.05 | 94.11 | 0.0039 | 0.2741 |
| WT | kg | Log10 | 2.01 | 0.15 | 103.25 | 1.93 | 0.07 | 85.58 | 0.0427 | 0.4810 |

FIG. 12

| | Single Markers | | 2 Marker Panels | | 3 Marker Panels | | 4 Marker Panels | |
|---|---|---|---|---|---|---|---|---|
| Total Possible Panels | 61 | 100.00% | 1,830 | 100.00% | 35,990 | 100.00% | 521,855 | 100.00% |
| All Panels with AUC Equal or Greater Than: | Count | % of Total | Count | % of Total | Count | % of Total | Count | % of Total |
| 0.05 | 61 | 100.00% | 1,830 | 100.00% | 35,990 | 100.00% | 521,855 | 100.00% |
| 0.10 | 61 | 100.00% | 1,830 | 100.00% | 35,990 | 100.00% | 521,855 | 100.00% |
| 0.15 | 61 | 100.00% | 1,830 | 100.00% | 35,990 | 100.00% | 521,855 | 100.00% |
| 0.20 | 61 | 100.00% | 1,830 | 100.00% | 35,990 | 100.00% | 521,855 | 100.00% |
| 0.25 | 61 | 100.00% | 1,830 | 100.00% | 35,990 | 100.00% | 521,855 | 100.00% |
| 0.30 | 61 | 100.00% | 1,830 | 100.00% | 35,990 | 100.00% | 521,855 | 100.00% |
| 0.35 | 61 | 100.00% | 1,830 | 100.00% | 35,990 | 100.00% | 521,855 | 100.00% |
| 0.40 | 61 | 100.00% | 1,830 | 100.00% | 35,990 | 100.00% | 521,855 | 100.00% |
| 0.45 | 60 | 98.36% | 1,829 | 99.95% | 35,988 | 99.99% | 521,855 | 100.00% |
| 0.50 | 51 | 83.61% | 1,760 | 96.17% | 35,740 | 99.31% | 521,104 | 99.86% |
| 0.55 | 25 | 40.98% | 1,244 | 67.98% | 30,169 | 83.83% | 481,357 | 92.24% |
| 0.60 | 10 | 16.39% | 672 | 36.72% | 19,747 | 54.87% | 363,849 | 69.72% |
| 0.65 | 2 | 3.28% | 200 | 10.93% | 7,970 | 22.15% | 184,389 | 35.33% |
| 0.70 | 1 | 1.64% | 69 | 3.77% | 2,573 | 7.15% | 62,489 | 11.97% |
| 0.75 | - | 0.00% | 2 | 0.11% | 198 | 0.55% | 8,153 | 1.56% |
| 0.80 | - | 0.00% | - | 0.00% | - | 0.00% | 29 | 0.01% |
| 0.85 | - | 0.00% | - | 0.00% | - | 0.00% | - | 0.00% |
| 0.90 | - | 0.00% | - | 0.00% | - | 0.00% | - | 0.00% |
| 0.95 | - | 0.00% | - | 0.00% | - | 0.00% | - | 0.00% |
| 1.00 | - | 0.00% | - | 0.00% | - | 0.00% | - | 0.00% |

| 2-Panel | Marker 1 | Marker 2 |
|---|---|---|
| 1 | ACE | Age |
| 2 | ACE | POMC |
| 3 | ADIPOQ | Age |
| 4 | ADIPOQ | POMC |
| 5 | Age | AGER |
| 6 | Age | AHSG |
| 7 | Age | ANG |
| 8 | Age | APOA1 |
| 9 | Age | APOE |
| 10 | Age | BAX |
| 11 | Age | BMI |
| 12 | Age | C3 |
| 13 | Age | CCL2 |
| 14 | Age | CD14 |
| 15 | Age | CD40 |
| 16 | Age | CDK5 |
| 17 | Age | CHOL |
| 18 | Age | CRP |
| 19 | Age | DBP |
| 20 | Age | DPP4 |
| 21 | Age | EGF |
| 22 | Age | ENG |
| 23 | Age | FamHX |
| 24 | Age | FGA |
| 25 | Age | FTH1 |
| 26 | Age | Gluc120 |
| 27 | Age | Glucose |
| 28 | Age | HBA1C |

| 2-Panel | Marker 1 | Marker 2 |
|---|---|---|
| 29 | Age | HDLC |
| 30 | Age | HGF |
| 31 | Age | Hip |
| 32 | Age | HP |
| 33 | Age | HT |
| 34 | Age | ICAM1 |
| 35 | Age | IGF1 |
| 36 | Age | IGFBP1 |
| 37 | Age | IGFBP3 |
| 38 | Age | IL18 |
| 39 | Age | IL2RA |
| 40 | Age | IL6R |
| 41 | Age | IL6ST |
| 42 | Age | IL8 |
| 43 | Age | INHBA |
| 44 | Age | Ins120 |
| 45 | Age | Insulin |
| 46 | Age | LDL |
| 47 | Age | LEP |
| 48 | Age | PLAT |
| 49 | Age | POMC |
| 50 | Age | SBP |
| 51 | Age | SCp |
| 52 | Age | SELE |
| 53 | Age | SELP |
| 54 | Age | Sex |
| 55 | Age | SHBG |
| 56 | Age | TNFRSF1B |

FIG. 13A

| 2-Panel | Marker 1 | Marker 2 |
|---|---|---|
| 57 | Age | TRIG |
| 58 | Age | VCAM1 |
| 59 | Age | VEGF |
| 60 | Age | VWF |
| 61 | Age | Waist |
| 62 | Age | WT |
| 63 | AGER | POMC |
| 64 | AHSG | POMC |
| 65 | ANG | APOA1 |
| 66 | ANG | BMI |
| 67 | ANG | CCL2 |
| 68 | ANG | CD40 |
| 69 | ANG | CRP |
| 70 | ANG | HDLC |
| 71 | ANG | Hip |
| 72 | ANG | IGF1 |
| 73 | ANG | IL2RA |
| 74 | ANG | IL6ST |
| 75 | ANG | Insulin |
| 76 | ANG | LEP |
| 77 | ANG | POMC |
| 78 | ANG | Sex |
| 79 | ANG | VCAM1 |
| 80 | ANG | VEGF |
| 81 | APOA1 | LEP |
| 82 | APOA1 | POMC |
| 83 | APOA1 | VEGF |
| 84 | APOE | LEP |

| 2-Panel | Marker 1 | Marker 2 |
|---|---|---|
| 85 | APOE | POMC |
| 86 | BAX | POMC |
| 87 | BMI | CD40 |
| 88 | BMI | CRP |
| 89 | BMI | HDLC |
| 90 | BMI | IGF1 |
| 91 | BMI | Ins120 |
| 92 | BMI | POMC |
| 93 | BMI | VEGF |
| 94 | BMI | Waist |
| 95 | C3 | POMC |
| 96 | CCL2 | POMC |
| 97 | CD14 | IL6ST |
| 98 | CD14 | LEP |
| 99 | CD14 | POMC |
| 100 | CD14 | Sex |
| 101 | CD14 | VEGF |
| 102 | CD40 | CDK5 |
| 103 | CD40 | HDLC |
| 104 | CD40 | IGF1 |
| 105 | CD40 | IL6ST |
| 106 | CD40 | Insulin |
| 107 | CD40 | LEP |
| 108 | CD40 | POMC |
| 109 | CD40 | Sex |
| 110 | CD40 | VEGF |
| 111 | CD40 | WT |
| 112 | CDK5 | POMC |

FIG. 13B

| 2-Panel | Marker 1 | Marker 2 |
|---|---|---|
| 113 | CHOL | POMC |
| 114 | CRP | Hip |
| 115 | CRP | IGF1 |
| 116 | CRP | IL6ST |
| 117 | CRP | Insulin |
| 118 | CRP | LEP |
| 119 | CRP | POMC |
| 120 | CRP | Sex |
| 121 | CRP | VEGF |
| 122 | CRP | WT |
| 123 | DBP | POMC |
| 124 | DPP4 | LEP |
| 125 | DPP4 | POMC |
| 126 | DPP4 | VEGF |
| 127 | EGF | POMC |
| 128 | ENG | POMC |
| 129 | FamHX | POMC |
| 130 | FGA | LEP |
| 131 | FGA | POMC |
| 132 | FTH1 | POMC |
| 133 | Gluc120 | POMC |
| 134 | Glucose | POMC |
| 135 | HBA1C | POMC |
| 136 | HDLC | Hip |
| 137 | HDLC | IGF1 |
| 138 | HDLC | IL6ST |
| 139 | HDLC | Insulin |
| 140 | HDLC | LEP |

| 2-Panel | Marker 1 | Marker 2 |
|---|---|---|
| 141 | HDLC | POMC |
| 142 | HDLC | Sex |
| 143 | HDLC | VEGF |
| 144 | HDLC | VWF |
| 145 | HDLC | WT |
| 146 | HGF | POMC |
| 147 | HGF | Sex |
| 148 | Hip | IGF1 |
| 149 | Hip | POMC |
| 150 | Hip | VEGF |
| 151 | HP | POMC |
| 152 | HP | Sex |
| 153 | HT | POMC |
| 154 | ICAM1 | POMC |
| 155 | IGF1 | IL6ST |
| 156 | IGF1 | LEP |
| 157 | IGF1 | POMC |
| 158 | IGF1 | Sex |
| 159 | IGF1 | VCAM1 |
| 160 | IGF1 | VEGF |
| 161 | IGFBP1 | POMC |
| 162 | IGFBP3 | POMC |
| 163 | IL18 | POMC |
| 164 | IL2RA | LEP |
| 165 | IL2RA | POMC |
| 166 | IL6R | POMC |
| 167 | IL6R | IL6ST |
| 168 | IL6ST | LEP |

FIG. 13C

| 2-Panel | Marker 1 | Marker 2 |
|---|---|---|
| 197 | POMC | WT |
| 198 | Sex | VEGF |
| 199 | VCAM1 | VEGF |
| 200 | VEGF | VWF |

| 2-Panel | Marker 1 | Marker 2 |
|---|---|---|
| 169 | IL6ST | POMC |
| 170 | IL6ST | Sex |
| 171 | IL6ST | VEGF |
| 172 | IL8 | POMC |
| 173 | INHBA | POMC |
| 174 | Ins120 | Insulin |
| 175 | Ins120 | POMC |
| 176 | Ins120 | Sex |
| 177 | Ins120 | VEGF |
| 178 | Insulin | POMC |
| 179 | Insulin | VEGF |
| 180 | LDL | POMC |
| 181 | LEP | POMC |
| 182 | LEP | VCAM1 |
| 183 | LEP | VEGF |
| 184 | PLAT | POMC |
| 185 | POMC | SBP |
| 186 | POMC | SCp |
| 187 | POMC | SELE |
| 188 | POMC | SELP |
| 189 | POMC | Sex |
| 190 | POMC | SHBG |
| 191 | POMC | TNFRSF1B |
| 192 | POMC | TRIG |
| 193 | POMC | VCAM1 |
| 194 | POMC | VEGF |
| 195 | POMC | VWF |
| 196 | POMC | Waist |

FIG. 13D

| 3-Panel | Marker 1 | Marker 2 | Marker 3 |
|---|---|---|---|
| 1 | ACE | ADIPOQ | Age |
| 2 | ACE | Age | AGER |
| 3 | ACE | Age | AHSG |
| 4 | ACE | Age | ANG |
| 5 | ACE | Age | APOA1 |
| 6 | ACE | Age | APOE |
| 7 | ACE | Age | BAX |
| 8 | ACE | Age | BMI |
| 9 | ACE | Age | C3 |
| 10 | ACE | Age | CCL2 |
| 11 | ACE | Age | CD14 |
| 12 | ACE | Age | CD40 |
| 13 | ACE | Age | CDK5 |
| 14 | ACE | Age | CHOL |
| 15 | ACE | Age | CRP |
| 16 | ACE | Age | DBP |
| 17 | ACE | Age | DPP4 |
| 18 | ACE | Age | EGF |
| 19 | ACE | Age | ENG |
| 20 | ACE | Age | FamHX |
| 21 | ACE | Age | FGA |
| 22 | ACE | Age | FTH1 |
| 23 | ACE | Age | Gluc120 |
| 24 | ACE | Age | Glucose |
| 25 | ACE | Age | HBA1C |
| 26 | ACE | Age | HDLC |
| 27 | ACE | Age | HGF |
| 28 | ACE | Age | Hip |
| 29 | ACE | Age | HP |
| 30 | ACE | Age | HT |
| 31 | ACE | Age | ICAM1 |
| 32 | ACE | Age | IGF1 |
| 33 | ACE | Age | IGFBP1 |
| 34 | ACE | Age | IGFBP3 |
| 35 | ACE | Age | IL18 |
| 36 | ACE | Age | IL2RA |
| 37 | ACE | Age | IL6R |
| 38 | ACE | Age | IL6ST |
| 39 | ACE | Age | IL8 |
| 40 | ACE | Age | INHBA |
| 41 | ACE | Age | Ins120 |
| 42 | ACE | Age | Insulin |
| 43 | ACE | Age | LDL |
| 44 | ACE | Age | LEP |
| 45 | ACE | Age | PLAT |
| 46 | ACE | Age | POMC |
| 47 | ACE | Age | SBP |
| 48 | ACE | Age | SCp |
| 49 | ACE | Age | SELE |
| 50 | ACE | Age | SELP |
| 51 | ACE | Age | Sex |
| 52 | ACE | Age | SHBG |
| 53 | ACE | Age | TNFRSF1B |
| 54 | ACE | Age | TRIG |
| 55 | ACE | Age | VCAM1 |
| 56 | ACE | Age | VEGF |

FIG. 14A

| 3-Panel | Marker 1 | Marker 2 | Marker 3 |
|---|---|---|---|
| 57 | ACE | Age | VWF |
| 58 | ACE | Age | Waist |
| 59 | ACE | Age | WT |
| 60 | ACE | ANG | POMC |
| 61 | ACE | APOE | POMC |
| 62 | ACE | BMI | POMC |
| 63 | ACE | CDK5 | POMC |
| 64 | ACE | CRP | POMC |
| 65 | ACE | FGA | POMC |
| 66 | ACE | HDLC | POMC |
| 67 | ACE | IGF1 | POMC |
| 68 | ACE | IL6ST | POMC |
| 69 | ACE | LEP | POMC |
| 70 | ACE | POMC | SBP |
| 71 | ACE | POMC | Sex |
| 72 | ACE | POMC | VCAM1 |
| 73 | ACE | POMC | VEGF |
| 74 | ADIPOQ | Age | AGER |
| 75 | ADIPOQ | Age | AHSG |
| 76 | ADIPOQ | Age | ANG |
| 77 | ADIPOQ | Age | APOA1 |
| 78 | ADIPOQ | Age | APOE |
| 79 | ADIPOQ | Age | BAX |
| 80 | ADIPOQ | Age | BMI |
| 81 | ADIPOQ | Age | C3 |
| 82 | ADIPOQ | Age | CCL2 |
| 83 | ADIPOQ | Age | CD14 |
| 84 | ADIPOQ | Age | CD40 |

| 3-Panel | Marker 1 | Marker 2 | Marker 3 |
|---|---|---|---|
| 85 | ADIPOQ | Age | CDK5 |
| 86 | ADIPOQ | Age | CHOL |
| 87 | ADIPOQ | Age | CRP |
| 88 | ADIPOQ | Age | DBP |
| 89 | ADIPOQ | Age | DPP4 |
| 90 | ADIPOQ | Age | EGF |
| 91 | ADIPOQ | Age | ENG |
| 92 | ADIPOQ | Age | FamHX |
| 93 | ADIPOQ | Age | FGA |
| 94 | ADIPOQ | Age | FTH1 |
| 95 | ADIPOQ | Age | Gluc120 |
| 96 | ADIPOQ | Age | Glucose |
| 97 | ADIPOQ | Age | HBA1C |
| 98 | ADIPOQ | Age | HDLC |
| 99 | ADIPOQ | Age | HGF |
| 100 | ADIPOQ | Age | Hip |
| 101 | ADIPOQ | Age | HP |
| 102 | ADIPOQ | Age | HT |
| 103 | ADIPOQ | Age | ICAM1 |
| 104 | ADIPOQ | Age | IGF1 |
| 105 | ADIPOQ | Age | IGFBP1 |
| 106 | ADIPOQ | Age | IGFBP3 |
| 107 | ADIPOQ | Age | IL18 |
| 108 | ADIPOQ | Age | IL2RA |
| 109 | ADIPOQ | Age | IL6R |
| 110 | ADIPOQ | Age | IL6ST |
| 111 | ADIPOQ | Age | IL8 |
| 112 | ADIPOQ | Age | INHBA |

FIG. 14B

| 3-Panel | Marker 1 | Marker 2 | Marker 3 |
|---|---|---|---|
| 141 | ADIPOQ | HT | POMC |
| 142 | ADIPOQ | IGF1 | POMC |
| 143 | ADIPOQ | IL6ST | POMC |
| 144 | ADIPOQ | Ins120 | POMC |
| 145 | ADIPOQ | LEP | POMC |
| 146 | ADIPOQ | POMC | Sex |
| 147 | ADIPOQ | POMC | VCAM1 |
| 148 | ADIPOQ | POMC | VEGF |
| 149 | Age | AGER | AHSG |
| 150 | Age | AGER | ANG |
| 151 | Age | AGER | APOA1 |
| 152 | Age | AGER | APOE |
| 153 | Age | AGER | BAX |
| 154 | Age | AGER | BMI |
| 155 | Age | AGER | C3 |
| 156 | Age | AGER | CCL2 |
| 157 | Age | AGER | CD14 |
| 158 | Age | AGER | CD40 |
| 159 | Age | AGER | CDK5 |
| 160 | Age | AGER | CHOL |
| 161 | Age | AGER | CRP |
| 162 | Age | AGER | DBP |
| 163 | Age | AGER | DPP4 |
| 164 | Age | AGER | EGF |
| 165 | Age | AGER | ENG |
| 166 | Age | AGER | FamHX |
| 167 | Age | AGER | FGA |
| 168 | Age | AGER | FTH1 |

| 3-Panel | Marker 1 | Marker 2 | Marker 3 |
|---|---|---|---|
| 113 | ADIPOQ | Age | Ins120 |
| 114 | ADIPOQ | Age | Insulin |
| 115 | ADIPOQ | Age | LDL |
| 116 | ADIPOQ | Age | LEP |
| 117 | ADIPOQ | Age | PLAT |
| 118 | ADIPOQ | Age | POMC |
| 119 | ADIPOQ | Age | SBP |
| 120 | ADIPOQ | Age | SCp |
| 121 | ADIPOQ | Age | SELE |
| 122 | ADIPOQ | Age | SELP |
| 123 | ADIPOQ | Age | Sex |
| 124 | ADIPOQ | Age | SHBG |
| 125 | ADIPOQ | Age | TNFRSF1B |
| 126 | ADIPOQ | Age | TRIG |
| 127 | ADIPOQ | Age | VCAM1 |
| 128 | ADIPOQ | Age | VEGF |
| 129 | ADIPOQ | Age | VWF |
| 130 | ADIPOQ | Age | Waist |
| 131 | ADIPOQ | Age | WT |
| 132 | ADIPOQ | ANG | POMC |
| 133 | ADIPOQ | APOE | POMC |
| 134 | ADIPOQ | BMI | CRP |
| 135 | ADIPOQ | CD14 | POMC |
| 136 | ADIPOQ | CDK5 | POMC |
| 137 | ADIPOQ | CRP | POMC |
| 138 | ADIPOQ | DPP4 | POMC |
| 139 | ADIPOQ | FGA | POMC |
| 140 | ADIPOQ | HDLC | POMC |

FIG. 14C

| 3-Panel | Marker 1 | Marker 2 | Marker 3 |
|---|---|---|---|
| 169 | Age | AGER | Gluc120 |
| 170 | Age | AGER | Glucose |
| 171 | Age | AGER | HBA1C |
| 172 | Age | AGER | HDLC |
| 173 | Age | AGER | HGF |
| 174 | Age | AGER | Hip |
| 175 | Age | AGER | HP |
| 176 | Age | AGER | HT |
| 177 | Age | AGER | ICAM1 |
| 178 | Age | AGER | IGF1 |
| 179 | Age | AGER | IGFBP1 |
| 180 | Age | AGER | IGFBP3 |
| 181 | Age | AGER | IL18 |
| 182 | Age | AGER | IL2RA |
| 183 | Age | AGER | IL6R |
| 184 | Age | AGER | IL6ST |
| 185 | Age | AGER | IL8 |
| 186 | Age | AGER | INHBA |
| 187 | Age | AGER | Ins120 |
| 188 | Age | AGER | Insulin |
| 189 | Age | AGER | LDL |
| 190 | Age | AGER | LEP |
| 191 | Age | AGER | PLAT |
| 192 | Age | AGER | POMC |
| 193 | Age | AGER | SBP |
| 194 | Age | AGER | SCp |
| 195 | Age | AGER | SELE |
| 196 | Age | AGER | SELP |

| 3-Panel | Marker 1 | Marker 2 | Marker 3 |
|---|---|---|---|
| 197 | Age | AGER | Sex |
| 198 | Age | AGER | SHBG |
| 199 | Age | AGER | TNFRSF1B |
| 200 | Age | AGER | TRIG |
| 201 | Age | AGER | VCAM1 |
| 202 | Age | AGER | VEGF |
| 203 | Age | AGER | VWF |
| 204 | Age | AGER | Waist |
| 205 | Age | AGER | WT |
| 206 | Age | AHSG | ANG |
| 207 | Age | AHSG | APOA1 |
| 208 | Age | AHSG | APOE |
| 209 | Age | AHSG | BAX |
| 210 | Age | AHSG | BMI |
| 211 | Age | AHSG | C3 |
| 212 | Age | AHSG | CCL2 |
| 213 | Age | AHSG | CD14 |
| 214 | Age | AHSG | CD40 |
| 215 | Age | AHSG | CDK5 |
| 216 | Age | AHSG | CHOL |
| 217 | Age | AHSG | CRP |
| 218 | Age | AHSG | DBP |
| 219 | Age | AHSG | DPP4 |
| 220 | Age | AHSG | EGF |
| 221 | Age | AHSG | ENG |
| 222 | Age | AHSG | FamHX |
| 223 | Age | AHSG | FGA |
| 224 | Age | AHSG | FTH1 |

FIG. 14D

| 3-Panel | Marker 1 | Marker 2 | Marker 3 |
|---|---|---|---|
| 225 | Age | AHSG | Gluc120 |
| 226 | Age | AHSG | Glucose |
| 227 | Age | AHSG | HBA1C |
| 228 | Age | AHSG | HDLC |
| 229 | Age | AHSG | HGF |
| 230 | Age | AHSG | Hip |
| 231 | Age | AHSG | HP |
| 232 | Age | AHSG | HT |
| 233 | Age | AHSG | ICAM1 |
| 234 | Age | AHSG | IGF1 |
| 235 | Age | AHSG | IGFBP1 |
| 236 | Age | AHSG | IGFBP3 |
| 237 | Age | AHSG | IL18 |
| 238 | Age | AHSG | IL2RA |
| 239 | Age | AHSG | IL6R |
| 240 | Age | AHSG | IL6ST |
| 241 | Age | AHSG | IL8 |
| 242 | Age | AHSG | INHBA |
| 243 | Age | AHSG | Ins120 |
| 244 | Age | AHSG | Insulin |
| 245 | Age | AHSG | LDL |
| 246 | Age | AHSG | LEP |
| 247 | Age | AHSG | PLAT |
| 248 | Age | AHSG | POMC |
| 249 | Age | AHSG | SBP |
| 250 | Age | AHSG | SCp |
| 251 | Age | AHSG | SELE |
| 252 | Age | AHSG | SELP |

| 3-Panel | Marker 1 | Marker 2 | Marker 3 |
|---|---|---|---|
| 253 | Age | AHSG | Sex |
| 254 | Age | AHSG | SHBG |
| 255 | Age | AHSG | TNFRSF1B |
| 256 | Age | AHSG | TRIG |
| 257 | Age | AHSG | VCAM1 |
| 258 | Age | AHSG | VEGF |
| 259 | Age | AHSG | VWF |
| 260 | Age | AHSG | Waist |
| 261 | Age | AHSG | WT |
| 262 | Age | ANG | APOA1 |
| 263 | Age | ANG | APOE |
| 264 | Age | ANG | BAX |
| 265 | Age | ANG | BMI |
| 266 | Age | ANG | C3 |
| 267 | Age | ANG | CCL2 |
| 268 | Age | ANG | CD14 |
| 269 | Age | ANG | CD40 |
| 270 | Age | ANG | CDK5 |
| 271 | Age | ANG | CHOL |
| 272 | Age | ANG | CRP |
| 273 | Age | ANG | DBP |
| 274 | Age | ANG | DPP4 |
| 275 | Age | ANG | EGF |
| 276 | Age | ANG | ENG |
| 277 | Age | ANG | FamHX |
| 278 | Age | ANG | FGA |
| 279 | Age | ANG | FTH1 |
| 280 | Age | ANG | Gluc120 |

FIG. 14E

| 3-Panel | Marker 1 | Marker 2 | Marker 3 |
|---|---|---|---|
| 281 | Age | ANG | Glucose |
| 282 | Age | ANG | HBA1C |
| 283 | Age | ANG | HDLC |
| 284 | Age | ANG | HGF |
| 285 | Age | ANG | Hip |
| 286 | Age | ANG | HP |
| 287 | Age | ANG | HT |
| 288 | Age | ANG | ICAM1 |
| 289 | Age | ANG | IGF1 |
| 290 | Age | ANG | IGFBP1 |
| 291 | Age | ANG | IGFBP3 |
| 292 | Age | ANG | IL18 |
| 293 | Age | ANG | IL2RA |
| 294 | Age | ANG | IL6R |
| 295 | Age | ANG | IL6ST |
| 296 | Age | ANG | IL8 |
| 297 | Age | ANG | INHBA |
| 298 | Age | ANG | Ins120 |
| 299 | Age | ANG | Insulin |
| 300 | Age | ANG | LDL |
| 301 | Age | ANG | LEP |
| 302 | Age | ANG | PLAT |
| 303 | Age | ANG | POMC |
| 304 | Age | ANG | SBP |
| 305 | Age | ANG | SCp |
| 306 | Age | ANG | SELE |
| 307 | Age | ANG | SELP |
| 308 | Age | ANG | Sex |

| 3-Panel | Marker 1 | Marker 2 | Marker 3 |
|---|---|---|---|
| 309 | Age | ANG | SHBG |
| 310 | Age | ANG | TNFRSF1B |
| 311 | Age | ANG | TRIG |
| 312 | Age | ANG | VCAM1 |
| 313 | Age | ANG | VEGF |
| 314 | Age | ANG | VWF |
| 315 | Age | ANG | Waist |
| 316 | Age | ANG | WT |
| 317 | Age | APOA1 | APOE |
| 318 | Age | APOA1 | BAX |
| 319 | Age | APOA1 | BMI |
| 320 | Age | APOA1 | C3 |
| 321 | Age | APOA1 | CCL2 |
| 322 | Age | APOA1 | CD14 |
| 323 | Age | APOA1 | CD40 |
| 324 | Age | APOA1 | CDK5 |
| 325 | Age | APOA1 | CHOL |
| 326 | Age | APOA1 | CRP |
| 327 | Age | APOA1 | DBP |
| 328 | Age | APOA1 | DPP4 |
| 329 | Age | APOA1 | EGF |
| 330 | Age | APOA1 | ENG |
| 331 | Age | APOA1 | FamHX |
| 332 | Age | APOA1 | FGA |
| 333 | Age | APOA1 | FTH1 |
| 334 | Age | APOA1 | Gluc120 |
| 335 | Age | APOA1 | Glucose |
| 336 | Age | APOA1 | HBA1C |

FIG. 14F

| 3-Panel | Marker 1 | Marker 2 | Marker 3 |
|---|---|---|---|
| 337 | Age | APOA1 | HDLC |
| 338 | Age | APOA1 | HGF |
| 339 | Age | APOA1 | Hip |
| 340 | Age | APOA1 | HP |
| 341 | Age | APOA1 | HT |
| 342 | Age | APOA1 | ICAM1 |
| 343 | Age | APOA1 | IGF1 |
| 344 | Age | APOA1 | IGFBP1 |
| 345 | Age | APOA1 | IGFBP3 |
| 346 | Age | APOA1 | IL18 |
| 347 | Age | APOA1 | IL2RA |
| 348 | Age | APOA1 | IL6R |
| 349 | Age | APOA1 | IL6ST |
| 350 | Age | APOA1 | IL8 |
| 351 | Age | APOA1 | INHBA |
| 352 | Age | APOA1 | Ins120 |
| 353 | Age | APOA1 | Insulin |
| 354 | Age | APOA1 | LDL |
| 355 | Age | APOA1 | LEP |
| 356 | Age | APOA1 | PLAT |
| 357 | Age | APOA1 | POMC |
| 358 | Age | APOA1 | SBP |
| 359 | Age | APOA1 | SCp |
| 360 | Age | APOA1 | SELE |
| 361 | Age | APOA1 | SELP |
| 362 | Age | APOA1 | Sex |
| 363 | Age | APOA1 | SHBG |
| 364 | Age | APOA1 | TNFRSF1B |

| 3-Panel | Marker 1 | Marker 2 | Marker 3 |
|---|---|---|---|
| 365 | Age | APOA1 | TRIG |
| 366 | Age | APOA1 | VCAM1 |
| 367 | Age | APOA1 | VEGF |
| 368 | Age | APOA1 | VWF |
| 369 | Age | APOA1 | Waist |
| 370 | Age | APOE | WT |
| 371 | Age | APOE | BAX |
| 372 | Age | APOE | BMI |
| 373 | Age | APOE | C3 |
| 374 | Age | APOE | CCL2 |
| 375 | Age | APOE | CD14 |
| 376 | Age | APOE | CD40 |
| 377 | Age | APOE | CDK5 |
| 378 | Age | APOE | CHOL |
| 379 | Age | APOE | CRP |
| 380 | Age | APOE | DBP |
| 381 | Age | APOE | DPP4 |
| 382 | Age | APOE | EGF |
| 383 | Age | APOE | ENG |
| 384 | Age | APOE | FamHX |
| 385 | Age | APOE | FGA |
| 386 | Age | APOE | FTH1 |
| 387 | Age | APOE | Gluc120 |
| 388 | Age | APOE | Glucose |
| 389 | Age | APOE | HBA1C |
| 390 | Age | APOE | HDLC |
| 391 | Age | APOE | HGF |
| 392 | Age | APOE | Hip |

FIG. 14G

| 3-Panel | Marker 1 | Marker 2 | Marker 3 |
|---|---|---|---|
| 393 | Age | APOE | HP |
| 394 | Age | APOE | HT |
| 395 | Age | APOE | ICAM1 |
| 396 | Age | APOE | IGF1 |
| 397 | Age | APOE | IGFBP1 |
| 398 | Age | APOE | IGFBP3 |
| 399 | Age | APOE | IL18 |
| 400 | Age | APOE | IL2RA |
| 401 | Age | APOE | IL6R |
| 402 | Age | APOE | IL6ST |
| 403 | Age | APOE | IL8 |
| 404 | Age | APOE | INHBA |
| 405 | Age | APOE | Ins120 |
| 406 | Age | APOE | Insulin |
| 407 | Age | APOE | LDL |
| 408 | Age | APOE | LEP |
| 409 | Age | APOE | PLAT |
| 410 | Age | APOE | POMC |
| 411 | Age | APOE | SBP |
| 412 | Age | APOE | SCp |
| 413 | Age | APOE | SELE |
| 414 | Age | APOE | SELP |
| 415 | Age | APOE | Sex |
| 416 | Age | APOE | SHBG |
| 417 | Age | APOE | TNFRSF1B |
| 418 | Age | APOE | TRIG |
| 419 | Age | APOE | VCAM1 |
| 420 | Age | APOE | VEGF |

| 3-Panel | Marker 1 | Marker 2 | Marker 3 |
|---|---|---|---|
| 421 | Age | APOE | VWF |
| 422 | Age | APOE | Waist |
| 423 | Age | APOE | WT |
| 424 | Age | BAX | BMI |
| 425 | Age | BAX | C3 |
| 426 | Age | BAX | CCL2 |
| 427 | Age | BAX | CD14 |
| 428 | Age | BAX | CD40 |
| 429 | Age | BAX | CDK5 |
| 430 | Age | BAX | CHOL |
| 431 | Age | BAX | CRP |
| 432 | Age | BAX | DBP |
| 433 | Age | BAX | DPP4 |
| 434 | Age | BAX | EGF |
| 435 | Age | BAX | ENG |
| 436 | Age | BAX | FamHX |
| 437 | Age | BAX | FGA |
| 438 | Age | BAX | FTH1 |
| 439 | Age | BAX | Gluc120 |
| 440 | Age | BAX | Glucose |
| 441 | Age | BAX | HBA1C |
| 442 | Age | BAX | HDLC |
| 443 | Age | BAX | HGF |
| 444 | Age | BAX | Hip |
| 445 | Age | BAX | HP |
| 446 | Age | BAX | HT |
| 447 | Age | BAX | ICAM1 |
| 448 | Age | BAX | IGF1 |

FIG. 14H

| 3-Panel | Marker 1 | Marker 2 | Marker 3 |
|---|---|---|---|
| 449 | Age | BAX | IGFBP1 |
| 450 | Age | BAX | IGFBP3 |
| 451 | Age | BAX | IL18 |
| 452 | Age | BAX | IL2RA |
| 453 | Age | BAX | IL6R |
| 454 | Age | BAX | IL6ST |
| 455 | Age | BAX | IL8 |
| 456 | Age | BAX | INHBA |
| 457 | Age | BAX | Ins120 |
| 458 | Age | BAX | insulin |
| 459 | Age | BAX | LDL |
| 460 | Age | BAX | LEP |
| 461 | Age | BAX | PLAT |
| 462 | Age | BAX | POMC |
| 463 | Age | BAX | SBP |
| 464 | Age | BAX | SCp |
| 465 | Age | BAX | SELE |
| 466 | Age | BAX | SELP |
| 467 | Age | BAX | Sex |
| 468 | Age | BAX | SHBG |
| 469 | Age | BAX | TNFRSF1B |
| 470 | Age | BAX | TRIG |
| 471 | Age | BAX | VCAM1 |
| 472 | Age | BAX | VEGF |
| 473 | Age | BAX | VWF |
| 474 | Age | BAX | Waist |
| 475 | Age | BAX | WT |
| 476 | Age | BMI | C3 |

| 3-Panel | Marker 1 | Marker 2 | Marker 3 |
|---|---|---|---|
| 477 | Age | BMI | CCL2 |
| 478 | Age | BMI | CD14 |
| 479 | Age | BMI | CD40 |
| 480 | Age | BMI | CDK5 |
| 481 | Age | BMI | CHOL |
| 482 | Age | BMI | CRP |
| 483 | Age | BMI | DBP |
| 484 | Age | BMI | DPP4 |
| 485 | Age | BMI | EGF |
| 486 | Age | BMI | ENG |
| 487 | Age | BMI | FamHX |
| 488 | Age | BMI | FGA |
| 489 | Age | BMI | FTH1 |
| 490 | Age | BMI | Gluc120 |
| 491 | Age | BMI | Glucose |
| 492 | Age | BMI | HBA1C |
| 493 | Age | BMI | HDLC |
| 494 | Age | BMI | HGF |
| 495 | Age | BMI | Hip |
| 496 | Age | BMI | HP |
| 497 | Age | BMI | HT |
| 498 | Age | BMI | ICAM1 |
| 499 | Age | BMI | IGF1 |
| 500 | Age | BMI | IGFBP1 |
| 501 | Age | BMI | IGFBP3 |
| 502 | Age | BMI | IL18 |
| 503 | Age | BMI | IL2RA |
| 504 | Age | BMI | IL6R |

FIG. 14I

| 3-Panel | Marker 1 | Marker 2 | Marker 3 |
|---|---|---|---|
| 533 | Age | C3 | DBP |
| 534 | Age | C3 | DPP4 |
| 535 | Age | C3 | EGF |
| 536 | Age | C3 | ENG |
| 537 | Age | C3 | FamHX |
| 538 | Age | C3 | FGA |
| 539 | Age | C3 | FTH1 |
| 540 | Age | C3 | Gluc120 |
| 541 | Age | C3 | Glucose |
| 542 | Age | C3 | HBA1C |
| 543 | Age | C3 | HDLC |
| 544 | Age | C3 | HGF |
| 545 | Age | C3 | Hp |
| 546 | Age | C3 | HP |
| 547 | Age | C3 | HT |
| 548 | Age | C3 | ICAM1 |
| 549 | Age | C3 | IGF1 |
| 550 | Age | C3 | IGFBP1 |
| 551 | Age | C3 | IGFBP3 |
| 552 | Age | C3 | IL18 |
| 553 | Age | C3 | IL2RA |
| 554 | Age | C3 | IL6R |
| 555 | Age | C3 | IL6ST |
| 556 | Age | C3 | IL8 |
| 557 | Age | C3 | INHBA |
| 558 | Age | C3 | Ins120 |
| 559 | Age | C3 | Insulin |
| 560 | Age | C3 | LDL |

| 3-Panel | Marker 1 | Marker 2 | Marker 3 |
|---|---|---|---|
| 505 | Age | BMI | IL8 |
| 506 | Age | BMI | INHBA |
| 507 | Age | BMI | Ins120 |
| 508 | Age | BMI | Insulin |
| 509 | Age | BMI | LDL |
| 510 | Age | BMI | LEP |
| 511 | Age | BMI | PLAT |
| 512 | Age | BMI | POMC |
| 513 | Age | BMI | SBP |
| 514 | Age | BMI | SCp |
| 515 | Age | BMI | SELE |
| 516 | Age | BMI | SELP |
| 517 | Age | BMI | Sex |
| 518 | Age | BMI | SHBG |
| 519 | Age | BMI | TNFRSF1B |
| 520 | Age | BMI | TRIG |
| 521 | Age | BMI | VCAM1 |
| 522 | Age | BMI | VEGF |
| 523 | Age | BMI | VWF |
| 524 | Age | BMI | Waist |
| 525 | Age | BMI | WT |
| 526 | Age | C3 | CCL2 |
| 527 | Age | C3 | CD14 |
| 528 | Age | C3 | CD40 |
| 529 | Age | C3 | CDK5 |
| 530 | Age | C3 | CHOL |
| 531 | Age | C3 | CRP |
| 532 | Age | C3 | |

FIG. 14J

| 3-Panel | Marker 1 | Marker 2 | Marker 3 |
|---|---|---|---|
| 561 | Age | C3 | LEP |
| 562 | Age | C3 | PLAT |
| 563 | Age | C3 | POMC |
| 564 | Age | C3 | SBP |
| 565 | Age | C3 | SCp |
| 566 | Age | C3 | SELE |
| 567 | Age | C3 | SELP |
| 568 | Age | C3 | Sex |
| 569 | Age | C3 | SHBG |
| 570 | Age | C3 | TNFRSF1B |
| 571 | Age | C3 | TRIG |
| 572 | Age | C3 | VCAM1 |
| 573 | Age | C3 | VEGF |
| 574 | Age | C3 | VWF |
| 575 | Age | C3 | Waist |
| 576 | Age | C3 | WT |
| 577 | Age | CCL2 | CD14 |
| 578 | Age | CCL2 | CD40 |
| 579 | Age | CCL2 | CDK5 |
| 580 | Age | CCL2 | CHOL |
| 581 | Age | CCL2 | CRP |
| 582 | Age | CCL2 | DBP |
| 583 | Age | CCL2 | DPP4 |
| 584 | Age | CCL2 | EGF |
| 585 | Age | CCL2 | ENG |
| 586 | Age | CCL2 | FamHX |
| 587 | Age | CCL2 | FGA |
| 588 | Age | CCL2 | FTH1 |

| 3-Panel | Marker 1 | Marker 2 | Marker 3 |
|---|---|---|---|
| 589 | Age | CCL2 | Gluc120 |
| 590 | Age | CCL2 | Glucose |
| 591 | Age | CCL2 | HBA1C |
| 592 | Age | CCL2 | HDLC |
| 593 | Age | CCL2 | HGF |
| 594 | Age | CCL2 | Hip |
| 595 | Age | CCL2 | HP |
| 596 | Age | CCL2 | HT |
| 597 | Age | CCL2 | ICAM1 |
| 598 | Age | CCL2 | IGF1 |
| 599 | Age | CCL2 | IGFBP1 |
| 600 | Age | CCL2 | IGFBP3 |
| 601 | Age | CCL2 | IL18 |
| 602 | Age | CCL2 | IL2RA |
| 603 | Age | CCL2 | IL6R |
| 604 | Age | CCL2 | IL6ST |
| 605 | Age | CCL2 | IL8 |
| 606 | Age | CCL2 | INHBA |
| 607 | Age | CCL2 | Ins120 |
| 608 | Age | CCL2 | Insulin |
| 609 | Age | CCL2 | LDL |
| 610 | Age | CCL2 | LEP |
| 611 | Age | CCL2 | PLAT |
| 612 | Age | CCL2 | POMC |
| 613 | Age | CCL2 | SBP |
| 614 | Age | CCL2 | SCp |
| 615 | Age | CCL2 | SELE |
| 616 | Age | CCL2 | SELP |

FIG. 14K

| 3-Panel | Marker 1 | Marker 2 | Marker 3 |
|---|---|---|---|
| 617 | Age | CCL2 | Sex |
| 618 | Age | CCL2 | SHBG |
| 619 | Age | CCL2 | TNFRSF1B |
| 620 | Age | CCL2 | TRIG |
| 621 | Age | CCL2 | VCAM1 |
| 622 | Age | CCL2 | VEGF |
| 623 | Age | CCL2 | VWF |
| 624 | Age | CCL2 | Waist |
| 625 | Age | CCL2 | WT |
| 626 | Age | CD14 | CD40 |
| 627 | Age | CD14 | CDK5 |
| 628 | Age | CD14 | CHOL |
| 629 | Age | CD14 | CRP |
| 630 | Age | CD14 | DBP |
| 631 | Age | CD14 | DPP4 |
| 632 | Age | CD14 | EGF |
| 633 | Age | CD14 | ENG |
| 634 | Age | CD14 | FamHX |
| 635 | Age | CD14 | FGA |
| 636 | Age | CD14 | FTH1 |
| 637 | Age | CD14 | Gluc120 |
| 638 | Age | CD14 | Glucose |
| 639 | Age | CD14 | HBA1C |
| 640 | Age | CD14 | HDLC |
| 641 | Age | CD14 | HGF |
| 642 | Age | CD14 | Hip |
| 643 | Age | CD14 | HP |
| 644 | Age | CD14 | HT |

| 3-Panel | Marker 1 | Marker 2 | Marker 3 |
|---|---|---|---|
| 645 | Age | CD14 | ICAM1 |
| 646 | Age | CD14 | IGF1 |
| 647 | Age | CD14 | IGFBP1 |
| 648 | Age | CD14 | IGFBP3 |
| 649 | Age | CD14 | IL18 |
| 650 | Age | CD14 | IL2RA |
| 651 | Age | CD14 | IL6R |
| 652 | Age | CD14 | IL6ST |
| 653 | Age | CD14 | IL8 |
| 654 | Age | CD14 | INHBA |
| 655 | Age | CD14 | Ins120 |
| 656 | Age | CD14 | Insulin |
| 657 | Age | CD14 | LDL |
| 658 | Age | CD14 | LEP |
| 659 | Age | CD14 | PLAT |
| 660 | Age | CD14 | POMC |
| 661 | Age | CD14 | SBP |
| 662 | Age | CD14 | SCp |
| 663 | Age | CD14 | SELE |
| 664 | Age | CD14 | SELP |
| 665 | Age | CD14 | Sex |
| 666 | Age | CD14 | SHBG |
| 667 | Age | CD14 | TNFRSF1B |
| 668 | Age | CD14 | TRIG |
| 669 | Age | CD14 | VCAM1 |
| 670 | Age | CD14 | VEGF |
| 671 | Age | CD14 | VWF |
| 672 | Age | CD14 | Waist |

FIG. 14L

| 3-Panel | Marker 1 | Marker 2 | Marker 3 |
|---|---|---|---|
| 673 | Age | CD14 | WT |
| 674 | Age | CD40 | CDK5 |
| 675 | Age | CD40 | CHOL |
| 676 | Age | CD40 | CRP |
| 677 | Age | CD40 | DBP |
| 678 | Age | CD40 | DPP4 |
| 679 | Age | CD40 | EGF |
| 680 | Age | CD40 | ENG |
| 681 | Age | CD40 | FamHX |
| 682 | Age | CD40 | FGA |
| 683 | Age | CD40 | FTH1 |
| 684 | Age | CD40 | Gluc120 |
| 685 | Age | CD40 | Glucose |
| 686 | Age | CD40 | HBA1C |
| 687 | Age | CD40 | HDLC |
| 688 | Age | CD40 | HGF |
| 689 | Age | CD40 | Hip |
| 690 | Age | CD40 | HP |
| 691 | Age | CD40 | HT |
| 692 | Age | CD40 | ICAM1 |
| 693 | Age | CD40 | IGF1 |
| 694 | Age | CD40 | IGFBP1 |
| 695 | Age | CD40 | IGFBP3 |
| 696 | Age | CD40 | IL18 |
| 697 | Age | CD40 | IL2RA |
| 698 | Age | CD40 | IL6R |
| 699 | Age | CD40 | IL6ST |
| 700 | Age | CD40 | IL8 |

| 3-Panel | Marker 1 | Marker 2 | Marker 3 |
|---|---|---|---|
| 701 | Age | CD40 | INHBA |
| 702 | Age | CD40 | Ins120 |
| 703 | Age | CD40 | Insulin |
| 704 | Age | CD40 | LDL |
| 705 | Age | CD40 | LEP |
| 706 | Age | CD40 | PLAT |
| 707 | Age | CD40 | POMC |
| 708 | Age | CD40 | SBP |
| 709 | Age | CD40 | SCp |
| 710 | Age | CD40 | SELE |
| 711 | Age | CD40 | SELP |
| 712 | Age | CD40 | Sex |
| 713 | Age | CD40 | SHBG |
| 714 | Age | CD40 | TNFRSF1B |
| 715 | Age | CD40 | TRIG |
| 716 | Age | CD40 | VCAM1 |
| 717 | Age | CD40 | VEGF |
| 718 | Age | CD40 | VWF |
| 719 | Age | CD40 | Waist |
| 720 | Age | CD40 | WT |
| 721 | Age | CDK5 | CHOL |
| 722 | Age | CDK5 | CRP |
| 723 | Age | CDK5 | DBP |
| 724 | Age | CDK5 | DPP4 |
| 725 | Age | CDK5 | EGF |
| 726 | Age | CDK5 | ENG |
| 727 | Age | CDK5 | FamHX |
| 728 | Age | CDK5 | FGA |

FIG. 14M

| 3-Panel | Marker 1 | Marker 2 | Marker 3 |
|---|---|---|---|
| 729 | Age | CDK5 | FTH1 |
| 730 | Age | CDK5 | Gluc120 |
| 731 | Age | CDK5 | Glucose |
| 732 | Age | CDK5 | HBA1C |
| 733 | Age | CDK5 | HDLC |
| 734 | Age | CDK5 | HGF |
| 735 | Age | CDK5 | Hip |
| 736 | Age | CDK5 | HP |
| 737 | Age | CDK5 | HT |
| 738 | Age | CDK5 | ICAM1 |
| 739 | Age | CDK5 | IGF1 |
| 740 | Age | CDK5 | IGFBP1 |
| 741 | Age | CDK5 | IGFBP3 |
| 742 | Age | CDK5 | IL18 |
| 743 | Age | CDK5 | IL2RA |
| 744 | Age | CDK5 | IL6R |
| 745 | Age | CDK5 | IL6ST |
| 746 | Age | CDK5 | IL8 |
| 747 | Age | CDK5 | INHBA |
| 748 | Age | CDK5 | Ins120 |
| 749 | Age | CDK5 | Insulin |
| 750 | Age | CDK5 | LDL |
| 751 | Age | CDK5 | LEP |
| 752 | Age | CDK5 | PLAT |
| 753 | Age | CDK5 | POMC |
| 754 | Age | CDK5 | SBP |
| 755 | Age | CDK5 | SCp |
| 756 | Age | CDK5 | SELE |
| 757 | Age | CDK5 | SELP |
| 758 | Age | CDK5 | Sex |
| 759 | Age | CDK5 | SHBG |
| 760 | Age | CDK5 | TNFRSF1B |
| 761 | Age | CDK5 | TRIG |
| 762 | Age | CDK5 | VCAM1 |
| 763 | Age | CDK5 | VEGF |
| 764 | Age | CDK5 | VWF |
| 765 | Age | CDK5 | Waist |
| 766 | Age | CDK5 | WT |
| 767 | Age | CHOL | CRP |
| 768 | Age | CHOL | DBP |
| 769 | Age | CHOL | DPP4 |
| 770 | Age | CHOL | EGF |
| 771 | Age | CHOL | ENG |
| 772 | Age | CHOL | FamHX |
| 773 | Age | CHOL | FGA |
| 774 | Age | CHOL | FTH1 |
| 775 | Age | CHOL | Gluc120 |
| 776 | Age | CHOL | Glucose |
| 777 | Age | CHOL | HBA1C |
| 778 | Age | CHOL | HDLC |
| 779 | Age | CHOL | HGF |
| 780 | Age | CHOL | Hip |
| 781 | Age | CHOL | HP |
| 782 | Age | CHOL | HT |
| 783 | Age | CHOL | ICAM1 |
| 784 | Age | CHOL | IGF1 |

FIG. 14N

| 3-Panel | Marker 1 | Marker 2 | Marker 3 |
|---|---|---|---|
| 785 | Age | CHOL | IGFBP1 |
| 786 | Age | CHOL | IGFBP3 |
| 787 | Age | CHOL | IL18 |
| 788 | Age | CHOL | IL2RA |
| 789 | Age | CHOL | IL6R |
| 790 | Age | CHOL | IL6ST |
| 791 | Age | CHOL | IL8 |
| 792 | Age | CHOL | INHBA |
| 793 | Age | CHOL | Ins120 |
| 794 | Age | CHOL | Insulin |
| 795 | Age | CHOL | LDL |
| 796 | Age | CHOL | LEP |
| 797 | Age | CHOL | PLAT |
| 798 | Age | CHOL | POMC |
| 799 | Age | CHOL | SBP |
| 800 | Age | CHOL | SCp |
| 801 | Age | CHOL | SELE |
| 802 | Age | CHOL | SELP |
| 803 | Age | CHOL | Sex |
| 804 | Age | CHOL | SHBG |
| 805 | Age | CHOL | TNFRSF1B |
| 806 | Age | CHOL | TRIG |
| 807 | Age | CHOL | VCAM1 |
| 808 | Age | CHOL | VEGF |
| 809 | Age | CHOL | VWF |
| 810 | Age | CHOL | Waist |
| 811 | Age | CHOL | WT |
| 812 | Age | CRP | DBP |

| 3-Panel | Marker 1 | Marker 2 | Marker 3 |
|---|---|---|---|
| 813 | Age | CRP | DPP4 |
| 814 | Age | CRP | EGF |
| 815 | Age | CRP | ENG |
| 816 | Age | CRP | FamHX |
| 817 | Age | CRP | FGA |
| 818 | Age | CRP | FTH1 |
| 819 | Age | CRP | Gluc120 |
| 820 | Age | CRP | Glucose |
| 821 | Age | CRP | HBA1C |
| 822 | Age | CRP | HDLC |
| 823 | Age | CRP | HGF |
| 824 | Age | CRP | Hip |
| 825 | Age | CRP | HP |
| 826 | Age | CRP | HT |
| 827 | Age | CRP | ICAM1 |
| 828 | Age | CRP | IGF1 |
| 829 | Age | CRP | IGFBP1 |
| 830 | Age | CRP | IGFBP3 |
| 831 | Age | CRP | IL18 |
| 832 | Age | CRP | IL2RA |
| 833 | Age | CRP | IL6R |
| 834 | Age | CRP | IL6ST |
| 835 | Age | CRP | IL8 |
| 836 | Age | CRP | INHBA |
| 837 | Age | CRP | Ins120 |
| 838 | Age | CRP | Insulin |
| 839 | Age | CRP | LDL |
| 840 | Age | CRP | LEP |

FIG. 140

| 3-Panel | Marker 1 | Marker 2 | Marker 3 |
|---|---|---|---|
| 841 | Age | CRP | PLAT |
| 842 | Age | CRP | POMC |
| 843 | Age | CRP | SBP |
| 844 | Age | CRP | SCp |
| 845 | Age | CRP | SELE |
| 846 | Age | CRP | SELP |
| 847 | Age | CRP | Sex |
| 848 | Age | CRP | SHBG |
| 849 | Age | CRP | TNFRSF1B |
| 850 | Age | CRP | TRIG |
| 851 | Age | CRP | VCAM1 |
| 852 | Age | CRP | VEGF |
| 853 | Age | CRP | VWF |
| 854 | Age | CRP | Waist |
| 855 | Age | CRP | WT |
| 856 | Age | DBP | DPP4 |
| 857 | Age | DBP | EGF |
| 858 | Age | DBP | ENG |
| 859 | Age | DBP | FamHX |
| 860 | Age | DBP | FGA |
| 861 | Age | DBP | FTH1 |
| 862 | Age | DBP | Gluc120 |
| 863 | Age | DBP | Glucose |
| 864 | Age | DBP | HBA1C |
| 865 | Age | DBP | HDLC |
| 866 | Age | DBP | HGF |
| 867 | Age | DBP | Hip |
| 868 | Age | DBP | HP |
| 869 | Age | DBP | HT |
| 870 | Age | DBP | ICAM1 |
| 871 | Age | DBP | IGF1 |
| 872 | Age | DBP | IGFBP1 |
| 873 | Age | DBP | IGFBP3 |
| 874 | Age | DBP | IL18 |
| 875 | Age | DBP | IL2RA |
| 876 | Age | DBP | IL6R |
| 877 | Age | DBP | IL6ST |
| 878 | Age | DBP | IL8 |
| 879 | Age | DBP | INHBA |
| 880 | Age | DBP | Ins120 |
| 881 | Age | DBP | Insulin |
| 882 | Age | DBP | LDL |
| 883 | Age | DBP | LEP |
| 884 | Age | DBP | PLAT |
| 885 | Age | DBP | POMC |
| 886 | Age | DBP | SBP |
| 887 | Age | DBP | SCp |
| 888 | Age | DBP | SELE |
| 889 | Age | DBP | SELP |
| 890 | Age | DBP | Sex |
| 891 | Age | DBP | SHBG |
| 892 | Age | DBP | TNFRSF1B |
| 893 | Age | DBP | TRIG |
| 894 | Age | DBP | VCAM1 |
| 895 | Age | DBP | VEGF |
| 896 | Age | DBP | VWF |

FIG. 14P

| 3-Panel | Marker 1 | Marker 2 | Marker 3 |
|---|---|---|---|
| 897 | Age | DBP | Waist |
| 898 | Age | DBP | WT |
| 899 | Age | DPP4 | EGF |
| 900 | Age | DPP4 | ENG |
| 901 | Age | DPP4 | FamHX |
| 902 | Age | DPP4 | FGA |
| 903 | Age | DPP4 | FTH1 |
| 904 | Age | DPP4 | Gluc120 |
| 905 | Age | DPP4 | Glucose |
| 906 | Age | DPP4 | HBA1C |
| 907 | Age | DPP4 | HDLC |
| 908 | Age | DPP4 | HGF |
| 909 | Age | DPP4 | Hip |
| 910 | Age | DPP4 | HP |
| 911 | Age | DPP4 | HT |
| 912 | Age | DPP4 | ICAM1 |
| 913 | Age | DPP4 | IGF1 |
| 914 | Age | DPP4 | IGFBP1 |
| 915 | Age | DPP4 | IGFBP3 |
| 916 | Age | DPP4 | IL18 |
| 917 | Age | DPP4 | IL2RA |
| 918 | Age | DPP4 | IL6R |
| 919 | Age | DPP4 | IL6ST |
| 920 | Age | DPP4 | IL8 |
| 921 | Age | DPP4 | INHBA |
| 922 | Age | DPP4 | Ins120 |
| 923 | Age | DPP4 | Insulin |
| 924 | Age | DPP4 | LDL |

| 3-Panel | Marker 1 | Marker 2 | Marker 3 |
|---|---|---|---|
| 925 | Age | DPP4 | LEP |
| 926 | Age | DPP4 | PLAT |
| 927 | Age | DPP4 | POMC |
| 928 | Age | DPP4 | SBP |
| 929 | Age | DPP4 | SCp |
| 930 | Age | DPP4 | SELE |
| 931 | Age | DPP4 | SELP |
| 932 | Age | DPP4 | Sex |
| 933 | Age | DPP4 | SHBG |
| 934 | Age | DPP4 | TNFRSF1B |
| 935 | Age | DPP4 | TRIG |
| 936 | Age | DPP4 | VCAM1 |
| 937 | Age | DPP4 | VEGF |
| 938 | Age | DPP4 | VWF |
| 939 | Age | DPP4 | Waist |
| 940 | Age | DPP4 | WT |
| 941 | Age | EGF | ENG |
| 942 | Age | EGF | FamHX |
| 943 | Age | EGF | FGA |
| 944 | Age | EGF | FTH1 |
| 945 | Age | EGF | Gluc120 |
| 946 | Age | EGF | Glucose |
| 947 | Age | EGF | HBA1C |
| 948 | Age | EGF | HDLC |
| 949 | Age | EGF | HGF |
| 950 | Age | EGF | Hip |
| 951 | Age | EGF | HP |
| 952 | Age | EGF | HT |

FIG. 14Q

| 3-Panel | Marker 1 | Marker 2 | Marker 3 |
|---|---|---|---|
| 953 | Age | EGF | ICAM1 |
| 954 | Age | EGF | IGF1 |
| 955 | Age | EGF | IGFBP1 |
| 956 | Age | EGF | IGFBP3 |
| 957 | Age | EGF | IL18 |
| 958 | Age | EGF | IL2RA |
| 959 | Age | EGF | IL6R |
| 960 | Age | EGF | IL6ST |
| 961 | Age | EGF | IL8 |
| 962 | Age | EGF | INHBA |
| 963 | Age | EGF | Ins120 |
| 964 | Age | EGF | Insulin |
| 965 | Age | EGF | LDL |
| 966 | Age | EGF | LEP |
| 967 | Age | EGF | PLAT |
| 968 | Age | EGF | POMC |
| 969 | Age | EGF | SBP |
| 970 | Age | EGF | SCp |
| 971 | Age | EGF | SELE |
| 972 | Age | EGF | SELP |
| 973 | Age | EGF | Sex |
| 974 | Age | EGF | SHBG |
| 975 | Age | EGF | TNFRSF1B |
| 976 | Age | EGF | TRIG |
| 977 | Age | EGF | VCAM1 |
| 978 | Age | EGF | VEGF |
| 979 | Age | EGF | VWF |
| 980 | Age | EGF | Waist |

| 3-Panel | Marker 1 | Marker 2 | Marker 3 |
|---|---|---|---|
| 981 | Age | EGF | WT |
| 982 | Age | ENG | FamHX |
| 983 | Age | ENG | FGA |
| 984 | Age | ENG | FTH1 |
| 985 | Age | ENG | Gluc120 |
| 986 | Age | ENG | Glucose |
| 987 | Age | ENG | HBA1C |
| 988 | Age | ENG | HDLC |
| 989 | Age | ENG | HGF |
| 990 | Age | ENG | Hip |
| 991 | Age | ENG | HP |
| 992 | Age | ENG | HT |
| 993 | Age | ENG | ICAM1 |
| 994 | Age | ENG | IGF1 |
| 995 | Age | ENG | IGFBP1 |
| 996 | Age | ENG | IGFBP3 |
| 997 | Age | ENG | IL18 |
| 998 | Age | ENG | IL2RA |
| 999 | Age | ENG | IL6R |
| 1000 | Age | ENG | IL6ST |
| 1001 | Age | ENG | IL8 |
| 1002 | Age | ENG | INHBA |
| 1003 | Age | ENG | Ins120 |
| 1004 | Age | ENG | Insulin |
| 1005 | Age | ENG | LDL |
| 1006 | Age | ENG | LEP |
| 1007 | Age | ENG | PLAT |
| 1008 | Age | ENG | POMC |

FIG. 14R

| 3-Panel | Marker 1 | Marker 2 | Marker 3 |
|---|---|---|---|
| 1009 | Age | ENG | SBP |
| 1010 | Age | ENG | SCp |
| 1011 | Age | ENG | SELE |
| 1012 | Age | ENG | SELP |
| 1013 | Age | ENG | Sex |
| 1014 | Age | ENG | SHBG |
| 1015 | Age | ENG | TNFRSF1B |
| 1016 | Age | ENG | TRIG |
| 1017 | Age | ENG | VCAM1 |
| 1018 | Age | ENG | VEGF |
| 1019 | Age | ENG | VWF |
| 1020 | Age | ENG | Waist |
| 1021 | Age | ENG | WT |
| 1022 | Age | FamHX | FGA |
| 1023 | Age | FamHX | FTH1 |
| 1024 | Age | FamHX | Gluc120 |
| 1025 | Age | FamHX | Glucose |
| 1026 | Age | FamHX | HBA1C |
| 1027 | Age | FamHX | HDLC |
| 1028 | Age | FamHX | HGF |
| 1029 | Age | FamHX | Hip |
| 1030 | Age | FamHX | HP |
| 1031 | Age | FamHX | HT |
| 1032 | Age | FamHX | ICAM1 |
| 1033 | Age | FamHX | IGF1 |
| 1034 | Age | FamHX | IGFBP1 |
| 1035 | Age | FamHX | IGFBP3 |
| 1036 | Age | FamHX | IL18 |

| 3-Panel | Marker 1 | Marker 2 | Marker 3 |
|---|---|---|---|
| 1037 | Age | FamHX | IL2RA |
| 1038 | Age | FamHX | IL6R |
| 1039 | Age | FamHX | IL6ST |
| 1040 | Age | FamHX | IL8 |
| 1041 | Age | FamHX | INHBA |
| 1042 | Age | FamHX | Ins120 |
| 1043 | Age | FamHX | Insulin |
| 1044 | Age | FamHX | LDL |
| 1045 | Age | FamHX | LEP |
| 1046 | Age | FamHX | PLAT |
| 1047 | Age | FamHX | POMC |
| 1048 | Age | FamHX | SBP |
| 1049 | Age | FamHX | SCp |
| 1050 | Age | FamHX | SELE |
| 1051 | Age | FamHX | SELP |
| 1052 | Age | FamHX | Sex |
| 1053 | Age | FamHX | SHBG |
| 1054 | Age | FamHX | TNFRSF1B |
| 1055 | Age | FamHX | TRIG |
| 1056 | Age | FamHX | VCAM1 |
| 1057 | Age | FamHX | VEGF |
| 1058 | Age | FamHX | VWF |
| 1059 | Age | FamHX | Waist |
| 1060 | Age | FamHX | WT |
| 1061 | Age | FGA | FTH1 |
| 1062 | Age | FGA | Gluc120 |
| 1063 | Age | FGA | Glucose |
| 1064 | Age | FGA | HBA1C |

FIG. 14S

| 3-Panel | Marker 1 | Marker 2 | Marker 3 |
|---|---|---|---|
| 1093 | Age | FGA | TRIG |
| 1094 | Age | FGA | VCAM1 |
| 1095 | Age | FGA | VEGF |
| 1096 | Age | FGA | VWF |
| 1097 | Age | FGA | Waist |
| 1098 | Age | FGA | WT |
| 1099 | Age | FTH1 | Gluc120 |
| 1100 | Age | FTH1 | Glucose |
| 1101 | Age | FTH1 | HBA1C |
| 1102 | Age | FTH1 | HDLC |
| 1103 | Age | FTH1 | HGF |
| 1104 | Age | FTH1 | Hip |
| 1105 | Age | FTH1 | HP |
| 1106 | Age | FTH1 | HT |
| 1107 | Age | FTH1 | ICAM1 |
| 1108 | Age | FTH1 | IGF1 |
| 1109 | Age | FTH1 | IGFBP1 |
| 1110 | Age | FTH1 | IGFBP3 |
| 1111 | Age | FTH1 | IL18 |
| 1112 | Age | FTH1 | IL2RA |
| 1113 | Age | FTH1 | IL6R |
| 1114 | Age | FTH1 | IL6ST |
| 1115 | Age | FTH1 | IL8 |
| 1116 | Age | FTH1 | INHBA |
| 1117 | Age | FTH1 | Ins120 |
| 1118 | Age | FTH1 | Insulin |
| 1119 | Age | FTH1 | LDL |
| 1120 | Age | FTH1 | LEP |

| 3-Panel | Marker 1 | Marker 2 | Marker 3 |
|---|---|---|---|
| 1065 | Age | FGA | HDLC |
| 1066 | Age | FGA | HGF |
| 1067 | Age | FGA | Hip |
| 1068 | Age | FGA | HP |
| 1069 | Age | FGA | HT |
| 1070 | Age | FGA | ICAM1 |
| 1071 | Age | FGA | IGF1 |
| 1072 | Age | FGA | IGFBP1 |
| 1073 | Age | FGA | IGFBP3 |
| 1074 | Age | FGA | IL18 |
| 1075 | Age | FGA | IL2RA |
| 1076 | Age | FGA | IL6R |
| 1077 | Age | FGA | IL6ST |
| 1078 | Age | FGA | IL8 |
| 1079 | Age | FGA | INHBA |
| 1080 | Age | FGA | Ins120 |
| 1081 | Age | FGA | Insulin |
| 1082 | Age | FGA | LDL |
| 1083 | Age | FGA | LEP |
| 1084 | Age | FGA | PLAT |
| 1085 | Age | FGA | POMC |
| 1086 | Age | FGA | SBP |
| 1087 | Age | FGA | SCp |
| 1088 | Age | FGA | SELE |
| 1089 | Age | FGA | SELP |
| 1090 | Age | FGA | Sex |
| 1091 | Age | FGA | SHBG |
| 1092 | Age | FGA | TNFRSF1B |

FIG. 14T

| 3-Panel | Marker 1 | Marker 2 | Marker 3 |
|---|---|---|---|
| 1121 | Age | FTH1 | PLAT |
| 1122 | Age | FTH1 | POMC |
| 1123 | Age | FTH1 | SBP |
| 1124 | Age | FTH1 | SCp |
| 1125 | Age | FTH1 | SELE |
| 1126 | Age | FTH1 | SELP |
| 1127 | Age | FTH1 | Sex |
| 1128 | Age | FTH1 | SHBG |
| 1129 | Age | FTH1 | TNFRSF1B |
| 1130 | Age | FTH1 | TRIG |
| 1131 | Age | FTH1 | VCAM1 |
| 1132 | Age | FTH1 | VEGF |
| 1133 | Age | FTH1 | VWF |
| 1134 | Age | FTH1 | Waist |
| 1135 | Age | FTH1 | WT |
| 1136 | Age | Gluc120 | Glucose |
| 1137 | Age | Gluc120 | HBA1C |
| 1138 | Age | Gluc120 | HDLC |
| 1139 | Age | Gluc120 | HGF |
| 1140 | Age | Gluc120 | Hip |
| 1141 | Age | Gluc120 | HP |
| 1142 | Age | Gluc120 | HT |
| 1143 | Age | Gluc120 | ICAM1 |
| 1144 | Age | Gluc120 | IGF1 |
| 1145 | Age | Gluc120 | IGFBP1 |
| 1146 | Age | Gluc120 | IGFBP3 |
| 1147 | Age | Gluc120 | IL18 |
| 1148 | Age | Gluc120 | IL2RA |

| 3-Panel | Marker 1 | Marker 2 | Marker 3 |
|---|---|---|---|
| 1149 | Age | Gluc120 | IL6R |
| 1150 | Age | Gluc120 | IL6ST |
| 1151 | Age | Gluc120 | IL8 |
| 1152 | Age | Gluc120 | INHBA |
| 1153 | Age | Gluc120 | Ins120 |
| 1154 | Age | Gluc120 | Insulin |
| 1155 | Age | Gluc120 | LDL |
| 1156 | Age | Gluc120 | LEP |
| 1157 | Age | Gluc120 | PLAT |
| 1158 | Age | Gluc120 | POMC |
| 1159 | Age | Gluc120 | SBP |
| 1160 | Age | Gluc120 | SCp |
| 1161 | Age | Gluc120 | SELE |
| 1162 | Age | Gluc120 | SELP |
| 1163 | Age | Gluc120 | Sex |
| 1164 | Age | Gluc120 | SHBG |
| 1165 | Age | Gluc120 | TNFRSF1B |
| 1166 | Age | Gluc120 | TRIG |
| 1167 | Age | Gluc120 | VCAM1 |
| 1168 | Age | Gluc120 | VEGF |
| 1169 | Age | Gluc120 | VWF |
| 1170 | Age | Gluc120 | Waist |
| 1171 | Age | Gluc120 | WT |
| 1172 | Age | Glucose | HBA1C |
| 1173 | Age | Glucose | HDLC |
| 1174 | Age | Glucose | HGF |
| 1175 | Age | Glucose | Hip |
| 1176 | Age | Glucose | HP |

FIG. 14U

| 3-Panel | Marker 1 | Marker 2 | Marker 3 |
|---|---|---|---|
| 1177 | Age | Glucose | HT |
| 1178 | Age | Glucose | ICAM1 |
| 1179 | Age | Glucose | IGF1 |
| 1180 | Age | Glucose | IGFBP1 |
| 1181 | Age | Glucose | IGFBP3 |
| 1182 | Age | Glucose | IL18 |
| 1183 | Age | Glucose | IL2RA |
| 1184 | Age | Glucose | IL6R |
| 1185 | Age | Glucose | IL6ST |
| 1186 | Age | Glucose | IL8 |
| 1187 | Age | Glucose | INHBA |
| 1188 | Age | Glucose | Ins120 |
| 1189 | Age | Glucose | Insulin |
| 1190 | Age | Glucose | LDL |
| 1191 | Age | Glucose | LEP |
| 1192 | Age | Glucose | PLAT |
| 1193 | Age | Glucose | POMC |
| 1194 | Age | Glucose | SBP |
| 1195 | Age | Glucose | SCp |
| 1196 | Age | Glucose | SELE |
| 1197 | Age | Glucose | SELP |
| 1198 | Age | Glucose | Sex |
| 1199 | Age | Glucose | SHBG |
| 1200 | Age | Glucose | TNFRSF1B |
| 1201 | Age | Glucose | TRIG |
| 1202 | Age | Glucose | VCAM1 |
| 1203 | Age | Glucose | VEGF |
| 1204 | Age | Glucose | VWF |

| 3-Panel | Marker 1 | Marker 2 | Marker 3 |
|---|---|---|---|
| 1205 | Age | Glucose | Waist |
| 1206 | Age | Glucose | WT |
| 1207 | Age | HBA1C | HDLC |
| 1208 | Age | HBA1C | HGF |
| 1209 | Age | HBA1C | Hip |
| 1210 | Age | HBA1C | HP |
| 1211 | Age | HBA1C | HT |
| 1212 | Age | HBA1C | ICAM1 |
| 1213 | Age | HBA1C | IGF1 |
| 1214 | Age | HBA1C | IGFBP1 |
| 1215 | Age | HBA1C | IGFBP3 |
| 1216 | Age | HBA1C | IL18 |
| 1217 | Age | HBA1C | IL2RA |
| 1218 | Age | HBA1C | IL6R |
| 1219 | Age | HBA1C | IL6ST |
| 1220 | Age | HBA1C | IL8 |
| 1221 | Age | HBA1C | INHBA |
| 1222 | Age | HBA1C | Ins120 |
| 1223 | Age | HBA1C | Insulin |
| 1224 | Age | HBA1C | LDL |
| 1225 | Age | HBA1C | LEP |
| 1226 | Age | HBA1C | PLAT |
| 1227 | Age | HBA1C | POMC |
| 1228 | Age | HBA1C | SBP |
| 1229 | Age | HBA1C | SCp |
| 1230 | Age | HBA1C | SELE |
| 1231 | Age | HBA1C | SELP |
| 1232 | Age | HBA1C | Sex |

| 3-Panel | Marker 1 | Marker 2 | Marker 3 |
|---|---|---|---|
| 1233 | Age | HBA1C | SHBG |
| 1234 | Age | HBA1C | TNFRSF1B |
| 1235 | Age | HBA1C | TRIG |
| 1236 | Age | HBA1C | VCAM1 |
| 1237 | Age | HBA1C | VEGF |
| 1238 | Age | HBA1C | VWF |
| 1239 | Age | HBA1C | Waist |
| 1240 | Age | HBA1C | WT |
| 1241 | Age | HDLC | HGF |
| 1242 | Age | HDLC | Hip |
| 1243 | Age | HDLC | HP |
| 1244 | Age | HDLC | HT |
| 1245 | Age | HDLC | ICAM1 |
| 1246 | Age | HDLC | IGF1 |
| 1247 | Age | HDLC | IGFBP1 |
| 1248 | Age | HDLC | IGFBP3 |
| 1249 | Age | HDLC | IL18 |
| 1250 | Age | HDLC | IL2RA |
| 1251 | Age | HDLC | IL6R |
| 1252 | Age | HDLC | IL6ST |
| 1253 | Age | HDLC | IL8 |
| 1254 | Age | HDLC | INHBA |
| 1255 | Age | HDLC | Ins120 |
| 1256 | Age | HDLC | Insulin |
| 1257 | Age | HDLC | LDL |
| 1258 | Age | HDLC | LEP |
| 1259 | Age | HDLC | PLAT |
| 1260 | Age | HDLC | POMC |

| 3-Panel | Marker 1 | Marker 2 | Marker 3 |
|---|---|---|---|
| 1261 | Age | HDLC | SBP |
| 1262 | Age | HDLC | SCp |
| 1263 | Age | HDLC | SELE |
| 1264 | Age | HDLC | SELP |
| 1265 | Age | HDLC | Sex |
| 1266 | Age | HDLC | SHBG |
| 1267 | Age | HDLC | TNFRSF1B |
| 1268 | Age | HDLC | TRIG |
| 1269 | Age | HDLC | VCAM1 |
| 1270 | Age | HDLC | VEGF |
| 1271 | Age | HDLC | VWF |
| 1272 | Age | HDLC | Waist |
| 1273 | Age | HDLC | WT |
| 1274 | Age | HGF | Hip |
| 1275 | Age | HGF | HP |
| 1276 | Age | HGF | HT |
| 1277 | Age | HGF | ICAM1 |
| 1278 | Age | HGF | IGF1 |
| 1279 | Age | HGF | IGFBP1 |
| 1280 | Age | HGF | IGFBP3 |
| 1281 | Age | HGF | IL18 |
| 1282 | Age | HGF | IL2RA |
| 1283 | Age | HGF | IL6R |
| 1284 | Age | HGF | IL6ST |
| 1285 | Age | HGF | IL8 |
| 1286 | Age | HGF | INHBA |
| 1287 | Age | HGF | Ins120 |
| 1288 | Age | HGF | Insulin |

| 3-Panel | Marker 1 | Marker 2 | Marker 3 |
|---|---|---|---|
| 1289 | Age | HGF | LDL |
| 1290 | Age | HGF | LEP |
| 1291 | Age | HGF | PLAT |
| 1292 | Age | HGF | POMC |
| 1293 | Age | HGF | SBP |
| 1294 | Age | HGF | SCp |
| 1295 | Age | HGF | SELE |
| 1296 | Age | HGF | SELP |
| 1297 | Age | HGF | Sex |
| 1298 | Age | HGF | SHBG |
| 1299 | Age | HGF | TNFRSF1B |
| 1300 | Age | HGF | TRIG |
| 1301 | Age | HGF | VCAM1 |
| 1302 | Age | HGF | VEGF |
| 1303 | Age | HGF | VWF |
| 1304 | Age | HGF | Waist |
| 1305 | Age | HGF | WT |
| 1306 | Age | Hip | HP |
| 1307 | Age | Hip | HT |
| 1308 | Age | Hip | ICAM1 |
| 1309 | Age | Hip | IGF1 |
| 1310 | Age | Hip | IGFBP1 |
| 1311 | Age | Hip | IGFBP3 |
| 1312 | Age | Hip | IL18 |
| 1313 | Age | Hip | IL2RA |
| 1314 | Age | Hip | IL6R |
| 1315 | Age | Hip | IL6ST |
| 1316 | Age | Hip | IL8 |

| 3-Panel | Marker 1 | Marker 2 | Marker 3 |
|---|---|---|---|
| 1317 | Age | Hip | INHBA |
| 1318 | Age | Hip | Ins120 |
| 1319 | Age | Hip | Insulin |
| 1320 | Age | Hip | LDL |
| 1321 | Age | Hip | LEP |
| 1322 | Age | Hip | PLAT |
| 1323 | Age | Hip | POMC |
| 1324 | Age | Hip | SBP |
| 1325 | Age | Hip | SCp |
| 1326 | Age | Hip | SELE |
| 1327 | Age | Hip | SELP |
| 1328 | Age | Hip | Sex |
| 1329 | Age | Hip | SHBG |
| 1330 | Age | Hip | TNFRSF1B |
| 1331 | Age | Hip | TRIG |
| 1332 | Age | Hip | VCAM1 |
| 1333 | Age | Hip | VEGF |
| 1334 | Age | Hip | VWF |
| 1335 | Age | Hip | Waist |
| 1336 | Age | Hip | WT |
| 1337 | Age | HP | HT |
| 1338 | Age | HP | ICAM1 |
| 1339 | Age | HP | IGF1 |
| 1340 | Age | HP | IGFBP1 |
| 1341 | Age | HP | IGFBP3 |
| 1342 | Age | HP | IL18 |
| 1343 | Age | HP | IL2RA |
| 1344 | Age | HP | IL6R |

FIG. 14X

| 3-Panel | Marker 1 | Marker 2 | Marker 3 |
|---|---|---|---|
| 1345 | Age | HP | IL6ST |
| 1346 | Age | HP | IL8 |
| 1347 | Age | HP | INHBA |
| 1348 | Age | HP | Ins120 |
| 1349 | Age | HP | Insulin |
| 1350 | Age | HP | LDL |
| 1351 | Age | HP | LEP |
| 1352 | Age | HP | PLAT |
| 1353 | Age | HP | POMC |
| 1354 | Age | HP | SBP |
| 1355 | Age | HP | SCp |
| 1356 | Age | HP | SELE |
| 1357 | Age | HP | SELP |
| 1358 | Age | HP | Sex |
| 1359 | Age | HP | SHBG |
| 1360 | Age | HP | TNFRSF1B |
| 1361 | Age | HP | TRIG |
| 1362 | Age | HP | VCAM1 |
| 1363 | Age | HP | VEGF |
| 1364 | Age | HP | VWF |
| 1365 | Age | HP | Waist |
| 1366 | Age | HP | WT |
| 1367 | Age | HT | ICAM1 |
| 1368 | Age | HT | IGF1 |
| 1369 | Age | HT | IGFBP1 |
| 1370 | Age | HT | IGFBP3 |
| 1371 | Age | HT | IL18 |
| 1372 | Age | HT | IL2RA |

| 3-Panel | Marker 1 | Marker 2 | Marker 3 |
|---|---|---|---|
| 1373 | Age | HT | IL6R |
| 1374 | Age | HT | IL6ST |
| 1375 | Age | HT | IL8 |
| 1376 | Age | HT | INHBA |
| 1377 | Age | HT | Ins120 |
| 1378 | Age | HT | Insulin |
| 1379 | Age | HT | LDL |
| 1380 | Age | HT | LEP |
| 1381 | Age | HT | PLAT |
| 1382 | Age | HT | POMC |
| 1383 | Age | HT | SBP |
| 1384 | Age | HT | SCp |
| 1385 | Age | HT | SELE |
| 1386 | Age | HT | SELP |
| 1387 | Age | HT | Sex |
| 1388 | Age | HT | SHBG |
| 1389 | Age | HT | TNFRSF1B |
| 1390 | Age | HT | TRIG |
| 1391 | Age | HT | VCAM1 |
| 1392 | Age | HT | VEGF |
| 1393 | Age | HT | VWF |
| 1394 | Age | HT | Waist |
| 1395 | Age | HT | WT |
| 1396 | Age | ICAM1 | IGF1 |
| 1397 | Age | ICAM1 | IGFBP1 |
| 1398 | Age | ICAM1 | IGFBP3 |
| 1399 | Age | ICAM1 | IL18 |
| 1400 | Age | ICAM1 | IL2RA |

FIG. 14Y

| 3-Panel | Marker 1 | Marker 2 | Marker 3 |
|---|---|---|---|
| 1401 | Age | ICAM1 | IL6R |
| 1402 | Age | ICAM1 | IL6ST |
| 1403 | Age | ICAM1 | IL8 |
| 1404 | Age | ICAM1 | INHBA |
| 1405 | Age | ICAM1 | Ins120 |
| 1406 | Age | ICAM1 | Insulin |
| 1407 | Age | ICAM1 | LDL |
| 1408 | Age | ICAM1 | LEP |
| 1409 | Age | ICAM1 | PLAT |
| 1410 | Age | ICAM1 | POMC |
| 1411 | Age | ICAM1 | SBP |
| 1412 | Age | ICAM1 | SCp |
| 1413 | Age | ICAM1 | SELE |
| 1414 | Age | ICAM1 | SELP |
| 1415 | Age | ICAM1 | Sex |
| 1416 | Age | ICAM1 | SHBG |
| 1417 | Age | ICAM1 | TNFRSF1B |
| 1418 | Age | ICAM1 | TRIG |
| 1419 | Age | ICAM1 | VCAM1 |
| 1420 | Age | ICAM1 | VEGF |
| 1421 | Age | ICAM1 | VWF |
| 1422 | Age | ICAM1 | Waist |
| 1423 | Age | ICAM1 | WT |
| 1424 | Age | IGF1 | IGFBP1 |
| 1425 | Age | IGF1 | IGFBP3 |
| 1426 | Age | IGF1 | IL18 |
| 1427 | Age | IGF1 | IL2RA |
| 1428 | Age | IGF1 | IL6R |

| 3-Panel | Marker 1 | Marker 2 | Marker 3 |
|---|---|---|---|
| 1429 | Age | IGF1 | IL6ST |
| 1430 | Age | IGF1 | IL8 |
| 1431 | Age | IGF1 | INHBA |
| 1432 | Age | IGF1 | Ins120 |
| 1433 | Age | IGF1 | Insulin |
| 1434 | Age | IGF1 | LDL |
| 1435 | Age | IGF1 | LEP |
| 1436 | Age | IGF1 | PLAT |
| 1437 | Age | IGF1 | POMC |
| 1438 | Age | IGF1 | SBP |
| 1439 | Age | IGF1 | SCp |
| 1440 | Age | IGF1 | SELE |
| 1441 | Age | IGF1 | SELP |
| 1442 | Age | IGF1 | Sex |
| 1443 | Age | IGF1 | SHBG |
| 1444 | Age | IGF1 | TNFRSF1B |
| 1445 | Age | IGF1 | TRIG |
| 1446 | Age | IGF1 | VCAM1 |
| 1447 | Age | IGF1 | VEGF |
| 1448 | Age | IGF1 | VWF |
| 1449 | Age | IGF1 | Waist |
| 1450 | Age | IGF1 | WT |
| 1451 | Age | IGFBP1 | IGFBP3 |
| 1452 | Age | IGFBP1 | IL18 |
| 1453 | Age | IGFBP1 | IL2RA |
| 1454 | Age | IGFBP1 | IL6R |
| 1455 | Age | IGFBP1 | IL6ST |
| 1456 | Age | IGFBP1 | IL8 |

FIG. 14Z

| 3-Panel | Marker 1 | Marker 2 | Marker 3 |
|---|---|---|---|
| 1457 | Age | IGFBP1 | INHBA |
| 1458 | Age | IGFBP1 | Ins120 |
| 1459 | Age | IGFBP1 | Insulin |
| 1460 | Age | IGFBP1 | LDL |
| 1461 | Age | IGFBP1 | LEP |
| 1462 | Age | IGFBP1 | PLAT |
| 1463 | Age | IGFBP1 | POMC |
| 1464 | Age | IGFBP1 | SBP |
| 1465 | Age | IGFBP1 | SCp |
| 1466 | Age | IGFBP1 | SELE |
| 1467 | Age | IGFBP1 | SELP |
| 1468 | Age | IGFBP1 | Sex |
| 1469 | Age | IGFBP1 | SHBG |
| 1470 | Age | IGFBP1 | TNFRSF1B |
| 1471 | Age | IGFBP1 | TRIG |
| 1472 | Age | IGFBP1 | VCAM1 |
| 1473 | Age | IGFBP1 | VEGF |
| 1474 | Age | IGFBP1 | VWF |
| 1475 | Age | IGFBP1 | Waist |
| 1476 | Age | IGFBP1 | WT |
| 1477 | Age | IGFBP3 | IL18 |
| 1478 | Age | IGFBP3 | IL2RA |
| 1479 | Age | IGFBP3 | IL6R |
| 1480 | Age | IGFBP3 | IL6ST |
| 1481 | Age | IGFBP3 | IL8 |
| 1482 | Age | IGFBP3 | INHBA |
| 1483 | Age | IGFBP3 | Ins120 |
| 1484 | Age | IGFBP3 | Insulin |
| 1485 | Age | IGFBP3 | LDL |
| 1486 | Age | IGFBP3 | LEP |
| 1487 | Age | IGFBP3 | PLAT |
| 1488 | Age | IGFBP3 | POMC |
| 1489 | Age | IGFBP3 | SBP |
| 1490 | Age | IGFBP3 | SCp |
| 1491 | Age | IGFBP3 | SELE |
| 1492 | Age | IGFBP3 | SELP |
| 1493 | Age | IGFBP3 | Sex |
| 1494 | Age | IGFBP3 | SHBG |
| 1495 | Age | IGFBP3 | TNFRSF1B |
| 1496 | Age | IGFBP3 | TRIG |
| 1497 | Age | IGFBP3 | VCAM1 |
| 1498 | Age | IGFBP3 | VEGF |
| 1499 | Age | IGFBP3 | VWF |
| 1500 | Age | IGFBP3 | Waist |
| 1501 | Age | IGFBP3 | WT |
| 1502 | Age | IL18 | IL2RA |
| 1503 | Age | IL18 | IL6R |
| 1504 | Age | IL18 | IL6ST |
| 1505 | Age | IL18 | IL8 |
| 1506 | Age | IL18 | INHBA |
| 1507 | Age | IL18 | Ins120 |
| 1508 | Age | IL18 | Insulin |
| 1509 | Age | IL18 | LDL |
| 1510 | Age | IL18 | LEP |
| 1511 | Age | IL18 | PLAT |
| 1512 | Age | IL18 | POMC |

FIG. 14AA

| 3-Panel | Marker 1 | Marker 2 | Marker 3 |
|---|---|---|---|
| 1513 | Age | IL18 | SBP |
| 1514 | Age | IL18 | SCp |
| 1515 | Age | IL18 | SELE |
| 1516 | Age | IL18 | SELP |
| 1517 | Age | IL18 | Sex |
| 1518 | Age | IL18 | SHBG |
| 1519 | Age | IL18 | TNFRSF1B |
| 1520 | Age | IL18 | TRIG |
| 1521 | Age | IL18 | VCAM1 |
| 1522 | Age | IL18 | VEGF |
| 1523 | Age | IL18 | VWF |
| 1524 | Age | IL18 | Waist |
| 1525 | Age | IL18 | WT |
| 1526 | Age | IL2RA | IL6R |
| 1527 | Age | IL2RA | IL6ST |
| 1528 | Age | IL2RA | IL8 |
| 1529 | Age | IL2RA | INHBA |
| 1530 | Age | IL2RA | Ins120 |
| 1531 | Age | IL2RA | Insulin |
| 1532 | Age | IL2RA | LDL |
| 1533 | Age | IL2RA | LEP |
| 1534 | Age | IL2RA | PLAT |
| 1535 | Age | IL2RA | POMC |
| 1536 | Age | IL2RA | SBP |
| 1537 | Age | IL2RA | SCp |
| 1538 | Age | IL2RA | SELE |
| 1539 | Age | IL2RA | SELP |
| 1540 | Age | IL2RA | Sex |

| 3-Panel | Marker 1 | Marker 2 | Marker 3 |
|---|---|---|---|
| 1541 | Age | IL2RA | SHBG |
| 1542 | Age | IL2RA | TNFRSF1B |
| 1543 | Age | IL2RA | TRIG |
| 1544 | Age | IL2RA | VCAM1 |
| 1545 | Age | IL2RA | VEGF |
| 1546 | Age | IL2RA | VWF |
| 1547 | Age | IL2RA | Waist |
| 1548 | Age | IL2RA | WT |
| 1549 | Age | IL6R | IL6ST |
| 1550 | Age | IL6R | IL8 |
| 1551 | Age | IL6R | INHBA |
| 1552 | Age | IL6R | Ins120 |
| 1553 | Age | IL6R | Insulin |
| 1554 | Age | IL6R | LDL |
| 1555 | Age | IL6R | LEP |
| 1556 | Age | IL6R | PLAT |
| 1557 | Age | IL6R | POMC |
| 1558 | Age | IL6R | SBP |
| 1559 | Age | IL6R | SCp |
| 1560 | Age | IL6R | SELE |
| 1561 | Age | IL6R | SELP |
| 1562 | Age | IL6R | Sex |
| 1563 | Age | IL6R | SHBG |
| 1564 | Age | IL6R | TNFRSF1B |
| 1565 | Age | IL6R | TRIG |
| 1566 | Age | IL6R | VCAM1 |
| 1567 | Age | IL6R | VEGF |
| 1568 | Age | IL6R | VWF |

FIG. 14BB

| 3-Panel | Marker 1 | Marker 2 | Marker 3 |
|---|---|---|---|
| 1569 | Age | IL6R | Waist |
| 1570 | Age | IL6R | WT |
| 1571 | Age | IL6ST | IL8 |
| 1572 | Age | IL6ST | INHBA |
| 1573 | Age | IL6ST | Ins120 |
| 1574 | Age | IL6ST | Insulin |
| 1575 | Age | IL6ST | LDL |
| 1576 | Age | IL6ST | LEP |
| 1577 | Age | IL6ST | PLAT |
| 1578 | Age | IL6ST | POMC |
| 1579 | Age | IL6ST | SBP |
| 1580 | Age | IL6ST | SCp |
| 1581 | Age | IL6ST | SELE |
| 1582 | Age | IL6ST | SELP |
| 1583 | Age | IL6ST | Sex |
| 1584 | Age | IL6ST | SHBG |
| 1585 | Age | IL6ST | TNFRSF1B |
| 1586 | Age | IL6ST | TRIG |
| 1587 | Age | IL6ST | VCAM1 |
| 1588 | Age | IL6ST | VEGF |
| 1589 | Age | IL6ST | VWF |
| 1590 | Age | IL6ST | Waist |
| 1591 | Age | IL6ST | WT |
| 1592 | Age | IL8 | INHBA |
| 1593 | Age | IL8 | Ins120 |
| 1594 | Age | IL8 | Insulin |
| 1595 | Age | IL8 | LDL |
| 1596 | Age | IL8 | LEP |
| 1597 | Age | IL8 | PLAT |
| 1598 | Age | IL8 | POMC |
| 1599 | Age | IL8 | SBP |
| 1600 | Age | IL8 | SCp |
| 1601 | Age | IL8 | SELE |
| 1602 | Age | IL8 | SELP |
| 1603 | Age | IL8 | Sex |
| 1604 | Age | IL8 | SHBG |
| 1605 | Age | IL8 | TNFRSF1B |
| 1606 | Age | IL8 | TRIG |
| 1607 | Age | IL8 | VCAM1 |
| 1608 | Age | IL8 | VEGF |
| 1609 | Age | IL8 | VWF |
| 1610 | Age | IL8 | Waist |
| 1611 | Age | IL8 | WT |
| 1612 | Age | INHBA | Ins120 |
| 1613 | Age | INHBA | Insulin |
| 1614 | Age | INHBA | LDL |
| 1615 | Age | INHBA | LEP |
| 1616 | Age | INHBA | PLAT |
| 1617 | Age | INHBA | POMC |
| 1618 | Age | INHBA | SBP |
| 1619 | Age | INHBA | SCp |
| 1620 | Age | INHBA | SELE |
| 1621 | Age | INHBA | SELP |
| 1622 | Age | INHBA | Sex |
| 1623 | Age | INHBA | SHBG |
| 1624 | Age | INHBA | TNFRSF1B |

FIG. 14CC

| 3-Panel | Marker 1 | Marker 2 | Marker 3 |
|---|---|---|---|
| 1625 | Age | INHBA | TRIG |
| 1626 | Age | INHBA | VCAM1 |
| 1627 | Age | INHBA | VEGF |
| 1628 | Age | INHBA | VWF |
| 1629 | Age | INHBA | Waist |
| 1630 | Age | INHBA | WT |
| 1631 | Age | Ins120 | Insulin |
| 1632 | Age | Ins120 | LDL |
| 1633 | Age | Ins120 | LEP |
| 1634 | Age | Ins120 | PLAT |
| 1635 | Age | Ins120 | POMC |
| 1636 | Age | Ins120 | SBP |
| 1637 | Age | Ins120 | SCp |
| 1638 | Age | Ins120 | SELE |
| 1639 | Age | Ins120 | SELP |
| 1640 | Age | Ins120 | Sex |
| 1641 | Age | Ins120 | SHBG |
| 1642 | Age | Ins120 | TNFRSF1B |
| 1643 | Age | Ins120 | TRIG |
| 1644 | Age | Ins120 | VCAM1 |
| 1645 | Age | Ins120 | VEGF |
| 1646 | Age | Ins120 | VWF |
| 1647 | Age | Ins120 | Waist |
| 1648 | Age | Ins120 | WT |
| 1649 | Age | Insulin | LDL |
| 1650 | Age | Insulin | LEP |
| 1651 | Age | Insulin | PLAT |
| 1652 | Age | Insulin | POMC |

| 3-Panel | Marker 1 | Marker 2 | Marker 3 |
|---|---|---|---|
| 1653 | Age | Insulin | SBP |
| 1654 | Age | Insulin | SCp |
| 1655 | Age | Insulin | SELE |
| 1656 | Age | Insulin | SELP |
| 1657 | Age | Insulin | Sex |
| 1658 | Age | Insulin | SHBG |
| 1659 | Age | Insulin | TNFRSF1B |
| 1660 | Age | Insulin | TRIG |
| 1661 | Age | Insulin | VCAM1 |
| 1662 | Age | Insulin | VEGF |
| 1663 | Age | Insulin | VWF |
| 1664 | Age | Insulin | Waist |
| 1665 | Age | Insulin | WT |
| 1666 | Age | LDL | LEP |
| 1667 | Age | LDL | PLAT |
| 1668 | Age | LDL | POMC |
| 1669 | Age | LDL | SBP |
| 1670 | Age | LDL | SCp |
| 1671 | Age | LDL | SELE |
| 1672 | Age | LDL | SELP |
| 1673 | Age | LDL | Sex |
| 1674 | Age | LDL | SHBG |
| 1675 | Age | LDL | TNFRSF1B |
| 1676 | Age | LDL | TRIG |
| 1677 | Age | LDL | VCAM1 |
| 1678 | Age | LDL | VEGF |
| 1679 | Age | LDL | VWF |
| 1680 | Age | LDL | Waist |

FIG. 14DD

| 3-Panel | Marker 1 | Marker 2 | Marker 3 |
|---|---|---|---|
| 1681 | Age | LDL | WT |
| 1682 | Age | LEP | PLAT |
| 1683 | Age | LEP | POMC |
| 1684 | Age | LEP | SBP |
| 1685 | Age | LEP | SCp |
| 1686 | Age | LEP | SELE |
| 1687 | Age | LEP | SELP |
| 1688 | Age | LEP | Sex |
| 1689 | Age | LEP | SHBG |
| 1690 | Age | LEP | TNFRSF1B |
| 1691 | Age | LEP | TRIG |
| 1692 | Age | LEP | VCAM1 |
| 1693 | Age | LEP | VEGF |
| 1694 | Age | LEP | VWF |
| 1695 | Age | LEP | Waist |
| 1696 | Age | LEP | WT |
| 1697 | Age | PLAT | POMC |
| 1698 | Age | PLAT | SBP |
| 1699 | Age | PLAT | SCp |
| 1700 | Age | PLAT | SELE |
| 1701 | Age | PLAT | SELP |
| 1702 | Age | PLAT | Sex |
| 1703 | Age | PLAT | SHBG |
| 1704 | Age | PLAT | TNFRSF1B |
| 1705 | Age | PLAT | TRIG |
| 1706 | Age | PLAT | VCAM1 |
| 1707 | Age | PLAT | VEGF |
| 1708 | Age | PLAT | VWF |

| 3-Panel | Marker 1 | Marker 2 | Marker 3 |
|---|---|---|---|
| 1709 | Age | PLAT | Waist |
| 1710 | Age | PLAT | WT |
| 1711 | Age | POMC | SBP |
| 1712 | Age | POMC | SCp |
| 1713 | Age | POMC | SELE |
| 1714 | Age | POMC | SELP |
| 1715 | Age | POMC | Sex |
| 1716 | Age | POMC | SHBG |
| 1717 | Age | POMC | TNFRSF1B |
| 1718 | Age | POMC | TRIG |
| 1719 | Age | POMC | VCAM1 |
| 1720 | Age | POMC | VEGF |
| 1721 | Age | POMC | VWF |
| 1722 | Age | POMC | Waist |
| 1723 | Age | POMC | WT |
| 1724 | Age | SBP | SCp |
| 1725 | Age | SBP | SELE |
| 1726 | Age | SBP | SELP |
| 1727 | Age | SBP | Sex |
| 1728 | Age | SBP | SHBG |
| 1729 | Age | SBP | TNFRSF1B |
| 1730 | Age | SBP | TRIG |
| 1731 | Age | SBP | VCAM1 |
| 1732 | Age | SBP | VEGF |
| 1733 | Age | SBP | VWF |
| 1734 | Age | SBP | Waist |
| 1735 | Age | SBP | WT |
| 1736 | Age | SCp | SELE |

FIG. 14EE

| 3-Panel | Marker 1 | Marker 2 | Marker 3 |
|---|---|---|---|
| 1737 | Age | SCp | SELP |
| 1738 | Age | SCp | Sex |
| 1739 | Age | SCp | SHBG |
| 1740 | Age | SCp | TNFRSF1B |
| 1741 | Age | SCp | TRIG |
| 1742 | Age | SCp | VCAM1 |
| 1743 | Age | SCp | VEGF |
| 1744 | Age | SCp | VWF |
| 1745 | Age | SCp | Waist |
| 1746 | Age | SCp | WT |
| 1747 | Age | SELE | SELP |
| 1748 | Age | SELE | Sex |
| 1749 | Age | SELE | SHBG |
| 1750 | Age | SELE | TNFRSF1B |
| 1751 | Age | SELE | TRIG |
| 1752 | Age | SELE | VCAM1 |
| 1753 | Age | SELE | VEGF |
| 1754 | Age | SELE | VWF |
| 1755 | Age | SELE | Waist |
| 1756 | Age | SELE | WT |
| 1757 | Age | SELP | Sex |
| 1758 | Age | SELP | SHBG |
| 1759 | Age | SELP | TNFRSF1B |
| 1760 | Age | SELP | TRIG |
| 1761 | Age | SELP | VCAM1 |
| 1762 | Age | SELP | VEGF |
| 1763 | Age | SELP | VWF |
| 1764 | Age | SELP | Waist |
| 1765 | Age | SELP | WT |
| 1766 | Age | Sex | SHBG |
| 1767 | Age | Sex | TNFRSF1B |
| 1768 | Age | Sex | TRIG |
| 1769 | Age | Sex | VCAM1 |
| 1770 | Age | Sex | VEGF |
| 1771 | Age | Sex | VWF |
| 1772 | Age | Sex | Waist |
| 1773 | Age | Sex | WT |
| 1774 | Age | SHBG | TNFRSF1B |
| 1775 | Age | SHBG | TRIG |
| 1776 | Age | SHBG | VCAM1 |
| 1777 | Age | SHBG | VEGF |
| 1778 | Age | SHBG | VWF |
| 1779 | Age | SHBG | Waist |
| 1780 | Age | SHBG | WT |
| 1781 | Age | TNFRSF1B | TRIG |
| 1782 | Age | TNFRSF1B | VCAM1 |
| 1783 | Age | TNFRSF1B | VEGF |
| 1784 | Age | TNFRSF1B | VWF |
| 1785 | Age | TNFRSF1B | Waist |
| 1786 | Age | TNFRSF1B | WT |
| 1787 | Age | TRIG | VCAM1 |
| 1788 | Age | TRIG | VEGF |
| 1789 | Age | TRIG | VWF |
| 1790 | Age | TRIG | Waist |
| 1791 | Age | TRIG | WT |
| 1792 | Age | VCAM1 | VEGF |

FIG. 14FF

| 3-Panel | Marker 1 | Marker 2 | Marker 3 |
|---|---|---|---|
| 1793 | Age | VCAM1 | VWF |
| 1794 | Age | VCAM1 | Waist |
| 1795 | Age | VCAM1 | WT |
| 1796 | Age | VEGF | VWF |
| 1797 | Age | VEGF | Waist |
| 1798 | Age | VEGF | WT |
| 1799 | Age | VWF | Waist |
| 1800 | Age | VWF | WT |
| 1801 | Age | Waist | WT |
| 1802 | AGER | ANG | POMC |
| 1803 | AGER | APOE | POMC |
| 1804 | AGER | BMI | POMC |
| 1805 | AGER | CD40 | POMC |
| 1806 | AGER | CDK5 | POMC |
| 1807 | AGER | CRP | POMC |
| 1808 | AGER | DPP4 | POMC |
| 1809 | AGER | FGA | POMC |
| 1810 | AGER | HDLC | POMC |
| 1811 | AGER | IGF1 | POMC |
| 1812 | AGER | IL6ST | POMC |
| 1813 | AGER | LEP | POMC |
| 1814 | AGER | POMC | SBP |
| 1815 | AGER | POMC | Sex |
| 1816 | AGER | POMC | VCAM1 |
| 1817 | AGER | POMC | VEGF |
| 1818 | AHSG | ANG | POMC |
| 1819 | AHSG | CDK5 | POMC |
| 1820 | AHSG | HDLC | POMC |

| 3-Panel | Marker 1 | Marker 2 | Marker 3 |
|---|---|---|---|
| 1821 | AHSG | IGF1 | POMC |
| 1822 | AHSG | IL6ST | POMC |
| 1823 | AHSG | LEP | POMC |
| 1824 | AHSG | POMC | Sex |
| 1825 | AHSG | POMC | VCAM1 |
| 1826 | AHSG | POMC | VEGF |
| 1827 | ANG | APOA1 | POMC |
| 1828 | ANG | APOA1 | VEGF |
| 1829 | ANG | APOE | POMC |
| 1830 | ANG | BAX | POMC |
| 1831 | ANG | BMI | CD40 |
| 1832 | ANG | BMI | CRP |
| 1833 | ANG | BMI | HDLC |
| 1834 | ANG | BMI | IGF1 |
| 1835 | ANG | BMI | IL6ST |
| 1836 | ANG | BMI | POMC |
| 1837 | ANG | BMI | VEGF |
| 1838 | ANG | BMI | Waist |
| 1839 | ANG | C3 | POMC |
| 1840 | ANG | CCL2 | IGF1 |
| 1841 | ANG | CCL2 | POMC |
| 1842 | ANG | CCL2 | Sex |
| 1843 | ANG | CD14 | POMC |
| 1844 | ANG | CD40 | IGF1 |
| 1845 | ANG | CD40 | IL6ST |
| 1846 | ANG | CD40 | Insulin |
| 1847 | ANG | CD40 | POMC |
| 1848 | ANG | CD40 | VEGF |

FIG. 14GG

| 3-Panel | Marker 1 | Marker 2 | Marker 3 |
|---|---|---|---|
| 1849 | ANG | CDK5 | POMC |
| 1850 | ANG | CHOL | POMC |
| 1851 | ANG | CRP | IL6ST |
| 1852 | ANG | CRP | Insulin |
| 1853 | ANG | CRP | POMC |
| 1854 | ANG | DBP | POMC |
| 1855 | ANG | DPP4 | POMC |
| 1856 | ANG | EGF | POMC |
| 1857 | ANG | ENG | POMC |
| 1858 | ANG | FamHX | POMC |
| 1859 | ANG | FGA | POMC |
| 1860 | ANG | FTH1 | POMC |
| 1861 | ANG | Gluc120 | POMC |
| 1862 | ANG | Glucose | POMC |
| 1863 | ANG | HBA1C | POMC |
| 1864 | ANG | HDLC | IGF1 |
| 1865 | ANG | HDLC | Insulin |
| 1866 | ANG | HDLC | POMC |
| 1867 | ANG | HDLC | VEGF |
| 1868 | ANG | HGF | POMC |
| 1869 | ANG | Hip | POMC |
| 1870 | ANG | HP | POMC |
| 1871 | ANG | HT | POMC |
| 1872 | ANG | ICAM1 | POMC |
| 1873 | ANG | IGF1 | IL6ST |
| 1874 | ANG | IGF1 | LEP |
| 1875 | ANG | IGF1 | POMC |
| 1876 | ANG | IGF1 | Sex |

| 3-Panel | Marker 1 | Marker 2 | Marker 3 |
|---|---|---|---|
| 1877 | ANG | IGF1 | VCAM1 |
| 1878 | ANG | IGF1 | VEGF |
| 1879 | ANG | IGFBP1 | POMC |
| 1880 | ANG | IGFBP3 | POMC |
| 1881 | ANG | IL18 | POMC |
| 1882 | ANG | IL2RA | POMC |
| 1883 | ANG | IL6R | IL6ST |
| 1884 | ANG | IL6R | POMC |
| 1885 | ANG | IL6ST | Insulin |
| 1886 | ANG | IL6ST | LEP |
| 1887 | ANG | IL6ST | POMC |
| 1888 | ANG | IL6ST | Sex |
| 1889 | ANG | IL6ST | VEGF |
| 1890 | ANG | IL8 | POMC |
| 1891 | ANG | INHBA | POMC |
| 1892 | ANG | Ins120 | POMC |
| 1893 | ANG | Insulin | POMC |
| 1894 | ANG | Insulin | VEGF |
| 1895 | ANG | LDL | POMC |
| 1896 | ANG | LEP | POMC |
| 1897 | ANG | PLAT | POMC |
| 1898 | ANG | POMC | SBP |
| 1899 | ANG | POMC | SCp |
| 1900 | ANG | POMC | SELE |
| 1901 | ANG | POMC | SELP |
| 1902 | ANG | POMC | Sex |
| 1903 | ANG | POMC | SHBG |
| 1904 | ANG | POMC | TNFRSF1B |

FIG. 14HH

| 3-Panel | Marker 1 | Marker 2 | Marker 3 |
|---|---|---|---|
| 1905 | ANG | POMC | TRIG |
| 1906 | ANG | POMC | VCAM1 |
| 1907 | ANG | POMC | VEGF |
| 1908 | ANG | POMC | vWF |
| 1909 | ANG | POMC | Waist |
| 1910 | ANG | POMC | WT |
| 1911 | ANG | Sex | VEGF |
| 1912 | ANG | VCAM1 | VEGF |
| 1913 | APOA1 | APOE | POMC |
| 1914 | APOA1 | CD40 | VEGF |
| 1915 | APOA1 | CDK5 | POMC |
| 1916 | APOA1 | CRP | LEP |
| 1917 | APOA1 | CRP | POMC |
| 1918 | APOA1 | CRP | Sex |
| 1919 | APOA1 | FGA | POMC |
| 1920 | APOA1 | HDLC | Insulin |
| 1921 | APOA1 | HDLC | POMC |
| 1922 | APOA1 | IGF1 | LEP |
| 1923 | APOA1 | IGF1 | POMC |
| 1924 | APOA1 | IL6ST | POMC |
| 1925 | APOA1 | LEP | POMC |
| 1926 | APOA1 | LEP | VEGF |
| 1927 | APOA1 | POMC | Sex |
| 1928 | APOA1 | POMC | VCAM1 |
| 1929 | APOA1 | POMC | VEGF |
| 1930 | APOA1 | Sex | VEGF |
| 1931 | APOE | BMI | CRP |
| 1932 | APOE | BMI | POMC |

| 3-Panel | Marker 1 | Marker 2 | Marker 3 |
|---|---|---|---|
| 1933 | APOE | CCL2 | POMC |
| 1934 | APOE | CD14 | POMC |
| 1935 | APOE | CD40 | POMC |
| 1936 | APOE | CDK5 | POMC |
| 1937 | APOE | CRP | POMC |
| 1938 | APOE | DBP | POMC |
| 1939 | APOE | DPP4 | POMC |
| 1940 | APOE | EGF | POMC |
| 1941 | APOE | FGA | POMC |
| 1942 | APOE | HDLC | POMC |
| 1943 | APOE | Hip | POMC |
| 1944 | APOE | HP | POMC |
| 1945 | APOE | HT | POMC |
| 1946 | APOE | IGF1 | POMC |
| 1947 | APOE | IGFBP1 | POMC |
| 1948 | APOE | IL18 | POMC |
| 1949 | APOE | IL2RA | POMC |
| 1950 | APOE | IL6ST | POMC |
| 1951 | APOE | Ins120 | POMC |
| 1952 | APOE | Insulin | POMC |
| 1953 | APOE | LEP | POMC |
| 1954 | APOE | PLAT | POMC |
| 1955 | APOE | POMC | SBP |
| 1956 | APOE | POMC | Sex |
| 1957 | APOE | POMC | TRIG |
| 1958 | APOE | POMC | VCAM1 |
| 1959 | APOE | POMC | VEGF |
| 1960 | APOE | POMC | WT |

FIG. 14II

| 3-Panel | Marker 1 | Marker 2 | Marker 3 |
|---|---|---|---|
| 1961 | BAX | CDK5 | POMC |
| 1962 | BAX | HDLC | POMC |
| 1963 | BAX | IGF1 | POMC |
| 1964 | BAX | IL6ST | POMC |
| 1965 | BAX | LEP | POMC |
| 1966 | BAX | POMC | Sex |
| 1967 | BAX | POMC | VCAM1 |
| 1968 | BAX | POMC | VEGF |
| 1969 | BMI | C3 | CRP |
| 1970 | BMI | C3 | POMC |
| 1971 | BMI | CCL2 | CRP |
| 1972 | BMI | CCL2 | POMC |
| 1973 | BMI | CD14 | HDLC |
| 1974 | BMI | CD14 | POMC |
| 1975 | BMI | CD40 | CRP |
| 1976 | BMI | CD40 | HDLC |
| 1977 | BMI | CD40 | Ins120 |
| 1978 | BMI | CD40 | POMC |
| 1979 | BMI | CD40 | VEGF |
| 1980 | BMI | CD40 | Waist |
| 1981 | BMI | CDK5 | CRP |
| 1982 | BMI | CDK5 | POMC |
| 1983 | BMI | CRP | DBP |
| 1984 | BMI | CRP | DPP4 |
| 1985 | BMI | CRP | ENG |
| 1986 | BMI | CRP | FamHX |
| 1987 | BMI | CRP | FGA |
| 1988 | BMI | CRP | Gluc120 |
| 1989 | BMI | CRP | Glucose |
| 1990 | BMI | CRP | HDLC |
| 1991 | BMI | CRP | HT |
| 1992 | BMI | CRP | ICAM1 |
| 1993 | BMI | CRP | IGF1 |
| 1994 | BMI | CRP | IL18 |
| 1995 | BMI | CRP | IL2RA |
| 1996 | BMI | CRP | IL6ST |
| 1997 | BMI | CRP | IL8 |
| 1998 | BMI | CRP | Ins120 |
| 1999 | BMI | CRP | LEP |
| 2000 | BMI | CRP | POMC |
| 2001 | BMI | CRP | Sex |
| 2002 | BMI | CRP | SHBG |
| 2003 | BMI | CRP | TRIG |
| 2004 | BMI | CRP | VEGF |
| 2005 | BMI | CRP | VWF |
| 2006 | BMI | CRP | Waist |
| 2007 | BMI | CRP | WT |
| 2008 | BMI | DBP | HDLC |
| 2009 | BMI | DBP | POMC |
| 2010 | BMI | DPP4 | HDLC |
| 2011 | BMI | DPP4 | POMC |
| 2012 | BMI | DPP4 | VEGF |
| 2013 | BMI | FGA | POMC |
| 2014 | BMI | Gluc120 | POMC |
| 2015 | BMI | HDLC | IGF1 |
| 2016 | BMI | HDLC | IL6ST |

FIG. 14JJ

| 3-Panel | Marker 1 | Marker 2 | Marker 3 |
|---|---|---|---|
| 2017 | BMI | HDLC | Ins120 |
| 2018 | BMI | HDLC | POMC |
| 2019 | BMI | HDLC | SBP |
| 2020 | BMI | HDLC | VEGF |
| 2021 | BMI | HDLC | VWF |
| 2022 | BMI | HDLC | Waist |
| 2023 | BMI | HGF | POMC |
| 2024 | BMI | HP | POMC |
| 2025 | BMI | HT | POMC |
| 2026 | BMI | IGF1 | IL6ST |
| 2027 | BMI | IGF1 | Ins120 |
| 2028 | BMI | IGF1 | POMC |
| 2029 | BMI | IGF1 | Waist |
| 2030 | BMI | IL2RA | POMC |
| 2031 | BMI | IL6R | POMC |
| 2032 | BMI | IL6ST | POMC |
| 2033 | BMI | IL6ST | VEGF |
| 2034 | BMI | Ins120 | POMC |
| 2035 | BMI | Ins120 | VEGF |
| 2036 | BMI | Ins120 | Waist |
| 2037 | BMI | LEP | POMC |
| 2038 | BMI | PLAT | POMC |
| 2039 | BMI | POMC | SBP |
| 2040 | BMI | POMC | SELP |
| 2041 | BMI | POMC | Sex |
| 2042 | BMI | POMC | TRIG |
| 2043 | BMI | POMC | VCAM1 |
| 2044 | BMI | POMC | VEGF |
| 2045 | BMI | POMC | VWF |
| 2046 | BMI | POMC | Waist |
| 2047 | BMI | POMC | WT |
| 2048 | BMI | Sex | VEGF |
| 2049 | BMI | VEGF | Waist |
| 2050 | C3 | CDK5 | POMC |
| 2051 | C3 | CRP | POMC |
| 2052 | C3 | DPP4 | POMC |
| 2053 | C3 | FGA | POMC |
| 2054 | C3 | HDLC | POMC |
| 2055 | C3 | IGF1 | POMC |
| 2056 | C3 | IL6ST | POMC |
| 2057 | C3 | LEP | POMC |
| 2058 | C3 | POMC | Sex |
| 2059 | C3 | POMC | VCAM1 |
| 2060 | C3 | POMC | VEGF |
| 2061 | CCL2 | CD40 | POMC |
| 2062 | CCL2 | CDK5 | POMC |
| 2063 | CCL2 | CRP | LEP |
| 2064 | CCL2 | CRP | POMC |
| 2065 | CCL2 | CRP | Sex |
| 2066 | CCL2 | DBP | POMC |
| 2067 | CCL2 | DPP4 | POMC |
| 2068 | CCL2 | FGA | POMC |
| 2069 | CCL2 | HDLC | POMC |
| 2070 | CCL2 | HT | POMC |
| 2071 | CCL2 | IGF1 | POMC |
| 2072 | CCL2 | IL6ST | LEP |

FIG. 14KK

| 3-Panel | Marker 1 | Marker 2 | Marker 3 |
|---|---|---|---|
| 2073 | CCL2 | IL6ST | POMC |
| 2074 | CCL2 | Ins120 | POMC |
| 2075 | CCL2 | LEP | POMC |
| 2076 | CCL2 | POMC | SBP |
| 2077 | CCL2 | POMC | Sex |
| 2078 | CCL2 | POMC | VCAM1 |
| 2079 | CCL2 | POMC | VEGF |
| 2080 | CD14 | CDK5 | POMC |
| 2081 | CD14 | CRP | POMC |
| 2082 | CD14 | DPP4 | POMC |
| 2083 | CD14 | FGA | POMC |
| 2084 | CD14 | HDLC | Insulin |
| 2085 | CD14 | HDLC | POMC |
| 2086 | CD14 | HT | POMC |
| 2087 | CD14 | IGF1 | POMC |
| 2088 | CD14 | IL6R | IL6ST |
| 2089 | CD14 | IL6ST | LEP |
| 2090 | CD14 | IL6ST | POMC |
| 2091 | CD14 | LEP | POMC |
| 2092 | CD14 | LEP | VEGF |
| 2093 | CD14 | POMC | SBP |
| 2094 | CD14 | POMC | Sex |
| 2095 | CD14 | POMC | VCAM1 |
| 2096 | CD14 | POMC | VEGF |
| 2097 | CD40 | CDK5 | POMC |
| 2098 | CD40 | CRP | Insulin |
| 2099 | CD40 | CRP | POMC |
| 2100 | CD40 | DPP4 | POMC |
| 2101 | CD40 | FGA | POMC |
| 2102 | CD40 | HDLC | IGF1 |
| 2103 | CD40 | HDLC | Insulin |
| 2104 | CD40 | HDLC | POMC |
| 2105 | CD40 | IGF1 | IL6ST |
| 2106 | CD40 | IGF1 | LEP |
| 2107 | CD40 | IGF1 | POMC |
| 2108 | CD40 | IGF1 | VCAM1 |
| 2109 | CD40 | IL6ST | LEP |
| 2110 | CD40 | IL6ST | POMC |
| 2111 | CD40 | IL6ST | VEGF |
| 2112 | CD40 | Ins120 | Insulin |
| 2113 | CD40 | Insulin | VEGF |
| 2114 | CD40 | LEP | POMC |
| 2115 | CD40 | PLAT | POMC |
| 2116 | CD40 | POMC | SBP |
| 2117 | CD40 | POMC | Sex |
| 2118 | CD40 | POMC | VCAM1 |
| 2119 | CD40 | POMC | VEGF |
| 2120 | CDK5 | CHOL | POMC |
| 2121 | CDK5 | CRP | POMC |
| 2122 | CDK5 | DBP | POMC |
| 2123 | CDK5 | DPP4 | POMC |
| 2124 | CDK5 | EGF | POMC |
| 2125 | CDK5 | ENG | POMC |
| 2126 | CDK5 | FamHX | POMC |
| 2127 | CDK5 | FGA | POMC |
| 2128 | CDK5 | FTH1 | POMC |

FIG. 14LL

| 3-Panel | Marker 1 | Marker 2 | Marker 3 |
|---|---|---|---|
| 2129 | CDK5 | Gluc120 | POMC |
| 2130 | CDK5 | Glucose | POMC |
| 2131 | CDK5 | HBA1C | POMC |
| 2132 | CDK5 | HDLC | POMC |
| 2133 | CDK5 | HGF | POMC |
| 2134 | CDK5 | Hip | POMC |
| 2135 | CDK5 | HP | POMC |
| 2136 | CDK5 | HT | POMC |
| 2137 | CDK5 | ICAM1 | POMC |
| 2138 | CDK5 | IGF1 | POMC |
| 2139 | CDK5 | IGFBP1 | POMC |
| 2140 | CDK5 | IGFBP3 | POMC |
| 2141 | CDK5 | IL18 | POMC |
| 2142 | CDK5 | IL2RA | POMC |
| 2143 | CDK5 | IL6R | POMC |
| 2144 | CDK5 | IL6ST | POMC |
| 2145 | CDK5 | IL8 | POMC |
| 2146 | CDK5 | INHBA | POMC |
| 2147 | CDK5 | Ins120 | POMC |
| 2148 | CDK5 | Insulin | POMC |
| 2149 | CDK5 | LDL | POMC |
| 2150 | CDK5 | LEP | POMC |
| 2151 | CDK5 | PLAT | POMC |
| 2152 | CDK5 | POMC | SBP |
| 2153 | CDK5 | POMC | SELE |
| 2154 | CDK5 | POMC | SELP |
| 2155 | CDK5 | POMC | Sex |
| 2156 | CDK5 | POMC | SHBG |

| 3-Panel | Marker 1 | Marker 2 | Marker 3 |
|---|---|---|---|
| 2157 | CDK5 | POMC | TNFRSF1B |
| 2158 | CDK5 | POMC | TRIG |
| 2159 | CDK5 | POMC | VCAM1 |
| 2160 | CDK5 | POMC | VEGF |
| 2161 | CDK5 | POMC | VWF |
| 2162 | CDK5 | POMC | Waist |
| 2163 | CDK5 | POMC | WT |
| 2164 | CHOL | HDLC | POMC |
| 2165 | CHOL | IGF1 | POMC |
| 2166 | CHOL | IL6ST | POMC |
| 2167 | CHOL | LDL | POMC |
| 2168 | CHOL | LEP | POMC |
| 2169 | CHOL | POMC | Sex |
| 2170 | CHOL | POMC | VCAM1 |
| 2171 | CHOL | POMC | VEGF |
| 2172 | CRP | DBP | POMC |
| 2173 | CRP | DPP4 | LEP |
| 2174 | CRP | DPP4 | POMC |
| 2175 | CRP | EGF | POMC |
| 2176 | CRP | ENG | POMC |
| 2177 | CRP | FGA | LEP |
| 2178 | CRP | FGA | POMC |
| 2179 | CRP | FTH1 | POMC |
| 2180 | CRP | Glucose | LEP |
| 2181 | CRP | Glucose | POMC |
| 2182 | CRP | HDLC | Insulin |
| 2183 | CRP | HDLC | POMC |
| 2184 | CRP | HGF | POMC |

FIG. 14MM

| 3-Panel | Marker 1 | Marker 2 | Marker 3 |
|---|---|---|---|
| 2185 | CRP | Hip | IL6ST |
| 2186 | CRP | Hip | LEP |
| 2187 | CRP | Hip | POMC |
| 2188 | CRP | Hip | Sex |
| 2189 | CRP | HT | POMC |
| 2190 | CRP | HT | WT |
| 2191 | CRP | IGF1 | IL6ST |
| 2192 | CRP | IGF1 | LEP |
| 2193 | CRP | IGF1 | POMC |
| 2194 | CRP | IGF1 | Sex |
| 2195 | CRP | IGF1 | VCAM1 |
| 2196 | CRP | IGFBP1 | POMC |
| 2197 | CRP | IL18 | POMC |
| 2198 | CRP | IL2RA | LEP |
| 2199 | CRP | IL2RA | POMC |
| 2200 | CRP | IL6R | IL6ST |
| 2201 | CRP | IL6R | POMC |
| 2202 | CRP | IL6ST | LEP |
| 2203 | CRP | IL6ST | POMC |
| 2204 | CRP | IL6ST | Sex |
| 2205 | CRP | INHBA | POMC |
| 2206 | CRP | Ins120 | POMC |
| 2207 | CRP | Insulin | LEP |
| 2208 | CRP | Insulin | POMC |
| 2209 | CRP | Insulin | Sex |
| 2210 | CRP | LDL | POMC |
| 2211 | CRP | LEP | POMC |
| 2212 | CRP | LEP | VCAM1 |
| 2213 | CRP | LEP | VEGF |
| 2214 | CRP | LEP | WT |
| 2215 | CRP | PLAT | POMC |
| 2216 | CRP | POMC | SBP |
| 2217 | CRP | POMC | Sex |
| 2218 | CRP | POMC | TNFRSF1B |
| 2219 | CRP | POMC | TRIG |
| 2220 | CRP | POMC | VCAM1 |
| 2221 | CRP | POMC | VEGF |
| 2222 | CRP | POMC | VWF |
| 2223 | CRP | POMC | WT |
| 2224 | CRP | Sex | VEGF |
| 2225 | CRP | Sex | Waist |
| 2226 | CRP | Sex | WT |
| 2227 | DBP | DPP4 | POMC |
| 2228 | DBP | FGA | POMC |
| 2229 | DBP | HDLC | POMC |
| 2230 | DBP | IGF1 | POMC |
| 2231 | DBP | IL6ST | POMC |
| 2232 | DBP | LEP | POMC |
| 2233 | DBP | POMC | Sex |
| 2234 | DBP | POMC | VCAM1 |
| 2235 | DBP | POMC | VEGF |
| 2236 | DPP4 | EGF | POMC |
| 2237 | DPP4 | FGA | POMC |
| 2238 | DPP4 | Gluc120 | POMC |
| 2239 | DPP4 | HDLC | POMC |
| 2240 | DPP4 | HP | POMC |

FIG. 14NN

| 3-Panel | Marker 1 | Marker 2 | Marker 3 |
|---|---|---|---|
| 2241 | DPP4 | HT | POMC |
| 2242 | DPP4 | IGF1 | LEP |
| 2243 | DPP4 | IGF1 | POMC |
| 2244 | DPP4 | IL18 | POMC |
| 2245 | DPP4 | IL2RA | POMC |
| 2246 | DPP4 | IL6ST | POMC |
| 2247 | DPP4 | Ins120 | POMC |
| 2248 | DPP4 | LDL | POMC |
| 2249 | DPP4 | LEP | POMC |
| 2250 | DPP4 | LEP | VEGF |
| 2251 | DPP4 | POMC | SBP |
| 2252 | DPP4 | POMC | Sex |
| 2253 | DPP4 | POMC | TNFRSF1B |
| 2254 | DPP4 | POMC | TRIG |
| 2255 | DPP4 | POMC | VCAM1 |
| 2256 | DPP4 | POMC | VEGF |
| 2257 | DPP4 | POMC | WT |
| 2258 | EGF | FGA | POMC |
| 2259 | EGF | HDLC | POMC |
| 2260 | EGF | IGF1 | POMC |
| 2261 | EGF | IL6ST | POMC |
| 2262 | EGF | LEP | POMC |
| 2263 | EGF | POMC | Sex |
| 2264 | EGF | POMC | VCAM1 |
| 2265 | EGF | POMC | VEGF |
| 2266 | ENG | FGA | POMC |
| 2267 | ENG | HDLC | POMC |
| 2268 | ENG | IGF1 | POMC |

| 3-Panel | Marker 1 | Marker 2 | Marker 3 |
|---|---|---|---|
| 2269 | ENG | IL6ST | POMC |
| 2270 | ENG | LEP | POMC |
| 2271 | ENG | POMC | Sex |
| 2272 | ENG | POMC | VCAM1 |
| 2273 | ENG | POMC | VEGF |
| 2274 | FamHX | HDLC | POMC |
| 2275 | FamHX | IGF1 | POMC |
| 2276 | FamHX | IL6ST | POMC |
| 2277 | FamHX | LEP | POMC |
| 2278 | FamHX | POMC | Sex |
| 2279 | FamHX | POMC | VCAM1 |
| 2280 | FamHX | POMC | VEGF |
| 2281 | FGA | FTH1 | POMC |
| 2282 | FGA | Gluc120 | POMC |
| 2283 | FGA | Glucose | POMC |
| 2284 | FGA | HDLC | POMC |
| 2285 | FGA | Hip | POMC |
| 2286 | FGA | HP | POMC |
| 2287 | FGA | HT | POMC |
| 2288 | FGA | IGF1 | POMC |
| 2289 | FGA | IGFBP1 | POMC |
| 2290 | FGA | IL18 | POMC |
| 2291 | FGA | IL2RA | POMC |
| 2292 | FGA | IL6R | POMC |
| 2293 | FGA | IL6ST | POMC |
| 2294 | FGA | Ins120 | POMC |
| 2295 | FGA | Insulin | POMC |
| 2296 | FGA | LEP | POMC |

FIG. 1400

| 3-Panel | Marker 1 | Marker 2 | Marker 3 |
|---|---|---|---|
| 2297 | FGA | PLAT | POMC |
| 2298 | FGA | POMC | SBP |
| 2299 | FGA | POMC | Sex |
| 2300 | FGA | POMC | TNFRSF1B |
| 2301 | FGA | POMC | TRIG |
| 2302 | FGA | POMC | VCAM1 |
| 2303 | FGA | POMC | VEGF |
| 2304 | FGA | POMC | WT |
| 2305 | FTH1 | HDLC | POMC |
| 2306 | FTH1 | IGF1 | POMC |
| 2307 | FTH1 | IL6ST | POMC |
| 2308 | FTH1 | LEP | POMC |
| 2309 | FTH1 | POMC | Sex |
| 2310 | FTH1 | POMC | VCAM1 |
| 2311 | FTH1 | POMC | VEGF |
| 2312 | Gluc120 | HDLC | POMC |
| 2313 | Gluc120 | IGF1 | POMC |
| 2314 | Gluc120 | IL6ST | POMC |
| 2315 | Gluc120 | LEP | POMC |
| 2316 | Gluc120 | POMC | Sex |
| 2317 | Gluc120 | POMC | VCAM1 |
| 2318 | Gluc120 | POMC | VEGF |
| 2319 | Glucose | HDLC | POMC |
| 2320 | Glucose | IGF1 | POMC |
| 2321 | Glucose | IL6ST | POMC |
| 2322 | Glucose | LEP | POMC |
| 2323 | Glucose | POMC | SBP |
| 2324 | Glucose | POMC | Sex |

| 3-Panel | Marker 1 | Marker 2 | Marker 3 |
|---|---|---|---|
| 2325 | Glucose | POMC | VCAM1 |
| 2326 | Glucose | POMC | VEGF |
| 2327 | HBA1C | HDLC | POMC |
| 2328 | HBA1C | IGF1 | POMC |
| 2329 | HBA1C | IL6ST | POMC |
| 2330 | HBA1C | LEP | POMC |
| 2331 | HBA1C | POMC | Sex |
| 2332 | HBA1C | POMC | VCAM1 |
| 2333 | HBA1C | POMC | VEGF |
| 2334 | HDLC | HGF | POMC |
| 2335 | HDLC | Hp | IGF1 |
| 2336 | HDLC | Hp | POMC |
| 2337 | HDLC | HP | POMC |
| 2338 | HDLC | HT | POMC |
| 2339 | HDLC | ICAM1 | POMC |
| 2340 | HDLC | IGF1 | IL6ST |
| 2341 | HDLC | IGF1 | IL6ST |
| 2342 | HDLC | IGF1 | LEP |
| 2343 | HDLC | IGF1 | POMC |
| 2344 | HDLC | IGFBP1 | POMC |
| 2345 | HDLC | IGFBP3 | POMC |
| 2346 | HDLC | IL18 | POMC |
| 2347 | HDLC | IL2RA | POMC |
| 2348 | HDLC | IL6R | POMC |
| 2349 | HDLC | IL6ST | POMC |
| 2350 | HDLC | IL8 | POMC |
| 2351 | HDLC | INHBA | POMC |
| 2352 | HDLC | Ins120 | POMC |

FIG. 14PP

| 3-Panel | Marker 1 | Marker 2 | Marker 3 |
|---|---|---|---|
| 2353 | HDLC | Insulin | POMC |
| 2354 | HDLC | LDL | POMC |
| 2355 | HDLC | LEP | POMC |
| 2356 | HDLC | PLAT | POMC |
| 2357 | HDLC | POMC | SBP |
| 2358 | HDLC | POMC | SCp |
| 2359 | HDLC | POMC | SELE |
| 2360 | HDLC | POMC | SELP |
| 2361 | HDLC | POMC | Sex |
| 2362 | HDLC | POMC | SHBG |
| 2363 | HDLC | POMC | TNFRSF1B |
| 2364 | HDLC | POMC | TRIG |
| 2365 | HDLC | POMC | VCAM1 |
| 2366 | HDLC | POMC | VEGF |
| 2367 | HDLC | POMC | VWF |
| 2368 | HDLC | POMC | Waist |
| 2369 | HDLC | POMC | WT |
| 2370 | HGF | HT | POMC |
| 2371 | HGF | IGF1 | POMC |
| 2372 | HGF | IL6ST | POMC |
| 2373 | HGF | LEP | POMC |
| 2374 | HGF | POMC | Sex |
| 2375 | HGF | POMC | VCAM1 |
| 2376 | HGF | POMC | VEGF |
| 2377 | Hip | IGF1 | IL6ST |
| 2378 | Hip | IGF1 | POMC |
| 2379 | Hip | IL6ST | POMC |
| 2380 | Hip | LEP | POMC |

| 3-Panel | Marker 1 | Marker 2 | Marker 3 |
|---|---|---|---|
| 2381 | Hip | POMC | Sex |
| 2382 | Hip | POMC | VCAM1 |
| 2383 | Hip | POMC | VEGF |
| 2384 | HP | HT | POMC |
| 2385 | HP | IGF1 | POMC |
| 2386 | HP | IL6ST | POMC |
| 2387 | HP | LEP | POMC |
| 2388 | HP | POMC | POMC |
| 2389 | HP | POMC | Sex |
| 2390 | HP | POMC | VCAM1 |
| 2391 | HP | IGF1 | VEGF |
| 2392 | HT | IL6ST | POMC |
| 2393 | HT | Ins120 | POMC |
| 2394 | HT | LEP | POMC |
| 2395 | HT | POMC | SBP |
| 2396 | HT | POMC | Sex |
| 2397 | HT | POMC | TRIG |
| 2398 | HT | POMC | VCAM1 |
| 2399 | HT | POMC | VEGF |
| 2400 | HT | POMC | WT |
| 2401 | ICAM1 | IGF1 | POMC |
| 2402 | ICAM1 | IL6ST | POMC |
| 2403 | ICAM1 | LEP | POMC |
| 2404 | ICAM1 | POMC | Sex |
| 2405 | ICAM1 | POMC | VCAM1 |
| 2406 | ICAM1 | POMC | VEGF |
| 2407 | IGF1 | IGFBP1 | POMC |
| 2408 | IGF1 | IGFBP3 | POMC |

FIG. 14QQ

| 3-Panel | Marker 1 | Marker 2 | Marker 3 |
|---|---|---|---|
| 2409 | IGF1 | IL18 | POMC |
| 2410 | IGF1 | IL2RA | LEP |
| 2411 | IGF1 | IL2RA | POMC |
| 2412 | IGF1 | IL6R | IL6ST |
| 2413 | IGF1 | IL6R | POMC |
| 2414 | IGF1 | IL6ST | LEP |
| 2415 | IGF1 | IL6ST | POMC |
| 2416 | IGF1 | IL6ST | Sex |
| 2417 | IGF1 | IL6ST | VCAM1 |
| 2418 | IGF1 | IL6ST | VEGF |
| 2419 | IGF1 | IL8 | POMC |
| 2420 | IGF1 | INHBA | POMC |
| 2421 | IGF1 | Ins120 | POMC |
| 2422 | IGF1 | Insulin | POMC |
| 2423 | IGF1 | LDL | POMC |
| 2424 | IGF1 | LEP | POMC |
| 2425 | IGF1 | LEP | VCAM1 |
| 2426 | IGF1 | LEP | VEGF |
| 2427 | IGF1 | LEP | vWF |
| 2428 | IGF1 | PLAT | POMC |
| 2429 | IGF1 | POMC | SBP |
| 2430 | IGF1 | POMC | SCp |
| 2431 | IGF1 | POMC | SELE |
| 2432 | IGF1 | POMC | SELP |
| 2433 | IGF1 | POMC | Sex |
| 2434 | IGF1 | POMC | SHBG |
| 2435 | IGF1 | POMC | TNFRSF1B |
| 2436 | IGF1 | POMC | TRIG |

| 3-Panel | Marker 1 | Marker 2 | Marker 3 |
|---|---|---|---|
| 2437 | IGF1 | POMC | VCAM1 |
| 2438 | IGF1 | POMC | VEGF |
| 2439 | IGF1 | POMC | vWF |
| 2440 | IGF1 | POMC | Waist |
| 2441 | IGF1 | POMC | WT |
| 2442 | IGF1 | Sex | VCAM1 |
| 2443 | IGF1 | VCAM1 | VEGF |
| 2444 | IGFBP1 | IL6ST | POMC |
| 2445 | IGFBP1 | LEP | POMC |
| 2446 | IGFBP1 | POMC | SBP |
| 2447 | IGFBP1 | POMC | Sex |
| 2448 | IGFBP1 | POMC | VCAM1 |
| 2449 | IGFBP1 | POMC | VEGF |
| 2450 | IGFBP3 | IL6ST | POMC |
| 2451 | IGFBP3 | LEP | POMC |
| 2452 | IGFBP3 | POMC | Sex |
| 2453 | IGFBP3 | POMC | VCAM1 |
| 2454 | IGFBP3 | POMC | VEGF |
| 2455 | IL18 | IL6ST | POMC |
| 2456 | IL18 | LEP | POMC |
| 2457 | IL18 | POMC | Sex |
| 2458 | IL18 | POMC | VCAM1 |
| 2459 | IL18 | POMC | VEGF |
| 2460 | IL2RA | IL6ST | POMC |
| 2461 | IL2RA | LEP | POMC |
| 2462 | IL2RA | POMC | Sex |
| 2463 | IL2RA | POMC | VCAM1 |
| 2464 | IL2RA | POMC | VEGF |

FIG. 14RR

| 3-Panel | Marker 1 | Marker 2 | Marker 3 |
|---|---|---|---|
| 2465 | IL6R | IL6ST | POMC |
| 2466 | IL6R | LEP | POMC |
| 2467 | IL6R | POMC | Sex |
| 2468 | IL6R | POMC | VCAM1 |
| 2469 | IL6R | POMC | VEGF |
| 2470 | IL6ST | IL8 | POMC |
| 2471 | IL6ST | INHBA | POMC |
| 2472 | IL6ST | Ins120 | LEP |
| 2473 | IL6ST | Ins120 | POMC |
| 2474 | IL6ST | Insulin | POMC |
| 2475 | IL6ST | LDL | POMC |
| 2476 | IL6ST | LEP | POMC |
| 2477 | IL6ST | LEP | VEGF |
| 2478 | IL6ST | PLAT | POMC |
| 2479 | IL6ST | POMC | SBP |
| 2480 | IL6ST | POMC | SCp |
| 2481 | IL6ST | POMC | SELE |
| 2482 | IL6ST | POMC | SELP |
| 2483 | IL6ST | POMC | Sex |
| 2484 | IL6ST | POMC | SHBG |
| 2485 | IL6ST | POMC | TNFRSF1B |
| 2486 | IL6ST | POMC | TRIG |
| 2487 | IL6ST | POMC | VCAM1 |
| 2488 | IL6ST | POMC | VEGF |
| 2489 | IL6ST | POMC | VWF |
| 2490 | IL6ST | POMC | Waist |
| 2491 | IL6ST | POMC | WT |
| 2492 | IL6ST | Sex | VEGF |

| 3-Panel | Marker 1 | Marker 2 | Marker 3 |
|---|---|---|---|
| 2493 | IL8 | LEP | POMC |
| 2494 | IL8 | POMC | Sex |
| 2495 | IL8 | POMC | VCAM1 |
| 2496 | IL8 | POMC | VEGF |
| 2497 | INHBA | LEP | POMC |
| 2498 | INHBA | POMC | Sex |
| 2499 | INHBA | POMC | VCAM1 |
| 2500 | INHBA | POMC | VEGF |
| 2501 | Ins120 | Insulin | POMC |
| 2502 | Ins120 | Insulin | Sex |
| 2503 | Ins120 | LEP | POMC |
| 2504 | Ins120 | PLAT | POMC |
| 2505 | Ins120 | POMC | Sex |
| 2506 | Ins120 | POMC | VCAM1 |
| 2507 | Ins120 | POMC | VEGF |
| 2508 | Insulin | LEP | POMC |
| 2509 | Insulin | POMC | SBP |
| 2510 | Insulin | POMC | Sex |
| 2511 | Insulin | POMC | VCAM1 |
| 2512 | Insulin | POMC | VEGF |
| 2513 | Insulin | Sex | VEGF |
| 2514 | LDL | LEP | POMC |
| 2515 | LDL | POMC | Sex |
| 2516 | LDL | POMC | VCAM1 |
| 2517 | LDL | POMC | VEGF |
| 2518 | LEP | PLAT | POMC |
| 2519 | LEP | POMC | SBP |
| 2520 | LEP | POMC | SCp |

FIG. 14SS

| 3-Panel | Marker 1 | Marker 2 | Marker 3 |
|---|---|---|---|
| 2521 | LEP | POMC | SELE |
| 2522 | LEP | POMC | SELP |
| 2523 | LEP | POMC | Sex |
| 2524 | LEP | POMC | SHBG |
| 2525 | LEP | POMC | TNFRSF1B |
| 2526 | LEP | POMC | TRIG |
| 2527 | LEP | POMC | VCAM1 |
| 2528 | LEP | POMC | VEGF |
| 2529 | LEP | POMC | VWF |
| 2530 | LEP | POMC | Waist |
| 2531 | LEP | POMC | WT |
| 2532 | LEP | VCAM1 | VEGF |
| 2533 | LEP | VEGF | VWF |
| 2534 | PLAT | POMC | Sex |
| 2535 | PLAT | POMC | VCAM1 |
| 2536 | PLAT | POMC | VEGF |
| 2537 | POMC | SBP | Sex |
| 2538 | POMC | SBP | VCAM1 |
| 2539 | POMC | SBP | VEGF |
| 2540 | POMC | SBP | VWF |
| 2541 | POMC | SCp | Sex |
| 2542 | POMC | SCp | VCAM1 |
| 2543 | POMC | SCp | VEGF |
| 2544 | POMC | SELE | Sex |
| 2545 | POMC | SELE | VCAM1 |
| 2546 | POMC | SELE | VEGF |
| 2547 | POMC | SELP | Sex |
| 2548 | POMC | SELP | VCAM1 |

| 3-Panel | Marker 1 | Marker 2 | Marker 3 |
|---|---|---|---|
| 2549 | POMC | SELP | VEGF |
| 2550 | POMC | Sex | SHBG |
| 2551 | POMC | Sex | TNFRSF1B |
| 2552 | POMC | Sex | TRIG |
| 2553 | POMC | Sex | VCAM1 |
| 2554 | POMC | Sex | VEGF |
| 2555 | POMC | Sex | VWF |
| 2556 | POMC | Sex | Waist |
| 2557 | POMC | Sex | WT |
| 2558 | POMC | SHBG | VCAM1 |
| 2559 | POMC | SHBG | VEGF |
| 2560 | POMC | TNFRSF1B | VCAM1 |
| 2561 | POMC | TNFRSF1B | VEGF |
| 2562 | POMC | TRIG | VCAM1 |
| 2563 | POMC | TRIG | VEGF |
| 2564 | POMC | VCAM1 | VEGF |
| 2565 | POMC | VCAM1 | VWF |
| 2566 | POMC | VCAM1 | Waist |
| 2567 | POMC | VCAM1 | WT |
| 2568 | POMC | VEGF | VWF |
| 2569 | POMC | VEGF | Waist |
| 2570 | POMC | VEGF | WT |
| 2571 | Sex | VCAM1 | VEGF |
| 2572 | Sex | VEGF | VWF |
| 2573 | Sex | VEGF | WT |

FIG. 14TT

| 4-Panel | Marker 1 | Marker 2 | Marker 3 | Marker 4 |
|---|---|---|---|---|
| 1 | ACE | ADIPOQ | Age | LEP |
| 2 | ACE | ADIPOQ | Age | POMC |
| 3 | ACE | Age | AGER | HDLC |
| 4 | ACE | Age | AGER | LEP |
| 5 | ACE | Age | AGER | POMC |
| 6 | ACE | Age | AGER | Sex |
| 7 | ACE | Age | AHSG | LEP |
| 8 | ACE | Age | AHSG | POMC |
| 9 | ACE | Age | ANG | BMI |
| 10 | ACE | Age | ANG | CCL2 |
| 11 | ACE | Age | ANG | Glucose |
| 12 | ACE | Age | ANG | HDLC |
| 13 | ACE | Age | ANG | IGF1 |
| 14 | ACE | Age | ANG | IL6ST |
| 15 | ACE | Age | ANG | LEP |
| 16 | ACE | Age | ANG | POMC |
| 17 | ACE | Age | ANG | VEGF |
| 18 | ACE | Age | APOA1 | HDLC |
| 19 | ACE | Age | APOA1 | IGF1 |
| 20 | ACE | Age | APOA1 | LEP |
| 21 | ACE | Age | APOA1 | POMC |
| 22 | ACE | Age | APOA1 | Sex |
| 23 | ACE | Age | APOA1 | VEGF |
| 24 | ACE | Age | APOE | LEP |
| 25 | ACE | Age | APOE | POMC |
| 26 | ACE | Age | BAX | LEP |
| 27 | ACE | Age | BAX | POMC |
| 28 | ACE | Age | BMI | CCL2 |
| 29 | ACE | Age | BMI | CD40 |
| 30 | ACE | Age | BMI | CRP |
| 31 | ACE | Age | BMI | HDLC |
| 32 | ACE | Age | BMI | HT |
| 33 | ACE | Age | BMI | IGF1 |
| 34 | ACE | Age | BMI | IL6ST |
| 35 | ACE | Age | BMI | Ins120 |
| 36 | ACE | Age | BMI | LEP |
| 37 | ACE | Age | BMI | POMC |
| 38 | ACE | Age | BMI | Sex |
| 39 | ACE | Age | BMI | VEGF |
| 40 | ACE | Age | BMI | Waist |
| 41 | ACE | Age | BMI | WT |
| 42 | ACE | Age | C3 | LEP |
| 43 | ACE | Age | C3 | POMC |
| 44 | ACE | Age | CCL2 | CD40 |
| 45 | ACE | Age | CCL2 | HDLC |
| 46 | ACE | Age | CCL2 | Hip |
| 47 | ACE | Age | CCL2 | HT |
| 48 | ACE | Age | CCL2 | IGF1 |
| 49 | ACE | Age | CCL2 | IL6ST |
| 50 | ACE | Age | CCL2 | LEP |
| 51 | ACE | Age | CCL2 | POMC |
| 52 | ACE | Age | CCL2 | Sex |
| 53 | ACE | Age | CCL2 | VEGF |
| 54 | ACE | Age | CD14 | LEP |
| 55 | ACE | Age | CD14 | POMC |
| 56 | ACE | Age | CD40 | Glucose |
| 57 | ACE | Age | CD40 | HDLC |
| 58 | ACE | Age | CD40 | IGF1 |
| 59 | ACE | Age | CD40 | IL6ST |

FIG. 15A

| 4-Panel | Marker 1 | Marker 2 | Marker 3 | Marker 4 |
|---|---|---|---|---|
| 60 | ACE | Age | CD40 | LEP |
| 61 | ACE | Age | CD40 | POMC |
| 62 | ACE | Age | CD40 | Sex |
| 63 | ACE | Age | CD40 | VEGF |
| 64 | ACE | Age | CDK5 | LEP |
| 65 | ACE | Age | CDK5 | POMC |
| 66 | ACE | Age | CHOL | HDLC |
| 67 | ACE | Age | CHOL | LEP |
| 68 | ACE | Age | CHOL | POMC |
| 69 | ACE | Age | CRP | LEP |
| 70 | ACE | Age | CRP | POMC |
| 71 | ACE | Age | DBP | LEP |
| 72 | ACE | Age | DBP | POMC |
| 73 | ACE | Age | DPP4 | HDLC |
| 74 | ACE | Age | DPP4 | IGF1 |
| 75 | ACE | Age | DPP4 | LEP |
| 76 | ACE | Age | DPP4 | POMC |
| 77 | ACE | Age | DPP4 | VEGF |
| 78 | ACE | Age | EGF | HDLC |
| 79 | ACE | Age | EGF | LEP |
| 80 | ACE | Age | EGF | POMC |
| 81 | ACE | Age | ENG | LEP |
| 82 | ACE | Age | ENG | POMC |
| 83 | ACE | Age | FamHX | LEP |
| 84 | ACE | Age | FamHX | POMC |
| 85 | ACE | Age | FGA | LEP |
| 86 | ACE | Age | FGA | POMC |
| 87 | ACE | Age | FTH1 | HDLC |
| 88 | ACE | Age | FTH1 | IGF1 |
| 89 | ACE | Age | FTH1 | LEP |
| 90 | ACE | Age | FTH1 | POMC |
| 91 | ACE | Age | FTH1 | Sex |
| 92 | ACE | Age | Gluc120 | LEP |
| 93 | ACE | Age | Gluc120 | POMC |
| 94 | ACE | Age | Glucose | HDLC |
| 95 | ACE | Age | Glucose | IGF1 |
| 96 | ACE | Age | Glucose | IL6ST |
| 97 | ACE | Age | Glucose | LEP |
| 98 | ACE | Age | Glucose | POMC |
| 99 | ACE | Age | Glucose | Sex |
| 100 | ACE | Age | Glucose | VEGF |
| 101 | ACE | Age | HBA1C | HDLC |
| 102 | ACE | Age | HBA1C | LEP |
| 103 | ACE | Age | HBA1C | POMC |
| 104 | ACE | Age | HDLC | Hip |
| 105 | ACE | Age | HDLC | IGF1 |
| 106 | ACE | Age | HDLC | IGFBP1 |
| 107 | ACE | Age | HDLC | IL18 |
| 108 | ACE | Age | HDLC | IL2RA |
| 109 | ACE | Age | HDLC | IL6ST |
| 110 | ACE | Age | HDLC | IL8 |
| 111 | ACE | Age | HDLC | Insulin |
| 112 | ACE | Age | HDLC | LEP |
| 113 | ACE | Age | HDLC | POMC |
| 114 | ACE | Age | HDLC | SCp |
| 115 | ACE | Age | HDLC | SELP |
| 116 | ACE | Age | HDLC | Sex |
| 117 | ACE | Age | HDLC | TRIG |
| 118 | ACE | Age | HDLC | VCAM1 |
| 119 | ACE | Age | HDLC | VEGF |

FIG. 15B

| 4-Panel | Marker 1 | Marker 2 | Marker 3 | Marker 4 |
|---|---|---|---|---|
| 120 | ACE | Age | HDLC | VWF |
| 121 | ACE | Age | HDLC | Waist |
| 122 | ACE | Age | HDLC | WT |
| 123 | ACE | Age | HGF | LEP |
| 124 | ACE | Age | HGF | POMC |
| 125 | ACE | Age | Hip | IGF1 |
| 126 | ACE | Age | Hip | LEP |
| 127 | ACE | Age | Hip | POMC |
| 128 | ACE | Age | HP | LEP |
| 129 | ACE | Age | HP | POMC |
| 130 | ACE | Age | HP | IGF1 |
| 131 | ACE | Age | HT | LEP |
| 132 | ACE | Age | HT | POMC |
| 133 | ACE | Age | HT | VEGF |
| 134 | ACE | Age | ICAM1 | LEP |
| 135 | ACE | Age | ICAM1 | POMC |
| 136 | ACE | Age | IGF1 | IL18 |
| 137 | ACE | Age | IGF1 | IL2RA |
| 138 | ACE | Age | IGF1 | IL6ST |
| 139 | ACE | Age | IGF1 | Ins120 |
| 140 | ACE | Age | IGF1 | Insulin |
| 141 | ACE | Age | IGF1 | LEP |
| 142 | ACE | Age | IGF1 | POMC |
| 143 | ACE | Age | IGF1 | SELP |
| 144 | ACE | Age | IGF1 | Sex |
| 145 | ACE | Age | IGF1 | VCAM1 |
| 146 | ACE | Age | IGF1 | VEGF |
| 147 | ACE | Age | IGFBP1 | LEP |
| 148 | ACE | Age | IGFBP1 | POMC |
| 149 | ACE | Age | IGFBP3 | LEP |

| 4-Panel | Marker 1 | Marker 2 | Marker 3 | Marker 4 |
|---|---|---|---|---|
| 150 | ACE | Age | IGFBP3 | POMC |
| 151 | ACE | Age | IL18 | LEP |
| 152 | ACE | Age | IL18 | POMC |
| 153 | ACE | Age | IL18 | Sex |
| 154 | ACE | Age | IL18 | VEGF |
| 155 | ACE | Age | IL2RA | LEP |
| 156 | ACE | Age | IL2RA | POMC |
| 157 | ACE | Age | IL2RA | Sex |
| 158 | ACE | Age | IL6R | LEP |
| 159 | ACE | Age | IL6R | POMC |
| 160 | ACE | Age | IL6ST | LEP |
| 161 | ACE | Age | IL6ST | POMC |
| 162 | ACE | Age | IL6ST | Sex |
| 163 | ACE | Age | IL6ST | TNFRSF1B |
| 164 | ACE | Age | IL6ST | VEGF |
| 165 | ACE | Age | IL8 | LEP |
| 166 | ACE | Age | IL8 | POMC |
| 167 | ACE | Age | IL8 | VEGF |
| 168 | ACE | Age | INHBA | LEP |
| 169 | ACE | Age | INHBA | POMC |
| 170 | ACE | Age | Ins120 | Insulin |
| 171 | ACE | Age | Ins120 | LEP |
| 172 | ACE | Age | Ins120 | POMC |
| 173 | ACE | Age | Insulin | LEP |
| 174 | ACE | Age | Insulin | POMC |
| 175 | ACE | Age | Insulin | Sex |
| 176 | ACE | Age | Insulin | VEGF |
| 177 | ACE | Age | LDL | LEP |
| 178 | ACE | Age | LDL | POMC |
| 179 | ACE | Age | LEP | PLAT |

FIG. 15C

| 4-Panel | Marker 1 | Marker 2 | Marker 3 | Marker 4 |
|---|---|---|---|---|
| 180 | ACE | Age | LEP | POMC |
| 181 | ACE | Age | LEP | SBP |
| 182 | ACE | Age | LEP | SCp |
| 183 | ACE | Age | LEP | SELE |
| 184 | ACE | Age | LEP | SELP |
| 185 | ACE | Age | LEP | Sex |
| 186 | ACE | Age | LEP | SHBG |
| 187 | ACE | Age | LEP | TNFRSF1B |
| 188 | ACE | Age | LEP | TRIG |
| 189 | ACE | Age | LEP | VCAM1 |
| 190 | ACE | Age | LEP | VEGF |
| 191 | ACE | Age | LEP | VWF |
| 192 | ACE | Age | LEP | Waist |
| 193 | ACE | Age | LEP | WT |
| 194 | ACE | Age | PLAT | POMC |
| 195 | ACE | Age | POMC | SBP |
| 196 | ACE | Age | POMC | SCp |
| 197 | ACE | Age | POMC | SELE |
| 198 | ACE | Age | POMC | SELP |
| 199 | ACE | Age | POMC | Sex |
| 200 | ACE | Age | POMC | SHBG |
| 201 | ACE | Age | POMC | TNFRSF1B |
| 202 | ACE | Age | POMC | TRIG |
| 203 | ACE | Age | POMC | VCAM1 |
| 204 | ACE | Age | POMC | VEGF |
| 205 | ACE | Age | POMC | VWF |
| 206 | ACE | Age | POMC | Waist |
| 207 | ACE | Age | POMC | WT |
| 208 | ACE | Age | SELP | VEGF |
| 209 | ACE | Age | Sex | VEGF |
| 210 | ACE | Age | Sex | Waist |
| 211 | ACE | Age | Sex | WT |
| 212 | ACE | BMI | HDLC | POMC |
| 213 | ACE | HDLC | IGF1 | POMC |
| 214 | ACE | HDLC | IL18 | POMC |
| 215 | ACE | HDLC | IL6ST | POMC |
| 216 | ACE | HDLC | Insulin | POMC |
| 217 | ACE | IGF1 | POMC | VEGF |
| 218 | ACE | IL6ST | POMC | VEGF |
| 219 | ACE | IL6ST | POMC | VEGF |
| 220 | ACE | LEP | POMC | VEGF |
| 221 | ACE | POMC | Sex | VEGF |
| 222 | ACE | POMC | VCAM1 | VEGF |
| 223 | ADIPOQ | Age | AGER | LEP |
| 224 | ADIPOQ | Age | AGER | POMC |
| 225 | ADIPOQ | Age | AGER | VEGF |
| 226 | ADIPOQ | Age | AHSG | LEP |
| 227 | ADIPOQ | Age | AHSG | POMC |
| 228 | ADIPOQ | Age | ANG | BMI |
| 229 | ADIPOQ | Age | ANG | CCL2 |
| 230 | ADIPOQ | Age | ANG | HDLC |
| 231 | ADIPOQ | Age | ANG | IGF1 |
| 232 | ADIPOQ | Age | ANG | IL6ST |
| 233 | ADIPOQ | Age | ANG | LEP |
| 234 | ADIPOQ | Age | ANG | POMC |
| 235 | ADIPOQ | Age | ANG | VEGF |
| 236 | ADIPOQ | Age | APOA1 | HDLC |
| 237 | ADIPOQ | Age | APOA1 | IGF1 |
| 238 | ADIPOQ | Age | APOA1 | LEP |
| 239 | ADIPOQ | Age | APOA1 | POMC |

FIG. 15D

| 4-Panel | Marker 1 | Marker 2 | Marker 3 | Marker 4 |
|---|---|---|---|---|
| 240 | ADIPOQ | Age | APOA1 | Sex |
| 241 | ADIPOQ | Age | APOA1 | VEGF |
| 242 | ADIPOQ | Age | APOE | LEP |
| 243 | ADIPOQ | Age | APOE | POMC |
| 244 | ADIPOQ | Age | APOE | VEGF |
| 245 | ADIPOQ | Age | BAX | LEP |
| 246 | ADIPOQ | Age | BAX | POMC |
| 247 | ADIPOQ | Age | BMI | CCL2 |
| 248 | ADIPOQ | Age | BMI | CD40 |
| 249 | ADIPOQ | Age | BMI | CRP |
| 250 | ADIPOQ | Age | BMI | DPP4 |
| 251 | ADIPOQ | Age | BMI | HDLC |
| 252 | ADIPOQ | Age | BMI | IGF1 |
| 253 | ADIPOQ | Age | BMI | IL6ST |
| 254 | ADIPOQ | Age | BMI | Ins120 |
| 255 | ADIPOQ | Age | BMI | LEP |
| 256 | ADIPOQ | Age | BMI | POMC |
| 257 | ADIPOQ | Age | BMI | Sex |
| 258 | ADIPOQ | Age | BMI | VEGF |
| 259 | ADIPOQ | Age | BMI | Waist |
| 260 | ADIPOQ | Age | C3 | LEP |
| 261 | ADIPOQ | Age | C3 | POMC |
| 262 | ADIPOQ | Age | CCL2 | CD40 |
| 263 | ADIPOQ | Age | CCL2 | CRP |
| 264 | ADIPOQ | Age | CCL2 | DPP4 |
| 265 | ADIPOQ | Age | CCL2 | Glucose |
| 266 | ADIPOQ | Age | CCL2 | HDLC |
| 267 | ADIPOQ | Age | CCL2 | HT |
| 268 | ADIPOQ | Age | CCL2 | IGF1 |
| 269 | ADIPOQ | Age | CCL2 | IL6ST |

| 4-Panel | Marker 1 | Marker 2 | Marker 3 | Marker 4 |
|---|---|---|---|---|
| 270 | ADIPOQ | Age | CCL2 | LEP |
| 271 | ADIPOQ | Age | CCL2 | POMC |
| 272 | ADIPOQ | Age | CCL2 | Sex |
| 273 | ADIPOQ | Age | CCL2 | VEGF |
| 274 | ADIPOQ | Age | CD14 | LEP |
| 275 | ADIPOQ | Age | CD14 | POMC |
| 276 | ADIPOQ | Age | CD14 | VEGF |
| 277 | ADIPOQ | Age | CD40 | Glucose |
| 278 | ADIPOQ | Age | CD40 | HDLC |
| 279 | ADIPOQ | Age | CD40 | IGF1 |
| 280 | ADIPOQ | Age | CD40 | IL6ST |
| 281 | ADIPOQ | Age | CD40 | LEP |
| 282 | ADIPOQ | Age | CD40 | POMC |
| 283 | ADIPOQ | Age | CD40 | Sex |
| 284 | ADIPOQ | Age | CD40 | VEGF |
| 285 | ADIPOQ | Age | CDK5 | LEP |
| 286 | ADIPOQ | Age | CDK5 | POMC |
| 287 | ADIPOQ | Age | CHOL | POMC |
| 288 | ADIPOQ | Age | CRP | Glucose |
| 289 | ADIPOQ | Age | CRP | IL6ST |
| 290 | ADIPOQ | Age | CRP | Insulin |
| 291 | ADIPOQ | Age | CRP | LEP |
| 292 | ADIPOQ | Age | CRP | POMC |
| 293 | ADIPOQ | Age | CRP | VEGF |
| 294 | ADIPOQ | Age | DBP | LEP |
| 295 | ADIPOQ | Age | DBP | POMC |
| 296 | ADIPOQ | Age | DPP4 | IGF1 |
| 297 | ADIPOQ | Age | DPP4 | LEP |
| 298 | ADIPOQ | Age | DPP4 | POMC |
| 299 | ADIPOQ | Age | DPP4 | VEGF |

FIG. 15E

| 4-Panel | Marker 1 | Marker 2 | Marker 3 | Marker 4 |
|---|---|---|---|---|
| 300 | ADIPOQ | Age | EGF | LEP |
| 301 | ADIPOQ | Age | EGF | POMC |
| 302 | ADIPOQ | Age | ENG | LEP |
| 303 | ADIPOQ | Age | ENG | POMC |
| 304 | ADIPOQ | Age | FamHX | LEP |
| 305 | ADIPOQ | Age | FamHX | POMC |
| 306 | ADIPOQ | Age | FGA | LEP |
| 307 | ADIPOQ | Age | FGA | POMC |
| 308 | ADIPOQ | Age | FTH1 | HDLC |
| 309 | ADIPOQ | Age | FTH1 | LEP |
| 310 | ADIPOQ | Age | FTH1 | POMC |
| 311 | ADIPOQ | Age | FTH1 | Sex |
| 312 | ADIPOQ | Age | Gluc120 | LEP |
| 313 | ADIPOQ | Age | Gluc120 | POMC |
| 314 | ADIPOQ | Age | Glucose | HDLC |
| 315 | ADIPOQ | Age | Glucose | HT |
| 316 | ADIPOQ | Age | Glucose | IGF1 |
| 317 | ADIPOQ | Age | Glucose | IL6ST |
| 318 | ADIPOQ | Age | Glucose | LEP |
| 319 | ADIPOQ | Age | Glucose | POMC |
| 320 | ADIPOQ | Age | Glucose | Sex |
| 321 | ADIPOQ | Age | Glucose | VEGF |
| 322 | ADIPOQ | Age | HBA1C | LEP |
| 323 | ADIPOQ | Age | HBA1C | POMC |
| 324 | ADIPOQ | Age | HBA1C | VEGF |
| 325 | ADIPOQ | Age | HDLC | Hip |
| 326 | ADIPOQ | Age | HDLC | IGF1 |
| 327 | ADIPOQ | Age | HDLC | IL18 |
| 328 | ADIPOQ | Age | HDLC | IL6ST |
| 329 | ADIPOQ | Age | HDLC | Insulin |
| 330 | ADIPOQ | Age | HDLC | LEP |
| 331 | ADIPOQ | Age | HDLC | POMC |
| 332 | ADIPOQ | Age | HDLC | VEGF |
| 333 | ADIPOQ | Age | HDLC | Waist |
| 334 | ADIPOQ | Age | HDLC | WT |
| 335 | ADIPOQ | Age | HGF | LEP |
| 336 | ADIPOQ | Age | HGF | POMC |
| 337 | ADIPOQ | Age | Hip | IGF1 |
| 338 | ADIPOQ | Age | Hip | LEP |
| 339 | ADIPOQ | Age | Hip | POMC |
| 340 | ADIPOQ | Age | Hip | VEGF |
| 341 | ADIPOQ | Age | HP | LEP |
| 342 | ADIPOQ | Age | HP | POMC |
| 343 | ADIPOQ | Age | HT | IGF1 |
| 344 | ADIPOQ | Age | HT | IL6ST |
| 345 | ADIPOQ | Age | HT | LEP |
| 346 | ADIPOQ | Age | HT | POMC |
| 347 | ADIPOQ | Age | HT | VEGF |
| 348 | ADIPOQ | Age | ICAM1 | LEP |
| 349 | ADIPOQ | Age | ICAM1 | POMC |
| 350 | ADIPOQ | Age | IGF1 | IL2RA |
| 351 | ADIPOQ | Age | IGF1 | IL6ST |
| 352 | ADIPOQ | Age | IGF1 | Insulin |
| 353 | ADIPOQ | Age | IGF1 | LEP |
| 354 | ADIPOQ | Age | IGF1 | POMC |
| 355 | ADIPOQ | Age | IGF1 | Sex |
| 356 | ADIPOQ | Age | IGF1 | VCAM1 |
| 357 | ADIPOQ | Age | IGF1 | VEGF |
| 358 | ADIPOQ | Age | IGFBP1 | LEP |
| 359 | ADIPOQ | Age | IGFBP1 | POMC |

FIG. 15F

| 4-Panel | Marker 1 | Marker 2 | Marker 3 | Marker 4 |
|---|---|---|---|---|
| 360 | ADIPOQ | Age | IGFBP3 | LEP |
| 361 | ADIPOQ | Age | IGFBP3 | POMC |
| 362 | ADIPOQ | Age | IL18 | IL6ST |
| 363 | ADIPOQ | Age | IL18 | LEP |
| 364 | ADIPOQ | Age | IL18 | POMC |
| 365 | ADIPOQ | Age | IL18 | VEGF |
| 366 | ADIPOQ | Age | IL2RA | LEP |
| 367 | ADIPOQ | Age | IL2RA | POMC |
| 368 | ADIPOQ | Age | IL6R | IL6ST |
| 369 | ADIPOQ | Age | IL6R | LEP |
| 370 | ADIPOQ | Age | IL6R | POMC |
| 371 | ADIPOQ | Age | IL6ST | LEP |
| 372 | ADIPOQ | Age | IL6ST | POMC |
| 373 | ADIPOQ | Age | IL6ST | Sex |
| 374 | ADIPOQ | Age | IL6ST | TNFRSF1B |
| 375 | ADIPOQ | Age | IL6ST | VEGF |
| 376 | ADIPOQ | Age | IL8 | LEP |
| 377 | ADIPOQ | Age | IL8 | POMC |
| 378 | ADIPOQ | Age | IL8 | VEGF |
| 379 | ADIPOQ | Age | INHBA | LEP |
| 380 | ADIPOQ | Age | INHBA | POMC |
| 381 | ADIPOQ | Age | Ins120 | Insulin |
| 382 | ADIPOQ | Age | Ins120 | LEP |
| 383 | ADIPOQ | Age | Ins120 | POMC |
| 384 | ADIPOQ | Age | Insulin | LEP |
| 385 | ADIPOQ | Age | Insulin | POMC |
| 386 | ADIPOQ | Age | Insulin | Sex |
| 387 | ADIPOQ | Age | Insulin | VEGF |
| 388 | ADIPOQ | Age | LDL | LEP |
| 389 | ADIPOQ | Age | LDL | POMC |
| 390 | ADIPOQ | Age | LEP | PLAT |
| 391 | ADIPOQ | Age | LEP | POMC |
| 392 | ADIPOQ | Age | LEP | SBP |
| 393 | ADIPOQ | Age | LEP | SELE |
| 394 | ADIPOQ | Age | LEP | SELP |
| 395 | ADIPOQ | Age | LEP | Sex |
| 396 | ADIPOQ | Age | LEP | SHBG |
| 397 | ADIPOQ | Age | LEP | TNFRSF1B |
| 398 | ADIPOQ | Age | LEP | TRIG |
| 399 | ADIPOQ | Age | LEP | VCAM1 |
| 400 | ADIPOQ | Age | LEP | VEGF |
| 401 | ADIPOQ | Age | LEP | VWF |
| 402 | ADIPOQ | Age | LEP | Waist |
| 403 | ADIPOQ | Age | LEP | WT |
| 404 | ADIPOQ | Age | PLAT | POMC |
| 405 | ADIPOQ | Age | POMC | SBP |
| 406 | ADIPOQ | Age | POMC | SCp |
| 407 | ADIPOQ | Age | POMC | SELE |
| 408 | ADIPOQ | Age | POMC | SELP |
| 409 | ADIPOQ | Age | POMC | Sex |
| 410 | ADIPOQ | Age | POMC | SHBG |
| 411 | ADIPOQ | Age | POMC | TNFRSF1B |
| 412 | ADIPOQ | Age | POMC | TRIG |
| 413 | ADIPOQ | Age | POMC | VCAM1 |
| 414 | ADIPOQ | Age | POMC | VEGF |
| 415 | ADIPOQ | Age | POMC | VWF |
| 416 | ADIPOQ | Age | POMC | Waist |
| 417 | ADIPOQ | Age | POMC | WT |
| 418 | ADIPOQ | Age | Sex | VEGF |
| 419 | ADIPOQ | Age | Sex | WT |

FIG. 15G

| 4-Panel | Marker 1 | Marker 2 | Marker 3 | Marker 4 |
|---|---|---|---|---|
| 420 | ADIPOQ | Age | VCAM1 | VEGF |
| 421 | ADIPOQ | Age | VEGF | VWF |
| 422 | ADIPOQ | BMI | HDLC | POMC |
| 423 | ADIPOQ | HDLC | IGF1 | POMC |
| 424 | ADIPOQ | HDLC | IL18 | POMC |
| 425 | ADIPOQ | HDLC | IL6ST | POMC |
| 426 | ADIPOQ | HDLC | Insulin | POMC |
| 427 | ADIPOQ | HDLC | POMC | VEGF |
| 428 | ADIPOQ | IGF1 | POMC | Sex |
| 429 | ADIPOQ | IGF1 | POMC | VEGF |
| 430 | ADIPOQ | IL6ST | POMC | VEGF |
| 431 | ADIPOQ | POMC | Sex | VEGF |
| 432 | ADIPOQ | POMC | VCAM1 | VEGF |
| 433 | Age | AGER | AHSG | LEP |
| 434 | Age | AGER | AHSG | POMC |
| 435 | Age | AGER | AHSG | Sex |
| 436 | Age | AGER | ANG | BMI |
| 437 | Age | AGER | ANG | CCL2 |
| 438 | Age | AGER | ANG | CD40 |
| 439 | Age | AGER | ANG | Glucose |
| 440 | Age | AGER | ANG | HDLC |
| 441 | Age | AGER | ANG | IGF1 |
| 442 | Age | AGER | ANG | IL6ST |
| 443 | Age | AGER | ANG | Insulin |
| 444 | Age | AGER | ANG | LEP |
| 445 | Age | AGER | ANG | POMC |
| 446 | Age | AGER | ANG | Sex |
| 447 | Age | AGER | ANG | VEGF |
| 448 | Age | AGER | APOA1 | HDLC |
| 449 | Age | AGER | APOA1 | IGF1 |

| 4-Panel | Marker 1 | Marker 2 | Marker 3 | Marker 4 |
|---|---|---|---|---|
| 450 | Age | AGER | APOA1 | LEP |
| 451 | Age | AGER | APOA1 | POMC |
| 452 | Age | AGER | APOA1 | Sex |
| 453 | Age | AGER | APOA1 | VEGF |
| 454 | Age | AGER | APOE | LEP |
| 455 | Age | AGER | APOE | POMC |
| 456 | Age | AGER | BAX | LEP |
| 457 | Age | AGER | BAX | POMC |
| 458 | Age | AGER | BMI | CCL2 |
| 459 | Age | AGER | BMI | CD40 |
| 460 | Age | AGER | BMI | CRP |
| 461 | Age | AGER | BMI | DPP4 |
| 462 | Age | AGER | BMI | HDLC |
| 463 | Age | AGER | BMI | IGF1 |
| 464 | Age | AGER | BMI | IL6ST |
| 465 | Age | AGER | BMI | Ins120 |
| 466 | Age | AGER | BMI | LEP |
| 467 | Age | AGER | BMI | POMC |
| 468 | Age | AGER | BMI | Sex |
| 469 | Age | AGER | BMI | VEGF |
| 470 | Age | AGER | BMI | Waist |
| 471 | Age | AGER | C3 | LEP |
| 472 | Age | AGER | C3 | POMC |
| 473 | Age | AGER | C3 | Sex |
| 474 | Age | AGER | CCL2 | CD40 |
| 475 | Age | AGER | CCL2 | DPP4 |
| 476 | Age | AGER | CCL2 | HDLC |
| 477 | Age | AGER | CCL2 | HT |
| 478 | Age | AGER | CCL2 | IGF1 |
| 479 | Age | AGER | CCL2 | IL6ST |

FIG. 15H

| 4-Panel | Marker 1 | Marker 2 | Marker 3 | Marker 4 |
|---|---|---|---|---|
| 480 | Age | AGER | CCL2 | LEP |
| 481 | Age | AGER | CCL2 | POMC |
| 482 | Age | AGER | CCL2 | Sex |
| 483 | Age | AGER | CCL2 | VEGF |
| 484 | Age | AGER | CD14 | LEP |
| 485 | Age | AGER | CD14 | POMC |
| 486 | Age | AGER | CD40 | Glucose |
| 487 | Age | AGER | CD40 | HDLC |
| 488 | Age | AGER | CD40 | IGF1 |
| 489 | Age | AGER | CD40 | IL6ST |
| 490 | Age | AGER | CD40 | LEP |
| 491 | Age | AGER | CD40 | POMC |
| 492 | Age | AGER | CD40 | Sex |
| 493 | Age | AGER | CD40 | VEGF |
| 494 | Age | AGER | CDK5 | HDLC |
| 495 | Age | AGER | CDK5 | LEP |
| 496 | Age | AGER | CDK5 | POMC |
| 497 | Age | AGER | CDK5 | Sex |
| 498 | Age | AGER | CHOL | HDLC |
| 499 | Age | AGER | CHOL | LEP |
| 500 | Age | AGER | CHOL | POMC |
| 501 | Age | AGER | CRP | HDLC |
| 502 | Age | AGER | CRP | IL6ST |
| 503 | Age | AGER | CRP | LEP |
| 504 | Age | AGER | CRP | POMC |
| 505 | Age | AGER | CRP | Sex |
| 506 | Age | AGER | DBP | HDLC |
| 507 | Age | AGER | DBP | LEP |
| 508 | Age | AGER | DBP | POMC |
| 509 | Age | AGER | DPP4 | HDLC |
| 510 | Age | AGER | DPP4 | IGF1 |
| 511 | Age | AGER | DPP4 | LEP |
| 512 | Age | AGER | DPP4 | POMC |
| 513 | Age | AGER | DPP4 | Sex |
| 514 | Age | AGER | DPP4 | VEGF |
| 515 | Age | AGER | EGF | HDLC |
| 516 | Age | AGER | EGF | LEP |
| 517 | Age | AGER | EGF | POMC |
| 518 | Age | AGER | ENG | LEP |
| 519 | Age | AGER | ENG | POMC |
| 520 | Age | AGER | FamHX | HDLC |
| 521 | Age | AGER | FamHX | LEP |
| 522 | Age | AGER | FamHX | POMC |
| 523 | Age | AGER | FamHX | Sex |
| 524 | Age | AGER | FGA | LEP |
| 525 | Age | AGER | FGA | POMC |
| 526 | Age | AGER | FTH1 | HDLC |
| 527 | Age | AGER | FTH1 | LEP |
| 528 | Age | AGER | FTH1 | POMC |
| 529 | Age | AGER | FTH1 | Sex |
| 530 | Age | AGER | Gluc120 | LEP |
| 531 | Age | AGER | Gluc120 | POMC |
| 532 | Age | AGER | Gluc120 | Sex |
| 533 | Age | AGER | Glucose | HDLC |
| 534 | Age | AGER | Glucose | IGF1 |
| 535 | Age | AGER | Glucose | IL6ST |
| 536 | Age | AGER | Glucose | LEP |
| 537 | Age | AGER | Glucose | POMC |
| 538 | Age | AGER | Glucose | Sex |
| 539 | Age | AGER | Glucose | VEGF |

FIG. 15I

| 4-Panel | Marker 1 | Marker 2 | Marker 3 | Marker 4 |
|---|---|---|---|---|
| 540 | Age | AGER | HBA1C | LEP |
| 541 | Age | AGER | HBA1C | POMC |
| 542 | Age | AGER | HBA1C | Sex |
| 543 | Age | AGER | HDLC | Hip |
| 544 | Age | AGER | HDLC | HT |
| 545 | Age | AGER | HDLC | IGF1 |
| 546 | Age | AGER | HDLC | IGFBP1 |
| 547 | Age | AGER | HDLC | IL18 |
| 548 | Age | AGER | HDLC | IL2RA |
| 549 | Age | AGER | HDLC | IL6ST |
| 550 | Age | AGER | HDLC | IL8 |
| 551 | Age | AGER | HDLC | INHBA |
| 552 | Age | AGER | HDLC | Insulin |
| 553 | Age | AGER | HDLC | LDL |
| 554 | Age | AGER | HDLC | LEP |
| 555 | Age | AGER | HDLC | POMC |
| 556 | Age | AGER | HDLC | SCp |
| 557 | Age | AGER | HDLC | Sex |
| 558 | Age | AGER | HDLC | TRIG |
| 559 | Age | AGER | HDLC | VCAM1 |
| 560 | Age | AGER | HDLC | VEGF |
| 561 | Age | AGER | HDLC | VWF |
| 562 | Age | AGER | HDLC | Waist |
| 563 | Age | AGER | HDLC | WT |
| 564 | Age | AGER | HGF | LEP |
| 565 | Age | AGER | HGF | POMC |
| 566 | Age | AGER | HGF | Sex |
| 567 | Age | AGER | HGF | IGF1 |
| 568 | Age | AGER | Hip | LEP |
| 569 | Age | AGER | Hip | POMC |

| 4-Panel | Marker 1 | Marker 2 | Marker 3 | Marker 4 |
|---|---|---|---|---|
| 570 | Age | AGER | Hip | Sex |
| 571 | Age | AGER | Hip | VEGF |
| 572 | Age | AGER | HP | LEP |
| 573 | Age | AGER | HP | POMC |
| 574 | Age | AGER | HP | Sex |
| 575 | Age | AGER | HT | IGF1 |
| 576 | Age | AGER | HT | IL6ST |
| 577 | Age | AGER | HT | LEP |
| 578 | Age | AGER | HT | POMC |
| 579 | Age | AGER | HT | VEGF |
| 580 | Age | AGER | ICAM1 | LEP |
| 581 | Age | AGER | ICAM1 | POMC |
| 582 | Age | AGER | IGF1 | IL18 |
| 583 | Age | AGER | IGF1 | IL2RA |
| 584 | Age | AGER | IGF1 | IL6ST |
| 585 | Age | AGER | IGF1 | Insulin |
| 586 | Age | AGER | IGF1 | LEP |
| 587 | Age | AGER | IGF1 | POMC |
| 588 | Age | AGER | IGF1 | Sex |
| 589 | Age | AGER | IGF1 | VCAM1 |
| 590 | Age | AGER | IGF1 | VEGF |
| 591 | Age | AGER | IGFBP1 | LEP |
| 592 | Age | AGER | IGFBP1 | POMC |
| 593 | Age | AGER | IGFBP1 | Sex |
| 594 | Age | AGER | IGFBP3 | LEP |
| 595 | Age | AGER | IGFBP3 | POMC |
| 596 | Age | AGER | IGFBP3 | Sex |
| 597 | Age | AGER | IL18 | IL6ST |
| 598 | Age | AGER | IL18 | LEP |
| 599 | Age | AGER | IL18 | POMC |

| 4-Panel | Marker 1 | Marker 2 | Marker 3 | Marker 4 |
|---|---|---|---|---|
| 600 | Age | AGER | IL18 | Sex |
| 601 | Age | AGER | IL18 | VEGF |
| 602 | Age | AGER | IL2RA | LEP |
| 603 | Age | AGER | IL2RA | POMC |
| 604 | Age | AGER | IL2RA | Sex |
| 605 | Age | AGER | IL6R | LEP |
| 606 | Age | AGER | IL6R | POMC |
| 607 | Age | AGER | IL6R | Sex |
| 608 | Age | AGER | IL6ST | LEP |
| 609 | Age | AGER | IL6ST | POMC |
| 610 | Age | AGER | IL6ST | Sex |
| 611 | Age | AGER | IL6ST | TNFRSF1B |
| 612 | Age | AGER | IL6ST | VEGF |
| 613 | Age | AGER | IL8 | LEP |
| 614 | Age | AGER | IL8 | POMC |
| 615 | Age | AGER | IL8 | Sex |
| 616 | Age | AGER | IL8 | VEGF |
| 617 | Age | AGER | INHBA | LEP |
| 618 | Age | AGER | INHBA | POMC |
| 619 | Age | AGER | INHBA | Sex |
| 620 | Age | AGER | Ins120 | Insulin |
| 621 | Age | AGER | Ins120 | LEP |
| 622 | Age | AGER | Ins120 | POMC |
| 623 | Age | AGER | Insulin | LEP |
| 624 | Age | AGER | Insulin | POMC |
| 625 | Age | AGER | Insulin | Sex |
| 626 | Age | AGER | Insulin | VEGF |
| 627 | Age | AGER | LDL | LEP |
| 628 | Age | AGER | LDL | POMC |
| 629 | Age | AGER | LEP | PLAT |
| 630 | Age | AGER | LEP | POMC |
| 631 | Age | AGER | LEP | SBP |
| 632 | Age | AGER | LEP | SCp |
| 633 | Age | AGER | LEP | SELE |
| 634 | Age | AGER | LEP | SELP |
| 635 | Age | AGER | LEP | Sex |
| 636 | Age | AGER | LEP | SHBG |
| 637 | Age | AGER | LEP | TNFRSF1B |
| 638 | Age | AGER | LEP | TRIG |
| 639 | Age | AGER | LEP | VCAM1 |
| 640 | Age | AGER | LEP | VEGF |
| 641 | Age | AGER | LEP | VWF |
| 642 | Age | AGER | LEP | Waist |
| 643 | Age | AGER | LEP | WT |
| 644 | Age | AGER | PLAT | POMC |
| 645 | Age | AGER | PLAT | Sex |
| 646 | Age | AGER | POMC | SBP |
| 647 | Age | AGER | POMC | SCp |
| 648 | Age | AGER | POMC | SELE |
| 649 | Age | AGER | POMC | SELP |
| 650 | Age | AGER | POMC | Sex |
| 651 | Age | AGER | POMC | SHBG |
| 652 | Age | AGER | POMC | TNFRSF1B |
| 653 | Age | AGER | POMC | TRIG |
| 654 | Age | AGER | POMC | VCAM1 |
| 655 | Age | AGER | POMC | VEGF |
| 656 | Age | AGER | POMC | VWF |
| 657 | Age | AGER | POMC | Waist |
| 658 | Age | AGER | POMC | WT |
| 659 | Age | AGER | SCp | Sex |

FIG. 15L

| 4-Panel | Marker 1 | Marker 2 | Marker 3 | Marker 4 |
|---|---|---|---|---|
| 660 | Age | AGER | SELE | Sex |
| 661 | Age | AGER | SELP | Sex |
| 662 | Age | AGER | SELP | VEGF |
| 663 | Age | AGER | Sex | TRIG |
| 664 | Age | AGER | Sex | VCAM1 |
| 665 | Age | AGER | Sex | VEGF |
| 666 | Age | AGER | Sex | Waist |
| 667 | Age | AGER | Sex | WT |
| 668 | Age | AGER | VCAM1 | VEGF |
| 669 | Age | AHSG | ANG | CCL2 |
| 670 | Age | AHSG | ANG | HDLC |
| 671 | Age | AHSG | ANG | LEP |
| 672 | Age | AHSG | ANG | POMC |
| 673 | Age | AHSG | ANG | VEGF |
| 674 | Age | AHSG | APOA1 | HDLC |
| 675 | Age | AHSG | APOA1 | IGF1 |
| 676 | Age | AHSG | APOA1 | LEP |
| 677 | Age | AHSG | APOA1 | POMC |
| 678 | Age | AHSG | APOA1 | Sex |
| 679 | Age | AHSG | APOA1 | VEGF |
| 680 | Age | AHSG | APOE | LEP |
| 681 | Age | AHSG | APOE | POMC |
| 682 | Age | AHSG | BAX | LEP |
| 683 | Age | AHSG | BAX | POMC |
| 684 | Age | AHSG | BMI | CCL2 |
| 685 | Age | AHSG | BMI | CRP |
| 686 | Age | AHSG | BMI | HDLC |
| 687 | Age | AHSG | BMI | IGF1 |
| 688 | Age | AHSG | BMI | IL6ST |
| 689 | Age | AHSG | BMI | LEP |

| 4-Panel | Marker 1 | Marker 2 | Marker 3 | Marker 4 |
|---|---|---|---|---|
| 690 | Age | AHSG | BMI | POMC |
| 691 | Age | AHSG | BMI | Sex |
| 692 | Age | AHSG | BMI | VEGF |
| 693 | Age | AHSG | BMI | Waist |
| 694 | Age | AHSG | C3 | LEP |
| 695 | Age | AHSG | C3 | POMC |
| 696 | Age | AHSG | C3 | CD40 |
| 697 | Age | AHSG | CCL2 | Glucose |
| 698 | Age | AHSG | CCL2 | HDLC |
| 699 | Age | AHSG | CCL2 | HT |
| 700 | Age | AHSG | CCL2 | IGF1 |
| 701 | Age | AHSG | CCL2 | IL6ST |
| 702 | Age | AHSG | CCL2 | LEP |
| 703 | Age | AHSG | CCL2 | POMC |
| 704 | Age | AHSG | CCL2 | Sex |
| 705 | Age | AHSG | CCL2 | VEGF |
| 706 | Age | AHSG | CD14 | LEP |
| 707 | Age | AHSG | CD14 | POMC |
| 708 | Age | AHSG | CD14 | Glucose |
| 709 | Age | AHSG | CD40 | HDLC |
| 710 | Age | AHSG | CD40 | IGF1 |
| 711 | Age | AHSG | CD40 | IL6ST |
| 712 | Age | AHSG | CD40 | LEP |
| 713 | Age | AHSG | CD40 | POMC |
| 714 | Age | AHSG | CD40 | Sex |
| 715 | Age | AHSG | CD40 | VEGF |
| 716 | Age | AHSG | CDK5 | LEP |
| 717 | Age | AHSG | CDK5 | POMC |
| 718 | Age | AHSG | CHOL | LEP |
| 719 | Age | AHSG | CHOL | POMC |

FIG. 15M

| 4-Panel | Marker 1 | Marker 2 | Marker 3 | Marker 4 |
|---|---|---|---|---|
| 720 | Age | AHSG | CRP | LEP |
| 721 | Age | AHSG | CRP | POMC |
| 722 | Age | AHSG | CRP | Sex |
| 723 | Age | AHSG | DBP | LEP |
| 724 | Age | AHSG | DBP | POMC |
| 725 | Age | AHSG | DPP4 | HDLC |
| 726 | Age | AHSG | DPP4 | IGF1 |
| 727 | Age | AHSG | DPP4 | LEP |
| 728 | Age | AHSG | DPP4 | POMC |
| 729 | Age | AHSG | DPP4 | VEGF |
| 730 | Age | AHSG | EGF | LEP |
| 731 | Age | AHSG | EGF | POMC |
| 732 | Age | AHSG | ENG | LEP |
| 733 | Age | AHSG | ENG | POMC |
| 734 | Age | AHSG | FamHX | LEP |
| 735 | Age | AHSG | FamHX | POMC |
| 736 | Age | AHSG | FGA | LEP |
| 737 | Age | AHSG | FGA | POMC |
| 738 | Age | AHSG | FTH1 | HDLC |
| 739 | Age | AHSG | FTH1 | LEP |
| 740 | Age | AHSG | FTH1 | POMC |
| 741 | Age | AHSG | FTH1 | Sex |
| 742 | Age | AHSG | Gluc120 | LEP |
| 743 | Age | AHSG | Gluc120 | POMC |
| 744 | Age | AHSG | Glucose | HDLC |
| 745 | Age | AHSG | Glucose | IGF1 |
| 746 | Age | AHSG | Glucose | IL6ST |
| 747 | Age | AHSG | Glucose | LEP |
| 748 | Age | AHSG | Glucose | POMC |
| 749 | Age | AHSG | Glucose | Sex |
| 750 | Age | AHSG | Glucose | VEGF |
| 751 | Age | AHSG | HBA1C | LEP |
| 752 | Age | AHSG | HBA1C | POMC |
| 753 | Age | AHSG | HDLC | Hip |
| 754 | Age | AHSG | HDLC | IGF1 |
| 755 | Age | AHSG | HDLC | IGFBP1 |
| 756 | Age | AHSG | HDLC | IL18 |
| 757 | Age | AHSG | HDLC | IL2RA |
| 758 | Age | AHSG | HDLC | IL6ST |
| 759 | Age | AHSG | HDLC | Insulin |
| 760 | Age | AHSG | HDLC | LEP |
| 761 | Age | AHSG | HDLC | POMC |
| 762 | Age | AHSG | HDLC | SCp |
| 763 | Age | AHSG | HDLC | Sex |
| 764 | Age | AHSG | HDLC | TRIG |
| 765 | Age | AHSG | HDLC | VCAM1 |
| 766 | Age | AHSG | HDLC | VEGF |
| 767 | Age | AHSG | HDLC | VWF |
| 768 | Age | AHSG | HDLC | Waist |
| 769 | Age | AHSG | HDLC | WT |
| 770 | Age | AHSG | HGF | LEP |
| 771 | Age | AHSG | HGF | POMC |
| 772 | Age | AHSG | Hip | IGF1 |
| 773 | Age | AHSG | Hip | LEP |
| 774 | Age | AHSG | Hip | POMC |
| 775 | Age | AHSG | HP | POMC |
| 776 | Age | AHSG | HT | IGF1 |
| 777 | Age | AHSG | HT | LEP |
| 778 | Age | AHSG | HT | POMC |
| 779 | Age | AHSG | HT | VEGF |

| 4-Panel | Marker 1 | Marker 2 | Marker 3 | Marker 4 |
|---|---|---|---|---|
| 780 | Age | AHSG | ICAM1 | LEP |
| 781 | Age | AHSG | ICAM1 | POMC |
| 782 | Age | AHSG | IGF1 | IL2RA |
| 783 | Age | AHSG | IGF1 | IL6ST |
| 784 | Age | AHSG | IGF1 | LEP |
| 785 | Age | AHSG | IGF1 | POMC |
| 786 | Age | AHSG | IGF1 | Sex |
| 787 | Age | AHSG | IGF1 | VCAM1 |
| 788 | Age | AHSG | IGF1 | VEGF |
| 789 | Age | AHSG | IGFBP1 | LEP |
| 790 | Age | AHSG | IGFBP1 | POMC |
| 791 | Age | AHSG | IGFBP3 | LEP |
| 792 | Age | AHSG | IGFBP3 | POMC |
| 793 | Age | AHSG | IL18 | LEP |
| 794 | Age | AHSG | IL18 | POMC |
| 795 | Age | AHSG | IL18 | VEGF |
| 796 | Age | AHSG | IL2RA | LEP |
| 797 | Age | AHSG | IL2RA | POMC |
| 798 | Age | AHSG | IL2RA | Sex |
| 799 | Age | AHSG | IL6R | LEP |
| 800 | Age | AHSG | IL6R | POMC |
| 801 | Age | AHSG | IL6ST | LEP |
| 802 | Age | AHSG | IL6ST | POMC |
| 803 | Age | AHSG | IL6ST | Sex |
| 804 | Age | AHSG | IL6ST | TNFRSF1B |
| 805 | Age | AHSG | IL6ST | VEGF |
| 806 | Age | AHSG | IL8 | LEP |
| 807 | Age | AHSG | IL8 | POMC |
| 808 | Age | AHSG | INHBA | LEP |
| 809 | Age | AHSG | INHBA | POMC |
| 810 | Age | AHSG | Ins120 | Insulin |
| 811 | Age | AHSG | Ins120 | LEP |
| 812 | Age | AHSG | Ins120 | POMC |
| 813 | Age | AHSG | Insulin | LEP |
| 814 | Age | AHSG | Insulin | POMC |
| 815 | Age | AHSG | Insulin | Sex |
| 816 | Age | AHSG | Insulin | VEGF |
| 817 | Age | AHSG | LDL | LEP |
| 818 | Age | AHSG | LDL | POMC |
| 819 | Age | AHSG | LEP | PLAT |
| 820 | Age | AHSG | LEP | POMC |
| 821 | Age | AHSG | LEP | SBP |
| 822 | Age | AHSG | LEP | SCp |
| 823 | Age | AHSG | LEP | SELE |
| 824 | Age | AHSG | LEP | SELP |
| 825 | Age | AHSG | LEP | Sex |
| 826 | Age | AHSG | LEP | SHBG |
| 827 | Age | AHSG | LEP | TNFRSF1B |
| 828 | Age | AHSG | LEP | TRIG |
| 829 | Age | AHSG | LEP | VCAM1 |
| 830 | Age | AHSG | LEP | VEGF |
| 831 | Age | AHSG | LEP | VWF |
| 832 | Age | AHSG | LEP | Waist |
| 833 | Age | AHSG | LEP | WT |
| 834 | Age | AHSG | PLAT | POMC |
| 835 | Age | AHSG | POMC | SBP |
| 836 | Age | AHSG | POMC | SCp |
| 837 | Age | AHSG | POMC | SELE |
| 838 | Age | AHSG | POMC | SELP |
| 839 | Age | AHSG | POMC | Sex |

FIG. 15N

| 4-Panel | Marker 1 | Marker 2 | Marker 3 | Marker 4 |
|---|---|---|---|---|
| 840 | Age | AHSG | POMC | SHBG |
| 841 | Age | AHSG | POMC | TNFRSF1B |
| 842 | Age | AHSG | POMC | TRIG |
| 843 | Age | AHSG | POMC | VCAM1 |
| 844 | Age | AHSG | POMC | VEGF |
| 845 | Age | AHSG | POMC | VWF |
| 846 | Age | AHSG | POMC | Waist |
| 847 | Age | AHSG | POMC | WT |
| 848 | Age | AHSG | Sex | VEGF |
| 849 | Age | AHSG | Sex | Waist |
| 850 | Age | AHSG | Sex | WT |
| 851 | Age | ANG | APOA1 | BMI |
| 852 | Age | ANG | APOA1 | CCL2 |
| 853 | Age | ANG | APOA1 | Glucose |
| 854 | Age | ANG | APOA1 | HDLC |
| 855 | Age | ANG | APOA1 | IGF1 |
| 856 | Age | ANG | APOA1 | IL6ST |
| 857 | Age | ANG | APOA1 | LEP |
| 858 | Age | ANG | APOA1 | POMC |
| 859 | Age | ANG | APOA1 | Sex |
| 860 | Age | ANG | APOA1 | VEGF |
| 861 | Age | ANG | APOE | BMI |
| 862 | Age | ANG | APOE | CCL2 |
| 863 | Age | ANG | APOE | HDLC |
| 864 | Age | ANG | APOE | IGF1 |
| 865 | Age | ANG | APOE | LEP |
| 866 | Age | ANG | APOE | POMC |
| 867 | Age | ANG | APOE | VEGF |
| 868 | Age | ANG | BAX | CCL2 |
| 869 | Age | ANG | BAX | IL6ST |

| 4-Panel | Marker 1 | Marker 2 | Marker 3 | Marker 4 |
|---|---|---|---|---|
| 870 | Age | ANG | BAX | LEP |
| 871 | Age | ANG | BAX | POMC |
| 872 | Age | ANG | BMI | CCL2 |
| 873 | Age | ANG | BMI | CD14 |
| 874 | Age | ANG | BMI | CD40 |
| 875 | Age | ANG | BMI | CHOL |
| 876 | Age | ANG | BMI | CRP |
| 877 | Age | ANG | BMI | DPP4 |
| 878 | Age | ANG | BMI | EGF |
| 879 | Age | ANG | BMI | ENG |
| 880 | Age | ANG | BMI | FamHX |
| 881 | Age | ANG | BMI | FGA |
| 882 | Age | ANG | BMI | FTH1 |
| 883 | Age | ANG | BMI | Gluc120 |
| 884 | Age | ANG | BMI | Glucose |
| 885 | Age | ANG | BMI | HBA1C |
| 886 | Age | ANG | BMI | HDLC |
| 887 | Age | ANG | BMI | HGF |
| 888 | Age | ANG | BMI | Hip |
| 889 | Age | ANG | BMI | HT |
| 890 | Age | ANG | BMI | ICAM1 |
| 891 | Age | ANG | BMI | IGF1 |
| 892 | Age | ANG | BMI | IL18 |
| 893 | Age | ANG | BMI | IL2RA |
| 894 | Age | ANG | BMI | IL6ST |
| 895 | Age | ANG | BMI | IL8 |
| 896 | Age | ANG | BMI | INHBA |
| 897 | Age | ANG | BMI | Ins120 |
| 898 | Age | ANG | BMI | Insulin |
| 899 | Age | ANG | BMI | LDL |

FIG. 150

| 4-Panel | Marker 1 | Marker 2 | Marker 3 | Marker 4 |
|---|---|---|---|---|
| 900 | Age | ANG | BMI | LEP |
| 901 | Age | ANG | BMI | POMC |
| 902 | Age | ANG | BMI | SCp |
| 903 | Age | ANG | BMI | SELE |
| 904 | Age | ANG | BMI | SELP |
| 905 | Age | ANG | BMI | Sex |
| 906 | Age | ANG | BMI | SHBG |
| 907 | Age | ANG | BMI | TRIG |
| 908 | Age | ANG | BMI | VEGF |
| 909 | Age | ANG | BMI | vWF |
| 910 | Age | ANG | BMI | Waist |
| 911 | Age | ANG | BMI | WT |
| 912 | Age | ANG | C3 | CCL2 |
| 913 | Age | ANG | C3 | HDLC |
| 914 | Age | ANG | C3 | POMC |
| 915 | Age | ANG | C3 | VEGF |
| 916 | Age | ANG | CCL2 | CD14 |
| 917 | Age | ANG | CCL2 | CD40 |
| 918 | Age | ANG | CCL2 | CDK5 |
| 919 | Age | ANG | CCL2 | CHOL |
| 920 | Age | ANG | CCL2 | CRP |
| 921 | Age | ANG | CCL2 | DBP |
| 922 | Age | ANG | CCL2 | DPP4 |
| 923 | Age | ANG | CCL2 | EGF |
| 924 | Age | ANG | CCL2 | ENG |
| 925 | Age | ANG | CCL2 | FamHX |
| 926 | Age | ANG | CCL2 | FGA |
| 927 | Age | ANG | CCL2 | FTH1 |
| 928 | Age | ANG | CCL2 | Gluc120 |
| 929 | Age | ANG | CCL2 | Glucose |
| 930 | Age | ANG | CCL2 | HBA1C |
| 931 | Age | ANG | CCL2 | HDLC |
| 932 | Age | ANG | CCL2 | HGF |
| 933 | Age | ANG | CCL2 | Hip |
| 934 | Age | ANG | CCL2 | HP |
| 935 | Age | ANG | CCL2 | HT |
| 936 | Age | ANG | CCL2 | ICAM1 |
| 937 | Age | ANG | CCL2 | IGF1 |
| 938 | Age | ANG | CCL2 | IGFBP1 |
| 939 | Age | ANG | CCL2 | IGFBP3 |
| 940 | Age | ANG | CCL2 | IL18 |
| 941 | Age | ANG | CCL2 | IL2RA |
| 942 | Age | ANG | CCL2 | IL6R |
| 943 | Age | ANG | CCL2 | IL6ST |
| 944 | Age | ANG | CCL2 | IL8 |
| 945 | Age | ANG | CCL2 | INHBA |
| 946 | Age | ANG | CCL2 | Ins120 |
| 947 | Age | ANG | CCL2 | Insulin |
| 948 | Age | ANG | CCL2 | LDL |
| 949 | Age | ANG | CCL2 | LEP |
| 950 | Age | ANG | CCL2 | PLAT |
| 951 | Age | ANG | CCL2 | POMC |
| 952 | Age | ANG | CCL2 | SBP |
| 953 | Age | ANG | CCL2 | SCp |
| 954 | Age | ANG | CCL2 | SELE |
| 955 | Age | ANG | CCL2 | SELP |
| 956 | Age | ANG | CCL2 | Sex |
| 957 | Age | ANG | CCL2 | SHBG |
| 958 | Age | ANG | CCL2 | TNFRSF1B |
| 959 | Age | ANG | CCL2 | TRIG |

FIG. 15P

| 4-Panel | Marker 1 | Marker 2 | Marker 3 | Marker 4 |
|---|---|---|---|---|
| 960 | Age | ANG | CCL2 | VCAM1 |
| 961 | Age | ANG | CCL2 | VEGF |
| 962 | Age | ANG | CCL2 | VWF |
| 963 | Age | ANG | CCL2 | Waist |
| 964 | Age | ANG | CCL2 | WT |
| 965 | Age | ANG | CD14 | HDLC |
| 966 | Age | ANG | CD14 | IL6ST |
| 967 | Age | ANG | CD14 | LEP |
| 968 | Age | ANG | CD14 | POMC |
| 969 | Age | ANG | CD14 | VEGF |
| 970 | Age | ANG | CD40 | DPP4 |
| 971 | Age | ANG | CD40 | Glucose |
| 972 | Age | ANG | CD40 | HDLC |
| 973 | Age | ANG | CD40 | HT |
| 974 | Age | ANG | CD40 | IGF1 |
| 975 | Age | ANG | CD40 | IL2RA |
| 976 | Age | ANG | CD40 | IL6ST |
| 977 | Age | ANG | CD40 | INHBA |
| 978 | Age | ANG | CD40 | Insulin |
| 979 | Age | ANG | CD40 | LEP |
| 980 | Age | ANG | CD40 | POMC |
| 981 | Age | ANG | CD40 | Sex |
| 982 | Age | ANG | CD40 | VEGF |
| 983 | Age | ANG | CDK5 | HDLC |
| 984 | Age | ANG | CDK5 | LEP |
| 985 | Age | ANG | CDK5 | POMC |
| 986 | Age | ANG | CDK5 | VEGF |
| 987 | Age | ANG | CHOL | Glucose |
| 988 | Age | ANG | CHOL | HDLC |
| 989 | Age | ANG | CHOL | IGF1 |
| 990 | Age | ANG | CHOL | IL6ST |
| 991 | Age | ANG | CHOL | Insulin |
| 992 | Age | ANG | CHOL | LEP |
| 993 | Age | ANG | CHOL | POMC |
| 994 | Age | ANG | CHOL | VEGF |
| 995 | Age | ANG | CRP | Glucose |
| 996 | Age | ANG | CRP | HDLC |
| 997 | Age | ANG | CRP | IL6ST |
| 998 | Age | ANG | CRP | Insulin |
| 999 | Age | ANG | CRP | LEP |
| 1000 | Age | ANG | CRP | POMC |
| 1001 | Age | ANG | CRP | Sex |
| 1002 | Age | ANG | CRP | VEGF |
| 1003 | Age | ANG | DBP | Glucose |
| 1004 | Age | ANG | DBP | HDLC |
| 1005 | Age | ANG | DBP | IGF1 |
| 1006 | Age | ANG | DBP | IL6ST |
| 1007 | Age | ANG | DBP | LEP |
| 1008 | Age | ANG | DBP | POMC |
| 1009 | Age | ANG | DBP | Sex |
| 1010 | Age | ANG | DBP | VEGF |
| 1011 | Age | ANG | DPP4 | FTH1 |
| 1012 | Age | ANG | DPP4 | Glucose |
| 1013 | Age | ANG | DPP4 | HDLC |
| 1014 | Age | ANG | DPP4 | IGF1 |
| 1015 | Age | ANG | DPP4 | Insulin |
| 1016 | Age | ANG | DPP4 | LEP |
| 1017 | Age | ANG | DPP4 | POMC |
| 1018 | Age | ANG | DPP4 | Sex |
| 1019 | Age | ANG | DPP4 | VEGF |

FIG. 15Q

| 4-Panel | Marker 1 | Marker 2 | Marker 3 | Marker 4 |
|---|---|---|---|---|
| 1020 | Age | ANG | EGF | Glucose |
| 1021 | Age | ANG | EGF | HDLC |
| 1022 | Age | ANG | EGF | IGF1 |
| 1023 | Age | ANG | EGF | IL6ST |
| 1024 | Age | ANG | EGF | Insulin |
| 1025 | Age | ANG | EGF | LEP |
| 1026 | Age | ANG | EGF | POMC |
| 1027 | Age | ANG | EGF | VEGF |
| 1028 | Age | ANG | ENG | Glucose |
| 1029 | Age | ANG | ENG | HDLC |
| 1030 | Age | ANG | ENG | IGF1 |
| 1031 | Age | ANG | ENG | IL6ST |
| 1032 | Age | ANG | ENG | Insulin |
| 1033 | Age | ANG | ENG | LEP |
| 1034 | Age | ANG | ENG | POMC |
| 1035 | Age | ANG | ENG | VEGF |
| 1036 | Age | ANG | FamHX | Glucose |
| 1037 | Age | ANG | FamHX | HDLC |
| 1038 | Age | ANG | FamHX | IGF1 |
| 1039 | Age | ANG | FamHX | IL6ST |
| 1040 | Age | ANG | FamHX | LEP |
| 1041 | Age | ANG | FamHX | POMC |
| 1042 | Age | ANG | FamHX | VEGF |
| 1043 | Age | ANG | FGA | HDLC |
| 1044 | Age | ANG | FGA | IGF1 |
| 1045 | Age | ANG | FGA | LEP |
| 1046 | Age | ANG | FGA | POMC |
| 1047 | Age | ANG | FGA | VEGF |
| 1048 | Age | ANG | FTH1 | Glucose |
| 1049 | Age | ANG | FTH1 | HDLC |

| 4-Panel | Marker 1 | Marker 2 | Marker 3 | Marker 4 |
|---|---|---|---|---|
| 1050 | Age | ANG | FTH1 | HT |
| 1051 | Age | ANG | FTH1 | IGF1 |
| 1052 | Age | ANG | FTH1 | IL6ST |
| 1053 | Age | ANG | FTH1 | Insulin |
| 1054 | Age | ANG | FTH1 | LEP |
| 1055 | Age | ANG | FTH1 | POMC |
| 1056 | Age | ANG | FTH1 | Sex |
| 1057 | Age | ANG | FTH1 | VEGF |
| 1058 | Age | ANG | Gluc120 | Glucose |
| 1059 | Age | ANG | Gluc120 | HDLC |
| 1060 | Age | ANG | Gluc120 | IGF1 |
| 1061 | Age | ANG | Gluc120 | IL6ST |
| 1062 | Age | ANG | Gluc120 | LEP |
| 1063 | Age | ANG | Gluc120 | POMC |
| 1064 | Age | ANG | Gluc120 | VEGF |
| 1065 | Age | ANG | Glucose | HBA1C |
| 1066 | Age | ANG | Glucose | HDLC |
| 1067 | Age | ANG | Glucose | Hip |
| 1068 | Age | ANG | Glucose | HP |
| 1069 | Age | ANG | Glucose | HT |
| 1070 | Age | ANG | Glucose | IGF1 |
| 1071 | Age | ANG | Glucose | IL18 |
| 1072 | Age | ANG | Glucose | IL2RA |
| 1073 | Age | ANG | Glucose | IL6ST |
| 1074 | Age | ANG | Glucose | IL8 |
| 1075 | Age | ANG | Glucose | INHBA |
| 1076 | Age | ANG | Glucose | Insulin |
| 1077 | Age | ANG | Glucose | LEP |
| 1078 | Age | ANG | Glucose | POMC |
| 1079 | Age | ANG | Glucose | SELP |

FIG. 15R

| 4-Panel | Marker 1 | Marker 2 | Marker 3 | Marker 4 |
|---|---|---|---|---|
| 1080 | Age | ANG | Glucose | Sex |
| 1081 | Age | ANG | Glucose | SHBG |
| 1082 | Age | ANG | Glucose | VEGF |
| 1083 | Age | ANG | HBA1C | HDLC |
| 1084 | Age | ANG | HBA1C | IGF1 |
| 1085 | Age | ANG | HBA1C | IL6ST |
| 1086 | Age | ANG | HBA1C | LEP |
| 1087 | Age | ANG | HBA1C | POMC |
| 1088 | Age | ANG | HBA1C | VEGF |
| 1089 | Age | ANG | HDLC | HGF |
| 1090 | Age | ANG | HDLC | Hip |
| 1091 | Age | ANG | HDLC | HP |
| 1092 | Age | ANG | HDLC | HT |
| 1093 | Age | ANG | HDLC | ICAM1 |
| 1094 | Age | ANG | HDLC | IGF1 |
| 1095 | Age | ANG | HDLC | IGFBP1 |
| 1096 | Age | ANG | HDLC | IGFBP3 |
| 1097 | Age | ANG | HDLC | IL18 |
| 1098 | Age | ANG | HDLC | IL2RA |
| 1099 | Age | ANG | HDLC | IL6R |
| 1100 | Age | ANG | HDLC | IL6ST |
| 1101 | Age | ANG | HDLC | IL8 |
| 1102 | Age | ANG | HDLC | INHBA |
| 1103 | Age | ANG | HDLC | Ins120 |
| 1104 | Age | ANG | HDLC | Insulin |
| 1105 | Age | ANG | HDLC | LDL |
| 1106 | Age | ANG | HDLC | LEP |
| 1107 | Age | ANG | HDLC | PLAT |
| 1108 | Age | ANG | HDLC | POMC |
| 1109 | Age | ANG | HDLC | SBP |

| 4-Panel | Marker 1 | Marker 2 | Marker 3 | Marker 4 |
|---|---|---|---|---|
| 1110 | Age | ANG | HDLC | SCp |
| 1111 | Age | ANG | HDLC | SELE |
| 1112 | Age | ANG | HDLC | SELP |
| 1113 | Age | ANG | HDLC | Sex |
| 1114 | Age | ANG | HDLC | SHBG |
| 1115 | Age | ANG | HDLC | TRIG |
| 1116 | Age | ANG | HDLC | VCAM1 |
| 1117 | Age | ANG | HDLC | VEGF |
| 1118 | Age | ANG | HDLC | VWF |
| 1119 | Age | ANG | HDLC | Waist |
| 1120 | Age | ANG | HDLC | WT |
| 1121 | Age | ANG | HGF | IGF1 |
| 1122 | Age | ANG | HGF | IL6ST |
| 1123 | Age | ANG | HGF | LEP |
| 1124 | Age | ANG | HGF | POMC |
| 1125 | Age | ANG | HGF | VEGF |
| 1126 | Age | ANG | Hip | IGF1 |
| 1127 | Age | ANG | Hip | IL6ST |
| 1128 | Age | ANG | Hip | LEP |
| 1129 | Age | ANG | Hip | POMC |
| 1130 | Age | ANG | Hip | Sex |
| 1131 | Age | ANG | Hip | VEGF |
| 1132 | Age | ANG | HP | IGF1 |
| 1133 | Age | ANG | HP | IL6ST |
| 1134 | Age | ANG | HP | LEP |
| 1135 | Age | ANG | HP | POMC |
| 1136 | Age | ANG | HP | VEGF |
| 1137 | Age | ANG | HT | IGF1 |
| 1138 | Age | ANG | HT | IL6ST |
| 1139 | Age | ANG | HT | Insulin |

FIG. 15S

| 4-Panel | Marker 1 | Marker 2 | Marker 3 | Marker 4 |
|---|---|---|---|---|
| 1140 | Age | ANG | HT | LEP |
| 1141 | Age | ANG | HT | POMC |
| 1142 | Age | ANG | HT | VEGF |
| 1143 | Age | ANG | HT | WT |
| 1144 | Age | ANG | ICAM1 | IGF1 |
| 1145 | Age | ANG | ICAM1 | IL6ST |
| 1146 | Age | ANG | ICAM1 | LEP |
| 1147 | Age | ANG | ICAM1 | POMC |
| 1148 | Age | ANG | ICAM1 | VEGF |
| 1149 | Age | ANG | IGF1 | IGFBP1 |
| 1150 | Age | ANG | IGF1 | IL18 |
| 1151 | Age | ANG | IGF1 | IL2RA |
| 1152 | Age | ANG | IGF1 | IL6ST |
| 1153 | Age | ANG | IGF1 | IL8 |
| 1154 | Age | ANG | IGF1 | INHBA |
| 1155 | Age | ANG | IGF1 | Insulin |
| 1156 | Age | ANG | IGF1 | LEP |
| 1157 | Age | ANG | IGF1 | PLAT |
| 1158 | Age | ANG | IGF1 | POMC |
| 1159 | Age | ANG | IGF1 | SBP |
| 1160 | Age | ANG | IGF1 | SELE |
| 1161 | Age | ANG | IGF1 | SELP |
| 1162 | Age | ANG | IGF1 | Sex |
| 1163 | Age | ANG | IGF1 | SHBG |
| 1164 | Age | ANG | IGF1 | TRIG |
| 1165 | Age | ANG | IGF1 | VCAM1 |
| 1166 | Age | ANG | IGF1 | VEGF |
| 1167 | Age | ANG | IGF1 | VWF |
| 1168 | Age | ANG | IGF1 | Waist |
| 1169 | Age | ANG | IGF1 | WT |

| 4-Panel | Marker 1 | Marker 2 | Marker 3 | Marker 4 |
|---|---|---|---|---|
| 1170 | Age | ANG | IGFBP1 | LEP |
| 1171 | Age | ANG | IGFBP1 | POMC |
| 1172 | Age | ANG | IGFBP1 | Sex |
| 1173 | Age | ANG | IGFBP1 | VEGF |
| 1174 | Age | ANG | IGFBP3 | IL6ST |
| 1175 | Age | ANG | IGFBP3 | LEP |
| 1176 | Age | ANG | IGFBP3 | POMC |
| 1177 | Age | ANG | IGFBP3 | VEGF |
| 1178 | Age | ANG | IL18 | IL6ST |
| 1179 | Age | ANG | IL18 | Insulin |
| 1180 | Age | ANG | IL18 | LEP |
| 1181 | Age | ANG | IL18 | POMC |
| 1182 | Age | ANG | IL18 | Sex |
| 1183 | Age | ANG | IL18 | VEGF |
| 1184 | Age | ANG | IL2RA | IL6ST |
| 1185 | Age | ANG | IL2RA | Insulin |
| 1186 | Age | ANG | IL2RA | LEP |
| 1187 | Age | ANG | IL2RA | POMC |
| 1188 | Age | ANG | IL2RA | Sex |
| 1189 | Age | ANG | IL2RA | VEGF |
| 1190 | Age | ANG | IL6R | IL6ST |
| 1191 | Age | ANG | IL6R | LEP |
| 1192 | Age | ANG | IL6R | POMC |
| 1193 | Age | ANG | IL6R | VEGF |
| 1194 | Age | ANG | IL6ST | IL8 |
| 1195 | Age | ANG | IL6ST | INHBA |
| 1196 | Age | ANG | IL6ST | Ins120 |
| 1197 | Age | ANG | IL6ST | Insulin |
| 1198 | Age | ANG | IL6ST | LDL |
| 1199 | Age | ANG | IL6ST | LEP |

| 4-Panel | Marker 1 | Marker 2 | Marker 3 | Marker 4 |
|---|---|---|---|---|
| 1200 | Age | ANG | IL6ST | POMC |
| 1201 | Age | ANG | IL6ST | SBP |
| 1202 | Age | ANG | IL6ST | SCp |
| 1203 | Age | ANG | IL6ST | SELP |
| 1204 | Age | ANG | IL6ST | Sex |
| 1205 | Age | ANG | IL6ST | SHBG |
| 1206 | Age | ANG | IL6ST | TNFRSF1B |
| 1207 | Age | ANG | IL6ST | VEGF |
| 1208 | Age | ANG | IL6ST | VWF |
| 1209 | Age | ANG | IL6ST | WT |
| 1210 | Age | ANG | IL8 | LEP |
| 1211 | Age | ANG | IL8 | POMC |
| 1212 | Age | ANG | IL8 | Sex |
| 1213 | Age | ANG | IL8 | VEGF |
| 1214 | Age | ANG | INHBA | Insulin |
| 1215 | Age | ANG | INHBA | LEP |
| 1216 | Age | ANG | INHBA | POMC |
| 1217 | Age | ANG | INHBA | Sex |
| 1218 | Age | ANG | INHBA | VEGF |
| 1219 | Age | ANG | Ins120 | Insulin |
| 1220 | Age | ANG | Ins120 | LEP |
| 1221 | Age | ANG | Ins120 | POMC |
| 1222 | Age | ANG | Ins120 | VEGF |
| 1223 | Age | ANG | Insulin | LEP |
| 1224 | Age | ANG | Insulin | POMC |
| 1225 | Age | ANG | Insulin | SCp |
| 1226 | Age | ANG | Insulin | Sex |
| 1227 | Age | ANG | Insulin | SHBG |
| 1228 | Age | ANG | Insulin | TRIG |
| 1229 | Age | ANG | Insulin | VEGF |
| 1230 | Age | ANG | LDL | LEP |
| 1231 | Age | ANG | LDL | POMC |
| 1232 | Age | ANG | LDL | VEGF |
| 1233 | Age | ANG | LEP | PLAT |
| 1234 | Age | ANG | LEP | POMC |
| 1235 | Age | ANG | LEP | SBP |
| 1236 | Age | ANG | LEP | SCp |
| 1237 | Age | ANG | LEP | SELE |
| 1238 | Age | ANG | LEP | SELP |
| 1239 | Age | ANG | LEP | Sex |
| 1240 | Age | ANG | LEP | SHBG |
| 1241 | Age | ANG | LEP | TRIG |
| 1242 | Age | ANG | LEP | VCAM1 |
| 1243 | Age | ANG | LEP | VEGF |
| 1244 | Age | ANG | LEP | VWF |
| 1245 | Age | ANG | LEP | Waist |
| 1246 | Age | ANG | LEP | WT |
| 1247 | Age | ANG | PLAT | POMC |
| 1248 | Age | ANG | PLAT | VEGF |
| 1249 | Age | ANG | POMC | SBP |
| 1250 | Age | ANG | POMC | SCp |
| 1251 | Age | ANG | POMC | SELE |
| 1252 | Age | ANG | POMC | SELP |
| 1253 | Age | ANG | POMC | Sex |
| 1254 | Age | ANG | POMC | SHBG |
| 1255 | Age | ANG | POMC | TNFRSF1B |
| 1256 | Age | ANG | POMC | TRIG |
| 1257 | Age | ANG | POMC | VCAM1 |
| 1258 | Age | ANG | POMC | VEGF |
| 1259 | Age | ANG | POMC | VWF |

FIG. 15V

| 4-Panel | Marker 1 | Marker 2 | Marker 3 | Marker 4 |
|---|---|---|---|---|
| 1260 | Age | ANG | POMC | Waist |
| 1261 | Age | ANG | POMC | WT |
| 1262 | Age | ANG | SBP | VEGF |
| 1263 | Age | ANG | SCp | VEGF |
| 1264 | Age | ANG | SELE | VEGF |
| 1265 | Age | ANG | SELP | VEGF |
| 1266 | Age | ANG | Sex | VCAM1 |
| 1267 | Age | ANG | Sex | VEGF |
| 1268 | Age | ANG | Sex | Waist |
| 1269 | Age | ANG | Sex | WT |
| 1270 | Age | ANG | SHBG | VEGF |
| 1271 | Age | ANG | TNFRSF1B | VEGF |
| 1272 | Age | ANG | TRIG | VEGF |
| 1273 | Age | ANG | VCAM1 | VEGF |
| 1274 | Age | ANG | VEGF | VWF |
| 1275 | Age | ANG | VEGF | Waist |
| 1276 | Age | ANG | VEGF | WT |
| 1277 | Age | APOA1 | APOE | HDLC |
| 1278 | Age | APOA1 | APOE | IGF1 |
| 1279 | Age | APOA1 | APOE | LEP |
| 1280 | Age | APOA1 | APOE | POMC |
| 1281 | Age | APOA1 | APOE | Sex |
| 1282 | Age | APOA1 | APOE | VEGF |
| 1283 | Age | APOA1 | BAX | HDLC |
| 1284 | Age | APOA1 | BAX | IGF1 |
| 1285 | Age | APOA1 | BAX | LEP |
| 1286 | Age | APOA1 | BAX | POMC |
| 1287 | Age | APOA1 | BAX | Sex |
| 1288 | Age | APOA1 | BAX | VEGF |
| 1289 | Age | APOA1 | BMI | CCL2 |

| 4-Panel | Marker 1 | Marker 2 | Marker 3 | Marker 4 |
|---|---|---|---|---|
| 1290 | Age | APOA1 | BMI | CD40 |
| 1291 | Age | APOA1 | BMI | CRP |
| 1292 | Age | APOA1 | BMI | HDLC |
| 1293 | Age | APOA1 | BMI | HT |
| 1294 | Age | APOA1 | BMI | IGF1 |
| 1295 | Age | APOA1 | BMI | IL6ST |
| 1296 | Age | APOA1 | BMI | Ins120 |
| 1297 | Age | APOA1 | BMI | LEP |
| 1298 | Age | APOA1 | BMI | POMC |
| 1299 | Age | APOA1 | BMI | Sex |
| 1300 | Age | APOA1 | BMI | VEGF |
| 1301 | Age | APOA1 | BMI | Waist |
| 1302 | Age | APOA1 | BMI | WT |
| 1303 | Age | APOA1 | C3 | HDLC |
| 1304 | Age | APOA1 | C3 | IGF1 |
| 1305 | Age | APOA1 | C3 | LEP |
| 1306 | Age | APOA1 | C3 | POMC |
| 1307 | Age | APOA1 | C3 | Sex |
| 1308 | Age | APOA1 | C3 | VEGF |
| 1309 | Age | APOA1 | CCL2 | CD40 |
| 1310 | Age | APOA1 | CCL2 | CRP |
| 1311 | Age | APOA1 | CCL2 | DPP4 |
| 1312 | Age | APOA1 | CCL2 | Glucose |
| 1313 | Age | APOA1 | CCL2 | HDLC |
| 1314 | Age | APOA1 | CCL2 | Hip |
| 1315 | Age | APOA1 | CCL2 | HT |
| 1316 | Age | APOA1 | CCL2 | IGF1 |
| 1317 | Age | APOA1 | CCL2 | IL18 |
| 1318 | Age | APOA1 | CCL2 | IL6ST |
| 1319 | Age | APOA1 | CCL2 | IL8 |

| 4-Panel | Marker 1 | Marker 2 | Marker 3 | Marker 4 |
|---|---|---|---|---|
| 1320 | Age | APOA1 | CCL2 | Ins120 |
| 1321 | Age | APOA1 | CCL2 | LEP |
| 1322 | Age | APOA1 | CCL2 | POMC |
| 1323 | Age | APOA1 | CCL2 | SELP |
| 1324 | Age | APOA1 | CCL2 | Sex |
| 1325 | Age | APOA1 | CCL2 | TNFRSF1B |
| 1326 | Age | APOA1 | CCL2 | VEGF |
| 1327 | Age | APOA1 | CD14 | HDLC |
| 1328 | Age | APOA1 | CD14 | IGF1 |
| 1329 | Age | APOA1 | CD14 | LEP |
| 1330 | Age | APOA1 | CD14 | POMC |
| 1331 | Age | APOA1 | CD14 | Sex |
| 1332 | Age | APOA1 | CD14 | VEGF |
| 1333 | Age | APOA1 | CD40 | CDK5 |
| 1334 | Age | APOA1 | CD40 | Glucose |
| 1335 | Age | APOA1 | CD40 | HDLC |
| 1336 | Age | APOA1 | CD40 | IGF1 |
| 1337 | Age | APOA1 | CD40 | IL6ST |
| 1338 | Age | APOA1 | CD40 | LEP |
| 1339 | Age | APOA1 | CD40 | POMC |
| 1340 | Age | APOA1 | CD40 | Sex |
| 1341 | Age | APOA1 | CD40 | VEGF |
| 1342 | Age | APOA1 | CDK5 | HDLC |
| 1343 | Age | APOA1 | CDK5 | IGF1 |
| 1344 | Age | APOA1 | CDK5 | LEP |
| 1345 | Age | APOA1 | CDK5 | POMC |
| 1346 | Age | APOA1 | CDK5 | Sex |
| 1347 | Age | APOA1 | CDK5 | VEGF |
| 1348 | Age | APOA1 | CHOL | HDLC |
| 1349 | Age | APOA1 | CHOL | IGF1 |
| 1350 | Age | APOA1 | CHOL | LEP |
| 1351 | Age | APOA1 | CHOL | POMC |
| 1352 | Age | APOA1 | CHOL | Sex |
| 1353 | Age | APOA1 | CHOL | VEGF |
| 1354 | Age | APOA1 | CRP | HDLC |
| 1355 | Age | APOA1 | CRP | IGF1 |
| 1356 | Age | APOA1 | CRP | IL6ST |
| 1357 | Age | APOA1 | CRP | LEP |
| 1358 | Age | APOA1 | CRP | POMC |
| 1359 | Age | APOA1 | CRP | Sex |
| 1360 | Age | APOA1 | CRP | VEGF |
| 1361 | Age | APOA1 | DBP | HDLC |
| 1362 | Age | APOA1 | DBP | IGF1 |
| 1363 | Age | APOA1 | DBP | LEP |
| 1364 | Age | APOA1 | DBP | POMC |
| 1365 | Age | APOA1 | DBP | Sex |
| 1366 | Age | APOA1 | DBP | VEGF |
| 1367 | Age | APOA1 | DPP4 | Glucose |
| 1368 | Age | APOA1 | DPP4 | HDLC |
| 1369 | Age | APOA1 | DPP4 | IGF1 |
| 1370 | Age | APOA1 | DPP4 | LEP |
| 1371 | Age | APOA1 | DPP4 | POMC |
| 1372 | Age | APOA1 | DPP4 | Sex |
| 1373 | Age | APOA1 | DPP4 | VEGF |
| 1374 | Age | APOA1 | EGF | HDLC |
| 1375 | Age | APOA1 | EGF | IGF1 |
| 1376 | Age | APOA1 | EGF | LEP |
| 1377 | Age | APOA1 | EGF | POMC |
| 1378 | Age | APOA1 | EGF | Sex |
| 1379 | Age | APOA1 | EGF | VEGF |

FIG. 15W

| 4-Panel | Marker 1 | Marker 2 | Marker 3 | Marker 4 |
|---|---|---|---|---|
| 1380 | Age | APOA1 | ENG | HDLC |
| 1381 | Age | APOA1 | ENG | IGF1 |
| 1382 | Age | APOA1 | ENG | LEP |
| 1383 | Age | APOA1 | ENG | POMC |
| 1384 | Age | APOA1 | ENG | Sex |
| 1385 | Age | APOA1 | ENG | VEGF |
| 1386 | Age | APOA1 | FamHX | HDLC |
| 1387 | Age | APOA1 | FamHX | IGF1 |
| 1388 | Age | APOA1 | FamHX | LEP |
| 1389 | Age | APOA1 | FamHX | POMC |
| 1390 | Age | APOA1 | FamHX | Sex |
| 1391 | Age | APOA1 | FamHX | VEGF |
| 1392 | Age | APOA1 | FGA | HDLC |
| 1393 | Age | APOA1 | FGA | IGF1 |
| 1394 | Age | APOA1 | FGA | LEP |
| 1395 | Age | APOA1 | FGA | POMC |
| 1396 | Age | APOA1 | FGA | Sex |
| 1397 | Age | APOA1 | FGA | VEGF |
| 1398 | Age | APOA1 | FTH1 | HDLC |
| 1399 | Age | APOA1 | FTH1 | IGF1 |
| 1400 | Age | APOA1 | FTH1 | LEP |
| 1401 | Age | APOA1 | FTH1 | POMC |
| 1402 | Age | APOA1 | FTH1 | Sex |
| 1403 | Age | APOA1 | FTH1 | VEGF |
| 1404 | Age | APOA1 | Gluc120 | HDLC |
| 1405 | Age | APOA1 | Gluc120 | IGF1 |
| 1406 | Age | APOA1 | Gluc120 | LEP |
| 1407 | Age | APOA1 | Gluc120 | POMC |
| 1408 | Age | APOA1 | Gluc120 | Sex |
| 1409 | Age | APOA1 | Gluc120 | VEGF |

| 4-Panel | Marker 1 | Marker 2 | Marker 3 | Marker 4 |
|---|---|---|---|---|
| 1410 | Age | APOA1 | Glucose | HDLC |
| 1411 | Age | APOA1 | Glucose | HT |
| 1412 | Age | APOA1 | Glucose | IGF1 |
| 1413 | Age | APOA1 | Glucose | IL6ST |
| 1414 | Age | APOA1 | Glucose | LEP |
| 1415 | Age | APOA1 | Glucose | POMC |
| 1416 | Age | APOA1 | Glucose | Sex |
| 1417 | Age | APOA1 | Glucose | VEGF |
| 1418 | Age | APOA1 | HBA1C | HDLC |
| 1419 | Age | APOA1 | HBA1C | IGF1 |
| 1420 | Age | APOA1 | HBA1C | LEP |
| 1421 | Age | APOA1 | HBA1C | POMC |
| 1422 | Age | APOA1 | HBA1C | Sex |
| 1423 | Age | APOA1 | HBA1C | VEGF |
| 1424 | Age | APOA1 | HDLC | HGF |
| 1425 | Age | APOA1 | HDLC | Hp |
| 1426 | Age | APOA1 | HDLC | HP |
| 1427 | Age | APOA1 | HDLC | HT |
| 1428 | Age | APOA1 | HDLC | iCAM1 |
| 1429 | Age | APOA1 | HDLC | IGF1 |
| 1430 | Age | APOA1 | HDLC | IGFBP1 |
| 1431 | Age | APOA1 | HDLC | IGFBP3 |
| 1432 | Age | APOA1 | HDLC | IL18 |
| 1433 | Age | APOA1 | HDLC | IL2RA |
| 1434 | Age | APOA1 | HDLC | IL6R |
| 1435 | Age | APOA1 | HDLC | IL6ST |
| 1436 | Age | APOA1 | HDLC | IL8 |
| 1437 | Age | APOA1 | HDLC | INHBA |
| 1438 | Age | APOA1 | HDLC | Ins120 |
| 1439 | Age | APOA1 | HDLC | Insulin |

FIG. 15X

| 4-Panel | Marker 1 | Marker 2 | Marker 3 | Marker 4 |
|---|---|---|---|---|
| 1440 | Age | APOA1 | HDLC | LDL |
| 1441 | Age | APOA1 | HDLC | LEP |
| 1442 | Age | APOA1 | HDLC | PLAT |
| 1443 | Age | APOA1 | HDLC | POMC |
| 1444 | Age | APOA1 | HDLC | SBP |
| 1445 | Age | APOA1 | HDLC | SCp |
| 1446 | Age | APOA1 | HDLC | SELE |
| 1447 | Age | APOA1 | HDLC | SELP |
| 1448 | Age | APOA1 | HDLC | Sex |
| 1449 | Age | APOA1 | HDLC | SHBG |
| 1450 | Age | APOA1 | HDLC | TNFRSF1B |
| 1451 | Age | APOA1 | HDLC | TRIG |
| 1452 | Age | APOA1 | HDLC | VCAM1 |
| 1453 | Age | APOA1 | HDLC | VEGF |
| 1454 | Age | APOA1 | HDLC | vWF |
| 1455 | Age | APOA1 | HDLC | Waist |
| 1456 | Age | APOA1 | HDLC | WT |
| 1457 | Age | APOA1 | HGF | IGF1 |
| 1458 | Age | APOA1 | HGF | LEP |
| 1459 | Age | APOA1 | HGF | POMC |
| 1460 | Age | APOA1 | HGF | Sex |
| 1461 | Age | APOA1 | HGF | VEGF |
| 1462 | Age | APOA1 | Hip | IGF1 |
| 1463 | Age | APOA1 | Hip | LEP |
| 1464 | Age | APOA1 | Hip | POMC |
| 1465 | Age | APOA1 | Hip | Sex |
| 1466 | Age | APOA1 | Hip | VEGF |
| 1467 | Age | APOA1 | HP | LEP |
| 1468 | Age | APOA1 | HP | POMC |
| 1469 | Age | APOA1 | HP | Sex |
| 1470 | Age | APOA1 | HP | VEGF |
| 1471 | Age | APOA1 | HT | IGF1 |
| 1472 | Age | APOA1 | HT | IL6ST |
| 1473 | Age | APOA1 | HT | LEP |
| 1474 | Age | APOA1 | HT | POMC |
| 1475 | Age | APOA1 | HT | Sex |
| 1476 | Age | APOA1 | HT | VEGF |
| 1477 | Age | APOA1 | HT | WT |
| 1478 | Age | APOA1 | ICAM1 | IGF1 |
| 1479 | Age | APOA1 | ICAM1 | LEP |
| 1480 | Age | APOA1 | ICAM1 | POMC |
| 1481 | Age | APOA1 | ICAM1 | Sex |
| 1482 | Age | APOA1 | ICAM1 | VEGF |
| 1483 | Age | APOA1 | IGF1 | IGFBP1 |
| 1484 | Age | APOA1 | IGF1 | IGFBP3 |
| 1485 | Age | APOA1 | IGF1 | IL18 |
| 1486 | Age | APOA1 | IGF1 | IL2RA |
| 1487 | Age | APOA1 | IGF1 | IL6R |
| 1488 | Age | APOA1 | IGF1 | IL6ST |
| 1489 | Age | APOA1 | IGF1 | IL8 |
| 1490 | Age | APOA1 | IGF1 | INHBA |
| 1491 | Age | APOA1 | IGF1 | Ins120 |
| 1492 | Age | APOA1 | IGF1 | Insulin |
| 1493 | Age | APOA1 | IGF1 | LDL |
| 1494 | Age | APOA1 | IGF1 | LEP |
| 1495 | Age | APOA1 | IGF1 | PLAT |
| 1496 | Age | APOA1 | IGF1 | POMC |
| 1497 | Age | APOA1 | IGF1 | SBP |
| 1498 | Age | APOA1 | IGF1 | SCp |
| 1499 | Age | APOA1 | IGF1 | SELE |

FIG. 15Y

| 4-Panel | Marker 1 | Marker 2 | Marker 3 | Marker 4 |
|---|---|---|---|---|
| 1500 | Age | APOA1 | IGF1 | SELP |
| 1501 | Age | APOA1 | IGF1 | Sex |
| 1502 | Age | APOA1 | IGF1 | SHBG |
| 1503 | Age | APOA1 | IGF1 | TNFRSF1B |
| 1504 | Age | APOA1 | IGF1 | TRIG |
| 1505 | Age | APOA1 | IGF1 | VCAM1 |
| 1506 | Age | APOA1 | IGF1 | VEGF |
| 1507 | Age | APOA1 | IGF1 | VWF |
| 1508 | Age | APOA1 | IGF1 | Waist |
| 1509 | Age | APOA1 | IGF1 | WT |
| 1510 | Age | APOA1 | IGFBP1 | LEP |
| 1511 | Age | APOA1 | IGFBP1 | POMC |
| 1512 | Age | APOA1 | IGFBP1 | Sex |
| 1513 | Age | APOA1 | IGFBP1 | VEGF |
| 1514 | Age | APOA1 | IGFBP3 | LEP |
| 1515 | Age | APOA1 | IGFBP3 | POMC |
| 1516 | Age | APOA1 | IGFBP3 | Sex |
| 1517 | Age | APOA1 | IGFBP3 | VEGF |
| 1518 | Age | APOA1 | IL18 | IL6ST |
| 1519 | Age | APOA1 | IL18 | LEP |
| 1520 | Age | APOA1 | IL18 | POMC |
| 1521 | Age | APOA1 | IL18 | Sex |
| 1522 | Age | APOA1 | IL18 | VEGF |
| 1523 | Age | APOA1 | IL2RA | LEP |
| 1524 | Age | APOA1 | IL2RA | POMC |
| 1525 | Age | APOA1 | IL2RA | Sex |
| 1526 | Age | APOA1 | IL2RA | VEGF |
| 1527 | Age | APOA1 | IL6R | IL6ST |
| 1528 | Age | APOA1 | IL6R | LEP |
| 1529 | Age | APOA1 | IL6R | POMC |
| 1530 | Age | APOA1 | IL6R | Sex |
| 1531 | Age | APOA1 | IL6R | VEGF |
| 1532 | Age | APOA1 | IL6ST | LEP |
| 1533 | Age | APOA1 | IL6ST | POMC |
| 1534 | Age | APOA1 | IL6ST | Sex |
| 1535 | Age | APOA1 | IL6ST | TNFRSF1B |
| 1536 | Age | APOA1 | IL6ST | VEGF |
| 1537 | Age | APOA1 | IL8 | LEP |
| 1538 | Age | APOA1 | IL8 | POMC |
| 1539 | Age | APOA1 | IL8 | Sex |
| 1540 | Age | APOA1 | IL8 | VEGF |
| 1541 | Age | APOA1 | INHBA | LEP |
| 1542 | Age | APOA1 | INHBA | POMC |
| 1543 | Age | APOA1 | INHBA | Sex |
| 1544 | Age | APOA1 | INHBA | VEGF |
| 1545 | Age | APOA1 | Ins120 | Insulin |
| 1546 | Age | APOA1 | Ins120 | LEP |
| 1547 | Age | APOA1 | Ins120 | POMC |
| 1548 | Age | APOA1 | Ins120 | Sex |
| 1549 | Age | APOA1 | Ins120 | VEGF |
| 1550 | Age | APOA1 | Insulin | LEP |
| 1551 | Age | APOA1 | Insulin | POMC |
| 1552 | Age | APOA1 | Insulin | Sex |
| 1553 | Age | APOA1 | Insulin | VEGF |
| 1554 | Age | APOA1 | LDL | LEP |
| 1555 | Age | APOA1 | LDL | POMC |
| 1556 | Age | APOA1 | LDL | Sex |
| 1557 | Age | APOA1 | LDL | VEGF |
| 1558 | Age | APOA1 | LEP | PLAT |
| 1559 | Age | APOA1 | LEP | POMC |

FIG. 15Z

| 4-Panel | Marker 1 | Marker 2 | Marker 3 | Marker 4 |
|---|---|---|---|---|
| 1560 | Age | APOA1 | LEP | SBP |
| 1561 | Age | APOA1 | LEP | SCp |
| 1562 | Age | APOA1 | LEP | SELE |
| 1563 | Age | APOA1 | LEP | SELP |
| 1564 | Age | APOA1 | LEP | Sex |
| 1565 | Age | APOA1 | LEP | SHBG |
| 1566 | Age | APOA1 | LEP | TNFRSF1B |
| 1567 | Age | APOA1 | LEP | TRIG |
| 1568 | Age | APOA1 | LEP | VCAM1 |
| 1569 | Age | APOA1 | LEP | VEGF |
| 1570 | Age | APOA1 | LEP | VWF |
| 1571 | Age | APOA1 | LEP | Waist |
| 1572 | Age | APOA1 | LEP | WT |
| 1573 | Age | APOA1 | PLAT | POMC |
| 1574 | Age | APOA1 | PLAT | Sex |
| 1575 | Age | APOA1 | PLAT | VEGF |
| 1576 | Age | APOA1 | POMC | SBP |
| 1577 | Age | APOA1 | POMC | SCp |
| 1578 | Age | APOA1 | POMC | SELE |
| 1579 | Age | APOA1 | POMC | SELP |
| 1580 | Age | APOA1 | POMC | Sex |
| 1581 | Age | APOA1 | POMC | SHBG |
| 1582 | Age | APOA1 | POMC | TNFRSF1B |
| 1583 | Age | APOA1 | POMC | TRIG |
| 1584 | Age | APOA1 | POMC | VCAM1 |
| 1585 | Age | APOA1 | POMC | VEGF |
| 1586 | Age | APOA1 | POMC | VWF |
| 1587 | Age | APOA1 | POMC | Waist |
| 1588 | Age | APOA1 | POMC | WT |
| 1589 | Age | APOA1 | SBP | Sex |
| 1590 | Age | APOA1 | SBP | VEGF |
| 1591 | Age | APOA1 | SCp | Sex |
| 1592 | Age | APOA1 | SCp | VEGF |
| 1593 | Age | APOA1 | SELE | Sex |
| 1594 | Age | APOA1 | SELE | VEGF |
| 1595 | Age | APOA1 | SELP | Sex |
| 1596 | Age | APOA1 | SELP | VEGF |
| 1597 | Age | APOA1 | Sex | SHBG |
| 1598 | Age | APOA1 | Sex | TNFRSF1B |
| 1599 | Age | APOA1 | Sex | TRIG |
| 1600 | Age | APOA1 | Sex | VCAM1 |
| 1601 | Age | APOA1 | Sex | VEGF |
| 1602 | Age | APOA1 | Sex | VWF |
| 1603 | Age | APOA1 | Sex | Waist |
| 1604 | Age | APOA1 | Sex | WT |
| 1605 | Age | APOA1 | SHBG | VEGF |
| 1606 | Age | APOA1 | TNFRSF1B | VEGF |
| 1607 | Age | APOA1 | TRIG | VEGF |
| 1608 | Age | APOA1 | VCAM1 | VEGF |
| 1609 | Age | APOA1 | VEGF | VWF |
| 1610 | Age | APOA1 | VEGF | Waist |
| 1611 | Age | APOA1 | VEGF | WT |
| 1612 | Age | APOE | BAX | LEP |
| 1613 | Age | APOE | BAX | POMC |
| 1614 | Age | APOE | BMI | CCL2 |
| 1615 | Age | APOE | BMI | CD40 |
| 1616 | Age | APOE | BMI | CRP |
| 1617 | Age | APOE | BMI | DPP4 |
| 1618 | Age | APOE | BMI | HDLC |
| 1619 | Age | APOE | BMI | HT |

FIG. 15AA

| 4-Panel | Marker 1 | Marker 2 | Marker 3 | Marker 4 |
|---|---|---|---|---|
| 1620 | Age | APOE | BMI | IGF1 |
| 1621 | Age | APOE | BMI | IL2RA |
| 1622 | Age | APOE | BMI | IL6ST |
| 1623 | Age | APOE | BMI | Ins120 |
| 1624 | Age | APOE | BMI | LEP |
| 1625 | Age | APOE | BMI | POMC |
| 1626 | Age | APOE | BMI | Sex |
| 1627 | Age | APOE | BMI | VEGF |
| 1628 | Age | APOE | BMI | Waist |
| 1629 | Age | APOE | BMI | WT |
| 1630 | Age | APOE | C3 | LEP |
| 1631 | Age | APOE | C3 | POMC |
| 1632 | Age | APOE | CCL2 | CD40 |
| 1633 | Age | APOE | CCL2 | CRP |
| 1634 | Age | APOE | CCL2 | Glucose |
| 1635 | Age | APOE | CCL2 | HDLC |
| 1636 | Age | APOE | CCL2 | Hip |
| 1637 | Age | APOE | CCL2 | HT |
| 1638 | Age | APOE | CCL2 | IGF1 |
| 1639 | Age | APOE | CCL2 | IL6ST |
| 1640 | Age | APOE | CCL2 | LEP |
| 1641 | Age | APOE | CCL2 | POMC |
| 1642 | Age | APOE | CCL2 | Sex |
| 1643 | Age | APOE | CCL2 | VEGF |
| 1644 | Age | APOE | CD14 | LEP |
| 1645 | Age | APOE | CD14 | POMC |
| 1646 | Age | APOE | CD40 | HDLC |
| 1647 | Age | APOE | CD40 | IGF1 |
| 1648 | Age | APOE | CD40 | IL6ST |
| 1649 | Age | APOE | CD40 | LEP |

| 4-Panel | Marker 1 | Marker 2 | Marker 3 | Marker 4 |
|---|---|---|---|---|
| 1650 | Age | APOE | CD40 | POMC |
| 1651 | Age | APOE | CD40 | Sex |
| 1652 | Age | APOE | CD40 | VEGF |
| 1653 | Age | APOE | CDK5 | LEP |
| 1654 | Age | APOE | CDK5 | POMC |
| 1655 | Age | APOE | CHOL | LEP |
| 1656 | Age | APOE | CHOL | POMC |
| 1657 | Age | APOE | CRP | LEP |
| 1658 | Age | APOE | CRP | POMC |
| 1659 | Age | APOE | DBP | LEP |
| 1660 | Age | APOE | DBP | POMC |
| 1661 | Age | APOE | DPP4 | HDLC |
| 1662 | Age | APOE | DPP4 | IGF1 |
| 1663 | Age | APOE | DPP4 | LEP |
| 1664 | Age | APOE | DPP4 | POMC |
| 1665 | Age | APOE | DPP4 | Sex |
| 1666 | Age | APOE | DPP4 | VEGF |
| 1667 | Age | APOE | EGF | LEP |
| 1668 | Age | APOE | EGF | POMC |
| 1669 | Age | APOE | ENG | LEP |
| 1670 | Age | APOE | ENG | POMC |
| 1671 | Age | APOE | FamHX | LEP |
| 1672 | Age | APOE | FamHX | POMC |
| 1673 | Age | APOE | FGA | LEP |
| 1674 | Age | APOE | FGA | POMC |
| 1675 | Age | APOE | FTH1 | HDLC |
| 1676 | Age | APOE | FTH1 | IGF1 |
| 1677 | Age | APOE | FTH1 | LEP |
| 1678 | Age | APOE | FTH1 | POMC |
| 1679 | Age | APOE | FTH1 | Sex |

FIG. 15BB

| 4-Panel | Marker 1 | Marker 2 | Marker 3 | Marker 4 |
|---|---|---|---|---|
| 1680 | Age | APOE | FTH1 | VEGF |
| 1681 | Age | APOE | Gluc120 | LEP |
| 1682 | Age | APOE | Gluc120 | POMC |
| 1683 | Age | APOE | Glucose | HDLC |
| 1684 | Age | APOE | Glucose | HT |
| 1685 | Age | APOE | Glucose | IGF1 |
| 1686 | Age | APOE | Glucose | IL6ST |
| 1687 | Age | APOE | Glucose | LEP |
| 1688 | Age | APOE | Glucose | POMC |
| 1689 | Age | APOE | Glucose | Sex |
| 1690 | Age | APOE | Glucose | VEGF |
| 1691 | Age | APOE | HBA1C | LEP |
| 1692 | Age | APOE | HBA1C | POMC |
| 1693 | Age | APOE | HDLC | Hip |
| 1694 | Age | APOE | HDLC | IGF1 |
| 1695 | Age | APOE | HDLC | IGFBP1 |
| 1696 | Age | APOE | HDLC | IL18 |
| 1697 | Age | APOE | HDLC | IL6ST |
| 1698 | Age | APOE | HDLC | Insulin |
| 1699 | Age | APOE | HDLC | LEP |
| 1700 | Age | APOE | HDLC | POMC |
| 1701 | Age | APOE | HDLC | SCp |
| 1702 | Age | APOE | HDLC | Sex |
| 1703 | Age | APOE | HDLC | TRIG |
| 1704 | Age | APOE | HDLC | VCAM1 |
| 1705 | Age | APOE | HDLC | VEGF |
| 1706 | Age | APOE | HDLC | Waist |
| 1707 | Age | APOE | HDLC | WT |
| 1708 | Age | APOE | HGF | LEP |
| 1709 | Age | APOE | HGF | POMC |
| 1710 | Age | APOE | Hip | IGF1 |
| 1711 | Age | APOE | Hip | LEP |
| 1712 | Age | APOE | Hip | POMC |
| 1713 | Age | APOE | Hip | VEGF |
| 1714 | Age | APOE | HP | LEP |
| 1715 | Age | APOE | HP | POMC |
| 1716 | Age | APOE | HT | IGF1 |
| 1717 | Age | APOE | HT | LEP |
| 1718 | Age | APOE | HT | POMC |
| 1719 | Age | APOE | HT | VEGF |
| 1720 | Age | APOE | HT | WT |
| 1721 | Age | APOE | ICAM1 | LEP |
| 1722 | Age | APOE | ICAM1 | POMC |
| 1723 | Age | APOE | IGF1 | IGFBP1 |
| 1724 | Age | APOE | IGF1 | IL18 |
| 1725 | Age | APOE | IGF1 | IL2RA |
| 1726 | Age | APOE | IGF1 | IL6ST |
| 1727 | Age | APOE | IGF1 | Insulin |
| 1728 | Age | APOE | IGF1 | LEP |
| 1729 | Age | APOE | IGF1 | POMC |
| 1730 | Age | APOE | IGF1 | SELP |
| 1731 | Age | APOE | IGF1 | Sex |
| 1732 | Age | APOE | IGF1 | VCAM1 |
| 1733 | Age | APOE | IGF1 | VEGF |
| 1734 | Age | APOE | IGF1 | VWF |
| 1735 | Age | APOE | IGFBP1 | LEP |
| 1736 | Age | APOE | IGFBP1 | POMC |
| 1737 | Age | APOE | IGFBP3 | Sex |
| 1738 | Age | APOE | IGFBP3 | LEP |
| 1739 | Age | APOE | IGFBP3 | POMC |

FIG. 15CC

| 4-Panel | Marker 1 | Marker 2 | Marker 3 | Marker 4 |
|---|---|---|---|---|
| 1740 | Age | APOE | IGFBP3 | VEGF |
| 1741 | Age | APOE | IL18 | LEP |
| 1742 | Age | APOE | IL18 | POMC |
| 1743 | Age | APOE | IL18 | Sex |
| 1744 | Age | APOE | IL18 | VEGF |
| 1745 | Age | APOE | IL2RA | LEP |
| 1746 | Age | APOE | IL2RA | POMC |
| 1747 | Age | APOE | IL2RA | Sex |
| 1748 | Age | APOE | IL6R | IL6ST |
| 1749 | Age | APOE | IL6R | LEP |
| 1750 | Age | APOE | IL6R | POMC |
| 1751 | Age | APOE | IL6ST | LEP |
| 1752 | Age | APOE | IL6ST | POMC |
| 1753 | Age | APOE | IL6ST | Sex |
| 1754 | Age | APOE | IL6ST | TNFRSF1B |
| 1755 | Age | APOE | IL6ST | VEGF |
| 1756 | Age | APOE | IL8 | LEP |
| 1757 | Age | APOE | IL8 | POMC |
| 1758 | Age | APOE | INHBA | LEP |
| 1759 | Age | APOE | INHBA | POMC |
| 1760 | Age | APOE | Ins120 | Insulin |
| 1761 | Age | APOE | Ins120 | LEP |
| 1762 | Age | APOE | Ins120 | POMC |
| 1763 | Age | APOE | Insulin | LEP |
| 1764 | Age | APOE | Insulin | POMC |
| 1765 | Age | APOE | Insulin | Sex |
| 1766 | Age | APOE | Insulin | VEGF |
| 1767 | Age | APOE | LDL | LEP |
| 1768 | Age | APOE | LDL | POMC |
| 1769 | Age | APOE | LEP | PLAT |
| 1770 | Age | APOE | LEP | POMC |
| 1771 | Age | APOE | LEP | SBP |
| 1772 | Age | APOE | LEP | SCp |
| 1773 | Age | APOE | LEP | SELE |
| 1774 | Age | APOE | LEP | SELP |
| 1775 | Age | APOE | LEP | Sex |
| 1776 | Age | APOE | LEP | SHBG |
| 1777 | Age | APOE | LEP | TNFRSF1B |
| 1778 | Age | APOE | LEP | TRIG |
| 1779 | Age | APOE | LEP | VCAM1 |
| 1780 | Age | APOE | LEP | VEGF |
| 1781 | Age | APOE | LEP | VWF |
| 1782 | Age | APOE | LEP | Waist |
| 1783 | Age | APOE | LEP | WT |
| 1784 | Age | APOE | PLAT | POMC |
| 1785 | Age | APOE | POMC | SBP |
| 1786 | Age | APOE | POMC | SCp |
| 1787 | Age | APOE | POMC | SELE |
| 1788 | Age | APOE | POMC | SELP |
| 1789 | Age | APOE | POMC | Sex |
| 1790 | Age | APOE | POMC | SHBG |
| 1791 | Age | APOE | POMC | TNFRSF1B |
| 1792 | Age | APOE | POMC | TRIG |
| 1793 | Age | APOE | POMC | VCAM1 |
| 1794 | Age | APOE | POMC | VEGF |
| 1795 | Age | APOE | POMC | VWF |
| 1796 | Age | APOE | POMC | Waist |
| 1797 | Age | APOE | POMC | WT |
| 1798 | Age | APOE | SELP | VEGF |
| 1799 | Age | APOE | Sex | VEGF |

FIG. 15DD

| 4-Panel | Marker 1 | Marker 2 | Marker 3 | Marker 4 |
|---|---|---|---|---|
| 1800 | Age | APOE | Sex | Waist |
| 1801 | Age | APOE | Sex | WT |
| 1802 | Age | APOE | VCAM1 | VEGF |
| 1803 | Age | BAX | BMI | CCL2 |
| 1804 | Age | BAX | BMI | HDLC |
| 1805 | Age | BAX | BMI | IGF1 |
| 1806 | Age | BAX | BMI | IL6ST |
| 1807 | Age | BAX | BMI | LEP |
| 1808 | Age | BAX | BMI | POMC |
| 1809 | Age | BAX | BMI | Sex |
| 1810 | Age | BAX | BMI | VEGF |
| 1811 | Age | BAX | BMI | Waist |
| 1812 | Age | BAX | C3 | LEP |
| 1813 | Age | BAX | C3 | POMC |
| 1814 | Age | BAX | CCL2 | CD40 |
| 1815 | Age | BAX | CCL2 | DPP4 |
| 1816 | Age | BAX | CCL2 | HDLC |
| 1817 | Age | BAX | CCL2 | HT |
| 1818 | Age | BAX | CCL2 | IGF1 |
| 1819 | Age | BAX | CCL2 | IL6ST |
| 1820 | Age | BAX | CCL2 | LEP |
| 1821 | Age | BAX | CCL2 | POMC |
| 1822 | Age | BAX | CCL2 | Sex |
| 1823 | Age | BAX | CCL2 | VEGF |
| 1824 | Age | BAX | CD14 | POMC |
| 1825 | Age | BAX | CD40 | Glucose |
| 1826 | Age | BAX | CD40 | HDLC |
| 1827 | Age | BAX | CD40 | IGF1 |
| 1828 | Age | BAX | CD40 | IL6ST |
| 1829 | Age | BAX | CD40 | LEP |

| 4-Panel | Marker 1 | Marker 2 | Marker 3 | Marker 4 |
|---|---|---|---|---|
| 1830 | Age | BAX | CD40 | POMC |
| 1831 | Age | BAX | CD40 | Sex |
| 1832 | Age | BAX | CDK5 | LEP |
| 1833 | Age | BAX | CDK5 | POMC |
| 1834 | Age | BAX | CHOL | LEP |
| 1835 | Age | BAX | CHOL | POMC |
| 1836 | Age | BAX | CRP | LEP |
| 1837 | Age | BAX | CRP | POMC |
| 1838 | Age | BAX | DBP | LEP |
| 1839 | Age | BAX | DBP | POMC |
| 1840 | Age | BAX | DPP4 | IGF1 |
| 1841 | Age | BAX | DPP4 | LEP |
| 1842 | Age | BAX | DPP4 | POMC |
| 1843 | Age | BAX | DPP4 | VEGF |
| 1844 | Age | BAX | EGF | LEP |
| 1845 | Age | BAX | EGF | POMC |
| 1846 | Age | BAX | ENG | LEP |
| 1847 | Age | BAX | ENG | POMC |
| 1848 | Age | BAX | FamHX | LEP |
| 1849 | Age | BAX | FamHX | POMC |
| 1850 | Age | BAX | FGA | LEP |
| 1851 | Age | BAX | FGA | POMC |
| 1852 | Age | BAX | FTH1 | HDLC |
| 1853 | Age | BAX | FTH1 | IL6ST |
| 1854 | Age | BAX | FTH1 | LEP |
| 1855 | Age | BAX | FTH1 | POMC |
| 1856 | Age | BAX | FTH1 | Sex |
| 1857 | Age | BAX | Gluc120 | LEP |
| 1858 | Age | BAX | Gluc120 | POMC |
| 1859 | Age | BAX | Glucose | HDLC |

FIG. 15EE

| 4-Panel | Marker 1 | Marker 2 | Marker 3 | Marker 4 |
|---|---|---|---|---|
| 1860 | Age | BAX | Glucose | IGF1 |
| 1861 | Age | BAX | Glucose | IL6ST |
| 1862 | Age | BAX | Glucose | LEP |
| 1863 | Age | BAX | Glucose | POMC |
| 1864 | Age | BAX | Glucose | Sex |
| 1865 | Age | BAX | Glucose | VEGF |
| 1866 | Age | BAX | HBA1C | LEP |
| 1867 | Age | BAX | HBA1C | POMC |
| 1868 | Age | BAX | HDLC | Hip |
| 1869 | Age | BAX | HDLC | IGF1 |
| 1870 | Age | BAX | HDLC | IL18 |
| 1871 | Age | BAX | HDLC | IL6ST |
| 1872 | Age | BAX | HDLC | Insulin |
| 1873 | Age | BAX | HDLC | LEP |
| 1874 | Age | BAX | HDLC | POMC |
| 1875 | Age | BAX | HDLC | Sex |
| 1876 | Age | BAX | HDLC | TRIG |
| 1877 | Age | BAX | HDLC | VEGF |
| 1878 | Age | BAX | HDLC | Waist |
| 1879 | Age | BAX | HDLC | WT |
| 1880 | Age | BAX | HGF | LEP |
| 1881 | Age | BAX | HGF | POMC |
| 1882 | Age | BAX | Hip | LEP |
| 1883 | Age | BAX | Hip | POMC |
| 1884 | Age | BAX | HP | POMC |
| 1885 | Age | BAX | HT | IGF1 |
| 1886 | Age | BAX | HT | LEP |
| 1887 | Age | BAX | HT | POMC |
| 1888 | Age | BAX | HT | VEGF |
| 1889 | Age | BAX | ICAM1 | LEP |

| 4-Panel | Marker 1 | Marker 2 | Marker 3 | Marker 4 |
|---|---|---|---|---|
| 1890 | Age | BAX | ICAM1 | POMC |
| 1891 | Age | BAX | IGF1 | IL6ST |
| 1892 | Age | BAX | IGF1 | LEP |
| 1893 | Age | BAX | IGF1 | POMC |
| 1894 | Age | BAX | IGF1 | Sex |
| 1895 | Age | BAX | IGF1 | VCAM1 |
| 1896 | Age | BAX | IGF1 | VEGF |
| 1897 | Age | BAX | IGFBP1 | LEP |
| 1898 | Age | BAX | IGFBP1 | POMC |
| 1899 | Age | BAX | IGFBP1 | Sex |
| 1900 | Age | BAX | IGFBP3 | LEP |
| 1901 | Age | BAX | IGFBP3 | POMC |
| 1902 | Age | BAX | IL18 | LEP |
| 1903 | Age | BAX | IL18 | POMC |
| 1904 | Age | BAX | IL18 | Sex |
| 1905 | Age | BAX | IL2RA | LEP |
| 1906 | Age | BAX | IL2RA | POMC |
| 1907 | Age | BAX | IL2RA | Sex |
| 1908 | Age | BAX | IL6R | LEP |
| 1909 | Age | BAX | IL6R | POMC |
| 1910 | Age | BAX | IL6R | LEP |
| 1911 | Age | BAX | IL6ST | POMC |
| 1912 | Age | BAX | IL6ST | LEP |
| 1913 | Age | BAX | IL6ST | POMC |
| 1914 | Age | BAX | IL6ST | Sex |
| 1915 | Age | BAX | IL6ST | TNFRSF1B |
| 1916 | Age | BAX | IL6ST | VEGF |
| 1917 | Age | BAX | IL8 | LEP |
| 1918 | Age | BAX | INHBA | LEP |
| 1919 | Age | BAX | INHBA | POMC |

| 4-Panel | Marker 1 | Marker 2 | Marker 3 | Marker 4 |
|---|---|---|---|---|
| 1920 | Age | BAX | Ins120 | LEP |
| 1921 | Age | BAX | Ins120 | POMC |
| 1922 | Age | BAX | Insulin | LEP |
| 1923 | Age | BAX | Insulin | POMC |
| 1924 | Age | BAX | Insulin | Sex |
| 1925 | Age | BAX | Insulin | VEGF |
| 1926 | Age | BAX | LDL | LEP |
| 1927 | Age | BAX | LDL | POMC |
| 1928 | Age | BAX | LEP | PLAT |
| 1929 | Age | BAX | LEP | POMC |
| 1930 | Age | BAX | LEP | SBP |
| 1931 | Age | BAX | LEP | SCp |
| 1932 | Age | BAX | LEP | SELE |
| 1933 | Age | BAX | LEP | SELP |
| 1934 | Age | BAX | LEP | Sex |
| 1935 | Age | BAX | LEP | SHBG |
| 1936 | Age | BAX | LEP | TNFRSF1B |
| 1937 | Age | BAX | LEP | TRIG |
| 1938 | Age | BAX | LEP | VCAM1 |
| 1939 | Age | BAX | LEP | VEGF |
| 1940 | Age | BAX | LEP | VWF |
| 1941 | Age | BAX | LEP | Waist |
| 1942 | Age | BAX | LEP | WT |
| 1943 | Age | BAX | PLAT | POMC |
| 1944 | Age | BAX | POMC | SBP |
| 1945 | Age | BAX | POMC | SCp |
| 1946 | Age | BAX | POMC | SELE |
| 1947 | Age | BAX | POMC | SELP |
| 1948 | Age | BAX | POMC | Sex |
| 1949 | Age | BAX | POMC | SHBG |

| 4-Panel | Marker 1 | Marker 2 | Marker 3 | Marker 4 |
|---|---|---|---|---|
| 1950 | Age | BAX | POMC | TNFRSF1B |
| 1951 | Age | BAX | POMC | TRIG |
| 1952 | Age | BAX | POMC | VCAM1 |
| 1953 | Age | BAX | POMC | VEGF |
| 1954 | Age | BAX | POMC | VWF |
| 1955 | Age | BAX | POMC | Waist |
| 1956 | Age | BAX | POMC | WT |
| 1957 | Age | BAX | Sex | VEGF |
| 1958 | Age | BAX | Sex | WT |
| 1959 | Age | BMI | C3 | CCL2 |
| 1960 | Age | BMI | C3 | CRP |
| 1961 | Age | BMI | C3 | HDLC |
| 1962 | Age | BMI | C3 | IGF1 |
| 1963 | Age | BMI | C3 | IL6ST |
| 1964 | Age | BMI | C3 | Ins120 |
| 1965 | Age | BMI | C3 | LEP |
| 1966 | Age | BMI | C3 | POMC |
| 1967 | Age | BMI | C3 | Sex |
| 1968 | Age | BMI | C3 | VEGF |
| 1969 | Age | BMI | C3 | Waist |
| 1970 | Age | BMI | CCL2 | CD14 |
| 1971 | Age | BMI | CCL2 | CD40 |
| 1972 | Age | BMI | CCL2 | CDK5 |
| 1973 | Age | BMI | CCL2 | CHOL |
| 1974 | Age | BMI | CCL2 | CRP |
| 1975 | Age | BMI | CCL2 | DBP |
| 1976 | Age | BMI | CCL2 | DPP4 |
| 1977 | Age | BMI | CCL2 | EGF |
| 1978 | Age | BMI | CCL2 | ENG |
| 1979 | Age | BMI | CCL2 | FamHX |

| 4-Panel | Marker 1 | Marker 2 | Marker 3 | Marker 4 |
|---|---|---|---|---|
| 1980 | Age | BMI | CCL2 | FGA |
| 1981 | Age | BMI | CCL2 | FTH1 |
| 1982 | Age | BMI | CCL2 | Gluc120 |
| 1983 | Age | BMI | CCL2 | Glucose |
| 1984 | Age | BMI | CCL2 | HBA1C |
| 1985 | Age | BMI | CCL2 | HDLC |
| 1986 | Age | BMI | CCL2 | HGF |
| 1987 | Age | BMI | CCL2 | Hip |
| 1988 | Age | BMI | CCL2 | HP |
| 1989 | Age | BMI | CCL2 | HT |
| 1990 | Age | BMI | CCL2 | ICAM1 |
| 1991 | Age | BMI | CCL2 | IGF1 |
| 1992 | Age | BMI | CCL2 | IGFBP1 |
| 1993 | Age | BMI | CCL2 | IGFBP3 |
| 1994 | Age | BMI | CCL2 | IL18 |
| 1995 | Age | BMI | CCL2 | IL2RA |
| 1996 | Age | BMI | CCL2 | IL6R |
| 1997 | Age | BMI | CCL2 | IL6ST |
| 1998 | Age | BMI | CCL2 | IL8 |
| 1999 | Age | BMI | CCL2 | INHBA |
| 2000 | Age | BMI | CCL2 | Ins120 |
| 2001 | Age | BMI | CCL2 | Insulin |
| 2002 | Age | BMI | CCL2 | LDL |
| 2003 | Age | BMI | CCL2 | LEP |
| 2004 | Age | BMI | CCL2 | PLAT |
| 2005 | Age | BMI | CCL2 | POMC |
| 2006 | Age | BMI | CCL2 | SBP |
| 2007 | Age | BMI | CCL2 | SCp |
| 2008 | Age | BMI | CCL2 | SELE |
| 2009 | Age | BMI | CCL2 | SELP |
| 2010 | Age | BMI | CCL2 | Sex |
| 2011 | Age | BMI | CCL2 | SHBG |
| 2012 | Age | BMI | CCL2 | TNFRSF1B |
| 2013 | Age | BMI | CCL2 | TRIG |
| 2014 | Age | BMI | CCL2 | VCAM1 |
| 2015 | Age | BMI | CCL2 | VEGF |
| 2016 | Age | BMI | CCL2 | VWF |
| 2017 | Age | BMI | CCL2 | Waist |
| 2018 | Age | BMI | CCL2 | WT |
| 2019 | Age | BMI | CD14 | CRP |
| 2020 | Age | BMI | CD14 | DPP4 |
| 2021 | Age | BMI | CD14 | HDLC |
| 2022 | Age | BMI | CD14 | IGF1 |
| 2023 | Age | BMI | CD14 | IL6ST |
| 2024 | Age | BMI | CD14 | LEP |
| 2025 | Age | BMI | CD14 | POMC |
| 2026 | Age | BMI | CD14 | Sex |
| 2027 | Age | BMI | CD14 | VEGF |
| 2028 | Age | BMI | CD14 | Waist |
| 2029 | Age | BMI | CD40 | CDK5 |
| 2030 | Age | BMI | CD40 | CRP |
| 2031 | Age | BMI | CD40 | DPP4 |
| 2032 | Age | BMI | CD40 | FamHX |
| 2033 | Age | BMI | CD40 | FGA |
| 2034 | Age | BMI | CD40 | Gluc120 |
| 2035 | Age | BMI | CD40 | Glucose |
| 2036 | Age | BMI | CD40 | HDLC |
| 2037 | Age | BMI | CD40 | HGF |
| 2038 | Age | BMI | CD40 | HT |
| 2039 | Age | BMI | CD40 | IGF1 |

FIG. 15HH

| 4-Panel | Marker 1 | Marker 2 | Marker 3 | Marker 4 |
|---|---|---|---|---|
| 2040 | Age | BMI | CD40 | IL2RA |
| 2041 | Age | BMI | CD40 | IL6ST |
| 2042 | Age | BMI | CD40 | IL8 |
| 2043 | Age | BMI | CD40 | INHBA |
| 2044 | Age | BMI | CD40 | Ins120 |
| 2045 | Age | BMI | CD40 | LEP |
| 2046 | Age | BMI | CD40 | PLAT |
| 2047 | Age | BMI | CD40 | POMC |
| 2048 | Age | BMI | CD40 | SCp |
| 2049 | Age | BMI | CD40 | SELE |
| 2050 | Age | BMI | CD40 | Sex |
| 2051 | Age | BMI | CD40 | TNFRSF1B |
| 2052 | Age | BMI | CD40 | TRIG |
| 2053 | Age | BMI | CD40 | VEGF |
| 2054 | Age | BMI | CD40 | VWF |
| 2055 | Age | BMI | CD40 | Waist |
| 2056 | Age | BMI | CD40 | WT |
| 2057 | Age | BMI | CDK5 | CRP |
| 2058 | Age | BMI | CDK5 | HDLC |
| 2059 | Age | BMI | CDK5 | IGF1 |
| 2060 | Age | BMI | CDK5 | IL6ST |
| 2061 | Age | BMI | CDK5 | Ins120 |
| 2062 | Age | BMI | CDK5 | LEP |
| 2063 | Age | BMI | CDK5 | POMC |
| 2064 | Age | BMI | CDK5 | Sex |
| 2065 | Age | BMI | CDK5 | VEGF |
| 2066 | Age | BMI | CDK5 | Waist |
| 2067 | Age | BMI | CHOL | CRP |
| 2068 | Age | BMI | CHOL | HDLC |
| 2069 | Age | BMI | CHOL | IGF1 |
| 2070 | Age | BMI | CHOL | IL6ST |
| 2071 | Age | BMI | CHOL | Ins120 |
| 2072 | Age | BMI | CHOL | LEP |
| 2073 | Age | BMI | CHOL | POMC |
| 2074 | Age | BMI | CHOL | Sex |
| 2075 | Age | BMI | CHOL | TRIG |
| 2076 | Age | BMI | CHOL | VEGF |
| 2077 | Age | BMI | CHOL | Waist |
| 2078 | Age | BMI | CRP | DBP |
| 2079 | Age | BMI | CRP | DPP4 |
| 2080 | Age | BMI | CRP | EGF |
| 2081 | Age | BMI | CRP | ENG |
| 2082 | Age | BMI | CRP | FamHX |
| 2083 | Age | BMI | CRP | FGA |
| 2084 | Age | BMI | CRP | FTH1 |
| 2085 | Age | BMI | CRP | Gluc120 |
| 2086 | Age | BMI | CRP | Glucose |
| 2087 | Age | BMI | CRP | HBA1C |
| 2088 | Age | BMI | CRP | HDLC |
| 2089 | Age | BMI | CRP | HGF |
| 2090 | Age | BMI | CRP | Hip |
| 2091 | Age | BMI | CRP | HP |
| 2092 | Age | BMI | CRP | HT |
| 2093 | Age | BMI | CRP | ICAM1 |
| 2094 | Age | BMI | CRP | IGF1 |
| 2095 | Age | BMI | CRP | IGFBP1 |
| 2096 | Age | BMI | CRP | IGFBP3 |
| 2097 | Age | BMI | CRP | IL18 |
| 2098 | Age | BMI | CRP | IL2RA |
| 2099 | Age | BMI | CRP | IL6R |

FIG. 15II

| 4-Panel | Marker 1 | Marker 2 | Marker 3 | Marker 4 |
|---|---|---|---|---|
| 2100 | Age | BMI | CRP | IL6ST |
| 2101 | Age | BMI | CRP | IL8 |
| 2102 | Age | BMI | CRP | INHBA |
| 2103 | Age | BMI | CRP | Ins120 |
| 2104 | Age | BMI | CRP | Insulin |
| 2105 | Age | BMI | CRP | LDL |
| 2106 | Age | BMI | CRP | LEP |
| 2107 | Age | BMI | CRP | PLAT |
| 2108 | Age | BMI | CRP | POMC |
| 2109 | Age | BMI | CRP | SBP |
| 2110 | Age | BMI | CRP | SCp |
| 2111 | Age | BMI | CRP | SELE |
| 2112 | Age | BMI | CRP | SELP |
| 2113 | Age | BMI | CRP | Sex |
| 2114 | Age | BMI | CRP | SHBG |
| 2115 | Age | BMI | CRP | TNFRSF1B |
| 2116 | Age | BMI | CRP | TRIG |
| 2117 | Age | BMI | CRP | VCAM1 |
| 2118 | Age | BMI | CRP | VEGF |
| 2119 | Age | BMI | CRP | VWF |
| 2120 | Age | BMI | CRP | Waist |
| 2121 | Age | BMI | CRP | WT |
| 2122 | Age | BMI | DBP | HDLC |
| 2123 | Age | BMI | DBP | IGF1 |
| 2124 | Age | BMI | DBP | IL6ST |
| 2125 | Age | BMI | DBP | LEP |
| 2126 | Age | BMI | DBP | POMC |
| 2127 | Age | BMI | DBP | Sex |
| 2128 | Age | BMI | DBP | VEGF |
| 2129 | Age | BMI | DBP | Waist |
| 2130 | Age | BMI | DPP4 | FTH1 |
| 2131 | Age | BMI | DPP4 | Gluc120 |
| 2132 | Age | BMI | DPP4 | Glucose |
| 2133 | Age | BMI | DPP4 | HDLC |
| 2134 | Age | BMI | DPP4 | HGF |
| 2135 | Age | BMI | DPP4 | HP |
| 2136 | Age | BMI | DPP4 | HT |
| 2137 | Age | BMI | DPP4 | IGF1 |
| 2138 | Age | BMI | DPP4 | IGFBP3 |
| 2139 | Age | BMI | DPP4 | IL18 |
| 2140 | Age | BMI | DPP4 | IL2RA |
| 2141 | Age | BMI | DPP4 | IL6ST |
| 2142 | Age | BMI | DPP4 | IL8 |
| 2143 | Age | BMI | DPP4 | Ins120 |
| 2144 | Age | BMI | DPP4 | LEP |
| 2145 | Age | BMI | DPP4 | POMC |
| 2146 | Age | BMI | DPP4 | SCp |
| 2147 | Age | BMI | DPP4 | SELP |
| 2148 | Age | BMI | DPP4 | Sex |
| 2149 | Age | BMI | DPP4 | SHBG |
| 2150 | Age | BMI | DPP4 | TNFRSF1B |
| 2151 | Age | BMI | DPP4 | TRIG |
| 2152 | Age | BMI | DPP4 | VEGF |
| 2153 | Age | BMI | DPP4 | VWF |
| 2154 | Age | BMI | DPP4 | Waist |
| 2155 | Age | BMI | DPP4 | WT |
| 2156 | Age | BMI | EGF | HDLC |
| 2157 | Age | BMI | EGF | IGF1 |
| 2158 | Age | BMI | EGF | IL6ST |
| 2159 | Age | BMI | EGF | Ins120 |

| 4-Panel | Marker 1 | Marker 2 | Marker 3 | Marker 4 |
|---|---|---|---|---|
| 2160 | Age | BMI | EGF | LEP |
| 2161 | Age | BMI | EGF | POMC |
| 2162 | Age | BMI | EGF | Sex |
| 2163 | Age | BMI | EGF | VEGF |
| 2164 | Age | BMI | EGF | Waist |
| 2165 | Age | BMI | ENG | HDLC |
| 2166 | Age | BMI | ENG | IGF1 |
| 2167 | Age | BMI | ENG | IL6ST |
| 2168 | Age | BMI | ENG | Ins120 |
| 2169 | Age | BMI | ENG | LEP |
| 2170 | Age | BMI | ENG | POMC |
| 2171 | Age | BMI | ENG | Sex |
| 2172 | Age | BMI | ENG | VEGF |
| 2173 | Age | BMI | ENG | Waist |
| 2174 | Age | BMI | FamHX | HDLC |
| 2175 | Age | BMI | FamHX | IGF1 |
| 2176 | Age | BMI | FamHX | IL6ST |
| 2177 | Age | BMI | FamHX | Ins120 |
| 2178 | Age | BMI | FamHX | LEP |
| 2179 | Age | BMI | FamHX | POMC |
| 2180 | Age | BMI | FamHX | Sex |
| 2181 | Age | BMI | FamHX | VEGF |
| 2182 | Age | BMI | FamHX | Waist |
| 2183 | Age | BMI | FGA | HDLC |
| 2184 | Age | BMI | FGA | IGF1 |
| 2185 | Age | BMI | FGA | IL6ST |
| 2186 | Age | BMI | FGA | LEP |
| 2187 | Age | BMI | FGA | POMC |
| 2188 | Age | BMI | FGA | Sex |
| 2189 | Age | BMI | FGA | VEGF |

| 4-Panel | Marker 1 | Marker 2 | Marker 3 | Marker 4 |
|---|---|---|---|---|
| 2190 | Age | BMI | FGA | Waist |
| 2191 | Age | BMI | FTH1 | HDLC |
| 2192 | Age | BMI | FTH1 | HT |
| 2193 | Age | BMI | FTH1 | IGF1 |
| 2194 | Age | BMI | FTH1 | IL6ST |
| 2195 | Age | BMI | FTH1 | Ins120 |
| 2196 | Age | BMI | FTH1 | LEP |
| 2197 | Age | BMI | FTH1 | POMC |
| 2198 | Age | BMI | FTH1 | Sex |
| 2199 | Age | BMI | FTH1 | TRIG |
| 2200 | Age | BMI | FTH1 | VEGF |
| 2201 | Age | BMI | FTH1 | Waist |
| 2202 | Age | BMI | FTH1 | WT |
| 2203 | Age | BMI | Gluc120 | Glucose |
| 2204 | Age | BMI | Gluc120 | HDLC |
| 2205 | Age | BMI | Gluc120 | IGF1 |
| 2206 | Age | BMI | Gluc120 | IL6ST |
| 2207 | Age | BMI | Gluc120 | Ins120 |
| 2208 | Age | BMI | Gluc120 | LEP |
| 2209 | Age | BMI | Gluc120 | POMC |
| 2210 | Age | BMI | Gluc120 | Sex |
| 2211 | Age | BMI | Gluc120 | VEGF |
| 2212 | Age | BMI | Gluc120 | Waist |
| 2213 | Age | BMI | Glucose | HBA1C |
| 2214 | Age | BMI | Glucose | HDLC |
| 2215 | Age | BMI | Glucose | HGF |
| 2216 | Age | BMI | Glucose | HT |
| 2217 | Age | BMI | Glucose | IGF1 |
| 2218 | Age | BMI | Glucose | IL18 |
| 2219 | Age | BMI | Glucose | IL6ST |

| 4-Panel | Marker 1 | Marker 2 | Marker 3 | Marker 4 |
|---|---|---|---|---|
| 2220 | Age | BMI | Glucose | Ins120 |
| 2221 | Age | BMI | Glucose | LEP |
| 2222 | Age | BMI | Glucose | POMC |
| 2223 | Age | BMI | Glucose | Sex |
| 2224 | Age | BMI | Glucose | TRIG |
| 2225 | Age | BMI | Glucose | VEGF |
| 2226 | Age | BMI | Glucose | Waist |
| 2227 | Age | BMI | Glucose | WT |
| 2228 | Age | BMI | HBA1C | HDLC |
| 2229 | Age | BMI | HBA1C | IGF1 |
| 2230 | Age | BMI | HBA1C | IL6ST |
| 2231 | Age | BMI | HBA1C | Ins120 |
| 2232 | Age | BMI | HBA1C | LEP |
| 2233 | Age | BMI | HBA1C | POMC |
| 2234 | Age | BMI | HBA1C | Sex |
| 2235 | Age | BMI | HBA1C | VEGF |
| 2236 | Age | BMI | HBA1C | Waist |
| 2237 | Age | BMI | HDLC | HGF |
| 2238 | Age | BMI | HDLC | Hip |
| 2239 | Age | BMI | HDLC | HP |
| 2240 | Age | BMI | HDLC | HT |
| 2241 | Age | BMI | HDLC | ICAM1 |
| 2242 | Age | BMI | HDLC | IGF1 |
| 2243 | Age | BMI | HDLC | IGFBP1 |
| 2244 | Age | BMI | HDLC | IGFBP3 |
| 2245 | Age | BMI | HDLC | IL18 |
| 2246 | Age | BMI | HDLC | IL2RA |
| 2247 | Age | BMI | HDLC | IL6R |
| 2248 | Age | BMI | HDLC | IL6ST |
| 2249 | Age | BMI | HDLC | IL8 |
| 2250 | Age | BMI | HDLC | INHBA |
| 2251 | Age | BMI | HDLC | Ins120 |
| 2252 | Age | BMI | HDLC | Insulin |
| 2253 | Age | BMI | HDLC | LDL |
| 2254 | Age | BMI | HDLC | LEP |
| 2255 | Age | BMI | HDLC | PLAT |
| 2256 | Age | BMI | HDLC | POMC |
| 2257 | Age | BMI | HDLC | SBP |
| 2258 | Age | BMI | HDLC | SCp |
| 2259 | Age | BMI | HDLC | SELE |
| 2260 | Age | BMI | HDLC | SELP |
| 2261 | Age | BMI | HDLC | Sex |
| 2262 | Age | BMI | HDLC | SHBG |
| 2263 | Age | BMI | HDLC | TNFRSF1B |
| 2264 | Age | BMI | HDLC | TRIG |
| 2265 | Age | BMI | HDLC | VCAM1 |
| 2266 | Age | BMI | HDLC | VEGF |
| 2267 | Age | BMI | HDLC | VWF |
| 2268 | Age | BMI | HDLC | Waist |
| 2269 | Age | BMI | HDLC | WT |
| 2270 | Age | BMI | HGF | HT |
| 2271 | Age | BMI | HGF | IGF1 |
| 2272 | Age | BMI | HGF | IL6ST |
| 2273 | Age | BMI | HGF | Ins120 |
| 2274 | Age | BMI | HGF | LEP |
| 2275 | Age | BMI | HGF | POMC |
| 2276 | Age | BMI | HGF | Sex |
| 2277 | Age | BMI | HGF | VEGF |
| 2278 | Age | BMI | HGF | Waist |
| 2279 | Age | BMI | HGF | WT |

| 4-Panel | Marker 1 | Marker 2 | Marker 3 | Marker 4 |
|---|---|---|---|---|
| 2280 | Age | BMI | Hip | IGF1 |
| 2281 | Age | BMI | Hip | IL6ST |
| 2282 | Age | BMI | Hip | Ins120 |
| 2283 | Age | BMI | Hip | LEP |
| 2284 | Age | BMI | Hip | POMC |
| 2285 | Age | BMI | Hip | Sex |
| 2286 | Age | BMI | Hip | VEGF |
| 2287 | Age | BMI | Hip | Waist |
| 2288 | Age | BMI | HP | IGF1 |
| 2289 | Age | BMI | HP | IL6ST |
| 2290 | Age | BMI | HP | Ins120 |
| 2291 | Age | BMI | HP | LEP |
| 2292 | Age | BMI | HP | POMC |
| 2293 | Age | BMI | HP | Sex |
| 2294 | Age | BMI | HP | VEGF |
| 2295 | Age | BMI | HP | Waist |
| 2296 | Age | BMI | HT | IGF1 |
| 2297 | Age | BMI | HT | IL2RA |
| 2298 | Age | BMI | HT | IL6ST |
| 2299 | Age | BMI | HT | Ins120 |
| 2300 | Age | BMI | HT | LEP |
| 2301 | Age | BMI | HT | POMC |
| 2302 | Age | BMI | HT | Sex |
| 2303 | Age | BMI | HT | TRIG |
| 2304 | Age | BMI | HT | VEGF |
| 2305 | Age | BMI | HT | VWF |
| 2306 | Age | BMI | HT | Waist |
| 2307 | Age | BMI | ICAM1 | IGF1 |
| 2308 | Age | BMI | ICAM1 | IL6ST |
| 2309 | Age | BMI | ICAM1 | Ins120 |

| 4-Panel | Marker 1 | Marker 2 | Marker 3 | Marker 4 |
|---|---|---|---|---|
| 2310 | Age | BMI | ICAM1 | LEP |
| 2311 | Age | BMI | ICAM1 | POMC |
| 2312 | Age | BMI | ICAM1 | Sex |
| 2313 | Age | BMI | ICAM1 | VEGF |
| 2314 | Age | BMI | ICAM1 | Waist |
| 2315 | Age | BMI | IGF1 | IGFBP1 |
| 2316 | Age | BMI | IGF1 | IGFBP3 |
| 2317 | Age | BMI | IGF1 | IL18 |
| 2318 | Age | BMI | IGF1 | IL2RA |
| 2319 | Age | BMI | IGF1 | IL6R |
| 2320 | Age | BMI | IGF1 | IL6ST |
| 2321 | Age | BMI | IGF1 | IL8 |
| 2322 | Age | BMI | IGF1 | INHBA |
| 2323 | Age | BMI | IGF1 | Ins120 |
| 2324 | Age | BMI | IGF1 | Insulin |
| 2325 | Age | BMI | IGF1 | LDL |
| 2326 | Age | BMI | IGF1 | LEP |
| 2327 | Age | BMI | IGF1 | PLAT |
| 2328 | Age | BMI | IGF1 | POMC |
| 2329 | Age | BMI | IGF1 | SBP |
| 2330 | Age | BMI | IGF1 | SCp |
| 2331 | Age | BMI | IGF1 | SELE |
| 2332 | Age | BMI | IGF1 | SELP |
| 2333 | Age | BMI | IGF1 | Sex |
| 2334 | Age | BMI | IGF1 | SHBG |
| 2335 | Age | BMI | IGF1 | TNFRSF1B |
| 2336 | Age | BMI | IGF1 | TRIG |
| 2337 | Age | BMI | IGF1 | VCAM1 |
| 2338 | Age | BMI | IGF1 | VEGF |
| 2339 | Age | BMI | IGF1 | VWF |

FIG. 15NN

| 4. Panel | Marker 1 | Marker 2 | Marker 3 | Marker 4 |
|---|---|---|---|---|
| 2340 | Age | BMI | IGF1 | Waist |
| 2341 | Age | BMI | IGF1 | WT |
| 2342 | Age | BMI | IGFBP1 | IL6ST |
| 2343 | Age | BMI | IGFBP1 | Ins120 |
| 2344 | Age | BMI | IGFBP1 | LEP |
| 2345 | Age | BMI | IGFBP1 | POMC |
| 2346 | Age | BMI | IGFBP1 | Sex |
| 2347 | Age | BMI | IGFBP1 | VEGF |
| 2348 | Age | BMI | IGFBP1 | Waist |
| 2349 | Age | BMI | IGFBP3 | IL6ST |
| 2350 | Age | BMI | IGFBP3 | Ins120 |
| 2351 | Age | BMI | IGFBP3 | LEP |
| 2352 | Age | BMI | IGFBP3 | POMC |
| 2353 | Age | BMI | IGFBP3 | Sex |
| 2354 | Age | BMI | IGFBP3 | VEGF |
| 2355 | Age | BMI | IGFBP3 | Waist |
| 2356 | Age | BMI | IL18 | IL6ST |
| 2357 | Age | BMI | IL18 | Ins120 |
| 2358 | Age | BMI | IL18 | LEP |
| 2359 | Age | BMI | IL18 | POMC |
| 2360 | Age | BMI | IL18 | Sex |
| 2361 | Age | BMI | IL18 | VEGF |
| 2362 | Age | BMI | IL18 | Waist |
| 2363 | Age | BMI | IL2RA | IL6ST |
| 2364 | Age | BMI | IL2RA | Ins120 |
| 2365 | Age | BMI | IL2RA | LEP |
| 2366 | Age | BMI | IL2RA | POMC |
| 2367 | Age | BMI | IL2RA | Sex |
| 2368 | Age | BMI | IL2RA | VEGF |
| 2369 | Age | BMI | IL2RA | Waist |
| 2370 | Age | BMI | IL2RA | WT |
| 2371 | Age | BMI | IL6R | IL6ST |
| 2372 | Age | BMI | IL6R | Ins120 |
| 2373 | Age | BMI | IL6R | LEP |
| 2374 | Age | BMI | IL6R | POMC |
| 2375 | Age | BMI | IL6R | Sex |
| 2376 | Age | BMI | IL6R | VEGF |
| 2377 | Age | BMI | IL6R | Waist |
| 2378 | Age | BMI | IL6ST | IL8 |
| 2379 | Age | BMI | IL6ST | INHBA |
| 2380 | Age | BMI | IL6ST | Ins120 |
| 2381 | Age | BMI | IL6ST | Insulin |
| 2382 | Age | BMI | IL6ST | LDL |
| 2383 | Age | BMI | IL6ST | LEP |
| 2384 | Age | BMI | IL6ST | PLAT |
| 2385 | Age | BMI | IL6ST | POMC |
| 2386 | Age | BMI | IL6ST | SBP |
| 2387 | Age | BMI | IL6ST | SCp |
| 2388 | Age | BMI | IL6ST | SELE |
| 2389 | Age | BMI | IL6ST | SELP |
| 2390 | Age | BMI | IL6ST | Sex |
| 2391 | Age | BMI | IL6ST | SHBG |
| 2392 | Age | BMI | IL6ST | TNFRSF1B |
| 2393 | Age | BMI | IL6ST | TRIG |
| 2394 | Age | BMI | IL6ST | VCAM1 |
| 2395 | Age | BMI | IL6ST | VEGF |
| 2396 | Age | BMI | IL6ST | VWF |
| 2397 | Age | BMI | IL6ST | Waist |
| 2398 | Age | BMI | IL6ST | WT |
| 2399 | Age | BMI | IL8 | Ins120 |

FIG. 1500

| 4-Panel | Marker 1 | Marker 2 | Marker 3 | Marker 4 |
|---|---|---|---|---|
| 2400 | Age | BMI | IL8 | LEP |
| 2401 | Age | BMI | IL8 | POMC |
| 2402 | Age | BMI | IL8 | Sex |
| 2403 | Age | BMI | IL8 | VEGF |
| 2404 | Age | BMI | IL8 | Waist |
| 2405 | Age | BMI | INHBA | Ins120 |
| 2406 | Age | BMI | INHBA | LEP |
| 2407 | Age | BMI | INHBA | POMC |
| 2408 | Age | BMI | INHBA | Sex |
| 2409 | Age | BMI | INHBA | VEGF |
| 2410 | Age | BMI | INHBA | Waist |
| 2411 | Age | BMI | Ins120 | Insulin |
| 2412 | Age | BMI | Ins120 | LDL |
| 2413 | Age | BMI | Ins120 | LEP |
| 2414 | Age | BMI | Ins120 | PLAT |
| 2415 | Age | BMI | Ins120 | POMC |
| 2416 | Age | BMI | Ins120 | SCp |
| 2417 | Age | BMI | Ins120 | SELE |
| 2418 | Age | BMI | Ins120 | SELP |
| 2419 | Age | BMI | Ins120 | Sex |
| 2420 | Age | BMI | Ins120 | SHBG |
| 2421 | Age | BMI | Ins120 | TNFRSF1B |
| 2422 | Age | BMI | Ins120 | TRIG |
| 2423 | Age | BMI | Ins120 | VCAM1 |
| 2424 | Age | BMI | Ins120 | VEGF |
| 2425 | Age | BMI | Ins120 | VWF |
| 2426 | Age | BMI | Ins120 | Waist |
| 2427 | Age | BMI | Ins120 | WT |
| 2428 | Age | BMI | Insulin | LEP |
| 2429 | Age | BMI | Insulin | POMC |
| 2430 | Age | BMI | Insulin | Sex |
| 2431 | Age | BMI | Insulin | VEGF |
| 2432 | Age | BMI | Insulin | Waist |
| 2433 | Age | BMI | LDL | LEP |
| 2434 | Age | BMI | LDL | POMC |
| 2435 | Age | BMI | LDL | Sex |
| 2436 | Age | BMI | LDL | VEGF |
| 2437 | Age | BMI | LDL | Waist |
| 2438 | Age | BMI | LEP | PLAT |
| 2439 | Age | BMI | LEP | POMC |
| 2440 | Age | BMI | LEP | SBP |
| 2441 | Age | BMI | LEP | SCp |
| 2442 | Age | BMI | LEP | SELE |
| 2443 | Age | BMI | LEP | SELP |
| 2444 | Age | BMI | LEP | Sex |
| 2445 | Age | BMI | LEP | SHBG |
| 2446 | Age | BMI | LEP | TNFRSF1B |
| 2447 | Age | BMI | LEP | TRIG |
| 2448 | Age | BMI | LEP | VCAM1 |
| 2449 | Age | BMI | LEP | VEGF |
| 2450 | Age | BMI | LEP | VWF |
| 2451 | Age | BMI | LEP | Waist |
| 2452 | Age | BMI | LEP | WT |
| 2453 | Age | BMI | PLAT | POMC |
| 2454 | Age | BMI | PLAT | Sex |
| 2455 | Age | BMI | PLAT | VEGF |
| 2456 | Age | BMI | PLAT | Waist |
| 2457 | Age | BMI | POMC | SBP |
| 2458 | Age | BMI | POMC | SCp |
| 2459 | Age | BMI | POMC | SELE |

| 4-Panel | Marker 1 | Marker 2 | Marker 3 | Marker 4 |
|---|---|---|---|---|
| 2460 | Age | BMI | POMC | SELP |
| 2461 | Age | BMI | POMC | Sex |
| 2462 | Age | BMI | POMC | SHBG |
| 2463 | Age | BMI | POMC | TNFRSF1B |
| 2464 | Age | BMI | POMC | TRIG |
| 2465 | Age | BMI | POMC | VCAM1 |
| 2466 | Age | BMI | POMC | VEGF |
| 2467 | Age | BMI | POMC | VWF |
| 2468 | Age | BMI | POMC | Waist |
| 2469 | Age | BMI | POMC | WT |
| 2470 | Age | BMI | SBP | Sex |
| 2471 | Age | BMI | SBP | VEGF |
| 2472 | Age | BMI | SBP | Waist |
| 2473 | Age | BMI | SCp | Sex |
| 2474 | Age | BMI | SCp | VEGF |
| 2475 | Age | BMI | SCp | Waist |
| 2476 | Age | BMI | SELE | Sex |
| 2477 | Age | BMI | SELE | VEGF |
| 2478 | Age | BMI | SELE | Waist |
| 2479 | Age | BMI | SELP | Sex |
| 2480 | Age | BMI | SELP | VEGF |
| 2481 | Age | BMI | SELP | Waist |
| 2482 | Age | BMI | Sex | SHBG |
| 2483 | Age | BMI | Sex | TNFRSF1B |
| 2484 | Age | BMI | Sex | TRIG |
| 2485 | Age | BMI | Sex | VCAM1 |
| 2486 | Age | BMI | Sex | VEGF |
| 2487 | Age | BMI | Sex | VWF |
| 2488 | Age | BMI | Sex | Waist |
| 2489 | Age | BMI | Sex | WT |
| 2490 | Age | BMI | SHBG | VEGF |
| 2491 | Age | BMI | SHBG | Waist |
| 2492 | Age | BMI | TNFRSF1B | WT |
| 2493 | Age | BMI | TNFRSF1B | Waist |
| 2494 | Age | BMI | TRIG | VEGF |
| 2495 | Age | BMI | TRIG | Waist |
| 2496 | Age | BMI | TRIG | WT |
| 2497 | Age | BMI | VCAM1 | VEGF |
| 2498 | Age | BMI | VCAM1 | Waist |
| 2499 | Age | BMI | VEGF | VWF |
| 2500 | Age | BMI | VEGF | Waist |
| 2501 | Age | BMI | VEGF | WT |
| 2502 | Age | BMI | VEGF | Waist |
| 2503 | Age | BMI | VWF | Waist |
| 2504 | Age | BMI | VWF | WT |
| 2505 | Age | BMI | Waist | WT |
| 2506 | Age | C3 | CCL2 | CD40 |
| 2507 | Age | C3 | CCL2 | HDLC |
| 2508 | Age | C3 | CCL2 | HT |
| 2509 | Age | C3 | CCL2 | IGF1 |
| 2510 | Age | C3 | CCL2 | IL6ST |
| 2511 | Age | C3 | CCL2 | LEP |
| 2512 | Age | C3 | CCL2 | POMC |
| 2513 | Age | C3 | CCL2 | Sex |
| 2514 | Age | C3 | CCL2 | VEGF |
| 2515 | Age | C3 | CD14 | POMC |
| 2516 | Age | C3 | CD40 | Glucose |
| 2517 | Age | C3 | CD40 | HDLC |
| 2518 | Age | C3 | CD40 | IGF1 |
| 2519 | Age | C3 | CD40 | IL6ST |
| 2519 | Age | C3 | CD40 | LEP |

FIG. 15PP

| 4-Panel | Marker 1 | Marker 2 | Marker 3 | Marker 4 |
|---|---|---|---|---|
| 2520 | Age | C3 | CD40 | POMC |
| 2521 | Age | C3 | CD40 | Sex |
| 2522 | Age | C3 | CD40 | VEGF |
| 2523 | Age | C3 | CDK5 | LEP |
| 2524 | Age | C3 | CDK5 | POMC |
| 2525 | Age | C3 | CHOL | HDLC |
| 2526 | Age | C3 | CHOL | LEP |
| 2527 | Age | C3 | CHOL | POMC |
| 2528 | Age | C3 | CRP | LEP |
| 2529 | Age | C3 | CRP | POMC |
| 2530 | Age | C3 | DBP | LEP |
| 2531 | Age | C3 | DBP | POMC |
| 2532 | Age | C3 | DPP4 | HDLC |
| 2533 | Age | C3 | DPP4 | IGF1 |
| 2534 | Age | C3 | DPP4 | LEP |
| 2535 | Age | C3 | DPP4 | POMC |
| 2536 | Age | C3 | DPP4 | VEGF |
| 2537 | Age | C3 | EGF | LEP |
| 2538 | Age | C3 | EGF | POMC |
| 2539 | Age | C3 | ENG | LEP |
| 2540 | Age | C3 | ENG | POMC |
| 2541 | Age | C3 | FamHX | LEP |
| 2542 | Age | C3 | FamHX | POMC |
| 2543 | Age | C3 | FGA | LEP |
| 2544 | Age | C3 | FGA | POMC |
| 2545 | Age | C3 | FTH1 | HDLC |
| 2546 | Age | C3 | FTH1 | LEP |
| 2547 | Age | C3 | FTH1 | POMC |
| 2548 | Age | C3 | FTH1 | Sex |
| 2549 | Age | C3 | Gluc120 | LEP |

| 4-Panel | Marker 1 | Marker 2 | Marker 3 | Marker 4 |
|---|---|---|---|---|
| 2550 | Age | C3 | Gluc120 | POMC |
| 2551 | Age | C3 | Glucose | HDLC |
| 2552 | Age | C3 | Glucose | IGF1 |
| 2553 | Age | C3 | Glucose | IL6ST |
| 2554 | Age | C3 | Glucose | LEP |
| 2555 | Age | C3 | Glucose | POMC |
| 2556 | Age | C3 | Glucose | Sex |
| 2557 | Age | C3 | Glucose | VEGF |
| 2558 | Age | C3 | HBA1C | LEP |
| 2559 | Age | C3 | HBA1C | POMC |
| 2560 | Age | C3 | HDLC | Hip |
| 2561 | Age | C3 | HDLC | IGF1 |
| 2562 | Age | C3 | HDLC | IGFBP1 |
| 2563 | Age | C3 | HDLC | IL18 |
| 2564 | Age | C3 | HDLC | IL2RA |
| 2565 | Age | C3 | HDLC | IL6ST |
| 2566 | Age | C3 | HDLC | Insulin |
| 2567 | Age | C3 | HDLC | LEP |
| 2568 | Age | C3 | HDLC | POMC |
| 2569 | Age | C3 | HDLC | SCp |
| 2570 | Age | C3 | HDLC | Sex |
| 2571 | Age | C3 | HDLC | TRIG |
| 2572 | Age | C3 | HDLC | VCAM1 |
| 2573 | Age | C3 | HDLC | VEGF |
| 2574 | Age | C3 | HDLC | Waist |
| 2575 | Age | C3 | HDLC | WT |
| 2576 | Age | C3 | HGF | LEP |
| 2577 | Age | C3 | HGF | POMC |
| 2578 | Age | C3 | Hip | IGF1 |
| 2579 | Age | C3 | Hip | LEP |

FIG. 15QQ

| 4-Panel | Marker 1 | Marker 2 | Marker 3 | Marker 4 |
|---|---|---|---|---|
| 2580 | Age | C3 | Hip | POMC |
| 2581 | Age | C3 | HP | POMC |
| 2582 | Age | C3 | HT | IGF1 |
| 2583 | Age | C3 | HT | LEP |
| 2584 | Age | C3 | HT | POMC |
| 2585 | Age | C3 | HT | VEGF |
| 2586 | Age | C3 | ICAM1 | LEP |
| 2587 | Age | C3 | ICAM1 | POMC |
| 2588 | Age | C3 | IGF1 | IL2RA |
| 2589 | Age | C3 | IGF1 | IL6ST |
| 2590 | Age | C3 | IGF1 | Insulin |
| 2591 | Age | C3 | IGF1 | LEP |
| 2592 | Age | C3 | IGF1 | POMC |
| 2593 | Age | C3 | IGF1 | Sex |
| 2594 | Age | C3 | IGF1 | VCAM1 |
| 2595 | Age | C3 | IGF1 | VEGF |
| 2596 | Age | C3 | IGFBP1 | LEP |
| 2597 | Age | C3 | IGFBP1 | POMC |
| 2598 | Age | C3 | IGFBP3 | LEP |
| 2599 | Age | C3 | IGFBP3 | POMC |
| 2600 | Age | C3 | IL18 | LEP |
| 2601 | Age | C3 | IL18 | POMC |
| 2602 | Age | C3 | IL2RA | LEP |
| 2603 | Age | C3 | IL2RA | POMC |
| 2604 | Age | C3 | IL2RA | Sex |
| 2605 | Age | C3 | IL6R | LEP |
| 2606 | Age | C3 | IL6R | POMC |
| 2607 | Age | C3 | IL6ST | LEP |
| 2608 | Age | C3 | IL6ST | POMC |
| 2609 | Age | C3 | IL6ST | Sex |

| 4-Panel | Marker 1 | Marker 2 | Marker 3 | Marker 4 |
|---|---|---|---|---|
| 2610 | Age | C3 | IL6ST | TNFRSF1B |
| 2611 | Age | C3 | IL6ST | VEGF |
| 2612 | Age | C3 | IL8 | LEP |
| 2613 | Age | C3 | IL8 | POMC |
| 2614 | Age | C3 | INHBA | LEP |
| 2615 | Age | C3 | INHBA | POMC |
| 2616 | Age | C3 | Ins120 | Insulin |
| 2617 | Age | C3 | Ins120 | LEP |
| 2618 | Age | C3 | Ins120 | POMC |
| 2619 | Age | C3 | Insulin | LEP |
| 2620 | Age | C3 | Insulin | POMC |
| 2621 | Age | C3 | Insulin | Sex |
| 2622 | Age | C3 | Insulin | VEGF |
| 2623 | Age | C3 | LDL | LEP |
| 2624 | Age | C3 | LDL | POMC |
| 2625 | Age | C3 | LEP | PLAT |
| 2626 | Age | C3 | LEP | POMC |
| 2627 | Age | C3 | LEP | SBP |
| 2628 | Age | C3 | LEP | SCp |
| 2629 | Age | C3 | LEP | SELE |
| 2630 | Age | C3 | LEP | SELP |
| 2631 | Age | C3 | LEP | Sex |
| 2632 | Age | C3 | LEP | SHBG |
| 2633 | Age | C3 | LEP | TNFRSF1B |
| 2634 | Age | C3 | LEP | TRIG |
| 2635 | Age | C3 | LEP | VCAM1 |
| 2636 | Age | C3 | LEP | VEGF |
| 2637 | Age | C3 | LEP | VWF |
| 2638 | Age | C3 | LEP | Waist |
| 2639 | Age | C3 | LEP | WT |

FIG. 15RR

| 4-Panel | Marker 1 | Marker 2 | Marker 3 | Marker 4 |
|---|---|---|---|---|
| 2640 | Age | C3 | PLAT | POMC |
| 2641 | Age | C3 | POMC | SBP |
| 2642 | Age | C3 | POMC | SCp |
| 2643 | Age | C3 | POMC | SELE |
| 2644 | Age | C3 | POMC | SELP |
| 2645 | Age | C3 | POMC | Sex |
| 2646 | Age | C3 | POMC | SHBG |
| 2647 | Age | C3 | POMC | TNFRSF1B |
| 2648 | Age | C3 | POMC | TRIG |
| 2649 | Age | C3 | POMC | VCAM1 |
| 2650 | Age | C3 | POMC | VEGF |
| 2651 | Age | C3 | POMC | VWF |
| 2652 | Age | C3 | POMC | Waist |
| 2653 | Age | C3 | POMC | WT |
| 2654 | Age | C3 | Sex | VEGF |
| 2655 | Age | C3 | Sex | Waist |
| 2656 | Age | C3 | Sex | WT |
| 2657 | Age | CCL2 | CD14 | CD40 |
| 2658 | Age | CCL2 | CD14 | DPP4 |
| 2659 | Age | CCL2 | CD14 | Glucose |
| 2660 | Age | CCL2 | CD14 | HDLC |
| 2661 | Age | CCL2 | CD14 | Hip |
| 2662 | Age | CCL2 | CD14 | HT |
| 2663 | Age | CCL2 | CD14 | IGF1 |
| 2664 | Age | CCL2 | CD14 | IL18 |
| 2665 | Age | CCL2 | CD14 | IL6ST |
| 2666 | Age | CCL2 | CD14 | IL8 |
| 2667 | Age | CCL2 | CD14 | LEP |
| 2668 | Age | CCL2 | CD14 | POMC |
| 2669 | Age | CCL2 | CD14 | Sex |

| 4-Panel | Marker 1 | Marker 2 | Marker 3 | Marker 4 |
|---|---|---|---|---|
| 2670 | Age | CCL2 | CD14 | VEGF |
| 2671 | Age | CCL2 | CD40 | CDK5 |
| 2672 | Age | CCL2 | CD40 | CHOL |
| 2673 | Age | CCL2 | CD40 | CRP |
| 2674 | Age | CCL2 | CD40 | DBP |
| 2675 | Age | CCL2 | CD40 | DPP4 |
| 2676 | Age | CCL2 | CD40 | EGF |
| 2677 | Age | CCL2 | CD40 | ENG |
| 2678 | Age | CCL2 | CD40 | FamHX |
| 2679 | Age | CCL2 | CD40 | FGA |
| 2680 | Age | CCL2 | CD40 | FTH1 |
| 2681 | Age | CCL2 | CD40 | Gluc120 |
| 2682 | Age | CCL2 | CD40 | Glucose |
| 2683 | Age | CCL2 | CD40 | HBA1C |
| 2684 | Age | CCL2 | CD40 | HDLC |
| 2685 | Age | CCL2 | CD40 | HGF |
| 2686 | Age | CCL2 | CD40 | Hip |
| 2687 | Age | CCL2 | CD40 | HP |
| 2688 | Age | CCL2 | CD40 | HT |
| 2689 | Age | CCL2 | CD40 | ICAM1 |
| 2690 | Age | CCL2 | CD40 | IGF1 |
| 2691 | Age | CCL2 | CD40 | IGFBP1 |
| 2692 | Age | CCL2 | CD40 | IGFBP3 |
| 2693 | Age | CCL2 | CD40 | IL18 |
| 2694 | Age | CCL2 | CD40 | IL2RA |
| 2695 | Age | CCL2 | CD40 | IL6R |
| 2696 | Age | CCL2 | CD40 | IL6ST |
| 2697 | Age | CCL2 | CD40 | IL8 |
| 2698 | Age | CCL2 | CD40 | INHBA |
| 2699 | Age | CCL2 | CD40 | Ins120 |

FIG. 15SS

| 4-Panel | Marker 1 | Marker 2 | Marker 3 | Marker 4 |
|---|---|---|---|---|
| 2700 | Age | CCL2 | CD40 | Insulin |
| 2701 | Age | CCL2 | CD40 | LDL |
| 2702 | Age | CCL2 | CD40 | LEP |
| 2703 | Age | CCL2 | CD40 | PLAT |
| 2704 | Age | CCL2 | CD40 | POMC |
| 2705 | Age | CCL2 | CD40 | SBP |
| 2706 | Age | CCL2 | CD40 | SCp |
| 2707 | Age | CCL2 | CD40 | SELE |
| 2708 | Age | CCL2 | CD40 | SELP |
| 2709 | Age | CCL2 | CD40 | Sex |
| 2710 | Age | CCL2 | CD40 | SHBG |
| 2711 | Age | CCL2 | CD40 | TNFRSF1B |
| 2712 | Age | CCL2 | CD40 | TRIG |
| 2713 | Age | CCL2 | CD40 | VCAM1 |
| 2714 | Age | CCL2 | CD40 | VEGF |
| 2715 | Age | CCL2 | CD40 | VWF |
| 2716 | Age | CCL2 | CD40 | Waist |
| 2717 | Age | CCL2 | CD40 | WT |
| 2718 | Age | CCL2 | CDK5 | HDLC |
| 2719 | Age | CCL2 | CDK5 | HT |
| 2720 | Age | CCL2 | CDK5 | IGF1 |
| 2721 | Age | CCL2 | CDK5 | IL6ST |
| 2722 | Age | CCL2 | CDK5 | LEP |
| 2723 | Age | CCL2 | CDK5 | POMC |
| 2724 | Age | CCL2 | CDK5 | Sex |
| 2725 | Age | CCL2 | CDK5 | VEGF |
| 2726 | Age | CCL2 | CHOL | HDLC |
| 2727 | Age | CCL2 | CHOL | HT |
| 2728 | Age | CCL2 | CHOL | IGF1 |
| 2729 | Age | CCL2 | CHOL | LEP |

| 4-Panel | Marker 1 | Marker 2 | Marker 3 | Marker 4 |
|---|---|---|---|---|
| 2730 | Age | CCL2 | CHOL | POMC |
| 2731 | Age | CCL2 | CHOL | Sex |
| 2732 | Age | CCL2 | CHOL | VEGF |
| 2733 | Age | CCL2 | CRP | DPP4 |
| 2734 | Age | CCL2 | CRP | Glucose |
| 2735 | Age | CCL2 | CRP | HDLC |
| 2736 | Age | CCL2 | CRP | Hip |
| 2737 | Age | CCL2 | CRP | HT |
| 2738 | Age | CCL2 | CRP | IGF1 |
| 2739 | Age | CCL2 | CRP | IL18 |
| 2740 | Age | CCL2 | CRP | IL6ST |
| 2741 | Age | CCL2 | CRP | IL8 |
| 2742 | Age | CCL2 | CRP | Insulin |
| 2743 | Age | CCL2 | CRP | LEP |
| 2744 | Age | CCL2 | CRP | POMC |
| 2745 | Age | CCL2 | CRP | SELP |
| 2746 | Age | CCL2 | CRP | Sex |
| 2747 | Age | CCL2 | CRP | VEGF |
| 2748 | Age | CCL2 | DBP | HDLC |
| 2749 | Age | CCL2 | DBP | HT |
| 2750 | Age | CCL2 | DBP | IGF1 |
| 2751 | Age | CCL2 | DBP | IL6ST |
| 2752 | Age | CCL2 | DBP | LEP |
| 2753 | Age | CCL2 | DBP | POMC |
| 2754 | Age | CCL2 | DBP | Sex |
| 2755 | Age | CCL2 | DBP | VEGF |
| 2756 | Age | CCL2 | DPP4 | EGF |
| 2757 | Age | CCL2 | DPP4 | FamHX |
| 2758 | Age | CCL2 | DPP4 | FTH1 |
| 2759 | Age | CCL2 | DPP4 | Glucose |

| 4-Panel | Marker 1 | Marker 2 | Marker 3 | Marker 4 |
|---|---|---|---|---|
| 2760 | Age | CCL2 | DPP4 | HDLC |
| 2761 | Age | CCL2 | DPP4 | Hip |
| 2762 | Age | CCL2 | DPP4 | HP |
| 2763 | Age | CCL2 | DPP4 | HT |
| 2764 | Age | CCL2 | DPP4 | ICAM1 |
| 2765 | Age | CCL2 | DPP4 | IGF1 |
| 2766 | Age | CCL2 | DPP4 | IL18 |
| 2767 | Age | CCL2 | DPP4 | IL2RA |
| 2768 | Age | CCL2 | DPP4 | IL6R |
| 2769 | Age | CCL2 | DPP4 | IL6ST |
| 2770 | Age | CCL2 | DPP4 | IL8 |
| 2771 | Age | CCL2 | DPP4 | Ins120 |
| 2772 | Age | CCL2 | DPP4 | LEP |
| 2773 | Age | CCL2 | DPP4 | POMC |
| 2774 | Age | CCL2 | DPP4 | SELP |
| 2775 | Age | CCL2 | DPP4 | Sex |
| 2776 | Age | CCL2 | DPP4 | TNFRSF1B |
| 2777 | Age | CCL2 | DPP4 | VEGF |
| 2778 | Age | CCL2 | EGF | Glucose |
| 2779 | Age | CCL2 | EGF | HDLC |
| 2780 | Age | CCL2 | EGF | Hip |
| 2781 | Age | CCL2 | EGF | HT |
| 2782 | Age | CCL2 | EGF | IGF1 |
| 2783 | Age | CCL2 | EGF | IL6ST |
| 2784 | Age | CCL2 | EGF | LEP |
| 2785 | Age | CCL2 | EGF | POMC |
| 2786 | Age | CCL2 | EGF | Sex |
| 2787 | Age | CCL2 | EGF | VEGF |
| 2788 | Age | CCL2 | ENG | HDLC |
| 2789 | Age | CCL2 | ENG | HT |
| 2790 | Age | CCL2 | ENG | IGF1 |
| 2791 | Age | CCL2 | ENG | IL6ST |
| 2792 | Age | CCL2 | ENG | LEP |
| 2793 | Age | CCL2 | ENG | POMC |
| 2794 | Age | CCL2 | ENG | Sex |
| 2795 | Age | CCL2 | ENG | VEGF |
| 2796 | Age | CCL2 | FamHX | Glucose |
| 2797 | Age | CCL2 | FamHX | HDLC |
| 2798 | Age | CCL2 | FamHX | Hip |
| 2799 | Age | CCL2 | FamHX | HT |
| 2800 | Age | CCL2 | FamHX | IGF1 |
| 2801 | Age | CCL2 | FamHX | IL6ST |
| 2802 | Age | CCL2 | FamHX | LEP |
| 2803 | Age | CCL2 | FamHX | POMC |
| 2804 | Age | CCL2 | FamHX | Sex |
| 2805 | Age | CCL2 | FamHX | VEGF |
| 2806 | Age | CCL2 | FGA | HDLC |
| 2807 | Age | CCL2 | FGA | Hip |
| 2808 | Age | CCL2 | FGA | HT |
| 2809 | Age | CCL2 | FGA | IGF1 |
| 2810 | Age | CCL2 | FGA | IL6ST |
| 2811 | Age | CCL2 | FGA | LEP |
| 2812 | Age | CCL2 | FGA | POMC |
| 2813 | Age | CCL2 | FGA | Sex |
| 2814 | Age | CCL2 | FGA | VEGF |
| 2815 | Age | CCL2 | FTH1 | HDLC |
| 2816 | Age | CCL2 | FTH1 | Hip |
| 2817 | Age | CCL2 | FTH1 | HT |
| 2818 | Age | CCL2 | FTH1 | IGF1 |
| 2819 | Age | CCL2 | FTH1 | IL6ST |
| 2819 | Age | CCL2 | FTH1 | LEP |

| 4-Panel | Marker 1 | Marker 2 | Marker 3 | Marker 4 |
|---|---|---|---|---|
| 2820 | Age | CCL2 | FTH1 | POMC |
| 2821 | Age | CCL2 | FTH1 | Sex |
| 2822 | Age | CCL2 | FTH1 | VEGF |
| 2823 | Age | CCL2 | Gluc120 | Glucose |
| 2824 | Age | CCL2 | Gluc120 | HDLC |
| 2825 | Age | CCL2 | Gluc120 | HT |
| 2826 | Age | CCL2 | Gluc120 | IGF1 |
| 2827 | Age | CCL2 | Gluc120 | IL6ST |
| 2828 | Age | CCL2 | Gluc120 | LEP |
| 2829 | Age | CCL2 | Gluc120 | POMC |
| 2830 | Age | CCL2 | Gluc120 | Sex |
| 2831 | Age | CCL2 | Gluc120 | VEGF |
| 2832 | Age | CCL2 | Glucose | HBA1C |
| 2833 | Age | CCL2 | Glucose | HDLC |
| 2834 | Age | CCL2 | Glucose | HGF |
| 2835 | Age | CCL2 | Glucose | Hip |
| 2836 | Age | CCL2 | Glucose | HP |
| 2837 | Age | CCL2 | Glucose | HT |
| 2838 | Age | CCL2 | Glucose | ICAM1 |
| 2839 | Age | CCL2 | Glucose | IGF1 |
| 2840 | Age | CCL2 | Glucose | IL18 |
| 2841 | Age | CCL2 | Glucose | IL6ST |
| 2842 | Age | CCL2 | Glucose | IL8 |
| 2843 | Age | CCL2 | Glucose | Ins120 |
| 2844 | Age | CCL2 | Glucose | LEP |
| 2845 | Age | CCL2 | Glucose | POMC |
| 2846 | Age | CCL2 | Glucose | SELP |
| 2847 | Age | CCL2 | Glucose | Sex |
| 2848 | Age | CCL2 | Glucose | TNFRSF1B |
| 2849 | Age | CCL2 | Glucose | TRIG |

| 4-Panel | Marker 1 | Marker 2 | Marker 3 | Marker 4 |
|---|---|---|---|---|
| 2850 | Age | CCL2 | Glucose | VCAM1 |
| 2851 | Age | CCL2 | Glucose | VEGF |
| 2852 | Age | CCL2 | HBA1C | HDLC |
| 2853 | Age | CCL2 | HBA1C | Hip |
| 2854 | Age | CCL2 | HBA1C | HT |
| 2855 | Age | CCL2 | HBA1C | IGF1 |
| 2856 | Age | CCL2 | HBA1C | IL6ST |
| 2857 | Age | CCL2 | HBA1C | LEP |
| 2858 | Age | CCL2 | HBA1C | POMC |
| 2859 | Age | CCL2 | HBA1C | Sex |
| 2860 | Age | CCL2 | HBA1C | VEGF |
| 2861 | Age | CCL2 | HDLC | HGF |
| 2862 | Age | CCL2 | HDLC | Hip |
| 2863 | Age | CCL2 | HDLC | HP |
| 2864 | Age | CCL2 | HDLC | HT |
| 2865 | Age | CCL2 | HDLC | ICAM1 |
| 2866 | Age | CCL2 | HDLC | IGF1 |
| 2867 | Age | CCL2 | HDLC | IGFBP1 |
| 2868 | Age | CCL2 | HDLC | IGFBP3 |
| 2869 | Age | CCL2 | HDLC | IL18 |
| 2870 | Age | CCL2 | HDLC | IL2RA |
| 2871 | Age | CCL2 | HDLC | IL6R |
| 2872 | Age | CCL2 | HDLC | IL6ST |
| 2873 | Age | CCL2 | HDLC | IL8 |
| 2874 | Age | CCL2 | HDLC | INHBA |
| 2875 | Age | CCL2 | HDLC | Ins120 |
| 2876 | Age | CCL2 | HDLC | Insulin |
| 2877 | Age | CCL2 | HDLC | LDL |
| 2878 | Age | CCL2 | HDLC | LEP |
| 2879 | Age | CCL2 | HDLC | PLAT |

FIG. 15VV

| 4-Panel | Marker 1 | Marker 2 | Marker 3 | Marker 4 |
|---|---|---|---|---|
| 2880 | Age | CCL2 | HDLC | POMC |
| 2881 | Age | CCL2 | HDLC | SBP |
| 2882 | Age | CCL2 | HDLC | SCp |
| 2883 | Age | CCL2 | HDLC | SELE |
| 2884 | Age | CCL2 | HDLC | SELP |
| 2885 | Age | CCL2 | HDLC | Sex |
| 2886 | Age | CCL2 | HDLC | SHBG |
| 2887 | Age | CCL2 | HDLC | TNFRSF1B |
| 2888 | Age | CCL2 | HDLC | TRIG |
| 2889 | Age | CCL2 | HDLC | VCAM1 |
| 2890 | Age | CCL2 | HDLC | VEGF |
| 2891 | Age | CCL2 | HDLC | VWF |
| 2892 | Age | CCL2 | HDLC | Waist |
| 2893 | Age | CCL2 | HDLC | WT |
| 2894 | Age | CCL2 | HGF | Hip |
| 2895 | Age | CCL2 | HGF | HT |
| 2896 | Age | CCL2 | HGF | IGF1 |
| 2897 | Age | CCL2 | HGF | IL6ST |
| 2898 | Age | CCL2 | HGF | LEP |
| 2899 | Age | CCL2 | HGF | POMC |
| 2900 | Age | CCL2 | HGF | Sex |
| 2901 | Age | CCL2 | HGF | VEGF |
| 2902 | Age | CCL2 | Hip | HP |
| 2903 | Age | CCL2 | Hip | HT |
| 2904 | Age | CCL2 | Hip | ICAM1 |
| 2905 | Age | CCL2 | Hip | IGF1 |
| 2906 | Age | CCL2 | Hip | IL18 |
| 2907 | Age | CCL2 | Hip | IL2RA |
| 2908 | Age | CCL2 | Hip | IL6ST |
| 2909 | Age | CCL2 | Hip | IL8 |
| 2910 | Age | CCL2 | Hip | Ins120 |
| 2911 | Age | CCL2 | Hip | LEP |
| 2912 | Age | CCL2 | Hip | POMC |
| 2913 | Age | CCL2 | Hip | Sex |
| 2914 | Age | CCL2 | Hip | TRIG |
| 2915 | Age | CCL2 | Hip | VEGF |
| 2916 | Age | CCL2 | Hip | VWF |
| 2917 | Age | CCL2 | Hip | Waist |
| 2918 | Age | CCL2 | HP | HT |
| 2919 | Age | CCL2 | HP | IGF1 |
| 2920 | Age | CCL2 | HP | IL6ST |
| 2921 | Age | CCL2 | HP | LEP |
| 2922 | Age | CCL2 | HP | POMC |
| 2923 | Age | CCL2 | HP | Sex |
| 2924 | Age | CCL2 | HP | VEGF |
| 2925 | Age | CCL2 | HT | ICAM1 |
| 2926 | Age | CCL2 | HT | IGF1 |
| 2927 | Age | CCL2 | HT | IGFBP1 |
| 2928 | Age | CCL2 | HT | IGFBP3 |
| 2929 | Age | CCL2 | HT | IL18 |
| 2930 | Age | CCL2 | HT | IL2RA |
| 2931 | Age | CCL2 | HT | IL6R |
| 2932 | Age | CCL2 | HT | IL6ST |
| 2933 | Age | CCL2 | HT | IL8 |
| 2934 | Age | CCL2 | HT | INHBA |
| 2935 | Age | CCL2 | HT | Ins120 |
| 2936 | Age | CCL2 | HT | Insulin |
| 2937 | Age | CCL2 | HT | LDL |
| 2938 | Age | CCL2 | HT | LEP |
| 2939 | Age | CCL2 | HT | PLAT |

FIG. 15WW

| 4-Panel | Marker 1 | Marker 2 | Marker 3 | Marker 4 |
|---|---|---|---|---|
| 2940 | Age | CCL2 | HT | POMC |
| 2941 | Age | CCL2 | HT | SBP |
| 2942 | Age | CCL2 | HT | SCp |
| 2943 | Age | CCL2 | HT | SELE |
| 2944 | Age | CCL2 | HT | SELP |
| 2945 | Age | CCL2 | HT | Sex |
| 2946 | Age | CCL2 | HT | SHBG |
| 2947 | Age | CCL2 | HT | TNFRSF1B |
| 2948 | Age | CCL2 | HT | TRIG |
| 2949 | Age | CCL2 | HT | VCAM1 |
| 2950 | Age | CCL2 | HT | VEGF |
| 2951 | Age | CCL2 | HT | VWF |
| 2952 | Age | CCL2 | HT | Waist |
| 2953 | Age | CCL2 | HT | WT |
| 2954 | Age | CCL2 | ICAM1 | IGF1 |
| 2955 | Age | CCL2 | ICAM1 | IL6ST |
| 2956 | Age | CCL2 | ICAM1 | LEP |
| 2957 | Age | CCL2 | ICAM1 | POMC |
| 2958 | Age | CCL2 | ICAM1 | Sex |
| 2959 | Age | CCL2 | ICAM1 | VEGF |
| 2960 | Age | CCL2 | IGF1 | IGFBP1 |
| 2961 | Age | CCL2 | IGF1 | IGFBP3 |
| 2962 | Age | CCL2 | IGF1 | IL18 |
| 2963 | Age | CCL2 | IGF1 | IL2RA |
| 2964 | Age | CCL2 | IGF1 | IL6R |
| 2965 | Age | CCL2 | IGF1 | IL6ST |
| 2966 | Age | CCL2 | IGF1 | IL8 |
| 2967 | Age | CCL2 | IGF1 | INHBA |
| 2968 | Age | CCL2 | IGF1 | Ins120 |
| 2969 | Age | CCL2 | IGF1 | Insulin |
| 2970 | Age | CCL2 | IGF1 | LDL |
| 2971 | Age | CCL2 | IGF1 | LEP |
| 2972 | Age | CCL2 | IGF1 | PLAT |
| 2973 | Age | CCL2 | IGF1 | POMC |
| 2974 | Age | CCL2 | IGF1 | SBP |
| 2975 | Age | CCL2 | IGF1 | SCp |
| 2976 | Age | CCL2 | IGF1 | SELE |
| 2977 | Age | CCL2 | IGF1 | SELP |
| 2978 | Age | CCL2 | IGF1 | Sex |
| 2979 | Age | CCL2 | IGF1 | SHBG |
| 2980 | Age | CCL2 | IGF1 | TNFRSF1B |
| 2981 | Age | CCL2 | IGF1 | TRIG |
| 2982 | Age | CCL2 | IGF1 | VCAM1 |
| 2983 | Age | CCL2 | IGF1 | VEGF |
| 2984 | Age | CCL2 | IGF1 | VWF |
| 2985 | Age | CCL2 | IGF1 | Waist |
| 2986 | Age | CCL2 | IGF1 | WT |
| 2987 | Age | CCL2 | IGFBP1 | IL6ST |
| 2988 | Age | CCL2 | IGFBP1 | LEP |
| 2989 | Age | CCL2 | IGFBP1 | POMC |
| 2990 | Age | CCL2 | IGFBP1 | Sex |
| 2991 | Age | CCL2 | IGFBP1 | VEGF |
| 2992 | Age | CCL2 | IGFBP3 | IL6ST |
| 2993 | Age | CCL2 | IGFBP3 | LEP |
| 2994 | Age | CCL2 | IGFBP3 | POMC |
| 2995 | Age | CCL2 | IGFBP3 | Sex |
| 2996 | Age | CCL2 | IGFBP3 | VEGF |
| 2997 | Age | CCL2 | IL18 | IL6ST |
| 2998 | Age | CCL2 | IL18 | Ins120 |
| 2999 | Age | CCL2 | IL18 | LEP |

| 4-Panel | Marker 1 | Marker 2 | Marker 3 | Marker 4 |
|---|---|---|---|---|
| 3000 | Age | CCL2 | IL18 | POMC |
| 3001 | Age | CCL2 | IL18 | Sex |
| 3002 | Age | CCL2 | IL18 | VEGF |
| 3003 | Age | CCL2 | IL2RA | IL6ST |
| 3004 | Age | CCL2 | IL2RA | LEP |
| 3005 | Age | CCL2 | IL2RA | POMC |
| 3006 | Age | CCL2 | IL2RA | Sex |
| 3007 | Age | CCL2 | IL2RA | VEGF |
| 3008 | Age | CCL2 | IL6R | IL6ST |
| 3009 | Age | CCL2 | IL6R | LEP |
| 3010 | Age | CCL2 | IL6R | POMC |
| 3011 | Age | CCL2 | IL6R | Sex |
| 3012 | Age | CCL2 | IL6R | VEGF |
| 3013 | Age | CCL2 | IL6ST | IL8 |
| 3014 | Age | CCL2 | IL6ST | INHBA |
| 3015 | Age | CCL2 | IL6ST | Ins120 |
| 3016 | Age | CCL2 | IL6ST | LEP |
| 3017 | Age | CCL2 | IL6ST | PLAT |
| 3018 | Age | CCL2 | IL6ST | POMC |
| 3019 | Age | CCL2 | IL6ST | SBP |
| 3020 | Age | CCL2 | IL6ST | SELP |
| 3021 | Age | CCL2 | IL6ST | Sex |
| 3022 | Age | CCL2 | IL6ST | SHBG |
| 3023 | Age | CCL2 | IL6ST | TNFRSF1B |
| 3024 | Age | CCL2 | IL6ST | TRIG |
| 3025 | Age | CCL2 | IL6ST | VEGF |
| 3026 | Age | CCL2 | IL6ST | VWF |
| 3027 | Age | CCL2 | IL8 | LEP |
| 3028 | Age | CCL2 | IL8 | POMC |
| 3029 | Age | CCL2 | IL8 | Sex |
| 3030 | Age | CCL2 | IL8 | VEGF |
| 3031 | Age | CCL2 | INHBA | LEP |
| 3032 | Age | CCL2 | INHBA | POMC |
| 3033 | Age | CCL2 | INHBA | Sex |
| 3034 | Age | CCL2 | INHBA | VEGF |
| 3035 | Age | CCL2 | Ins120 | Insulin |
| 3036 | Age | CCL2 | Ins120 | LEP |
| 3037 | Age | CCL2 | Ins120 | POMC |
| 3038 | Age | CCL2 | Ins120 | Sex |
| 3039 | Age | CCL2 | Ins120 | VEGF |
| 3040 | Age | CCL2 | Ins120 | LEP |
| 3041 | Age | CCL2 | Insulin | POMC |
| 3042 | Age | CCL2 | Insulin | Sex |
| 3043 | Age | CCL2 | Insulin | VEGF |
| 3044 | Age | CCL2 | LDL | LEP |
| 3045 | Age | CCL2 | LDL | POMC |
| 3046 | Age | CCL2 | LDL | Sex |
| 3047 | Age | CCL2 | LDL | VEGF |
| 3048 | Age | CCL2 | LEP | PLAT |
| 3049 | Age | CCL2 | LEP | POMC |
| 3050 | Age | CCL2 | LEP | SBP |
| 3051 | Age | CCL2 | LEP | SCp |
| 3052 | Age | CCL2 | LEP | SELE |
| 3053 | Age | CCL2 | LEP | SELP |
| 3054 | Age | CCL2 | LEP | Sex |
| 3055 | Age | CCL2 | LEP | SHBG |
| 3056 | Age | CCL2 | LEP | TNFRSF1B |
| 3057 | Age | CCL2 | LEP | TRIG |
| 3058 | Age | CCL2 | LEP | VCAM1 |
| 3059 | Age | CCL2 | LEP | VEGF |

| 4-Panel | Marker 1 | Marker 2 | Marker 3 | Marker 4 |
|---|---|---|---|---|
| 3060 | Age | CCL2 | LEP | VWF |
| 3061 | Age | CCL2 | LEP | Waist |
| 3062 | Age | CCL2 | LEP | WT |
| 3063 | Age | CCL2 | PLAT | POMC |
| 3064 | Age | CCL2 | PLAT | Sex |
| 3065 | Age | CCL2 | PLAT | VEGF |
| 3066 | Age | CCL2 | POMC | SBP |
| 3067 | Age | CCL2 | POMC | SCp |
| 3068 | Age | CCL2 | POMC | SELE |
| 3069 | Age | CCL2 | POMC | SELP |
| 3070 | Age | CCL2 | POMC | Sex |
| 3071 | Age | CCL2 | POMC | SHBG |
| 3072 | Age | CCL2 | POMC | TNFRSF1B |
| 3073 | Age | CCL2 | POMC | TRIG |
| 3074 | Age | CCL2 | POMC | VCAM1 |
| 3075 | Age | CCL2 | POMC | VEGF |
| 3076 | Age | CCL2 | POMC | VWF |
| 3077 | Age | CCL2 | POMC | Waist |
| 3078 | Age | CCL2 | POMC | WT |
| 3079 | Age | CCL2 | SBP | Sex |
| 3080 | Age | CCL2 | SBP | VEGF |
| 3081 | Age | CCL2 | SCp | Sex |
| 3082 | Age | CCL2 | SCp | VEGF |
| 3083 | Age | CCL2 | SELE | Sex |
| 3084 | Age | CCL2 | SELE | VEGF |
| 3085 | Age | CCL2 | SELP | Sex |
| 3086 | Age | CCL2 | SELP | VEGF |
| 3087 | Age | CCL2 | Sex | SHBG |
| 3088 | Age | CCL2 | Sex | TNFRSF1B |
| 3089 | Age | CCL2 | Sex | TRIG |
| 3090 | Age | CCL2 | Sex | VCAM1 |
| 3091 | Age | CCL2 | Sex | VEGF |
| 3092 | Age | CCL2 | Sex | VWF |
| 3093 | Age | CCL2 | Sex | Waist |
| 3094 | Age | CCL2 | Sex | WT |
| 3095 | Age | CCL2 | SHBG | VEGF |
| 3096 | Age | CCL2 | TNFRSF1B | VEGF |
| 3097 | Age | CCL2 | TRIG | VEGF |
| 3098 | Age | CCL2 | VCAM1 | VEGF |
| 3099 | Age | CCL2 | VEGF | VWF |
| 3100 | Age | CCL2 | VEGF | Waist |
| 3101 | Age | CCL2 | VEGF | WT |
| 3102 | Age | CD14 | CD40 | HDLC |
| 3103 | Age | CD14 | CD40 | IGF1 |
| 3104 | Age | CD14 | CD40 | IL6ST |
| 3105 | Age | CD14 | CD40 | LEP |
| 3106 | Age | CD14 | CD40 | POMC |
| 3107 | Age | CD14 | CDK5 | LEP |
| 3108 | Age | CD14 | CDK5 | POMC |
| 3109 | Age | CD14 | CDK5 | Sex |
| 3110 | Age | CD14 | CHOL | POMC |
| 3111 | Age | CD14 | CRP | LEP |
| 3112 | Age | CD14 | CRP | POMC |
| 3113 | Age | CD14 | DBP | LEP |
| 3114 | Age | CD14 | DBP | POMC |
| 3115 | Age | CD14 | DPP4 | LEP |
| 3116 | Age | CD14 | DPP4 | HDLC |
| 3117 | Age | CD14 | DPP4 | IGF1 |
| 3118 | Age | CD14 | DPP4 | LEP |
| 3119 | Age | CD14 | DPP4 | POMC |
| | Age | CD14 | DPP4 | VEGF |

FIG. 15ZZ

| 4-Panel | Marker 1 | Marker 2 | Marker 3 | Marker 4 |
|---|---|---|---|---|
| 3120 | Age | CD14 | EGF | POMC |
| 3121 | Age | CD14 | ENG | POMC |
| 3122 | Age | CD14 | FamHX | LEP |
| 3123 | Age | CD14 | FamHX | POMC |
| 3124 | Age | CD14 | FGA | LEP |
| 3125 | Age | CD14 | FGA | POMC |
| 3126 | Age | CD14 | FTH1 | HDLC |
| 3127 | Age | CD14 | FTH1 | IL6ST |
| 3128 | Age | CD14 | FTH1 | LEP |
| 3129 | Age | CD14 | FTH1 | POMC |
| 3130 | Age | CD14 | FTH1 | Sex |
| 3131 | Age | CD14 | Gluc120 | LEP |
| 3132 | Age | CD14 | Gluc120 | POMC |
| 3133 | Age | CD14 | Glucose | HDLC |
| 3134 | Age | CD14 | Glucose | IGF1 |
| 3135 | Age | CD14 | Glucose | IL6ST |
| 3136 | Age | CD14 | Glucose | LEP |
| 3137 | Age | CD14 | Glucose | POMC |
| 3138 | Age | CD14 | Glucose | Sex |
| 3139 | Age | CD14 | Glucose | VEGF |
| 3140 | Age | CD14 | HBA1C | LEP |
| 3141 | Age | CD14 | HBA1C | POMC |
| 3142 | Age | CD14 | HDLC | Hip |
| 3143 | Age | CD14 | HDLC | IGF1 |
| 3144 | Age | CD14 | HDLC | IGFBP1 |
| 3145 | Age | CD14 | HDLC | IL18 |
| 3146 | Age | CD14 | HDLC | IL6ST |
| 3147 | Age | CD14 | HDLC | IL8 |
| 3148 | Age | CD14 | HDLC | Insulin |
| 3149 | Age | CD14 | HDLC | LEP |

| 4-Panel | Marker 1 | Marker 2 | Marker 3 | Marker 4 |
|---|---|---|---|---|
| 3150 | Age | CD14 | HDLC | POMC |
| 3151 | Age | CD14 | HDLC | SCp |
| 3152 | Age | CD14 | HDLC | Sex |
| 3153 | Age | CD14 | HDLC | TRIG |
| 3154 | Age | CD14 | HDLC | VEGF |
| 3155 | Age | CD14 | HDLC | Waist |
| 3156 | Age | CD14 | HDLC | WT |
| 3157 | Age | CD14 | HGF | LEP |
| 3158 | Age | CD14 | HGF | POMC |
| 3159 | Age | CD14 | Hip | IGF1 |
| 3160 | Age | CD14 | Hip | LEP |
| 3161 | Age | CD14 | Hip | POMC |
| 3162 | Age | CD14 | HP | POMC |
| 3163 | Age | CD14 | HT | IGF1 |
| 3164 | Age | CD14 | HT | IL6ST |
| 3165 | Age | CD14 | HT | POMC |
| 3166 | Age | CD14 | HT | VEGF |
| 3167 | Age | CD14 | ICAM1 | LEP |
| 3168 | Age | CD14 | ICAM1 | POMC |
| 3169 | Age | CD14 | IGF1 | IL18 |
| 3170 | Age | CD14 | IGF1 | IL2RA |
| 3171 | Age | CD14 | IGF1 | IL6ST |
| 3172 | Age | CD14 | IGF1 | Insulin |
| 3173 | Age | CD14 | IGF1 | LEP |
| 3174 | Age | CD14 | IGF1 | POMC |
| 3175 | Age | CD14 | IGF1 | Sex |
| 3176 | Age | CD14 | IGF1 | VCAM1 |
| 3177 | Age | CD14 | IGF1 | VEGF |
| 3178 | Age | CD14 | IGFBP1 | LEP |
| 3179 | Age | CD14 | IGFBP1 | POMC |

FIG. 15AAA

| 4-Panel | Marker 1 | Marker 2 | Marker 3 | Marker 4 |
|---|---|---|---|---|
| 3180 | Age | CD14 | IGFBP3 | POMC |
| 3181 | Age | CD14 | IL18 | IL6ST |
| 3182 | Age | CD14 | IL18 | LEP |
| 3183 | Age | CD14 | IL18 | POMC |
| 3184 | Age | CD14 | IL18 | Sex |
| 3185 | Age | CD14 | IL18 | VEGF |
| 3186 | Age | CD14 | IL2RA | LEP |
| 3187 | Age | CD14 | IL2RA | POMC |
| 3188 | Age | CD14 | IL2RA | Sex |
| 3189 | Age | CD14 | IL6R | IL6ST |
| 3190 | Age | CD14 | IL6R | LEP |
| 3191 | Age | CD14 | IL6R | POMC |
| 3192 | Age | CD14 | IL6ST | IL8 |
| 3193 | Age | CD14 | IL6ST | LEP |
| 3194 | Age | CD14 | IL6ST | POMC |
| 3195 | Age | CD14 | IL6ST | SELP |
| 3196 | Age | CD14 | IL6ST | Sex |
| 3197 | Age | CD14 | IL6ST | TNFRSF1B |
| 3198 | Age | CD14 | IL6ST | VEGF |
| 3199 | Age | CD14 | IL8 | LEP |
| 3200 | Age | CD14 | IL8 | POMC |
| 3201 | Age | CD14 | IL8 | Sex |
| 3202 | Age | CD14 | INHBA | LEP |
| 3203 | Age | CD14 | INHBA | POMC |
| 3204 | Age | CD14 | Ins120 | LEP |
| 3205 | Age | CD14 | Ins120 | POMC |
| 3206 | Age | CD14 | Insulin | LEP |
| 3207 | Age | CD14 | Insulin | POMC |
| 3208 | Age | CD14 | Insulin | Sex |
| 3209 | Age | CD14 | Insulin | VEGF |

| 4-Panel | Marker 1 | Marker 2 | Marker 3 | Marker 4 |
|---|---|---|---|---|
| 3210 | Age | CD14 | LDL | POMC |
| 3211 | Age | CD14 | LEP | PLAT |
| 3212 | Age | CD14 | LEP | POMC |
| 3213 | Age | CD14 | LEP | SELE |
| 3214 | Age | CD14 | LEP | Sex |
| 3215 | Age | CD14 | LEP | TRIG |
| 3216 | Age | CD14 | LEP | VCAM1 |
| 3217 | Age | CD14 | LEP | VEGF |
| 3218 | Age | CD14 | LEP | VWF |
| 3219 | Age | CD14 | LEP | Waist |
| 3220 | Age | CD14 | LEP | WT |
| 3221 | Age | CD14 | PLAT | POMC |
| 3222 | Age | CD14 | POMC | SBP |
| 3223 | Age | CD14 | POMC | SCp |
| 3224 | Age | CD14 | POMC | SELE |
| 3225 | Age | CD14 | POMC | SELP |
| 3226 | Age | CD14 | POMC | Sex |
| 3227 | Age | CD14 | POMC | SHBG |
| 3228 | Age | CD14 | POMC | TNFRSF1B |
| 3229 | Age | CD14 | POMC | TRIG |
| 3230 | Age | CD14 | POMC | VCAM1 |
| 3231 | Age | CD14 | POMC | VEGF |
| 3232 | Age | CD14 | POMC | VWF |
| 3233 | Age | CD14 | POMC | Waist |
| 3234 | Age | CD14 | POMC | WT |
| 3235 | Age | CD14 | Sex | VEGF |
| 3236 | Age | CD14 | Sex | Waist |
| 3237 | Age | CD14 | Sex | WT |
| 3238 | Age | CD40 | CDK5 | Glucose |
| 3239 | Age | CD40 | CDK5 | HDLC |

| 4-Panel | Marker 1 | Marker 2 | Marker 3 | Marker 4 |
|---|---|---|---|---|
| 3240 | Age | CD40 | CDK5 | IGF1 |
| 3241 | Age | CD40 | CDK5 | IL6ST |
| 3242 | Age | CD40 | CDK5 | Insulin |
| 3243 | Age | CD40 | CDK5 | LEP |
| 3244 | Age | CD40 | CDK5 | POMC |
| 3245 | Age | CD40 | CDK5 | Sex |
| 3246 | Age | CD40 | CDK5 | VEGF |
| 3247 | Age | CD40 | CHOL | Glucose |
| 3248 | Age | CD40 | CHOL | HDLC |
| 3249 | Age | CD40 | CHOL | IGF1 |
| 3250 | Age | CD40 | CHOL | LEP |
| 3251 | Age | CD40 | CHOL | POMC |
| 3252 | Age | CD40 | CHOL | Sex |
| 3253 | Age | CD40 | CHOL | Glucose |
| 3254 | Age | CD40 | CRP | HDLC |
| 3255 | Age | CD40 | CRP | IGF1 |
| 3256 | Age | CD40 | CRP | IL6ST |
| 3257 | Age | CD40 | CRP | Insulin |
| 3258 | Age | CD40 | CRP | LEP |
| 3259 | Age | CD40 | CRP | POMC |
| 3260 | Age | CD40 | CRP | Sex |
| 3261 | Age | CD40 | CRP | VEGF |
| 3262 | Age | CD40 | DBP | Glucose |
| 3263 | Age | CD40 | DBP | HDLC |
| 3264 | Age | CD40 | DBP | IGF1 |
| 3265 | Age | CD40 | DBP | IL6ST |
| 3266 | Age | CD40 | DBP | LEP |
| 3267 | Age | CD40 | DBP | POMC |
| 3268 | Age | CD40 | DBP | Sex |
| 3269 | Age | CD40 | DBP | VEGF |
| 3270 | Age | CD40 | DPP4 | Glucose |
| 3271 | Age | CD40 | DPP4 | HDLC |
| 3272 | Age | CD40 | DPP4 | IGF1 |
| 3273 | Age | CD40 | DPP4 | IL6ST |
| 3274 | Age | CD40 | DPP4 | Insulin |
| 3275 | Age | CD40 | DPP4 | LEP |
| 3276 | Age | CD40 | DPP4 | POMC |
| 3277 | Age | CD40 | DPP4 | Sex |
| 3278 | Age | CD40 | DPP4 | VEGF |
| 3279 | Age | CD40 | EGF | Glucose |
| 3280 | Age | CD40 | EGF | HDLC |
| 3281 | Age | CD40 | EGF | IGF1 |
| 3282 | Age | CD40 | EGF | IL6ST |
| 3283 | Age | CD40 | EGF | LEP |
| 3284 | Age | CD40 | EGF | POMC |
| 3285 | Age | CD40 | EGF | Sex |
| 3286 | Age | CD40 | EGF | VEGF |
| 3287 | Age | CD40 | ENG | HDLC |
| 3288 | Age | CD40 | ENG | IGF1 |
| 3289 | Age | CD40 | ENG | IL6ST |
| 3290 | Age | CD40 | ENG | LEP |
| 3291 | Age | CD40 | ENG | POMC |
| 3292 | Age | CD40 | ENG | Sex |
| 3293 | Age | CD40 | ENG | VEGF |
| 3294 | Age | CD40 | FamHX | Glucose |
| 3295 | Age | CD40 | FamHX | HDLC |
| 3296 | Age | CD40 | FamHX | IGF1 |
| 3297 | Age | CD40 | FamHX | IL6ST |
| 3298 | Age | CD40 | FamHX | LEP |
| 3299 | Age | CD40 | FamHX | POMC |

FIG. 15DDD

| 4-Panel | Marker 1 | Marker 2 | Marker 3 | Marker 4 |
|---|---|---|---|---|
| 3300 | Age | CD40 | FamHX | Sex |
| 3301 | Age | CD40 | FamHX | VEGF |
| 3302 | Age | CD40 | FGA | HDLC |
| 3303 | Age | CD40 | FGA | IGF1 |
| 3304 | Age | CD40 | FGA | IL6ST |
| 3305 | Age | CD40 | FGA | LEP |
| 3306 | Age | CD40 | FGA | POMC |
| 3307 | Age | CD40 | FGA | Sex |
| 3308 | Age | CD40 | FGA | VEGF |
| 3309 | Age | CD40 | FTH1 | Glucose |
| 3310 | Age | CD40 | FTH1 | HDLC |
| 3311 | Age | CD40 | FTH1 | IGF1 |
| 3312 | Age | CD40 | FTH1 | IL6ST |
| 3313 | Age | CD40 | FTH1 | LEP |
| 3314 | Age | CD40 | FTH1 | POMC |
| 3315 | Age | CD40 | FTH1 | Sex |
| 3316 | Age | CD40 | FTH1 | VEGF |
| 3317 | Age | CD40 | Gluc120 | Glucose |
| 3318 | Age | CD40 | Gluc120 | HDLC |
| 3319 | Age | CD40 | Gluc120 | IGF1 |
| 3320 | Age | CD40 | Gluc120 | IL6ST |
| 3321 | Age | CD40 | Gluc120 | LEP |
| 3322 | Age | CD40 | Gluc120 | POMC |
| 3323 | Age | CD40 | Gluc120 | Sex |
| 3324 | Age | CD40 | Gluc120 | VEGF |
| 3325 | Age | CD40 | Glucose | HBA1C |
| 3326 | Age | CD40 | Glucose | HDLC |
| 3327 | Age | CD40 | Glucose | HGF |
| 3328 | Age | CD40 | Glucose | HP |
| 3329 | Age | CD40 | Glucose | HT |

| 4-Panel | Marker 1 | Marker 2 | Marker 3 | Marker 4 |
|---|---|---|---|---|
| 3330 | Age | CD40 | Glucose | ICAM1 |
| 3331 | Age | CD40 | Glucose | IGF1 |
| 3332 | Age | CD40 | Glucose | IGFBP1 |
| 3333 | Age | CD40 | Glucose | IGFBP3 |
| 3334 | Age | CD40 | Glucose | IL18 |
| 3335 | Age | CD40 | Glucose | IL2RA |
| 3336 | Age | CD40 | Glucose | IL6R |
| 3337 | Age | CD40 | Glucose | IL6ST |
| 3338 | Age | CD40 | Glucose | IL8 |
| 3339 | Age | CD40 | Glucose | INHBA |
| 3340 | Age | CD40 | Glucose | Ins120 |
| 3341 | Age | CD40 | Glucose | Insulin |
| 3342 | Age | CD40 | Glucose | LDL |
| 3343 | Age | CD40 | Glucose | LEP |
| 3344 | Age | CD40 | Glucose | PLAT |
| 3345 | Age | CD40 | Glucose | POMC |
| 3346 | Age | CD40 | Glucose | SBP |
| 3347 | Age | CD40 | Glucose | SCp |
| 3348 | Age | CD40 | Glucose | SELE |
| 3349 | Age | CD40 | Glucose | SELP |
| 3350 | Age | CD40 | Glucose | Sex |
| 3351 | Age | CD40 | Glucose | SHBG |
| 3352 | Age | CD40 | Glucose | TNFRSF1B |
| 3353 | Age | CD40 | Glucose | TRIG |
| 3354 | Age | CD40 | Glucose | VCAM1 |
| 3355 | Age | CD40 | Glucose | VEGF |
| 3356 | Age | CD40 | Glucose | Waist |
| 3357 | Age | CD40 | HBA1C | HDLC |
| 3358 | Age | CD40 | HBA1C | IGF1 |
| 3359 | Age | CD40 | HBA1C | IL6ST |

| 4-Panel | Marker 1 | Marker 2 | Marker 3 | Marker 4 |
|---|---|---|---|---|
| 3360 | Age | CD40 | HBA1C | LEP |
| 3361 | Age | CD40 | HBA1C | POMC |
| 3362 | Age | CD40 | HBA1C | Sex |
| 3363 | Age | CD40 | HBA1C | VEGF |
| 3364 | Age | CD40 | HDLC | HGF |
| 3365 | Age | CD40 | HDLC | Hip |
| 3366 | Age | CD40 | HDLC | HP |
| 3367 | Age | CD40 | HDLC | HT |
| 3368 | Age | CD40 | HDLC | ICAM1 |
| 3369 | Age | CD40 | HDLC | IGF1 |
| 3370 | Age | CD40 | HDLC | IGFBP1 |
| 3371 | Age | CD40 | HDLC | IGFBP3 |
| 3372 | Age | CD40 | HDLC | IL18 |
| 3373 | Age | CD40 | HDLC | IL2RA |
| 3374 | Age | CD40 | HDLC | IL6R |
| 3375 | Age | CD40 | HDLC | IL6ST |
| 3376 | Age | CD40 | HDLC | IL8 |
| 3377 | Age | CD40 | HDLC | INHBA |
| 3378 | Age | CD40 | HDLC | Ins120 |
| 3379 | Age | CD40 | HDLC | Insulin |
| 3380 | Age | CD40 | HDLC | LDL |
| 3381 | Age | CD40 | HDLC | LEP |
| 3382 | Age | CD40 | HDLC | PLAT |
| 3383 | Age | CD40 | HDLC | POMC |
| 3384 | Age | CD40 | HDLC | SBP |
| 3385 | Age | CD40 | HDLC | SCp |
| 3386 | Age | CD40 | HDLC | SELE |
| 3387 | Age | CD40 | HDLC | SELP |
| 3388 | Age | CD40 | HDLC | Sex |
| 3389 | Age | CD40 | HDLC | SHBG |
| 3390 | Age | CD40 | HDLC | TNFRSF1B |
| 3391 | Age | CD40 | HDLC | TRIG |
| 3392 | Age | CD40 | HDLC | VCAM1 |
| 3393 | Age | CD40 | HDLC | VEGF |
| 3394 | Age | CD40 | HDLC | VWF |
| 3395 | Age | CD40 | HDLC | Waist |
| 3396 | Age | CD40 | HDLC | WT |
| 3397 | Age | CD40 | HGF | IGF1 |
| 3398 | Age | CD40 | HGF | IL6ST |
| 3399 | Age | CD40 | HGF | Insulin |
| 3400 | Age | CD40 | HGF | LEP |
| 3401 | Age | CD40 | HGF | POMC |
| 3402 | Age | CD40 | HGF | Sex |
| 3403 | Age | CD40 | HGF | VEGF |
| 3404 | Age | CD40 | Hip | IGF1 |
| 3405 | Age | CD40 | Hip | IL6ST |
| 3406 | Age | CD40 | Hip | LEP |
| 3407 | Age | CD40 | Hip | POMC |
| 3408 | Age | CD40 | Hip | Sex |
| 3409 | Age | CD40 | Hip | VEGF |
| 3410 | Age | CD40 | HP | IL6ST |
| 3411 | Age | CD40 | HP | LEP |
| 3412 | Age | CD40 | HP | POMC |
| 3413 | Age | CD40 | HP | VEGF |
| 3414 | Age | CD40 | HT | IGF1 |
| 3415 | Age | CD40 | HT | IL6ST |
| 3416 | Age | CD40 | HT | Insulin |
| 3417 | Age | CD40 | HT | LEP |
| 3418 | Age | CD40 | HT | POMC |
| 3419 | Age | CD40 | HT | Sex |

FIG. 15EEE

| 4-Panel | Marker 1 | Marker 2 | Marker 3 | Marker 4 |
|---|---|---|---|---|
| 3420 | Age | CD40 | HT | VEGF |
| 3421 | Age | CD40 | HT | WT |
| 3422 | Age | CD40 | ICAM1 | IGF1 |
| 3423 | Age | CD40 | ICAM1 | IL6ST |
| 3424 | Age | CD40 | ICAM1 | LEP |
| 3425 | Age | CD40 | ICAM1 | POMC |
| 3426 | Age | CD40 | ICAM1 | Sex |
| 3427 | Age | CD40 | IGF1 | IGFBP1 |
| 3428 | Age | CD40 | IGF1 | IGFBP3 |
| 3429 | Age | CD40 | IGF1 | IL18 |
| 3430 | Age | CD40 | IGF1 | IL2RA |
| 3431 | Age | CD40 | IGF1 | IL6R |
| 3432 | Age | CD40 | IGF1 | IL6ST |
| 3433 | Age | CD40 | IGF1 | IL8 |
| 3434 | Age | CD40 | IGF1 | INHBA |
| 3435 | Age | CD40 | IGF1 | Ins120 |
| 3436 | Age | CD40 | IGF1 | Insulin |
| 3437 | Age | CD40 | IGF1 | LDL |
| 3438 | Age | CD40 | IGF1 | LEP |
| 3439 | Age | CD40 | IGF1 | PLAT |
| 3440 | Age | CD40 | IGF1 | POMC |
| 3441 | Age | CD40 | IGF1 | SBP |
| 3442 | Age | CD40 | IGF1 | SCp |
| 3443 | Age | CD40 | IGF1 | SELE |
| 3444 | Age | CD40 | IGF1 | SELP |
| 3445 | Age | CD40 | IGF1 | Sex |
| 3446 | Age | CD40 | IGF1 | SHBG |
| 3447 | Age | CD40 | IGF1 | TNFRSF1B |
| 3448 | Age | CD40 | IGF1 | TRIG |
| 3449 | Age | CD40 | IGF1 | VCAM1 |

| 4-Panel | Marker 1 | Marker 2 | Marker 3 | Marker 4 |
|---|---|---|---|---|
| 3450 | Age | CD40 | IGF1 | VEGF |
| 3451 | Age | CD40 | IGF1 | VWF |
| 3452 | Age | CD40 | IGF1 | Waist |
| 3453 | Age | CD40 | IGF1 | WT |
| 3454 | Age | CD40 | IGFBP1 | IL6ST |
| 3455 | Age | CD40 | IGFBP1 | LEP |
| 3456 | Age | CD40 | IGFBP1 | POMC |
| 3457 | Age | CD40 | IGFBP1 | Sex |
| 3458 | Age | CD40 | IGFBP1 | VEGF |
| 3459 | Age | CD40 | IGFBP3 | IL6ST |
| 3460 | Age | CD40 | IGFBP3 | LEP |
| 3461 | Age | CD40 | IGFBP3 | POMC |
| 3462 | Age | CD40 | IGFBP3 | Sex |
| 3463 | Age | CD40 | IL18 | IL6ST |
| 3464 | Age | CD40 | IL18 | LEP |
| 3465 | Age | CD40 | IL18 | POMC |
| 3466 | Age | CD40 | IL18 | Sex |
| 3467 | Age | CD40 | IL18 | VEGF |
| 3468 | Age | CD40 | IL2RA | IL6ST |
| 3469 | Age | CD40 | IL2RA | Insulin |
| 3470 | Age | CD40 | IL2RA | LEP |
| 3471 | Age | CD40 | IL2RA | POMC |
| 3472 | Age | CD40 | IL2RA | Sex |
| 3473 | Age | CD40 | IL2RA | VEGF |
| 3474 | Age | CD40 | IL2RA | IL6ST |
| 3475 | Age | CD40 | IL6R | LEP |
| 3476 | Age | CD40 | IL6R | POMC |
| 3477 | Age | CD40 | IL6R | Sex |
| 3478 | Age | CD40 | IL6R | VEGF |
| 3479 | Age | CD40 | IL6ST | IL8 |

FIG. 15FFF

| 4-Panel | Marker 1 | Marker 2 | Marker 3 | Marker 4 |
|---|---|---|---|---|
| 3480 | Age | CD40 | IL6ST | INHBA |
| 3481 | Age | CD40 | IL6ST | Ins120 |
| 3482 | Age | CD40 | IL6ST | Insulin |
| 3483 | Age | CD40 | IL6ST | LEP |
| 3484 | Age | CD40 | IL6ST | PLAT |
| 3485 | Age | CD40 | IL6ST | POMC |
| 3486 | Age | CD40 | IL6ST | SBP |
| 3487 | Age | CD40 | IL6ST | SCp |
| 3488 | Age | CD40 | IL6ST | SELE |
| 3489 | Age | CD40 | IL6ST | SELP |
| 3490 | Age | CD40 | IL6ST | Sex |
| 3491 | Age | CD40 | IL6ST | SHBG |
| 3492 | Age | CD40 | IL6ST | TNFRSF1B |
| 3493 | Age | CD40 | IL6ST | TRIG |
| 3494 | Age | CD40 | IL6ST | VEGF |
| 3495 | Age | CD40 | IL6ST | VWF |
| 3496 | Age | CD40 | IL6ST | WT |
| 3497 | Age | CD40 | IL8 | LEP |
| 3498 | Age | CD40 | IL8 | POMC |
| 3499 | Age | CD40 | IL8 | Sex |
| 3500 | Age | CD40 | IL8 | VEGF |
| 3501 | Age | CD40 | INHBA | LEP |
| 3502 | Age | CD40 | INHBA | POMC |
| 3503 | Age | CD40 | INHBA | Sex |
| 3504 | Age | CD40 | INHBA | VEGF |
| 3505 | Age | CD40 | Ins120 | Insulin |
| 3506 | Age | CD40 | Ins120 | LEP |
| 3507 | Age | CD40 | Ins120 | POMC |
| 3508 | Age | CD40 | Ins120 | Sex |
| 3509 | Age | CD40 | Ins120 | VEGF |

| 4-Panel | Marker 1 | Marker 2 | Marker 3 | Marker 4 |
|---|---|---|---|---|
| 3510 | Age | CD40 | Insulin | LEP |
| 3511 | Age | CD40 | Insulin | POMC |
| 3512 | Age | CD40 | Insulin | Sex |
| 3513 | Age | CD40 | Insulin | TRIG |
| 3514 | Age | CD40 | Insulin | VEGF |
| 3515 | Age | CD40 | LDL | LEP |
| 3516 | Age | CD40 | LDL | POMC |
| 3517 | Age | CD40 | LDL | Sex |
| 3518 | Age | CD40 | LDL | VEGF |
| 3519 | Age | CD40 | LDL | PLAT |
| 3520 | Age | CD40 | LEP | POMC |
| 3521 | Age | CD40 | LEP | SBP |
| 3522 | Age | CD40 | LEP | SCp |
| 3523 | Age | CD40 | LEP | SELE |
| 3524 | Age | CD40 | LEP | SELP |
| 3525 | Age | CD40 | LEP | Sex |
| 3526 | Age | CD40 | LEP | SHBG |
| 3527 | Age | CD40 | LEP | TNFRSF1B |
| 3528 | Age | CD40 | LEP | TRIG |
| 3529 | Age | CD40 | LEP | VCAM1 |
| 3530 | Age | CD40 | LEP | VEGF |
| 3531 | Age | CD40 | LEP | VWF |
| 3532 | Age | CD40 | LEP | Waist |
| 3533 | Age | CD40 | LEP | WT |
| 3534 | Age | CD40 | LEP | POMC |
| 3535 | Age | CD40 | PLAT | Sex |
| 3536 | Age | CD40 | PLAT | VEGF |
| 3537 | Age | CD40 | PLAT | SBP |
| 3538 | Age | CD40 | POMC | SCp |
| 3539 | Age | CD40 | POMC | SELE |

FIG. 15GGG

| 4-Panel | Marker 1 | Marker 2 | Marker 3 | Marker 4 |
|---|---|---|---|---|
| 3540 | Age | CD40 | POMC | SELP |
| 3541 | Age | CD40 | POMC | Sex |
| 3542 | Age | CD40 | POMC | SHBG |
| 3543 | Age | CD40 | POMC | TNFRSF1B |
| 3544 | Age | CD40 | POMC | TRIG |
| 3545 | Age | CD40 | POMC | VCAM1 |
| 3546 | Age | CD40 | POMC | VEGF |
| 3547 | Age | CD40 | POMC | VWF |
| 3548 | Age | CD40 | POMC | Waist |
| 3549 | Age | CD40 | POMC | WT |
| 3550 | Age | CD40 | SBP | Sex |
| 3551 | Age | CD40 | SBP | VEGF |
| 3552 | Age | CD40 | SCp | Sex |
| 3553 | Age | CD40 | SCp | VEGF |
| 3554 | Age | CD40 | SELE | Sex |
| 3555 | Age | CD40 | SELE | VEGF |
| 3556 | Age | CD40 | SELP | Sex |
| 3557 | Age | CD40 | SELP | VEGF |
| 3558 | Age | CD40 | Sex | TNFRSF1B |
| 3559 | Age | CD40 | Sex | TRIG |
| 3560 | Age | CD40 | Sex | VCAM1 |
| 3561 | Age | CD40 | Sex | VEGF |
| 3562 | Age | CD40 | Sex | VWF |
| 3563 | Age | CD40 | Sex | Waist |
| 3564 | Age | CD40 | Sex | WT |
| 3565 | Age | CD40 | SHBG | VEGF |
| 3566 | Age | CD40 | TNFRSF1B | VEGF |
| 3567 | Age | CD40 | TRIG | VEGF |
| 3568 | Age | CD40 | VCAM1 | VEGF |
| 3569 | Age | CD40 | VEGF | VWF |

| 4-Panel | Marker 1 | Marker 2 | Marker 3 | Marker 4 |
|---|---|---|---|---|
| 3570 | Age | CD40 | VEGF | Waist |
| 3571 | Age | CD40 | VEGF | WT |
| 3572 | Age | CDK5 | CHOL | HDLC |
| 3573 | Age | CDK5 | CHOL | LEP |
| 3574 | Age | CDK5 | CHOL | POMC |
| 3575 | Age | CDK5 | CHOL | Sex |
| 3576 | Age | CDK5 | CRP | IL6ST |
| 3577 | Age | CDK5 | CRP | LEP |
| 3578 | Age | CDK5 | CRP | POMC |
| 3579 | Age | CDK5 | CRP | Sex |
| 3580 | Age | CDK5 | DBP | LEP |
| 3581 | Age | CDK5 | DBP | POMC |
| 3582 | Age | CDK5 | DBP | Sex |
| 3583 | Age | CDK5 | DPP4 | HDLC |
| 3584 | Age | CDK5 | DPP4 | IGF1 |
| 3585 | Age | CDK5 | DPP4 | LEP |
| 3586 | Age | CDK5 | DPP4 | POMC |
| 3587 | Age | CDK5 | DPP4 | Sex |
| 3588 | Age | CDK5 | DPP4 | VEGF |
| 3589 | Age | CDK5 | EGF | HDLC |
| 3590 | Age | CDK5 | EGF | LEP |
| 3591 | Age | CDK5 | EGF | POMC |
| 3592 | Age | CDK5 | ENG | LEP |
| 3593 | Age | CDK5 | ENG | POMC |
| 3594 | Age | CDK5 | FamHX | LEP |
| 3595 | Age | CDK5 | FamHX | POMC |
| 3596 | Age | CDK5 | FGA | LEP |
| 3597 | Age | CDK5 | FGA | POMC |
| 3598 | Age | CDK5 | FTH1 | HDLC |
| 3599 | Age | CDK5 | FTH1 | LEP |

FIG. 15HHH

| 4-Panel | Marker 1 | Marker 2 | Marker 3 | Marker 4 |
|---|---|---|---|---|
| 3600 | Age | CDK5 | FTH1 | POMC |
| 3601 | Age | CDK5 | FTH1 | Sex |
| 3602 | Age | CDK5 | Gluc120 | LEP |
| 3603 | Age | CDK5 | Gluc120 | POMC |
| 3604 | Age | CDK5 | Glucose | HDLC |
| 3605 | Age | CDK5 | Glucose | IGF1 |
| 3606 | Age | CDK5 | Glucose | IL6ST |
| 3607 | Age | CDK5 | Glucose | LEP |
| 3608 | Age | CDK5 | Glucose | POMC |
| 3609 | Age | CDK5 | Glucose | Sex |
| 3610 | Age | CDK5 | Glucose | VEGF |
| 3611 | Age | CDK5 | HBA1C | HDLC |
| 3612 | Age | CDK5 | HBA1C | LEP |
| 3613 | Age | CDK5 | HBA1C | POMC |
| 3614 | Age | CDK5 | HDLC | Hip |
| 3615 | Age | CDK5 | HDLC | HT |
| 3616 | Age | CDK5 | HDLC | IGF1 |
| 3617 | Age | CDK5 | HDLC | IGFBP1 |
| 3618 | Age | CDK5 | HDLC | IL18 |
| 3619 | Age | CDK5 | HDLC | IL2RA |
| 3620 | Age | CDK5 | HDLC | IL6R |
| 3621 | Age | CDK5 | HDLC | IL6ST |
| 3622 | Age | CDK5 | HDLC | IL8 |
| 3623 | Age | CDK5 | HDLC | Insulin |
| 3624 | Age | CDK5 | HDLC | LEP |
| 3625 | Age | CDK5 | HDLC | POMC |
| 3626 | Age | CDK5 | HDLC | SCp |
| 3627 | Age | CDK5 | HDLC | SELP |
| 3628 | Age | CDK5 | HDLC | Sex |
| 3629 | Age | CDK5 | HDLC | TRIG |

| 4-Panel | Marker 1 | Marker 2 | Marker 3 | Marker 4 |
|---|---|---|---|---|
| 3630 | Age | CDK5 | HDLC | VEGF |
| 3631 | Age | CDK5 | HDLC | VWF |
| 3632 | Age | CDK5 | HDLC | Waist |
| 3633 | Age | CDK5 | HDLC | WT |
| 3634 | Age | CDK5 | HGF | LEP |
| 3635 | Age | CDK5 | HGF | POMC |
| 3636 | Age | CDK5 | HGF | Sex |
| 3637 | Age | CDK5 | Hip | IGF1 |
| 3638 | Age | CDK5 | Hip | LEP |
| 3639 | Age | CDK5 | Hip | POMC |
| 3640 | Age | CDK5 | Hip | Sex |
| 3641 | Age | CDK5 | Hip | VEGF |
| 3642 | Age | CDK5 | HP | LEP |
| 3643 | Age | CDK5 | HP | POMC |
| 3644 | Age | CDK5 | HP | Sex |
| 3645 | Age | CDK5 | HT | IGF1 |
| 3646 | Age | CDK5 | HT | IL6ST |
| 3647 | Age | CDK5 | HT | LEP |
| 3648 | Age | CDK5 | HT | POMC |
| 3649 | Age | CDK5 | HT | VEGF |
| 3650 | Age | CDK5 | ICAM1 | LEP |
| 3651 | Age | CDK5 | ICAM1 | POMC |
| 3652 | Age | CDK5 | IGF1 | IL2RA |
| 3653 | Age | CDK5 | IGF1 | IL6ST |
| 3654 | Age | CDK5 | IGF1 | Insulin |
| 3655 | Age | CDK5 | IGF1 | LEP |
| 3656 | Age | CDK5 | IGF1 | POMC |
| 3657 | Age | CDK5 | IGF1 | Sex |
| 3658 | Age | CDK5 | IGF1 | VCAM1 |
| 3659 | Age | CDK5 | IGF1 | VEGF |

FIG. 15III

| 4- Panel | Marker 1 | Marker 2 | Marker 3 | Marker 4 |
|---|---|---|---|---|
| 3660 | Age | CDK5 | IGFBP1 | LEP |
| 3661 | Age | CDK5 | IGFBP1 | POMC |
| 3662 | Age | CDK5 | IGFBP1 | Sex |
| 3663 | Age | CDK5 | IGFBP3 | LEP |
| 3664 | Age | CDK5 | IGFBP3 | POMC |
| 3665 | Age | CDK5 | IL18 | LEP |
| 3666 | Age | CDK5 | IL18 | POMC |
| 3667 | Age | CDK5 | IL18 | Sex |
| 3668 | Age | CDK5 | IL18 | VEGF |
| 3669 | Age | CDK5 | IL2RA | LEP |
| 3670 | Age | CDK5 | IL2RA | POMC |
| 3671 | Age | CDK5 | IL2RA | Sex |
| 3672 | Age | CDK5 | IL6R | IL6ST |
| 3673 | Age | CDK5 | IL6R | LEP |
| 3674 | Age | CDK5 | IL6R | POMC |
| 3675 | Age | CDK5 | IL6ST | LEP |
| 3676 | Age | CDK5 | IL6ST | POMC |
| 3677 | Age | CDK5 | IL6ST | SELP |
| 3678 | Age | CDK5 | IL6ST | Sex |
| 3679 | Age | CDK5 | IL6ST | TNFRSF1B |
| 3680 | Age | CDK5 | IL6ST | VEGF |
| 3681 | Age | CDK5 | IL8 | LEP |
| 3682 | Age | CDK5 | IL8 | POMC |
| 3683 | Age | CDK5 | IL8 | Sex |
| 3684 | Age | CDK5 | INHBA | LEP |
| 3685 | Age | CDK5 | INHBA | POMC |
| 3686 | Age | CDK5 | INHBA | Sex |
| 3687 | Age | CDK5 | Ins120 | Insulin |
| 3688 | Age | CDK5 | Ins120 | LEP |
| 3689 | Age | CDK5 | Ins120 | POMC |

| 4- Panel | Marker 1 | Marker 2 | Marker 3 | Marker 4 |
|---|---|---|---|---|
| 3690 | Age | CDK5 | Insulin | LEP |
| 3691 | Age | CDK5 | Insulin | POMC |
| 3692 | Age | CDK5 | Insulin | Sex |
| 3693 | Age | CDK5 | Insulin | VEGF |
| 3694 | Age | CDK5 | LDL | LEP |
| 3695 | Age | CDK5 | LEP | POMC |
| 3696 | Age | CDK5 | LEP | PLAT |
| 3697 | Age | CDK5 | LEP | POMC |
| 3698 | Age | CDK5 | LEP | SBP |
| 3699 | Age | CDK5 | LEP | SCp |
| 3700 | Age | CDK5 | LEP | SELE |
| 3701 | Age | CDK5 | LEP | SELP |
| 3702 | Age | CDK5 | LEP | Sex |
| 3703 | Age | CDK5 | LEP | SHBG |
| 3704 | Age | CDK5 | LEP | TNFRSF1B |
| 3705 | Age | CDK5 | LEP | TRIG |
| 3706 | Age | CDK5 | LEP | VCAM1 |
| 3707 | Age | CDK5 | LEP | VEGF |
| 3708 | Age | CDK5 | LEP | vWF |
| 3709 | Age | CDK5 | LEP | Waist |
| 3710 | Age | CDK5 | LEP | WT |
| 3711 | Age | CDK5 | PLAT | POMC |
| 3712 | Age | CDK5 | POMC | SBP |
| 3713 | Age | CDK5 | POMC | SCp |
| 3714 | Age | CDK5 | POMC | SELE |
| 3715 | Age | CDK5 | POMC | SELP |
| 3716 | Age | CDK5 | POMC | Sex |
| 3717 | Age | CDK5 | POMC | SHBG |
| 3718 | Age | CDK5 | POMC | TNFRSF1B |
| 3719 | Age | CDK5 | POMC | TRIG |

FIG. 15JJJ

| 4-Panel | Marker 1 | Marker 2 | Marker 3 | Marker 4 |
|---|---|---|---|---|
| 3720 | Age | CDK5 | POMC | VCAM1 |
| 3721 | Age | CDK5 | POMC | VEGF |
| 3722 | Age | CDK5 | POMC | VWF |
| 3723 | Age | CDK5 | POMC | Waist |
| 3724 | Age | CDK5 | POMC | WT |
| 3725 | Age | CDK5 | SELP | VEGF |
| 3726 | Age | CDK5 | Sex | VCAM1 |
| 3727 | Age | CDK5 | Sex | VEGF |
| 3728 | Age | CDK5 | Sex | Waist |
| 3729 | Age | CDK5 | Sex | WT |
| 3730 | Age | CDK5 | VCAM1 | VEGF |
| 3731 | Age | CHOL | CRP | HDLC |
| 3732 | Age | CHOL | CRP | LEP |
| 3733 | Age | CHOL | CRP | POMC |
| 3734 | Age | CHOL | CRP | Sex |
| 3735 | Age | CHOL | DBP | LEP |
| 3736 | Age | CHOL | DBP | POMC |
| 3737 | Age | CHOL | DPP4 | HDLC |
| 3738 | Age | CHOL | DPP4 | IGF1 |
| 3739 | Age | CHOL | DPP4 | LEP |
| 3740 | Age | CHOL | DPP4 | POMC |
| 3741 | Age | CHOL | DPP4 | Sex |
| 3742 | Age | CHOL | DPP4 | VEGF |
| 3743 | Age | CHOL | EGF | LEP |
| 3744 | Age | CHOL | EGF | POMC |
| 3745 | Age | CHOL | ENG | LEP |
| 3746 | Age | CHOL | ENG | POMC |
| 3747 | Age | CHOL | FamHX | HDLC |
| 3748 | Age | CHOL | FamHX | LEP |
| 3749 | Age | CHOL | FamHX | POMC |

| 4-Panel | Marker 1 | Marker 2 | Marker 3 | Marker 4 |
|---|---|---|---|---|
| 3750 | Age | CHOL | FGA | HDLC |
| 3751 | Age | CHOL | FGA | LEP |
| 3752 | Age | CHOL | FGA | POMC |
| 3753 | Age | CHOL | FTH1 | HDLC |
| 3754 | Age | CHOL | FTH1 | LEP |
| 3755 | Age | CHOL | FTH1 | POMC |
| 3756 | Age | CHOL | FTH1 | Sex |
| 3757 | Age | CHOL | Gluc120 | HDLC |
| 3758 | Age | CHOL | Gluc120 | LEP |
| 3759 | Age | CHOL | Gluc120 | POMC |
| 3760 | Age | CHOL | Glucose | HDLC |
| 3761 | Age | CHOL | Glucose | IGF1 |
| 3762 | Age | CHOL | Glucose | IL6ST |
| 3763 | Age | CHOL | Glucose | LEP |
| 3764 | Age | CHOL | Glucose | POMC |
| 3765 | Age | CHOL | Glucose | Sex |
| 3766 | Age | CHOL | Glucose | VEGF |
| 3767 | Age | CHOL | HBA1C | LEP |
| 3768 | Age | CHOL | HBA1C | POMC |
| 3769 | Age | CHOL | HBA1C | Sex |
| 3770 | Age | CHOL | HDLC | Hip |
| 3771 | Age | CHOL | HDLC | HT |
| 3772 | Age | CHOL | HDLC | ICAM1 |
| 3773 | Age | CHOL | HDLC | IGF1 |
| 3774 | Age | CHOL | HDLC | IGFBP1 |
| 3775 | Age | CHOL | HDLC | IL18 |
| 3776 | Age | CHOL | HDLC | IL2RA |
| 3777 | Age | CHOL | HDLC | IL6R |
| 3778 | Age | CHOL | HDLC | IL6ST |
| 3779 | Age | CHOL | HDLC | IL8 |

FIG. 15KKK

| 4-Panel | Marker 1 | Marker 2 | Marker 3 | Marker 4 |
|---|---|---|---|---|
| 3780 | Age | CHOL | HDLC | INHBA |
| 3781 | Age | CHOL | HDLC | Ins120 |
| 3782 | Age | CHOL | HDLC | Insulin |
| 3783 | Age | CHOL | HDLC | LDL |
| 3784 | Age | CHOL | HDLC | LEP |
| 3785 | Age | CHOL | HDLC | POMC |
| 3786 | Age | CHOL | HDLC | SCp |
| 3787 | Age | CHOL | HDLC | SELP |
| 3788 | Age | CHOL | HDLC | Sex |
| 3789 | Age | CHOL | HDLC | TRIG |
| 3790 | Age | CHOL | HDLC | VCAM1 |
| 3791 | Age | CHOL | HDLC | VEGF |
| 3792 | Age | CHOL | HDLC | VWF |
| 3793 | Age | CHOL | HDLC | Waist |
| 3794 | Age | CHOL | HDLC | WT |
| 3795 | Age | CHOL | HGF | LEP |
| 3796 | Age | CHOL | HGF | POMC |
| 3797 | Age | CHOL | Hip | LEP |
| 3798 | Age | CHOL | Hip | POMC |
| 3799 | Age | CHOL | HP | POMC |
| 3800 | Age | CHOL | HT | IGF1 |
| 3801 | Age | CHOL | HT | POMC |
| 3802 | Age | CHOL | HT | VEGF |
| 3803 | Age | CHOL | ICAM1 | LEP |
| 3804 | Age | CHOL | ICAM1 | POMC |
| 3805 | Age | CHOL | IGF1 | IL2RA |
| 3806 | Age | CHOL | IGF1 | IL6ST |
| 3807 | Age | CHOL | IGF1 | LDL |
| 3808 | Age | CHOL | IGF1 | LEP |
| 3809 | Age | CHOL | IGF1 | POMC |

| 4-Panel | Marker 1 | Marker 2 | Marker 3 | Marker 4 |
|---|---|---|---|---|
| 3810 | Age | CHOL | IGF1 | Sex |
| 3811 | Age | CHOL | IGF1 | VCAM1 |
| 3812 | Age | CHOL | IGF1 | VEGF |
| 3813 | Age | CHOL | IGF1 | VWF |
| 3814 | Age | CHOL | IGFBP1 | LEP |
| 3815 | Age | CHOL | IGFBP1 | POMC |
| 3816 | Age | CHOL | IGFBP1 | Sex |
| 3817 | Age | CHOL | IGFBP3 | LEP |
| 3818 | Age | CHOL | IGFBP3 | POMC |
| 3819 | Age | CHOL | IGFBP3 | LEP |
| 3820 | Age | CHOL | IL18 | POMC |
| 3821 | Age | CHOL | IL18 | Sex |
| 3822 | Age | CHOL | IL2RA | LEP |
| 3823 | Age | CHOL | IL2RA | POMC |
| 3824 | Age | CHOL | IL2RA | Sex |
| 3825 | Age | CHOL | IL6R | LEP |
| 3826 | Age | CHOL | IL6R | POMC |
| 3827 | Age | CHOL | IL6ST | LEP |
| 3828 | Age | CHOL | IL6ST | POMC |
| 3829 | Age | CHOL | IL6ST | Sex |
| 3830 | Age | CHOL | IL6ST | TNFRSF1B |
| 3831 | Age | CHOL | IL6ST | VEGF |
| 3832 | Age | CHOL | IL8 | LEP |
| 3833 | Age | CHOL | IL8 | POMC |
| 3834 | Age | CHOL | IL8 | Sex |
| 3835 | Age | CHOL | IL8 | LEP |
| 3836 | Age | CHOL | INHBA | POMC |
| 3837 | Age | CHOL | INHBA | Sex |
| 3838 | Age | CHOL | Ins120 | Insulin |
| 3839 | Age | CHOL | Ins120 | LEP |

FIG. 15LLL

| 4-Panel | Marker 1 | Marker 2 | Marker 3 | Marker 4 |
|---|---|---|---|---|
| 3840 | Age | CHOL | Ins120 | POMC |
| 3841 | Age | CHOL | Ins120 | Sex |
| 3842 | Age | CHOL | Insulin | LEP |
| 3843 | Age | CHOL | Insulin | POMC |
| 3844 | Age | CHOL | Insulin | Sex |
| 3845 | Age | CHOL | LDL | POMC |
| 3846 | Age | CHOL | LEP | PLAT |
| 3847 | Age | CHOL | LEP | POMC |
| 3848 | Age | CHOL | LEP | SBP |
| 3849 | Age | CHOL | LEP | SELE |
| 3850 | Age | CHOL | LEP | SELP |
| 3851 | Age | CHOL | LEP | Sex |
| 3852 | Age | CHOL | LEP | TNFRSF1B |
| 3853 | Age | CHOL | LEP | TRIG |
| 3854 | Age | CHOL | LEP | VCAM1 |
| 3855 | Age | CHOL | LEP | VEGF |
| 3856 | Age | CHOL | LEP | VWF |
| 3857 | Age | CHOL | LEP | Waist |
| 3858 | Age | CHOL | PLAT | POMC |
| 3859 | Age | CHOL | POMC | SBP |
| 3860 | Age | CHOL | POMC | SCp |
| 3861 | Age | CHOL | POMC | SELE |
| 3862 | Age | CHOL | POMC | SELP |
| 3863 | Age | CHOL | POMC | Sex |
| 3864 | Age | CHOL | POMC | SHBG |
| 3865 | Age | CHOL | POMC | TNFRSF1B |
| 3866 | Age | CHOL | POMC | TRIG |
| 3867 | Age | CHOL | POMC | VCAM1 |
| 3868 | Age | CHOL | POMC | VEGF |
| 3869 | Age | CHOL | POMC | VWF |
| 3870 | Age | CHOL | POMC | Waist |
| 3871 | Age | CHOL | POMC | WT |
| 3872 | Age | CHOL | Sex | VEGF |
| 3873 | Age | CHOL | Sex | Waist |
| 3874 | Age | CHOL | Sex | WT |
| 3875 | Age | CRP | DBP | LEP |
| 3876 | Age | CRP | DBP | POMC |
| 3877 | Age | CRP | DBP | Sex |
| 3878 | Age | CRP | DPP4 | Glucose |
| 3879 | Age | CRP | DPP4 | HDLC |
| 3880 | Age | CRP | DPP4 | Hip |
| 3881 | Age | CRP | DPP4 | IGF1 |
| 3882 | Age | CRP | DPP4 | Insulin |
| 3883 | Age | CRP | DPP4 | LEP |
| 3884 | Age | CRP | DPP4 | POMC |
| 3885 | Age | CRP | DPP4 | Sex |
| 3886 | Age | CRP | DPP4 | VEGF |
| 3887 | Age | CRP | EGF | IL6ST |
| 3888 | Age | CRP | EGF | LEP |
| 3889 | Age | CRP | EGF | POMC |
| 3890 | Age | CRP | EGF | Sex |
| 3891 | Age | CRP | ENG | LEP |
| 3892 | Age | CRP | ENG | POMC |
| 3893 | Age | CRP | FamHX | LEP |
| 3894 | Age | CRP | FamHX | POMC |
| 3895 | Age | CRP | FGA | LEP |
| 3896 | Age | CRP | FGA | POMC |
| 3897 | Age | CRP | FTH1 | HDLC |
| 3898 | Age | CRP | FTH1 | IL6ST |
| 3899 | Age | CRP | FTH1 | LEP |

| 4-Panel | Marker 1 | Marker 2 | Marker 3 | Marker 4 |
|---|---|---|---|---|
| 3900 | Age | CRP | FTH1 | POMC |
| 3901 | Age | CRP | FTH1 | Sex |
| 3902 | Age | CRP | Gluc120 | LEP |
| 3903 | Age | CRP | Gluc120 | POMC |
| 3904 | Age | CRP | Glucose | HDLC |
| 3905 | Age | CRP | Glucose | HT |
| 3906 | Age | CRP | Glucose | IGF1 |
| 3907 | Age | CRP | Glucose | IL18 |
| 3908 | Age | CRP | Glucose | IL6ST |
| 3909 | Age | CRP | Glucose | Insulin |
| 3910 | Age | CRP | Glucose | LEP |
| 3911 | Age | CRP | Glucose | POMC |
| 3912 | Age | CRP | Glucose | Sex |
| 3913 | Age | CRP | Glucose | VEGF |
| 3914 | Age | CRP | HBA1C | LEP |
| 3915 | Age | CRP | HBA1C | POMC |
| 3916 | Age | CRP | HBA1C | Sex |
| 3917 | Age | CRP | HDLC | Hip |
| 3918 | Age | CRP | HDLC | HT |
| 3919 | Age | CRP | HDLC | IGF1 |
| 3920 | Age | CRP | HDLC | IGFBP1 |
| 3921 | Age | CRP | HDLC | IL18 |
| 3922 | Age | CRP | HDLC | IL2RA |
| 3923 | Age | CRP | HDLC | IL6ST |
| 3924 | Age | CRP | HDLC | Insulin |
| 3925 | Age | CRP | HDLC | LEP |
| 3926 | Age | CRP | HDLC | POMC |
| 3927 | Age | CRP | HDLC | SCp |
| 3928 | Age | CRP | HDLC | Sex |
| 3929 | Age | CRP | HDLC | TRIG |
| 3930 | Age | CRP | HDLC | VCAM1 |
| 3931 | Age | CRP | HDLC | VEGF |
| 3932 | Age | CRP | HDLC | Waist |
| 3933 | Age | CRP | HDLC | WT |
| 3934 | Age | CRP | HGF | LEP |
| 3935 | Age | CRP | HGF | POMC |
| 3936 | Age | CRP | Hip | HT |
| 3937 | Age | CRP | Hip | IGF1 |
| 3938 | Age | CRP | Hip | IL6ST |
| 3939 | Age | CRP | Hip | LEP |
| 3940 | Age | CRP | Hip | POMC |
| 3941 | Age | CRP | Hip | Sex |
| 3942 | Age | CRP | Hip | VEGF |
| 3943 | Age | CRP | HP | IL6ST |
| 3944 | Age | CRP | HP | LEP |
| 3945 | Age | CRP | HP | POMC |
| 3946 | Age | CRP | HP | IGF1 |
| 3947 | Age | CRP | HT | IL6ST |
| 3948 | Age | CRP | HT | Insulin |
| 3949 | Age | CRP | HT | LEP |
| 3950 | Age | CRP | HT | POMC |
| 3951 | Age | CRP | HT | VEGF |
| 3952 | Age | CRP | HT | WT |
| 3953 | Age | CRP | ICAM1 | IL6ST |
| 3954 | Age | CRP | ICAM1 | LEP |
| 3955 | Age | CRP | ICAM1 | POMC |
| 3956 | Age | CRP | IGF1 | IL2RA |
| 3957 | Age | CRP | IGF1 | IL6ST |
| 3958 | Age | CRP | IGF1 | Insulin |
| 3959 | Age | CRP | IGF1 | LEP |

| 4-Panel | Marker 1 | Marker 2 | Marker 3 | Marker 4 |
|---|---|---|---|---|
| 3960 | Age | CRP | IGF1 | POMC |
| 3961 | Age | CRP | IGF1 | Sex |
| 3962 | Age | CRP | IGF1 | VCAM1 |
| 3963 | Age | CRP | IGF1 | VEGF |
| 3964 | Age | CRP | IGFBP1 | LEP |
| 3965 | Age | CRP | IGFBP1 | POMC |
| 3966 | Age | CRP | IGFBP1 | Sex |
| 3967 | Age | CRP | IGFBP3 | LEP |
| 3968 | Age | CRP | IGFBP3 | POMC |
| 3969 | Age | CRP | IL18 | IL6ST |
| 3970 | Age | CRP | IL18 | Insulin |
| 3971 | Age | CRP | IL18 | LEP |
| 3972 | Age | CRP | IL18 | POMC |
| 3973 | Age | CRP | IL18 | Sex |
| 3974 | Age | CRP | IL2RA | LEP |
| 3975 | Age | CRP | IL2RA | POMC |
| 3976 | Age | CRP | IL2RA | Sex |
| 3977 | Age | CRP | IL6R | IL6ST |
| 3978 | Age | CRP | IL6R | LEP |
| 3979 | Age | CRP | IL6R | POMC |
| 3980 | Age | CRP | IL6ST | IL8 |
| 3981 | Age | CRP | IL6ST | Insulin |
| 3982 | Age | CRP | IL6ST | LEP |
| 3983 | Age | CRP | IL6ST | POMC |
| 3984 | Age | CRP | IL6ST | SELP |
| 3985 | Age | CRP | IL6ST | Sex |
| 3986 | Age | CRP | IL6ST | TNFRSF1B |
| 3987 | Age | CRP | IL6ST | VEGF |
| 3988 | Age | CRP | IL6ST | WT |
| 3989 | Age | CRP | IL8 | LEP |

| 4-Panel | Marker 1 | Marker 2 | Marker 3 | Marker 4 |
|---|---|---|---|---|
| 3990 | Age | CRP | IL8 | POMC |
| 3991 | Age | CRP | IL8 | Sex |
| 3992 | Age | CRP | INHBA | LEP |
| 3993 | Age | CRP | INHBA | POMC |
| 3994 | Age | CRP | INHBA | Sex |
| 3995 | Age | CRP | Ins120 | Insulin |
| 3996 | Age | CRP | Ins120 | LEP |
| 3997 | Age | CRP | Ins120 | POMC |
| 3998 | Age | CRP | Insulin | LEP |
| 3999 | Age | CRP | Insulin | POMC |
| 4000 | Age | CRP | Insulin | Sex |
| 4001 | Age | CRP | Insulin | VEGF |
| 4002 | Age | CRP | LDL | LEP |
| 4003 | Age | CRP | LDL | POMC |
| 4004 | Age | CRP | LEP | PLAT |
| 4005 | Age | CRP | LEP | POMC |
| 4006 | Age | CRP | LEP | SBP |
| 4007 | Age | CRP | LEP | SCp |
| 4008 | Age | CRP | LEP | SELE |
| 4009 | Age | CRP | LEP | SELP |
| 4010 | Age | CRP | LEP | Sex |
| 4011 | Age | CRP | LEP | SHBG |
| 4012 | Age | CRP | LEP | TNFRSF1B |
| 4013 | Age | CRP | LEP | TRIG |
| 4014 | Age | CRP | LEP | VCAM1 |
| 4015 | Age | CRP | LEP | VEGF |
| 4016 | Age | CRP | LEP | VWF |
| 4017 | Age | CRP | LEP | Waist |
| 4018 | Age | CRP | LEP | WT |
| 4019 | Age | CRP | PLAT | POMC |

FIG. 15000

| 4-Panel | Marker 1 | Marker 2 | Marker 3 | Marker 4 |
|---|---|---|---|---|
| 4020 | Age | CRP | POMC | SBP |
| 4021 | Age | CRP | POMC | SCp |
| 4022 | Age | CRP | POMC | SELE |
| 4023 | Age | CRP | POMC | SELP |
| 4024 | Age | CRP | POMC | Sex |
| 4025 | Age | CRP | POMC | SHBG |
| 4026 | Age | CRP | POMC | TNFRSF1B |
| 4027 | Age | CRP | POMC | TRIG |
| 4028 | Age | CRP | POMC | VCAM1 |
| 4029 | Age | CRP | POMC | VEGF |
| 4030 | Age | CRP | POMC | VWF |
| 4031 | Age | CRP | POMC | Waist |
| 4032 | Age | CRP | POMC | WT |
| 4033 | Age | CRP | SCp | Sex |
| 4034 | Age | CRP | Sex | VCAM1 |
| 4035 | Age | CRP | Sex | VEGF |
| 4036 | Age | CRP | Sex | Waist |
| 4037 | Age | CRP | Sex | WT |
| 4038 | Age | CRP | VCAM1 | VEGF |
| 4039 | Age | DBP | DPP4 | HDLC |
| 4040 | Age | DBP | DPP4 | IGF1 |
| 4041 | Age | DBP | DPP4 | LEP |
| 4042 | Age | DBP | DPP4 | POMC |
| 4043 | Age | DBP | DPP4 | Sex |
| 4044 | Age | DBP | DPP4 | VEGF |
| 4045 | Age | DBP | EGF | LEP |
| 4046 | Age | DBP | EGF | POMC |
| 4047 | Age | DBP | ENG | LEP |
| 4048 | Age | DBP | ENG | POMC |
| 4049 | Age | DBP | FamHX | LEP |

| 4-Panel | Marker 1 | Marker 2 | Marker 3 | Marker 4 |
|---|---|---|---|---|
| 4050 | Age | DBP | FamHX | POMC |
| 4051 | Age | DBP | FGA | LEP |
| 4052 | Age | DBP | FGA | POMC |
| 4053 | Age | DBP | FTH1 | HDLC |
| 4054 | Age | DBP | FTH1 | LEP |
| 4055 | Age | DBP | FTH1 | POMC |
| 4056 | Age | DBP | FTH1 | Sex |
| 4057 | Age | DBP | Gluc120 | LEP |
| 4058 | Age | DBP | Gluc120 | POMC |
| 4059 | Age | DBP | Glucose | HDLC |
| 4060 | Age | DBP | Glucose | IGF1 |
| 4061 | Age | DBP | Glucose | IL6ST |
| 4062 | Age | DBP | Glucose | LEP |
| 4063 | Age | DBP | Glucose | POMC |
| 4064 | Age | DBP | Glucose | Sex |
| 4065 | Age | DBP | Glucose | VEGF |
| 4066 | Age | DBP | HBA1C | LEP |
| 4067 | Age | DBP | HBA1C | POMC |
| 4068 | Age | DBP | HBA1C | Sex |
| 4069 | Age | DBP | HDLC | Hip |
| 4070 | Age | DBP | HDLC | IGF1 |
| 4071 | Age | DBP | HDLC | IGFBP1 |
| 4072 | Age | DBP | HDLC | IL18 |
| 4073 | Age | DBP | HDLC | IL2RA |
| 4074 | Age | DBP | HDLC | IL6ST |
| 4075 | Age | DBP | HDLC | IL8 |
| 4076 | Age | DBP | HDLC | Insulin |
| 4077 | Age | DBP | HDLC | LEP |
| 4078 | Age | DBP | HDLC | POMC |
| 4079 | Age | DBP | HDLC | SCp |

FIG. 15PPP

| 4-Panel | Marker 1 | Marker 2 | Marker 3 | Marker 4 |
|---|---|---|---|---|
| 4080 | Age | DBP | HDLC | Sex |
| 4081 | Age | DBP | HDLC | TRIG |
| 4082 | Age | DBP | HDLC | VCAM1 |
| 4083 | Age | DBP | HDLC | VEGF |
| 4084 | Age | DBP | HDLC | VWF |
| 4085 | Age | DBP | HDLC | Waist |
| 4086 | Age | DBP | HDLC | WT |
| 4087 | Age | DBP | HGF | LEP |
| 4088 | Age | DBP | HGF | POMC |
| 4089 | Age | DBP | Hip | IGF1 |
| 4090 | Age | DBP | Hip | LEP |
| 4091 | Age | DBP | Hip | POMC |
| 4092 | Age | DBP | HP | LEP |
| 4093 | Age | DBP | HP | POMC |
| 4094 | Age | DBP | HT | IGF1 |
| 4095 | Age | DBP | HT | IL6ST |
| 4096 | Age | DBP | HT | LEP |
| 4097 | Age | DBP | HT | POMC |
| 4098 | Age | DBP | HT | VEGF |
| 4099 | Age | DBP | ICAM1 | LEP |
| 4100 | Age | DBP | ICAM1 | POMC |
| 4101 | Age | DBP | IGF1 | IL2RA |
| 4102 | Age | DBP | IGF1 | IL6ST |
| 4103 | Age | DBP | IGF1 | Ins120 |
| 4104 | Age | DBP | IGF1 | Insulin |
| 4105 | Age | DBP | IGF1 | LEP |
| 4106 | Age | DBP | IGF1 | POMC |
| 4107 | Age | DBP | IGF1 | Sex |
| 4108 | Age | DBP | IGF1 | VCAM1 |
| 4109 | Age | DBP | IGF1 | VEGF |

| 4-Panel | Marker 1 | Marker 2 | Marker 3 | Marker 4 |
|---|---|---|---|---|
| 4110 | Age | DBP | IGFBP1 | LEP |
| 4111 | Age | DBP | IGFBP1 | POMC |
| 4112 | Age | DBP | IGFBP1 | Sex |
| 4113 | Age | DBP | IGFBP3 | LEP |
| 4114 | Age | DBP | IGFBP3 | POMC |
| 4115 | Age | DBP | IL18 | LEP |
| 4116 | Age | DBP | IL18 | POMC |
| 4117 | Age | DBP | IL18 | Sex |
| 4118 | Age | DBP | IL18 | VEGF |
| 4119 | Age | DBP | IL2RA | LEP |
| 4120 | Age | DBP | IL2RA | POMC |
| 4121 | Age | DBP | IL2RA | Sex |
| 4122 | Age | DBP | IL6R | LEP |
| 4123 | Age | DBP | IL6R | POMC |
| 4124 | Age | DBP | IL6ST | LEP |
| 4125 | Age | DBP | IL6ST | POMC |
| 4126 | Age | DBP | IL6ST | Sex |
| 4127 | Age | DBP | IL6ST | TNFRSF1B |
| 4128 | Age | DBP | IL6ST | VEGF |
| 4129 | Age | DBP | IL8 | LEP |
| 4130 | Age | DBP | IL8 | POMC |
| 4131 | Age | DBP | IL8 | Sex |
| 4132 | Age | DBP | INHBA | LEP |
| 4133 | Age | DBP | INHBA | POMC |
| 4134 | Age | DBP | INHBA | Sex |
| 4135 | Age | DBP | Ins120 | Insulin |
| 4136 | Age | DBP | Ins120 | LEP |
| 4137 | Age | DBP | Ins120 | POMC |
| 4138 | Age | DBP | Insulin | LEP |
| 4139 | Age | DBP | Insulin | POMC |

FIG. 15QQQ

| 4-Panel | Marker 1 | Marker 2 | Marker 3 | Marker 4 |
|---|---|---|---|---|
| 4140 | Age | DBP | Insulin | Sex |
| 4141 | Age | DBP | Insulin | VEGF |
| 4142 | Age | DBP | LDL | LEP |
| 4143 | Age | DBP | LDL | POMC |
| 4144 | Age | DBP | LEP | PLAT |
| 4145 | Age | DBP | LEP | POMC |
| 4146 | Age | DBP | LEP | SBP |
| 4147 | Age | DBP | LEP | SCp |
| 4148 | Age | DBP | LEP | SELE |
| 4149 | Age | DBP | LEP | SELP |
| 4150 | Age | DBP | LEP | Sex |
| 4151 | Age | DBP | LEP | SHBG |
| 4152 | Age | DBP | LEP | TNFRSF1B |
| 4153 | Age | DBP | LEP | TRIG |
| 4154 | Age | DBP | LEP | VCAM1 |
| 4155 | Age | DBP | LEP | VEGF |
| 4156 | Age | DBP | LEP | VWF |
| 4157 | Age | DBP | LEP | Waist |
| 4158 | Age | DBP | LEP | WT |
| 4159 | Age | DBP | PLAT | POMC |
| 4160 | Age | DBP | POMC | SBP |
| 4161 | Age | DBP | POMC | SCp |
| 4162 | Age | DBP | POMC | SELE |
| 4163 | Age | DBP | POMC | SELP |
| 4164 | Age | DBP | POMC | Sex |
| 4165 | Age | DBP | POMC | SHBG |
| 4166 | Age | DBP | POMC | TNFRSF1B |
| 4167 | Age | DBP | POMC | TRIG |
| 4168 | Age | DBP | POMC | VCAM1 |
| 4169 | Age | DBP | POMC | VEGF |
| 4170 | Age | DBP | POMC | VWF |
| 4171 | Age | DBP | POMC | Waist |
| 4172 | Age | DBP | POMC | WT |
| 4173 | Age | DBP | Sex | VCAM1 |
| 4174 | Age | DBP | Sex | VEGF |
| 4175 | Age | DBP | Sex | Waist |
| 4176 | Age | DBP | Sex | WT |
| 4177 | Age | DPP4 | EGF | HDLC |
| 4178 | Age | DPP4 | EGF | IGF1 |
| 4179 | Age | DPP4 | EGF | LEP |
| 4180 | Age | DPP4 | EGF | POMC |
| 4181 | Age | DPP4 | EGF | Sex |
| 4182 | Age | DPP4 | EGF | VEGF |
| 4183 | Age | DPP4 | ENG | HDLC |
| 4184 | Age | DPP4 | ENG | IGF1 |
| 4185 | Age | DPP4 | ENG | LEP |
| 4186 | Age | DPP4 | ENG | POMC |
| 4187 | Age | DPP4 | ENG | VEGF |
| 4188 | Age | DPP4 | FamHX | HDLC |
| 4189 | Age | DPP4 | FamHX | IGF1 |
| 4190 | Age | DPP4 | FamHX | LEP |
| 4191 | Age | DPP4 | FamHX | POMC |
| 4192 | Age | DPP4 | FamHX | VEGF |
| 4193 | Age | DPP4 | FGA | HDLC |
| 4194 | Age | DPP4 | FGA | IGF1 |
| 4195 | Age | DPP4 | FGA | LEP |
| 4196 | Age | DPP4 | FGA | POMC |
| 4197 | Age | DPP4 | FGA | VEGF |
| 4198 | Age | DPP4 | FTH1 | HDLC |
| 4199 | Age | DPP4 | FTH1 | HT |

FIG. 15RRRR

FIG. 15SSS

| 4-Panel | Marker 1 | Marker 2 | Marker 3 | Marker 4 |
|---|---|---|---|---|
| 4200 | Age | DPP4 | FTH1 | IGF1 |
| 4201 | Age | DPP4 | FTH1 | LEP |
| 4202 | Age | DPP4 | FTH1 | POMC |
| 4203 | Age | DPP4 | FTH1 | Sex |
| 4204 | Age | DPP4 | FTH1 | VEGF |
| 4205 | Age | DPP4 | Gluc120 | Glucose |
| 4206 | Age | DPP4 | Gluc120 | HDLC |
| 4207 | Age | DPP4 | Gluc120 | IGF1 |
| 4208 | Age | DPP4 | Gluc120 | LEP |
| 4209 | Age | DPP4 | Gluc120 | POMC |
| 4210 | Age | DPP4 | Gluc120 | VEGF |
| 4211 | Age | DPP4 | Glucose | HBA1C |
| 4212 | Age | DPP4 | Glucose | HDLC |
| 4213 | Age | DPP4 | Glucose | HP |
| 4214 | Age | DPP4 | Glucose | HT |
| 4215 | Age | DPP4 | Glucose | IGF1 |
| 4216 | Age | DPP4 | Glucose | IL18 |
| 4217 | Age | DPP4 | Glucose | IL6ST |
| 4218 | Age | DPP4 | Glucose | IL8 |
| 4219 | Age | DPP4 | Glucose | Ins120 |
| 4220 | Age | DPP4 | Glucose | LEP |
| 4221 | Age | DPP4 | Glucose | POMC |
| 4222 | Age | DPP4 | Glucose | SELP |
| 4223 | Age | DPP4 | Glucose | Sex |
| 4224 | Age | DPP4 | Glucose | VEGF |
| 4225 | Age | DPP4 | HBA1C | HDLC |
| 4226 | Age | DPP4 | HBA1C | IGF1 |
| 4227 | Age | DPP4 | HBA1C | LEP |
| 4228 | Age | DPP4 | HBA1C | POMC |
| 4229 | Age | DPP4 | HBA1C | Sex |

| 4-Panel | Marker 1 | Marker 2 | Marker 3 | Marker 4 |
|---|---|---|---|---|
| 4230 | Age | DPP4 | HBA1C | VEGF |
| 4231 | Age | DPP4 | HDLC | HGF |
| 4232 | Age | DPP4 | HDLC | Hip |
| 4233 | Age | DPP4 | HDLC | HP |
| 4234 | Age | DPP4 | HDLC | HT |
| 4235 | Age | DPP4 | HDLC | ICAM1 |
| 4236 | Age | DPP4 | HDLC | IGF1 |
| 4237 | Age | DPP4 | HDLC | IGFBP1 |
| 4238 | Age | DPP4 | HDLC | IGFBP3 |
| 4239 | Age | DPP4 | HDLC | IL18 |
| 4240 | Age | DPP4 | HDLC | IL2RA |
| 4241 | Age | DPP4 | HDLC | IL6R |
| 4242 | Age | DPP4 | HDLC | IL6ST |
| 4243 | Age | DPP4 | HDLC | IL8 |
| 4244 | Age | DPP4 | HDLC | INHBA |
| 4245 | Age | DPP4 | HDLC | Ins120 |
| 4246 | Age | DPP4 | HDLC | Insulin |
| 4247 | Age | DPP4 | HDLC | LDL |
| 4248 | Age | DPP4 | HDLC | LEP |
| 4249 | Age | DPP4 | HDLC | PLAT |
| 4250 | Age | DPP4 | HDLC | POMC |
| 4251 | Age | DPP4 | HDLC | SBP |
| 4252 | Age | DPP4 | HDLC | SCp |
| 4253 | Age | DPP4 | HDLC | SELE |
| 4254 | Age | DPP4 | HDLC | SELP |
| 4255 | Age | DPP4 | HDLC | Sex |
| 4256 | Age | DPP4 | HDLC | SHBG |
| 4257 | Age | DPP4 | HDLC | TNFRSF1B |
| 4258 | Age | DPP4 | HDLC | TRIG |
| 4259 | Age | DPP4 | HDLC | VCAM1 |

| 4-Panel | Marker 1 | Marker 2 | Marker 3 | Marker 4 |
|---|---|---|---|---|
| 4260 | Age | DPP4 | HDLC | VEGF |
| 4261 | Age | DPP4 | HDLC | VWF |
| 4262 | Age | DPP4 | HDLC | Waist |
| 4263 | Age | DPP4 | HDLC | WT |
| 4264 | Age | DPP4 | HGF | IGF1 |
| 4265 | Age | DPP4 | HGF | LEP |
| 4266 | Age | DPP4 | HGF | POMC |
| 4267 | Age | DPP4 | HGF | Sex |
| 4268 | Age | DPP4 | HGF | VEGF |
| 4269 | Age | DPP4 | Hip | HT |
| 4270 | Age | DPP4 | Hip | IGF1 |
| 4271 | Age | DPP4 | Hip | LEP |
| 4272 | Age | DPP4 | Hip | POMC |
| 4273 | Age | DPP4 | Hip | Sex |
| 4274 | Age | DPP4 | Hip | VEGF |
| 4275 | Age | DPP4 | HP | IGF1 |
| 4276 | Age | DPP4 | HP | LEP |
| 4277 | Age | DPP4 | HP | POMC |
| 4278 | Age | DPP4 | HP | Sex |
| 4279 | Age | DPP4 | HP | VEGF |
| 4280 | Age | DPP4 | HT | IGF1 |
| 4281 | Age | DPP4 | HT | Insulin |
| 4282 | Age | DPP4 | HT | LEP |
| 4283 | Age | DPP4 | HT | POMC |
| 4284 | Age | DPP4 | HT | VEGF |
| 4285 | Age | DPP4 | HT | WT |
| 4286 | Age | DPP4 | ICAM1 | IGF1 |
| 4287 | Age | DPP4 | ICAM1 | LEP |
| 4288 | Age | DPP4 | ICAM1 | POMC |
| 4289 | Age | DPP4 | ICAM1 | Sex |

| 4-Panel | Marker 1 | Marker 2 | Marker 3 | Marker 4 |
|---|---|---|---|---|
| 4290 | Age | DPP4 | ICAM1 | VEGF |
| 4291 | Age | DPP4 | IGF1 | IGFBP1 |
| 4292 | Age | DPP4 | IGF1 | IGFBP3 |
| 4293 | Age | DPP4 | IGF1 | IL18 |
| 4294 | Age | DPP4 | IGF1 | IL2RA |
| 4295 | Age | DPP4 | IGF1 | IL6R |
| 4296 | Age | DPP4 | IGF1 | IL6ST |
| 4297 | Age | DPP4 | IGF1 | IL8 |
| 4298 | Age | DPP4 | IGF1 | INHBA |
| 4299 | Age | DPP4 | IGF1 | Ins120 |
| 4300 | Age | DPP4 | IGF1 | Insulin |
| 4301 | Age | DPP4 | IGF1 | LDL |
| 4302 | Age | DPP4 | IGF1 | LEP |
| 4303 | Age | DPP4 | IGF1 | PLAT |
| 4304 | Age | DPP4 | IGF1 | POMC |
| 4305 | Age | DPP4 | IGF1 | SBP |
| 4306 | Age | DPP4 | IGF1 | SCp |
| 4307 | Age | DPP4 | IGF1 | SELE |
| 4308 | Age | DPP4 | IGF1 | SELP |
| 4309 | Age | DPP4 | IGF1 | Sex |
| 4310 | Age | DPP4 | IGF1 | SHBG |
| 4311 | Age | DPP4 | IGF1 | TNFRSF1B |
| 4312 | Age | DPP4 | IGF1 | TRIG |
| 4313 | Age | DPP4 | IGF1 | VCAM1 |
| 4314 | Age | DPP4 | IGF1 | VEGF |
| 4315 | Age | DPP4 | IGF1 | VWF |
| 4316 | Age | DPP4 | IGF1 | Waist |
| 4317 | Age | DPP4 | IGF1 | WT |
| 4318 | Age | DPP4 | IGFBP1 | LEP |
| 4319 | Age | DPP4 | IGFBP1 | POMC |

| 4-Panel | Marker 1 | Marker 2 | Marker 3 | Marker 4 |
|---|---|---|---|---|
| 4320 | Age | DPP4 | IGFBP1 | Sex |
| 4321 | Age | DPP4 | IGFBP1 | VEGF |
| 4322 | Age | DPP4 | IGFBP3 | LEP |
| 4323 | Age | DPP4 | IGFBP3 | POMC |
| 4324 | Age | DPP4 | IGFBP3 | VEGF |
| 4325 | Age | DPP4 | IL18 | LEP |
| 4326 | Age | DPP4 | IL18 | POMC |
| 4327 | Age | DPP4 | IL18 | Sex |
| 4328 | Age | DPP4 | IL18 | VEGF |
| 4329 | Age | DPP4 | IL2RA | LEP |
| 4330 | Age | DPP4 | IL2RA | POMC |
| 4331 | Age | DPP4 | IL2RA | Sex |
| 4332 | Age | DPP4 | IL2RA | VEGF |
| 4333 | Age | DPP4 | IL6R | IL6ST |
| 4334 | Age | DPP4 | IL6R | LEP |
| 4335 | Age | DPP4 | IL6R | POMC |
| 4336 | Age | DPP4 | IL6R | Sex |
| 4337 | Age | DPP4 | IL6R | VEGF |
| 4338 | Age | DPP4 | IL6ST | LEP |
| 4339 | Age | DPP4 | IL6ST | POMC |
| 4340 | Age | DPP4 | IL6ST | Sex |
| 4341 | Age | DPP4 | IL6ST | TNFRSF1B |
| 4342 | Age | DPP4 | IL6ST | VEGF |
| 4343 | Age | DPP4 | IL8 | LEP |
| 4344 | Age | DPP4 | IL8 | POMC |
| 4345 | Age | DPP4 | IL8 | Sex |
| 4346 | Age | DPP4 | IL8 | VEGF |
| 4347 | Age | DPP4 | INHBA | LEP |
| 4348 | Age | DPP4 | INHBA | POMC |
| 4349 | Age | DPP4 | INHBA | Sex |
| 4350 | Age | DPP4 | INHBA | VEGF |
| 4351 | Age | DPP4 | Ins120 | Insulin |
| 4352 | Age | DPP4 | Ins120 | LEP |
| 4353 | Age | DPP4 | Ins120 | POMC |
| 4354 | Age | DPP4 | Ins120 | Sex |
| 4355 | Age | DPP4 | Ins120 | VEGF |
| 4356 | Age | DPP4 | Insulin | LEP |
| 4357 | Age | DPP4 | Insulin | POMC |
| 4358 | Age | DPP4 | Insulin | Sex |
| 4359 | Age | DPP4 | Insulin | VEGF |
| 4360 | Age | DPP4 | LDL | LEP |
| 4361 | Age | DPP4 | LDL | POMC |
| 4362 | Age | DPP4 | LDL | VEGF |
| 4363 | Age | DPP4 | LEP | PLAT |
| 4364 | Age | DPP4 | LEP | POMC |
| 4365 | Age | DPP4 | LEP | SBP |
| 4366 | Age | DPP4 | LEP | SCp |
| 4367 | Age | DPP4 | LEP | SELE |
| 4368 | Age | DPP4 | LEP | SELP |
| 4369 | Age | DPP4 | LEP | Sex |
| 4370 | Age | DPP4 | LEP | SHBG |
| 4371 | Age | DPP4 | LEP | TNFRSF1B |
| 4372 | Age | DPP4 | LEP | TRIG |
| 4373 | Age | DPP4 | LEP | VCAM1 |
| 4374 | Age | DPP4 | LEP | VEGF |
| 4375 | Age | DPP4 | LEP | VWF |
| 4376 | Age | DPP4 | LEP | Waist |
| 4377 | Age | DPP4 | LEP | WT |
| 4378 | Age | DPP4 | PLAT | POMC |
| 4379 | Age | DPP4 | PLAT | VEGF |

| 4-Panel | Marker 1 | Marker 2 | Marker 3 | Marker 4 |
|---|---|---|---|---|
| 4380 | Age | DPP4 | POMC | SBP |
| 4381 | Age | DPP4 | POMC | SCp |
| 4382 | Age | DPP4 | POMC | SELE |
| 4383 | Age | DPP4 | POMC | SELP |
| 4384 | Age | DPP4 | POMC | Sex |
| 4385 | Age | DPP4 | POMC | SHBG |
| 4386 | Age | DPP4 | POMC | TNFRSF1B |
| 4387 | Age | DPP4 | POMC | TRIG |
| 4388 | Age | DPP4 | POMC | VCAM1 |
| 4389 | Age | DPP4 | POMC | VEGF |
| 4390 | Age | DPP4 | POMC | VWF |
| 4391 | Age | DPP4 | POMC | Waist |
| 4392 | Age | DPP4 | POMC | WT |
| 4393 | Age | DPP4 | SBP | VEGF |
| 4394 | Age | DPP4 | SCp | VEGF |
| 4395 | Age | DPP4 | SELE | VEGF |
| 4396 | Age | DPP4 | SELP | Sex |
| 4397 | Age | DPP4 | SELP | VEGF |
| 4398 | Age | DPP4 | Sex | VCAM1 |
| 4399 | Age | DPP4 | Sex | VEGF |
| 4400 | Age | DPP4 | Sex | Waist |
| 4401 | Age | DPP4 | Sex | WT |
| 4402 | Age | DPP4 | SHBG | VEGF |
| 4403 | Age | DPP4 | TNFRSF1B | VEGF |
| 4404 | Age | DPP4 | TRIG | VEGF |
| 4405 | Age | DPP4 | VCAM1 | VEGF |
| 4406 | Age | DPP4 | VEGF | VWF |
| 4407 | Age | DPP4 | VEGF | Waist |
| 4408 | Age | DPP4 | VEGF | WT |
| 4409 | Age | EGF | ENG | LEP |

| 4-Panel | Marker 1 | Marker 2 | Marker 3 | Marker 4 |
|---|---|---|---|---|
| 4410 | Age | EGF | ENG | POMC |
| 4411 | Age | EGF | FamHX | LEP |
| 4412 | Age | EGF | FamHX | POMC |
| 4413 | Age | EGF | FGA | LEP |
| 4414 | Age | EGF | FGA | POMC |
| 4415 | Age | EGF | FTH1 | HDLC |
| 4416 | Age | EGF | FTH1 | LEP |
| 4417 | Age | EGF | FTH1 | POMC |
| 4418 | Age | EGF | FTH1 | Sex |
| 4419 | Age | EGF | Gluc120 | LEP |
| 4420 | Age | EGF | Gluc120 | POMC |
| 4421 | Age | EGF | Glucose | HDLC |
| 4422 | Age | EGF | Glucose | IGF1 |
| 4423 | Age | EGF | Glucose | IL6ST |
| 4424 | Age | EGF | Glucose | LEP |
| 4425 | Age | EGF | Glucose | POMC |
| 4426 | Age | EGF | Glucose | Sex |
| 4427 | Age | EGF | Glucose | VEGF |
| 4428 | Age | EGF | HBA1C | LEP |
| 4429 | Age | EGF | HBA1C | POMC |
| 4430 | Age | EGF | HDLC | Hip |
| 4431 | Age | EGF | HDLC | HT |
| 4432 | Age | EGF | HDLC | IGF1 |
| 4433 | Age | EGF | HDLC | IGFBP1 |
| 4434 | Age | EGF | HDLC | IL18 |
| 4435 | Age | EGF | HDLC | IL2RA |
| 4436 | Age | EGF | HDLC | IL6ST |
| 4437 | Age | EGF | HDLC | Insulin |
| 4438 | Age | EGF | HDLC | LEP |
| 4439 | Age | EGF | HDLC | POMC |

FIG. 15VVV

| 4-Panel | Marker 1 | Marker 2 | Marker 3 | Marker 4 |
|---|---|---|---|---|
| 4440 | Age | EGF | HDLC | SCp |
| 4441 | Age | EGF | HDLC | Sex |
| 4442 | Age | EGF | HDLC | TRIG |
| 4443 | Age | EGF | HDLC | VCAM1 |
| 4444 | Age | EGF | HDLC | VEGF |
| 4445 | Age | EGF | HDLC | VWF |
| 4446 | Age | EGF | HDLC | Waist |
| 4447 | Age | EGF | HDLC | WT |
| 4448 | Age | EGF | HGF | LEP |
| 4449 | Age | EGF | HGF | POMC |
| 4450 | Age | EGF | Hip | IGF1 |
| 4451 | Age | EGF | Hip | LEP |
| 4452 | Age | EGF | Hip | POMC |
| 4453 | Age | EGF | Hip | Sex |
| 4454 | Age | EGF | HP | POMC |
| 4455 | Age | EGF | HT | IGF1 |
| 4456 | Age | EGF | HT | IL6ST |
| 4457 | Age | EGF | HT | LEP |
| 4458 | Age | EGF | HT | POMC |
| 4459 | Age | EGF | HT | VEGF |
| 4460 | Age | EGF | ICAM1 | LEP |
| 4461 | Age | EGF | ICAM1 | POMC |
| 4462 | Age | EGF | IGF1 | IL2RA |
| 4463 | Age | EGF | IGF1 | IL6ST |
| 4464 | Age | EGF | IGF1 | Ins120 |
| 4465 | Age | EGF | IGF1 | Insulin |
| 4466 | Age | EGF | IGF1 | LEP |
| 4467 | Age | EGF | IGF1 | POMC |
| 4468 | Age | EGF | IGF1 | Sex |
| 4469 | Age | EGF | IGF1 | VCAM1 |
| 4470 | Age | EGF | IGF1 | VEGF |
| 4471 | Age | EGF | IGFBP1 | LEP |
| 4472 | Age | EGF | IGFBP1 | POMC |
| 4473 | Age | EGF | IGFBP3 | LEP |
| 4474 | Age | EGF | IGFBP3 | POMC |
| 4475 | Age | EGF | IL18 | LEP |
| 4476 | Age | EGF | IL18 | POMC |
| 4477 | Age | EGF | IL2RA | LEP |
| 4478 | Age | EGF | IL2RA | POMC |
| 4479 | Age | EGF | IL2RA | Sex |
| 4480 | Age | EGF | IL6R | LEP |
| 4481 | Age | EGF | IL6R | POMC |
| 4482 | Age | EGF | IL6ST | LEP |
| 4483 | Age | EGF | IL6ST | POMC |
| 4484 | Age | EGF | IL6ST | Sex |
| 4485 | Age | EGF | IL6ST | TNFRSF1B |
| 4486 | Age | EGF | IL6ST | VEGF |
| 4487 | Age | EGF | IL8 | LEP |
| 4488 | Age | EGF | IL8 | POMC |
| 4489 | Age | EGF | INHBA | LEP |
| 4490 | Age | EGF | INHBA | POMC |
| 4491 | Age | EGF | Ins120 | LEP |
| 4492 | Age | EGF | Ins120 | POMC |
| 4493 | Age | EGF | Insulin | LEP |
| 4494 | Age | EGF | Insulin | POMC |
| 4495 | Age | EGF | Insulin | Sex |
| 4496 | Age | EGF | Insulin | VEGF |
| 4497 | Age | EGF | LDL | LEP |
| 4498 | Age | EGF | LDL | POMC |
| 4499 | Age | EGF | LEP | PLAT |

FIG. 15WWW

| 4-Panel | Marker 1 | Marker 2 | Marker 3 | Marker 4 |
|---|---|---|---|---|
| 4500 | Age | EGF | LEP | POMC |
| 4501 | Age | EGF | LEP | SBP |
| 4502 | Age | EGF | LEP | SCp |
| 4503 | Age | EGF | LEP | SELE |
| 4504 | Age | EGF | LEP | SELP |
| 4505 | Age | EGF | LEP | Sex |
| 4506 | Age | EGF | LEP | TNFRSF1B |
| 4507 | Age | EGF | LEP | TRIG |
| 4508 | Age | EGF | LEP | VCAM1 |
| 4509 | Age | EGF | LEP | VEGF |
| 4510 | Age | EGF | LEP | VWF |
| 4511 | Age | EGF | LEP | Waist |
| 4512 | Age | EGF | LEP | WT |
| 4513 | Age | EGF | PLAT | POMC |
| 4514 | Age | EGF | POMC | SBP |
| 4515 | Age | EGF | POMC | SCp |
| 4516 | Age | EGF | POMC | SELE |
| 4517 | Age | EGF | POMC | SELP |
| 4518 | Age | EGF | POMC | Sex |
| 4519 | Age | EGF | POMC | SHBG |
| 4520 | Age | EGF | POMC | TNFRSF1B |
| 4521 | Age | EGF | POMC | TRIG |
| 4522 | Age | EGF | POMC | VCAM1 |
| 4523 | Age | EGF | POMC | VEGF |
| 4524 | Age | EGF | POMC | VWF |
| 4525 | Age | EGF | POMC | Waist |
| 4526 | Age | EGF | POMC | WT |
| 4527 | Age | EGF | Sex | VEGF |
| 4528 | Age | EGF | Sex | Waist |
| 4529 | Age | EGF | Sex | WT |
| 4530 | Age | EGF | VCAM1 | VEGF |
| 4531 | Age | EGF | VEGF | VWF |
| 4532 | Age | ENG | FamHX | LEP |
| 4533 | Age | ENG | FamHX | POMC |
| 4534 | Age | ENG | FGA | LEP |
| 4535 | Age | ENG | FGA | POMC |
| 4536 | Age | ENG | FTH1 | HDLC |
| 4537 | Age | ENG | FTH1 | LEP |
| 4538 | Age | ENG | FTH1 | POMC |
| 4539 | Age | ENG | FTH1 | Sex |
| 4540 | Age | ENG | Gluc120 | LEP |
| 4541 | Age | ENG | Gluc120 | POMC |
| 4542 | Age | ENG | Glucose | HDLC |
| 4543 | Age | ENG | Glucose | IGF1 |
| 4544 | Age | ENG | Glucose | IL6ST |
| 4545 | Age | ENG | Glucose | LEP |
| 4546 | Age | ENG | Glucose | POMC |
| 4547 | Age | ENG | Glucose | Sex |
| 4548 | Age | ENG | Glucose | VEGF |
| 4549 | Age | ENG | HBA1C | LEP |
| 4550 | Age | ENG | HBA1C | POMC |
| 4551 | Age | ENG | HDLC | Hp |
| 4552 | Age | ENG | HDLC | IGF1 |
| 4553 | Age | ENG | HDLC | IGFBP1 |
| 4554 | Age | ENG | HDLC | IL18 |
| 4555 | Age | ENG | HDLC | IL2RA |
| 4556 | Age | ENG | HDLC | IL6ST |
| 4557 | Age | ENG | HDLC | Insulin |
| 4558 | Age | ENG | HDLC | LEP |
| 4559 | Age | ENG | HDLC | POMC |

FIG. 15XXX

| 4-Panel | Marker 1 | Marker 2 | Marker 3 | Marker 4 |
|---|---|---|---|---|
| 4560 | Age | ENG | HDLC | SCp |
| 4561 | Age | ENG | HDLC | Sex |
| 4562 | Age | ENG | HDLC | TRIG |
| 4563 | Age | ENG | HDLC | VCAM1 |
| 4564 | Age | ENG | HDLC | VEGF |
| 4565 | Age | ENG | HDLC | Waist |
| 4566 | Age | ENG | HDLC | WT |
| 4567 | Age | ENG | HGF | LEP |
| 4568 | Age | ENG | HGF | POMC |
| 4569 | Age | ENG | Hip | IGF1 |
| 4570 | Age | ENG | Hip | LEP |
| 4571 | Age | ENG | Hip | POMC |
| 4572 | Age | ENG | HP | LEP |
| 4573 | Age | ENG | HP | POMC |
| 4574 | Age | ENG | HP | IGF1 |
| 4575 | Age | ENG | HT | IL6ST |
| 4576 | Age | ENG | HT | LEP |
| 4577 | Age | ENG | HT | POMC |
| 4578 | Age | ENG | HT | VEGF |
| 4579 | Age | ENG | ICAM1 | LEP |
| 4580 | Age | ENG | ICAM1 | POMC |
| 4581 | Age | ENG | IGF1 | IL2RA |
| 4582 | Age | ENG | IGF1 | IL6ST |
| 4583 | Age | ENG | IGF1 | Insulin |
| 4584 | Age | ENG | IGF1 | LEP |
| 4585 | Age | ENG | IGF1 | POMC |
| 4586 | Age | ENG | IGF1 | Sex |
| 4587 | Age | ENG | IGF1 | VCAM1 |
| 4588 | Age | ENG | IGF1 | VEGF |
| 4589 | Age | ENG | IGFBP1 | LEP |

| 4-Panel | Marker 1 | Marker 2 | Marker 3 | Marker 4 |
|---|---|---|---|---|
| 4590 | Age | ENG | IGFBP1 | POMC |
| 4591 | Age | ENG | IGFBP3 | LEP |
| 4592 | Age | ENG | IGFBP3 | POMC |
| 4593 | Age | ENG | IL18 | LEP |
| 4594 | Age | ENG | IL18 | POMC |
| 4595 | Age | ENG | IL18 | VEGF |
| 4596 | Age | ENG | IL2RA | LEP |
| 4597 | Age | ENG | IL2RA | POMC |
| 4598 | Age | ENG | IL2RA | Sex |
| 4599 | Age | ENG | IL6R | LEP |
| 4600 | Age | ENG | IL6R | POMC |
| 4601 | Age | ENG | IL6ST | LEP |
| 4602 | Age | ENG | IL6ST | POMC |
| 4603 | Age | ENG | IL6ST | Sex |
| 4604 | Age | ENG | IL6ST | TNFRSF1B |
| 4605 | Age | ENG | IL6ST | VEGF |
| 4606 | Age | ENG | IL8 | LEP |
| 4607 | Age | ENG | IL8 | POMC |
| 4608 | Age | ENG | INHBA | LEP |
| 4609 | Age | ENG | INHBA | POMC |
| 4610 | Age | ENG | Ins120 | Insulin |
| 4611 | Age | ENG | Ins120 | LEP |
| 4612 | Age | ENG | Ins120 | POMC |
| 4613 | Age | ENG | Insulin | LEP |
| 4614 | Age | ENG | Insulin | POMC |
| 4615 | Age | ENG | Insulin | Sex |
| 4616 | Age | ENG | Insulin | VEGF |
| 4617 | Age | ENG | LDL | LEP |
| 4618 | Age | ENG | LDL | POMC |
| 4619 | Age | ENG | LEP | PLAT |

FIG. 15YYY

| 4-Panel | Marker 1 | Marker 2 | Marker 3 | Marker 4 |
|---|---|---|---|---|
| 4620 | Age | ENG | LEP | POMC |
| 4621 | Age | ENG | LEP | SBP |
| 4622 | Age | ENG | LEP | SCp |
| 4623 | Age | ENG | LEP | SELE |
| 4624 | Age | ENG | LEP | SELP |
| 4625 | Age | ENG | LEP | Sex |
| 4626 | Age | ENG | LEP | SHBG |
| 4627 | Age | ENG | LEP | TNFRSF1B |
| 4628 | Age | ENG | LEP | TRIG |
| 4629 | Age | ENG | LEP | VCAM1 |
| 4630 | Age | ENG | LEP | VEGF |
| 4631 | Age | ENG | LEP | vWF |
| 4632 | Age | ENG | LEP | Waist |
| 4633 | Age | ENG | LEP | WT |
| 4634 | Age | ENG | PLAT | POMC |
| 4635 | Age | ENG | POMC | SBP |
| 4636 | Age | ENG | POMC | SCp |
| 4637 | Age | ENG | POMC | SELE |
| 4638 | Age | ENG | POMC | SELP |
| 4639 | Age | ENG | POMC | Sex |
| 4640 | Age | ENG | POMC | SHBG |
| 4641 | Age | ENG | POMC | TNFRSF1B |
| 4642 | Age | ENG | POMC | TRIG |
| 4643 | Age | ENG | POMC | VCAM1 |
| 4644 | Age | ENG | POMC | VEGF |
| 4645 | Age | ENG | POMC | vWF |
| 4646 | Age | ENG | POMC | Waist |
| 4647 | Age | ENG | POMC | WT |
| 4648 | Age | ENG | Sex | VEGF |
| 4649 | Age | ENG | Sex | Waist |

| 4-Panel | Marker 1 | Marker 2 | Marker 3 | Marker 4 |
|---|---|---|---|---|
| 4650 | Age | ENG | Sex | WT |
| 4651 | Age | FamHX | FGA | LEP |
| 4652 | Age | FamHX | FGA | POMC |
| 4653 | Age | FamHX | FTH1 | HDLC |
| 4654 | Age | FamHX | FTH1 | LEP |
| 4655 | Age | FamHX | FTH1 | POMC |
| 4656 | Age | FamHX | FTH1 | Sex |
| 4657 | Age | FamHX | Gluc120 | LEP |
| 4658 | Age | FamHX | Gluc120 | POMC |
| 4659 | Age | FamHX | Glucose | HDLC |
| 4660 | Age | FamHX | Glucose | HT |
| 4661 | Age | FamHX | Glucose | IGF1 |
| 4662 | Age | FamHX | Glucose | IL6ST |
| 4663 | Age | FamHX | Glucose | LEP |
| 4664 | Age | FamHX | Glucose | POMC |
| 4665 | Age | FamHX | Glucose | Sex |
| 4666 | Age | FamHX | Glucose | VEGF |
| 4667 | Age | FamHX | HBA1C | LEP |
| 4668 | Age | FamHX | HBA1C | POMC |
| 4669 | Age | FamHX | HDLC | Hip |
| 4670 | Age | FamHX | HDLC | IGF1 |
| 4671 | Age | FamHX | HDLC | IGFBP1 |
| 4672 | Age | FamHX | HDLC | IL18 |
| 4673 | Age | FamHX | HDLC | IL2RA |
| 4674 | Age | FamHX | HDLC | IL6ST |
| 4675 | Age | FamHX | HDLC | Insulin |
| 4676 | Age | FamHX | HDLC | LEP |
| 4677 | Age | FamHX | HDLC | POMC |
| 4678 | Age | FamHX | HDLC | SCp |
| 4679 | Age | FamHX | HDLC | Sex |

FIG. 15ZZZ

| 4-Panel | Marker 1 | Marker 2 | Marker 3 | Marker 4 |
|---|---|---|---|---|
| 4680 | Age | FamHX | HDLC | TRIG |
| 4681 | Age | FamHX | HDLC | VCAM1 |
| 4682 | Age | FamHX | HDLC | VEGF |
| 4683 | Age | FamHX | HDLC | vWF |
| 4684 | Age | FamHX | HDLC | Waist |
| 4685 | Age | FamHX | HDLC | WT |
| 4686 | Age | FamHX | HGF | LEP |
| 4687 | Age | FamHX | HGF | POMC |
| 4688 | Age | FamHX | Hip | IGF1 |
| 4689 | Age | FamHX | Hip | LEP |
| 4690 | Age | FamHX | Hip | POMC |
| 4691 | Age | FamHX | HP | LEP |
| 4692 | Age | FamHX | HP | POMC |
| 4693 | Age | FamHX | HT | IGF1 |
| 4694 | Age | FamHX | HT | LEP |
| 4695 | Age | FamHX | HT | POMC |
| 4696 | Age | FamHX | HT | VEGF |
| 4697 | Age | FamHX | ICAM1 | LEP |
| 4698 | Age | FamHX | ICAM1 | POMC |
| 4699 | Age | FamHX | IGF1 | IL2RA |
| 4700 | Age | FamHX | IGF1 | IL6ST |
| 4701 | Age | FamHX | IGF1 | Ins120 |
| 4702 | Age | FamHX | IGF1 | Insulin |
| 4703 | Age | FamHX | IGF1 | LEP |
| 4704 | Age | FamHX | IGF1 | POMC |
| 4705 | Age | FamHX | IGF1 | Sex |
| 4706 | Age | FamHX | IGF1 | VCAM1 |
| 4707 | Age | FamHX | IGF1 | VEGF |
| 4708 | Age | FamHX | IGFBP1 | LEP |
| 4709 | Age | FamHX | IGFBP1 | POMC |

| 4-Panel | Marker 1 | Marker 2 | Marker 3 | Marker 4 |
|---|---|---|---|---|
| 4710 | Age | FamHX | IGFBP3 | LEP |
| 4711 | Age | FamHX | IGFBP3 | POMC |
| 4712 | Age | FamHX | IL18 | LEP |
| 4713 | Age | FamHX | IL18 | POMC |
| 4714 | Age | FamHX | IL18 | VEGF |
| 4715 | Age | FamHX | IL2RA | LEP |
| 4716 | Age | FamHX | IL2RA | POMC |
| 4717 | Age | FamHX | IL2RA | Sex |
| 4718 | Age | FamHX | IL6R | LEP |
| 4719 | Age | FamHX | IL6R | POMC |
| 4720 | Age | FamHX | IL6ST | LEP |
| 4721 | Age | FamHX | IL6ST | POMC |
| 4722 | Age | FamHX | IL6ST | Sex |
| 4723 | Age | FamHX | IL6ST | TNFRSF1B |
| 4724 | Age | FamHX | IL6ST | VEGF |
| 4725 | Age | FamHX | IL8 | LEP |
| 4726 | Age | FamHX | IL8 | POMC |
| 4727 | Age | FamHX | INHBA | LEP |
| 4728 | Age | FamHX | INHBA | POMC |
| 4729 | Age | FamHX | Ins120 | Insulin |
| 4730 | Age | FamHX | Ins120 | LEP |
| 4731 | Age | FamHX | Ins120 | POMC |
| 4732 | Age | FamHX | Insulin | LEP |
| 4733 | Age | FamHX | Insulin | POMC |
| 4734 | Age | FamHX | Insulin | Sex |
| 4735 | Age | FamHX | Insulin | VEGF |
| 4736 | Age | FamHX | LDL | LEP |
| 4737 | Age | FamHX | LDL | POMC |
| 4738 | Age | FamHX | LEP | PLAT |
| 4739 | Age | FamHX | LEP | POMC |

FIG. 15AAAA

FIG. 15BBBB

| 4-Panel | Marker 1 | Marker 2 | Marker 3 | Marker 4 |
|---|---|---|---|---|
| 4740 | Age | FamHX | LEP | SBP |
| 4741 | Age | FamHX | LEP | SCp |
| 4742 | Age | FamHX | LEP | SELE |
| 4743 | Age | FamHX | LEP | SELP |
| 4744 | Age | FamHX | LEP | Sex |
| 4745 | Age | FamHX | LEP | SHBG |
| 4746 | Age | FamHX | LEP | TNFRSF1B |
| 4747 | Age | FamHX | LEP | TRIG |
| 4748 | Age | FamHX | LEP | VCAM1 |
| 4749 | Age | FamHX | LEP | VEGF |
| 4750 | Age | FamHX | LEP | VWF |
| 4751 | Age | FamHX | LEP | Waist |
| 4752 | Age | FamHX | LEP | WT |
| 4753 | Age | FamHX | PLAT | POMC |
| 4754 | Age | FamHX | POMC | SBP |
| 4755 | Age | FamHX | POMC | SCp |
| 4756 | Age | FamHX | POMC | SELE |
| 4757 | Age | FamHX | POMC | SELP |
| 4758 | Age | FamHX | POMC | Sex |
| 4759 | Age | FamHX | POMC | SHBG |
| 4760 | Age | FamHX | POMC | TNFRSF1B |
| 4761 | Age | FamHX | POMC | TRIG |
| 4762 | Age | FamHX | POMC | VCAM1 |
| 4763 | Age | FamHX | POMC | VEGF |
| 4764 | Age | FamHX | POMC | VWF |
| 4765 | Age | FamHX | POMC | Waist |
| 4766 | Age | FamHX | POMC | WT |
| 4767 | Age | FamHX | Sex | VEGF |
| 4768 | Age | FamHX | Sex | Waist |
| 4769 | Age | FamHX | Sex | WT |

| 4-Panel | Marker 1 | Marker 2 | Marker 3 | Marker 4 |
|---|---|---|---|---|
| 4770 | Age | FGA | FTH1 | HDLC |
| 4771 | Age | FGA | FTH1 | LEP |
| 4772 | Age | FGA | FTH1 | POMC |
| 4773 | Age | FGA | FTH1 | Sex |
| 4774 | Age | FGA | Gluc120 | LEP |
| 4775 | Age | FGA | Gluc120 | POMC |
| 4776 | Age | FGA | Glucose | HDLC |
| 4777 | Age | FGA | Glucose | IGF1 |
| 4778 | Age | FGA | Glucose | LEP |
| 4779 | Age | FGA | Glucose | POMC |
| 4780 | Age | FGA | Glucose | Sex |
| 4781 | Age | FGA | Glucose | VEGF |
| 4782 | Age | FGA | HBA1C | LEP |
| 4783 | Age | FGA | HBA1C | POMC |
| 4784 | Age | FGA | HDLC | Hip |
| 4785 | Age | FGA | HDLC | IGF1 |
| 4786 | Age | FGA | HDLC | IGFBP1 |
| 4787 | Age | FGA | HDLC | IL18 |
| 4788 | Age | FGA | HDLC | IL6ST |
| 4789 | Age | FGA | HDLC | Insulin |
| 4790 | Age | FGA | HDLC | LEP |
| 4791 | Age | FGA | HDLC | POMC |
| 4792 | Age | FGA | HDLC | Sex |
| 4793 | Age | FGA | HDLC | TRIG |
| 4794 | Age | FGA | HDLC | VCAM1 |
| 4795 | Age | FGA | HDLC | VEGF |
| 4796 | Age | FGA | HDLC | Waist |
| 4797 | Age | FGA | HDLC | WT |
| 4798 | Age | FGA | HGF | LEP |
| 4799 | Age | FGA | HGF | POMC |

| 4-Panel | Marker 1 | Marker 2 | Marker 3 | Marker 4 |
|---|---|---|---|---|
| 4800 | Age | FGA | Hip | IGF1 |
| 4801 | Age | FGA | Hip | LEP |
| 4802 | Age | FGA | Hip | POMC |
| 4803 | Age | FGA | Hip | VEGF |
| 4804 | Age | FGA | HP | LEP |
| 4805 | Age | FGA | HP | POMC |
| 4806 | Age | FGA | HT | IGF1 |
| 4807 | Age | FGA | HT | LEP |
| 4808 | Age | FGA | HT | POMC |
| 4809 | Age | FGA | HT | VEGF |
| 4810 | Age | FGA | ICAM1 | LEP |
| 4811 | Age | FGA | ICAM1 | POMC |
| 4812 | Age | FGA | IGF1 | IL2RA |
| 4813 | Age | FGA | IGF1 | IL6ST |
| 4814 | Age | FGA | IGF1 | Insulin |
| 4815 | Age | FGA | IGF1 | LEP |
| 4816 | Age | FGA | IGF1 | POMC |
| 4817 | Age | FGA | IGF1 | Sex |
| 4818 | Age | FGA | IGF1 | VCAM1 |
| 4819 | Age | FGA | IGF1 | VEGF |
| 4820 | Age | FGA | IGFBP1 | LEP |
| 4821 | Age | FGA | IGFBP1 | POMC |
| 4822 | Age | FGA | IGFBP3 | LEP |
| 4823 | Age | FGA | IGFBP3 | POMC |
| 4824 | Age | FGA | IL18 | LEP |
| 4825 | Age | FGA | IL18 | POMC |
| 4826 | Age | FGA | IL18 | Sex |
| 4827 | Age | FGA | IL18 | VEGF |
| 4828 | Age | FGA | IL2RA | LEP |
| 4829 | Age | FGA | IL2RA | POMC |
| 4830 | Age | FGA | IL2RA | Sex |
| 4831 | Age | FGA | IL6R | LEP |
| 4832 | Age | FGA | IL6R | POMC |
| 4833 | Age | FGA | IL6ST | LEP |
| 4834 | Age | FGA | IL6ST | POMC |
| 4835 | Age | FGA | IL6ST | Sex |
| 4836 | Age | FGA | IL6ST | TNFRSF1B |
| 4837 | Age | FGA | IL6ST | VEGF |
| 4838 | Age | FGA | IL8 | LEP |
| 4839 | Age | FGA | IL8 | POMC |
| 4840 | Age | FGA | INHBA | LEP |
| 4841 | Age | FGA | INHBA | POMC |
| 4842 | Age | FGA | Ins120 | LEP |
| 4843 | Age | FGA | Ins120 | POMC |
| 4844 | Age | FGA | Insulin | LEP |
| 4845 | Age | FGA | Insulin | POMC |
| 4846 | Age | FGA | Insulin | Sex |
| 4847 | Age | FGA | Insulin | VEGF |
| 4848 | Age | FGA | LDL | LEP |
| 4849 | Age | FGA | LDL | POMC |
| 4850 | Age | FGA | LEP | PLAT |
| 4851 | Age | FGA | LEP | POMC |
| 4852 | Age | FGA | LEP | SBP |
| 4853 | Age | FGA | LEP | SCp |
| 4854 | Age | FGA | LEP | SELE |
| 4855 | Age | FGA | LEP | SELP |
| 4856 | Age | FGA | LEP | Sex |
| 4857 | Age | FGA | LEP | SHBG |
| 4858 | Age | FGA | LEP | TNFRSF1B |
| 4859 | Age | FGA | LEP | TRIG |

FIG. 15CCCC

| 4-Panel | Marker 1 | Marker 2 | Marker 3 | Marker 4 |
|---|---|---|---|---|
| 4860 | Age | FGA | LEP | VCAM1 |
| 4861 | Age | FGA | LEP | VEGF |
| 4862 | Age | FGA | LEP | VWF |
| 4863 | Age | FGA | LEP | Waist |
| 4864 | Age | FGA | LEP | WT |
| 4865 | Age | FGA | PLAT | POMC |
| 4866 | Age | FGA | POMC | SBP |
| 4867 | Age | FGA | POMC | SCp |
| 4868 | Age | FGA | POMC | SELE |
| 4869 | Age | FGA | POMC | SELP |
| 4870 | Age | FGA | POMC | Sex |
| 4871 | Age | FGA | POMC | SHBG |
| 4872 | Age | FGA | POMC | TNFRSF1B |
| 4873 | Age | FGA | POMC | TRIG |
| 4874 | Age | FGA | POMC | VCAM1 |
| 4875 | Age | FGA | POMC | VEGF |
| 4876 | Age | FGA | POMC | VWF |
| 4877 | Age | FGA | POMC | Waist |
| 4878 | Age | FGA | POMC | WT |
| 4879 | Age | FGA | Sex | VEGF |
| 4880 | Age | FGA | Sex | Waist |
| 4881 | Age | FGA | Sex | WT |
| 4882 | Age | FGA | VCAM1 | VEGF |
| 4883 | Age | FTH1 | Gluc120 | HDLC |
| 4884 | Age | FTH1 | Gluc120 | LEP |
| 4885 | Age | FTH1 | Gluc120 | POMC |
| 4886 | Age | FTH1 | Gluc120 | Sex |
| 4887 | Age | FTH1 | Glucose | HDLC |
| 4888 | Age | FTH1 | Glucose | HT |
| 4889 | Age | FTH1 | Glucose | IGF1 |

| 4-Panel | Marker 1 | Marker 2 | Marker 3 | Marker 4 |
|---|---|---|---|---|
| 4890 | Age | FTH1 | Glucose | IL6ST |
| 4891 | Age | FTH1 | Glucose | LEP |
| 4892 | Age | FTH1 | Glucose | POMC |
| 4893 | Age | FTH1 | Glucose | Sex |
| 4894 | Age | FTH1 | Glucose | VEGF |
| 4895 | Age | FTH1 | HBA1C | HDLC |
| 4896 | Age | FTH1 | HBA1C | LEP |
| 4897 | Age | FTH1 | HBA1C | POMC |
| 4898 | Age | FTH1 | HBA1C | Sex |
| 4899 | Age | FTH1 | HDLC | HGF |
| 4900 | Age | FTH1 | HDLC | Hip |
| 4901 | Age | FTH1 | HDLC | HP |
| 4902 | Age | FTH1 | HDLC | HT |
| 4903 | Age | FTH1 | HDLC | ICAM1 |
| 4904 | Age | FTH1 | HDLC | IGF1 |
| 4905 | Age | FTH1 | HDLC | IGFBP1 |
| 4906 | Age | FTH1 | HDLC | IGFBP3 |
| 4907 | Age | FTH1 | HDLC | IL18 |
| 4908 | Age | FTH1 | HDLC | IL2RA |
| 4909 | Age | FTH1 | HDLC | IL6R |
| 4910 | Age | FTH1 | HDLC | IL6ST |
| 4911 | Age | FTH1 | HDLC | IL8 |
| 4912 | Age | FTH1 | HDLC | INHBA |
| 4913 | Age | FTH1 | HDLC | Ins120 |
| 4914 | Age | FTH1 | HDLC | Insulin |
| 4915 | Age | FTH1 | HDLC | LDL |
| 4916 | Age | FTH1 | HDLC | LEP |
| 4917 | Age | FTH1 | HDLC | PLAT |
| 4918 | Age | FTH1 | HDLC | POMC |
| 4919 | Age | FTH1 | HDLC | SBP |

FIG. 15DDDD

| 4-Panel | Marker 1 | Marker 2 | Marker 3 | Marker 4 |
|---|---|---|---|---|
| 4920 | Age | FTH1 | HDLC | SCp |
| 4921 | Age | FTH1 | HDLC | SELE |
| 4922 | Age | FTH1 | HDLC | SELP |
| 4923 | Age | FTH1 | HDLC | Sex |
| 4924 | Age | FTH1 | HDLC | SHBG |
| 4925 | Age | FTH1 | HDLC | TNFRSF1B |
| 4926 | Age | FTH1 | HDLC | TRIG |
| 4927 | Age | FTH1 | HDLC | VCAM1 |
| 4928 | Age | FTH1 | HDLC | VEGF |
| 4929 | Age | FTH1 | HDLC | VWF |
| 4930 | Age | FTH1 | HDLC | Waist |
| 4931 | Age | FTH1 | HDLC | WT |
| 4932 | Age | FTH1 | HGF | LEP |
| 4933 | Age | FTH1 | HGF | POMC |
| 4934 | Age | FTH1 | HGF | Sex |
| 4935 | Age | FTH1 | Hip | IGF1 |
| 4936 | Age | FTH1 | Hip | IL6ST |
| 4937 | Age | FTH1 | Hip | LEP |
| 4938 | Age | FTH1 | Hip | POMC |
| 4939 | Age | FTH1 | Hip | Sex |
| 4940 | Age | FTH1 | Hip | VEGF |
| 4941 | Age | FTH1 | HP | LEP |
| 4942 | Age | FTH1 | HP | POMC |
| 4943 | Age | FTH1 | HP | Sex |
| 4944 | Age | FTH1 | HT | IGF1 |
| 4945 | Age | FTH1 | HT | IL6ST |
| 4946 | Age | FTH1 | HT | LEP |
| 4947 | Age | FTH1 | HT | POMC |
| 4948 | Age | FTH1 | HT | Sex |
| 4949 | Age | FTH1 | HT | VEGF |

| 4-Panel | Marker 1 | Marker 2 | Marker 3 | Marker 4 |
|---|---|---|---|---|
| 4950 | Age | FTH1 | HT | WT |
| 4951 | Age | FTH1 | ICAM1 | LEP |
| 4952 | Age | FTH1 | ICAM1 | POMC |
| 4953 | Age | FTH1 | ICAM1 | Sex |
| 4954 | Age | FTH1 | IGF1 | IGFBP1 |
| 4955 | Age | FTH1 | IGF1 | IL2RA |
| 4956 | Age | FTH1 | IGF1 | IL6ST |
| 4957 | Age | FTH1 | IGF1 | Ins120 |
| 4958 | Age | FTH1 | IGF1 | Insulin |
| 4959 | Age | FTH1 | IGF1 | LEP |
| 4960 | Age | FTH1 | IGF1 | POMC |
| 4961 | Age | FTH1 | IGF1 | Sex |
| 4962 | Age | FTH1 | IGF1 | VCAM1 |
| 4963 | Age | FTH1 | IGF1 | VEGF |
| 4964 | Age | FTH1 | IGFBP1 | LEP |
| 4965 | Age | FTH1 | IGFBP1 | POMC |
| 4966 | Age | FTH1 | IGFBP1 | Sex |
| 4967 | Age | FTH1 | IGFBP3 | LEP |
| 4968 | Age | FTH1 | IGFBP3 | POMC |
| 4969 | Age | FTH1 | IGFBP3 | Sex |
| 4970 | Age | FTH1 | IL18 | IL6ST |
| 4971 | Age | FTH1 | IL18 | LEP |
| 4972 | Age | FTH1 | IL18 | POMC |
| 4973 | Age | FTH1 | IL18 | Sex |
| 4974 | Age | FTH1 | IL18 | VEGF |
| 4975 | Age | FTH1 | IL2RA | LEP |
| 4976 | Age | FTH1 | IL2RA | POMC |
| 4977 | Age | FTH1 | IL2RA | Sex |
| 4978 | Age | FTH1 | IL6R | IL6ST |
| 4979 | Age | FTH1 | IL6R | LEP |

FIG. 15EEEE

| 4-Panel | Marker 1 | Marker 2 | Marker 3 | Marker 4 |
|---|---|---|---|---|
| 4980 | Age | FTH1 | IL6R | POMC |
| 4981 | Age | FTH1 | IL6R | Sex |
| 4982 | Age | FTH1 | IL6ST | IL8 |
| 4983 | Age | FTH1 | IL6ST | Ins120 |
| 4984 | Age | FTH1 | IL6ST | LEP |
| 4985 | Age | FTH1 | IL6ST | POMC |
| 4986 | Age | FTH1 | IL6ST | SELP |
| 4987 | Age | FTH1 | IL6ST | Sex |
| 4988 | Age | FTH1 | IL6ST | TNFRSF1B |
| 4989 | Age | FTH1 | IL6ST | VEGF |
| 4990 | Age | FTH1 | IL8 | LEP |
| 4991 | Age | FTH1 | IL8 | POMC |
| 4992 | Age | FTH1 | IL8 | Sex |
| 4993 | Age | FTH1 | INHBA | LEP |
| 4994 | Age | FTH1 | INHBA | POMC |
| 4995 | Age | FTH1 | INHBA | Sex |
| 4996 | Age | FTH1 | Ins120 | Insulin |
| 4997 | Age | FTH1 | Ins120 | LEP |
| 4998 | Age | FTH1 | Ins120 | POMC |
| 4999 | Age | FTH1 | Ins120 | Sex |
| 5000 | Age | FTH1 | Insulin | LEP |
| 5001 | Age | FTH1 | Insulin | POMC |
| 5002 | Age | FTH1 | Insulin | Sex |
| 5003 | Age | FTH1 | Insulin | VEGF |
| 5004 | Age | FTH1 | LDL | LEP |
| 5005 | Age | FTH1 | LDL | POMC |
| 5006 | Age | FTH1 | LDL | Sex |
| 5007 | Age | FTH1 | LEP | PLAT |
| 5008 | Age | FTH1 | LEP | POMC |
| 5009 | Age | FTH1 | LEP | SBP |

| 4-Panel | Marker 1 | Marker 2 | Marker 3 | Marker 4 |
|---|---|---|---|---|
| 5010 | Age | FTH1 | LEP | SELE |
| 5011 | Age | FTH1 | LEP | SELP |
| 5012 | Age | FTH1 | LEP | Sex |
| 5013 | Age | FTH1 | LEP | SHBG |
| 5014 | Age | FTH1 | LEP | TNFRSF1B |
| 5015 | Age | FTH1 | LEP | TRIG |
| 5016 | Age | FTH1 | LEP | VCAM1 |
| 5017 | Age | FTH1 | LEP | VEGF |
| 5018 | Age | FTH1 | LEP | VWF |
| 5019 | Age | FTH1 | LEP | Waist |
| 5020 | Age | FTH1 | LEP | WT |
| 5021 | Age | FTH1 | PLAT | POMC |
| 5022 | Age | FTH1 | PLAT | Sex |
| 5023 | Age | FTH1 | POMC | SBP |
| 5024 | Age | FTH1 | POMC | SCp |
| 5025 | Age | FTH1 | POMC | SELE |
| 5026 | Age | FTH1 | POMC | SELP |
| 5027 | Age | FTH1 | POMC | Sex |
| 5028 | Age | FTH1 | POMC | SHBG |
| 5029 | Age | FTH1 | POMC | TNFRSF1B |
| 5030 | Age | FTH1 | POMC | TRIG |
| 5031 | Age | FTH1 | POMC | VCAM1 |
| 5032 | Age | FTH1 | POMC | VEGF |
| 5033 | Age | FTH1 | POMC | VWF |
| 5034 | Age | FTH1 | POMC | Waist |
| 5035 | Age | FTH1 | POMC | WT |
| 5036 | Age | FTH1 | SBP | Sex |
| 5037 | Age | FTH1 | SCp | Sex |
| 5038 | Age | FTH1 | SELE | Sex |
| 5039 | Age | FTH1 | SELP | Sex |

FIG. 15FFFF

| 4-Panel | Marker 1 | Marker 2 | Marker 3 | Marker 4 |
|---|---|---|---|---|
| 5040 | Age | FTH1 | Sex | SHBG |
| 5041 | Age | FTH1 | Sex | TNFRSF1B |
| 5042 | Age | FTH1 | Sex | TRIG |
| 5043 | Age | FTH1 | Sex | VCAM1 |
| 5044 | Age | FTH1 | Sex | VEGF |
| 5045 | Age | FTH1 | Sex | VWF |
| 5046 | Age | FTH1 | Sex | Waist |
| 5047 | Age | FTH1 | Sex | WT |
| 5048 | Age | FTH1 | VCAM1 | VEGF |
| 5049 | Age | FTH1 | VEGF | VWF |
| 5050 | Age | Gluc120 | Glucose | HDLC |
| 5051 | Age | Gluc120 | Glucose | HT |
| 5052 | Age | Gluc120 | Glucose | IGF1 |
| 5053 | Age | Gluc120 | Glucose | IL6ST |
| 5054 | Age | Gluc120 | Glucose | LEP |
| 5055 | Age | Gluc120 | Glucose | POMC |
| 5056 | Age | Gluc120 | Glucose | Sex |
| 5057 | Age | Gluc120 | Glucose | VEGF |
| 5058 | Age | Gluc120 | HBA1C | LEP |
| 5059 | Age | Gluc120 | HBA1C | POMC |
| 5060 | Age | Gluc120 | HDLC | Hip |
| 5061 | Age | Gluc120 | HDLC | IGF1 |
| 5062 | Age | Gluc120 | HDLC | IGFBP1 |
| 5063 | Age | Gluc120 | HDLC | IL18 |
| 5064 | Age | Gluc120 | HDLC | IL6ST |
| 5065 | Age | Gluc120 | HDLC | Insulin |
| 5066 | Age | Gluc120 | HDLC | LEP |
| 5067 | Age | Gluc120 | HDLC | POMC |
| 5068 | Age | Gluc120 | HDLC | SCp |
| 5069 | Age | Gluc120 | HDLC | Sex |

| 4-Panel | Marker 1 | Marker 2 | Marker 3 | Marker 4 |
|---|---|---|---|---|
| 5070 | Age | Gluc120 | HDLC | TRIG |
| 5071 | Age | Gluc120 | HDLC | VCAM1 |
| 5072 | Age | Gluc120 | HDLC | VEGF |
| 5073 | Age | Gluc120 | HDLC | Waist |
| 5074 | Age | Gluc120 | HDLC | WT |
| 5075 | Age | Gluc120 | HGF | LEP |
| 5076 | Age | Gluc120 | HGF | POMC |
| 5077 | Age | Gluc120 | Hip | IGF1 |
| 5078 | Age | Gluc120 | Hip | LEP |
| 5079 | Age | Gluc120 | Hip | POMC |
| 5080 | Age | Gluc120 | Hip | Sex |
| 5081 | Age | Gluc120 | HP | LEP |
| 5082 | Age | Gluc120 | HP | POMC |
| 5083 | Age | Gluc120 | HT | IGF1 |
| 5084 | Age | Gluc120 | HT | LEP |
| 5085 | Age | Gluc120 | HT | POMC |
| 5086 | Age | Gluc120 | HT | VEGF |
| 5087 | Age | Gluc120 | ICAM1 | LEP |
| 5088 | Age | Gluc120 | ICAM1 | POMC |
| 5089 | Age | Gluc120 | IGF1 | IL2RA |
| 5090 | Age | Gluc120 | IGF1 | IL6ST |
| 5091 | Age | Gluc120 | IGF1 | Insulin |
| 5092 | Age | Gluc120 | IGF1 | LEP |
| 5093 | Age | Gluc120 | IGF1 | POMC |
| 5094 | Age | Gluc120 | IGF1 | Sex |
| 5095 | Age | Gluc120 | IGF1 | VCAM1 |
| 5096 | Age | Gluc120 | IGF1 | VEGF |
| 5097 | Age | Gluc120 | IGFBP1 | LEP |
| 5098 | Age | Gluc120 | IGFBP1 | POMC |
| 5099 | Age | Gluc120 | IGFBP3 | LEP |

FIG. 15GGGG

| 4-Panel | Marker 1 | Marker 2 | Marker 3 | Marker 4 |
|---|---|---|---|---|
| 5100 | Age | Gluc120 | IGFBP3 | POMC |
| 5101 | Age | Gluc120 | IL18 | LEP |
| 5102 | Age | Gluc120 | IL18 | POMC |
| 5103 | Age | Gluc120 | IL18 | Sex |
| 5104 | Age | Gluc120 | IL18 | VEGF |
| 5105 | Age | Gluc120 | IL2RA | LEP |
| 5106 | Age | Gluc120 | IL2RA | POMC |
| 5107 | Age | Gluc120 | IL2RA | Sex |
| 5108 | Age | Gluc120 | IL6R | LEP |
| 5109 | Age | Gluc120 | IL6R | POMC |
| 5110 | Age | Gluc120 | IL6ST | LEP |
| 5111 | Age | Gluc120 | IL6ST | POMC |
| 5112 | Age | Gluc120 | IL6ST | Sex |
| 5113 | Age | Gluc120 | IL6ST | TNFRSF1B |
| 5114 | Age | Gluc120 | IL6ST | VEGF |
| 5115 | Age | Gluc120 | IL8 | LEP |
| 5116 | Age | Gluc120 | IL8 | POMC |
| 5117 | Age | Gluc120 | INHBA | LEP |
| 5118 | Age | Gluc120 | INHBA | POMC |
| 5119 | Age | Gluc120 | Ins120 | Insulin |
| 5120 | Age | Gluc120 | Ins120 | LEP |
| 5121 | Age | Gluc120 | Insulin | POMC |
| 5122 | Age | Gluc120 | Insulin | LEP |
| 5123 | Age | Gluc120 | Insulin | POMC |
| 5124 | Age | Gluc120 | Insulin | Sex |
| 5125 | Age | Gluc120 | Insulin | VEGF |
| 5126 | Age | Gluc120 | LDL | LEP |
| 5127 | Age | Gluc120 | LDL | POMC |
| 5128 | Age | Gluc120 | LEP | PLAT |
| 5129 | Age | Gluc120 | LEP | POMC |
| 5130 | Age | Gluc120 | LEP | SBP |
| 5131 | Age | Gluc120 | LEP | SCp |
| 5132 | Age | Gluc120 | LEP | SELE |
| 5133 | Age | Gluc120 | LEP | SELP |
| 5134 | Age | Gluc120 | LEP | Sex |
| 5135 | Age | Gluc120 | LEP | SHBG |
| 5136 | Age | Gluc120 | LEP | TNFRSF1B |
| 5137 | Age | Gluc120 | LEP | TRIG |
| 5138 | Age | Gluc120 | LEP | VCAM1 |
| 5139 | Age | Gluc120 | LEP | VEGF |
| 5140 | Age | Gluc120 | LEP | VWF |
| 5141 | Age | Gluc120 | LEP | Waist |
| 5142 | Age | Gluc120 | LEP | WT |
| 5143 | Age | Gluc120 | PLAT | POMC |
| 5144 | Age | Gluc120 | POMC | SBP |
| 5145 | Age | Gluc120 | POMC | SCp |
| 5146 | Age | Gluc120 | POMC | SELE |
| 5147 | Age | Gluc120 | POMC | SELP |
| 5148 | Age | Gluc120 | POMC | Sex |
| 5149 | Age | Gluc120 | POMC | SHBG |
| 5150 | Age | Gluc120 | POMC | TNFRSF1B |
| 5151 | Age | Gluc120 | POMC | TRIG |
| 5152 | Age | Gluc120 | POMC | VCAM1 |
| 5153 | Age | Gluc120 | POMC | VEGF |
| 5154 | Age | Gluc120 | POMC | VWF |
| 5155 | Age | Gluc120 | POMC | Waist |
| 5156 | Age | Gluc120 | POMC | WT |
| 5157 | Age | Gluc120 | Sex | VEGF |
| 5158 | Age | Gluc120 | Sex | Waist |
| 5159 | Age | Gluc120 | Sex | WT |

FIG. 15HHHH

FIG. 15IIII

| 4-Panel | Marker 1 | Marker 2 | Marker 3 | Marker 4 |
|---|---|---|---|---|
| 5160 | Age | Glucose | HBA1C | HDLC |
| 5161 | Age | Glucose | HBA1C | HT |
| 5162 | Age | Glucose | HBA1C | IGF1 |
| 5163 | Age | Glucose | HBA1C | IL6ST |
| 5164 | Age | Glucose | HBA1C | LEP |
| 5165 | Age | Glucose | HBA1C | POMC |
| 5166 | Age | Glucose | HBA1C | Sex |
| 5167 | Age | Glucose | HBA1C | VEGF |
| 5168 | Age | Glucose | HDLC | HGF |
| 5169 | Age | Glucose | HDLC | Hip |
| 5170 | Age | Glucose | HDLC | HP |
| 5171 | Age | Glucose | HDLC | HT |
| 5172 | Age | Glucose | HDLC | ICAM1 |
| 5173 | Age | Glucose | HDLC | IGF1 |
| 5174 | Age | Glucose | HDLC | IGFBP1 |
| 5175 | Age | Glucose | HDLC | IGFBP3 |
| 5176 | Age | Glucose | HDLC | IL18 |
| 5177 | Age | Glucose | HDLC | IL2RA |
| 5178 | Age | Glucose | HDLC | IL6R |
| 5179 | Age | Glucose | HDLC | IL6ST |
| 5180 | Age | Glucose | HDLC | IL8 |
| 5181 | Age | Glucose | HDLC | INHBA |
| 5182 | Age | Glucose | HDLC | Ins120 |
| 5183 | Age | Glucose | HDLC | Insulin |
| 5184 | Age | Glucose | HDLC | LDL |
| 5185 | Age | Glucose | HDLC | LEP |
| 5186 | Age | Glucose | HDLC | PLAT |
| 5187 | Age | Glucose | HDLC | POMC |
| 5188 | Age | Glucose | HDLC | SBP |
| 5189 | Age | Glucose | HDLC | SCp |

| 4-Panel | Marker 1 | Marker 2 | Marker 3 | Marker 4 |
|---|---|---|---|---|
| 5190 | Age | Glucose | HDLC | SELE |
| 5191 | Age | Glucose | HDLC | SELP |
| 5192 | Age | Glucose | HDLC | Sex |
| 5193 | Age | Glucose | HDLC | SHBG |
| 5194 | Age | Glucose | HDLC | TNFRSF1B |
| 5195 | Age | Glucose | HDLC | TRIG |
| 5196 | Age | Glucose | HDLC | VCAM1 |
| 5197 | Age | Glucose | HDLC | VEGF |
| 5198 | Age | Glucose | HDLC | VWF |
| 5199 | Age | Glucose | HDLC | Waist |
| 5200 | Age | Glucose | HDLC | WT |
| 5201 | Age | Glucose | HGF | HT |
| 5202 | Age | Glucose | HGF | IGF1 |
| 5203 | Age | Glucose | HGF | IL6ST |
| 5204 | Age | Glucose | HGF | LEP |
| 5205 | Age | Glucose | HGF | POMC |
| 5206 | Age | Glucose | HGF | Sex |
| 5207 | Age | Glucose | HGF | VEGF |
| 5208 | Age | Glucose | Hip | HT |
| 5209 | Age | Glucose | Hip | IGF1 |
| 5210 | Age | Glucose | Hip | IL6ST |
| 5211 | Age | Glucose | Hip | LEP |
| 5212 | Age | Glucose | Hip | POMC |
| 5213 | Age | Glucose | Hip | Sex |
| 5214 | Age | Glucose | Hip | VEGF |
| 5215 | Age | Glucose | HP | HT |
| 5216 | Age | Glucose | HP | IGF1 |
| 5217 | Age | Glucose | HP | IL6ST |
| 5218 | Age | Glucose | HP | LEP |
| 5219 | Age | Glucose | HP | POMC |

FIG. 15JJJJ

| 4-Panel | Marker 1 | Marker 2 | Marker 3 | Marker 4 |
|---|---|---|---|---|
| 5220 | Age | Glucose | HP | Sex |
| 5221 | Age | Glucose | HP | VEGF |
| 5222 | Age | Glucose | HT | IGF1 |
| 5223 | Age | Glucose | HT | IL18 |
| 5224 | Age | Glucose | HT | IL2RA |
| 5225 | Age | Glucose | HT | IL6ST |
| 5226 | Age | Glucose | HT | IL8 |
| 5227 | Age | Glucose | HT | Ins120 |
| 5228 | Age | Glucose | HT | Insulin |
| 5229 | Age | Glucose | HT | LEP |
| 5230 | Age | Glucose | HT | POMC |
| 5231 | Age | Glucose | HT | SELE |
| 5232 | Age | Glucose | HT | Sex |
| 5233 | Age | Glucose | HT | TRIG |
| 5234 | Age | Glucose | HT | VCAM1 |
| 5235 | Age | Glucose | HT | VEGF |
| 5236 | Age | Glucose | HT | WT |
| 5237 | Age | Glucose | ICAM1 | IGF1 |
| 5238 | Age | Glucose | ICAM1 | IL6ST |
| 5239 | Age | Glucose | ICAM1 | LEP |
| 5240 | Age | Glucose | ICAM1 | POMC |
| 5241 | Age | Glucose | ICAM1 | Sex |
| 5242 | Age | Glucose | ICAM1 | VEGF |
| 5243 | Age | Glucose | IGF1 | IGFBP1 |
| 5244 | Age | Glucose | IGF1 | IGFBP3 |
| 5245 | Age | Glucose | IGF1 | IL18 |
| 5246 | Age | Glucose | IGF1 | IL2RA |
| 5247 | Age | Glucose | IGF1 | IL6R |
| 5248 | Age | Glucose | IGF1 | IL6ST |
| 5249 | Age | Glucose | IGF1 | IL8 |

| 4-Panel | Marker 1 | Marker 2 | Marker 3 | Marker 4 |
|---|---|---|---|---|
| 5250 | Age | Glucose | IGF1 | INHBA |
| 5251 | Age | Glucose | IGF1 | Ins120 |
| 5252 | Age | Glucose | IGF1 | Insulin |
| 5253 | Age | Glucose | IGF1 | LDL |
| 5254 | Age | Glucose | IGF1 | LEP |
| 5255 | Age | Glucose | IGF1 | PLAT |
| 5256 | Age | Glucose | IGF1 | POMC |
| 5257 | Age | Glucose | IGF1 | SBP |
| 5258 | Age | Glucose | IGF1 | SCp |
| 5259 | Age | Glucose | IGF1 | SELE |
| 5260 | Age | Glucose | IGF1 | SELP |
| 5261 | Age | Glucose | IGF1 | Sex |
| 5262 | Age | Glucose | IGF1 | SHBG |
| 5263 | Age | Glucose | IGF1 | TNFRSF1B |
| 5264 | Age | Glucose | IGF1 | TRIG |
| 5265 | Age | Glucose | IGF1 | VCAM1 |
| 5266 | Age | Glucose | IGF1 | VEGF |
| 5267 | Age | Glucose | IGF1 | VWF |
| 5268 | Age | Glucose | IGF1 | Waist |
| 5269 | Age | Glucose | IGF1 | WT |
| 5270 | Age | Glucose | IGFBP1 | IL6ST |
| 5271 | Age | Glucose | IGFBP1 | LEP |
| 5272 | Age | Glucose | IGFBP1 | POMC |
| 5273 | Age | Glucose | IGFBP1 | Sex |
| 5274 | Age | Glucose | IGFBP1 | VEGF |
| 5275 | Age | Glucose | IGFBP3 | IL6ST |
| 5276 | Age | Glucose | IGFBP3 | LEP |
| 5277 | Age | Glucose | IGFBP3 | POMC |
| 5278 | Age | Glucose | IGFBP3 | Sex |
| 5279 | Age | Glucose | IGFBP3 | VEGF |

| 4-Panel | Marker 1 | Marker 2 | Marker 3 | Marker 4 |
|---|---|---|---|---|
| 5280 | Age | Glucose | IL18 | IL6ST |
| 5281 | Age | Glucose | IL18 | Ins120 |
| 5282 | Age | Glucose | IL18 | LEP |
| 5283 | Age | Glucose | IL18 | POMC |
| 5284 | Age | Glucose | IL18 | Sex |
| 5285 | Age | Glucose | IL18 | VEGF |
| 5286 | Age | Glucose | IL2RA | IL6ST |
| 5287 | Age | Glucose | IL2RA | LEP |
| 5288 | Age | Glucose | IL2RA | POMC |
| 5289 | Age | Glucose | IL2RA | Sex |
| 5290 | Age | Glucose | IL2RA | VEGF |
| 5291 | Age | Glucose | IL6R | IL6ST |
| 5292 | Age | Glucose | IL6R | LEP |
| 5293 | Age | Glucose | IL6R | POMC |
| 5294 | Age | Glucose | IL6R | Sex |
| 5295 | Age | Glucose | IL6R | VEGF |
| 5296 | Age | Glucose | IL6ST | IL8 |
| 5297 | Age | Glucose | IL6ST | INHBA |
| 5298 | Age | Glucose | IL6ST | Ins120 |
| 5299 | Age | Glucose | IL6ST | Insulin |
| 5300 | Age | Glucose | IL6ST | LEP |
| 5301 | Age | Glucose | IL6ST | PLAT |
| 5302 | Age | Glucose | IL6ST | POMC |
| 5303 | Age | Glucose | IL6ST | SBP |
| 5304 | Age | Glucose | IL6ST | SCp |
| 5305 | Age | Glucose | IL6ST | SELE |
| 5306 | Age | Glucose | IL6ST | SELP |
| 5307 | Age | Glucose | IL6ST | Sex |
| 5308 | Age | Glucose | IL6ST | SHBG |
| 5309 | Age | Glucose | IL6ST | TNFRSF1B |
| 5310 | Age | Glucose | IL6ST | TRIG |
| 5311 | Age | Glucose | IL6ST | VCAM1 |
| 5312 | Age | Glucose | IL6ST | VEGF |
| 5313 | Age | Glucose | IL6ST | VWF |
| 5314 | Age | Glucose | IL6ST | Waist |
| 5315 | Age | Glucose | IL8 | LEP |
| 5316 | Age | Glucose | IL8 | POMC |
| 5317 | Age | Glucose | IL8 | Sex |
| 5318 | Age | Glucose | IL8 | VEGF |
| 5319 | Age | Glucose | INHBA | LEP |
| 5320 | Age | Glucose | INHBA | POMC |
| 5321 | Age | Glucose | INHBA | Sex |
| 5322 | Age | Glucose | INHBA | VEGF |
| 5323 | Age | Glucose | Ins120 | Insulin |
| 5324 | Age | Glucose | Ins120 | LEP |
| 5325 | Age | Glucose | Ins120 | POMC |
| 5326 | Age | Glucose | Ins120 | Sex |
| 5327 | Age | Glucose | Ins120 | VEGF |
| 5328 | Age | Glucose | Insulin | LEP |
| 5329 | Age | Glucose | Insulin | POMC |
| 5330 | Age | Glucose | Insulin | Sex |
| 5331 | Age | Glucose | Insulin | VEGF |
| 5332 | Age | Glucose | LDL | LEP |
| 5333 | Age | Glucose | LDL | POMC |
| 5334 | Age | Glucose | LDL | Sex |
| 5335 | Age | Glucose | LDL | VEGF |
| 5336 | Age | Glucose | LEP | PLAT |
| 5337 | Age | Glucose | LEP | POMC |
| 5338 | Age | Glucose | LEP | SBP |
| 5339 | Age | Glucose | LEP | SCp |

FIG. 15KKKK

| 4-Panel | Marker 1 | Marker 2 | Marker 3 | Marker 4 |
|---|---|---|---|---|
| 5340 | Age | Glucose | LEP | SELE |
| 5341 | Age | Glucose | LEP | SELP |
| 5342 | Age | Glucose | LEP | Sex |
| 5343 | Age | Glucose | LEP | SHBG |
| 5344 | Age | Glucose | LEP | TNFRSF1B |
| 5345 | Age | Glucose | LEP | TRIG |
| 5346 | Age | Glucose | LEP | VCAM1 |
| 5347 | Age | Glucose | LEP | VEGF |
| 5348 | Age | Glucose | LEP | VWF |
| 5349 | Age | Glucose | LEP | Waist |
| 5350 | Age | Glucose | LEP | WT |
| 5351 | Age | Glucose | PLAT | POMC |
| 5352 | Age | Glucose | PLAT | Sex |
| 5353 | Age | Glucose | PLAT | VEGF |
| 5354 | Age | Glucose | POMC | SBP |
| 5355 | Age | Glucose | POMC | SCp |
| 5356 | Age | Glucose | POMC | SELE |
| 5357 | Age | Glucose | POMC | SELP |
| 5358 | Age | Glucose | POMC | Sex |
| 5359 | Age | Glucose | POMC | SHBG |
| 5360 | Age | Glucose | POMC | TNFRSF1B |
| 5361 | Age | Glucose | POMC | TRIG |
| 5362 | Age | Glucose | POMC | VCAM1 |
| 5363 | Age | Glucose | POMC | VEGF |
| 5364 | Age | Glucose | POMC | VWF |
| 5365 | Age | Glucose | POMC | Waist |
| 5366 | Age | Glucose | POMC | WT |
| 5367 | Age | Glucose | SBP | Sex |
| 5368 | Age | Glucose | SBP | VEGF |
| 5369 | Age | Glucose | SCp | Sex |
| 5370 | Age | Glucose | SCp | VEGF |
| 5371 | Age | Glucose | SELE | Sex |
| 5372 | Age | Glucose | SELE | VEGF |
| 5373 | Age | Glucose | SELP | Sex |
| 5374 | Age | Glucose | SELP | VEGF |
| 5375 | Age | Glucose | Sex | SHBG |
| 5376 | Age | Glucose | Sex | TNFRSF1B |
| 5377 | Age | Glucose | Sex | TRIG |
| 5378 | Age | Glucose | Sex | VCAM1 |
| 5379 | Age | Glucose | Sex | VEGF |
| 5380 | Age | Glucose | Sex | VWF |
| 5381 | Age | Glucose | Sex | Waist |
| 5382 | Age | Glucose | Sex | WT |
| 5383 | Age | Glucose | SHBG | VEGF |
| 5384 | Age | Glucose | TNFRSF1B | VEGF |
| 5385 | Age | Glucose | TRIG | VEGF |
| 5386 | Age | Glucose | VCAM1 | VEGF |
| 5387 | Age | Glucose | VEGF | VWF |
| 5388 | Age | Glucose | VEGF | Waist |
| 5389 | Age | Glucose | VEGF | WT |
| 5390 | Age | HBA1C | HDLC | Hip |
| 5391 | Age | HBA1C | HDLC | HT |
| 5392 | Age | HBA1C | HDLC | IGF1 |
| 5393 | Age | HBA1C | HDLC | IGFBP1 |
| 5394 | Age | HBA1C | HDLC | IL18 |
| 5395 | Age | HBA1C | HDLC | IL6ST |
| 5396 | Age | HBA1C | HDLC | IL8 |
| 5397 | Age | HBA1C | HDLC | Insulin |
| 5398 | Age | HBA1C | HDLC | LEP |
| 5399 | Age | HBA1C | HDLC | POMC |

FIG. 15LLLL

| 4-Panel | Marker 1 | Marker 2 | Marker 3 | Marker 4 |
|---|---|---|---|---|
| 5400 | Age | HBA1C | HDLC | SCp |
| 5401 | Age | HBA1C | HDLC | Sex |
| 5402 | Age | HBA1C | HDLC | TRIG |
| 5403 | Age | HBA1C | HDLC | VEGF |
| 5404 | Age | HBA1C | HDLC | Waist |
| 5405 | Age | HBA1C | HDLC | WT |
| 5406 | Age | HBA1C | HGF | LEP |
| 5407 | Age | HBA1C | HGF | POMC |
| 5408 | Age | HBA1C | Hip | IGF1 |
| 5409 | Age | HBA1C | Hip | LEP |
| 5410 | Age | HBA1C | Hip | POMC |
| 5411 | Age | HBA1C | Hip | VEGF |
| 5412 | Age | HBA1C | HP | LEP |
| 5413 | Age | HBA1C | HP | POMC |
| 5414 | Age | HBA1C | HT | IGF1 |
| 5415 | Age | HBA1C | HT | LEP |
| 5416 | Age | HBA1C | HT | POMC |
| 5417 | Age | HBA1C | HT | VEGF |
| 5418 | Age | HBA1C | ICAM1 | LEP |
| 5419 | Age | HBA1C | ICAM1 | POMC |
| 5420 | Age | HBA1C | IGF1 | IL18 |
| 5421 | Age | HBA1C | IGF1 | IL2RA |
| 5422 | Age | HBA1C | IGF1 | IL6ST |
| 5423 | Age | HBA1C | IGF1 | Insulin |
| 5424 | Age | HBA1C | IGF1 | LEP |
| 5425 | Age | HBA1C | IGF1 | POMC |
| 5426 | Age | HBA1C | IGF1 | Sex |
| 5427 | Age | HBA1C | IGF1 | VCAM1 |
| 5428 | Age | HBA1C | IGF1 | VEGF |
| 5429 | Age | HBA1C | IGFBP1 | LEP |

| 4-Panel | Marker 1 | Marker 2 | Marker 3 | Marker 4 |
|---|---|---|---|---|
| 5430 | Age | HBA1C | IGFBP1 | POMC |
| 5431 | Age | HBA1C | IGFBP1 | Sex |
| 5432 | Age | HBA1C | IGFBP3 | LEP |
| 5433 | Age | HBA1C | IGFBP3 | POMC |
| 5434 | Age | HBA1C | IL18 | LEP |
| 5435 | Age | HBA1C | IL18 | POMC |
| 5436 | Age | HBA1C | IL18 | Sex |
| 5437 | Age | HBA1C | IL18 | VEGF |
| 5438 | Age | HBA1C | IL2RA | LEP |
| 5439 | Age | HBA1C | IL2RA | POMC |
| 5440 | Age | HBA1C | IL2RA | Sex |
| 5441 | Age | HBA1C | IL6R | IL6ST |
| 5442 | Age | HBA1C | IL6R | LEP |
| 5443 | Age | HBA1C | IL6R | POMC |
| 5444 | Age | HBA1C | IL6ST | LEP |
| 5445 | Age | HBA1C | IL6ST | POMC |
| 5446 | Age | HBA1C | IL6ST | Sex |
| 5447 | Age | HBA1C | IL6ST | TNFRSF1B |
| 5448 | Age | HBA1C | IL6ST | VEGF |
| 5449 | Age | HBA1C | IL8 | LEP |
| 5450 | Age | HBA1C | IL8 | POMC |
| 5451 | Age | HBA1C | IL8 | VEGF |
| 5452 | Age | HBA1C | INHBA | LEP |
| 5453 | Age | HBA1C | INHBA | POMC |
| 5454 | Age | HBA1C | Ins120 | LEP |
| 5455 | Age | HBA1C | Ins120 | POMC |
| 5456 | Age | HBA1C | Insulin | LEP |
| 5457 | Age | HBA1C | Insulin | POMC |
| 5458 | Age | HBA1C | Insulin | Sex |
| 5459 | Age | HBA1C | Insulin | VEGF |

FIG. 15MMMM

| 4-Panel | Marker 1 | Marker 2 | Marker 3 | Marker 4 |
|---|---|---|---|---|
| 5460 | Age | HBA1C | LDL | LEP |
| 5461 | Age | HBA1C | LDL | POMC |
| 5462 | Age | HBA1C | LEP | PLAT |
| 5463 | Age | HBA1C | LEP | POMC |
| 5464 | Age | HBA1C | LEP | SBP |
| 5465 | Age | HBA1C | LEP | SCp |
| 5466 | Age | HBA1C | LEP | SELE |
| 5467 | Age | HBA1C | LEP | SELP |
| 5468 | Age | HBA1C | LEP | Sex |
| 5469 | Age | HBA1C | LEP | SHBG |
| 5470 | Age | HBA1C | LEP | TNFRSF1B |
| 5471 | Age | HBA1C | LEP | TRIG |
| 5472 | Age | HBA1C | LEP | VCAM1 |
| 5473 | Age | HBA1C | LEP | VEGF |
| 5474 | Age | HBA1C | LEP | VWF |
| 5475 | Age | HBA1C | LEP | Waist |
| 5476 | Age | HBA1C | LEP | WT |
| 5477 | Age | HBA1C | PLAT | POMC |
| 5478 | Age | HBA1C | POMC | SBP |
| 5479 | Age | HBA1C | POMC | SCp |
| 5480 | Age | HBA1C | POMC | SELE |
| 5481 | Age | HBA1C | POMC | SELP |
| 5482 | Age | HBA1C | POMC | Sex |
| 5483 | Age | HBA1C | POMC | SHBG |
| 5484 | Age | HBA1C | POMC | TNFRSF1B |
| 5485 | Age | HBA1C | POMC | TRIG |
| 5486 | Age | HBA1C | POMC | VCAM1 |
| 5487 | Age | HBA1C | POMC | VEGF |
| 5488 | Age | HBA1C | POMC | VWF |
| 5489 | Age | HBA1C | POMC | Waist |
| 5490 | Age | HBA1C | POMC | WT |
| 5491 | Age | HBA1C | Sex | VEGF |
| 5492 | Age | HBA1C | Sex | Waist |
| 5493 | Age | HBA1C | Sex | WT |
| 5494 | Age | HDLC | HGF | Hip |
| 5495 | Age | HDLC | HGF | IGF1 |
| 5496 | Age | HDLC | HGF | IGFBP1 |
| 5497 | Age | HDLC | HGF | IL18 |
| 5498 | Age | HDLC | HGF | IL2RA |
| 5499 | Age | HDLC | HGF | IL6ST |
| 5500 | Age | HDLC | HGF | Insulin |
| 5501 | Age | HDLC | HGF | LEP |
| 5502 | Age | HDLC | HGF | POMC |
| 5503 | Age | HDLC | HGF | SCp |
| 5504 | Age | HDLC | HGF | Sex |
| 5505 | Age | HDLC | HGF | TRIG |
| 5506 | Age | HDLC | HGF | VCAM1 |
| 5507 | Age | HDLC | HGF | VEGF |
| 5508 | Age | HDLC | HGF | Waist |
| 5509 | Age | HDLC | HGF | WT |
| 5510 | Age | HDLC | Hip | HP |
| 5511 | Age | HDLC | Hip | HT |
| 5512 | Age | HDLC | Hip | ICAM1 |
| 5513 | Age | HDLC | Hip | IGF1 |
| 5514 | Age | HDLC | Hip | IGFBP1 |
| 5515 | Age | HDLC | Hip | IGFBP3 |
| 5516 | Age | HDLC | Hip | IL18 |
| 5517 | Age | HDLC | Hip | IL2RA |
| 5518 | Age | HDLC | Hip | IL6R |
| 5519 | Age | HDLC | Hip | IL6ST |

FIG. 15NNNN

| 4-Panel | Marker 1 | Marker 2 | Marker 3 | Marker 4 |
|---|---|---|---|---|
| 5520 | Age | HDLC | Hip | IL8 |
| 5521 | Age | HDLC | Hip | INHBA |
| 5522 | Age | HDLC | Hip | Ins120 |
| 5523 | Age | HDLC | Hip | Insulin |
| 5524 | Age | HDLC | Hip | LDL |
| 5525 | Age | HDLC | Hip | LEP |
| 5526 | Age | HDLC | Hip | PLAT |
| 5527 | Age | HDLC | Hip | POMC |
| 5528 | Age | HDLC | Hip | SBP |
| 5529 | Age | HDLC | Hip | SCp |
| 5530 | Age | HDLC | Hip | SELE |
| 5531 | Age | HDLC | Hip | SELP |
| 5532 | Age | HDLC | Hip | Sex |
| 5533 | Age | HDLC | Hip | SHBG |
| 5534 | Age | HDLC | Hip | TNFRSF1B |
| 5535 | Age | HDLC | Hip | TRIG |
| 5536 | Age | HDLC | Hip | VCAM1 |
| 5537 | Age | HDLC | Hip | VEGF |
| 5538 | Age | HDLC | Hip | vWF |
| 5539 | Age | HDLC | Hip | Waist |
| 5540 | Age | HDLC | Hip | WT |
| 5541 | Age | HDLC | Hip | IGF1 |
| 5542 | Age | HDLC | Hip | IGFBP1 |
| 5543 | Age | HDLC | Hip | IL18 |
| 5544 | Age | HDLC | Hip | IL6ST |
| 5545 | Age | HDLC | Hip | Insulin |
| 5546 | Age | HDLC | Hip | LEP |
| 5547 | Age | HDLC | Hip | POMC |
| 5548 | Age | HDLC | HP | SCp |
| 5549 | Age | HDLC | HP | Sex |
| 5550 | Age | HDLC | HP | TRIG |
| 5551 | Age | HDLC | HP | VCAM1 |
| 5552 | Age | HDLC | HP | VEGF |
| 5553 | Age | HDLC | HP | Waist |
| 5554 | Age | HDLC | HP | WT |
| 5555 | Age | HDLC | HT | IGF1 |
| 5556 | Age | HDLC | HT | IGFBP1 |
| 5557 | Age | HDLC | HT | IL18 |
| 5558 | Age | HDLC | HT | IL2RA |
| 5559 | Age | HDLC | HT | IL6ST |
| 5560 | Age | HDLC | HT | IL8 |
| 5561 | Age | HDLC | HT | Insulin |
| 5562 | Age | HDLC | HT | LDL |
| 5563 | Age | HDLC | HT | LEP |
| 5564 | Age | HDLC | HT | POMC |
| 5565 | Age | HDLC | HT | SCp |
| 5566 | Age | HDLC | HT | Sex |
| 5567 | Age | HDLC | HT | TRIG |
| 5568 | Age | HDLC | HT | VCAM1 |
| 5569 | Age | HDLC | HT | VEGF |
| 5570 | Age | HDLC | HT | vWF |
| 5571 | Age | HDLC | HT | Waist |
| 5572 | Age | HDLC | HT | WT |
| 5573 | Age | HDLC | ICAM1 | IGF1 |
| 5574 | Age | HDLC | ICAM1 | IGFBP1 |
| 5575 | Age | HDLC | ICAM1 | IL18 |
| 5576 | Age | HDLC | ICAM1 | IL2RA |
| 5577 | Age | HDLC | ICAM1 | IL6ST |
| 5578 | Age | HDLC | ICAM1 | Insulin |
| 5579 | Age | HDLC | ICAM1 | LEP |

FIG. 150000

FIG. 15PPPP

| 4-Panel | Marker 1 | Marker 2 | Marker 3 | Marker 4 |
|---|---|---|---|---|
| 5580 | Age | HDLC | ICAM1 | POMC |
| 5581 | Age | HDLC | ICAM1 | SCp |
| 5582 | Age | HDLC | ICAM1 | Sex |
| 5583 | Age | HDLC | ICAM1 | TRIG |
| 5584 | Age | HDLC | ICAM1 | VCAM1 |
| 5585 | Age | HDLC | ICAM1 | VEGF |
| 5586 | Age | HDLC | ICAM1 | Waist |
| 5587 | Age | HDLC | ICAM1 | WT |
| 5588 | Age | HDLC | IGF1 | IGFBP1 |
| 5589 | Age | HDLC | IGF1 | IGFBP3 |
| 5590 | Age | HDLC | IGF1 | IL18 |
| 5591 | Age | HDLC | IGF1 | IL2RA |
| 5592 | Age | HDLC | IGF1 | IL6R |
| 5593 | Age | HDLC | IGF1 | IL6ST |
| 5594 | Age | HDLC | IGF1 | IL8 |
| 5595 | Age | HDLC | IGF1 | INHBA |
| 5596 | Age | HDLC | IGF1 | Ins120 |
| 5597 | Age | HDLC | IGF1 | Insulin |
| 5598 | Age | HDLC | IGF1 | LDL |
| 5599 | Age | HDLC | IGF1 | LEP |
| 5600 | Age | HDLC | IGF1 | PLAT |
| 5601 | Age | HDLC | IGF1 | POMC |
| 5602 | Age | HDLC | IGF1 | SBP |
| 5603 | Age | HDLC | IGF1 | SCp |
| 5604 | Age | HDLC | IGF1 | SELE |
| 5605 | Age | HDLC | IGF1 | SELP |
| 5606 | Age | HDLC | IGF1 | Sex |
| 5607 | Age | HDLC | IGF1 | SHBG |
| 5608 | Age | HDLC | IGF1 | TNFRSF1B |
| 5609 | Age | HDLC | IGF1 | TRIG |

| 4-Panel | Marker 1 | Marker 2 | Marker 3 | Marker 4 |
|---|---|---|---|---|
| 5610 | Age | HDLC | IGF1 | VCAM1 |
| 5611 | Age | HDLC | IGF1 | VEGF |
| 5612 | Age | HDLC | IGF1 | VWF |
| 5613 | Age | HDLC | IGF1 | Waist |
| 5614 | Age | HDLC | IGF1 | WT |
| 5615 | Age | HDLC | IGFBP1 | IGFBP3 |
| 5616 | Age | HDLC | IGFBP1 | IL18 |
| 5617 | Age | HDLC | IGFBP1 | IL2RA |
| 5618 | Age | HDLC | IGFBP1 | IL6R |
| 5619 | Age | HDLC | IGFBP1 | IL6ST |
| 5620 | Age | HDLC | IGFBP1 | IL8 |
| 5621 | Age | HDLC | IGFBP1 | INHBA |
| 5622 | Age | HDLC | IGFBP1 | Ins120 |
| 5623 | Age | HDLC | IGFBP1 | Insulin |
| 5624 | Age | HDLC | IGFBP1 | LDL |
| 5625 | Age | HDLC | IGFBP1 | LEP |
| 5626 | Age | HDLC | IGFBP1 | PLAT |
| 5627 | Age | HDLC | IGFBP1 | POMC |
| 5628 | Age | HDLC | IGFBP1 | SBP |
| 5629 | Age | HDLC | IGFBP1 | SCp |
| 5630 | Age | HDLC | IGFBP1 | SELE |
| 5631 | Age | HDLC | IGFBP1 | SELP |
| 5632 | Age | HDLC | IGFBP1 | Sex |
| 5633 | Age | HDLC | IGFBP1 | TNFRSF1B |
| 5634 | Age | HDLC | IGFBP1 | TRIG |
| 5635 | Age | HDLC | IGFBP1 | VCAM1 |
| 5636 | Age | HDLC | IGFBP1 | VEGF |
| 5637 | Age | HDLC | IGFBP1 | VWF |
| 5638 | Age | HDLC | IGFBP1 | Waist |
| 5639 | Age | HDLC | IGFBP1 | WT |

| 4-Panel | Marker 1 | Marker 2 | Marker 3 | Marker 4 |
|---|---|---|---|---|
| 5640 | Age | HDLC | IGFBP3 | IL18 |
| 5641 | Age | HDLC | IGFBP3 | IL6ST |
| 5642 | Age | HDLC | IGFBP3 | Insulin |
| 5643 | Age | HDLC | IGFBP3 | LEP |
| 5644 | Age | HDLC | IGFBP3 | POMC |
| 5645 | Age | HDLC | IGFBP3 | SCp |
| 5646 | Age | HDLC | IGFBP3 | Sex |
| 5647 | Age | HDLC | IGFBP3 | TRIG |
| 5648 | Age | HDLC | IGFBP3 | VCAM1 |
| 5649 | Age | HDLC | IGFBP3 | VEGF |
| 5650 | Age | HDLC | IGFBP3 | Waist |
| 5651 | Age | HDLC | IGFBP3 | WT |
| 5652 | Age | HDLC | IL18 | IL2RA |
| 5653 | Age | HDLC | IL18 | IL6R |
| 5654 | Age | HDLC | IL18 | IL6ST |
| 5655 | Age | HDLC | IL18 | IL8 |
| 5656 | Age | HDLC | IL18 | INHBA |
| 5657 | Age | HDLC | IL18 | Ins120 |
| 5658 | Age | HDLC | IL18 | Insulin |
| 5659 | Age | HDLC | IL18 | LDL |
| 5660 | Age | HDLC | IL18 | LEP |
| 5661 | Age | HDLC | IL18 | PLAT |
| 5662 | Age | HDLC | IL18 | POMC |
| 5663 | Age | HDLC | IL18 | SBP |
| 5664 | Age | HDLC | IL18 | SCp |
| 5665 | Age | HDLC | IL18 | SELE |
| 5666 | Age | HDLC | IL18 | SELP |
| 5667 | Age | HDLC | IL18 | Sex |
| 5668 | Age | HDLC | IL18 | SHBG |
| 5669 | Age | HDLC | IL18 | TNFRSF1B |

| 4-Panel | Marker 1 | Marker 2 | Marker 3 | Marker 4 |
|---|---|---|---|---|
| 5670 | Age | HDLC | IL18 | TRIG |
| 5671 | Age | HDLC | IL18 | VCAM1 |
| 5672 | Age | HDLC | IL18 | VEGF |
| 5673 | Age | HDLC | IL18 | VWF |
| 5674 | Age | HDLC | IL18 | Waist |
| 5675 | Age | HDLC | IL18 | WT |
| 5676 | Age | HDLC | IL2RA | IL6R |
| 5677 | Age | HDLC | IL2RA | IL6ST |
| 5678 | Age | HDLC | IL2RA | IL8 |
| 5679 | Age | HDLC | IL2RA | INHBA |
| 5680 | Age | HDLC | IL2RA | Ins120 |
| 5681 | Age | HDLC | IL2RA | Insulin |
| 5682 | Age | HDLC | IL2RA | LDL |
| 5683 | Age | HDLC | IL2RA | LEP |
| 5684 | Age | HDLC | IL2RA | POMC |
| 5685 | Age | HDLC | IL2RA | SBP |
| 5686 | Age | HDLC | IL2RA | SCp |
| 5687 | Age | HDLC | IL2RA | SELP |
| 5688 | Age | HDLC | IL2RA | Sex |
| 5689 | Age | HDLC | IL2RA | TNFRSF1B |
| 5690 | Age | HDLC | IL2RA | TRIG |
| 5691 | Age | HDLC | IL2RA | VCAM1 |
| 5692 | Age | HDLC | IL2RA | VEGF |
| 5693 | Age | HDLC | IL2RA | VWF |
| 5694 | Age | HDLC | IL2RA | Waist |
| 5695 | Age | HDLC | IL2RA | WT |
| 5696 | Age | HDLC | IL6R | IL6ST |
| 5697 | Age | HDLC | IL6R | Insulin |
| 5698 | Age | HDLC | IL6R | LEP |
| 5699 | Age | HDLC | IL6R | POMC |

FIG. 15QQQQ

| 4-Panel | Marker 1 | Marker 2 | Marker 3 | Marker 4 |
|---|---|---|---|---|
| 5700 | Age | HDLC | IL6R | SCp |
| 5701 | Age | HDLC | IL6R | Sex |
| 5702 | Age | HDLC | IL6R | TRIG |
| 5703 | Age | HDLC | IL6R | VCAM1 |
| 5704 | Age | HDLC | IL6R | VEGF |
| 5705 | Age | HDLC | IL6R | Waist |
| 5706 | Age | HDLC | IL6R | WT |
| 5707 | Age | HDLC | IL6ST | IL8 |
| 5708 | Age | HDLC | IL6ST | INHBA |
| 5709 | Age | HDLC | IL6ST | Ins120 |
| 5710 | Age | HDLC | IL6ST | Insulin |
| 5711 | Age | HDLC | IL6ST | LDL |
| 5712 | Age | HDLC | IL6ST | LEP |
| 5713 | Age | HDLC | IL6ST | PLAT |
| 5714 | Age | HDLC | IL6ST | POMC |
| 5715 | Age | HDLC | IL6ST | SBP |
| 5716 | Age | HDLC | IL6ST | SCp |
| 5717 | Age | HDLC | IL6ST | SELE |
| 5718 | Age | HDLC | IL6ST | SELP |
| 5719 | Age | HDLC | IL6ST | Sex |
| 5720 | Age | HDLC | IL6ST | SHBG |
| 5721 | Age | HDLC | IL6ST | TNFRSF1B |
| 5722 | Age | HDLC | IL6ST | TRIG |
| 5723 | Age | HDLC | IL6ST | VCAM1 |
| 5724 | Age | HDLC | IL6ST | VEGF |
| 5725 | Age | HDLC | IL6ST | VWF |
| 5726 | Age | HDLC | IL6ST | Waist |
| 5727 | Age | HDLC | IL6ST | WT |
| 5728 | Age | HDLC | IL8 | INHBA |
| 5729 | Age | HDLC | IL8 | Insulin |

| 4-Panel | Marker 1 | Marker 2 | Marker 3 | Marker 4 |
|---|---|---|---|---|
| 5730 | Age | HDLC | IL8 | LDL |
| 5731 | Age | HDLC | IL8 | LEP |
| 5732 | Age | HDLC | IL8 | POMC |
| 5733 | Age | HDLC | IL8 | SCp |
| 5734 | Age | HDLC | IL8 | Sex |
| 5735 | Age | HDLC | IL8 | TRIG |
| 5736 | Age | HDLC | IL8 | VCAM1 |
| 5737 | Age | HDLC | IL8 | VEGF |
| 5738 | Age | HDLC | IL8 | VWF |
| 5739 | Age | HDLC | IL8 | Waist |
| 5740 | Age | HDLC | IL8 | WT |
| 5741 | Age | HDLC | INHBA | Insulin |
| 5742 | Age | HDLC | INHBA | LEP |
| 5743 | Age | HDLC | INHBA | POMC |
| 5744 | Age | HDLC | INHBA | SCp |
| 5745 | Age | HDLC | INHBA | Sex |
| 5746 | Age | HDLC | INHBA | TRIG |
| 5747 | Age | HDLC | INHBA | VCAM1 |
| 5748 | Age | HDLC | INHBA | VEGF |
| 5749 | Age | HDLC | INHBA | VWF |
| 5750 | Age | HDLC | INHBA | Waist |
| 5751 | Age | HDLC | INHBA | WT |
| 5752 | Age | HDLC | Ins120 | Insulin |
| 5753 | Age | HDLC | Ins120 | LEP |
| 5754 | Age | HDLC | Ins120 | POMC |
| 5755 | Age | HDLC | Ins120 | SCp |
| 5756 | Age | HDLC | Ins120 | Sex |
| 5757 | Age | HDLC | Ins120 | TRIG |
| 5758 | Age | HDLC | Ins120 | VCAM1 |
| 5759 | Age | HDLC | Ins120 | VEGF |

FIG. 15RRRR

| 4-Panel | Marker 1 | Marker 2 | Marker 3 | Marker 4 |
|---|---|---|---|---|
| 5760 | Age | HDLC | Ins120 | VWF |
| 5761 | Age | HDLC | Ins120 | Waist |
| 5762 | Age | HDLC | Ins120 | WT |
| 5763 | Age | HDLC | Insulin | LDL |
| 5764 | Age | HDLC | Insulin | LEP |
| 5765 | Age | HDLC | Insulin | PLAT |
| 5766 | Age | HDLC | Insulin | POMC |
| 5767 | Age | HDLC | Insulin | SBP |
| 5768 | Age | HDLC | Insulin | SCp |
| 5769 | Age | HDLC | Insulin | SELE |
| 5770 | Age | HDLC | Insulin | SELP |
| 5771 | Age | HDLC | Insulin | Sex |
| 5772 | Age | HDLC | Insulin | SHBG |
| 5773 | Age | HDLC | Insulin | TNFRSF1B |
| 5774 | Age | HDLC | Insulin | TRIG |
| 5775 | Age | HDLC | Insulin | VCAM1 |
| 5776 | Age | HDLC | Insulin | VEGF |
| 5777 | Age | HDLC | Insulin | VWF |
| 5778 | Age | HDLC | Insulin | Waist |
| 5779 | Age | HDLC | Insulin | WT |
| 5780 | Age | HDLC | LDL | LEP |
| 5781 | Age | HDLC | LDL | POMC |
| 5782 | Age | HDLC | LDL | SCp |
| 5783 | Age | HDLC | LDL | Sex |
| 5784 | Age | HDLC | LDL | TRIG |
| 5785 | Age | HDLC | LDL | VCAM1 |
| 5786 | Age | HDLC | LDL | VEGF |
| 5787 | Age | HDLC | LDL | VWF |
| 5788 | Age | HDLC | LDL | Waist |
| 5789 | Age | HDLC | LDL | WT |
| 5790 | Age | HDLC | LEP | PLAT |
| 5791 | Age | HDLC | LEP | POMC |
| 5792 | Age | HDLC | LEP | SBP |
| 5793 | Age | HDLC | LEP | SCp |
| 5794 | Age | HDLC | LEP | SELE |
| 5795 | Age | HDLC | LEP | SELP |
| 5796 | Age | HDLC | LEP | Sex |
| 5797 | Age | HDLC | LEP | SHBG |
| 5798 | Age | HDLC | LEP | TNFRSF1B |
| 5799 | Age | HDLC | LEP | TRIG |
| 5800 | Age | HDLC | LEP | VCAM1 |
| 5801 | Age | HDLC | LEP | VEGF |
| 5802 | Age | HDLC | LEP | VWF |
| 5803 | Age | HDLC | LEP | Waist |
| 5804 | Age | HDLC | LEP | WT |
| 5805 | Age | HDLC | PLAT | POMC |
| 5806 | Age | HDLC | PLAT | SCp |
| 5807 | Age | HDLC | PLAT | Sex |
| 5808 | Age | HDLC | PLAT | TRIG |
| 5809 | Age | HDLC | PLAT | VEGF |
| 5810 | Age | HDLC | PLAT | Waist |
| 5811 | Age | HDLC | PLAT | WT |
| 5812 | Age | HDLC | POMC | SBP |
| 5813 | Age | HDLC | POMC | SCp |
| 5814 | Age | HDLC | POMC | SELE |
| 5815 | Age | HDLC | POMC | SELP |
| 5816 | Age | HDLC | POMC | Sex |
| 5817 | Age | HDLC | POMC | SHBG |
| 5818 | Age | HDLC | POMC | TNFRSF1B |
| 5819 | Age | HDLC | POMC | TRIG |

FIG. 15SSSS

FIG. 15TTTT

| 4-Panel | Marker 1 | Marker 2 | Marker 3 | Marker 4 |
|---|---|---|---|---|
| 5820 | Age | HDLC | POMC | VCAM1 |
| 5821 | Age | HDLC | POMC | VEGF |
| 5822 | Age | HDLC | POMC | VWF |
| 5823 | Age | HDLC | POMC | Waist |
| 5824 | Age | HDLC | POMC | WT |
| 5825 | Age | HDLC | SBP | SCp |
| 5826 | Age | HDLC | SBP | Sex |
| 5827 | Age | HDLC | SBP | TRIG |
| 5828 | Age | HDLC | SBP | VCAM1 |
| 5829 | Age | HDLC | SBP | VEGF |
| 5830 | Age | HDLC | SBP | VWF |
| 5831 | Age | HDLC | SBP | Waist |
| 5832 | Age | HDLC | SBP | WT |
| 5833 | Age | HDLC | SCp | SELE |
| 5834 | Age | HDLC | SCp | SELP |
| 5835 | Age | HDLC | SCp | Sex |
| 5836 | Age | HDLC | SCp | TNFRSF1B |
| 5837 | Age | HDLC | SCp | TRIG |
| 5838 | Age | HDLC | SCp | VCAM1 |
| 5839 | Age | HDLC | SCp | VEGF |
| 5840 | Age | HDLC | SCp | VWF |
| 5841 | Age | HDLC | SCp | Waist |
| 5842 | Age | HDLC | SCp | WT |
| 5843 | Age | HDLC | SELE | Sex |
| 5844 | Age | HDLC | SELE | TRIG |
| 5845 | Age | HDLC | SELE | VCAM1 |
| 5846 | Age | HDLC | SELE | VEGF |
| 5847 | Age | HDLC | SELE | Waist |
| 5848 | Age | HDLC | SELE | WT |
| 5849 | Age | HDLC | SELP | TRIG |
| 5850 | Age | HDLC | SELP | VCAM1 |
| 5851 | Age | HDLC | SELP | VEGF |
| 5852 | Age | HDLC | SELP | VWF |
| 5853 | Age | HDLC | SELP | Waist |
| 5854 | Age | HDLC | SELP | WT |
| 5855 | Age | HDLC | Sex | TNFRSF1B |
| 5856 | Age | HDLC | Sex | TRIG |
| 5857 | Age | HDLC | Sex | VCAM1 |
| 5858 | Age | HDLC | Sex | VEGF |
| 5859 | Age | HDLC | Sex | VWF |
| 5860 | Age | HDLC | Sex | Waist |
| 5861 | Age | HDLC | Sex | WT |
| 5862 | Age | HDLC | SHBG | VCAM1 |
| 5863 | Age | HDLC | SHBG | VEGF |
| 5864 | Age | HDLC | SHBG | Waist |
| 5865 | Age | HDLC | SHBG | WT |
| 5866 | Age | HDLC | TNFRSF1B | TRIG |
| 5867 | Age | HDLC | TNFRSF1B | VCAM1 |
| 5868 | Age | HDLC | TNFRSF1B | VEGF |
| 5869 | Age | HDLC | TNFRSF1B | VWF |
| 5870 | Age | HDLC | TNFRSF1B | Waist |
| 5871 | Age | HDLC | TRIG | WT |
| 5872 | Age | HDLC | TRIG | VCAM1 |
| 5873 | Age | HDLC | TRIG | VEGF |
| 5874 | Age | HDLC | TRIG | VWF |
| 5875 | Age | HDLC | TRIG | Waist |
| 5876 | Age | HDLC | TRIG | WT |
| 5877 | Age | HDLC | VCAM1 | VEGF |
| 5878 | Age | HDLC | VCAM1 | VWF |
| 5879 | Age | HDLC | VCAM1 | Waist |

| 4-Panel | Marker 1 | Marker 2 | Marker 3 | Marker 4 |
|---|---|---|---|---|
| 5880 | Age | HDLC | VEGF | VWF |
| 5881 | Age | HDLC | VEGF | Waist |
| 5882 | Age | HDLC | VEGF | WT |
| 5883 | Age | HDLC | VWF | Waist |
| 5884 | Age | HDLC | VWF | WT |
| 5885 | Age | HDLC | Waist | WT |
| 5886 | Age | HGF | Hip | IGF1 |
| 5887 | Age | HGF | Hip | LEP |
| 5888 | Age | HGF | Hip | POMC |
| 5889 | Age | HGF | Hip | Sex |
| 5890 | Age | HGF | HP | LEP |
| 5891 | Age | HGF | HP | POMC |
| 5892 | Age | HGF | HT | IGF1 |
| 5893 | Age | HGF | HT | IL6ST |
| 5894 | Age | HGF | HT | Insulin |
| 5895 | Age | HGF | HT | LEP |
| 5896 | Age | HGF | HT | POMC |
| 5897 | Age | HGF | HT | VEGF |
| 5898 | Age | HGF | HT | WT |
| 5899 | Age | HGF | ICAM1 | LEP |
| 5900 | Age | HGF | ICAM1 | POMC |
| 5901 | Age | HGF | IGF1 | IL2RA |
| 5902 | Age | HGF | IGF1 | IL6ST |
| 5903 | Age | HGF | IGF1 | Insulin |
| 5904 | Age | HGF | IGF1 | LEP |
| 5905 | Age | HGF | IGF1 | POMC |
| 5906 | Age | HGF | IGF1 | Sex |
| 5907 | Age | HGF | IGF1 | VCAM1 |
| 5908 | Age | HGF | IGF1 | VEGF |
| 5909 | Age | HGF | IGFBP1 | LEP |
| 5910 | Age | HGF | IGFBP1 | POMC |
| 5911 | Age | HGF | IGFBP1 | Sex |
| 5912 | Age | HGF | IGFBP3 | LEP |
| 5913 | Age | HGF | IGFBP3 | POMC |
| 5914 | Age | HGF | IL18 | LEP |
| 5915 | Age | HGF | IL18 | POMC |
| 5916 | Age | HGF | IL18 | Sex |
| 5917 | Age | HGF | IL18 | VEGF |
| 5918 | Age | HGF | IL2RA | LEP |
| 5919 | Age | HGF | IL2RA | POMC |
| 5920 | Age | HGF | IL2RA | Sex |
| 5921 | Age | HGF | IL6R | IL6ST |
| 5922 | Age | HGF | IL6R | LEP |
| 5923 | Age | HGF | IL6R | POMC |
| 5924 | Age | HGF | IL6ST | LEP |
| 5925 | Age | HGF | IL6ST | POMC |
| 5926 | Age | HGF | IL6ST | SELP |
| 5927 | Age | HGF | IL6ST | Sex |
| 5928 | Age | HGF | IL6ST | TNFRSF1B |
| 5929 | Age | HGF | IL6ST | VEGF |
| 5930 | Age | HGF | IL8 | LEP |
| 5931 | Age | HGF | IL8 | POMC |
| 5932 | Age | HGF | IL8 | Sex |
| 5933 | Age | HGF | IL8 | LEP |
| 5934 | Age | HGF | INHBA | POMC |
| 5935 | Age | HGF | INHBA | Insulin |
| 5936 | Age | HGF | Ins120 | Insulin |
| 5937 | Age | HGF | Ins120 | LEP |
| 5938 | Age | HGF | Insulin | POMC |
| 5939 | Age | HGF | Insulin | LEP |

FIG. 15UUUU

| 4-Panel | Marker 1 | Marker 2 | Marker 3 | Marker 4 |
|---|---|---|---|---|
| 5940 | Age | HGF | Insulin | Sex |
| 5941 | Age | HGF | Insulin | VEGF |
| 5942 | Age | HGF | LDL | LEP |
| 5943 | Age | HGF | LDL | POMC |
| 5944 | Age | HGF | LEP | PLAT |
| 5945 | Age | HGF | LEP | POMC |
| 5946 | Age | HGF | LEP | SBP |
| 5947 | Age | HGF | LEP | SCp |
| 5948 | Age | HGF | LEP | SELE |
| 5949 | Age | HGF | LEP | SELP |
| 5950 | Age | HGF | LEP | Sex |
| 5951 | Age | HGF | LEP | SHBG |
| 5952 | Age | HGF | LEP | TNFRSF1B |
| 5953 | Age | HGF | LEP | TRIG |
| 5954 | Age | HGF | LEP | VCAM1 |
| 5955 | Age | HGF | LEP | VEGF |
| 5956 | Age | HGF | LEP | VWF |
| 5957 | Age | HGF | LEP | Waist |
| 5958 | Age | HGF | LEP | WT |
| 5959 | Age | HGF | PLAT | POMC |
| 5960 | Age | HGF | POMC | SBP |
| 5961 | Age | HGF | POMC | SCp |
| 5962 | Age | HGF | POMC | SELE |
| 5963 | Age | HGF | POMC | SELP |
| 5964 | Age | HGF | POMC | Sex |
| 5965 | Age | HGF | POMC | SHBG |
| 5966 | Age | HGF | POMC | TNFRSF1B |
| 5967 | Age | HGF | POMC | TRIG |
| 5968 | Age | HGF | POMC | VCAM1 |
| 5969 | Age | HGF | POMC | VEGF |
| 5970 | Age | HGF | POMC | VWF |
| 5971 | Age | HGF | POMC | Waist |
| 5972 | Age | HGF | POMC | WT |
| 5973 | Age | HGF | Sex | VCAM1 |
| 5974 | Age | HGF | Sex | VEGF |
| 5975 | Age | HGF | Sex | Waist |
| 5976 | Age | HGF | Sex | WT |
| 5977 | Age | Hip | HP | POMC |
| 5978 | Age | Hip | HP | Sex |
| 5979 | Age | Hip | HP | VEGF |
| 5980 | Age | Hip | HP | IGF1 |
| 5981 | Age | Hip | HT | IL6ST |
| 5982 | Age | Hip | HT | LEP |
| 5983 | Age | Hip | HT | POMC |
| 5984 | Age | Hip | HT | VEGF |
| 5985 | Age | Hip | ICAM1 | IGF1 |
| 5986 | Age | Hip | ICAM1 | LEP |
| 5987 | Age | Hip | ICAM1 | POMC |
| 5988 | Age | Hip | IGF1 | IGFBP1 |
| 5989 | Age | Hip | IGF1 | IL18 |
| 5990 | Age | Hip | IGF1 | IL2RA |
| 5991 | Age | Hip | IGF1 | IL6R |
| 5992 | Age | Hip | IGF1 | IL6ST |
| 5993 | Age | Hip | IGF1 | IL8 |
| 5994 | Age | Hip | IGF1 | Ins120 |
| 5995 | Age | Hip | IGF1 | Insulin |
| 5996 | Age | Hip | IGF1 | LEP |
| 5997 | Age | Hip | IGF1 | PLAT |
| 5998 | Age | Hip | IGF1 | POMC |
| 5999 | Age | Hip | IGF1 | SCp |

FIG. 15VVVV

| 4-Panel | Marker 1 | Marker 2 | Marker 3 | Marker 4 |
|---|---|---|---|---|
| 6000 | Age | Hip | IGF1 | SELE |
| 6001 | Age | Hip | IGF1 | SELP |
| 6002 | Age | Hip | IGF1 | Sex |
| 6003 | Age | Hip | IGF1 | SHBG |
| 6004 | Age | Hip | IGF1 | TNFRSF1B |
| 6005 | Age | Hip | IGF1 | TRIG |
| 6006 | Age | Hip | IGF1 | VCAM1 |
| 6007 | Age | Hip | IGF1 | VEGF |
| 6008 | Age | Hip | IGF1 | VWF |
| 6009 | Age | Hip | IGF1 | Waist |
| 6010 | Age | Hip | IGF1 | WT |
| 6011 | Age | Hip | IGFBP1 | LEP |
| 6012 | Age | Hip | IGFBP1 | POMC |
| 6013 | Age | Hip | IGFBP1 | Sex |
| 6014 | Age | Hip | IGFBP3 | LEP |
| 6015 | Age | Hip | IGFBP3 | POMC |
| 6016 | Age | Hip | IL18 | IL6ST |
| 6017 | Age | Hip | IL18 | LEP |
| 6018 | Age | Hip | IL18 | POMC |
| 6019 | Age | Hip | IL18 | Sex |
| 6020 | Age | Hip | IL18 | VEGF |
| 6021 | Age | Hip | IL2RA | LEP |
| 6022 | Age | Hip | IL2RA | POMC |
| 6023 | Age | Hip | IL2RA | Sex |
| 6024 | Age | Hip | IL2RA | VEGF |
| 6025 | Age | Hip | IL6R | IL6ST |
| 6026 | Age | Hip | IL6R | LEP |
| 6027 | Age | Hip | IL6R | POMC |
| 6028 | Age | Hip | IL6ST | IL8 |
| 6029 | Age | Hip | IL6ST | Ins120 |
| 6030 | Age | Hip | IL6ST | LEP |
| 6031 | Age | Hip | IL6ST | POMC |
| 6032 | Age | Hip | IL6ST | SELP |
| 6033 | Age | Hip | IL6ST | Sex |
| 6034 | Age | Hip | IL6ST | TNFRSF1B |
| 6035 | Age | Hip | IL6ST | VEGF |
| 6036 | Age | Hip | IL6ST | Waist |
| 6037 | Age | Hip | IL8 | LEP |
| 6038 | Age | Hip | IL8 | POMC |
| 6039 | Age | Hip | IL8 | Sex |
| 6040 | Age | Hip | IL8 | VEGF |
| 6041 | Age | Hip | INHBA | LEP |
| 6042 | Age | Hip | INHBA | POMC |
| 6043 | Age | Hip | Ins120 | LEP |
| 6044 | Age | Hip | Ins120 | POMC |
| 6045 | Age | Hip | Ins120 | Sex |
| 6046 | Age | Hip | Ins120 | VEGF |
| 6047 | Age | Hip | Insulin | LEP |
| 6048 | Age | Hip | Insulin | POMC |
| 6049 | Age | Hip | Insulin | Sex |
| 6050 | Age | Hip | Insulin | VEGF |
| 6051 | Age | Hip | LDL | LEP |
| 6052 | Age | Hip | LDL | POMC |
| 6053 | Age | Hip | LEP | PLAT |
| 6054 | Age | Hip | LEP | POMC |
| 6055 | Age | Hip | LEP | SBP |
| 6056 | Age | Hip | LEP | SCp |
| 6057 | Age | Hip | LEP | SELE |
| 6058 | Age | Hip | LEP | SELP |
| 6059 | Age | Hip | LEP | Sex |

FIG. 15WWWW

| 4-Panel | Marker 1 | Marker 2 | Marker 3 | Marker 4 |
|---|---|---|---|---|
| 6060 | Age | Hip | LEP | SHBG |
| 6061 | Age | Hip | LEP | TNFRSF1B |
| 6062 | Age | Hip | LEP | TRIG |
| 6063 | Age | Hip | LEP | VCAM1 |
| 6064 | Age | Hip | LEP | VEGF |
| 6065 | Age | Hip | LEP | VWF |
| 6066 | Age | Hip | LEP | Waist |
| 6067 | Age | Hip | LEP | WT |
| 6068 | Age | Hip | PLAT | POMC |
| 6069 | Age | Hip | POMC | SBP |
| 6070 | Age | Hip | POMC | SCp |
| 6071 | Age | Hip | POMC | SELE |
| 6072 | Age | Hip | POMC | SELP |
| 6073 | Age | Hip | POMC | Sex |
| 6074 | Age | Hip | POMC | SHBG |
| 6075 | Age | Hip | POMC | TNFRSF1B |
| 6076 | Age | Hip | POMC | TRIG |
| 6077 | Age | Hip | POMC | VCAM1 |
| 6078 | Age | Hip | POMC | VEGF |
| 6079 | Age | Hip | POMC | VWF |
| 6080 | Age | Hip | POMC | Waist |
| 6081 | Age | Hip | POMC | WT |
| 6082 | Age | Hip | SELP | Sex |
| 6083 | Age | Hip | SELP | VEGF |
| 6084 | Age | Hip | Sex | VCAM1 |
| 6085 | Age | Hip | Sex | VEGF |
| 6086 | Age | Hip | Sex | WT |
| 6087 | Age | Hip | TRIG | VEGF |
| 6088 | Age | Hip | VCAM1 | VEGF |
| 6089 | Age | Hip | VEGF | VWF |

| 4-Panel | Marker 1 | Marker 2 | Marker 3 | Marker 4 |
|---|---|---|---|---|
| 6090 | Age | Hip | VEGF | Waist |
| 6091 | Age | HP | HT | IL6ST |
| 6092 | Age | HP | HT | Insulin |
| 6093 | Age | HP | HT | POMC |
| 6094 | Age | HP | HT | VEGF |
| 6095 | Age | HP | ICAM1 | POMC |
| 6096 | Age | HP | IGF1 | IL6ST |
| 6097 | Age | HP | IGF1 | Insulin |
| 6098 | Age | HP | IGF1 | LEP |
| 6099 | Age | HP | IGF1 | POMC |
| 6100 | Age | HP | IGF1 | Sex |
| 6101 | Age | HP | IGF1 | VCAM1 |
| 6102 | Age | HP | IGF1 | VEGF |
| 6103 | Age | HP | IGFBP1 | LEP |
| 6104 | Age | HP | IGFBP1 | POMC |
| 6105 | Age | HP | IGFBP1 | Sex |
| 6106 | Age | HP | IGFBP3 | POMC |
| 6107 | Age | HP | IL18 | POMC |
| 6108 | Age | HP | IL2RA | LEP |
| 6109 | Age | HP | IL2RA | POMC |
| 6110 | Age | HP | IL2RA | Sex |
| 6111 | Age | HP | IL6R | IL6ST |
| 6112 | Age | HP | IL6R | LEP |
| 6113 | Age | HP | IL6R | POMC |
| 6114 | Age | HP | IL6ST | Insulin |
| 6115 | Age | HP | IL6ST | LEP |
| 6116 | Age | HP | IL6ST | POMC |
| 6117 | Age | HP | IL6ST | SELP |
| 6118 | Age | HP | IL6ST | Sex |
| 6119 | Age | HP | IL6ST | TNFRSF1B |

FIG. 15XXXX

| 4-Panel | Marker 1 | Marker 2 | Marker 3 | Marker 4 |
|---|---|---|---|---|
| 6120 | Age | HP | IL6ST | VEGF |
| 6121 | Age | HP | IL8 | LEP |
| 6122 | Age | HP | IL8 | POMC |
| 6123 | Age | HP | INHBA | LEP |
| 6124 | Age | HP | INHBA | POMC |
| 6125 | Age | HP | INHBA | Sex |
| 6126 | Age | HP | Ins120 | Insulin |
| 6127 | Age | HP | Ins120 | LEP |
| 6128 | Age | HP | Ins120 | POMC |
| 6129 | Age | HP | Insulin | LEP |
| 6130 | Age | HP | Insulin | POMC |
| 6131 | Age | HP | Insulin | Sex |
| 6132 | Age | HP | Insulin | VEGF |
| 6133 | Age | HP | LDL | POMC |
| 6134 | Age | HP | LEP | PLAT |
| 6135 | Age | HP | LEP | POMC |
| 6136 | Age | HP | LEP | SBP |
| 6137 | Age | HP | LEP | SELE |
| 6138 | Age | HP | LEP | SELP |
| 6139 | Age | HP | LEP | Sex |
| 6140 | Age | HP | LEP | SHBG |
| 6141 | Age | HP | LEP | TRIG |
| 6142 | Age | HP | LEP | VCAM1 |
| 6143 | Age | HP | LEP | VEGF |
| 6144 | Age | HP | LEP | VWF |
| 6145 | Age | HP | LEP | Waist |
| 6146 | Age | HP | PLAT | POMC |
| 6147 | Age | HP | POMC | SBP |
| 6148 | Age | HP | POMC | SCp |
| 6149 | Age | HP | POMC | SELE |
| 6150 | Age | HP | POMC | SELP |
| 6151 | Age | HP | POMC | Sex |
| 6152 | Age | HP | POMC | SHBG |
| 6153 | Age | HP | POMC | TNFRSF1B |
| 6154 | Age | HP | POMC | TRIG |
| 6155 | Age | HP | POMC | VCAM1 |
| 6156 | Age | HP | POMC | VEGF |
| 6157 | Age | HP | POMC | VWF |
| 6158 | Age | HP | POMC | Waist |
| 6159 | Age | HP | POMC | WT |
| 6160 | Age | HP | Sex | VCAM1 |
| 6161 | Age | HP | Sex | VEGF |
| 6162 | Age | HP | Sex | Waist |
| 6163 | Age | HP | Sex | WT |
| 6164 | Age | HT | VCAM1 | VEGF |
| 6165 | Age | HT | ICAM1 | IGF1 |
| 6166 | Age | HT | ICAM1 | IL6ST |
| 6167 | Age | HT | ICAM1 | LEP |
| 6168 | Age | HT | ICAM1 | POMC |
| 6169 | Age | HT | ICAM1 | VEGF |
| 6170 | Age | HT | IGF1 | IGFBP1 |
| 6171 | Age | HT | IGF1 | IGFBP3 |
| 6172 | Age | HT | IGF1 | IL18 |
| 6173 | Age | HT | IGF1 | IL2RA |
| 6174 | Age | HT | IGF1 | IL6R |
| 6175 | Age | HT | IGF1 | IL6ST |
| 6176 | Age | HT | IGF1 | IL8 |
| 6177 | Age | HT | IGF1 | INHBA |
| 6178 | Age | HT | IGF1 | Ins120 |
| 6179 | Age | HT | IGF1 | Insulin |

FIG. 15YYYY

| 4-Panel | Marker 1 | Marker 2 | Marker 3 | Marker 4 |
|---|---|---|---|---|
| 6180 | Age | HT | IGF1 | LDL |
| 6181 | Age | HT | IGF1 | LEP |
| 6182 | Age | HT | IGF1 | PLAT |
| 6183 | Age | HT | IGF1 | POMC |
| 6184 | Age | HT | IGF1 | SBP |
| 6185 | Age | HT | IGF1 | SCp |
| 6186 | Age | HT | IGF1 | SELE |
| 6187 | Age | HT | IGF1 | SELP |
| 6188 | Age | HT | IGF1 | Sex |
| 6189 | Age | HT | IGF1 | SHBG |
| 6190 | Age | HT | IGF1 | TNFRSF1B |
| 6191 | Age | HT | IGF1 | TRIG |
| 6192 | Age | HT | IGF1 | VCAM1 |
| 6193 | Age | HT | IGF1 | VEGF |
| 6194 | Age | HT | IGF1 | VWF |
| 6195 | Age | HT | IGF1 | Waist |
| 6196 | Age | HT | IGF1 | WT |
| 6197 | Age | HT | IGFBP1 | LEP |
| 6198 | Age | HT | IGFBP1 | POMC |
| 6199 | Age | HT | IGFBP1 | VEGF |
| 6200 | Age | HT | IGFBP3 | LEP |
| 6201 | Age | HT | IGFBP3 | POMC |
| 6202 | Age | HT | IGFBP3 | VEGF |
| 6203 | Age | HT | IL18 | IL6ST |
| 6204 | Age | HT | IL18 | LEP |
| 6205 | Age | HT | IL18 | POMC |
| 6206 | Age | HT | IL18 | VEGF |
| 6207 | Age | HT | IL2RA | IL6ST |
| 6208 | Age | HT | IL2RA | LEP |
| 6209 | Age | HT | IL2RA | POMC |
| 6210 | Age | HT | IL2RA | Sex |
| 6211 | Age | HT | IL2RA | VEGF |
| 6212 | Age | HT | IL2RA | WT |
| 6213 | Age | HT | IL6R | IL6ST |
| 6214 | Age | HT | IL6R | LEP |
| 6215 | Age | HT | IL6R | POMC |
| 6216 | Age | HT | IL6R | VEGF |
| 6217 | Age | HT | IL6ST | IL8 |
| 6218 | Age | HT | IL6ST | INHBA |
| 6219 | Age | HT | IL6ST | Ins120 |
| 6220 | Age | HT | IL6ST | Insulin |
| 6221 | Age | HT | IL6ST | LDL |
| 6222 | Age | HT | IL6ST | LEP |
| 6223 | Age | HT | IL6ST | POMC |
| 6224 | Age | HT | IL6ST | SELP |
| 6225 | Age | HT | IL6ST | Sex |
| 6226 | Age | HT | IL6ST | TNFRSF1B |
| 6227 | Age | HT | IL6ST | VEGF |
| 6228 | Age | HT | IL6ST | Waist |
| 6229 | Age | HT | IL6ST | WT |
| 6230 | Age | HT | IL8 | LEP |
| 6231 | Age | HT | IL8 | POMC |
| 6232 | Age | HT | IL8 | VEGF |
| 6233 | Age | HT | INHBA | LEP |
| 6234 | Age | HT | INHBA | POMC |
| 6235 | Age | HT | INHBA | VEGF |
| 6236 | Age | HT | Ins120 | Insulin |
| 6237 | Age | HT | Ins120 | LEP |
| 6238 | Age | HT | Ins120 | POMC |
| 6239 | Age | HT | Ins120 | VEGF |

FIG. 15ZZZZ

| 4-Panel | Marker 1 | Marker 2 | Marker 3 | Marker 4 |
|---|---|---|---|---|
| 6240 | Age | HT | Ins120 | WT |
| 6241 | Age | HT | Insulin | LEP |
| 6242 | Age | HT | Insulin | POMC |
| 6243 | Age | HT | Insulin | Sex |
| 6244 | Age | HT | Insulin | VEGF |
| 6245 | Age | HT | LDL | LEP |
| 6246 | Age | HT | LDL | POMC |
| 6247 | Age | HT | LDL | VEGF |
| 6248 | Age | HT | LEP | PLAT |
| 6249 | Age | HT | LEP | POMC |
| 6250 | Age | HT | LEP | SBP |
| 6251 | Age | HT | LEP | SCp |
| 6252 | Age | HT | LEP | SELE |
| 6253 | Age | HT | LEP | SELP |
| 6254 | Age | HT | LEP | Sex |
| 6255 | Age | HT | LEP | SHBG |
| 6256 | Age | HT | LEP | TNFRSF1B |
| 6257 | Age | HT | LEP | TRIG |
| 6258 | Age | HT | LEP | VCAM1 |
| 6259 | Age | HT | LEP | VEGF |
| 6260 | Age | HT | LEP | VWF |
| 6261 | Age | HT | LEP | Waist |
| 6262 | Age | HT | LEP | WT |
| 6263 | Age | HT | PLAT | POMC |
| 6264 | Age | HT | PLAT | VEGF |
| 6265 | Age | HT | POMC | SBP |
| 6266 | Age | HT | POMC | SCp |
| 6267 | Age | HT | POMC | SELE |
| 6268 | Age | HT | POMC | SELP |
| 6269 | Age | HT | POMC | Sex |
| 6270 | Age | HT | POMC | SHBG |
| 6271 | Age | HT | POMC | TNFRSF1B |
| 6272 | Age | HT | POMC | TRIG |
| 6273 | Age | HT | POMC | VCAM1 |
| 6274 | Age | HT | POMC | VEGF |
| 6275 | Age | HT | POMC | VWF |
| 6276 | Age | HT | POMC | Waist |
| 6277 | Age | HT | POMC | WT |
| 6278 | Age | HT | SBP | VEGF |
| 6279 | Age | HT | SCp | VEGF |
| 6280 | Age | HT | SELE | VEGF |
| 6281 | Age | HT | SELP | VEGF |
| 6282 | Age | HT | Sex | VEGF |
| 6283 | Age | HT | Sex | WT |
| 6284 | Age | HT | SHBG | VEGF |
| 6285 | Age | HT | TNFRSF1B | VEGF |
| 6286 | Age | HT | TRIG | VEGF |
| 6287 | Age | HT | TRIG | WT |
| 6288 | Age | HT | VCAM1 | VEGF |
| 6289 | Age | HT | VEGF | VWF |
| 6290 | Age | HT | VEGF | Waist |
| 6291 | Age | HT | VEGF | WT |
| 6292 | Age | HT | Waist | WT |
| 6293 | Age | ICAM1 | IGF1 | IL2RA |
| 6294 | Age | ICAM1 | IGF1 | IL6ST |
| 6295 | Age | ICAM1 | IGF1 | Insulin |
| 6296 | Age | ICAM1 | IGF1 | LEP |
| 6297 | Age | ICAM1 | IGF1 | POMC |
| 6298 | Age | ICAM1 | IGF1 | Sex |
| 6299 | Age | ICAM1 | IGF1 | VCAM1 |

FIG. 15AAAAA

| 4-Panel | Marker 1 | Marker 2 | Marker 3 | Marker 4 |
|---|---|---|---|---|
| 6300 | Age | ICAM1 | IGF1 | VEGF |
| 6301 | Age | ICAM1 | IGFBP1 | LEP |
| 6302 | Age | ICAM1 | IGFBP1 | POMC |
| 6303 | Age | ICAM1 | IGFBP3 | LEP |
| 6304 | Age | ICAM1 | IGFBP3 | POMC |
| 6305 | Age | ICAM1 | IL18 | LEP |
| 6306 | Age | ICAM1 | IL18 | POMC |
| 6307 | Age | ICAM1 | IL18 | VEGF |
| 6308 | Age | ICAM1 | IL2RA | LEP |
| 6309 | Age | ICAM1 | IL2RA | POMC |
| 6310 | Age | ICAM1 | IL2RA | Sex |
| 6311 | Age | ICAM1 | IL6R | LEP |
| 6312 | Age | ICAM1 | IL6R | POMC |
| 6313 | Age | ICAM1 | IL6ST | LEP |
| 6314 | Age | ICAM1 | IL6ST | POMC |
| 6315 | Age | ICAM1 | IL6ST | Sex |
| 6316 | Age | ICAM1 | IL6ST | TNFRSF1B |
| 6317 | Age | ICAM1 | IL8 | VEGF |
| 6318 | Age | ICAM1 | IL8 | LEP |
| 6319 | Age | ICAM1 | IL8 | POMC |
| 6320 | Age | ICAM1 | INHBA | LEP |
| 6321 | Age | ICAM1 | INHBA | POMC |
| 6322 | Age | ICAM1 | Ins120 | Insulin |
| 6323 | Age | ICAM1 | Ins120 | LEP |
| 6324 | Age | ICAM1 | Ins120 | POMC |
| 6325 | Age | ICAM1 | Insulin | LEP |
| 6326 | Age | ICAM1 | Insulin | POMC |
| 6327 | Age | ICAM1 | Insulin | Sex |
| 6328 | Age | ICAM1 | Insulin | VEGF |
| 6329 | Age | ICAM1 | LDL | LEP |
| 6330 | Age | ICAM1 | LDL | POMC |
| 6331 | Age | ICAM1 | LEP | PLAT |
| 6332 | Age | ICAM1 | LEP | POMC |
| 6333 | Age | ICAM1 | LEP | SBP |
| 6334 | Age | ICAM1 | LEP | SCp |
| 6335 | Age | ICAM1 | LEP | SELE |
| 6336 | Age | ICAM1 | LEP | SELP |
| 6337 | Age | ICAM1 | LEP | Sex |
| 6338 | Age | ICAM1 | LEP | SHBG |
| 6339 | Age | ICAM1 | LEP | TNFRSF1B |
| 6340 | Age | ICAM1 | LEP | TRIG |
| 6341 | Age | ICAM1 | LEP | VCAM1 |
| 6342 | Age | ICAM1 | LEP | VEGF |
| 6343 | Age | ICAM1 | LEP | VWF |
| 6344 | Age | ICAM1 | LEP | Waist |
| 6345 | Age | ICAM1 | LEP | WT |
| 6346 | Age | ICAM1 | PLAT | POMC |
| 6347 | Age | ICAM1 | POMC | SBP |
| 6348 | Age | ICAM1 | POMC | SCp |
| 6349 | Age | ICAM1 | POMC | SELE |
| 6350 | Age | ICAM1 | POMC | SELP |
| 6351 | Age | ICAM1 | POMC | Sex |
| 6352 | Age | ICAM1 | POMC | SHBG |
| 6353 | Age | ICAM1 | POMC | TNFRSF1B |
| 6354 | Age | ICAM1 | POMC | TRIG |
| 6355 | Age | ICAM1 | POMC | VCAM1 |
| 6356 | Age | ICAM1 | POMC | VEGF |
| 6357 | Age | ICAM1 | POMC | VWF |
| 6358 | Age | ICAM1 | POMC | Waist |
| 6359 | Age | ICAM1 | POMC | WT |

FIG. 15BBBBB

FIG. 15CCCCC

| 4-Panel | Marker 1 | Marker 2 | Marker 3 | Marker 4 |
|---|---|---|---|---|
| 6360 | Age | ICAM1 | Sex | VCAM1 |
| 6361 | Age | ICAM1 | Sex | VEGF |
| 6362 | Age | ICAM1 | Sex | Waist |
| 6363 | Age | ICAM1 | Sex | WT |
| 6364 | Age | IGF1 | IGFBP1 | IL2RA |
| 6365 | Age | IGF1 | IGFBP1 | IL6ST |
| 6366 | Age | IGF1 | IGFBP1 | INHBA |
| 6367 | Age | IGF1 | IGFBP1 | Ins120 |
| 6368 | Age | IGF1 | IGFBP1 | Insulin |
| 6369 | Age | IGF1 | IGFBP1 | LEP |
| 6370 | Age | IGF1 | IGFBP1 | POMC |
| 6371 | Age | IGF1 | IGFBP1 | Sex |
| 6372 | Age | IGF1 | IGFBP1 | VCAM1 |
| 6373 | Age | IGF1 | IGFBP1 | VEGF |
| 6374 | Age | IGF1 | IGFBP3 | IL6ST |
| 6375 | Age | IGF1 | IGFBP3 | Insulin |
| 6376 | Age | IGF1 | IGFBP3 | LEP |
| 6377 | Age | IGF1 | IGFBP3 | POMC |
| 6378 | Age | IGF1 | IGFBP3 | Sex |
| 6379 | Age | IGF1 | IGFBP3 | VCAM1 |
| 6380 | Age | IGF1 | IGFBP3 | VEGF |
| 6381 | Age | IGF1 | IL18 | IL2RA |
| 6382 | Age | IGF1 | IL18 | IL6ST |
| 6383 | Age | IGF1 | IL18 | Ins120 |
| 6384 | Age | IGF1 | IL18 | Insulin |
| 6385 | Age | IGF1 | IL18 | LEP |
| 6386 | Age | IGF1 | IL18 | POMC |
| 6387 | Age | IGF1 | IL18 | Sex |
| 6388 | Age | IGF1 | IL18 | VCAM1 |
| 6389 | Age | IGF1 | IL18 | VEGF |

| 4-Panel | Marker 1 | Marker 2 | Marker 3 | Marker 4 |
|---|---|---|---|---|
| 6390 | Age | IGF1 | IL18 | VWF |
| 6391 | Age | IGF1 | IL2RA | IL6R |
| 6392 | Age | IGF1 | IL2RA | IL6ST |
| 6393 | Age | IGF1 | IL2RA | IL8 |
| 6394 | Age | IGF1 | IL2RA | INHBA |
| 6395 | Age | IGF1 | IL2RA | Ins120 |
| 6396 | Age | IGF1 | IL2RA | Insulin |
| 6397 | Age | IGF1 | IL2RA | LDL |
| 6398 | Age | IGF1 | IL2RA | LEP |
| 6399 | Age | IGF1 | IL2RA | PLAT |
| 6400 | Age | IGF1 | IL2RA | POMC |
| 6401 | Age | IGF1 | IL2RA | SBP |
| 6402 | Age | IGF1 | IL2RA | SCp |
| 6403 | Age | IGF1 | IL2RA | SELE |
| 6404 | Age | IGF1 | IL2RA | SELP |
| 6405 | Age | IGF1 | IL2RA | Sex |
| 6406 | Age | IGF1 | IL2RA | TNFRSF1B |
| 6407 | Age | IGF1 | IL2RA | TRIG |
| 6408 | Age | IGF1 | IL2RA | VCAM1 |
| 6409 | Age | IGF1 | IL2RA | VEGF |
| 6410 | Age | IGF1 | IL2RA | VWF |
| 6411 | Age | IGF1 | IL2RA | Waist |
| 6412 | Age | IGF1 | IL2RA | WT |
| 6413 | Age | IGF1 | IL6R | IL6ST |
| 6414 | Age | IGF1 | IL6R | Insulin |
| 6415 | Age | IGF1 | IL6R | LEP |
| 6416 | Age | IGF1 | IL6R | POMC |
| 6417 | Age | IGF1 | IL6R | Sex |
| 6418 | Age | IGF1 | IL6R | VCAM1 |
| 6419 | Age | IGF1 | IL6R | VEGF |

FIG. 15DDDDD

| 4-Panel | Marker 1 | Marker 2 | Marker 3 | Marker 4 |
|---|---|---|---|---|
| 6420 | Age | IGF1 | IL6ST | IL8 |
| 6421 | Age | IGF1 | IL6ST | INHBA |
| 6422 | Age | IGF1 | IL6ST | Ins120 |
| 6423 | Age | IGF1 | IL6ST | Insulin |
| 6424 | Age | IGF1 | IL6ST | LDL |
| 6425 | Age | IGF1 | IL6ST | LEP |
| 6426 | Age | IGF1 | IL6ST | PLAT |
| 6427 | Age | IGF1 | IL6ST | POMC |
| 6428 | Age | IGF1 | IL6ST | SBP |
| 6429 | Age | IGF1 | IL6ST | SCp |
| 6430 | Age | IGF1 | IL6ST | SELE |
| 6431 | Age | IGF1 | IL6ST | SELP |
| 6432 | Age | IGF1 | IL6ST | Sex |
| 6433 | Age | IGF1 | IL6ST | SHBG |
| 6434 | Age | IGF1 | IL6ST | TNFRSF1B |
| 6435 | Age | IGF1 | IL6ST | TRIG |
| 6436 | Age | IGF1 | IL6ST | VCAM1 |
| 6437 | Age | IGF1 | IL6ST | VEGF |
| 6438 | Age | IGF1 | IL6ST | VWF |
| 6439 | Age | IGF1 | IL6ST | Waist |
| 6440 | Age | IGF1 | IL6ST | WT |
| 6441 | Age | IGF1 | IL8 | Insulin |
| 6442 | Age | IGF1 | IL8 | LEP |
| 6443 | Age | IGF1 | IL8 | POMC |
| 6444 | Age | IGF1 | IL8 | Sex |
| 6445 | Age | IGF1 | IL8 | VCAM1 |
| 6446 | Age | IGF1 | IL8 | VEGF |
| 6447 | Age | IGF1 | INHBA | Insulin |
| 6448 | Age | IGF1 | INHBA | LEP |
| 6449 | Age | IGF1 | INHBA | POMC |

| 4-Panel | Marker 1 | Marker 2 | Marker 3 | Marker 4 |
|---|---|---|---|---|
| 6450 | Age | IGF1 | INHBA | Sex |
| 6451 | Age | IGF1 | INHBA | VCAM1 |
| 6452 | Age | IGF1 | INHBA | VEGF |
| 6453 | Age | IGF1 | Ins120 | Insulin |
| 6454 | Age | IGF1 | Ins120 | LEP |
| 6455 | Age | IGF1 | Ins120 | POMC |
| 6456 | Age | IGF1 | Ins120 | SCp |
| 6457 | Age | IGF1 | Ins120 | Sex |
| 6458 | Age | IGF1 | Ins120 | VCAM1 |
| 6459 | Age | IGF1 | Ins120 | VEGF |
| 6460 | Age | IGF1 | Ins120 | Waist |
| 6461 | Age | IGF1 | Ins120 | WT |
| 6462 | Age | IGF1 | Insulin | LDL |
| 6463 | Age | IGF1 | Insulin | LEP |
| 6464 | Age | IGF1 | Insulin | PLAT |
| 6465 | Age | IGF1 | Insulin | POMC |
| 6466 | Age | IGF1 | Insulin | SBP |
| 6467 | Age | IGF1 | Insulin | SCp |
| 6468 | Age | IGF1 | Insulin | SELE |
| 6469 | Age | IGF1 | Insulin | SELP |
| 6470 | Age | IGF1 | Insulin | Sex |
| 6471 | Age | IGF1 | Insulin | SHBG |
| 6472 | Age | IGF1 | Insulin | TRIG |
| 6473 | Age | IGF1 | Insulin | VCAM1 |
| 6474 | Age | IGF1 | Insulin | VEGF |
| 6475 | Age | IGF1 | Insulin | VWF |
| 6476 | Age | IGF1 | Insulin | Waist |
| 6477 | Age | IGF1 | LDL | LEP |
| 6478 | Age | IGF1 | LDL | POMC |
| 6479 | Age | IGF1 | LDL | Sex |

| 4-Panel | Marker 1 | Marker 2 | Marker 3 | Marker 4 |
|---|---|---|---|---|
| 6480 | Age | IGF1 | LDL | VCAM1 |
| 6481 | Age | IGF1 | LDL | VEGF |
| 6482 | Age | IGF1 | LEP | PLAT |
| 6483 | Age | IGF1 | LEP | POMC |
| 6484 | Age | IGF1 | LEP | SBP |
| 6485 | Age | IGF1 | LEP | SCp |
| 6486 | Age | IGF1 | LEP | SELE |
| 6487 | Age | IGF1 | LEP | SELP |
| 6488 | Age | IGF1 | LEP | Sex |
| 6489 | Age | IGF1 | LEP | SHBG |
| 6490 | Age | IGF1 | LEP | TNFRSF1B |
| 6491 | Age | IGF1 | LEP | TRIG |
| 6492 | Age | IGF1 | LEP | VCAM1 |
| 6493 | Age | IGF1 | LEP | VEGF |
| 6494 | Age | IGF1 | LEP | VWF |
| 6495 | Age | IGF1 | LEP | Waist |
| 6496 | Age | IGF1 | LEP | WT |
| 6497 | Age | IGF1 | PLAT | POMC |
| 6498 | Age | IGF1 | PLAT | Sex |
| 6499 | Age | IGF1 | PLAT | VCAM1 |
| 6500 | Age | IGF1 | PLAT | VEGF |
| 6501 | Age | IGF1 | POMC | SBP |
| 6502 | Age | IGF1 | POMC | SCp |
| 6503 | Age | IGF1 | POMC | SELE |
| 6504 | Age | IGF1 | POMC | SELP |
| 6505 | Age | IGF1 | POMC | Sex |
| 6506 | Age | IGF1 | POMC | SHBG |
| 6507 | Age | IGF1 | POMC | TNFRSF1B |
| 6508 | Age | IGF1 | POMC | TRIG |
| 6509 | Age | IGF1 | POMC | VCAM1 |
| 6510 | Age | IGF1 | POMC | VEGF |
| 6511 | Age | IGF1 | POMC | VWF |
| 6512 | Age | IGF1 | POMC | Waist |
| 6513 | Age | IGF1 | POMC | WT |
| 6514 | Age | IGF1 | SBP | Sex |
| 6515 | Age | IGF1 | SBP | VCAM1 |
| 6516 | Age | IGF1 | SBP | VEGF |
| 6517 | Age | IGF1 | SCp | Sex |
| 6518 | Age | IGF1 | SCp | VCAM1 |
| 6519 | Age | IGF1 | SCp | VEGF |
| 6520 | Age | IGF1 | SELE | Sex |
| 6521 | Age | IGF1 | SELE | VCAM1 |
| 6522 | Age | IGF1 | SELE | VEGF |
| 6523 | Age | IGF1 | SELP | Sex |
| 6524 | Age | IGF1 | SELP | VCAM1 |
| 6525 | Age | IGF1 | SELP | VEGF |
| 6526 | Age | IGF1 | Sex | SHBG |
| 6527 | Age | IGF1 | Sex | TNFRSF1B |
| 6528 | Age | IGF1 | Sex | TRIG |
| 6529 | Age | IGF1 | Sex | VCAM1 |
| 6530 | Age | IGF1 | Sex | VEGF |
| 6531 | Age | IGF1 | Sex | VWF |
| 6532 | Age | IGF1 | Sex | Waist |
| 6533 | Age | IGF1 | Sex | WT |
| 6534 | Age | IGF1 | SHBG | VCAM1 |
| 6535 | Age | IGF1 | SHBG | VEGF |
| 6536 | Age | IGF1 | TNFRSF1B | VCAM1 |
| 6537 | Age | IGF1 | TNFRSF1B | VEGF |
| 6538 | Age | IGF1 | TRIG | VCAM1 |
| 6539 | Age | IGF1 | TRIG | VEGF |

FIG. 15EEEEE

| 4-Panel | Marker 1 | Marker 2 | Marker 3 | Marker 4 |
|---|---|---|---|---|
| 6540 | Age | IGF1 | VCAM1 | VEGF |
| 6541 | Age | IGF1 | VCAM1 | VWF |
| 6542 | Age | IGF1 | VCAM1 | Waist |
| 6543 | Age | IGF1 | VCAM1 | WT |
| 6544 | Age | IGF1 | VEGF | VWF |
| 6545 | Age | IGF1 | VEGF | Waist |
| 6546 | Age | IGF1 | VEGF | WT |
| 6547 | Age | IGFBP1 | IGFBP3 | LEP |
| 6548 | Age | IGFBP1 | IGFBP3 | POMC |
| 6549 | Age | IGFBP1 | IL18 | LEP |
| 6550 | Age | IGFBP1 | IL18 | POMC |
| 6551 | Age | IGFBP1 | IL18 | Sex |
| 6552 | Age | IGFBP1 | IL18 | VEGF |
| 6553 | Age | IGFBP1 | IL2RA | LEP |
| 6554 | Age | IGFBP1 | IL2RA | POMC |
| 6555 | Age | IGFBP1 | IL2RA | Sex |
| 6556 | Age | IGFBP1 | IL6R | LEP |
| 6557 | Age | IGFBP1 | IL6R | POMC |
| 6558 | Age | IGFBP1 | IL6ST | LEP |
| 6559 | Age | IGFBP1 | IL6ST | POMC |
| 6560 | Age | IGFBP1 | IL6ST | Sex |
| 6561 | Age | IGFBP1 | IL6ST | TNFRSF1B |
| 6562 | Age | IGFBP1 | IL6ST | VEGF |
| 6563 | Age | IGFBP1 | IL8 | LEP |
| 6564 | Age | IGFBP1 | IL8 | POMC |
| 6565 | Age | IGFBP1 | IL8 | Sex |
| 6566 | Age | IGFBP1 | INHBA | LEP |
| 6567 | Age | IGFBP1 | INHBA | POMC |
| 6568 | Age | IGFBP1 | Ins120 | Insulin |
| 6569 | Age | IGFBP1 | Ins120 | LEP |
| 6570 | Age | IGFBP1 | Ins120 | POMC |
| 6571 | Age | IGFBP1 | Ins120 | Sex |
| 6572 | Age | IGFBP1 | Insulin | LEP |
| 6573 | Age | IGFBP1 | Insulin | POMC |
| 6574 | Age | IGFBP1 | Insulin | Sex |
| 6575 | Age | IGFBP1 | Insulin | VEGF |
| 6576 | Age | IGFBP1 | LDL | LEP |
| 6577 | Age | IGFBP1 | LDL | POMC |
| 6578 | Age | IGFBP1 | LDL | Sex |
| 6579 | Age | IGFBP1 | LEP | PLAT |
| 6580 | Age | IGFBP1 | LEP | POMC |
| 6581 | Age | IGFBP1 | LEP | SBP |
| 6582 | Age | IGFBP1 | LEP | SCp |
| 6583 | Age | IGFBP1 | LEP | SELE |
| 6584 | Age | IGFBP1 | LEP | SELP |
| 6585 | Age | IGFBP1 | LEP | Sex |
| 6586 | Age | IGFBP1 | LEP | SHBG |
| 6587 | Age | IGFBP1 | LEP | TNFRSF1B |
| 6588 | Age | IGFBP1 | LEP | TRIG |
| 6589 | Age | IGFBP1 | LEP | VCAM1 |
| 6590 | Age | IGFBP1 | LEP | VEGF |
| 6591 | Age | IGFBP1 | LEP | VWF |
| 6592 | Age | IGFBP1 | LEP | Waist |
| 6593 | Age | IGFBP1 | LEP | WT |
| 6594 | Age | IGFBP1 | PLAT | POMC |
| 6595 | Age | IGFBP1 | POMC | SBP |
| 6596 | Age | IGFBP1 | POMC | SCp |
| 6597 | Age | IGFBP1 | POMC | SELE |
| 6598 | Age | IGFBP1 | POMC | SELP |
| 6599 | Age | IGFBP1 | POMC | Sex |

FIG. 15FFFFFF

FIG. 15GGGGG

| 4-Panel | Marker 1 | Marker 2 | Marker 3 | Marker 4 |
|---|---|---|---|---|
| 6600 | Age | IGFBP1 | POMC | SHBG |
| 6601 | Age | IGFBP1 | POMC | TNFRSF1B |
| 6602 | Age | IGFBP1 | POMC | TRIG |
| 6603 | Age | IGFBP1 | POMC | VCAM1 |
| 6604 | Age | IGFBP1 | POMC | VEGF |
| 6605 | Age | IGFBP1 | POMC | VWF |
| 6606 | Age | IGFBP1 | POMC | Waist |
| 6607 | Age | IGFBP1 | POMC | WT |
| 6608 | Age | IGFBP1 | SELP | Sex |
| 6609 | Age | IGFBP1 | Sex | TNFRSF1B |
| 6610 | Age | IGFBP1 | Sex | VCAM1 |
| 6611 | Age | IGFBP1 | Sex | VEGF |
| 6612 | Age | IGFBP1 | Sex | Waist |
| 6613 | Age | IGFBP1 | Sex | WT |
| 6614 | Age | IGFBP3 | IL18 | LEP |
| 6615 | Age | IGFBP3 | IL18 | POMC |
| 6616 | Age | IGFBP3 | IL2RA | LEP |
| 6617 | Age | IGFBP3 | IL2RA | POMC |
| 6618 | Age | IGFBP3 | IL2RA | Sex |
| 6619 | Age | IGFBP3 | IL6R | LEP |
| 6620 | Age | IGFBP3 | IL6R | POMC |
| 6621 | Age | IGFBP3 | IL6ST | LEP |
| 6622 | Age | IGFBP3 | IL6ST | POMC |
| 6623 | Age | IGFBP3 | IL6ST | Sex |
| 6624 | Age | IGFBP3 | IL6ST | TNFRSF1B |
| 6625 | Age | IGFBP3 | IL6ST | VEGF |
| 6626 | Age | IGFBP3 | IL8 | LEP |
| 6627 | Age | IGFBP3 | IL8 | POMC |
| 6628 | Age | IGFBP3 | INHBA | LEP |
| 6629 | Age | IGFBP3 | INHBA | POMC |

| 4-Panel | Marker 1 | Marker 2 | Marker 3 | Marker 4 |
|---|---|---|---|---|
| 6630 | Age | IGFBP3 | Ins120 | LEP |
| 6631 | Age | IGFBP3 | Ins120 | POMC |
| 6632 | Age | IGFBP3 | Insulin | LEP |
| 6633 | Age | IGFBP3 | Insulin | POMC |
| 6634 | Age | IGFBP3 | Insulin | Sex |
| 6635 | Age | IGFBP3 | Insulin | VEGF |
| 6636 | Age | IGFBP3 | LDL | LEP |
| 6637 | Age | IGFBP3 | LDL | POMC |
| 6638 | Age | IGFBP3 | LEP | PLAT |
| 6639 | Age | IGFBP3 | LEP | POMC |
| 6640 | Age | IGFBP3 | LEP | SBP |
| 6641 | Age | IGFBP3 | LEP | SCp |
| 6642 | Age | IGFBP3 | LEP | SELE |
| 6643 | Age | IGFBP3 | LEP | SELP |
| 6644 | Age | IGFBP3 | LEP | Sex |
| 6645 | Age | IGFBP3 | LEP | SHBG |
| 6646 | Age | IGFBP3 | LEP | TNFRSF1B |
| 6647 | Age | IGFBP3 | LEP | TRIG |
| 6648 | Age | IGFBP3 | LEP | VCAM1 |
| 6649 | Age | IGFBP3 | LEP | VEGF |
| 6650 | Age | IGFBP3 | LEP | VWF |
| 6651 | Age | IGFBP3 | LEP | Waist |
| 6652 | Age | IGFBP3 | LEP | WT |
| 6653 | Age | IGFBP3 | PLAT | POMC |
| 6654 | Age | IGFBP3 | POMC | SBP |
| 6655 | Age | IGFBP3 | POMC | SCp |
| 6656 | Age | IGFBP3 | POMC | SELE |
| 6657 | Age | IGFBP3 | POMC | SELP |
| 6658 | Age | IGFBP3 | POMC | Sex |
| 6659 | Age | IGFBP3 | POMC | SHBG |

| 4-Panel | Marker 1 | Marker 2 | Marker 3 | Marker 4 |
|---|---|---|---|---|
| 6660 | Age | IGFBP3 | POMC | TNFRSF1B |
| 6661 | Age | IGFBP3 | POMC | TRIG |
| 6662 | Age | IGFBP3 | POMC | VCAM1 |
| 6663 | Age | IGFBP3 | POMC | VEGF |
| 6664 | Age | IGFBP3 | POMC | VWF |
| 6665 | Age | IGFBP3 | POMC | Waist |
| 6666 | Age | IGFBP3 | POMC | WT |
| 6667 | Age | IGFBP3 | Sex | VCAM1 |
| 6668 | Age | IGFBP3 | Sex | VEGF |
| 6669 | Age | IGFBP3 | Sex | Waist |
| 6670 | Age | IGFBP3 | Sex | WT |
| 6671 | Age | IGFBP3 | VCAM1 | VEGF |
| 6672 | Age | IL18 | IL2RA | IL6ST |
| 6673 | Age | IL18 | IL2RA | LEP |
| 6674 | Age | IL18 | IL2RA | POMC |
| 6675 | Age | IL18 | IL2RA | Sex |
| 6676 | Age | IL18 | IL2RA | VEGF |
| 6677 | Age | IL18 | IL6R | IL6ST |
| 6678 | Age | IL18 | IL6R | LEP |
| 6679 | Age | IL18 | IL6R | POMC |
| 6680 | Age | IL18 | IL6R | VEGF |
| 6681 | Age | IL18 | IL6ST | IL8 |
| 6682 | Age | IL18 | IL6ST | Ins120 |
| 6683 | Age | IL18 | IL6ST | LEP |
| 6684 | Age | IL18 | IL6ST | POMC |
| 6685 | Age | IL18 | IL6ST | SELP |
| 6686 | Age | IL18 | IL6ST | Sex |
| 6687 | Age | IL18 | IL6ST | TNFRSF1B |
| 6688 | Age | IL18 | IL6ST | TRIG |
| 6689 | Age | IL18 | IL6ST | VEGF |

| 4-Panel | Marker 1 | Marker 2 | Marker 3 | Marker 4 |
|---|---|---|---|---|
| 6690 | Age | IL18 | IL8 | LEP |
| 6691 | Age | IL18 | IL8 | POMC |
| 6692 | Age | IL18 | IL8 | Sex |
| 6693 | Age | IL18 | IL8 | VEGF |
| 6694 | Age | IL18 | INHBA | LEP |
| 6695 | Age | IL18 | INHBA | POMC |
| 6696 | Age | IL18 | INHBA | Sex |
| 6697 | Age | IL18 | INHBA | VEGF |
| 6698 | Age | IL18 | Ins120 | Insulin |
| 6699 | Age | IL18 | Ins120 | LEP |
| 6700 | Age | IL18 | Ins120 | POMC |
| 6701 | Age | IL18 | Ins120 | Sex |
| 6702 | Age | IL18 | Ins120 | VEGF |
| 6703 | Age | IL18 | Insulin | LEP |
| 6704 | Age | IL18 | Insulin | POMC |
| 6705 | Age | IL18 | Insulin | Sex |
| 6706 | Age | IL18 | Insulin | VEGF |
| 6707 | Age | IL18 | LDL | LEP |
| 6708 | Age | IL18 | LDL | POMC |
| 6709 | Age | IL18 | LEP | PLAT |
| 6710 | Age | IL18 | LEP | POMC |
| 6711 | Age | IL18 | LEP | SBP |
| 6712 | Age | IL18 | LEP | SCp |
| 6713 | Age | IL18 | LEP | SELE |
| 6714 | Age | IL18 | LEP | SELP |
| 6715 | Age | IL18 | LEP | Sex |
| 6716 | Age | IL18 | LEP | SHBG |
| 6717 | Age | IL18 | LEP | TNFRSF1B |
| 6718 | Age | IL18 | LEP | TRIG |
| 6719 | Age | IL18 | LEP | VCAM1 |

FIG. 15HHHHH

FIG. 15IIIIII

| 4-Panel | Marker 1 | Marker 2 | Marker 3 | Marker 4 |
|---|---|---|---|---|
| 6720 | Age | IL18 | LEP | VEGF |
| 6721 | Age | IL18 | LEP | VWF |
| 6722 | Age | IL18 | LEP | Waist |
| 6723 | Age | IL18 | LEP | WT |
| 6724 | Age | IL18 | PLAT | POMC |
| 6725 | Age | IL18 | PLAT | VEGF |
| 6726 | Age | IL18 | POMC | SBP |
| 6727 | Age | IL18 | POMC | SCp |
| 6728 | Age | IL18 | POMC | SELE |
| 6729 | Age | IL18 | POMC | SELP |
| 6730 | Age | IL18 | POMC | Sex |
| 6731 | Age | IL18 | POMC | SHBG |
| 6732 | Age | IL18 | POMC | TNFRSF1B |
| 6733 | Age | IL18 | POMC | TRIG |
| 6734 | Age | IL18 | POMC | VCAM1 |
| 6735 | Age | IL18 | POMC | VEGF |
| 6736 | Age | IL18 | POMC | VWF |
| 6737 | Age | IL18 | POMC | Waist |
| 6738 | Age | IL18 | POMC | WT |
| 6739 | Age | IL18 | SBP | Sex |
| 6740 | Age | IL18 | SBP | VEGF |
| 6741 | Age | IL18 | SCp | VEGF |
| 6742 | Age | IL18 | SELE | VEGF |
| 6743 | Age | IL18 | SELP | Sex |
| 6744 | Age | IL18 | SELP | VEGF |
| 6745 | Age | IL18 | Sex | VCAM1 |
| 6746 | Age | IL18 | Sex | VEGF |
| 6747 | Age | IL18 | Sex | VWF |
| 6748 | Age | IL18 | Sex | Waist |
| 6749 | Age | IL18 | Sex | WT |

| 4-Panel | Marker 1 | Marker 2 | Marker 3 | Marker 4 |
|---|---|---|---|---|
| 6750 | Age | IL18 | SHBG | VEGF |
| 6751 | Age | IL18 | TNFRSF1B | VEGF |
| 6752 | Age | IL18 | TRIG | VEGF |
| 6753 | Age | IL18 | VCAM1 | VEGF |
| 6754 | Age | IL18 | VEGF | VWF |
| 6755 | Age | IL18 | VEGF | WT |
| 6756 | Age | IL2RA | IL6R | LEP |
| 6757 | Age | IL2RA | IL6R | POMC |
| 6758 | Age | IL2RA | IL6R | Sex |
| 6759 | Age | IL2RA | IL6ST | LEP |
| 6760 | Age | IL2RA | IL6ST | POMC |
| 6761 | Age | IL2RA | IL6ST | Sex |
| 6762 | Age | IL2RA | IL6ST | TNFRSF1B |
| 6763 | Age | IL2RA | IL6ST | VEGF |
| 6764 | Age | IL2RA | IL8 | LEP |
| 6765 | Age | IL2RA | IL8 | POMC |
| 6766 | Age | IL2RA | IL8 | Sex |
| 6767 | Age | IL2RA | INHBA | LEP |
| 6768 | Age | IL2RA | INHBA | POMC |
| 6769 | Age | IL2RA | INHBA | Sex |
| 6770 | Age | IL2RA | Ins120 | Insulin |
| 6771 | Age | IL2RA | Ins120 | LEP |
| 6772 | Age | IL2RA | Ins120 | POMC |
| 6773 | Age | IL2RA | Ins120 | Sex |
| 6774 | Age | IL2RA | Insulin | LEP |
| 6775 | Age | IL2RA | Insulin | POMC |
| 6776 | Age | IL2RA | Insulin | Sex |
| 6777 | Age | IL2RA | Insulin | VEGF |
| 6778 | Age | IL2RA | LDL | LEP |
| 6779 | Age | IL2RA | LDL | POMC |

| 4-Panel | Marker 1 | Marker 2 | Marker 3 | Marker 4 |
|---|---|---|---|---|
| 6780 | Age | IL2RA | LDL | Sex |
| 6781 | Age | IL2RA | LEP | PLAT |
| 6782 | Age | IL2RA | LEP | POMC |
| 6783 | Age | IL2RA | LEP | SBP |
| 6784 | Age | IL2RA | LEP | SCp |
| 6785 | Age | IL2RA | LEP | SELE |
| 6786 | Age | IL2RA | LEP | SELP |
| 6787 | Age | IL2RA | LEP | Sex |
| 6788 | Age | IL2RA | LEP | SHBG |
| 6789 | Age | IL2RA | LEP | TNFRSF1B |
| 6790 | Age | IL2RA | LEP | TRIG |
| 6791 | Age | IL2RA | LEP | VCAM1 |
| 6792 | Age | IL2RA | LEP | VEGF |
| 6793 | Age | IL2RA | LEP | VWF |
| 6794 | Age | IL2RA | LEP | Waist |
| 6795 | Age | IL2RA | LEP | WT |
| 6796 | Age | IL2RA | PLAT | POMC |
| 6797 | Age | IL2RA | PLAT | Sex |
| 6798 | Age | IL2RA | POMC | SBP |
| 6799 | Age | IL2RA | POMC | SCp |
| 6800 | Age | IL2RA | POMC | SELE |
| 6801 | Age | IL2RA | POMC | SELP |
| 6802 | Age | IL2RA | POMC | Sex |
| 6803 | Age | IL2RA | POMC | SHBG |
| 6804 | Age | IL2RA | POMC | TNFRSF1B |
| 6805 | Age | IL2RA | POMC | TRIG |
| 6806 | Age | IL2RA | POMC | VCAM1 |
| 6807 | Age | IL2RA | POMC | VEGF |
| 6808 | Age | IL2RA | POMC | VWF |
| 6809 | Age | IL2RA | POMC | Waist |

| 4-Panel | Marker 1 | Marker 2 | Marker 3 | Marker 4 |
|---|---|---|---|---|
| 6810 | Age | IL2RA | POMC | WT |
| 6811 | Age | IL2RA | SBP | Sex |
| 6812 | Age | IL2RA | SCp | Sex |
| 6813 | Age | IL2RA | SELE | Sex |
| 6814 | Age | IL2RA | SELP | Sex |
| 6815 | Age | IL2RA | Sex | TNFRSF1B |
| 6816 | Age | IL2RA | Sex | TRIG |
| 6817 | Age | IL2RA | Sex | VCAM1 |
| 6818 | Age | IL2RA | Sex | VEGF |
| 6819 | Age | IL2RA | Sex | VWF |
| 6820 | Age | IL2RA | Sex | Waist |
| 6821 | Age | IL2RA | Sex | WT |
| 6822 | Age | IL6R | IL6ST | IL8 |
| 6823 | Age | IL6R | IL6ST | Ins120 |
| 6824 | Age | IL6R | IL6ST | Insulin |
| 6825 | Age | IL6R | IL6ST | LEP |
| 6826 | Age | IL6R | IL6ST | POMC |
| 6827 | Age | IL6R | IL6ST | SELP |
| 6828 | Age | IL6R | IL6ST | Sex |
| 6829 | Age | IL6R | IL6ST | TNFRSF1B |
| 6830 | Age | IL6R | IL6ST | TRIG |
| 6831 | Age | IL6R | IL6ST | VEGF |
| 6832 | Age | IL6R | IL8 | LEP |
| 6833 | Age | IL6R | IL8 | POMC |
| 6834 | Age | IL6R | INHBA | LEP |
| 6835 | Age | IL6R | INHBA | POMC |
| 6836 | Age | IL6R | Ins120 | LEP |
| 6837 | Age | IL6R | Ins120 | POMC |
| 6838 | Age | IL6R | Insulin | LEP |
| 6839 | Age | IL6R | Insulin | POMC |

FIG. 15JJJJJ

| 4-Panel | Marker 1 | Marker 2 | Marker 3 | Marker 4 |
|---|---|---|---|---|
| 6840 | Age | IL6R | Insulin | Sex |
| 6841 | Age | IL6R | Insulin | VEGF |
| 6842 | Age | IL6R | LDL | LEP |
| 6843 | Age | IL6R | LDL | POMC |
| 6844 | Age | IL6R | LEP | PLAT |
| 6845 | Age | IL6R | LEP | POMC |
| 6846 | Age | IL6R | LEP | SBP |
| 6847 | Age | IL6R | LEP | SCp |
| 6848 | Age | IL6R | LEP | SELE |
| 6849 | Age | IL6R | LEP | SELP |
| 6850 | Age | IL6R | LEP | Sex |
| 6851 | Age | IL6R | LEP | SHBG |
| 6852 | Age | IL6R | LEP | TNFRSF1B |
| 6853 | Age | IL6R | LEP | TRIG |
| 6854 | Age | IL6R | LEP | VCAM1 |
| 6855 | Age | IL6R | LEP | VEGF |
| 6856 | Age | IL6R | LEP | VWF |
| 6857 | Age | IL6R | LEP | Waist |
| 6858 | Age | IL6R | LEP | WT |
| 6859 | Age | IL6R | PLAT | POMC |
| 6860 | Age | IL6R | POMC | SBP |
| 6861 | Age | IL6R | POMC | SCp |
| 6862 | Age | IL6R | POMC | SELE |
| 6863 | Age | IL6R | POMC | SELP |
| 6864 | Age | IL6R | POMC | Sex |
| 6865 | Age | IL6R | POMC | SHBG |
| 6866 | Age | IL6R | POMC | TNFRSF1B |
| 6867 | Age | IL6R | POMC | TRIG |
| 6868 | Age | IL6R | POMC | VCAM1 |
| 6869 | Age | IL6R | POMC | VEGF |
| 6870 | Age | IL6R | POMC | VWF |
| 6871 | Age | IL6R | POMC | Waist |
| 6872 | Age | IL6R | POMC | WT |
| 6873 | Age | IL6R | Sex | VEGF |
| 6874 | Age | IL6R | Sex | Waist |
| 6875 | Age | IL6R | Sex | WT |
| 6876 | Age | IL6ST | IL8 | LEP |
| 6877 | Age | IL6ST | IL8 | POMC |
| 6878 | Age | IL6ST | IL8 | SELP |
| 6879 | Age | IL6ST | IL8 | Sex |
| 6880 | Age | IL6ST | IL8 | TNFRSF1B |
| 6881 | Age | IL6ST | IL8 | VEGF |
| 6882 | Age | IL6ST | INHBA | LEP |
| 6883 | Age | IL6ST | INHBA | POMC |
| 6884 | Age | IL6ST | INHBA | Sex |
| 6885 | Age | IL6ST | INHBA | TNFRSF1B |
| 6886 | Age | IL6ST | INHBA | VEGF |
| 6887 | Age | IL6ST | Ins120 | Insulin |
| 6888 | Age | IL6ST | Ins120 | LEP |
| 6889 | Age | IL6ST | Ins120 | POMC |
| 6890 | Age | IL6ST | Ins120 | SELP |
| 6891 | Age | IL6ST | Ins120 | Sex |
| 6892 | Age | IL6ST | Ins120 | TNFRSF1B |
| 6893 | Age | IL6ST | Ins120 | VEGF |
| 6894 | Age | IL6ST | Insulin | LEP |
| 6895 | Age | IL6ST | Insulin | POMC |
| 6896 | Age | IL6ST | Insulin | Sex |
| 6897 | Age | IL6ST | Insulin | TNFRSF1B |
| 6898 | Age | IL6ST | Insulin | VEGF |
| 6899 | Age | IL6ST | LDL | LEP |

FIG. 15KKKKK

FIG. 15LLLLL

| 4-Panel | Marker 1 | Marker 2 | Marker 3 | Marker 4 |
|---|---|---|---|---|
| 6900 | Age | IL6ST | LDL | POMC |
| 6901 | Age | IL6ST | LDL | Sex |
| 6902 | Age | IL6ST | LDL | TNFRSF1B |
| 6903 | Age | IL6ST | LDL | VEGF |
| 6904 | Age | IL6ST | LEP | PLAT |
| 6905 | Age | IL6ST | LEP | POMC |
| 6906 | Age | IL6ST | LEP | SBP |
| 6907 | Age | IL6ST | LEP | SCp |
| 6908 | Age | IL6ST | LEP | SELE |
| 6909 | Age | IL6ST | LEP | SELP |
| 6910 | Age | IL6ST | LEP | Sex |
| 6911 | Age | IL6ST | LEP | SHBG |
| 6912 | Age | IL6ST | LEP | TNFRSF1B |
| 6913 | Age | IL6ST | LEP | TRIG |
| 6914 | Age | IL6ST | LEP | VCAM1 |
| 6915 | Age | IL6ST | LEP | VEGF |
| 6916 | Age | IL6ST | LEP | VWF |
| 6917 | Age | IL6ST | LEP | Waist |
| 6918 | Age | IL6ST | LEP | WT |
| 6919 | Age | IL6ST | PLAT | POMC |
| 6920 | Age | IL6ST | PLAT | Sex |
| 6921 | Age | IL6ST | PLAT | TNFRSF1B |
| 6922 | Age | IL6ST | PLAT | VEGF |
| 6923 | Age | IL6ST | POMC | SBP |
| 6924 | Age | IL6ST | POMC | SCp |
| 6925 | Age | IL6ST | POMC | SELE |
| 6926 | Age | IL6ST | POMC | SELP |
| 6927 | Age | IL6ST | POMC | Sex |
| 6928 | Age | IL6ST | POMC | SHBG |
| 6929 | Age | IL6ST | POMC | TNFRSF1B |

| 4-Panel | Marker 1 | Marker 2 | Marker 3 | Marker 4 |
|---|---|---|---|---|
| 6930 | Age | IL6ST | POMC | TRIG |
| 6931 | Age | IL6ST | POMC | VCAM1 |
| 6932 | Age | IL6ST | POMC | VEGF |
| 6933 | Age | IL6ST | POMC | VWF |
| 6934 | Age | IL6ST | POMC | Waist |
| 6935 | Age | IL6ST | POMC | WT |
| 6936 | Age | IL6ST | SBP | Sex |
| 6937 | Age | IL6ST | SBP | TNFRSF1B |
| 6938 | Age | IL6ST | SBP | VEGF |
| 6939 | Age | IL6ST | SCp | Sex |
| 6940 | Age | IL6ST | SCp | TNFRSF1B |
| 6941 | Age | IL6ST | SCp | VEGF |
| 6942 | Age | IL6ST | SELE | Sex |
| 6943 | Age | IL6ST | SELE | TNFRSF1B |
| 6944 | Age | IL6ST | SELE | VEGF |
| 6945 | Age | IL6ST | SELP | Sex |
| 6946 | Age | IL6ST | SELP | TNFRSF1B |
| 6947 | Age | IL6ST | SELP | VEGF |
| 6948 | Age | IL6ST | Sex | SHBG |
| 6949 | Age | IL6ST | Sex | TNFRSF1B |
| 6950 | Age | IL6ST | Sex | TRIG |
| 6951 | Age | IL6ST | Sex | VCAM1 |
| 6952 | Age | IL6ST | Sex | VEGF |
| 6953 | Age | IL6ST | Sex | VWF |
| 6954 | Age | IL6ST | Sex | Waist |
| 6955 | Age | IL6ST | Sex | WT |
| 6956 | Age | IL6ST | SHBG | TNFRSF1B |
| 6957 | Age | IL6ST | SHBG | VEGF |
| 6958 | Age | IL6ST | TNFRSF1B | TRIG |
| 6959 | Age | IL6ST | TNFRSF1B | VCAM1 |

| 4-Panel | Marker 1 | Marker 2 | Marker 3 | Marker 4 |
|---|---|---|---|---|
| 6960 | Age | IL6ST | TNFRSF1B | VEGF |
| 6961 | Age | IL6ST | TNFRSF1B | VWF |
| 6962 | Age | IL6ST | TNFRSF1B | Waist |
| 6963 | Age | IL6ST | TNFRSF1B | WT |
| 6964 | Age | IL6ST | TRIG | VEGF |
| 6965 | Age | IL6ST | VCAM1 | VEGF |
| 6966 | Age | IL6ST | VEGF | VWF |
| 6967 | Age | IL6ST | VEGF | Waist |
| 6968 | Age | IL6ST | VEGF | WT |
| 6969 | Age | IL8 | INHBA | LEP |
| 6970 | Age | IL8 | INHBA | POMC |
| 6971 | Age | IL8 | Ins120 | Insulin |
| 6972 | Age | IL8 | Ins120 | LEP |
| 6973 | Age | IL8 | Ins120 | POMC |
| 6974 | Age | IL8 | Insulin | LEP |
| 6975 | Age | IL8 | Insulin | POMC |
| 6976 | Age | IL8 | Insulin | Sex |
| 6977 | Age | IL8 | Insulin | VEGF |
| 6978 | Age | IL8 | LDL | LEP |
| 6979 | Age | IL8 | LDL | POMC |
| 6980 | Age | IL8 | LEP | PLAT |
| 6981 | Age | IL8 | LEP | POMC |
| 6982 | Age | IL8 | LEP | SBP |
| 6983 | Age | IL8 | LEP | SCp |
| 6984 | Age | IL8 | LEP | SELE |
| 6985 | Age | IL8 | LEP | SELP |
| 6986 | Age | IL8 | LEP | Sex |
| 6987 | Age | IL8 | LEP | SHBG |
| 6988 | Age | IL8 | LEP | TNFRSF1B |
| 6989 | Age | IL8 | LEP | TRIG |
| 6990 | Age | IL8 | LEP | VCAM1 |
| 6991 | Age | IL8 | LEP | VEGF |
| 6992 | Age | IL8 | LEP | VWF |
| 6993 | Age | IL8 | LEP | Waist |
| 6994 | Age | IL8 | LEP | WT |
| 6995 | Age | IL8 | PLAT | POMC |
| 6996 | Age | IL8 | POMC | SBP |
| 6997 | Age | IL8 | POMC | SCp |
| 6998 | Age | IL8 | POMC | SELE |
| 6999 | Age | IL8 | POMC | SELP |
| 7000 | Age | IL8 | POMC | Sex |
| 7001 | Age | IL8 | POMC | SHBG |
| 7002 | Age | IL8 | POMC | TNFRSF1B |
| 7003 | Age | IL8 | POMC | TRIG |
| 7004 | Age | IL8 | POMC | VCAM1 |
| 7005 | Age | IL8 | POMC | VEGF |
| 7006 | Age | IL8 | POMC | VWF |
| 7007 | Age | IL8 | POMC | Waist |
| 7008 | Age | IL8 | POMC | WT |
| 7009 | Age | IL8 | SELP | VEGF |
| 7010 | Age | IL8 | Sex | VCAM1 |
| 7011 | Age | IL8 | Sex | VEGF |
| 7012 | Age | IL8 | Sex | Waist |
| 7013 | Age | IL8 | Sex | WT |
| 7014 | Age | IL8 | VCAM1 | VEGF |
| 7015 | Age | IL8 | VEGF | VWF |
| 7016 | Age | INHBA | Ins120 | Insulin |
| 7017 | Age | INHBA | Ins120 | LEP |
| 7018 | Age | INHBA | Ins120 | POMC |
| 7019 | Age | INHBA | Insulin | LEP |

FIG. 15MMMMM

| 4-Panel | Marker 1 | Marker 2 | Marker 3 | Marker 4 |
|---|---|---|---|---|
| 7020 | Age | INHBA | Insulin | POMC |
| 7021 | Age | INHBA | Insulin | Sex |
| 7022 | Age | INHBA | Insulin | VEGF |
| 7023 | Age | INHBA | LDL | LEP |
| 7024 | Age | INHBA | LDL | POMC |
| 7025 | Age | INHBA | LEP | PLAT |
| 7026 | Age | INHBA | LEP | POMC |
| 7027 | Age | INHBA | LEP | SBP |
| 7028 | Age | INHBA | LEP | SCp |
| 7029 | Age | INHBA | LEP | SELE |
| 7030 | Age | INHBA | LEP | SELP |
| 7031 | Age | INHBA | LEP | Sex |
| 7032 | Age | INHBA | LEP | SHBG |
| 7033 | Age | INHBA | LEP | TNFRSF1B |
| 7034 | Age | INHBA | LEP | TRIG |
| 7035 | Age | INHBA | LEP | VCAM1 |
| 7036 | Age | INHBA | LEP | VEGF |
| 7037 | Age | INHBA | LEP | VWF |
| 7038 | Age | INHBA | LEP | Waist |
| 7039 | Age | INHBA | LEP | WT |
| 7040 | Age | INHBA | PLAT | POMC |
| 7041 | Age | INHBA | POMC | SBP |
| 7042 | Age | INHBA | POMC | SCp |
| 7043 | Age | INHBA | POMC | SELE |
| 7044 | Age | INHBA | POMC | SELP |
| 7045 | Age | INHBA | POMC | Sex |
| 7046 | Age | INHBA | POMC | SHBG |
| 7047 | Age | INHBA | POMC | TNFRSF1B |
| 7048 | Age | INHBA | POMC | TRIG |
| 7049 | Age | INHBA | POMC | VCAM1 |

| 4-Panel | Marker 1 | Marker 2 | Marker 3 | Marker 4 |
|---|---|---|---|---|
| 7050 | Age | INHBA | POMC | VEGF |
| 7051 | Age | INHBA | POMC | VWF |
| 7052 | Age | INHBA | POMC | Waist |
| 7053 | Age | INHBA | POMC | WT |
| 7054 | Age | INHBA | Sex | VCAM1 |
| 7055 | Age | INHBA | Sex | VEGF |
| 7056 | Age | INHBA | Sex | Waist |
| 7057 | Age | INHBA | Sex | WT |
| 7058 | Age | Ins120 | Insulin | LEP |
| 7059 | Age | Ins120 | Insulin | PLAT |
| 7060 | Age | Ins120 | Insulin | POMC |
| 7061 | Age | Ins120 | Insulin | SBP |
| 7062 | Age | Ins120 | Insulin | SCp |
| 7063 | Age | Ins120 | Insulin | SELE |
| 7064 | Age | Ins120 | Insulin | SELP |
| 7065 | Age | Ins120 | Insulin | Sex |
| 7066 | Age | Ins120 | Insulin | SHBG |
| 7067 | Age | Ins120 | Insulin | TNFRSF1B |
| 7068 | Age | Ins120 | Insulin | TRIG |
| 7069 | Age | Ins120 | Insulin | VEGF |
| 7070 | Age | Ins120 | Insulin | Waist |
| 7071 | Age | Ins120 | LDL | LEP |
| 7072 | Age | Ins120 | LDL | POMC |
| 7073 | Age | Ins120 | LEP | PLAT |
| 7074 | Age | Ins120 | LEP | POMC |
| 7075 | Age | Ins120 | LEP | SBP |
| 7076 | Age | Ins120 | LEP | SCp |
| 7077 | Age | Ins120 | LEP | SELE |
| 7078 | Age | Ins120 | LEP | SELP |
| 7079 | Age | Ins120 | LEP | Sex |

FIG. 15NNNNN

| 4-Panel | Marker 1 | Marker 2 | Marker 3 | Marker 4 |
|---|---|---|---|---|
| 7080 | Age | Ins120 | LEP | SHBG |
| 7081 | Age | Ins120 | LEP | TNFRSF1B |
| 7082 | Age | Ins120 | LEP | TRIG |
| 7083 | Age | Ins120 | LEP | VCAM1 |
| 7084 | Age | Ins120 | LEP | VEGF |
| 7085 | Age | Ins120 | LEP | VWF |
| 7086 | Age | Ins120 | LEP | Waist |
| 7087 | Age | Ins120 | LEP | WT |
| 7088 | Age | Ins120 | PLAT | POMC |
| 7089 | Age | Ins120 | POMC | SBP |
| 7090 | Age | Ins120 | POMC | SCp |
| 7091 | Age | Ins120 | POMC | SELE |
| 7092 | Age | Ins120 | POMC | SELP |
| 7093 | Age | Ins120 | POMC | Sex |
| 7094 | Age | Ins120 | POMC | SHBG |
| 7095 | Age | Ins120 | POMC | TNFRSF1B |
| 7096 | Age | Ins120 | POMC | TRIG |
| 7097 | Age | Ins120 | POMC | VCAM1 |
| 7098 | Age | Ins120 | POMC | VEGF |
| 7099 | Age | Ins120 | POMC | VWF |
| 7100 | Age | Ins120 | POMC | Waist |
| 7101 | Age | Ins120 | POMC | WT |
| 7102 | Age | Ins120 | Sex | VCAM1 |
| 7103 | Age | Ins120 | Sex | VEGF |
| 7104 | Age | Ins120 | Sex | Waist |
| 7105 | Age | Ins120 | Sex | WT |
| 7106 | Age | Ins120 | VCAM1 | VEGF |
| 7107 | Age | Insulin | LDL | LEP |
| 7108 | Age | Insulin | LDL | POMC |
| 7109 | Age | Insulin | LDL | Sex |

| 4-Panel | Marker 1 | Marker 2 | Marker 3 | Marker 4 |
|---|---|---|---|---|
| 7110 | Age | Insulin | LDL | VEGF |
| 7111 | Age | Insulin | LEP | PLAT |
| 7112 | Age | Insulin | LEP | POMC |
| 7113 | Age | Insulin | LEP | SBP |
| 7114 | Age | Insulin | LEP | SCp |
| 7115 | Age | Insulin | LEP | SELE |
| 7116 | Age | Insulin | LEP | SELP |
| 7117 | Age | Insulin | LEP | Sex |
| 7118 | Age | Insulin | LEP | SHBG |
| 7119 | Age | Insulin | LEP | TNFRSF1B |
| 7120 | Age | Insulin | LEP | TRIG |
| 7121 | Age | Insulin | LEP | VCAM1 |
| 7122 | Age | Insulin | LEP | VEGF |
| 7123 | Age | Insulin | LEP | VWF |
| 7124 | Age | Insulin | LEP | Waist |
| 7125 | Age | Insulin | LEP | WT |
| 7126 | Age | Insulin | PLAT | POMC |
| 7127 | Age | Insulin | PLAT | Sex |
| 7128 | Age | Insulin | PLAT | VEGF |
| 7129 | Age | Insulin | POMC | SBP |
| 7130 | Age | Insulin | POMC | SCp |
| 7131 | Age | Insulin | POMC | SELE |
| 7132 | Age | Insulin | POMC | SELP |
| 7133 | Age | Insulin | POMC | Sex |
| 7134 | Age | Insulin | POMC | SHBG |
| 7135 | Age | Insulin | POMC | TNFRSF1B |
| 7136 | Age | Insulin | POMC | TRIG |
| 7137 | Age | Insulin | POMC | VCAM1 |
| 7138 | Age | Insulin | POMC | VEGF |
| 7139 | Age | Insulin | POMC | VWF |

FIG. 1500000

| 4-Panel | Marker 1 | Marker 2 | Marker 3 | Marker 4 |
|---|---|---|---|---|
| 7140 | Age | Insulin | POMC | Waist |
| 7141 | Age | Insulin | POMC | WT |
| 7142 | Age | Insulin | SBP | Sex |
| 7143 | Age | Insulin | SBP | VEGF |
| 7144 | Age | Insulin | SCp | Sex |
| 7145 | Age | Insulin | SCp | VEGF |
| 7146 | Age | Insulin | SELE | Sex |
| 7147 | Age | Insulin | SELE | VEGF |
| 7148 | Age | Insulin | SELP | Sex |
| 7149 | Age | Insulin | SELP | VEGF |
| 7150 | Age | Insulin | Sex | SHBG |
| 7151 | Age | Insulin | Sex | TNFRSF1B |
| 7152 | Age | Insulin | Sex | TRIG |
| 7153 | Age | Insulin | Sex | VCAM1 |
| 7154 | Age | Insulin | Sex | VEGF |
| 7155 | Age | Insulin | Sex | VWF |
| 7156 | Age | Insulin | Sex | Waist |
| 7157 | Age | Insulin | Sex | WT |
| 7158 | Age | Insulin | SHBG | VEGF |
| 7159 | Age | Insulin | TNFRSF1B | VEGF |
| 7160 | Age | Insulin | TRIG | VEGF |
| 7161 | Age | Insulin | VCAM1 | VEGF |
| 7162 | Age | Insulin | VEGF | VWF |
| 7163 | Age | Insulin | VEGF | Waist |
| 7164 | Age | Insulin | VEGF | WT |
| 7165 | Age | LDL | LEP | PLAT |
| 7166 | Age | LDL | LEP | POMC |
| 7167 | Age | LDL | LEP | SBP |
| 7168 | Age | LDL | LEP | SCp |
| 7169 | Age | LDL | LEP | SELE |
| 7170 | Age | LDL | LEP | SELP |
| 7171 | Age | LDL | LEP | Sex |
| 7172 | Age | LDL | LEP | SHBG |
| 7173 | Age | LDL | LEP | TNFRSF1B |
| 7174 | Age | LDL | LEP | TRIG |
| 7175 | Age | LDL | LEP | VCAM1 |
| 7176 | Age | LDL | LEP | VEGF |
| 7177 | Age | LDL | LEP | VWF |
| 7178 | Age | LDL | LEP | Waist |
| 7179 | Age | LDL | LEP | WT |
| 7180 | Age | LDL | PLAT | POMC |
| 7181 | Age | LDL | POMC | SBP |
| 7182 | Age | LDL | POMC | SCp |
| 7183 | Age | LDL | POMC | SELE |
| 7184 | Age | LDL | POMC | SELP |
| 7185 | Age | LDL | POMC | Sex |
| 7186 | Age | LDL | POMC | SHBG |
| 7187 | Age | LDL | POMC | TNFRSF1B |
| 7188 | Age | LDL | POMC | TRIG |
| 7189 | Age | LDL | POMC | VCAM1 |
| 7190 | Age | LDL | POMC | VEGF |
| 7191 | Age | LDL | POMC | VWF |
| 7192 | Age | LDL | POMC | Waist |
| 7193 | Age | LDL | POMC | WT |
| 7194 | Age | LDL | POMC | VEGF |
| 7195 | Age | LDL | Sex | Waist |
| 7196 | Age | LDL | Sex | WT |
| 7197 | Age | LEP | PLAT | POMC |
| 7198 | Age | LEP | PLAT | SBP |
| 7199 | Age | LEP | PLAT | SCp |

FIG. 15PPPPP

FIG. 15QQQQQ

| 4-Panel | Marker 1 | Marker 2 | Marker 3 | Marker 4 |
|---|---|---|---|---|
| 7200 | Age | LEP | PLAT | SELE |
| 7201 | Age | LEP | PLAT | SELP |
| 7202 | Age | LEP | PLAT | Sex |
| 7203 | Age | LEP | PLAT | SHBG |
| 7204 | Age | LEP | PLAT | TNFRSF1B |
| 7205 | Age | LEP | PLAT | TRIG |
| 7206 | Age | LEP | PLAT | VCAM1 |
| 7207 | Age | LEP | PLAT | VEGF |
| 7208 | Age | LEP | PLAT | VWF |
| 7209 | Age | LEP | PLAT | Waist |
| 7210 | Age | LEP | PLAT | WT |
| 7211 | Age | LEP | POMC | SBP |
| 7212 | Age | LEP | POMC | SCp |
| 7213 | Age | LEP | POMC | SELE |
| 7214 | Age | LEP | POMC | SELP |
| 7215 | Age | LEP | POMC | Sex |
| 7216 | Age | LEP | POMC | SHBG |
| 7217 | Age | LEP | POMC | TNFRSF1B |
| 7218 | Age | LEP | POMC | TRIG |
| 7219 | Age | LEP | POMC | VCAM1 |
| 7220 | Age | LEP | POMC | VEGF |
| 7221 | Age | LEP | POMC | VWF |
| 7222 | Age | LEP | POMC | Waist |
| 7223 | Age | LEP | POMC | WT |
| 7224 | Age | LEP | SBP | SCp |
| 7225 | Age | LEP | SBP | SELE |
| 7226 | Age | LEP | SBP | SELP |
| 7227 | Age | LEP | SBP | Sex |
| 7228 | Age | LEP | SBP | SHBG |
| 7229 | Age | LEP | SBP | TNFRSF1B |
| 7230 | Age | LEP | SBP | TRIG |
| 7231 | Age | LEP | SBP | VCAM1 |
| 7232 | Age | LEP | SBP | VEGF |
| 7233 | Age | LEP | SBP | VWF |
| 7234 | Age | LEP | SBP | Waist |
| 7235 | Age | LEP | SBP | WT |
| 7236 | Age | LEP | SCp | SELE |
| 7237 | Age | LEP | SCp | SELP |
| 7238 | Age | LEP | SCp | Sex |
| 7239 | Age | LEP | SCp | SHBG |
| 7240 | Age | LEP | SCp | TNFRSF1B |
| 7241 | Age | LEP | SCp | TRIG |
| 7242 | Age | LEP | SCp | VCAM1 |
| 7243 | Age | LEP | SCp | VEGF |
| 7244 | Age | LEP | SCp | VWF |
| 7245 | Age | LEP | SCp | Waist |
| 7246 | Age | LEP | SCp | WT |
| 7247 | Age | LEP | SELE | SELP |
| 7248 | Age | LEP | SELE | Sex |
| 7249 | Age | LEP | SELE | SHBG |
| 7250 | Age | LEP | SELE | TNFRSF1B |
| 7251 | Age | LEP | SELE | TRIG |
| 7252 | Age | LEP | SELE | VCAM1 |
| 7253 | Age | LEP | SELE | VEGF |
| 7254 | Age | LEP | SELE | VWF |
| 7255 | Age | LEP | SELE | Waist |
| 7256 | Age | LEP | SELE | WT |
| 7257 | Age | LEP | SELP | Sex |
| 7258 | Age | LEP | SELP | SHBG |
| 7259 | Age | LEP | SELP | TNFRSF1B |

| 4-Panel | Marker 1 | Marker 2 | Marker 3 | Marker 4 |
|---|---|---|---|---|
| 7260 | Age | LEP | SELP | TRIG |
| 7261 | Age | LEP | SELP | VCAM1 |
| 7262 | Age | LEP | SELP | VEGF |
| 7263 | Age | LEP | SELP | VWF |
| 7264 | Age | LEP | SELP | Waist |
| 7265 | Age | LEP | SELP | WT |
| 7266 | Age | LEP | Sex | SHBG |
| 7267 | Age | LEP | Sex | TNFRSF1B |
| 7268 | Age | LEP | Sex | TRIG |
| 7269 | Age | LEP | Sex | VCAM1 |
| 7270 | Age | LEP | Sex | VEGF |
| 7271 | Age | LEP | Sex | VWF |
| 7272 | Age | LEP | Sex | Waist |
| 7273 | Age | LEP | Sex | WT |
| 7274 | Age | LEP | SHBG | TNFRSF1B |
| 7275 | Age | LEP | SHBG | TRIG |
| 7276 | Age | LEP | SHBG | VCAM1 |
| 7277 | Age | LEP | SHBG | VEGF |
| 7278 | Age | LEP | SHBG | VWF |
| 7279 | Age | LEP | SHBG | Waist |
| 7280 | Age | LEP | SHBG | WT |
| 7281 | Age | LEP | TNFRSF1B | TRIG |
| 7282 | Age | LEP | TNFRSF1B | VCAM1 |
| 7283 | Age | LEP | TNFRSF1B | VEGF |
| 7284 | Age | LEP | TNFRSF1B | VWF |
| 7285 | Age | LEP | TNFRSF1B | Waist |
| 7286 | Age | LEP | TNFRSF1B | WT |
| 7287 | Age | LEP | TRIG | 1B |
| 7288 | Age | LEP | TRIG | VCAM1 |
| 7289 | Age | LEP | TRIG | VEGF |
| 7290 | Age | LEP | TRIG | VWF |
| 7291 | Age | LEP | TRIG | Waist |
| 7292 | Age | LEP | TRIG | WT |
| 7293 | Age | LEP | VCAM1 | VEGF |
| 7294 | Age | LEP | VCAM1 | VWF |
| 7295 | Age | LEP | VCAM1 | Waist |
| 7296 | Age | LEP | VCAM1 | WT |
| 7297 | Age | LEP | VEGF | VWF |
| 7298 | Age | LEP | VEGF | Waist |
| 7299 | Age | LEP | VEGF | WT |
| 7300 | Age | LEP | VWF | Waist |
| 7301 | Age | LEP | VWF | WT |
| 7302 | Age | LEP | Waist | WT |
| 7303 | Age | PLAT | POMC | SBP |
| 7304 | Age | PLAT | POMC | SCp |
| 7305 | Age | PLAT | POMC | SELE |
| 7306 | Age | PLAT | POMC | SELP |
| 7307 | Age | PLAT | POMC | Sex |
| 7308 | Age | PLAT | POMC | SHBG |
| 7309 | Age | PLAT | POMC | TNFRSF1B |
| 7310 | Age | PLAT | POMC | TRIG |
| 7311 | Age | PLAT | POMC | VCAM1 |
| 7312 | Age | PLAT | POMC | VEGF |
| 7313 | Age | PLAT | POMC | VWF |
| 7314 | Age | PLAT | POMC | Waist |
| 7315 | Age | PLAT | Sex | VEGF |

FIG. 15RRRRR

| 4-Panel | Marker 1 | Marker 2 | Marker 3 | Marker 4 |
|---|---|---|---|---|
| 7316 | Age | PLAT | Sex | WT |
| 7317 | Age | POMC | SBP | SCp |
| 7318 | Age | POMC | SBP | SELE |
| 7319 | Age | POMC | SBP | SELP |
| 7320 | Age | POMC | SBP | Sex |
| 7321 | Age | POMC | SBP | SHBG |
| 7322 | Age | POMC | SBP | TNFRSF1B |
| 7323 | Age | POMC | SBP | TRIG |
| 7324 | Age | POMC | SBP | VCAM1 |
| 7325 | Age | POMC | SBP | VEGF |
| 7326 | Age | POMC | SBP | VWF |
| 7327 | Age | POMC | SBP | Waist |
| 7328 | Age | POMC | SBP | WT |
| 7329 | Age | POMC | SCp | SELE |
| 7330 | Age | POMC | SCp | SELP |
| 7331 | Age | POMC | SCp | Sex |
| 7332 | Age | POMC | SCp | SHBG |
| 7333 | Age | POMC | SCp | TNFRSF1B |
| 7334 | Age | POMC | SCp | TRIG |
| 7335 | Age | POMC | SCp | VCAM1 |
| 7336 | Age | POMC | SCp | VEGF |
| 7337 | Age | POMC | SCp | VWF |
| 7338 | Age | POMC | SCp | Waist |
| 7339 | Age | POMC | SCp | WT |
| 7340 | Age | POMC | SELE | SELP |
| 7341 | Age | POMC | SELE | Sex |
| 7342 | Age | POMC | SELE | SHBG |
| 7343 | Age | POMC | SELE | TNFRSF1B |
| 7344 | Age | POMC | SELE | TRIG |
| 7345 | Age | POMC | SELE | VCAM1 |
| 7346 | Age | POMC | SELE | VEGF |
| 7347 | Age | POMC | SELE | VWF |
| 7348 | Age | POMC | SELE | Waist |
| 7349 | Age | POMC | SELE | WT |
| 7350 | Age | POMC | SELP | Sex |
| 7351 | Age | POMC | SELP | SHBG |
| 7352 | Age | POMC | SELP | TNFRSF1B |
| 7353 | Age | POMC | SELP | TRIG |
| 7354 | Age | POMC | SELP | VCAM1 |
| 7355 | Age | POMC | SELP | VEGF |
| 7356 | Age | POMC | SELP | VWF |
| 7357 | Age | POMC | SELP | Waist |
| 7358 | Age | POMC | SELP | WT |
| 7359 | Age | POMC | Sex | SHBG |
| 7360 | Age | POMC | Sex | TNFRSF1B |
| 7361 | Age | POMC | Sex | TRIG |
| 7362 | Age | POMC | Sex | VCAM1 |
| 7363 | Age | POMC | Sex | VEGF |
| 7364 | Age | POMC | Sex | VWF |
| 7365 | Age | POMC | Sex | Waist |
| 7366 | Age | POMC | Sex | WT |
| 7367 | Age | POMC | SHBG | TNFRSF1B |
| 7368 | Age | POMC | SHBG | TRIG |
| 7369 | Age | POMC | SHBG | VCAM1 |
| 7370 | Age | POMC | SHBG | VEGF |
| 7371 | Age | POMC | SHBG | VWF |
| 7372 | Age | POMC | SHBG | Waist |
| 7373 | Age | POMC | SHBG | WT |
| 7374 | Age | POMC | TNFRSF1B | TRIG |
| 7375 | Age | POMC | TNFRSF1B | VCAM1 |

FIG. 15SSSSS

| 4-Panel | Marker 1 | Marker 2 | Marker 3 | Marker 4 |
|---|---|---|---|---|
| 7376 | Age | POMC | TNFRSF1B | VEGF |
| 7377 | Age | POMC | TNFRSF1B | VWF |
| 7378 | Age | POMC | TNFRSF1B | Waist |
| 7379 | Age | POMC | TNFRSF1B | WT |
| 7380 | Age | POMC | TRIG | VCAM1 |
| 7381 | Age | POMC | TRIG | VEGF |
| 7382 | Age | POMC | TRIG | VWF |
| 7383 | Age | POMC | TRIG | Waist |
| 7384 | Age | POMC | TRIG | WT |
| 7385 | Age | POMC | VCAM1 | VEGF |
| 7386 | Age | POMC | VCAM1 | VWF |
| 7387 | Age | POMC | VCAM1 | Waist |
| 7388 | Age | POMC | VCAM1 | WT |
| 7389 | Age | POMC | VEGF | VWF |
| 7390 | Age | POMC | VEGF | Waist |
| 7391 | Age | POMC | VEGF | WT |
| 7392 | Age | POMC | VWF | Waist |
| 7393 | Age | POMC | VWF | WT |
| 7394 | Age | POMC | Waist | WT |
| 7395 | Age | SBP | Sex | VEGF |
| 7396 | Age | SBP | Sex | Waist |
| 7397 | Age | SBP | Sex | WT |
| 7398 | Age | SCp | Sex | VEGF |
| 7399 | Age | SCp | Sex | WT |
| 7400 | Age | SCp | VCAM1 | VEGF |
| 7401 | Age | SELE | Sex | VEGF |
| 7402 | Age | SELE | Sex | Waist |
| 7403 | Age | SELE | Sex | WT |
| 7404 | Age | SELP | Sex | VCAM1 |
| 7405 | Age | SELP | Sex | VEGF |
| 7406 | Age | SELP | Sex | Waist |
| 7407 | Age | SELP | Sex | WT |
| 7408 | Age | SELP | VCAM1 | VEGF |
| 7409 | Age | SELP | VEGF | VWF |
| 7410 | Age | Sex | SHBG | VEGF |
| 7411 | Age | Sex | SHBG | Waist |
| 7412 | Age | Sex | SHBG | WT |
| 7413 | Age | Sex | TNFRSF1B | VCAM1 |
| 7414 | Age | Sex | TNFRSF1B | VEGF |
| 7415 | Age | Sex | TNFRSF1B | Waist |
| 7416 | Age | Sex | TNFRSF1B | WT |
| 7417 | Age | Sex | TRIG | VEGF |
| 7418 | Age | Sex | TRIG | Waist |
| 7419 | Age | Sex | TRIG | WT |
| 7420 | Age | Sex | VCAM1 | VEGF |
| 7421 | Age | Sex | VCAM1 | Waist |
| 7422 | Age | Sex | VCAM1 | WT |
| 7423 | Age | Sex | VEGF | VWF |
| 7424 | Age | Sex | VEGF | Waist |
| 7425 | Age | Sex | VEGF | WT |
| 7426 | Age | Sex | VWF | Waist |
| 7427 | Age | Sex | VWF | WT |
| 7428 | Age | Sex | Waist | WT |
| 7429 | Age | SHBG | VCAM1 | VEGF |
| 7430 | Age | TNFRSF1B | VCAM1 | VEGF |
| 7431 | AGER | ANG | IL6ST | POMC |
| 7432 | AGER | BMI | HDLC | POMC |
| 7433 | AGER | CDK5 | HDLC | POMC |
| 7434 | AGER | HDLC | IGF1 | POMC |
| 7435 | AGER | HDLC | IL1B | POMC |

FIG. 15TTTTT

FIG. 15UUUUU

| 4-Panel | Marker 1 | Marker 2 | Marker 3 | Marker 4 |
|---|---|---|---|---|
| 7436 | AGER | HDLC | IL6ST | POMC |
| 7437 | AGER | HDLC | Insulin | POMC |
| 7438 | AGER | HDLC | POMC | VCAM1 |
| 7439 | AGER | HDLC | POMC | VEGF |
| 7440 | AGER | IGF1 | IL6ST | POMC |
| 7441 | AGER | IL6ST | POMC | VEGF |
| 7442 | AGER | POMC | Sex | VEGF |
| 7443 | AGER | POMC | VCAM1 | VEGF |
| 7444 | AHSG | BMI | HDLC | POMC |
| 7445 | AHSG | HDLC | IGF1 | POMC |
| 7446 | AHSG | HDLC | IL6ST | VEGF |
| 7447 | AHSG | IL6ST | POMC | VEGF |
| 7448 | AHSG | POMC | Sex | VEGF |
| 7449 | AHSG | POMC | VCAM1 | VEGF |
| 7450 | ANG | APOE | POMC | POMC |
| 7451 | ANG | BMI | HDLC | POMC |
| 7452 | ANG | BMI | IL6ST | VEGF |
| 7453 | ANG | BMI | POMC | VEGF |
| 7454 | ANG | CCL2 | HDLC | POMC |
| 7455 | ANG | CCL2 | IGF1 | POMC |
| 7456 | ANG | CCL2 | IL6ST | POMC |
| 7457 | ANG | CCL2 | POMC | Sex |
| 7458 | ANG | CD40 | IGF1 | IL6ST |
| 7459 | ANG | CD40 | IL6ST | POMC |
| 7460 | ANG | CDK5 | IL6ST | POMC |
| 7461 | ANG | CDK5 | POMC | VEGF |
| 7462 | ANG | CRP | IL6ST | POMC |
| 7463 | ANG | DPP4 | POMC | VEGF |
| 7464 | ANG | EGF | HDLC | POMC |
| 7465 | ANG | EGF | IL6ST | POMC |

| 4-Panel | Marker 1 | Marker 2 | Marker 3 | Marker 4 |
|---|---|---|---|---|
| 7466 | ANG | EGF | POMC | VEGF |
| 7467 | ANG | FGA | IL6ST | POMC |
| 7468 | ANG | HDLC | IGF1 | POMC |
| 7469 | ANG | HDLC | IL18 | POMC |
| 7470 | ANG | HDLC | IL6ST | POMC |
| 7471 | ANG | HDLC | Insulin | POMC |
| 7472 | ANG | HDLC | POMC | VCAM1 |
| 7473 | ANG | HDLC | POMC | VEGF |
| 7474 | ANG | HT | IL6ST | POMC |
| 7475 | ANG | IGF1 | IL6R | IL6ST |
| 7476 | ANG | IGF1 | IL6ST | LEP |
| 7477 | ANG | IGF1 | IL6ST | POMC |
| 7478 | ANG | IGF1 | POMC | Sex |
| 7479 | ANG | IGF1 | POMC | VCAM1 |
| 7480 | ANG | IGF1 | POMC | VEGF |
| 7481 | ANG | IL18 | IL6ST | POMC |
| 7482 | ANG | IL6R | IL6ST | POMC |
| 7483 | ANG | IL6ST | Insulin | POMC |
| 7484 | ANG | IL6ST | LEP | POMC |
| 7485 | ANG | IL6ST | PLAT | POMC |
| 7486 | ANG | IL6ST | POMC | SBP |
| 7487 | ANG | IL6ST | POMC | Sex |
| 7488 | ANG | IL6ST | POMC | TNFRSF1B |
| 7489 | ANG | IL6ST | POMC | VCAM1 |
| 7490 | ANG | IL6ST | POMC | VEGF |
| 7491 | ANG | Insulin | Insulin | VEGF |
| 7492 | ANG | LEP | LEP | VEGF |
| 7493 | ANG | POMC | Sex | VCAM1 |
| 7494 | ANG | POMC | Sex | VEGF |
| 7495 | ANG | POMC | VCAM1 | VEGF |

| 4-Panel | Marker 1 | Marker 2 | Marker 3 | Marker 4 |
|---|---|---|---|---|
| 7496 | APOA1 | BMI | HDLC | POMC |
| 7497 | APOA1 | CCL2 | CRP | LEP |
| 7498 | APOA1 | CCL2 | HDLC | POMC |
| 7499 | APOA1 | CDK5 | HDLC | POMC |
| 7500 | APOA1 | CRP | IL6ST | LEP |
| 7501 | APOA1 | EGF | HDLC | POMC |
| 7502 | APOA1 | HDLC | Hip | POMC |
| 7503 | APOA1 | HDLC | IGF1 | POMC |
| 7504 | APOA1 | HDLC | IGFBP1 | POMC |
| 7505 | APOA1 | HDLC | IL18 | POMC |
| 7506 | APOA1 | HDLC | IL6ST | POMC |
| 7507 | APOA1 | HDLC | Insulin | POMC |
| 7508 | APOA1 | HDLC | LEP | POMC |
| 7509 | APOA1 | HDLC | POMC | SBP |
| 7510 | APOA1 | HDLC | POMC | Sex |
| 7511 | APOA1 | HDLC | POMC | VCAM1 |
| 7512 | APOA1 | HDLC | POMC | VEGF |
| 7513 | APOA1 | HDLC | POMC | WT |
| 7514 | APOA1 | IGF1 | IL6ST | POMC |
| 7515 | APOA1 | IGF1 | POMC | Sex |
| 7516 | APOA1 | IGF1 | POMC | VEGF |
| 7517 | APOA1 | IL6ST | POMC | VEGF |
| 7518 | APOA1 | LEP | POMC | VEGF |
| 7519 | APOA1 | POMC | Sex | VEGF |
| 7520 | APOA1 | POMC | VCAM1 | VEGF |
| 7521 | APOE | BMI | HDLC | POMC |
| 7522 | APOE | BMI | POMC | VEGF |
| 7523 | APOE | CCL2 | HDLC | POMC |
| 7524 | APOE | CDK5 | HDLC | POMC |
| 7525 | APOE | CDK5 | IL6ST | POMC |

| 4-Panel | Marker 1 | Marker 2 | Marker 3 | Marker 4 |
|---|---|---|---|---|
| 7526 | APOE | CDK5 | POMC | VEGF |
| 7527 | APOE | EGF | POMC | VEGF |
| 7528 | APOE | HDLC | IGF1 | POMC |
| 7529 | APOE | HDLC | IL18 | POMC |
| 7530 | APOE | HDLC | IL6ST | POMC |
| 7531 | APOE | HDLC | Insulin | POMC |
| 7532 | APOE | HDLC | POMC | VEGF |
| 7533 | APOE | IGF1 | IL6ST | POMC |
| 7534 | APOE | IGF1 | POMC | VEGF |
| 7535 | APOE | IL6ST | POMC | VEGF |
| 7536 | APOE | LEP | POMC | VEGF |
| 7537 | APOE | POMC | SBP | VEGF |
| 7538 | APOE | POMC | Sex | VEGF |
| 7539 | APOE | POMC | VCAM1 | VEGF |
| 7540 | BAX | BMI | HDLC | POMC |
| 7541 | BAX | HDLC | IGF1 | POMC |
| 7542 | BAX | HDLC | IL6ST | POMC |
| 7543 | BAX | IGF1 | IL6ST | POMC |
| 7544 | BAX | IL6ST | POMC | VEGF |
| 7545 | BAX | POMC | Sex | VEGF |
| 7546 | BAX | POMC | VCAM1 | VEGF |
| 7547 | BMI | C3 | HDLC | POMC |
| 7548 | BMI | CCL2 | CD40 | CRP |
| 7549 | BMI | CCL2 | CRP | HDLC |
| 7550 | BMI | CCL2 | CRP | LEP |
| 7551 | BMI | CCL2 | CRP | Sex |
| 7552 | BMI | CCL2 | CRP | Waist |
| 7553 | BMI | CCL2 | HDLC | POMC |
| 7554 | BMI | CCL2 | POMC | Waist |
| 7555 | BMI | CD14 | HDLC | POMC |

FIG. 15VVVVV

| 4. Panel | Marker 1 | Marker 2 | Marker 3 | Marker 4 |
|---|---|---|---|---|
| 7556 | BMI | CD40 | CRP | HDLC |
| 7557 | BMI | CD40 | HDLC | POMC |
| 7558 | BMI | CDK5 | HDLC | POMC |
| 7559 | BMI | CDK5 | IL6ST | POMC |
| 7560 | BMI | CDK5 | POMC | VEGF |
| 7561 | BMI | CDK5 | POMC | Waist |
| 7562 | BMI | CHOL | HDLC | POMC |
| 7563 | BMI | CRP | Glucose | Sex |
| 7564 | BMI | CRP | HDLC | IL6ST |
| 7565 | BMI | CRP | HDLC | Insulin |
| 7566 | BMI | CRP | HDLC | POMC |
| 7567 | BMI | CRP | IGF1 | POMC |
| 7568 | BMI | CRP | IL6ST | LEP |
| 7569 | BMI | CRP | IL6ST | POMC |
| 7570 | BMI | CRP | IL6ST | Sex |
| 7571 | BMI | CRP | IL6ST | Waist |
| 7572 | BMI | CRP | POMC | Sex |
| 7573 | BMI | CRP | POMC | VEGF |
| 7574 | BMI | CRP | POMC | Waist |
| 7575 | BMI | CRP | Sex | VEGF |
| 7576 | BMI | DBP | HDLC | POMC |
| 7577 | BMI | DPP4 | HDLC | POMC |
| 7578 | BMI | DPP4 | POMC | VEGF |
| 7579 | BMI | EGF | HDLC | POMC |
| 7580 | BMI | ENG | HDLC | POMC |
| 7581 | BMI | FamHX | HDLC | POMC |
| 7582 | BMI | FGA | HDLC | POMC |
| 7583 | BMI | FTH1 | HDLC | POMC |
| 7584 | BMI | Gluc120 | HDLC | POMC |
| 7585 | BMI | Glucose | HDLC | POMC |

| 4. Panel | Marker 1 | Marker 2 | Marker 3 | Marker 4 |
|---|---|---|---|---|
| 7586 | BMI | HBA1C | HDLC | POMC |
| 7587 | BMI | HDLC | HGF | POMC |
| 7588 | BMI | HDLC | Hp | POMC |
| 7589 | BMI | HDLC | HP | POMC |
| 7590 | BMI | HDLC | HT | POMC |
| 7591 | BMI | HDLC | ICAM1 | POMC |
| 7592 | BMI | HDLC | IGF1 | POMC |
| 7593 | BMI | HDLC | IGFBP1 | POMC |
| 7594 | BMI | HDLC | IGFBP3 | POMC |
| 7595 | BMI | HDLC | IL18 | POMC |
| 7596 | BMI | HDLC | IL2RA | POMC |
| 7597 | BMI | HDLC | IL6R | POMC |
| 7598 | BMI | HDLC | IL6ST | POMC |
| 7599 | BMI | HDLC | IL8 | POMC |
| 7600 | BMI | HDLC | INHBA | POMC |
| 7601 | BMI | HDLC | Ins120 | POMC |
| 7602 | BMI | HDLC | Insulin | POMC |
| 7603 | BMI | HDLC | LDL | POMC |
| 7604 | BMI | HDLC | LEP | POMC |
| 7605 | BMI | HDLC | PLAT | POMC |
| 7606 | BMI | HDLC | POMC | SBP |
| 7607 | BMI | HDLC | POMC | SCp |
| 7608 | BMI | HDLC | POMC | SELE |
| 7609 | BMI | HDLC | POMC | SELP |
| 7610 | BMI | HDLC | POMC | Sex |
| 7611 | BMI | HDLC | POMC | SHBG |
| 7612 | BMI | HDLC | POMC | TNFRSF1B |
| 7613 | BMI | HDLC | POMC | TRIG |
| 7614 | BMI | HDLC | POMC | VCAM1 |
| 7615 | BMI | HDLC | POMC | VEGF |

FIG. 15WWWWWW

| 4-Panel | Marker 1 | Marker 2 | Marker 3 | Marker 4 |
|---|---|---|---|---|
| 7616 | BMI | HDLC | POMC | VWF |
| 7617 | BMI | HDLC | POMC | Waist |
| 7618 | BMI | HDLC | POMC | WT |
| 7619 | BMI | IGF1 | IL6ST | POMC |
| 7620 | BMI | IGF1 | POMC | VCAM1 |
| 7621 | BMI | IGF1 | POMC | VEGF |
| 7622 | BMI | IGF1 | POMC | Waist |
| 7623 | BMI | IL6ST | Ins120 | POMC |
| 7624 | BMI | IL6ST | POMC | Sex |
| 7625 | BMI | IL6ST | POMC | VEGF |
| 7626 | BMI | IL6ST | POMC | Waist |
| 7627 | BMI | Ins120 | POMC | VEGF |
| 7628 | BMI | POMC | SBP | VEGF |
| 7629 | BMI | POMC | Sex | VCAM1 |
| 7630 | BMI | POMC | Sex | VEGF |
| 7631 | BMI | POMC | VCAM1 | VEGF |
| 7632 | BMI | POMC | VCAM1 | Waist |
| 7633 | BMI | POMC | VEGF | Waist |
| 7634 | C3 | HDLC | IGF1 | POMC |
| 7635 | C3 | HDLC | IL6ST | POMC |
| 7636 | C3 | IGF1 | IL6ST | POMC |
| 7637 | C3 | IGF1 | POMC | Sex |
| 7638 | C3 | IL6ST | POMC | VEGF |
| 7639 | C3 | POMC | Sex | VEGF |
| 7640 | C3 | POMC | VCAM1 | VEGF |
| 7641 | CCL2 | CD40 | HDLC | POMC |
| 7642 | CCL2 | CDK5 | HDLC | POMC |
| 7643 | CCL2 | CDK5 | POMC | Sex |
| 7644 | CCL2 | CRP | HDLC | POMC |
| 7645 | CCL2 | CRP | IGF1 | LEP |
| 7646 | CCL2 | CRP | IL6ST | LEP |
| 7647 | CCL2 | CRP | LEP | POMC |
| 7648 | CCL2 | CRP | POMC | Sex |
| 7649 | CCL2 | CRP | Sex | WT |
| 7650 | CCL2 | DBP | HDLC | POMC |
| 7651 | CCL2 | DPP4 | HDLC | POMC |
| 7652 | CCL2 | EGF | HDLC | POMC |
| 7653 | CCL2 | HDLC | Hip | POMC |
| 7654 | CCL2 | HDLC | HT | POMC |
| 7655 | CCL2 | HDLC | IGF1 | POMC |
| 7656 | CCL2 | HDLC | IL18 | POMC |
| 7657 | CCL2 | HDLC | IL6ST | POMC |
| 7658 | CCL2 | HDLC | Insulin | POMC |
| 7659 | CCL2 | HDLC | LEP | POMC |
| 7660 | CCL2 | HDLC | POMC | SBP |
| 7661 | CCL2 | HDLC | POMC | Sex |
| 7662 | CCL2 | HDLC | POMC | VCAM1 |
| 7663 | CCL2 | HDLC | POMC | VEGF |
| 7664 | CCL2 | HDLC | POMC | WT |
| 7665 | CCL2 | IGF1 | IL6ST | POMC |
| 7666 | CCL2 | IGF1 | LEP | POMC |
| 7667 | CCL2 | IGF1 | POMC | Sex |
| 7668 | CCL2 | IGF1 | POMC | VCAM1 |
| 7669 | CCL2 | IL6ST | POMC | VEGF |
| 7670 | CCL2 | IL6ST | POMC | VEGF |
| 7671 | CCL2 | IL6ST | POMC | POMC |
| 7672 | CCL2 | LEP | POMC | Sex |
| 7673 | CCL2 | LEP | POMC | VEGF |
| 7674 | CCL2 | LEP | POMC | VCAM1 |
| 7675 | CCL2 | POMC | Sex | VCAM1 |

FIG. 15XXXXX

| 4-Panel | Marker 1 | Marker 2 | Marker 3 | Marker 4 |
|---|---|---|---|---|
| 7676 | CCL2 | POMC | Sex | VEGF |
| 7677 | CCL2 | POMC | VCAM1 | VEGF |
| 7678 | CD14 | CDK5 | IL6ST | POMC |
| 7679 | CD14 | HDLC | IGF1 | POMC |
| 7680 | CD14 | HDLC | IL18 | POMC |
| 7681 | CD14 | HDLC | IL6ST | POMC |
| 7682 | CD14 | HDLC | Insulin | POMC |
| 7683 | CD14 | IGF1 | IL6ST | POMC |
| 7684 | CD14 | IL6ST | POMC | VEGF |
| 7685 | CD14 | POMC | Sex | VEGF |
| 7686 | CD14 | POMC | VCAM1 | VEGF |
| 7687 | CD40 | CDK5 | HDLC | POMC |
| 7688 | CD40 | CDK5 | IL6ST | VEGF |
| 7689 | CD40 | CDK5 | POMC | VEGF |
| 7690 | CD40 | HDLC | IGF1 | POMC |
| 7691 | CD40 | HDLC | IL6ST | POMC |
| 7692 | CD40 | HDLC | Insulin | POMC |
| 7693 | CD40 | IGF1 | IL6ST | POMC |
| 7694 | CD40 | IGF1 | POMC | VEGF |
| 7695 | CD40 | IL6ST | POMC | VEGF |
| 7696 | CD40 | POMC | Sex | VEGF |
| 7697 | CD40 | POMC | VCAM1 | Sex |
| 7698 | CDK5 | CRP | HDLC | POMC |
| 7699 | CDK5 | CRP | IL6ST | POMC |
| 7700 | CDK5 | CRP | POMC | POMC |
| 7701 | CDK5 | DBP | IL6ST | POMC |
| 7702 | CDK5 | DPP4 | HDLC | POMC |
| 7703 | CDK5 | DPP4 | POMC | VEGF |
| 7704 | CDK5 | EGF | HDLC | POMC |
| 7705 | CDK5 | EGF | IL6ST | POMC |

| 4-Panel | Marker 1 | Marker 2 | Marker 3 | Marker 4 |
|---|---|---|---|---|
| 7706 | CDK5 | EGF | POMC | VEGF |
| 7707 | CDK5 | FGA | IL6ST | POMC |
| 7708 | CDK5 | HDLC | Hip | POMC |
| 7709 | CDK5 | HDLC | HT | POMC |
| 7710 | CDK5 | HDLC | IGF1 | POMC |
| 7711 | CDK5 | HDLC | IGFBP1 | POMC |
| 7712 | CDK5 | HDLC | IL18 | POMC |
| 7713 | CDK5 | HDLC | IL6ST | POMC |
| 7714 | CDK5 | HDLC | Insulin | POMC |
| 7715 | CDK5 | HDLC | LEP | POMC |
| 7716 | CDK5 | HDLC | PLAT | POMC |
| 7717 | CDK5 | HDLC | POMC | SBP |
| 7718 | CDK5 | HDLC | POMC | Sex |
| 7719 | CDK5 | HDLC | POMC | VCAM1 |
| 7720 | CDK5 | HDLC | POMC | VEGF |
| 7721 | CDK5 | HDLC | POMC | WT |
| 7722 | CDK5 | HGF | IL6ST | POMC |
| 7723 | CDK5 | HP | IL6ST | POMC |
| 7724 | CDK5 | HT | IL6ST | POMC |
| 7725 | CDK5 | HT | POMC | VEGF |
| 7726 | CDK5 | IGF1 | IL6ST | POMC |
| 7727 | CDK5 | IGF1 | POMC | VEGF |
| 7728 | CDK5 | IGF1 | POMC | VCAM1 |
| 7729 | CDK5 | IL18 | IL6ST | VEGF |
| 7730 | CDK5 | IL6R | IL6ST | POMC |
| 7731 | CDK5 | IL6ST | LDL | POMC |
| 7732 | CDK5 | IL6ST | LEP | POMC |
| 7733 | CDK5 | IL6ST | POMC | POMC |
| 7734 | CDK5 | IL6ST | POMC | SBP |
| 7735 | CDK5 | IL6ST | POMC | Sex |

FIG. 15YYYYY

| 4-Panel | Marker 1 | Marker 2 | Marker 3 | Marker 4 |
|---|---|---|---|---|
| 7736 | CDK5 | IL6ST | POMC | TNFRSF1B |
| 7737 | CDK5 | IL6ST | POMC | VCAM1 |
| 7738 | CDK5 | IL6ST | POMC | VEGF |
| 7739 | CDK5 | LEP | POMC | VCAM1 |
| 7740 | CDK5 | LEP | POMC | VEGF |
| 7741 | CDK5 | POMC | Sex | VCAM1 |
| 7742 | CDK5 | POMC | Sex | VEGF |
| 7743 | CDK5 | POMC | VCAM1 | VEGF |
| 7744 | CHOL | HDLC | IGF1 | POMC |
| 7745 | CHOL | HDLC | IL6ST | POMC |
| 7746 | CHOL | HDLC | Insulin | POMC |
| 7747 | CHOL | IGF1 | IL6ST | VEGF |
| 7748 | CHOL | IL6ST | POMC | POMC |
| 7749 | CHOL | POMC | Sex | VEGF |
| 7750 | CRP | EGF | HDLC | POMC |
| 7751 | CRP | Glucose | IL6ST | LEP |
| 7752 | CRP | HDLC | Hip | POMC |
| 7753 | CRP | HDLC | IGF1 | POMC |
| 7754 | CRP | HDLC | IL18 | POMC |
| 7755 | CRP | HDLC | IL6ST | POMC |
| 7756 | CRP | HDLC | Insulin | POMC |
| 7757 | CRP | HDLC | LEP | POMC |
| 7758 | CRP | HDLC | POMC | Sex |
| 7759 | CRP | HDLC | POMC | VCAM1 |
| 7760 | CRP | HDLC | POMC | VEGF |
| 7761 | CRP | HDLC | POMC | WT |
| 7762 | CRP | IGF1 | IL6ST | LEP |
| 7763 | CRP | IGF1 | IL6ST | POMC |
| 7764 | CRP | IGF1 | LEP | VCAM1 |
| 7765 | CRP | IGF1 | POMC | Sex |
| 7766 | CRP | IGF1 | POMC | VCAM1 |
| 7767 | CRP | IGFBP1 | POMC | Sex |
| 7768 | CRP | IL2RA | IL6ST | LEP |
| 7769 | CRP | IL6ST | Insulin | LEP |
| 7770 | CRP | IL6ST | LEP | POMC |
| 7771 | CRP | IL6ST | LEP | VEGF |
| 7772 | CRP | IL6ST | LEP | WT |
| 7773 | CRP | IL6ST | POMC | Sex |
| 7774 | CRP | IL6ST | POMC | TNFRSF1B |
| 7775 | CRP | IL6ST | POMC | VEGF |
| 7776 | CRP | Insulin | POMC | Sex |
| 7777 | CRP | Insulin | Sex | VCAM1 |
| 7778 | CRP | LEP | POMC | VCAM1 |
| 7779 | CRP | POMC | Sex | VCAM1 |
| 7780 | CRP | POMC | Sex | VCAM1 |
| 7781 | CRP | POMC | Sex | VEGF |
| 7782 | CRP | POMC | VCAM1 | WT |
| 7783 | DBP | HDLC | IL6ST | VEGF |
| 7784 | DBP | HDLC | IL6ST | POMC |
| 7785 | DBP | IGF1 | POMC | POMC |
| 7786 | DBP | IGF1 | IL6ST | VEGF |
| 7787 | DBP | IL6ST | POMC | VEGF |
| 7788 | DBP | POMC | Sex | VEGF |
| 7789 | DBP | POMC | VCAM1 | VEGF |
| 7790 | DPP4 | EGF | HDLC | VEGF |
| 7791 | DPP4 | EGF | POMC | VEGF |
| 7792 | DPP4 | HDLC | IGF1 | POMC |
| 7793 | DPP4 | HDLC | IL18 | POMC |
| 7794 | DPP4 | HDLC | IL6ST | POMC |
| 7795 | DPP4 | HDLC | LEP | POMC |

FIG. 15ZZZZZ

| 4-Panel | Marker 1 | Marker 2 | Marker 3 | Marker 4 |
|---|---|---|---|---|
| 7796 | DPP4 | HDLC | POMC | Sex |
| 7797 | DPP4 | HDLC | POMC | VEGF |
| 7798 | DPP4 | HT | POMC | VEGF |
| 7799 | DPP4 | IGF1 | IL6ST | POMC |
| 7800 | DPP4 | IGF1 | POMC | Sex |
| 7801 | DPP4 | IGF1 | POMC | VEGF |
| 7802 | DPP4 | IL6ST | POMC | VEGF |
| 7803 | DPP4 | LEP | POMC | VEGF |
| 7804 | DPP4 | POMC | SBP | VEGF |
| 7805 | DPP4 | POMC | Sex | VEGF |
| 7806 | DPP4 | POMC | VCAM1 | VEGF |
| 7807 | EGF | FGA | HDLC | POMC |
| 7808 | EGF | HDLC | IGF1 | POMC |
| 7809 | EGF | HDLC | IGFBP1 | POMC |
| 7810 | EGF | HDLC | IL18 | POMC |
| 7811 | EGF | HDLC | IL6ST | POMC |
| 7812 | EGF | HDLC | Insulin | VCAM1 |
| 7813 | EGF | HDLC | LEP | VEGF |
| 7814 | EGF | HDLC | PLAT | POMC |
| 7815 | EGF | HDLC | POMC | Sex |
| 7816 | EGF | HDLC | POMC | VCAM1 |
| 7817 | EGF | HDLC | POMC | VEGF |
| 7818 | EGF | IGF1 | IL6ST | POMC |
| 7819 | EGF | IGF1 | POMC | VEGF |
| 7820 | EGF | IL6ST | POMC | VEGF |
| 7821 | EGF | POMC | Sex | VCAM1 |
| 7822 | EGF | POMC | Sex | VEGF |
| 7823 | EGF | POMC | VCAM1 | VEGF |
| 7824 | ENG | HDLC | IGF1 | POMC |
| 7825 | ENG | HDLC | IL6ST | POMC |

| 4-Panel | Marker 1 | Marker 2 | Marker 3 | Marker 4 |
|---|---|---|---|---|
| 7826 | ENG | HDLC | Insulin | POMC |
| 7827 | ENG | HDLC | POMC | VCAM1 |
| 7828 | ENG | HDLC | POMC | VEGF |
| 7829 | ENG | IL6ST | POMC | VEGF |
| 7830 | ENG | POMC | Sex | VEGF |
| 7831 | ENG | POMC | VCAM1 | VEGF |
| 7832 | FamHX | HDLC | IGF1 | POMC |
| 7833 | FamHX | HDLC | IL6ST | POMC |
| 7834 | FamHX | IL6ST | POMC | VEGF |
| 7835 | FamHX | POMC | Sex | VEGF |
| 7836 | FamHX | POMC | VCAM1 | VEGF |
| 7837 | FGA | HDLC | IL18 | POMC |
| 7838 | FGA | HDLC | IL6ST | POMC |
| 7839 | FGA | IGF1 | IL6ST | VEGF |
| 7840 | FGA | IGF1 | POMC | Sex |
| 7841 | FGA | IL6ST | LEP | POMC |
| 7842 | FGA | IL6ST | POMC | SBP |
| 7843 | FGA | IL6ST | POMC | Sex |
| 7844 | FGA | IL6ST | POMC | TNFRSF1B |
| 7845 | FGA | IL6ST | POMC | VEGF |
| 7846 | FGA | LEP | POMC | VEGF |
| 7847 | FGA | POMC | POMC | VCAM1 |
| 7848 | FGA | POMC | Sex | VEGF |
| 7849 | FGA | POMC | Sex | VEGF |
| 7850 | FTH1 | HDLC | VCAM1 | VEGF |
| 7851 | FTH1 | HDLC | IGF1 | POMC |
| 7852 | FTH1 | HDLC | IL6ST | POMC |
| 7853 | FTH1 | HDLC | POMC | Sex |
| 7854 | FTH1 | IL6ST | POMC | VCAM1 |
| 7855 | FTH1 | POMC | Sex | VEGF |

FIG. 15AAAAAA

| 4-Panel | Marker 1 | Marker 2 | Marker 3 | Marker 4 |
|---|---|---|---|---|
| 7856 | FTH1 | POMC | VCAM1 | VEGF |
| 7857 | Gluc120 | HDLC | IL6ST | POMC |
| 7858 | Gluc120 | IGF1 | IL6ST | POMC |
| 7859 | Gluc120 | IL6ST | POMC | VEGF |
| 7860 | Gluc120 | POMC | Sex | VEGF |
| 7861 | Gluc120 | POMC | VCAM1 | VEGF |
| 7862 | Glucose | HDLC | IGF1 | POMC |
| 7863 | Glucose | HDLC | IL18 | POMC |
| 7864 | Glucose | HDLC | IL6ST | POMC |
| 7865 | Glucose | IGF1 | IL6ST | POMC |
| 7866 | Glucose | IGF1 | POMC | VEGF |
| 7867 | Glucose | IL6ST | POMC | VEGF |
| 7868 | Glucose | POMC | Sex | VCAM1 |
| 7869 | Glucose | POMC | Sex | VEGF |
| 7870 | HBA1C | HDLC | IGF1 | POMC |
| 7871 | HBA1C | HDLC | IL6ST | POMC |
| 7872 | HBA1C | HDLC | Insulin | POMC |
| 7873 | HBA1C | HDLC | POMC | VEGF |
| 7874 | HBA1C | IGF1 | IL6ST | POMC |
| 7875 | HBA1C | IL6ST | POMC | VEGF |
| 7876 | HBA1C | POMC | Sex | VCAM1 |
| 7877 | HBA1C | POMC | VCAM1 | VEGF |
| 7878 | HDLC | HGF | IL6ST | POMC |
| 7879 | HDLC | Hp | IGF1 | POMC |
| 7880 | HDLC | Hp | IL18 | POMC |
| 7881 | HDLC | Hp | IL6ST | POMC |
| 7882 | HDLC | Hp | Insulin | POMC |
| 7883 | HDLC | Hp | POMC | SBP |
| 7884 | HDLC | Hp | POMC | VCAM1 |
| 7885 | HDLC | Hp | POMC | VEGF |

| 4-Panel | Marker 1 | Marker 2 | Marker 3 | Marker 4 |
|---|---|---|---|---|
| 7886 | HDLC | Hp | IGF1 | POMC |
| 7887 | HDLC | Hp | IL6ST | POMC |
| 7888 | HDLC | HT | IGF1 | POMC |
| 7889 | HDLC | HT | IL18 | POMC |
| 7890 | HDLC | HT | IL6ST | POMC |
| 7891 | HDLC | HT | Insulin | POMC |
| 7892 | HDLC | HT | POMC | VCAM1 |
| 7893 | HDLC | HT | POMC | VEGF |
| 7894 | HDLC | HT | POMC | WT |
| 7895 | HDLC | ICAM1 | IGF1 | POMC |
| 7896 | HDLC | ICAM1 | IL6ST | POMC |
| 7897 | HDLC | IGF1 | IGFBP1 | POMC |
| 7898 | HDLC | IGF1 | IGFBP3 | POMC |
| 7899 | HDLC | IGF1 | IL18 | POMC |
| 7900 | HDLC | IGF1 | IL2RA | POMC |
| 7901 | HDLC | IGF1 | IL6R | POMC |
| 7902 | HDLC | IGF1 | IL6ST | POMC |
| 7903 | HDLC | IGF1 | IL8 | POMC |
| 7904 | HDLC | IGF1 | INHBA | POMC |
| 7905 | HDLC | IGF1 | Insulin | POMC |
| 7906 | HDLC | IGF1 | LDL | POMC |
| 7907 | HDLC | IGF1 | LEP | POMC |
| 7908 | HDLC | IGF1 | PLAT | POMC |
| 7909 | HDLC | IGF1 | POMC | SBP |
| 7910 | HDLC | IGF1 | POMC | SCp |
| 7911 | HDLC | IGF1 | POMC | SELE |
| 7912 | HDLC | IGF1 | POMC | SELP |
| 7913 | HDLC | IGF1 | POMC | Sex |
| 7914 | HDLC | IGF1 | POMC | SHBG |
| 7915 | HDLC | IGF1 | POMC | TNFRSF1B |

FIG. 15BBBBB

FIG. 15BBBBBB

| 4-Panel | Marker 1 | Marker 2 | Marker 3 | Marker 4 |
|---|---|---|---|---|
| 7916 | HDLC | IGF1 | POMC | TRIG |
| 7917 | HDLC | IGF1 | POMC | VCAM1 |
| 7918 | HDLC | IGF1 | POMC | VEGF |
| 7919 | HDLC | IGF1 | POMC | Waist |
| 7920 | HDLC | IGF1 | POMC | WT |
| 7921 | HDLC | IGFBP1 | IL18 | POMC |
| 7922 | HDLC | IGFBP1 | IL6ST | POMC |
| 7923 | HDLC | IGFBP1 | Insulin | POMC |
| 7924 | HDLC | IGFBP1 | LEP | POMC |
| 7925 | HDLC | IGFBP1 | POMC | SBP |
| 7926 | HDLC | IGFBP1 | POMC | Sex |
| 7927 | HDLC | IGFBP1 | POMC | VCAM1 |
| 7928 | HDLC | IGFBP1 | POMC | VEGF |
| 7929 | HDLC | IGFBP3 | IL6ST | POMC |
| 7930 | HDLC | IL18 | IL2RA | POMC |
| 7931 | HDLC | IL18 | IL6ST | POMC |
| 7932 | HDLC | IL18 | INHBA | POMC |
| 7933 | HDLC | IL18 | Insulin | POMC |
| 7934 | HDLC | IL18 | LDL | POMC |
| 7935 | HDLC | IL18 | LEP | POMC |
| 7936 | HDLC | IL18 | PLAT | POMC |
| 7937 | HDLC | IL18 | POMC | SBP |
| 7938 | HDLC | IL18 | POMC | SELE |
| 7939 | HDLC | IL18 | POMC | Sex |
| 7940 | HDLC | IL18 | POMC | VCAM1 |
| 7941 | HDLC | IL18 | POMC | VEGF |
| 7942 | HDLC | IL18 | POMC | WT |
| 7943 | HDLC | IL2RA | IL6ST | POMC |
| 7944 | HDLC | IL2RA | Insulin | POMC |
| 7945 | HDLC | IL2RA | POMC | Sex |

| 4-Panel | Marker 1 | Marker 2 | Marker 3 | Marker 4 |
|---|---|---|---|---|
| 7946 | HDLC | IL6R | IL6ST | POMC |
| 7947 | HDLC | IL6ST | IL8 | POMC |
| 7948 | HDLC | IL6ST | INHBA | POMC |
| 7949 | HDLC | IL6ST | Ins120 | POMC |
| 7950 | HDLC | IL6ST | Insulin | POMC |
| 7951 | HDLC | IL6ST | LDL | POMC |
| 7952 | HDLC | IL6ST | LEP | POMC |
| 7953 | HDLC | IL6ST | PLAT | POMC |
| 7954 | HDLC | IL6ST | POMC | SBP |
| 7955 | HDLC | IL6ST | POMC | SCp |
| 7956 | HDLC | IL6ST | POMC | SELE |
| 7957 | HDLC | IL6ST | POMC | SELP |
| 7958 | HDLC | IL6ST | POMC | Sex |
| 7959 | HDLC | IL6ST | POMC | SHBG |
| 7960 | HDLC | IL6ST | POMC | TNFRSF1B |
| 7961 | HDLC | IL6ST | POMC | TRIG |
| 7962 | HDLC | IL6ST | POMC | VCAM1 |
| 7963 | HDLC | IL6ST | POMC | VEGF |
| 7964 | HDLC | IL6ST | POMC | vWF |
| 7965 | HDLC | IL6ST | POMC | Waist |
| 7966 | HDLC | IL6ST | POMC | WT |
| 7967 | HDLC | IL6ST | POMC | Sex |
| 7968 | HDLC | INHBA | Insulin | POMC |
| 7969 | HDLC | Ins120 | Insulin | POMC |
| 7970 | HDLC | Insulin | LDL | POMC |
| 7971 | HDLC | Insulin | LEP | POMC |
| 7972 | HDLC | Insulin | PLAT | POMC |
| 7973 | HDLC | Insulin | POMC | SBP |
| 7974 | HDLC | Insulin | POMC | SELE |
| 7975 | HDLC | Insulin | POMC | Sex |
| | HDLC | Insulin | POMC | TNFRSF1B |

FIG. 15CCCCCC

| 4-Panel | Marker 1 | Marker 2 | Marker 3 | Marker 4 |
|---|---|---|---|---|
| 7976 | HDLC | Insulin | POMC | VCAM1 |
| 7977 | HDLC | Insulin | POMC | VEGF |
| 7978 | HDLC | Insulin | POMC | WT |
| 7979 | HDLC | LDL | POMC | VEGF |
| 7980 | HDLC | LEP | PLAT | POMC |
| 7981 | HDLC | LEP | POMC | VCAM1 |
| 7982 | HDLC | LEP | POMC | VEGF |
| 7983 | HDLC | PLAT | POMC | Sex |
| 7984 | HDLC | PLAT | POMC | VCAM1 |
| 7985 | HDLC | PLAT | POMC | VEGF |
| 7986 | HDLC | POMC | SBP | VCAM1 |
| 7987 | HDLC | POMC | SBP | VEGF |
| 7988 | HDLC | POMC | SBP | WT |
| 7989 | HDLC | POMC | SCp | VEGF |
| 7990 | HDLC | POMC | Sex | VCAM1 |
| 7991 | HDLC | POMC | Sex | VEGF |
| 7992 | HDLC | POMC | Sex | Waist |
| 7993 | HDLC | POMC | Sex | WT |
| 7994 | HDLC | POMC | SHBG | VEGF |
| 7995 | HDLC | POMC | VCAM1 | VEGF |
| 7996 | HDLC | POMC | VCAM1 | WT |
| 7997 | HDLC | POMC | VEGF | Waist |
| 7998 | HDLC | POMC | VEGF | WT |
| 7999 | HGF | IGF1 | IL6ST | POMC |
| 8000 | HGF | IL6ST | POMC | VEGF |
| 8001 | HGF | POMC | Sex | VEGF |
| 8002 | HGF | POMC | VCAM1 | VEGF |
| 8003 | Hip | IGF1 | IL6ST | POMC |
| 8004 | Hip | IGF1 | POMC | VEGF |
| 8005 | Hip | IL6ST | POMC | VEGF |

| 4-Panel | Marker 1 | Marker 2 | Marker 3 | Marker 4 |
|---|---|---|---|---|
| 8006 | Hip | POMC | Sex | VEGF |
| 8007 | Hip | POMC | VCAM1 | VEGF |
| 8008 | HP | IGF1 | IL6ST | POMC |
| 8009 | HP | IL6ST | POMC | VEGF |
| 8010 | HP | POMC | Sex | VEGF |
| 8011 | HP | POMC | VCAM1 | VEGF |
| 8012 | HT | IGF1 | IL6ST | POMC |
| 8013 | HT | IGF1 | POMC | VCAM1 |
| 8014 | HT | IGF1 | POMC | VEGF |
| 8015 | HT | IL6ST | POMC | VEGF |
| 8016 | HT | POMC | Sex | VEGF |
| 8017 | HT | POMC | VCAM1 | VEGF |
| 8018 | ICAM1 | IGF1 | IL6ST | POMC |
| 8019 | ICAM1 | IL6ST | POMC | VEGF |
| 8020 | ICAM1 | POMC | Sex | VEGF |
| 8021 | ICAM1 | POMC | VCAM1 | VEGF |
| 8022 | IGF1 | IGFBP1 | IL6ST | POMC |
| 8023 | IGF1 | IGFBP1 | POMC | Sex |
| 8024 | IGF1 | IGFBP1 | POMC | VEGF |
| 8025 | IGF1 | IGFBP3 | IL6ST | POMC |
| 8026 | IGF1 | IL18 | IL6ST | POMC |
| 8027 | IGF1 | IL18 | POMC | Sex |
| 8028 | IGF1 | IL18 | POMC | VCAM1 |
| 8029 | IGF1 | IL18 | POMC | VEGF |
| 8030 | IGF1 | IL2RA | IL6ST | POMC |
| 8031 | IGF1 | IL2RA | POMC | Sex |
| 8032 | IGF1 | IL2RA | POMC | VCAM1 |
| 8033 | IGF1 | IL2RA | POMC | VEGF |
| 8034 | IGF1 | IL6R | IL6ST | POMC |
| 8035 | IGF1 | IL6R | POMC | VEGF |

FIG. 15DDDDDD

| 4-Panel | Marker 1 | Marker 2 | Marker 3 | Marker 4 |
|---|---|---|---|---|
| 8036 | IGF1 | IL6ST | IL8 | POMC |
| 8037 | IGF1 | IL6ST | INHBA | POMC |
| 8038 | IGF1 | IL6ST | Ins120 | POMC |
| 8039 | IGF1 | IL6ST | Insulin | POMC |
| 8040 | IGF1 | IL6ST | LDL | POMC |
| 8041 | IGF1 | IL6ST | LEP | POMC |
| 8042 | IGF1 | IL6ST | LEP | VEGF |
| 8043 | IGF1 | IL6ST | LEP | POMC |
| 8044 | IGF1 | IL6ST | PLAT | SBP |
| 8045 | IGF1 | IL6ST | POMC | SCp |
| 8046 | IGF1 | IL6ST | POMC | SELE |
| 8047 | IGF1 | IL6ST | POMC | SELP |
| 8048 | IGF1 | IL6ST | POMC | Sex |
| 8049 | IGF1 | IL6ST | POMC | TNFRSF1B |
| 8050 | IGF1 | IL6ST | POMC | TRIG |
| 8051 | IGF1 | IL6ST | POMC | VCAM1 |
| 8052 | IGF1 | IL6ST | POMC | VEGF |
| 8053 | IGF1 | IL6ST | POMC | VWF |
| 8054 | IGF1 | IL6ST | POMC | Waist |
| 8055 | IGF1 | IL6ST | POMC | WT |
| 8056 | IGF1 | Ins120 | POMC | VEGF |
| 8057 | IGF1 | Insulin | POMC | VEGF |
| 8058 | IGF1 | LEP | POMC | VCAM1 |
| 8059 | IGF1 | LEP | POMC | VEGF |
| 8060 | IGF1 | PLAT | POMC | VEGF |
| 8061 | IGF1 | POMC | SBP | VCAM1 |
| 8062 | IGF1 | POMC | SBP | VEGF |
| 8063 | IGF1 | POMC | Sex | VCAM1 |
| 8064 | IGF1 | POMC | Sex | VEGF |
| 8065 | IGF1 | POMC | Sex | WT |
| 8066 | IGF1 | POMC | SHBG | VEGF |
| 8067 | IGF1 | POMC | TRIG | VEGF |
| 8068 | IGF1 | POMC | VCAM1 | VEGF |
| 8069 | IGF1 | POMC | VEGF | Waist |
| 8070 | IGF1 | POMC | VEGF | WT |
| 8071 | IGFBP1 | IL6ST | POMC | VEGF |
| 8072 | IGFBP1 | POMC | Sex | VCAM1 |
| 8073 | IGFBP1 | POMC | Sex | VEGF |
| 8074 | IGFBP1 | POMC | VCAM1 | VEGF |
| 8075 | IGFBP3 | IL6ST | POMC | VEGF |
| 8076 | IGFBP3 | POMC | Sex | VEGF |
| 8077 | IGFBP3 | POMC | VCAM1 | VEGF |
| 8078 | IL18 | IL6ST | POMC | VEGF |
| 8079 | IL18 | POMC | Sex | VCAM1 |
| 8080 | IL18 | POMC | Sex | VEGF |
| 8081 | IL18 | POMC | VCAM1 | VEGF |
| 8082 | IL2RA | IL6ST | POMC | VEGF |
| 8083 | IL2RA | POMC | Sex | VEGF |
| 8084 | IL2RA | POMC | Sex | VCAM1 |
| 8085 | IL2RA | POMC | VCAM1 | VEGF |
| 8086 | IL6R | IL6ST | POMC | VEGF |
| 8087 | IL6R | LEP | POMC | VEGF |
| 8088 | IL6R | POMC | Sex | VEGF |
| 8089 | IL6ST | IL8 | POMC | VEGF |
| 8090 | IL6ST | INHBA | POMC | VEGF |
| 8091 | IL6ST | Ins120 | POMC | VEGF |
| 8092 | IL6ST | Insulin | POMC | VEGF |
| 8093 | IL6ST | LDL | POMC | VEGF |
| 8094 | IL6ST | LEP | POMC | VCAM1 |
| 8095 | IL6ST | LEP | POMC | VEGF |

FIG. 15EEEEEE

| 4-Panel | Marker 1 | Marker 2 | Marker 3 | Marker 4 |
|---|---|---|---|---|
| 8096 | IL6ST | PLAT | POMC | VEGF |
| 8097 | IL6ST | POMC | SBP | Sex |
| 8098 | IL6ST | POMC | SBP | VEGF |
| 8099 | IL6ST | POMC | SCp | VEGF |
| 8100 | IL6ST | POMC | SELE | VEGF |
| 8101 | IL6ST | POMC | SELP | VEGF |
| 8102 | IL6ST | POMC | Sex | TNFRSF1B |
| 8103 | IL6ST | POMC | Sex | VCAM1 |
| 8104 | IL6ST | POMC | Sex | VEGF |
| 8105 | IL6ST | POMC | Sex | WT |
| 8106 | IL6ST | POMC | SHBG | VEGF |
| 8107 | IL6ST | POMC | TNFRSF1B | VEGF |
| 8108 | IL6ST | POMC | TRIG | VEGF |
| 8109 | IL6ST | POMC | VCAM1 | VEGF |
| 8110 | IL6ST | POMC | VEGF | VWF |
| 8111 | IL6ST | POMC | VEGF | Waist |
| 8112 | IL6ST | POMC | VEGF | WT |
| 8113 | IL8 | POMC | Sex | VEGF |
| 8114 | IL8 | POMC | Sex | VCAM1 |
| 8115 | INHBA | POMC | Sex | VEGF |
| 8116 | INHBA | POMC | Sex | VEGF |
| 8117 | INHBA | POMC | VCAM1 | VEGF |
| 8118 | Ins120 | POMC | Sex | VEGF |
| 8119 | Ins120 | POMC | VCAM1 | VEGF |
| 8120 | Insulin | POMC | SBP | VEGF |
| 8121 | Insulin | POMC | Sex | VEGF |
| 8122 | Insulin | POMC | VCAM1 | VEGF |
| 8123 | LDL | POMC | Sex | VEGF |
| 8124 | LDL | POMC | VCAM1 | VEGF |
| 8125 | LEP | POMC | SBP | VEGF |

| 4-Panel | Marker 1 | Marker 2 | Marker 3 | Marker 4 |
|---|---|---|---|---|
| 8126 | LEP | POMC | Sex | VEGF |
| 8127 | LEP | POMC | TRIG | VEGF |
| 8128 | LEP | POMC | VCAM1 | VEGF |
| 8129 | LEP | POMC | VEGF | VWF |
| 8130 | PLAT | POMC | Sex | VCAM1 |
| 8131 | PLAT | POMC | Sex | VEGF |
| 8132 | PLAT | POMC | VCAM1 | VEGF |
| 8133 | POMC | SBP | Sex | VCAM1 |
| 8134 | POMC | SBP | Sex | VEGF |
| 8135 | POMC | SBP | VCAM1 | VEGF |
| 8136 | POMC | SCp | Sex | VEGF |
| 8137 | POMC | SELE | Sex | VEGF |
| 8138 | POMC | SELE | VCAM1 | VEGF |
| 8139 | POMC | SELP | Sex | VEGF |
| 8140 | POMC | SELP | VCAM1 | VEGF |
| 8141 | POMC | Sex | SHBG | VEGF |
| 8142 | POMC | Sex | TNFRSF1B | VEGF |
| 8143 | POMC | Sex | TRIG | VEGF |
| 8144 | POMC | Sex | VCAM1 | VEGF |
| 8145 | POMC | Sex | VCAM1 | VEGF |
| 8146 | POMC | Sex | VEGF | WT |
| 8147 | POMC | Sex | VEGF | VWF |
| 8148 | POMC | Sex | VEGF | Waist |
| 8149 | POMC | SHBG | VCAM1 | WT |
| 8150 | POMC | TNFRSF1B | VCAM1 | VEGF |
| 8151 | POMC | TRIG | VCAM1 | VEGF |
| 8152 | POMC | VCAM1 | VEGF | VEGF |
| 8153 | POMC | VCAM1 | VEGF | WT |

FIG. 15FFFFFF

FIG. 19A

| Excluding Stroke, Blood | LDA-FWD | LDA-BWD | LDA-SWS | SVMI-KW5 | SVMI-RF9 | LDA-ELDA3 | LDA-ELDA2 | |
|---|---|---|---|---|---|---|---|---|
| ANG | X | X | X | X | X | X | X | 7 |
| APOA1 | | | | | X | | X | 2 |
| APOE | | | | | | | X | 1 |
| C3 | | | | | X | | | 1 |
| CCL2 | X | X | X | | | | | 3 |
| CD14 | | | | | | | X | 1 |
| CD40 | | | | X | | X | X | 3 |
| CRP | X | X | X | | | X | | 4 |
| DPP4 | | X | | | | | | 1 |
| EGF | X | X | X | | | | | 3 |
| FGA | | | | | | | X | 1 |
| FTH1 | X | X | X | | | | | 3 |
| HDLC | X | X | X | | | | X | 4 |
| HGF | | | | | X | | | 1 |
| HP | | | | | | | X | 1 |
| IGF1 | X | X | X | | X | X | X | 6 |
| IGFBP3 | | | | | X | | | 1 |
| IL18 | X | X | X | | | | | 3 |
| IL6R | X | X | X | | | | | 3 |
| IL6ST | X | X | X | | | | X | 4 |
| IL8 | | | | | X | | | 1 |
| Ins120 | X | X | X | | X | | X | 5 |
| LEP | X | X | X | X | X | X | X | 7 |
| POMC | X | X | X | X | | X | X | 6 |
| Sex | | | | | | X | | 1 |
| VCAM1 | X | X | X | | | | X | 4 |
| VEGF | X | X | X | X | | X | X | 6 |
| | 15 | 16 | 15 | 5 | 9 | 8 | 15 | |
| AUC | 0.86 | 0.86 | 0.86 | 0.75 | 0.75 | 0.77 | 0.81 | |

FIG. 19B

| Including Stroke, Blood | LDA-FWD | LDA-BWD | LDA-SWS | SVMi-KW5 | SVMi-RF9 | LDA-ELDA3 | LDA-ELDA2 | |
|---|---|---|---|---|---|---|---|---|
| ANG | | X | | | | X | X | 3 |
| APOA1 | | | | | | | X | 1 |
| APOE | | | | | | | X | 1 |
| C3 | | | | | X | | | 1 |
| CCL2 | X | X | X | | | | X | 4 |
| CD14 | | | | | | X | | 1 |
| CD40 | X | X | X | X | | X | X | 6 |
| CRP | X | X | X | X | | X | X | 6 |
| ENG | | | | | | | X | 1 |
| FGA | | | | | | X | X | 2 |
| FTH1 | X | X | X | | | | | 3 |
| HBA1C | | | | | | | X | 1 |
| HDLC | X | X | X | X | | | X | 5 |
| HGF | | | | | X | | | 1 |
| HP | | | | | | X | X | 2 |
| ICAM1 | X | X | | | | | | 2 |
| IGF1 | X | X | X | | X | X | X | 6 |
| IL6ST | X | X | X | | | X | X | 5 |
| IL8 | | | | | X | | | 1 |
| LEP | | | | | X | | X | 2 |
| PLAT | X | X | | | X | | | 3 |
| POMC | X | X | X | X | | X | | 5 |
| SELE | | | | | X | | | 1 |
| Sex | X | X | X | X | X | X | | 6 |
| SHBG | | | | | X | | | 1 |
| TNFRSF1B | X | X | X | | | | | 3 |
| VCAM1 | X | X | | | | | X | 3 |
| VEGF | X | X | X | | | X | X | 5 |
| | 14 | 15 | 11 | 5 | 9 | 11 | 16 | |
| AUC | 0.87 | 0.87 | 0.84 | 0.78 | NA | 0.80 | 0.82 | |

FIG. 19C

| Excluding Stroke, All | LDA-FWD | LDA-BWD | LDA-SWS | SVMI-KW5 | SVMI-RF9 | LDA-ELDA3 | LDA-ELDA2 | |
|---|---|---|---|---|---|---|---|---|
| ADIPOQ | | | | | X | | | 1 |
| Age | X | X | X | X | | X | X | 6 |
| ANG | X | X | X | X | | | X | 5 |
| APOA1 | | | | | X | | | 1 |
| BMI | X | | X | | | | | 2 |
| C3 | | | | | X | | | 1 |
| CCL2 | X | X | X | | | | | 3 |
| CRP | X | X | | | X | | X | 4 |
| DBP | | | | | X | | | 1 |
| DPP4 | X | X | | | | | | 2 |
| EGF | X | X | X | | | | | 3 |
| FTH1 | X | X | | | | | | 2 |
| HDLC | X | X | X | | | | | 3 |
| HGF | | | | | X | | | 1 |
| IGF1 | X | X | | | | | X | 3 |
| IL18 | X | X | X | | | | | 3 |
| IL2RA | | | | | X | | | 1 |
| IL6R | X | X | | | | | | 2 |
| IL6ST | X | X | X | | | | | 3 |
| Ins120 | X | X | | | | | | 2 |
| Insulin | | X | | | | | | 1 |
| LEP | X | X | | X | X | | X | 5 |
| POMC | X | X | X | X | | | X | 5 |
| Sex | X | | | | | | X | 2 |
| TNFRSF1B | | | | | X | | | 1 |
| VCAM1 | X | X | | | | | | 2 |
| VEGF | X | X | X | X | | | X | 5 |
| | 19 | 18 | 10 | 5 | 9 | 1 | 8 | |
| AUC | 0.90 | 0.89 | 0.88 | 0.80 | 0.74 | 0.72 | 0.80 | |

FIG. 19D

| Including Stroke, All | LDA-FWD | LDA-BWD | LDA-SWS | SVMI-KW5 | SVMI-RF9 | LDA-ELDA3 | LDA-ELDA2 | |
|---|---|---|---|---|---|---|---|---|
| Age | X | X | X | X | | X | X | 6 |
| ANG | | | | | | | X | 1 |
| C3 | | | | | X | | | 1 |
| CCL2 | X | X | X | | | | | 3 |
| CD40 | | X | | X | | | X | 3 |
| CDK5 | | X | | | | | | 1 |
| CRP | X | X | X | | | | X | 4 |
| FTH1 | X | X | X | | | | | 3 |
| Glucose | | | | | X | | | 1 |
| HDLC | X | X | X | X | | | | 4 |
| HGF | | | | | X | | | 1 |
| HP | | | | | | | X | 1 |
| HT | | | | | | | X | 1 |
| ICAM1 | | X | | | | | | 1 |
| IGF1 | X | X | X | | X | | X | 5 |
| IL18 | X | | | | | | | 1 |
| IL6ST | X | X | X | | | | X | 4 |
| IL8 | | | | | X | | | 1 |
| Ins120 | | | | | X | | | 1 |
| LEP | X | | | | X | | X | 3 |
| POMC | X | X | X | X | | | X | 5 |
| Sex | X | X | X | X | | X | X | 6 |
| SHBG | | | | | X | | | 1 |
| TNFRSF1B | X | X | X | | | | | 3 |
| VEGF | X | X | X | | | | X | 4 |
| VWF | | | | | X | | | 1 |
| | 13 | 14 | 11 | 5 | 9 | 2 | 12 | |
| AUC | 0.85 | 0.87 | 0.85 | 0.80 | NA | 0.73 | 0.81 | |

MARKERS ASSOCIATED WITH ARTERIOVASCULAR EVENTS AND METHODS OF USE THEREOF

INCORPORATION BY REFERENCE

This is a continuation of application Ser. No. 12/755,146, filed Apr. 6, 2010, which is a continuation of application Ser. No. 11/811,441, filed Jun. 7, 2007 and claims the benefit of U.S. Provisional Application Ser. No. 60/811,996, filed on Jun. 7, 2006. Each of the applications and patents cited in this text, as well as each document or reference cited in each of the applications and patents (including during the prosecution of each issued patent; "application cited documents"), and each of the U.S. and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference. Documents incorporated by reference into this text may be employed in the practice of the invention.

FIELD OF THE INVENTION

The present invention relates generally to the identification of biological markers associated with arteriovascular events and methods of using such biological markers in screening, prevention, diagnosis, therapy, monitoring, and prognosis of arteriovascular disease.

BACKGROUND OF THE INVENTION

Arteriovascular disease continues to be a leading cause of morbidity and mortality among adults in Europe and North America. Although age-adjusted death rates have declined over the past two decades, the absolute mortality rate from arteriovascular disease has not. Arteriovascular disease accounts for over one-half million deaths (1 out of every 5) in the U.S. yearly. The lifetime risk of arteriovascular disease after age 40 has been estimated at 49% for men and 32% for women. Even for those who survive to age 70 years, the lifetime risk for arteriovascular disease has been estimated at 35% for men and 24% for women. Arteriovascular diseases include atherosclerosis and atherothrombosis, coronary artery disease (CAD), peripheral artery disease (PAD), and cerebrovascular disease (CVD).

Risk factors for arteriovascular disease currently account for a large proportion of the burden of heart disease in the United States, suggesting that risk-factor identification and risk-lowering treatments could postpone or prevent the majority of arteriovascular events. Identified risk factors for arteriovascular disease include independent risk factors, such as cigarette smoking, elevated blood pressure (hypertension), elevated serum total cholesterol (CHOL) and low-density lipoprotein (LDL) cholesterol, low serum high-density lipoprotein (HDL) cholesterol, diabetes mellitus, and advancing age. Conditional risk factors for arteriovascular disease include elevated serum triglycerides (TRIG), small LDL particles, elevated serum homocysteine levels, elevated serum lipoprotein (a) (LPA), prothrombotic factors such as fibrinogen (FGA), and inflammatory markers like C-reactive protein (CRP), whose contribution to risk may vary upon their relationship to other identified risk factors. Other risk factors include obesity (measured by weight (WT), height (HT), Body Mass Index (BMI), and abdominal girth comparisons such as waist ("Waist") or hip ("Hip") circumference, ankle-brachial index, physical inactivity, family history of arteriovascular disease, ethnicity, and psychosocial factors. Arteriovascular disease risk factors have been the subject of many studies, including those presented in Pasternak, R. C. et al (2003) JACC 41(11): 1855-1917 and Grundy, S. M. (1999) Circulation 100: 988-998.

Typically, a patient suspected of having arteriovascular disease is assessed on several of the "traditional" or "conventional" risk factors: age, sex, total cholesterol concentration, HDL and LDL cholesterol concentration, smoking status, diabetic status, and blood pressure (systolic and diastolic), as well as many of the above conditional risk factors, such as LPA, FGA, CRP, and homocysteine, amongst others. These risk factors have been incorporated into useful predictive models of future arteriovascular events, such as the Framingham Risk Score presented in Wilson, P. W, et al (1998) Circulation 97: 1837-1847, however this "evidence-based" multiple risk factor or "global risk assessment" approach is only moderately accurate for predicting short- and long-term risk of manifesting a major arteriovascular event, particularly an event such as acute coronary syndromes (ACS, comprising myocardial infarction and unstable angina), stroke or sudden death, in healthy populations or asymptomatic individuals. In particular, while such approaches may, at typical clinical measurement cut-off levels, be relatively sensitive to individuals who have multiple risk factors, experienced past arteriovascular events or who have already confirmed arteriovascular disease (who would be "true positives" if they subsequently experience an acute arteriovascular event), they suffer from specificity, also identifying large portions of the population who do not subsequently experience acute arteriovascular events ("false positives"). In the typical adult population, these algorithms yield many more false positives than true positives, particularly in the low (<6% ten year risk of an acute event) and intermediate risk (6-20% ten year risk of an acute event) populations that make up the majority of those tested. While performance metrics for global risk assessment indices may evidence high clinical utility in the population in which the index algorithm was trained, occasionally exhibiting an AUC as high as 0.8, but more commonly an AUC around 0.7 (Wilson et al. above reported 0.74 for men and 0.77 for females for the Framingham Risk Score), such predictive models show relatively low transferability between populations, which may differ based on genetic and other factors, and absent substantial recalibration and re-optimization, often the AUC will drop to below 0.65, as shown in the example. They also are often difficult for clinicians to effectively implement and perform within an active clinical environment, involving complex calculations and numerical manipulations.

Thus, the general concept of applying one or more biomarkers to the task of classifying current and predicting future arteriovascular disease or risk of future arteriovascular events is not new in the clinical practice, literature or patent art. Several specific biomarkers, biomarker combinations, and methods have been proposed over time, with limited adoption to date due to several issues including technical difficulty, analytical performance, clinical performance, reliability, and practical clinician application of complex algorithms combining more than one such biomarker. By way of example, Ridker, P. et al. in U.S. Pat. No. 6,040,147 dated Mar. 21, 2000, suggested the use of a marker of systemic inflammation (including the use of CRP, a cytokine or a cellular adhesion marker such as soluble ICAM-1) could be useful in assessing the risk profile of an apparently healthy individuals risk profile for developing a future myocardial infarction, either alone or in combination with traditional risk factors such as CHOL or HDLC; such use of CRP has now become routine. Schönbeck, U. et al., in U.S. Pat. No. 7,189,518 B2 dated Mar. 13, 2007, suggested similar usage for soluble CD40 ligand (CD40LG) in predicting future cardiovascular disorders, such as myocardial infarction or stroke, in apparently healthy individuals; this has not been clinically adopted due to inadequate performance as a single marker. Anderson, L. (2004) in J. Physiological Society 563.1: 23-60, suggested 177 individual candidate biomarker proteins with reported associations to cardiovascular disease and stroke that might be of use in constructing panels of disease-related proteins for several applications, including the anticipation of future myocardial infarction or stroke, if it were found that several of the biomarkers were independent and not strongly correlated with each other, and thus able to be combined together into panels and "composite indices" more useful than the information gathered from the single biomarkers used individually; beyond referencing the previously mentioned relationships with CRP and cholesterol, no such useful individual panel involving was disclosed by Anderson, and several technical barriers and shortcomings of existing multi-marker analytical techniques in future discovery of such multi-marker associations were mentioned. Puskas, R. et al., in US Patent Publication 2006/0078998 A1 published Apr. 13, 2006, disclosed an technical technique useful for such single or multiplexed biomarker single molecule counting in samples, and mentions a wide analytical range of potential biomarkers and functional biomarker groupings potentially useful in multiple diseases, including cardiovascular disease; no specific combination of biomarkers for predicting the future risk of arteriovascular events was mentioned, nor were all of the individual biomarkers of the current invention disclosed therein.

Tabibiazar, R. et al., in US Patent Publication 2007/0070099239 A1 published May 3, 2007, disclosed the use of several specific panels of biomarkers combined with various algorithms and analytical processes, in the discrimination and classification of atherosclerotic patients with past acute myocardial infarction from such patients with known stable cardiovascular disease, from those with no history of cardiovascular disease or atherosclerosis, or amongst various classification of atherosclerotic staging and current medication use within known atherosclerotic patients. Although various "predictive" algorithms are mentioned therein, and the suggestion made that certain of such disclosed biomarker panels may be useful in the prediction of future cardiovascular events, no specific panel for prediction of future cardiovascular events or future cardiovascular status tested within an asymptomatic and previously undiagnosed population is disclosed. Nor is such clearly claimed in the application as filed, nor are any examples given within the published patent of study designs involving the measurement of apparently healthy and asymptomatic individuals prior to known cardiovascular events (or confirmed symptoms and/or diagnosed atherosclerosis) and then subsequently following their health status for a sufficient longitudinal time period allowing the development of subsequent cardiovascular events. Although certain of the individual panels of biomarkers disclosed therein may be useful in such applications, it is unlikely that the panels, algorithms and analytical processes disclosed therein, selected and trained on past events and known symptomatic disease, will successfully predict the future risk of cardiovascular events in asymptomatic and previously undiagnosed subjects with as high a degree of diagnostic accuracy as is presented and claimed in Tabibiazar over a specific multi-year time horizon, absent substantial and predictive model re-training, re-modeling, optimization and re-purposing likely not possible absent inputs from such longitudinal studies, which may include changes to cutoffs, reference values and other formula. Although overlap of certain individual biomarkers disclosed in Tabibiazar with individual biomarkers and a subset of the panels of the current invention is acknowledged, each of the individual biomarkers mentioned in Tabibiazar which are also claimed herein in specific panel combinations of the current invention (and specifically CCL2, IGF1, LEP, VEGF, and IL8) were also previously disclosed in the prior published art as associated with cardiovascular disease (each of them were notably mentioned and reviewed in the aforementioned Anderson reference, amongst others). Such specific clinical applications, additional biomarkers, specific biomarker combination panels, study designs, and analytical techniques and formula are key aspects of the current invention.

Recently, several studies in the scientific literature have been published examining various individual and multiple biomarker strategies, most notably Folsom, A. R. et al. (2006) Arch. Intern Med 166:1368-1373 and Wang, T. J. et al. (2006) N Eng J Med 355: 2631-2639. These studies, utilizing retrospective samples from longitudinal clinical studies such as the Atherosclerosis Risk in Communities Study and the Framingham Heart Study, combined subject clinical parameters and traditional laboratory risk factors (including using such traditional laboratory based biomarkers such as CHOL, CRP, FGA, HDLC, LPA, and Homocysteine), as well as novel markers such as Albumin-to-creatine ratios, Aldosterone, ANP (NPPA), BNP (NPPB), D-dimer, ICAM1, IL6, LEP, MMP1, PLA2G7, PLAT, PLG, REN, SELE, SERPINE1, TIMP1, THBD, amongst others, both as individual markers and incrementally as additions to multi-marker indices. Both studies found little improvement in the ability to predict future arteriovascular events with novel markers over the models incorporating the basic clinical parameters and traditional laboratory risk factors. As a result, the use of such novel markers remains clinically controversial.

Given the foregoing, it is clear that an important discrepancy has arisen in understanding the role of the aforementioned risk factors and biomarkers compared to the development of arteriovascular disease events. In contrast to the relative ease of recognition and clarity of treatment and prevention strategies in patients with symptomatic arteriovascular disease (i.e., exhibit symptoms such as active chest pain, claudication, transient ischemic attacks (TIAs) or mild cognitive impairment (MCI), a major problem of detection, treatment, and prevention of arteriovascular disease exists in the large, apparently healthy, population who have no symptoms, yet are at an increased risk to develop arteriovascular disease or experience major arteriovascular events. A large number of victims of the disease who are apparently healthy die or have initial acute arteriovascular events suddenly without prior symptoms. Despite the many available risk assessment approaches, a substantial gap remains in the detection of asymptomatic individuals who ultimately develop arteriovascular disease. Currently available screening and diagnostic methods are insufficient to identify asymptomatic individuals before such acute events associated with arteriovascular disease occur. Of those who experience a major arteriovascular event as many as 20% have none of the traditional risk factors. There remains an unmet need in the art to directly diagnose and predict the risk of arteriovascular disease and events, particularly in those individuals who do not exhibit symptoms or few or none of the traditional risk factors currently measured by physicians.

All of the foregoing references, including Tabibiazar, are herein referred to and incorporated in their entirety.

SUMMARY OF THE INVENTION

The present invention relates in part to the discovery that certain biological markers, such as proteins, nucleic acids, polymorphisms, metabolites, and other analytes, as well as certain physiological conditions and states, are present in subjects with an increased risk of arteriovascular events, such as, but not limited to, acute coronary syndromes such as myocardial infarction and unstable angina, as well as other acute events associated with an arteriovascular disease, including those associated with atherosclerosis, atherothrombosis, coronary artery disease (CAD), peripheral artery disease (PAD), and cerebrovascular disease (CVD), but where such subjects do not exhibit some or all of the traditional risk factors of these diseases, or subjects who are asymptomatic for these diseases.

Accordingly, the invention provides biological markers of arteriovascular events that, when used together in combinations of three or more such biomarker combinations, or "panels," can be used to assess the risk of subjects experiencing said arteriovascular events, to diagnose or identify subjects with an arteriovascular disease, to monitor the risk factors for development of an arteriovascular disease, to monitor subjects that are undergoing therapies for an arteriovascular disease, to differentially diagnose disease states associated with an arteriovascular disease from other diseases or within sub-classifications of arteriovascular diseases, to evaluate changes in the risk of arteriovascular events in subjects with an arteriovascular disease, and to select or modify therapies or interventions for use in treating subjects with an arteriovascular disease, or for use in subjects who are at risk for developing an arteriovascular disease.

An aspect of the present invention provides use of a panel of biological markers, some of which are unrelated to arteriovascular disease or have not heretofore been identified as related to the risk of future arteriovascular disease or events, but are related to early biological changes that can lead to the development of arteriovascular disease or arteriovascular events, to detect and identify subjects who exhibit none of the symptoms or few or none of the traditional risk factors for arteriovascular disease, i.e., who are asymptomatic for arteriovascular disease and have only non-specific indicators of potential arteriovascular events, such as arteriovascular risk factors, or who exhibit none or few of the traditional risk factors of arteriovascular disease, yet remain at risk.

Significantly, many of the individual biomarkers disclosed herein have shown little individual significance in the diagnosis of arteriovascular disease, or individually for assessing the risk of arteriovascular disease or events, but when used in combination with other disclosed biomarkers and combined with the various herein disclosed algorithms, traditional laboratory risk factors of arteriovascular disease, and other clinical parameters of arteriovascular disease, become significant discriminates of a subject having arteriovascular disease or a subject who is at risk for developing an arteriovascular event, from one who is not at risk for arteriovascular disease or is not at significant risk of developing arteriovascular disease or an arteriovascular event. The Methods of the present invention provide an improvement over currently available methods of risk evaluation of the development of arteriovascular disease and/or arteriovascular events in a subject by measurement of the biomarkers defined herein.

Accordingly, in certain embodiments an aspect of the invention is directed to a method for assessing a risk of developing an arteriovascular disease in a subject. In certain embodiments, the method allows for assessing risk with a predetermined level of predictability. In certain embodiments, the method includes, measuring a level of an effective amount of two or more ARTERIORISKMARKERS. For instance, the ARTERIORISKMARKERS may include one or more of the ARTERIORISKMARKERS 1-1023, which markers are in a sample obtained from the subject. In certain embodiments, the level of expression of five or more, ten or more, twenty-five or more, or fifty or more ARTERIORISKMARKERS are measured. The method may further include measuring a clinically significant alteration in the level of the two or more ARTERIORISKMARKERS in the sample, for instance, where the alteration indicates an increased risk of developing an arteriovascular disease in the subject.

In certain embodiments, an aspect of the subject invention is directed to a method of diagnosing or identifying a subject having an arteriovascular disease. In certain embodiments, the method allows for assessing risk with a predetermined level of predictability. In certain embodiments, the method includes measuring the level of an effective amount of two or more ARTERIORISKMARKERS that are selected from ARTERIORISKMARKERS 1-1023 in a sample from the subject. The method may further include comparing the level of the effective amount of the two or more ARTERIORISKMARKERS to a reference value. The reference value may be an index value or may be may be derived from one or more risk prediction algorithms or computed indices for the arteriovascular disease.

In certain embodiments, an aspect of the subject invention is directed to a method for assessing the progression of an arteriovascular disease in a subject. In certain embodiments, the method allows for assessing the progression of an arteriovascular disease in a subject with a predetermined level of predictability. In certain embodiments, the method includes detecting the level of an effective amount of two or more ARTERIORISKMARKERS selected from ARTERIORISKMARKERS 1-1023 in a first sample from the subject at a first period of time, detecting the level of an effective amount of two or more ARTERIORISKMARKERS in a second sample from the subject at a second period of time, and comparing the level of the effective amount of the two or more ARTERIORISKMARKERS detected in the first step to the amount detected in second step, or to a reference value. In certain embodiments, the first sample is taken from the subject prior to being treated for the arteriovascular disease and/or the second sample is taken from the subject after being treated for the arteriovascular disease. Further, in certain embodiments, the reference value is derived from one or more subjects who have suffered from an arteriovascular event.

In certain embodiments, an aspect of the subject invention is directed to a method for monitoring the effectiveness of treatment for an arteriovascular disease. In certain embodiments, the method allows for monitoring the effectiveness of treatment for an arteriovascular disease in a subject with a predetermined level of predictability. In certain embodiments, the method includes detecting the level of an effective amount of two or more ARTERIORISKMARKERS selected from ARTERIORISKMARKERS 1-1023 in a first sample from a subject at a first period of time; detecting the level of an effective amount of two or more ARTERIORISKMARKERS in a second sample from the subject at a second period of time; and comparing the level of the effective amount of the two or more ARTERIORISKMARKERS detected in the first step to the amount detected in the second step, or to a reference value, wherein the effectiveness of treatment is monitored by a change in the level of the effective amount of two or more ARTERIORISKMARKERS from the subject. In certain embodiments, the treatment for the arteriovascular disease to be monitored includes exercise regimens, dietary supplements, therapeutic agents, surgical intervention, and prophylactic agents. In certain embodiments, the effectiveness of treatment is additionally monitored by detecting changes in body mass index (BMI), total cholesterol levels, LDL levels, HDL levels, systolic and/or diastolic blood pressure, or combinations thereof. Further, the reference value is derived from one or more subjects who show an improvement in arteriovascular risk factors as a result of one or more treatments for arteriovascular disease.

In certain embodiments, an aspect of the subject invention is directed to a method for selecting a treatment regimen for a subject diagnosed with or at risk for an arteriovascular disease. In certain embodiments, the method allows for selecting a treatment regimen for a subject diagnosed with or at risk for an arteriovascular disease with a predetermined level of predictability. In certain embodiments, the method includes detecting the level of an effective amount of two or more ARTERIORISKMARKERS selected from ARTERIORISKMARKERS 1-1023 in a first sample from the subject at a first period of time, optionally detecting the level of an effective amount of two or more ARTERIORISKMARKERS in a second sample from the subject at a second period of time and comparing the level of the effective amount of the two or more ARTERIORISKMARKERS detected in the first step to a reference value, or optionally to an amount detected in the second step. In certain embodiments, the reference value is derived from one or more subjects who show an improvement in arteriovascular disease risk factors as a result of one or more treatments for the arteriovascular disease. For instance, the improvement may be monitored by an imaging modality, by detecting a reduction in body mass index (BMI), a reduction in total cholesterol levels, a reduction in LDL levels, an increase in HDL levels, a reduction in systolic and/or diastolic blood pressure, or combinations thereof. In certain embodiments, the imaging modality may include one or more of: computed tomography (CT), optical coherence tomography (OCT), intravascular ultrasonography (IVUS), high-resolution IVUS, elastography (palpography), angioscopy, electron beam computed tomography (EBCT), magnetic resonance imaging (MRI), positron emission tomography (PET), single photon emission computed tomography (SPECT), immunoscintigraphy, and invasive angiography.

In certain embodiments, an aspect of the subject invention is directed to a method for treating one or more subjects at risk for developing an arteriovascular disease. In certain embodiments, the method includes, detecting the presence of increased levels of at least two different ARTERIORISKMARKERS that are present in a sample from the one or more subjects; and treating the one or more subjects. For instance, the one or more subjects may be treated with one or more arteriovascular disease-modulating drugs until altered levels of the at least two different ARTERIORISKMARKERS return to a baseline value measured in one or more subjects at low risk for developing the arteriovascular disease, or a baseline value measured in one or more subjects who show improvements in arteriovascular risk markers as a result of treatment with one or more arteriovascular disease-modulating drugs. In certain embodiments, the arteriovascular disease-modulating drug comprises β-blockers, angiotensin-converting enzyme (ACE) inhibitors, diuretics, calcium channel blockers, angiotensin II receptor blockers, antiplatelet agents, anti-coagulant agents, sulfonylureas, biguanides, insulin, thiazolidinediones, nitrates, non-steroidal anti-inflammatory agents, statins, cilostazol, pentoxifylline, buflomedil, naftidrofuryl, and combinations thereof. Additionally, the improvements in arteriovascular risk markers may be as a result of treatment with the one or more arteriovascular disease-modulating drugs and may include a reduction in body mass index (BMI), a reduction in total cholesterol levels, a reduction in LDL levels, an increase in HDL levels, a reduction in systolic and/or diastolic blood pressure, or combinations thereof.

In certain embodiments, an aspect of the subject invention is directed to a method of differentially diagnosing disease states associated with an arteriovascular disease in a subject. In certain embodiments, the method includes detecting the level of an effective amount of two or more ARTERIORISKMARKERS selected from ARTERIORISKMARKERS 1-1023 in a sample from the subject; and comparing the level of the effective amount of the two or more ARTERIORISKMARKERS detected in the first step to a arteriovascular disease subject expression profile, or to a reference value.

The arteriovascular disease may include a metabolic syndrome, Syndrome X, atherosclerosis, atherothrombosis, coronary artery disease, heart valve disease, arrhythmia, angina pectoris, cardiomyopathy, congestive heart failure, hypertension, orthostatic hypotension, shock, endocarditis, aortic stenosis, peripheral artery disease, cerebrovascular disease, and/or congenital heart disease. The arteriovascular disease may be measured by any method well known in the art, for instance, such as electrophoretically or immunochemically, for instance, by radio-immunoassay, immunofluorescence assay or by an enzyme-linked immunosorbent assay. Additionally, the level of ARTERIORISKMARKERS may be measured by specific oligonucleotide hybridization.

The subject maybe a subject that has not been previously diagnosed or identified as having or suffering from the arteriovascular disease or the subject may be one that is asymptomatic for the arteriovascular disease. Further, the subject may be one that has previously been identified and/or treated or has not previously been identified and/or treated for the arteriovascular disease. Additionally, the sample may be obtained by any means known in the art and may be serum, blood plasma, blood cells, endothelial cells, tissue biopsies, ascites fluid, bone marrow, interstitial fluid, sputum, urine, or the like.

In certain embodiments, an aspect of the subject invention is directed to a method for assessing a risk of plaque development in a subject. In certain embodiments, the method allows for assessing risk with a predetermined level of predictability. In certain embodiments, the method includes measuring the level of an effective amount of two or more ARTERIORISKMARKERS, such as 1-1023, in a sample from the subject. The method may further include measuring a clinically significant alteration in the level of the two or more ARTERIORISKMARKERS in the sample, for instance, wherein the alteration indicates an increased risk of developing a plaque in the subject. In certain embodiments, the subject has not been previously diagnosed as having a plaque, while in other embodiments the subject is asymptomatic for the plaque.

In certain embodiments, an aspect of the subject invention is directed to a method of diagnosing or identifying a subject having a plaque. In certain embodiments, the method allows for diagnosing or identifying a subject having a plaque with a predetermined level of predictability. In certain embodiments, the method includes measuring the level of an effective amount of two or more ARTERIORISKMARKERS selected from ARTERIORISKMARKERS 1-1023 in a sample from the subject. The method may further include comparing the level of the effective amount of the two or more ARTERIORISKMARKERS to a reference value. In certain embodiments, the reference value is an index value and in other embodiments, the reference value is derived from one or more risk prediction algorithms or computed indices for plaque development.

In certain embodiments, an aspect of the subject invention is directed to a method for assessing the progression of a plaque formation that associated with atherosclerosis or atherothrombosis in a subject. In certain embodiments, the method allows for assessing the progression of a plaque formation that associated with atherosclerosis or atherothrombosis in a subject with a predetermined level of predictability. In certain embodiments, the method includes detecting the level of an effective amount of two or more ARTERIORISKMARKERS selected from ARTERIORISKMARKERS 1-1023 in a first sample from the subject at a first period of time; detecting a level of an effective amount of two or more ARTERIORISKMARKERS in a second sample from the subject at a second period of time; and comparing the level of the effective amount of the two or more ARTERIORISKMARKERS detected in the first step to the amount detected in the second step, or to a reference value. In certain embodiments, the reference value is derived from one or more subjects who have suffered from plaque rupture.

In certain embodiments, an aspect of the subject invention is directed to a method for evaluating changes in the risk of plaque formation in a subject diagnosed with or at risk for developing atherosclerosis or atherothrombosis. In certain embodiments, the method includes detecting the level of an effective amount of two or more ARTERIORISKMARKERS selected from ARTERIORISKMARKERS 1-1023 in a first sample from the subject at a first period of time; optionally detecting the level of an effective amount of two or more ARTERIORISKMARKERS in a second sample from the subject at a second period of time; and comparing the level of the effective amount of the two or more ARTERIORISKMARKERS detected in the first step to a reference value, or optionally, to the amount in the second step. In certain embodiments, the first sample is taken from the subject prior to being treated for the atherosclerosis or atherothrombosis and/or the second sample is taken from the subject after being treated for the atherosclerosis or atherothrombosis. Additionally, in certain embodiments, the treatment for atherosclerosis or atherothrombosis comprises exercise regimens, dietary supplements, therapeutic agents, surgical intervention, and prophylactic agents. Furthermore, in certain embodiments, the reference value is derived from one or more subjects who have suffered from plaque rupture.

In certain embodiments, the subject is suffering from atherosclerosis or atherothrombosis. In certain embodiments, the subject may or may not have been previously diagnosed or identified as having a plaque, suffering from atherosclerosis and/or atherothrombosis; and/or may or may not have been previously treated for atherosclerosis or atherothrombosis. Further, the subject may be asymptomatic for the plaque, atherosclerosis or atherothrombosis. In certain embodiments, the first sample is taken from the subject prior to being treated for the atherosclerosis or atherothrombosis and/or the second sample is taken from the subject after being treated for the atherosclerosis or atherothrombosis.

In certain embodiments, an aspect of the subject invention is directed to an arteriovascular disease reference expression profile that includes a pattern of marker levels of an effective amount of two or more markers selected from ARTERIORISKMARKERS 1-1023, which is taken from one or more subjects who do not have the arteriovascular disease. In certain embodiments, the subject invention is directed to an atherosclerosis or atherothrombosis reference expression profile that includes a pattern of marker levels of an effective amount of two or more markers selected from ARTERIORISKMARKERS 1-1023, which are taken from one or more subjects who do not have atherosclerosis or atherothrombosis. In certain embodiments, the subject invention is directed to an arteriovascular disease subject expression profile, that includes a pattern of marker levels of an effective amount of two or more markers selected from ARTERIORISKMARKERS 1-1023, which are taken from one or more subjects who have the arteriovascular disease, are at risk for developing the arteriovascular disease, or are being treated for the arteriovascular disease. In certain embodiments, the subject invention is directed to an atherosclerosis or atherothrombosis subject expression profile, that includes a pattern of marker levels of an effective amount of two ore more markers selected from ARTERIORISKMARKERS 1-1023, which are taken from one or more subjects who have atherosclerosis or atherothrombosis and maybe at risk for developing atherosclerosis or atherothrombosis, or may be being treated for atherosclerosis or atherothrombosis.

In certain embodiments, an aspect of the subject invention is directed to an array that includes a plurality of ARTERIORISKMARKER detection reagents, which detect the corresponding ARTERIORISKMARKERS selected from ARTERIORISKMARKERS 1-1023, and are sufficient to generate a profile(s). In certain embodiments, the detection reagent includes one or more antibodies or fragments thereof, one or more oligonucleotides, one or more aptamers, one or more arteriovascular disease reference expression profiles and/or optionally, additional test results and subject information. In certain embodiments, an aspect of the subject invention is directed to a machine readable media containing one or more of the atherosclerosis or atherothrombosis reference expression profiles and optionally, additional test results and subject information. In certain embodiments, an aspect of the subject invention is directed to a method of tracking a subject's status that includes collecting an arteriovascular disease reference expression profile and reporting the expression profile to a center.

In certain embodiments, an aspect of the subject invention is directed to an ARTERIORISKMARKER panel. In certain embodiments, the one or more ARTERIORISKMARKERS are indicative of a physiological pathway associated with an arteriovascular disease. In certain embodiments, the physiological pathway comprises inflammation, platelet aggregation, apoptosis, angiogenesis, lipid metabolism, necrosis, or vascular calcification.

In certain embodiments, an aspect of the subject invention is directed to an ARTERIORISKMARKER panel that includes one or more ARTERIORISKMARKERS that are indicative of a site associated with an arteriovascular disease. In certain embodiments, the site includes one or more coronary arteries, peripheral arteries, or cerebrovascular arteries.

In certain embodiments, an aspect of the subject invention is directed to an ARTERIORISKMARKER panel that includes one or more ARTERIORISKMARKERS that are indicative of the progression of an arteriovascular disease.

In certain embodiments, an aspect of the subject invention is directed to an ARTERIORISKMARKER panel that includes one or more ARTERIORISKMARKERS that are indicative of the speed of progression of an arteriovascular disease.

In certain embodiments, an aspect of the subject invention is directed to an ARTERIORISKMARKER panel that includes one or more ARTERIORISKMARKERS that are specific to one or more arteriovascular diseases.

In certain embodiments, an aspect of the subject invention is directed to a method of evaluating changes in the risk of an arteriovascular event in a subject diagnosed with an arteriovascular disease. The method includes detecting the level of an effective amount of two or more ARTERIORISKMARKERS selected from ARTERIORISKMARKERS 1-1023 in a first sample from the subject at a first period of time; optionally detecting the level of an effective amount of two or more ARTERIORISKMARKERS in a second sample from the subject at a second period of time and comparing the level of the effective amount of the two or more ARTERIORISKMARKERS detected in the first step to a reference value, or optionally, to the amount in the second step.

In certain embodiments, the subject has previously been treated for the arteriovascular disease. In certain embodiments, the subject is asymptomatic for the arteriovascular disease. In certain embodiments, the first sample is taken from the subject prior to being treated for the arteriovascular disease and/or the second sample is taken from the subject after being treated for the arteriovascular disease. In certain embodiments, the reference value is derived from one or more subjects who have suffered from an arteriovascular event. In certain embodiments, the arteriovascular event includes plaque rupture, myocardial infarction, unstable angina, blood clots of the leg, stroke, or aneurysm.

Aspects of the invention include methods for evaluating the risk of a cardiovascular event for a subject. In certain embodiments, the method comprises measuring at least three component ARTERIORISKMARKERS for the individual selected from the component ARTERIORISKMARKERS within the groups consisting of Core Markers I, Core Markers II, Traditional Laboratory Risk Factors, Clinical Parameters, Supplemental Markers I, and Supplemental Markers II, provided at least one component ARTERIORISKMARKER is selected from the component ARTERIORISKMARKERS within Core Markers I. In a further embodiment, the method comprises any combination comprising at least two or more component ARTERIORISKMARKERS, providing at least two of such are selected from within Core Markers I.

In certain aspects, we contemplate the use of POMC alone, while in other aspects POMC is used with other markers. In some embodiments, POMC is measured by itself and in other embodiments, POMC is used with markers selected from the group comprising HDLC, VEGF, CCL2, IL6ST, IL8, and LEP. In another embodiment, POMC is measured along with an additional clinical parameter. In certain embodiments, the additional parameters are selected from Age or BMI. In another embodiment, the invention includes a kit comprising at least one reagent for the detection or quantification of POMC.

In a particular preferred embodiment, the invention relates to the use of four or more biomarkers from a given subject, with three or more of such biomarkers measured in samples from the subject, and two or more of such markers chosen from a set including angiogenin (ANG), CD40 molecule aka TNF receptor superfamily member 5 (CD40), dipeptidyl-peptidase 4 aka CD26 (DPP4), interleukin 6 signal transducer (IL6ST), proopiomelanocortin aka adrenocorticotropin/beta-lipotropin/alpha-melanocyte stimulating hormone/beta-melanocyte stimulating hormone/beta-endorphin (POMC), vascular cell adhesion molecule 1 (VCAM1), monocyte chemoattractant protein-1 aka MCP-1 (CCL2), insulin-like growth factor 1 aka somatomedin C(IGF1), leptin (LEP), vascular endothelial growth factor A (VEGF), and a third or more additional biomarker measurements optionally chosen from any of the subject's clinical parameters, traditional laboratory risk factors (including, without limitation, any ARTERIORISKMARKERS or other biomarkers, identified herein), in the subject's sample. These four or more biomarkers are combined together by a mathematical process or formula into a single number reflecting the subject's risk for developing an arteriovascular event, or for use in selecting, tailoring, and monitoring effectiveness of various therapeutic interventions, such as treatment of subjects with arteriovascular disease and risk modulating drugs, for said conditions.

Another embodiment is a method of performance improvement to an existing combination of biomarkers used in multi-biomarker global risk assessment of a patient, and in particular combinations drawing three or more biomarker from the combined groups of Traditional Laboratory Risk Factors and Clinical Parameters, wherein that improvement comprises the addition of at least one, of the ARTERIORISKMARKERS chosen from the groups of Core Markers I or Core Markers 2, and the combination of the results in a new analytical process. For example, the invention would cover the addition of POMC to the Framingham Risk Score, or of LEP to a risk factor counting algorithm for the multiple criterias defining metabolic syndrome under NCEP ATP III, or other existing clinical algorithm using the three or more such biomarkers, including the combination of Age, BMI, and CHOL, as well as the combination of such modifiable risk factors as LDL, HDLC, TRIG, CHOL, together with those of SBP, DBP, and Glucose, where such was combined using an analytical process.

Additional biomarkers beyond any of the starting amounts of biomarkers cited in these preceding preferred embodiments may also be added to the panel from any of ARTERIORISKMARKERS, clinical parameters, and traditional laboratory risk factors.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

BRIEF DESCRIPTION OF THE DRAWINGS

The following Detailed Description, given by way of example, but not intended to limit the invention to specific embodiments described, may be understood in conjunction with the accompanying Figures, incorporated herein by reference, in which:

FIG. 1 is a table containing key ARTERIORISKMARK-ERS, including clinical parameters, traditional laboratory risk factors, and together with core, supplemental and additional biomarkers, that are used in the predictive models according to the present invention. These are identified based on the commonly used gene symbol as described in the detailed description on the invention.

FIGS. 2-1 and 2-2 are flow charts depicting ARTERIOR-ISKMARKER pathophysiology and progression and biomarker functions, pathways and other categories over the spectrum of arteriovascular disease, including numerical references to the canonical molecular pathways as currently listed within the Kyoto University Encyclopedia of Genes and Genomes (KEGG) web site. Such pathway diagrams listed at the KEGG web site include references to each of the various biomarker participants within the given pathway, relating biomarkers both directly and indirectly associated with arteriovascular disease. These KEGG pathways are depicted in the following FIGS. 2-A through 2-P.

FIGS. 2A-1 and 2A-2 are KEGG 4920, depicting the adipocytokine signaling pathway.

FIG. 2-B is KEGG 4910, depicting the insulin signaling pathway.

FIGS. 2C-1 to 2C-3 are KEGG 4060, depicting cytokine-cytokine receptor interaction pathways.

FIGS. 2D-1 to 2D-3 are KEGG 4514, depicting pathways and interactions between cell adhesion molecules.

FIGS. 2E-1 and 2E-2 are KEGG 4670, depicting leukocyte transendothelial migration pathways.

FIGS. 2F-1 and 2F-2 are KEGG 4660, which depicts the T-cell receptor signaling pathway.

FIGS. 2G-1 and 2G-2 are KEGG 4370, depicting the vascular endothelial growth factor (VEGF) signaling pathway.

FIGS. 2H-1 and 2H-2 are KEGG 4110, which depicts pathways involved in the cell cycle.

FIGS. 2I-1 to 2I-3 are KEGG 4010, depicting mitogen-activated protein kinase (MAPK) signaling pathways.

FIGS. 2J-1 to 2J-3 are KEGG 4210 and depicts pathways involved in apoptosis.

FIGS. 2K-1 and 2K-2 are KEGG 4020, depicting the calcium signaling pathway.

FIGS. 2L-1 and 2L-2 are KEGG 4610, and depicts the complement and coagulation cascades.

FIGS. 2M-1 and 2M-2 are KEGG 4512, depicting interactions between the extracellular matrix (ECM) and their receptors.

FIGS. 2N-1 to 2N-3 are KEGG 0564, which depicts pathways involved in glycerophospholipid metabolism.

FIGS. 2O-1 to 2O-3 are KEGG 0590, depicting pathways involved in arachidonic acid metabolism.

FIGS. 2P-1 to 2P-3 are KEGG 4810 and depicts pathways involved in regulation of the actin cytoskeleton.

FIG. 3 is a table detailing the clinical study design of the various Examples given, showing the design and study subject clinical characteristics, both excluding stroke events (Cases per Example 1, n=26) and including stroke events (Cases per Example 2, n=33) within the Case (Converter to Arteriovascular Events) arms, and for the Control (Non-Converter to Cardiovascular Events, n=724) arm shared for both Examples.

FIGS. 4A and 4B are tables summarizing the measured values and variances of certain selected ARTERIORISK-MARKERS studied within the Examples given, including their concentration or other measurement units, mathematical normalization transformations (used in model formula and multi-biomarker index construction), transformed mean and standard deviation values, and back-transformed (raw) mean biomarker concentration or other value as measured for both the Total Cases (Converter to Arteriovascular Events, n=33) and Total Controls (Non-Converter to Cardiovascular Events, n=724) of the Examples, as well as a comparison of the mean values with a statistical p-value given, using a two-tailed t-test for the null hypothesis (the probability that means are equal).

FIGS. 5A to 5F are tables further dividing the Cases cohort into sub-groupings based on the event type and, for the non-stroke subjects, based on the time elapsed from the baseline entry date to the study (also the sample collection date for the samples tested for ARTERIORISKMARKERS) to the earliest arteriovascular event date. The table also provides the measured means and variances for each sub-group as otherwise described in FIG. 4 applying the same summary statistics, additionally providing statistical p-values for a one-way Analysis of Variance (ANOVA) and non-parametric Kruskal-Wallis analysis of variance (KW). Several markers show statistically significant differences across the sub-groups, indicating an ability to both distinguish stroke from other arteriovascular events and also to distinguish between early and late converters to arteriovascular events.

FIG. 12 is a table summarizing the complete enumeration of fitted LDA models for all single, two, three, and four ARTERIORISKMARKER combinations possible from a starting set of 61 selected ARTERIORISKMARKERS, including both blood-bourne analytes and clinical parameters. The table indicates first the total possible panel combinations, which expands from 61 for single ARTERIORISKMARKERS to 521,855 for four ARTERIORISKMARKER combinations. It then gives the number of combinations which produce fitted LDA models that achieve an equal or greater AUC than that shown as the hurdle in the leftmost column of the table (all as calculated in the populations of Example 1). For example, in the row indicated 0.75, from all possible two ARTERIORISKMARKER combinations (1,830 combinations), only 2 combinations (0.11% of the total two ARTERIORISKMARKER combinations possible) resulted in a fitted LDA model that equalled or exceeded an AUC of 0.75, while only 198 three ARTERIORISKMARKER combinations (0.55% of 35,990 possible three ARTERIORISKMARKER combinations) resulted in fitted LDA models exceeding the same hurdle, and so on. No single markers reached this hurdle; in fact, in the data set used only Age and POMC equaled or exceeded an AUC of 0.65.

FIGS. 13A to 13D are tables listing all 200 individual two marker combinations (10.93% out of a total 1,830 unique combinations possible) achieving an AUC of 0.65 or better according to the analysis summarized previously.

FIGS. 14A to 14TT list all 2,573 individual three marker combinations (7.15% out of a total 1,830 unique combinations possible) achieving an AUC of 0.70 or better according to the analysis summarized previously.

FIGS. 15A to 15FFFFFF list all 8,153 individual four marker combinations (1.56% out of a total 521,855 unique combinations possible) achieving an AUC of 0.75 or better according to the analysis summarized previously.

FIGS. 19A to 19D provide information on the inputs used under different ARTERIORISKMARKER model types and selection techniques, with resulting "best" models given model design and constraints, within both of the different case populations of Example 1 (excluding stroke from the Case arm) and Example 2 (including stroke in the Case arm). Of particular note is the consistency of selection of certain markers, which are the Core Markers of the invention, across three or more model types, multiple model constraints, and marker selection techniques.

Figures 1, 2:
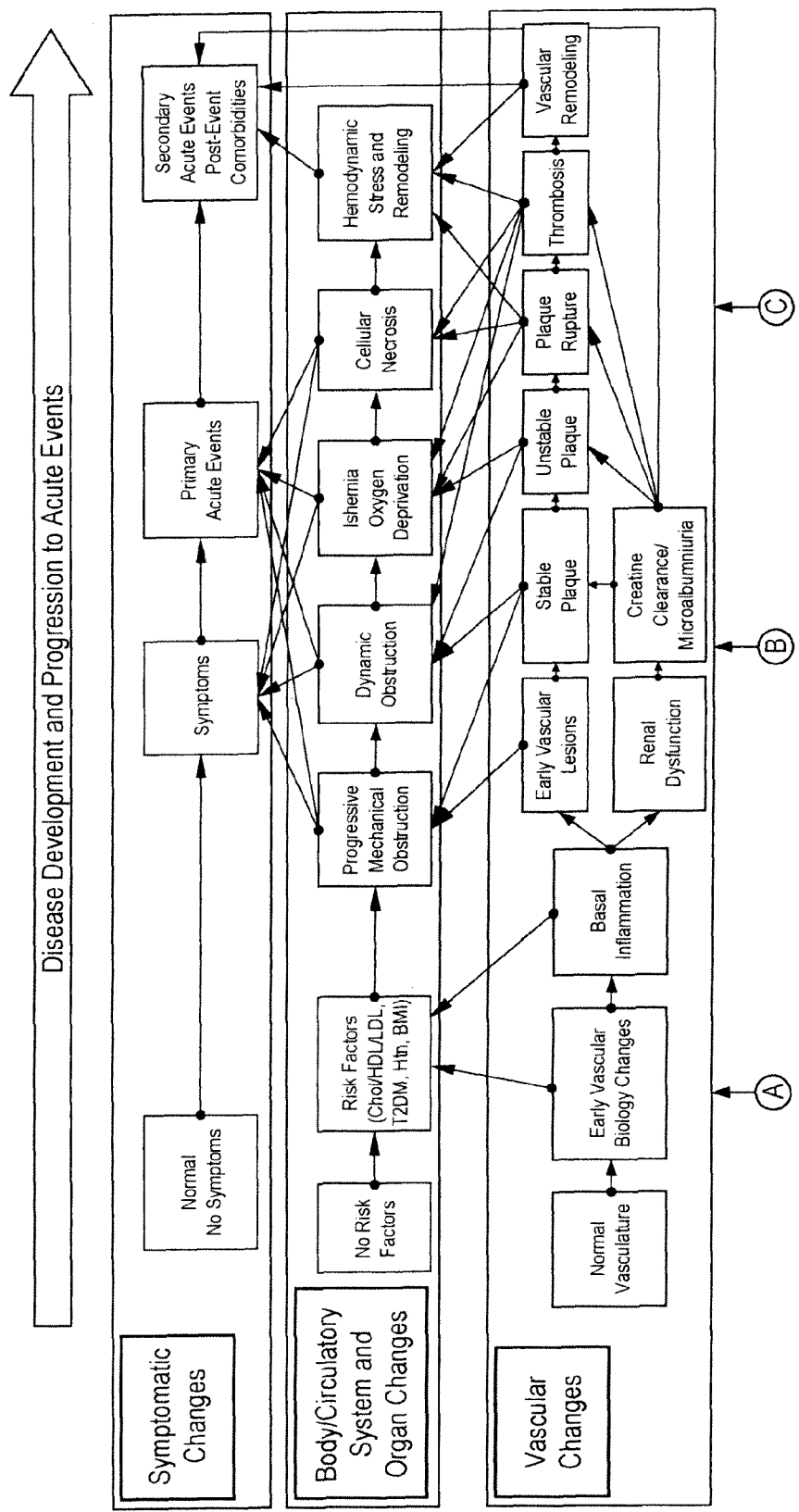
Figure 2:
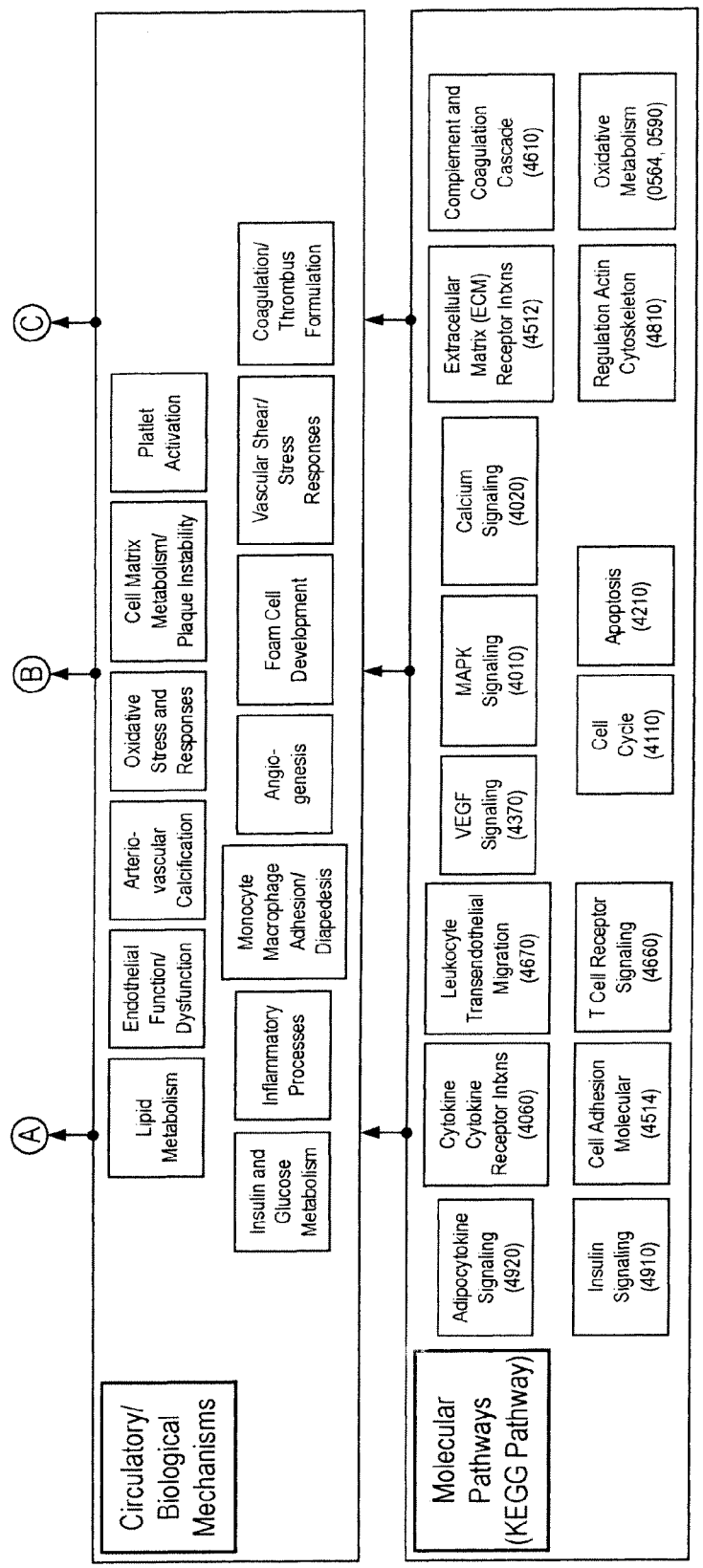

Differences in marker selection using the same models and marker selection criteria across the different cohorts excluding versus including stroke converters, and amongst the markers when restricted to blood-bourne markers only versus allowed to select all variables, may demonstrate both the substitutability of certain biomarkers, where multiple solutions to the model optimization are likely, and the impact of population and diagnostic indication/intended use on the best fitted models. Several techniques of result normalization, model cross-validation, and model calibration are disclosed herein which may be employed in various scenarios as appropriate.

DETAILED DESCRIPTION OF THE INVENTION

The present invention relates to the identification of biomarkers associated with subjects having an arteriovascular disease such as atherosclerosis, atherothrombosis, CAD, PAD, and CVD, are predisposed to or at risk for developing an arteriovascular disease or are predisposed to or at risk of experiencing an acute arteriovascular event. Accordingly, the invention provides methods for identifying subjects who have an arteriovascular disease, or who are predisposed to or at risk for experiencing an arteriovascular event by the detection of biomarkers associated with an arteriovascular disease, including those subjects who are asymptomatic for an arteriovascular disease. These biomarkers are also useful for monitoring subjects undergoing treatments and therapies for an arteriovascular disease, and for selecting or modifying therapies and treatments that would be efficacious in subjects having an arteriovascular disease, wherein selection and use of such treatments and therapies slow the progression of an arteriovascular disease, or substantially delay or prevent its onset, or reduce or prevent the incidence of arteriovascular events.

DEFINITIONS

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), or as a likelihood, odds ratio, among other measures.

As used herein, "atherosclerosis" and "atherothrombosis" refer to systemic inflammatory disease states associated with complex inflammatory responses to multifaceted vascular pathologies involving inflammatory activation of the endothelium, inflammatory leukocytes as a source of thrombogenic stimuli, smooth muscle cells as a source of procoagulants and amplifier of the inflammatory response during thrombosis, and platelets as mediators of inflammation. Arteries harden and narrow due to buildup of a material called "plaque" on their inner walls. As the plaque develops and increases in size, the insides of the arteries get narrower ("stenosis") and less blood can flow through them. Stenosis or plaque rupture may cause partial or complete occlusion of the affected vasculature. Tissues supplied by the vasculature are thus deprived of their source of oxygenation (ischemia) and cell death (necrosis) can occur.

"Arteriovascular disease" as defined herein is a general term used to classify numerous conditions affecting the heart, heart valves, blood, and vasculature of the body and encompasses any disease affecting the heart or blood vessels, including, but not limited to, Metabolic Syndrome, Syndrome X, arteriosclerosis, atherosclerosis, atherothrombosis, coronary artery disease, heart valve disease, arrhythmia, angina pectoris (stable and unstable), cardiomyopathy, congestive heart failure, hypertension, orthostatic hypotension, shock, endocarditis, diseases of the aorta and its branches (such as aortic stenosis), peripheral artery disease, peripheral vascular disease, cerebrovascular disease, and congenital heart disease, and including, without limitation, any acute ischemic arteriovascular event. Arteriovascular disease as used herein is meant to most commonly refer to the ischemic or pro-ischemic disease, rather than generally to non-ischemic disease.

"Arteriovascular event" is used interchangeably herein with the term "acute arteriovascular event", "cardiac event", or "cardiovascular event" and refers to sudden cardiac death, acute coronary syndromes such as, but not limited to, plaque rupture, myocardial infarction, unstable angina, as well as non-cardiac acute arteriovascular events such as blood clots of the leg, aneurysms, stroke and other arteriovascular ischemic events where arteriovascular blood flow and oxygenation is interrupted.

"Biomarker" in the context of the present invention encompasses, without limitation, proteins, nucleic acids, and metabolites, together with their polymorphisms, mutations, variants, modifications, subunits, fragments, protein-ligand complexes, and degradation products, protein-ligand complexes, elements, related metabolites, and other analytes or sample-derived measures. Biomarkers can also include mutated proteins or mutated nucleic acids. Biomarkers also encompass non-blood borne factors or non-analyte physiological markers of health status, such as "clinical parameters" defined herein, as well as "traditional laboratory risk factors", also defined herein. Biomarkers also include any calculated indices created mathematically or combinations of any one or more of the foregoing measurements, including temporal trends and differences. The term "analyte" as used herein can mean any substance to be measured and can encompass electrolytes and elements, such as calcium.

Where available, and unless otherwise described herein, biomarkers which are gene products are identified based on the official letter abbreviation or gene symbol assigned by the international Human Genome Organization Naming Committee (HGNC) and listed at the date of this filing at the US National Center for Biotechnology Information (NCBI) web site (http://www.ncbi.nlm.nih.gov/sites/entrez?db=gene), also known as Entrez Gene.

"CAD" or "coronary' artery disease" is an arteriovascular disease which occurs when the arteries that supply blood to the heart muscle (the coronary arteries) become calcified and/or narrowed. Eventually, blood flow to the heart muscle is reduced, and, because blood carries much-needed oxygen, the heart muscle is not able to receive the amount of oxygen it needs, and often undergoes necrosis. CAD encompasses disease states such as acute coronary syndromes (ACS), myocardial infarction (heart attack), angina (stable and unstable), and atherosclerosis and atherothrombosis that occurs in the blood vessels that supply the heart with oxygen-rich blood. An estimated 13 million Americans are currently diagnosed with CAD, with approximately 7 million being the survivors of past acute events. Over 1 million new acute CAD events occur each year, many resulting in death. The lifetime risk of CAD after age 40 is 49 percent for men and 32 percent for women.

Subjects who are deemed clinically to be at low risk or no risk for developing arteriovascular disease such as CAD often exhibit none or few of the traditional risk factors for the arteriovascular disease, but nevertheless may still be at risk for an acute arteriovascular event. Approximately 20% of all acute CAD events occur in subjects with none of the traditional risk factors, and the majority of all acute CAD occur in subjects who have not been previously diagnosed with CAD. Often these subjects do not exhibit the symptoms of an acute CAD event, i.e. shortness of breath and/or chest pain, until the actual occurrence of such an acute event. A substantial detection gap remains for those who are at risk for an acute CAD event yet are asymptomatic, without traditional risk factors, or are currently deemed clinically to be at low risk and have not yet been diagnosed with CAD.

"ARTERIORISKMARKER" OR "ARTERIORISK-MARKERS" encompass one or more of all biomarkers whose levels are changed in subjects who have an arteriovascular disease or are predisposed to developing an arteriovascular disease, or at risk of an arteriovascular event.

Individual analyte-based ARTERIORISKMARKERS are summarized in Table 2 and are collectively referred to herein as, inter alia, "arteriovascular event risk-associated proteins", "ARTERIORISKMARKER polypeptides", or "ARTERIORISKMARKER proteins". The corresponding nucleic acids encoding the polypeptides are referred to as "cardiac event risk-associated nucleic acids", "cardiac event risk-associated genes", "ARTERIORISKMARKER nucleic acids", or "ARTERIORISKMARKER genes". Unless indicated otherwise, "ARTERIORISKMARKER", "cardiac event risk-associated proteins", "cardiac event risk-associated nucleic acids" are meant to refer to any of the sequences disclosed herein. The corresponding metabolites of the ARTERIORISKMARKER proteins or nucleic acids can also be measured, as well as any of the aforementioned traditional risk marker metabolites previously disclosed, including, without limitation, such metabolites as total cholesterol (CHOL), LDL, HDLC, cholesterol sub-fractions, and glucose, herein referred to as "ARTERIORISK-MARKER metabolites".

Non-analyte physiological markers of health status (e.g., such as age, diastolic or systolic blood pressure, body-mass index, and other non-analyte measurements commonly used as traditional risk factors) are referred to as "ARTERIOR-ISKMARKER physiology". Calculated indices created from mathematically combining measurements of one or more, preferably two or more of the aforementioned classes of ARTERIORISKMARKERS are referred to as "ARTERI-ORISKMARKER indices".

"Clinical parameters" encompasses all non-sample or non-analyte biomarkers of subject health status or other characteristics, such as, without limitation, age (Age), ethnicity (RACE), gender (Sex), diastolic blood pressure (DBP) and systolic blood pressure (SBP), family history (FamHX), height (HT), weight (WT), waist (Waist) and hip (Hip) circumference, body-mass index (BMI), as well as others such as Type I or Type II Diabetes Mellitus or Gestational Diabetes Mellitus (DM or GDM, collectively referred to here as Diabetes), and resting heart rate.

"CVD" or "cerebrovascular disease" is an arteriovascular disease in the blood vessels that feed oxygen-rich blood to the face and brain, such as atherosclerosis and atherothrombosis. This term is often used to describe "hardening" of the carotid arteries, which supply the brain with blood. It is a common comorbid disease with CAD and/or PAD. It is also referred to as an ischemic disease, or a disease that causes a lack of blood flow. CVD encompasses disease states such as "cerebrovascular ischemia," "acute cerebral infarction," "stroke," "ischemic stroke," "hemorrhagic stroke," "aneurysm," "mild cognitive impairment (MCI)" and "transient ischemic attacks" (TIA). Ischemic CVD is believed to closely related to CAD and PAD; non-ischemic CVD may have multiple pathophysiologies. An estimated 5 million Americans are the survivors of past diagnosed acute CVD events, with an estimated 700 thousand acute CVD events occurring each year. As disclosed herein, subjects deemed to be at low risk or no risk of CVD based on clinical assessments of traditional arteriovascular disease risk factors, or without symptoms such as TIAs, MCI or severe headache, may still be at risk for an acute CVD event.

"FN" is false negative, which for a disease state test means classifying a disease subject incorrectly as non-disease or normal.

"FP" is false positive, which for a disease state test means classifying a normal subject incorrectly as having disease.

A "formula," "algorithm," or "model" is any mathematical equation, algorithmic, analytical or programmed process, or statistical technique that takes one or more continuous or categorical inputs (herein called "parameters") and calculates an output value, sometimes referred to as an "index" or "index value." Non-limiting examples of "formulas" include sums, ratios, and regression operators, such as coefficients or exponents, biomarker value transformations and normalizations (including, without limitation, those normalization schemes based on clinical parameters, such as gender, age, or ethnicity), rules and guidelines, statistical classification models, and neural networks trained on historical populations. Of particular use in combining ARTERIORISK-MARKERS and other biomarkers are linear and non-linear equations and statistical classification analyses to determine the relationship between levels of ARTERIORISKMARK-ERS detected in a subject sample and the subject's risk of arteriovascular disease. In panel and combination construction, of particular interest are structural and synactic statistical classification algorithms, and methods of risk index construction, utilizing pattern recognition features, including established techniques such as cross-correlation, Principal Components Analysis (PCA), factor rotation, Logistic Regression (Log Reg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, Support Vector Machines, and Hidden Markov Models, among others. Other techniques may be used in survival and time to event hazard analysis, including Cox, Weibull, Kaplan-Meier and Greenwood models well known to those of skill in the art. Many of these techniques are useful either combined with a ARTERIORISKMARKER selection technique, such as forward selection, backwards selection, or stepwise selection, complete enumeration of all potential panels of a given size, genetic algorithms, or they may themselves include biomarker selection methodologies in their own technique. These may be coupled with information criteria, such as Akaike's Information Criterion (AIC) or Bayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as Bootstrap, Leave-One-Out (LOO) and 10-Fold cross-validation (10-Fold CV). At various steps, false discovery rates may be estimated by value permutation according to techniques known in the art. A "health economic utility function" is a formula that is derived from a combination of the expected probability of a range of clinical outcomes in an idealized applicable patient population, both before and after the introduction of a diagnostic or therapeutic intervention into the standard of care. It encompasses estimates of the accuracy, effectiveness and performance characteristics of such intervention, and a cost and/or value measurement (a utility) associated with each outcome, which may be derived from actual health system costs of care (services, supplies, devices and drugs, etc.) and/or as an estimated acceptable value per quality adjusted life year (QALY) resulting in each outcome. The sum, across all predicted outcomes, of the product of the predicted population size for an outcome multiplied by the respective outcome's expected utility is the total health economic utility of a given standard of care. The difference between (i) the total health economic utility calculated for the standard of care with the intervention versus (ii) the total health economic utility for the standard of care without the intervention results in an overall measure of the health economic cost or value of the intervention. This may itself be divided amongst the entire patient group being analyzed (or solely amongst the intervention group) to arrive at a cost per unit intervention, and to guide such decisions as market positioning, pricing, and assumptions of health system acceptance. Such health economic utility functions are commonly used to compare the cost-effectiveness of the intervention, but may also be transformed to estimate the acceptable value per QALY the health care system is willing to pay, or the acceptable cost-effective clinical performance characteristics required of a new intervention.

For diagnostic (or prognostic) interventions of the invention, as each outcome (which in a disease classifying diagnostic test may be a TP, FP, TN, or FN) bears a different cost, a health economic utility function may preferentially favor sensitivity over specificity, or PPV over NPV based on the clinical situation and individual outcome costs and value, and thus provides another measure of health economic performance and value which may be different from more direct clinical or analytical performance measures. These different measurements and relative trade-offs generally will converge only in the case of a perfect test, with zero error rate (a.k.a., zero predicted subject outcome misclassifications or FP and FN), which all performance measures will favor over imperfection, but to differing degrees.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's non-analyte clinical parameters.

"Negative predictive value" or "NPV" is calculated by TN/(TN FN) or the true negative fraction of all negative test results. It also is inherently impacted by the prevalence of the disease and pre-test probability of the population intended to be tested. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test. Often, for binary disease state classification approaches using a continuous diagnostic test measurement, the sensitivity and specificity is summarized by Receiver Operating Characteristics (ROC) curves according to Pepe et al, "Limitations of the Odds Ratio in Gauging the Performance of a Diagnostic, Prognostic, or Screening Marker," Am. J. Epidemiol 2004, 159 (9): 882-890, and summarized by the Area Under the Curve (AUC) or c-statistic, an indicator that allows representation of the sensitivity and specificity of a test, assay, or method over the entire range of test (or assay) cut points with just a single value. See also, e.g., Shultz, "Clinical Interpretation Of Laboratory Procedures," chapter 14 in Teitz, Fundamentals of Clinical Chemistry, Burtis and Ashwood (eds.), $4^{th}$ edition 1996, W.B. Saunders Company, pages 192-199; and Zweig et al., "ROC Curve Analysis: An Example Showing The Relationships Among Serum Lipid And Apolipoprotein Concentrations In Identifying Subjects With Coronory Artery Disease," Clin. Chem., 1992, 38(8): 1425-1428. An alternative approach using likelihood functions, odds ratios, information theory, predictive values, calibration (including goodness-of-fit), and reclassification measurements is summarized according to Cook, "Use and Misuse of the Receiver Operating Characteristic Curve in Risk Prediction," Circulation 2007, 115: 928-935.

Finally, hazard ratios and absolute and relative risk ratios within subject cohorts defined by a test are a further measurement of clinical accuracy and utility. Multiple methods are frequently used to defining abnormal or disease values, including reference limits, discrimination limits, and risk thresholds as per Vasan, "Biomarkers of Cardiovascular Disease: Molecular Basis and Practical Considerations," Circulation 2006, 113: 2335-2362.

Analytical accuracy refers to the reproducibility and predictability of the measurement process itself, and may be summarized in such measurements as coefficients of variation, and tests of concordance and calibration of the same samples or controls with different times, users, equipment and/or reagents. These and other considerations in evaluating new biomarkers are also summarized in Vasan, 2006.

"PAD" or "peripheral artery disease" encompasses disease states such as atherosclerosis and atherothrombosis that occur outside the heart and brain. It is a common comorbid disease with CAD. Subjects who are deemed to be at low risk or no risk of PAD based upon an assessment of traditional risk factors of PAD (or arteriovascular disease), or who are asymptomatic for PAD or an arteriovascular disease may nevertheless be at risk for an arteriovascular event, even in the absence of claudication. Claudication can be defined as pain or discomfort in the muscles of the legs occurring due to a decreased amount of blood flowing to a muscle from narrowing of the peripheral arteries, producing ischemia and often arterial occlusion, causing skeletal muscle and limb necrosis. The pain or discomfort often occurs when walking and dissipates under resting conditions (intermittent claudication). Pain, tightness, cramping, tiredness or weakness is often experienced as a result of claudication. An estimated 8 to 12 million Americans are estimated to have PAD, but only 25% or less are currently diagnosed and treated.

PAD not only causes the hemodynamic alterations common in CAD, but also results in metabolic changes in skeletal muscle. When PAD has progressed to severe chronic and acute peripheral arterial occlusion, surgery and limb amputation often become the sole therapeutic options. PAD is widely considered to be an underdiagnosed disease, with the majority of confirmed diagnoses occurring only after symptoms are manifested, or only with other arteriovascular disease, and irreversible arteriovascular damage due to such ischemic events has already occurred.

"Performance" is a term that relates to the overall usefulness and quality of a diagnostic or prognostic test, including, among others, clinical and analytical accuracy, other analytical and process characteristics, such as use characteristics (e.g., stability, ease of use), health economic value, and relative costs of components of the test. Any of these factors may be the source of superior performance and thus usefulness of the test, and may be measured by appropriate "performance metrics," such as AUC, time to result, shelf life, etc. as relevant.

"Positive predictive value" or "PPV" is calculated by TP/(TP+FP) or the true positive fraction of all positive test results. It is inherently impacted by the prevalence of the disease and pre-test probability of the population intended to be tested.

"Risk" in the context of the present invention, relates to the probability that an event will occur over a specific time period, as in the conversion to arteriovascular events, and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula $p/(1-p)$ where p is the probability of event and $(1-p)$ is the probability of no event) to no-conversion. Alternative continuous measures which may be assessed in the context of the present invention include time to arteriovascular disease conversion and therapeutic arteriovascular disease conversion risk reduction ratios.

"Risk evaluation," or "evaluation of risk" in the context of the present invention encompasses making a prediction of the probability, odds, or likelihood that an event or disease state may occur, the rate of occurrence of the event or conversion from one disease state to another, i.e., from a normal condition to an arteriovascular condition or to one at risk of developing an arteriovascular event, or from at risk of an arteriovascular event to a more stable arteriovascular condition. Risk evaluation can also comprise prediction of future clinical parameters, traditional laboratory risk factor values, or other indices of arteriovascular disease, such as coronary calcium scores, other imaging or treadmill scores, passive or provocative testing results, arteriovasculature percentage stenosis or occlusion and other measurements of plaque burden and activity, either in absolute or relative terms in reference to a previously measured population. The methods of the present invention may be used to make continuous or categorical measurements of the risk of conversion to arteriovascular disease and events, thus diagnosing and defining the risk spectrum of a category of subjects defined as being at risk for an arteriovascular event. In the categorical scenario, the invention can be used to discriminate between normal and other subject cohorts at higher risk for arteriovascular events. In other embodiments, the present invention may be used so as to discriminate those at risk for developing an arteriovascular event from those having arteriovascular disease, or those having arteriovascular disease from normal. Such differing use may require different ARTERIORISKMARKER combinations and individualized panels, mathematical algorithms, and/or cut-off points, but be subject to the same aforementioned measurements of accuracy and performance for the respective intended use.

A "sample" in the context of the present invention is a biological sample isolated from a subject and can include, by way of example and not limitation, whole blood, serum, plasma, blood cells, endothelial cells, tissue biopsies, lymphatic fluid, ascites fluid, interstitial fluid (also known as "extracellular fluid" and encompasses the fluid found in spaces between cells, including, inter alia, gingival crevicular fluid), bone marrow, cerebrospinal fluid (CSF), saliva, mucous, sputum, sweat, urine, or any other secretion, excretion, or other bodily fluids.

"Sensitivity" is calculated by TP/(TP+FN) or the true positive fraction of disease subjects.

"Specificity" is calculated by TN/(TN+FP) or the true negative fraction of non-disease or normal subjects.

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is often considered highly significant at a p-value of 0.05 or less.

A "subject" in the context of the present invention is preferably a mammal. The mammal can be a human, non-human primate, mouse, rat, dog, cat, horse, or cow, but are not limited to these examples. Mammals other than humans can be advantageously used as subjects that represent animal models of arteriovascular disease or arteriovascular events. A subject can be male or female. A subject can be one who has been previously diagnosed or identified as having arteriovascular disease or an arteriovascular event, and optionally has already undergone, or is undergoing, a therapeutic intervention for the arteriovascular disease or arteriovascular event. Alternatively, a subject can also be one who has not been previously diagnosed as having arteriovascular disease. For example, a subject can be one who exhibits one or more risk factors for arteriovascular disease, or a subject who does not exhibit arteriovascular risk factors, or a subject who is asymptomatic for arteriovascular disease or arteriovascular events. A subject can also be one who is suffering from or at risk of developing arteriovascular disease or an arteriovascular event.

"TN" is true negative, which for a disease state test means classifying a non-disease or normal subject correctly.

"TP" is true positive, which for a disease state test means correctly classifying a disease subject.

"Traditional laboratory risk factors" correspond to biomarkers isolated or derived from subject samples and which are currently evaluated in the clinical laboratory and used in traditional global risk assessment algorithms, such as those from the San Antonio Heart Study, the Framingham Heart Study, and the National Cholesterol Education Program Expert Panel on Detection, Evaluation, and Treatment of High Blood Cholesterol in Adults (Adult Treatment Panel III), also known as NCEP/ATP III. Traditional laboratory risk factors commonly tested from subject blood samples include, but are not limited to, total cholesterol (CHOL), LDL (LDL), HDL (HDLC), VLDL (VLDL), triglycerides (TRIG), glucose, insulin and hemoglobin A1c (HBA1C). Glucose as used herein includes, without limitation, fasting glucose (Glucose) as well as glucose levels taken during and after the oral glucose tolerance test (OGTT), such as 120 minute Glucose (herein labeled "Gluc120"). Insulin (INS) as used herein includes, without limitation, fasting insulin (Insulin) and insulin levels taken during and after the OGTT, such as 120 minute Insulin (herein labeled "Ins120"), as well as insulin's precursors (such as pro-insulin) and their cleavage products such as soluble c-peptide (SCp). Traditional laboratory risk factors are also understood to encompass those ARTERIORISKMARKERS frequently tested in those at risk of arteriovascular or other thrombotic diseases, specifically including, without limitation, fibrinogen (FGA), lipoprotein (a) (LPA), c-reactive protein (CRP), D-dimer, and homocysteine.

Methods and Uses of the Invention

The methods disclosed herein are used with subjects at risk for experiencing an arteriovascular event, subjects who may or may not have already been diagnosed with an arteriovascular disease, and subjects undergoing treatment and/or therapies for an arteriovascular disease. The methods of the present invention can also be used to monitor or select a treatment regimen for a subject who has an arteriovascular disease, and to screen subjects who have not been previously diagnosed as having an arteriovascular disease, such as subjects who exhibit risk factors for an arteriovascular disease, or to assess a subject's future risk of an arteriovascular event, Preferably, the methods of the present invention are used to identify and/or diagnose subjects who are asymptomatic for an arteriovascular disease. "Asymptomatic" means not exhibiting the traditional symptoms, including chest pain and shortness of breath for CAD, claudication for PAD, and TIAs, MCI and severe headache for CVD.

The methods of the present invention may also used to identify and/or diagnose subjects already at higher risk of arteriovascular disease based on solely on the traditional risk factors including, without limitation, gender; race, wherein the chances of developing an arteriovascular disease can be greater in certain ethnic groups; family history, wherein risk of developing an arteriovascular disease is thought to be due, in part, to genetics. Other traditional risk factors for developing an arteriovascular disease include cigarette smoking, elevated systolic (SBP) and diastolic blood pressure (DBP) aka hypertension, elevated serum total (CHOL) and LDL cholesterol levels, low serum HDL cholesterol (HDLG), diabetes mellitus (Diabetes), advancing age, obesity, physical inactivity, abnormal blood glucose (Glucose, Gluc120) and insulin (Insulin, Ins120, SCp) levels, elevated serum triglyceride (TRIG) levels, small LDL particles, elevated serum homocysteine, elevated serum lipoprotein (a) (LPA), prothrombotic factors such as fibrinogen (FGA), and inflammatory markers, such as C-reactive protein (CRP). Each of these may be used as an input variable and/or ARTERIORISKMARKER to multiple-ARTERIORISKMARKER models of the invention.

A subject having an arteriovascular disease such as atherosclerosis, atherothrombosis, CAD, PAD, or CVD can be identified by measuring the amounts (including the presence or absence) of an effective number (which can be two or more) of ARTERIORISKMARKERS in a subject-derived sample and the amounts are then compared to a reference value. Alterations in the amounts and patterns of expression of biomarkers, such as proteins, polypeptides, nucleic acids and polynucleotides, polymorphisms of proteins, polypeptides, nucleic acids, and polynucleotides, mutated proteins, polypeptides, nucleic acids, and polynucleotides, or alterations in the molecular quantities of metabolites or other analytes (such as elemental calcium) in the subject sample compared to the reference value are then identified.

A reference value can be relative to a number or value derived from population studies, including without limitation, such subjects having similar body mass index, total cholesterol levels, LDL/HDL levels, systolic or diastolic blood pressure, subjects of the same or similar age range, subjects in the same or similar ethnic group, subjects having family histories of atherosclerosis, atherothrombosis, or CAD, PAD, or CVD, or relative to the starting sample of a subject undergoing treatment for an arteriovascular disease, such as atherosclerosis, atherothrombosis, CAD, PAD, or CVD, Such reference values can be derived from statistical analyses and/or risk prediction data of populations obtained from mathematical algorithms and computed indices of arteriovascular disease, such as but not limited to, algorithms reported in the Framingham Study, NCEP/ATP III, among others. Reference ARTERIORISKMARKER indices can also be constructed and used using algorithms and other methods of statistical and structural classification.

In one embodiment of the present invention, the reference value is the amount of ARTERIORISKMARKERS in a control sample derived from one or more subjects who are both asymptomatic and lack traditional risk factors for an arteriovascular disease. Such subjects who lack traditional risk factors for an arteriovascular disease can be verified as those subjects having a serum cholesterol level less than 200 mg/dl, systolic blood pressure less than or equal to 120 mm Hg, diastolic blood pressure less than or equal to 80 mm Hg, non-current smoker, no history of diagnosed diabetes, no previously diagnosed acute coronary syndrome or hypertension, among other aforementioned other risk factors, or can be verified by another invasive or non-invasive diagnostic test of arteriovascular disease known in the art, such as but not limited to, electrocardiogram (ECG), carotid B-mode ultrasound (for intima-medial thickness measurement), electron beam computed tomography (EBCT), coronary calcium scoring, multi-slice high resolution computed tomography, nuclear magnetic resonance, stress exercise testing, angiography, intra-vascular ultrasound (IVUS), other contrast and/or radioisotopic imaging techniques, or other provocative testing techniques. In a further embodiment, such subjects are monitored and/or periodically retested for a diagnostically relevant period of time ("longitudinal studies") following such test to verify continued absence from arteriovascular disease or acute arteriovascular events (disease or event free survival). Such period of time may be one year, two years, two to five years, five years, five to ten years, ten years, or ten or more years from the initial testing date for determination of the reference value. Furthermore, retrospective measurement of ARTERIORISKMARKERS in properly banked historical subject samples may be used in establishing these reference values, thus shortening the study time required, presuming the subjects have been appropriately followed during the intervening period through the intended horizon of the product claim.

A reference value can also comprise the amounts of ARTERIORISKMARKERS derived from subjects who show an improvement in arteriovascular risk factors as a result of treatments and/or therapies for arteriovascular diseases. Such improvements include a reduction in body mass index, a reduction in total cholesterol, a reduction in LDL levels, an increase in HDLC levels, a reduction in systolic and/or diastolic blood pressure, or other aforementioned risk factor or combinations thereof. A reference value can also comprise the amounts of ARTERIORISKMARKERS derived from subjects who have confirmed disease by one of the above invasive or non-invasive techniques, or are at high risk for developing an arteriovascular event, or who are at high risk for developing an atherosclerotic or atherothrombotic plaque rupture, or who have suffered from an arteriovascular event or plaque rupture.

A subject predisposed to developing an arteriovascular disease such as atherosclerosis, atherothrombosis, CAD, PAD, or CVD, or at increased risk of experiencing an arteriovascular event can be identified by measuring the levels of an effective amount (which may be two or more) of ARTERIORISKMARKERS in a subject-derived sample and the levels are then compared to a reference value. Alterations in the level of expression of proteins, polypeptides, nucleic acids and polynucleotides, polymorphisms of proteins, polypeptides, nucleic acids, and polynucleotides, or alterations in the molecular quantities of metabolites or other analytes in the subject sample compared to the reference value are then identified.

A reference value can be relative to a number or value derived from population studies including without limitation, such subjects having the same or similar arteriovascular risk factors, which include atherosclerosis and/or atherothrombosis risk factors, such as similar body mass index or similar total cholesterol levels, similar LDL/HDLC levels, similar blood glucose levels, similar systolic or diastolic blood pressure, subjects of the same or similar age range, subjects in the same or similar ethnic group, subjects having family histories of atherosclerosis, atherothrombosis, or CAD, PAD, or CVD, subjects who exhibit similar symptoms of an arteriovascular disease, or relative to a value obtained from a starting sample of a subject undergoing treatment for an arteriovascular disease, subjects who have shown improvement in arteriovascular risk factors as a result of treatment for the arteriovascular disease, or subjects who are not at risk or at low risk for developing an arteriovascular disease, or subjects who are asymptomatic for arteriovascular disease.

In one embodiment of the present invention, the reference value is the amount of ARTERIORISKMARKERS in a control sample derived from one or more subjects who are not at risk or at low risk for developing an arteriovascular disease, or subjects who are asymptomatic for arteriovascular disease. Such subjects who are not at risk or at low risk for developing an arteriovascular disease, or who are asymptomatic for arteriovascular disease can be verified by comparing the risk factors of the subjects against a number derived from longitudinal studies of subjects from which the likelihood of arteriovascular disease progression can be determined, including without limitation, such subjects having similar body mass index or similar total cholesterol levels, similar LDL/HDLC levels, similar blood glucose levels, similar systolic or diastolic blood pressure, subjects of the same or similar age range, subjects in the same or similar ethnic group, subjects who exhibit similar symptoms of an arteriovascular disease, or subjects having family histories of atherosclerosis, atherothrombosis, CAD, PAD, or CVD.

In another embodiment, the reference value is an index value or a baseline value. An index value or baseline value is a composite sample of an effective amount of ARTERIORISKMARKERS from one or more subjects who do not have an arteriovascular disease, such as atherosclerosis, atherothrombosis, CAD, PAD, or CVD, or subjects who are asymptomatic for an arteriovascular disease. A baseline value can also comprise the amounts of ARTERIORISKMARKERS in a sample derived from a subject who has shown an improvement in arteriovascular risk factors (encompassing atherosclerosis and/or atherothrombosis risk factors) as a result of arteriovascular treatments or therapies. Such improvements include, without limitation, a reduction in body mass index, a reduction in total cholesterol, a reduction in LDL levels, an increase in HDLC levels, a reduction in systolic and/or diastolic blood pressure, or combinations thereof. In this embodiment, to make comparisons to the subject-derived sample, the amounts of ARTERIORISKMARKERS are similarly calculated and compared to the index value. Optionally, subjects identified as having an arteriovascular disease, or being at increased risk of developing an arteriovascular disease are chosen to receive a therapeutic regimen to slow the progression of an arteriovascular disease, or decrease or prevent the risk of developing an arteriovascular disease.

The progression of an arteriovascular disease, or effectiveness of an arteriovascular disease treatment regimen can be monitored by detecting a ARTERIORISKMARKER in an effective amount (which may be two or more) of samples obtained from a subject over time and comparing the amount of ARTERIORISKMARKERS detected. For example, a first sample can be obtained prior to the subject receiving treatment and one or more subsequent samples are taken after or during treatment of the subject. Arteriovascular diseases are considered to be progressive (or, alternatively, the treatment does not prevent progression) if the amount of ARTERIORISKMARKER changes over time relative to the reference value, whereas the arteriovascular disease is not progressive if the amount of ARTERIORISKMARKERS remains constant over time (relative to the reference population, or "constant" as used herein). The term "constant" as used in the context of the present invention is construed to include changes over time with respect to the reference value.

Additionally, therapeutic or prophylactic agents suitable for administration to a particular subject can be identified by detecting a ARTERIORISKMARKER in an effective amount (which may be two or more) in a sample obtained from a subject, exposing the subject-derived sample to a test compound that determines the amount (which may be two or more) of ARTERIORISKMARKERS in the subject-derived sample. Accordingly, treatments or therapeutic regimens for use in subjects having an arteriovascular disease, or subjects at risk for developing an arteriovascular disease can be selected based on the amounts of ARTERIORISKMARKERS in samples obtained from the subjects and compared to a reference value. Two or more treatments or therapeutic regimens can be evaluated in parallel to determine which treatment or therapeutic regimen would be the most efficacious for use in a subject to delay onset, or slow progression of an arteriovascular disease.

The present invention further provides a method for screening for changes in marker expression associated with an arteriovascular disease, by determining the amount (which may be two or more) of ARTERIORISKMARKERS in a subject-derived sample, comparing the amounts of the ARTERIORISKMARKERS in a reference sample, and identifying alterations in amounts in the subject sample compared to the reference sample.

If the reference sample, e.g., a control sample, is from a subject that does not have an arteriovascular disease, or if the reference sample reflects a value that is relative to a person that has a high likelihood of rapid progression to an arteriovascular disease, a similarity in the amount of the ARTERIORISKMARKER analytes in the test sample and the reference sample indicates that the treatment is efficacious. However, a difference in the amount of the ARTERIORISKMARKER in the test sample and the reference sample indicates a less favorable clinical outcome or prognosis.

By "efficacious", it is meant that the treatment leads to a decrease in the amount of a ARTERIORISKMARKER protein, nucleic acid, polymorphism, metabolite, or other analyte, decreases in systolic and/or diastolic blood pressure, decreases in total serum cholesterol and LDL cholesterol levels, increases in HDL cholesterol levels, or decreases in BMI. Assessment of the risk factors disclosed herein can be achieved using standard clinical protocols. Efficacy can be determined in association with any known method for diagnosing, identifying, or treating an arteriovascular disease.

The present invention further encompasses methods of differentially diagnosing and distinguishing arteriovascular diseases, such as, but not limited to, Metabolic Syndrome, Syndrome X, arteriosclerosis, atherosclerosis, atherothrombosis, coronary artery disease, heart valve disease, arrhythmia, angina pectoris (stable and unstable), cardiomyopathy, congestive heart failure, hypertension, orthostatic hypotension, shock, endocarditis, diseases of the aorta and its branches (such as aortic stenosis), peripheral artery disease, cerebrovascular disease, and congenital heart disease. One embodiment of the invention provides a method of differentially diagnosing and distinguishing the progressive stages of atherosclerosis and atherothrombosis based on the development of an occlusive or subocclusive thrombus (also known as a "plaque"), which may be ruptured or non-ruptured. Plaque rupture is the most common type of plaque complication, accounting for ~70% of fatal acute myocardial infarctions and/or sudden coronary deaths. Thus, there is an interdependent relationship between plaque growth and arterial thrombosis, providing the framework for precipitation of an acute arteriovascular event. Plaques within the arteriovascular system become "high-risk," "unstable,", or "vulnerable" in response to a wide array of local and systemic influences, such as inflammation, composition of the plaque, prothrombotic milieu, among others (Wasserman, E. J. and Shipley, N. M. (2006) Mt. Sinai J. Med. 73L: 431-439). Plaque composition is a major pathophysiological determinant of arteriovascular disease. Measurement of plaque components can determine the probability of an arteriovascular event, and can be useful in diagnosing or identifying asymptomatic subjects.

The earliest changes begin within the endothelium, where activated endothelial cells (ECs) recruit monocytes and T-lymphocytes to the vessel wall (Springer, T. A. (1994) Cell 76: 301-314). Endothelial dysfunction drives this process, which is marked by endothelial cell expression of leukocyte and vascular cell adhesion molecules (VCAMs) and increased endothelial permeability to lipoproteins, leukocytes, and other inflammatory mediators, Increasing number of atherogenic lipoproteins and T-cells within the intima stimulate monocytes to differentiate to macrophages, which then become lipid-laden foam cells as they engulf and ingest modified lipoproteins. Smooth muscle cells (SMCs) migrate and proliferate, leukocyte recruitment amplifies, and platelet aggregates adhere to injured endothelium in response to a variety of inflammatory mediators secreted by ECs, activated leukocytes, SMCs, and platelets (Springer, T. A. and Cybulsky, M. I., (1996) In: *Atherosclerosis and coronary artery disease* Vol. 1 Lippincott-Raven (Philadelphia), pp. 511-538). These lesions are commonly referred to in the art as "fatty streaks". With continued progression, these plaques accumulate pools of extracellular lipid deposits that surround increasing numbers of inflammatory cells, SMCs, and connective tissue elements, all of which comprise a pro-atherogenic, pro-thrombotic, dynamic extracellular matrix (ECM). In response to cytokines and growth factors, such as but not limited to transforming growth factor-β (TGFβ), a fibrous cap, composed primarily of SMCs and collagen, develops around the expanding lipid core, walling it off from the lumen. The atheromatous core accumulates larger, more confluent amounts of extracellular lipids along with pro-inflammatory mediators (e.g., interferon-γ) and proteolytic enzymes (e.g., matrix metalloproteinases (MMPs)) that contribute to the erosion of the fibrous cap by digesting its components.

Plaques are identified by several criteria, such as but not limited to plaque cap thickness, plaque lipid core size, presence or absence of a necrotic core, plaque stenosis (luminal narrowing), remodeling (expansive vs. constrictive remodeling), color (yellow, glistening yellow, red, etc.), collagen content vs. lipid content, mechanical stability (stiffness and elasticity), calcification burden and pattern (nodule vs. scattered, superficial vs. deep, etc.), plaque activity/function, such as plaque inflammation (comprising macrophage density, rate of monocyte infiltration, and density of activated T-cell), endothelial dysfunction measured by local nitric oxide production, anti-procoagulation properties of the endothelium, plaque oxidative stress, superficial platelet aggregation and fibrin deposition, rate of apoptosis, angiogenesis, leaking vasa vasorum, and intraplaque hemorrhage, the presence of matrix metalloproteinase activity in the cap, and the present of certain microbial antigens. Other criteria include pan-arterial measurements, such as transcoronary gradients of serum markers of vulnerability, total coronary calcium burden, total coronary vasoreactivity (endothelial function), total arterial burden of plaque including peripheral arterial burden, among others.

Plaques which often, but do not always, create significant degrees of arterial luminal stenosis are characterized by a degraded fibrous cap with superimposed organizing thrombus and a well-formed, mostly acellular necrotic core containing oxygen radicals, oxidized lipids, dying foam cells, erythrocyte membranes, and apoptotic cellular debris (referred to in the art as "thin-cap fibroatheroma"). These high-risk atheromas may progress to largely occlusive and calcified or fibrotic atheromas, which may in turn trigger signs and symptoms of more progressive arteriovascular diseases, such as angina pectoris and which occur secondary to acute thrombosis or during periods of inadequate collateral/luminal blood flow.

The progression of a fatty streak to a high-risk atheroma occurs through a continuous process of ECM remodeling. Dysregulation of ECM metabolism may result in an accelerated accumulation of lipids and foam cells, a net increase in collagen resorption with subsequent weakening of the fibrous cap and compensatory changes in vessel wall architecture. Neovascularization in atherosclerotic arteries introduces fragile intimal microvessels (also known as "vasa vasorum"), which may rupture into the core, resulting in repeated, often subclinical, intraplaque hemorrhage. As these clots reorganize and are layered with fibrous tissue, the lesion advances. Expansive ECM remodeling results in outward growth of the plaque, increasing the circumference of the diseased section of artery. The extent of luminal narrowing has been found to be inversely proportional to the degree of expansive remodeling (Pasterkamp, G. et al (1995) Circulation 91: 1444-1449).

Inflammation plays a key role during thrombogenesis, or disruption of the plaque. Procoagulant factors within the ECM are exposed to luminal blood flow at sites where plaque disruption has occurred. Stimulated by inflammatory mediators, circulating platelets adhere to damaged endothelium and form aggregates that become trapped in fibrin. Given the appropriate mixture of disturbed blood flow, inflammation, and thrombogenic potential, occlusive thrombi may occur, causing an arteriovascular event even in the absence of visible plaque disruption. Hyperlipoproteinemia, hypertension, diabetes, elevated levels of homocysteine as well as C-reactive protein, smoking, apoptosis, elevated levels of lipoprotein A, elevated levels of plasminogen activator inhibitor type-1 (PAI-1), high levels of MMPs, the presence of tissue factor, as well as other conditions, augment the inflammatory and hemodynamic response to vascular injury and feed the coagulation cascade, resulting in accelerated thrombogenesis.

The present invention also provides ARTERIORISK-MARKER panels including one or more ARTERIORISK-MARKERS that are indicative of a general physiological pathway associated with an arteriovascular disease (such as inflammation, coagulation, necrosis), an arteriovascular disease site (such as the heart or brain), the particular stage of the arteriovascular disease (such as platelet aggregation or plaque rupture), the rate of progression of the arteriovascular disease (i.e., speed or kinetics that the arteriovascular disease is progressing at), and one or more ARTERIORISK-MARKERS that can be used to exclude or distinguish between different disease states or sequelae associated with arteriovascular disease. The ARTERIORISKMARKERS of the invention also provides categories or clusters of analytes that can be measured and detected according to signaling pathway or physiological pathway. A single ARTERIORISKMARKER may have several of the aforementioned characteristics according to the present invention, and may alternatively be used in replacement of one or more other ARTERIORISKMARKERS where appropriate for the given application of the invention.

The present invention also comprises a kit with a detection reagent that binds to two or more ARTERIORISK-MARKER proteins, nucleic acids, polymorphisms, metabolites, or other analytes. Also provided by the invention is an array of detection reagents, e.g., antibodies and/or oligonucleotides that can bind to two or more ARTERIORISK-MARKER proteins or nucleic acids, respectively. In one embodiment, the ARTERIORISKMARKER are proteins and the array contains antibodies that bind an effective amount of ARTERIORISKMARKERS 1-1023 sufficient to measure a statistically significant alteration in ARTERIORISKMARKER expression compared to a reference value. In another embodiment, the ARTERIORISKMARKERS are nucleic acids and the array contains oligonucleotides or aptamers that bind an effective amount of ARTERIORISKMARKERS 1-1023 sufficient to measure a statistically significant alteration in ARTERIORISKMARKER expression compared to a reference value.

Also provided by the present invention is a method for treating one or more subjects at risk for developing an arteriovascular disease, comprising: detecting the presence of altered amounts of an effective amount of ARTERIORISKMARKERS present in a sample from the one or more subjects; and treating the one or more subjects with one or more arteriovascular disease-modulating drugs until altered amounts of the ARTERIORISKMARKERS return to a baseline value measured in one or more subjects at low risk for developing an arteriovascular disease, or alternatively, in subjects who do not exhibit any of the traditional risk factors for arteriovascular disease.

Also provided by the present invention is a method for treating one or more subjects having an arteriovascular disease comprising: detecting the presence of altered levels of an effective amount of ARTERIORISKMARKERS present in a sample from the one or more subjects; and treating the one or more subjects with one or more arteriovascular disease-modulating drugs until altered amounts of the ARTERIORISKMARKERS return to a baseline value measured in one or more subjects at low risk for developing an arteriovascular disease.

Also provided by the present invention is a method for evaluating changes in the risk of an arteriovascular event in a subject diagnosed with an arteriovascular disease, comprising detecting an effective amount of ARTERIORISK-MARKERS (which may be two or more) in a first sample from the subject at a first period of time, detecting the amounts of the ARTERIORISKMARKERS in a second sample from the subject at a second period of time, and comparing the amounts of the ARTERIORISKMARKERS detected at the first and second periods of time.

The present invention also encompasses a method for evaluating the risk of plaque rupture in a subject diagnosed with atherosclerosis or atherothrombosis, comprising detecting an effective amount of ARTERIORISKMARKERS (which may be two or more) in a first sample from the subject at a first period of time, detecting the ARTERIORISKMARKERS in a second sample from the subject at a second period of time, and comparing the amounts of the ARTERIORISKMARKERS detected at the first and second periods of time.

A method for differentially diagnosing disease states associated with an arteriovascular disease in a subject is provided, comprising detecting an effective amount of ARTERIORISKMARKERS selected from the group consisting of ARTERIORISKMARKERS 1-1023, or the ARTERIORISKMARKER panels of the invention, in a sample from the subject; and comparing the amounts of the ARTERIORISKMARKERS to the arteriovascular disease subject profiles of the present invention, or to a reference value.

Also provided by the present invention is a method of monitoring the progression of plaque formation in a subject comprising detecting an effective amount of ARTERIORISKMARKERS selected from the group consisting of CARDIORISKMARKERS 1-1023, or the ARTERIORISKMARKER panels of the invention, in a sample from the subject; and comparing the amounts of the two or more ARTERIORISKMARKERS, or the ARTERIORISKMARKER panel, to the arteriovascular disease subject profiles of the present invention, or to a reference value.

Diagnostic and Prognostic Indications of the Invention

The invention allows the diagnosis and prognosis of arteriovascular disease or arteriovascular events. The risk of developing an arteriovascular disease can be detected by measuring an effective amount of ARTERIORISK-MARKER proteins, nucleic acids, polymorphisms, metabolites, and other analytes (which may be two or more) in a test sample (e.g., a subject derived sample), and comparing the effective amounts to reference or index values, often utilizing mathematical algorithms or formula in order to combine information from results of multiple individual ARTERIORISKMARKERS and from non-analyte clinical parameters into a single measurement or index. Subjects identified as having an increased risk of an arteriovascular disease can optionally be selected to receive treatment regimens, such as administration of prophylactic or therapeutic compounds such as "arteriovascular disease-modulating agents" as defined herein, or implementation of exercise regimens, surgical interventions as defined elsewhere in this disclosure, or dietary supplements to prevent or delay the onset of an arteriovascular disease.

The amount of the ARTERIORISKMARKER protein, nucleic acid, polymorphism, metabolite, or other analyte can be measured in a test sample and compared to the "normal control level," utilizing techniques such as reference limits, discrimination limits, or risk defining thresholds to define cutoff points and abnormal values for arteriovascular disease or arteriovascular events, all as described in Vasan, 2006. The "normal control level" means the level of one or more ARTERIORISKMARKERS or combined ARTERIORISKMARKER indices typically found in a subject not suffering from an arteriovascular disease. Such normal control level and cutoff points may vary based on whether a ARTERIORISKMARKER is used alone or in a formula combining with other ARTERIORISKMARKERS into an index. Alternatively, the normal control level can be a database of ARTERIORISKMARKER patterns from previously tested subjects who did not convert to arteriovascular disease over a clinically relevant time horizon.

The present invention may be used to make continuous or categorical measurements of the risk of conversion to arteriovascular disease, thus diagnosing and defining the risk spectrum of a category of subjects defined as at risk for having an arteriovascular event. In the categorical scenario, the methods of the present invention can be used to discriminate between normal and arteriovascular disease subject cohorts. In other embodiments, the present invention may be used so as to discriminate those at risk for having an arteriovascular event from those having more stable arteriovascular disease, those more rapidly progressing (or alternatively those with a shorter probable time horizon to an arteriovascular event) to an arteriovascular event from those more slowly progressing (or with a longer time horizon to an arteriovascular event), or those having arteriovascular disease from normal. Such differing use may require different ARTERIORISKMARKER combinations in individual panel, mathematical algorithm, and/or cut-off points, but be subject to the same aforementioned measurements of accuracy and other performance metrics relevant for the intended use.

Identifying the subject at risk of having an arteriovascular event enables the selection and initiation of various therapeutic interventions or treatment regimens in order to delay, reduce or prevent that subject's conversion to an arteriovascular disease state. Levels of an effective amount of ARTERIORISKMARKER proteins, nucleic acids, polymorphisms, metabolites, or other analytes also allows for the course of treatment of arteriovascular disease or arteriovascular event to be monitored. In this method, a biological sample can be provided from a subject undergoing treatment regimens, e.g., drug treatments, for arteriovascular disease. Such treatment regimens can include, but are not limited to, exercise regimens, dietary supplementation, bariatric surgical intervention, and treatment with therapeutics or prophylactics used in subjects diagnosed or identified with arteriovascular disease or at risk of having an arteriovascular event. If desired, biological samples are obtained from the subject at various time points before, during, or after treatment.

The present invention can also be used to screen patient or subject populations in any number of settings. For example, a health maintenance organization, public health entity or school health program can screen a group of subjects to identify those requiring interventions, as described above, or for the collection of epidemiological data. Insurance companies (e.g., health, life or disability) may screen applicants in the process of determining coverage or pricing, or existing clients for possible intervention. Data collected in such population screens, particularly when tied to any clinical progression to conditions like arteriovascular disease or arteriovascular events, will be of value in the operations of, for example, health maintenance organizations, public health programs and insurance companies. Such data arrays or collections can be stored in machine-readable media and used in any number of health-related data management systems to provide improved healthcare services, cost effective healthcare, improved insurance operation, etc. See, for example, U.S. Patent Application No. 2002/0038227; U.S. Patent Application No. US 2004/0122296; U.S. Patent Application No. US 2004/0122297; and U.S. Pat. No. 5,018,067. Such systems can access the data directly from internal data storage or remotely from one or more data storage sites as further detailed herein. Thus, in a health-related data management system, wherein risk of developing a arteriovascular condition for a subject or a population comprises analyzing arteriovascular disease risk factors, the present invention provides an improvement comprising use of a data array encompassing the biomarker measurements as defined herein and/or the resulting evaluation of risk from those biomarker measurements.

A machine-readable storage medium can comprise a data storage material encoded with machine readable data or data arrays which, when using a machine programmed with instructions for using said data, is capable of use for a variety of purposes, such as, without limitation, subject information relating to arteriovascular disease risk factors over time or in response to arteriovascular disease-modulating drug therapies, drug discovery, and the like. Measurements of effective amounts of the biomarkers of the invention and/or the resulting evaluation of risk from those biomarkers can implemented in computer programs executing on programmable computers, comprising, inter alia, a processor, a data storage system (including volatile and non-volatile memory and/or storage elements), at least one input device, and at least one output device. Program code can be applied to input data to perform the functions described above and generate output information. The output information can be applied to one or more output devices, according to methods known in the art. The computer may be, for example, a personal computer, microcomputer, or workstation of conventional design.

Each program can be implemented in a high level procedural or object oriented programming language to communicate with a computer system. However, the programs can be implemented in assembly or machine language, if desired. The language can be a compiled or interpreted language. Each such computer program can be stored on a storage media or device (e.g., ROM or magnetic diskette or others as defined elsewhere in this disclosure) readable by a general or special purpose programmable computer, for configuring and operating the computer when the storage media or device is read by the computer to perform the procedures described herein. The health-related data management system of the invention may also be considered to be implemented as a computer-readable storage medium, configured with a computer program, where the storage medium so configured causes a computer to operate in a specific and predefined manner to perform various functions described herein.

Levels of an effective amount of ARTERIORISK-MARKER proteins, nucleic acids, polymorphisms, metabolites, or other analytes can then be determined and compared to a reference value, e.g. a control subject or population whose athersclerotic state is known or an index value or baseline value. The reference sample or index value or baseline value may be taken or derived from one or more subjects who have been exposed to the treatment, or may be taken or derived from one or more subjects who are at low risk of developing arteriovascular disease or an arteriovascular event, or may be taken or derived from subjects who have shown improvements in arteriovascular disease risk factors (such as clinical parameters or traditional laboratory risk factors as defined herein) as a result of exposure to treatment. Alternatively, the reference sample or index value or baseline value may be taken or derived from one or more subjects who have not been exposed to the treatment. For example, samples may be collected from subjects who have received initial treatment for arteriovascular disease or an arteriovascular event and subsequent treatment for arteriovascular disease or an arteriovascular event to monitor the progress of the treatment. A reference value can also comprise a value derived from risk prediction algorithms or computed indices from population studies such as those disclosed herein.

The ARTERIORISKMARKERS of the present invention can thus be used to generate a "reference ARTERIORISK-MARKER profile" of those subjects who do not have arteriovascular disease or are not at risk of having an arteriovascular event, and would not be expected to develop arteriovascular disease or an arteriovascular event. The ARTERIORISKMARKERS disclosed herein can also be used to generate a "subject ARTERIORISKMARKER profile" taken from subjects who have arteriovascular disease or are at risk for having an arteriovascular event. The subject ARTERIORISKMARKER profiles can be compared to a reference ARTERIORISKMARKER profile to diagnose or identify subjects at risk for developing arteriovascular disease or an arteriovascular event, to monitor the progression of disease, as well as the rate of progression of disease, and to monitor the effectiveness of arteriovascular treatment modalities. The reference and subject ARTERIORISK-MARKER profiles of the present invention can be contained in a machine-readable medium, such as but not limited to, analog tapes like those readable by a VCR, CD-ROM, DVD-ROM, USB flash media, among others, Such machine-readable media can also contain additional test results, such as, without limitation, measurements of clinical parameters and traditional laboratory risk factors. Alternatively or additionally, the machine-readable media can also comprise subject information such as medical history and any relevant family history. The machine-readable media can also contain information relating to other arteriovascular disease-risk algorithms and computed indices such as those described herein.

Differences in the genetic makeup of subjects can result in differences in their relative abilities to metabolize various drugs, which may modulate the symptoms or risk factors of arteriovascular disease or arteriovascular events. Subjects that have arteriovascular disease, or at risk for developing arteriovascular disease or an arteriovascular event can vary in age, ethnicity, body mass index (BMI), total cholesterol levels, blood glucose levels, blood pressure, LDL and HDL levels, and other parameters. Accordingly, use of the ARTE-RIORISKMARKERS disclosed herein, both alone and together in combination with known genetic factors for drug metabolism, allow for a pre-determined level of predictability that a putative therapeutic or prophylactic to be tested in a selected subject will be suitable for treating or preventing arteriovascular disease or an arteriovascular event in the subject.

To identify therapeutics or drugs that are appropriate for a specific subject, a test sample from the subject can also be exposed to a therapeutic agent or a drug, and the level of one or more of ARTERIORISKMARKER proteins, nucleic acids, polymorphisms, metabolites or other analytes can be determined. The level of one or more ARTERIORISK-MARKERS can be compared to sample derived from the subject before and after treatment or exposure to a therapeutic agent or a drug, or can be compared to samples derived from one or more subjects who have shown improvements in arteriovascular risk factors (e.g., clinical parameters or traditional laboratory risk factors) as a result of such treatment or exposure.

Agents for reducing the risk of arteriovascular disease, an arteriovascular event, or arteriovascular complications include, without limitation of the following, insulin, hypoglycemic agents, anti-inflammatory agents, lipid reducing agents, anti-hypertensives such as calcium channel blockers, beta-adrenergic receptor blockers, cyclooxygenase-2 inhibitors, angiotensin system inhibitors, ACE inhibitors, rennin inhibitors, together with other common risk factor modifying agents (herein "arteriovascular disease-modulating drugs").

"Insulin" includes rapid acting forms, such as Insulin lispro rDNA origin: HUMALOG (1.5 mL, 10 mL, Eli Lilly and Company, Indianapolis, Ind.), Insulin Injection (Regular Insulin) form beef and pork (regular ILETIN I, Eli Lilly], human: rDNA: HUMULIN R (Eli Lilly), NOVOLIN R (Novo Nordisk, New York, N.Y.), Semisynthetic: VELO-SULIN Human (Novo Nordisk), rDNA Human, Buffered: VELOSULIN BR, pork: regular Insulin (Novo Nordisk), purified pork: Pork Regular ILETIN II (Eli Lilly), Regular Purified Pork Insulin (Novo Nordisk), and Regular (Concentrated) ILETIN II U-500 (500 units/mL, Eli Lilly); intermediate-acting forms such as Insulin Zinc Suspension, beef and pork: LENTE ILETIN G I (Eli Lilly), Human, rDNA: HUMULIN L (Eli Lilly), NOVOLIN L (Novo Nordisk), purified pork: LENTE ILETIN II (Eli Lilly), Isophane Insulin Suspension (NPH): beef and pork: NPH ILETIN I (Eli Lilly), Human, rDNA: HUMULIN N (Eli Lilly), Novolin N (Novo Nordisk), purified pork: Pork NPH Iletin II (Eli Lilly), NPH-N (Novo Nordisk); and long-acting forms such as Insulin zinc suspension, extended (ULTRALENTE, Eli Lilly), human, rDNA: HUMULIN U (Eli Lilly).

"Hypoglycemic" agents are preferably oral hypoglycemic agents and include, without limitation, first-generation sulfonylureas: Acetohexamide (Dymelor), Chlorpropamide (Diabinese), Tolbutamide (Orinase); second-generation sulfonylureas: Glipizide (Glucotrol, Glucotrol XL), Glyburide (Diabeta; Micronase; Glynase), Glimepiride (Amaryl); Biguanides: Metformin (Glucophage); Alpha-glucosidase inhibitors: Acarbose (Precose), Miglitol (Glyset), Thiazolidinediones: Rosiglitazone (Avandia), Pioglitazone (Actos), Troglitazone (Rezulin); Meglitinides: Repaglinide (Prandin); and other hypoglycemics such as Acarbose; Buformin; Butoxamine Hydrochloride; Camiglibose; Ciglitazone; Englitazone Sodium; Darglitazone Sodium; Etoformin Hydrochloride; Gliamflide; Glibomuride; Glicetanile Gliclazide Sodium; Gliflumide; Glucagon; Glyhexamide; Glymidine Sodium; Glyoctamide; Glyparamide; Linogliride; Linogliride Fumarate; Methyl Palmoxirate; Palmoxirate Sodium; Pirogliride Tartrate; Proinsulin Human; Seglitide Acetate; Tolazamide; Tolpyrramide; Zopolrestat.

"Anti-inflammatory" agents include Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cot methasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Momiflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; Zomepirac Sodium. An important anti-inflammatory agent is aspirin.

Preferred anti-inflammatory agents are cytokine inhibitors. Important cytokine inhibitors include cytokine antagonists (e.g., IL-6 receptor antagonists), aza-alkyl lysophospholipids (AALP), and Tumor Necrosis Factor-alpha (TNF-alpha) inhibitors, such as anti-TNF-alpha antibodies, soluble TNF receptor, TNF-alpha, anti-sense nucleic acid molecules, multivalent guanylhydrazone (CNI-1493), N-acetylcysteine, pentoxiphylline, oxpentifylline, carbocyclic nucleoside analogues, small molecule S9a, RP 55778 (a TNF-alpha synthesis inhibitor), Dexanabinol (HU-211, is a synthetic cannabinoid devoid of cannabimimetic effects, inhibits TNF-alpha production at a post-transcriptional stage), MDL 201,449A (9-[(1R,3R)-trans-cyclopentan-3-ol] adenine, and trichodimerol (BMS-182123). Preferred TNF-alpha inhibitors are Etanercept (ENBREL, Immunex, Seattle) and Infliximab (REMICADE, Centocor, Malvern, Pa.).

"Lipid reducing agents" include gemfibrozil, cholystyramine, colestipol, nicotinic acid, and HMG-CoA reductase inhibitors. HMG-CoA reductase inhibitors useful for administration, or co-administration with other agents according to the invention include, but are not limited to, simvastatin (U.S. Pat. No. 4,444,784), lovastatin (U.S. Pat. No. 4,231,938), pravastatin sodium (U.S. Pat. No. 4,346,227), fluvastatin (U.S. Pat. No. 4,739,073), atorvastatin (U.S. Pat. No. 5,273,995), cerivastatin, and numerous others described in U.S. Pat. No. 5,622,985, U.S. Pat. No. 5,135,935, U.S. Pat. No. 5,356,896, U.S. Pat. No. 4,920,109, U.S. Pat. No. 5,286,895, U.S. Pat. No. 5,262,435, U.S. Pat. No. 5,260,332, U.S. Pat. No. 5,317,031, U.S. Pat. No. 5,283,256, U.S. Pat. No. 5,256,689, U.S. Pat. No. 5,182,298, U.S. Pat. No. 5,369,125, U.S. Pat. No. 5,302,604, U.S. Pat. No. 5,166,171, U.S. Pat. No. 5,202,327, U.S. Pat. No. 5,276,021, U.S. Pat. No. 5,196,440, U.S. Pat. No. 5,091,386, U.S. Pat. No. 5,091,378, U.S. Pat. No. 4,904,646, U.S. Pat. No. 5,385,932, U.S. Pat. No. 5,250,435, U.S. Pat. No. 5,132,312, U.S. Pat. No. 5,130,306, U.S. Pat. No. 5,116,870, U.S. Pat. No. 5,112,857, U.S. Pat. No. 5,102,911, U.S. Pat. No. 5,098,931, U.S. Pat. No. 5,081,136, U.S. Pat. No. 5,025,000, U.S. Pat. No. 5,021,453, U.S. Pat. No. 5,017,716, U.S. Pat. No. 5,001,144, U.S. Pat. No. 5,001,128, U.S. Pat. No. 4,997,837, U.S. Pat. No. 4,996,234, U.S. Pat. No. 4,994,494, U.S. Pat. No. 4,992,429, U.S. Pat. No. 4,970,231, U.S. Pat. No. 4,968,693, U.S. Pat. No. 4,963,538, U.S. Pat. No. 4,957,940, U.S. Pat. No. 4,950,675, U.S. Pat. No. 4,946,864, U.S. Pat. No. 4,946,860, U.S. Pat. No. 4,940,800, U.S. Pat. No. 4,940,727, U.S. Pat. No. 4,939,143, U.S. Pat. No. 4,929,620, U.S. Pat. No. 4,923,861, U.S. Pat. No. 4,906,657, U.S. Pat. No. 4,906,624 and U.S. Pat. No. 4,897,402, the disclosures of which patents are incorporated herein by reference.

Anti-thrombotic and/or fibrinolytic agents include Plasminogen (to plasmin via interactions of prekallikrein, kininogens, Factors XII, XIIIa, plasminogen proactivator, and tissue plasminogen activator[TPA]) Streptokinase; Urokinase: Anisoylated Plasminogen-Streptokinase Activator Complex; Pro-Urokinase; (Pro-UK); rTPA (alteplase or activase; r denotes recombinant), rPro-UK; Abbokinase; Eminase; Sreptase Anagrelide Hydrochloride; Bivalirudin; Dalteparin Sodium; Danaparoid Sodium; Dazoxiben Hydrochloride; Efegatran Sulfate; Enoxaparin Sodium; Ifetroban; Ifetroban Sodium; Tinzaparin Sodium; retaplase; Trifenagrel; Warfarin; Dextrans.

Anti-platelet agents include Clopridogrel; Sulfinpyrazone; Aspirin; Dipyridamole; Clofibrate; Pyridinol Carbamate; PGE; Glucagon; Antiserotonin drugs; Caffeine; Theophyllin Pentoxifyllin; Ticlopidine; Anagrelide.

Lipid reducing agents include gemfibrozil, cholystyramine, colestipol, nicotinic acid, probucol lovastatin, fluvastatin, simvastatin, atorvastatin, pravastatin, cirivastatin.

Direct thrombin inhibitors include hirudin, hirugen, hirulog, agatroban, PPACK, thrombin aptamers.

Glycoprotein IIb/IIIa receptor Inhibitors are both antibodies and non-antibodies, and include but are not limited to ReoPro (abcixamab), lamifiban, tirofiban.

One preferred agent is aspirin.

"Calcium channel blockers" are a chemically diverse class of compounds having important therapeutic value in the control of a variety of diseases including several cardiovascular disorders, such as hypertension, angina, and cardiac arrhythmias (Fleckenstein, Cir. Res. v. 52, (suppl. 1), p. 13-16 (1983); Fleckenstein, Experimental Facts and Therapeutic Prospects, John Wiley, New York (1983); McCall, D., Curr Pract Cardiol, v. 10, p. 1-11 (1985)). Calcium channel blockers are a heterogeneous group of drugs that belong to one of three major chemical groups of drugs, the dihydropyridines, such as nifedipine, the phenyl alkyl amines, such as verapamil, and the benzothiazepines, such as diltiazem. Other calcium channel blockers useful according to the invention, include, but are not limited to, amrinone, amlodipine, bencyclane, felodipine, fendiline, flunarizine, isradipine, nicardipine, nimodipine, perhexilene, gallopamil, tiapamil and tiapamil analogues (such as 1993RO-11-2933), phenytoin, barbiturates, and the peptides dynorphin, omega-conotoxin, and omega-agatoxin, and the like and/or pharmaceutically acceptable salts thereof.

"Beta-adrenergic receptor blocking agents" are a class of drugs that antagonize the cardiovascular effects of catecholamines in angina pectoris, hypertension, and cardiac arrhythmias. Beta-adrenergic receptor blockers include, but are not limited to, atenolol, acebutolol, alprenolol, befunolol, betaxolol, bunitrolol, carteolol, celiprolol, hedroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hydroxypropoxy)-3-pyridenecarbonitrilHCl, 1-butylamino-3-(2,5-dichlorophenoxy-)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazol, 7-(2-hydroxy-3-t-butylaminpropoxy) phthalide. The above-identified compounds can be used as isomeric mixtures, or in their respective levorotating or dextrorotating form.

A number of selective "COX-2 inhibitors" are known in the art and include, but are not limited to, COX-2 inhibitors described in U.S. Pat. No. 5,474,995 "Phenyl heterocycles as cox-2 inhibitors"; U.S. Pat. No. 5,521,213 "Diaryl bicyclic heterocycles as inhibitors of cyclooxygenase-2"; U.S. Pat. No. 5,536,752 "Phenyl heterocycles as COX-2 inhibitors"; U.S. Pat. No. 5,550,142 "Phenyl heterocycles as COX-2 inhibitors"; U.S. Pat. No. 5,552,422 "Aryl substituted 5,5 fused aromatic nitrogen compounds as anti-inflammatory agents"; U.S. Pat. No. 5,604,253 "N-benzylindol-3-yl propanoic acid derivatives as cyclooxygenase inhibitors"; U.S. Pat. No. 5,604,260 "5-methanesulfonamido-1-indanones as an inhibitor of cyclooxygenase-2"; U.S. Pat. No. 5,639,780 "N-benzyl indol-3-yl butanoic acid derivatives as cyclooxygenase inhibitors"; U.S. Pat. No. 5,677,318 "Diphenyl-1,2-3-thiadiazoles as anti-inflammatory agents"; U.S. Pat. No. 5,691,374 "Diaryl-5-oxygenated-2-(5H)-furanones as COX-2 inhibitors"; U.S. Pat. No. 5,698,584 "3,4-diaryl-2-hydroxy-2,5-dihy-drofurans as prodrugs to COX-2 inhibitors"; U.S. Pat. No. 5,710,140 "Phenyl heterocycles as COX-2 inhibitors"; U.S. Pat. No. 5,733,909 "Diphenyl stilbenes as prodrugs to COX-2 inhibitors"; U.S. Pat. No. 5,789,413 "Alkylated styrenes as prodrugs to COX-2 inhibitors"; U.S. Pat. No. 5,817,700 "Bisaryl cyclobutenes derivatives as cyclooxygenase inhibitors"; U.S. Pat. No. 5,849,943 "Stilbene derivatives useful as cyclooxygenase-2 inhibitors"; U.S. Pat. No. 5,861,419 "Substituted pyridines as selective cyclooxygenase-2 inhibitors"; U.S. Pat. No. 5,922,742 "Pyridinyl-2-cyclopenten-1-ones as selective cyclooxygenase-2 inhibitors"; U.S. Pat. No. 5,925,631 "Alkylated styrenes as prodrugs to COX-2 inhibitors"; all of which are commonly assigned to Merck Frosst Canada, Inc. (Kirkland, Calif.). Additional COX-2 inhibitors are also described in U.S. Pat. No. 5,643,933, assigned to G. D. Searle & Co. (Skokie, Ill.), entitled: "Substituted sulfonylphenyl-heterocycles as cyclooxygenase-2 and 5-lipoxygenase inhibitors."

A number of the above-identified COX-2 inhibitors are prodrugs of selective COX-2 inhibitors, and exert their action by conversion in vivo to the active and selective COX-2 inhibitors. The active and selective COX-2 inhibitors formed from the above-identified COX-2 inhibitor prodrugs are described in detail in WO 95/00501, published Jan. 5, 1995, WO 95/18799, published Jul. 13, 1995 and U.S. Pat. No. 5,474,995, issued Dec. 12, 1995. Given the teachings of U.S. Pat. No. 5,543,297, entitled: "Human cyclooxygenase-2 cDNA and assays for evaluating cyclooxygenase-2 activity," a person of ordinary skill in the art would be able to determine whether an agent is a selective COX-2 inhibitor or a precursor of a COX-2 inhibitor, and therefore part of the present invention.

"Angiotensin II antagonists" are compounds which interfere with the activity of angiotensin II by binding to angiotensin II receptors and interfering with its activity. Angiotensin II antagonists are well known and include peptide compounds and non-peptide compounds. Most angiotensin II antagonists are slightly modified congeners in which agonist activity is attenuated by replacement of phenylalanine in position 8 with some other amino acid; stability can be enhanced by other replacements that slow degeneration in vivo. Examples of angiotensin II antagonists include: peptidic compounds (e.g., saralasin, [(San$^1$)(Val$^5$)(Ala$^8$)] angiotensin-(1-8) octapeptide and related analogs); N-substituted imidazole-2-one (U.S. Pat. No. 5,087,634); imidazole acetate derivatives including 2-N-butyl-4-chloro-1-(2-chlorobenzile) imidazole-5-acetic acid (see Long et al., J. Pharmacol. Exp. Ther. 247(1), 1-7 (1988)); 4,5,6,7-tetrahydro-1H-imidazo[4,5-c]pyridine-6-carboxylic acid and analog derivatives (U.S. Pat. No. 4,816,463); N2-tetrazole beta-glucuronide analogs (U.S. Pat. No. 5,085,992); substituted pyrroles, pyrazoles, and tryazoles (U.S. Pat. No. 5,081,127); phenol and heterocyclic derivatives such as 1,3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP Number 253,310, Jan. 20, 1988); ES8891 (N-morpholinoacetyl-(-1-naphthyl)-L-alany-1-(4, thiazolyl)-L-alanyl (35,45)-4-amino-3-hydroxy-5-cyclo-hexapentanoyl-N-hexylamide, Sankyo Company, Ltd., Tokyo, Japan); SKF108566 (E-alpha-2-[2-butyl-1-(carboxy phenyl) methyl] 1H-imidazole-5-yl[methylan-e]-2-thiophenepropanoic acid, Smith Kline Beecham Pharmaceuticals, Pa.); Losartan (DUP753/MK954, DuPont Merck Pharmaceutical Company); Remikirin (RO42-5892, F. Hoffman LaRoche AG); A.sub.2 agonists (Marion Merrill Dow) and certain non-peptide heterocycles (G. D. Searle and Company).

"Angiotensin converting enzyme (ACE) inhibitors" include amino acids and derivatives thereof, peptides, including di- and tri-peptides and antibodies to ACE which intervene in the renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410,520), phosphinylalkanoyl prolines such as fosinopril (U.S. Pat. No. 4,337,201) and trandolopril.

"Renin inhibitors" are compounds which interfere with the activity of renin. Renin inhibitors include amino acids and derivatives thereof, peptides and derivatives thereof, and antibodies to renin. Examples of renin inhibitors that are the subject of United States patents are as follows: urea derivatives of peptides (U.S. Pat. No. 5,116,835); amino acids connected by nonpeptide bonds (U.S. Pat. No. 5,114,937); di- and tri-peptide derivatives (U.S. Pat. No. 5,106,835); amino acids and derivatives thereof (U.S. Pat. Nos. 5,104,869 and 5,095,119); diol sulfonamides and sulfinyls (U.S. Pat. No. 5,098,924); modified peptides (U.S. Pat. No. 5,095,006); peptidyl beta-aminoacyl aminodiol carbamates (U.S. Pat. No. 5,089,471); pyrolimidazolones (U.S. Pat. No. 5,075,451); fluorine and chlorine statine or statone containing peptides (U.S. Pat. No. 5,066,643); peptidyl amino diols (U.S. Pat. Nos. 5,063,208 and 4,845,079); N-morpholino derivatives (U.S. Pat. No. 5,055,466); pepstatin derivatives (U.S. Pat. No. 4,980,283); N-heterocyclic alcohols (U.S. Pat. No. 4,885,292); monoclonal antibodies to renin (U.S. Pat. No. 4,780,401); and a variety of other peptides and analogs thereof (U.S. Pat. Nos. 5,071,837, 5,064,965, 5,063,207, 5,036,054, 5,036,053, 5,034,512, and 4,894,437).

Anti-platelet" agents include but are not limited to, Clopridogrel; Sulfinpyrazone; Aspirin; Dipyridamole; Clofibrate; Pyridinol Carbamate; PGE; Glucagon; Antiserotonin drugs; Caffeine; Theophyllin Pentoxifyllin; Ticlopidine; Anagrelide.

Other arteriovascular disease-modulating drugs include, but are not limited to, lipase inhibitors such as cetilistat (ATL-962); synthetic amylin analogs such as Symlin pramlintide with or without recombinant leptin; sodium-glucose cotransporter 2 (SGLT2) inhibitors like sergliflozin (869682; KGT-1251), YM543, dapagliflozin, GlaxoSmithKline molecule 189075, and Sanofi-Aventis molecule AVE2268; dual adipose triglyceride lipase and PI3 kinase activators like Adyvia (ID 1101); antagonists of neuropeptide Y2, Y4, and Y5 receptors like Nastech molecule PYY3-36, synthetic analog of human hormones PYY3-36 and pancreatic polypeptide (7TM molecule TM30338); Shionogi molecule S-2367; cannabinoid CB I receptor antagonists such as rimonabant (Acomplia), taranabant, CP-945,598, Solvay molecule SLV319, Vernalis molecule V24343; hormones like oleoyl-estrone; inhibitors of serotonin, dopamine, and norepinephrine (also known in the art as "triple monoamine reuptake inhibitors") like tesofensine (Neurosearch molecule NS2330); inhibitors of norepinephrine and dopamine reuptake, like Contrave (bupropion plus opioid antagonist naltrexone) and Excalia (bupropion plus anticonvulsant zonisaminde); inhibitors of 11β-hydroxysteroid dehydrogenase type I (11b-HSDI) like Incyte molecule INCB13739; inhibitors of cortisol synthesis such as ketoconazole (Di-Obex molecule DIO-902); inhibitors of gluconeogenesis such as Metabasis/Daiichi molecule CS-917; glucokinase activators like Roche molecule R1440; antisense inhibitors of protein tyrosine phosphatase-1B such as ISIS 113715; as well as other agents like NicOx molecule NCX 4016; injections of gastrin and epidermal growth factor (EGF) analogs such as Islet Neogenesis Therapy (E1-I.N.T.); and betahistine (Obecure molecule OBE101).

A subject cell (i.e., a cell isolated from a subject) can be incubated in the presence of a candidate agent and the pattern of ARTERIORISKMARKER expression in the test sample is measured and compared to a reference profile, e.g., an arteriovascular disease reference expression profile or a non-arteriovascular disease reference expression profile or an index value or baseline value. The test agent can be any compound or composition or combination thereof, including, dietary supplements. For example, the test agents are agents frequently used in arteriovascular treatment regimens and are described herein.

The aforementioned methods of the invention can be used to evaluate or monitor the progression and/or improvement of subjects who have been diagnosed with an arteriovascular disease, and who have undergone surgical interventions for these diseases, such as, for example, angioplasty, arteriovascular grafting of stems, including self expanding stents and drug-eluting stents comprising for example paclitaxel, atherectomy, coronary artery bypass, aortic and mitral valve replacement, heart transplantation, ventricular remodeling, transmyocardial laser therapy, aneurysm repair, aortic dissection, pacemaker devices, and Maze procedure.

Additionally, any of the aforementioned methods can be used separately or in combination to assess if a subject has shown an "improvement in arteriovascular disease risk factors" or moved within the risk spectrum of subjects at risk for having an arteriovascular event. Such improvements include, without limitation, a reduction in body mass index, a reduction in blood glucose levels, an increase in HDL levels, a decrease in LDL or total cholesterol levels, a reduction in systolic and/or diastolic blood pressure, an increase in insulin levels, or combinations thereof.

A subject suffering from or at risk of developing arteriovascular disease or an arteriovascular event may also be suffering from or at risk of developing Type 2 Diabetes, hypertension, or obesity. Type 2 Diabetes in particular and arteriovascular disease have many risk factors in common, and many of these risk factors are highly correlated with one another. The relationships among these risk factors may be attributable to a small number of physiological phenomena, perhaps even a single phenomenon. Subjects suffering from or at risk of developing Diabetes, arteriovascular disease, hypertension or obesity are identified by methods known in the art.

Because of the interrelationship between Diabetes and arteriovascular disease, some or all of the individual ARTERIORISKMARKERS and ARTERIORISKMARKER panels of the present invention may overlap or be encompassed by biomarkers of Type 2 Diabetes, Pre-Diabetes, or pre-diabetic conditions, and indeed may be useful in the diagnosis of the risk of Diabetes, Pre-Diabetes, or pre-diabetic conditions.

Performance and Accuracy Measures of the Invention

The performance and thus absolute and relative clinical usefulness of the invention may be assessed in multiple ways as noted above. Amongst the various assessments of performance, the invention is intended to provide accuracy in clinical diagnosis and prognosis. The accuracy of a diagnostic or prognostic test, assay, or method concerns the ability of the test, assay, or method to distinguish between subjects having arteriovascular disease, or at risk for arteriovascular disease or an arteriovascular event, is based on whether the subjects have an "effective amount" or a "significant alteration" in the levels of a ARTERIORISKMARKER. By "effective amount" or "significant alteration," it is meant that the measurement of an appropriate number of ARTERIORISKMARKERS (which may be one or more) is different than the predetermined cut-off point (or threshold value) for that ARTERIORISKMARKER(S) and therefore indicates that the subject has arteriovascular disease or is at risk for having an arteriovascular event for which the ARTERIORISKMARKER(S) is a determinant. The difference in the level of ARTERIORISKMARKER between normal and abnormal is preferably statistically significant. As noted below, and without any limitation of the invention, achieving statistical significance, and thus the preferred analytical and clinical accuracy, generally but not always requires that combinations of several ARTERIOR-ISKMARKERS be used together in panels and combined with mathematical algorithms in order to achieve a statistically significant ARTERIORISKMARKER index.

In the categorical diagnosis of a disease state, changing the cut point or threshold value of a test (or assay) usually changes the sensitivity and specificity, but in a qualitatively inverse relationship. Therefore, in assessing the accuracy and usefulness of a proposed medical test, assay, or method for assessing a subject's condition, one should always take both sensitivity and specificity into account and be mindful of what the cut point is at which the sensitivity and specificity are being reported because sensitivity and specificity may vary significantly over the range of cut points. Use of statistics such as AUC, encompassing all potential cut point values, is preferred for most categorical risk measures using the invention, while for continuous risk measures, statistics of goodness-of-fit and calibration to observed results or other gold standards, are preferred.

Using such statistics, an "acceptable degree of diagnostic accuracy", is herein defined as a test or assay (such as the test of the invention for determining the clinically significant presence of ARTERIORISKMARKERS, which thereby indicates the presence of arteriovascular disease and/or a risk of having an arteriovascular event) in which the AUC (area under the ROC curve for the test or assay) is at least 0.60, desirably at least 0.65, more desirably at least 0.70, preferably at least 0.75, more preferably at least 0.80, and most preferably at least 0.85.

By a "very high degree of diagnostic accuracy", it is meant a test or assay in which the AUC (area under the ROC curve for the test or assay) is at least 0.80, desirably at least 0.85, more desirably at least 0.875, preferably at least 0.90, more preferably at least 0.925, and most preferably at least 0.95.

The predictive value of any test depends on the sensitivity and specificity of the test, and on the prevalence of the condition in the population being tested. This notion, based on Bayes' theorem, provides that the greater the likelihood that the condition being screened for is present in an individual or in the population (pre-test probability), the greater the validity of a positive test and the greater the likelihood that the result is a true positive. Thus, the problem with using a test in any population where there is a low likelihood of the condition being present is that a positive result has limited value (i.e., more likely to be a false positive). Similarly, in populations at very high risk, a negative test result is more likely to be a false negative.

As a result, ROC and AUC can be misleading as to the clinical utility of a test in low disease prevalence tested populations (defined as those with less than 1% rate of occurrences (incidence) per annum, or less than 10% cumulative prevalence over a specified time horizon). Alternatively, absolute risk and relative risk ratios as defined elsewhere in this disclosure can be employed to determine the degree of clinical utility. Populations of subjects to be tested can also be categorized into quartiles by the test's measurement values, where the top quartile (25% of the population) comprises the group of subjects with the highest relative risk for developing arteriovascular disease or an arteriovascular event, and the bottom quartile comprising the group of subjects having the lowest relative risk for developing arteriovascular disease or an arteriovascular event. Generally, values derived from tests or assays having over 2.5 times the relative risk from top to bottom quartile in a low prevalence population are considered to have a "high degree of diagnostic accuracy," and those with five to seven times the relative risk for each quartile are considered to have a "very high degree of diagnostic accuracy." Nonetheless, values derived from tests or assays having only 1.2 to 2.5 times the relative risk for each quartile remain clinically useful are widely used as risk factors for a disease; such is the case with total cholesterol and for many inflammatory biomarkers with respect to their prediction of future arteriovascular events. Often such lower diagnostic accuracy tests must be combined with additional parameters in order to derive meaningful clinical thresholds for therapeutic intervention, as is done with the aforementioned global risk assessment indices.

A health economic utility function is an yet another means of measuring the performance and clinical value of a given test, consisting of weighting the potential categorical test outcomes based on actual measures of clinical and economic value for each. Health economic performance is closely related to accuracy, as a health economic utility function specifically assigns an economic value for the benefits of correct classification and the costs of misclassification of tested subjects. As a performance measure, it is not unusual to require a test to achieve a level of performance which results in an increase in health economic value per test (prior to testing costs) in excess of the target price of the test.

In general, alternative methods of determining diagnostic accuracy are commonly used for continuous measures, when a disease category or risk category (such as those ati risk for having an arteriovascular event) has not yet been clearly defined by the relevant medical societies and practice of medicine, where thresholds for therapeutic use are not yet established, or where there is no existing gold standard for diagnosis of the pre-disease. For continuous measures of risk, measures of diagnostic accuracy for a calculated index are typically based on curve fit and calibration between the predicted continuous value and the actual observed values (or a historical index calculated value) and utilize measures such as R squared, Hosmer-Lemeshow P-value statistics and confidence intervals. It is not unusual for predicted values using such algorithms to be reported including a confidence interval (usually 90% or 95% CI) based on a historical observed cohort's predictions, as in the test for risk of future breast cancer recurrence commercialized by Genomic Health, Inc. (Redwood City, Calif.).

In general, by defining the degree of diagnostic accuracy, i.e., cut points on a ROC curve, defining an acceptable AUC value, and determining the acceptable ranges in relative concentration of what constitutes an effective amount of the ARTERIORISKMARKERS of the invention allows for one of skill in the art to use the ARTERIORISKMARKERS to identify, diagnose, or prognose subjects with a pre-determined level of predictability and performance.

Relative Performance of the Invention

Only a minority of individual ARTERIORISKMARKERS achieve an acceptable degree of prognostic accuracy for future arteriovascular events. A representative list of 61 ARTERIORISKMARKERS, chosen as high priority based on the quality of the published scientific literature associating them with arteriovascular disease, was tested in the study design of Example 1 below. An exhaustive enumerative analysis of all potential single biomarker, two biomarker, and three biomarker and four biomarker panel combinations of this 61 ARTERIORISKMARKERS was used to derive individual best fit LDA models to predict risk of conversion to arteriovascular events in the Example 1 populations (see FIG. 12 and Table 1 below). A fitted LDA model was developed for every possible ARTERIORISKMARKER combination of a given panel size and then analyzed for its AUC statistic.

It is immediately apparent from the table below that there was a very low likelihood of finding individual prognostic biomarkers with an acceptable diagnostic accuracy, even from such an enriched population of ARTERIORISKMARKERS as those cited in literature with evidence of an association with frank arteriovascular disease.

vascular events (such as in the Framingham Risk Score), and furthermore remains the primary identification method and definition of appropriate categories of subjects for the testing and diagnosis of asymptomatic arteriovascular disease.

Even larger combinations utilizing multiple biomarkers infrequently achieve high model accuracy. A minimum combination of two or more biomarkers (as taught in the invention herein) was required to achieve a level of accuracy defined by an AUC of 0.75 or above within the Example 1

TABLE 1

Exhaustive Enumeration of All Single, Two, Three and Four Marker Combination of ARTERIORISKMARKERS and Their Best Fit LDA Model AUC Statistics

| | Single Markers | | 2 Marker Panels | | 3 Marker Panels | | 4 Marker Panels | |
|---|---|---|---|---|---|---|---|---|
| | Total Possible Panels | | | | | | | |
| All Panels with AUC Equal or Greater Than: | 61 Count | 100 00% % of Total | 1,830 Count | 100.00% % of Total | 35,990 Count | 100.00% % of Total | 521,855 Count | 100.00% % of Total |
| 0.05 | 61 | 100.00% | 1,830 | 100.00% | 35,990 | 100.00% | 521,855 | 100.00% |
| 0.10 | 61 | 100.00% | 1,830 | 100.00% | 35,990 | 100.00% | 521,855 | 100.00% |
| 0.15 | 61 | 100.00% | 1,830 | 100.00% | 35,990 | 100.00% | 521,855 | 100.00% |
| 0.20 | 61 | 100.00% | 1,830 | 100.00% | 35,990 | 100.00% | 521,855 | 100.00% |
| 0.25 | 61 | 100.00% | 1,830 | 100.00% | 35,990 | 100.00% | 521,855 | 100.00% |
| 0.30 | 61 | 100.00% | 1,830 | 100.00% | 35,990 | 100.00% | 521,855 | 100.00% |
| 0.35 | 61 | 100.00% | 1,830 | 100.00% | 35,990 | 100.00% | 521,855 | 100.00% |
| 0.40 | 61 | 100.00% | 1,830 | 100.00% | 35,990 | 100.00% | 521,855 | 100.00% |
| 0.45 | 60 | 98.36% | 1,829 | 99.95% | 35,988 | 99.99% | 521,855 | 100.00% |
| 0.50 | 51 | 83.61% | 1,760 | 96.17% | 35,740 | 99.31% | 521,104 | 99.86% |
| 0.55 | 25 | 40.98% | 1,244 | 67.98% | 30,169 | 83.83% | 481,357 | 92.24% |
| 0.60 | 10 | 16.39% | 672 | 36.72% | 19,747 | 54.67% | 363,849 | 69.72% |
| 0.65 | 2 | 3.28% | 200 | 10.93% | 7,970 | 22.15% | 184,389 | 35.33% |
| 0.70 | 1 | 1.64% | 69 | 3.77% | 2,573 | 7.15% | 62,489 | 11.97% |
| 0.75 | — | 0.00% | 2 | 0.11% | 198 | 0.55% | 8,153 | 1.56% |
| 0.80 | — | 0.00% | — | 0.00% | — | 0.00% | 29 | 0.01% |
| 0.85 | — | 0.00% | — | 0.00% | — | 0.00% | — | 0.00% |
| 0.90 | — | 0.00% | — | 0.00% | — | 0.00% | — | 0.00% |
| 0.95 | — | 0.00% | — | 0.00% | — | 0.00% | — | 0.00% |
| 1.00 | — | 0.00% | — | 0.00% | — | 0.00% | — | 0.00% |

As shown in FIG. 12, none of the individual ARTERIORISKMARKERS, out of the total 61 ARTERIORISKMARKERS tested in Example 1, achieved an AUC of 0.75 for the prediction of arteriovascular events even using a best fit univariate LDA model. The individual ARTERIORISKMARKER parameters tested included many of the traditional laboratory risk factors and clinical parameters commonly used in global risk assessment and indices for arteriovascular disease. Taken alone in a univariate best fit LDA model, only ten of the 61 selected ARTERIORISKMARKERS achieved an acceptable AUC of 0.6 or better; this was less than one in five markers. Many of the ARTERIORISKMARKERS most useful in constructing panels of multiple ARTERIORISKMARKERS were not in this group.

This analysis indicates that documented evidence of associations with arteriovascular disease, as was found in the published literature for each of the ARTERIORISKMARKERS, does not necessarily grant a biomarker prognostic utility for future arteriovascular events. In fact, only two ARTERIORISKMARKERS, Age and POMC, achieved an AUC of even 0.65 in a univariate best fit LDA model, representing less than one in twenty of the total ARTERIORISKMARKERS tested in this relatively enriched literature selected grouping of ARTERISKMARKERS. Despite this lack of a very high level of diagnostic accuracy in any single ARTERIORISKMARKER, Age remains the most dominant factor in global risk assessment algorithms for predicting the risk of arteriovascular disease or of arteriodata set. Across all 1,830 unique possible combinations, only two combinations of two ARTERIORISKMARKERS yielded bivariate best fit LDA models which met this hurdle. Such two ARTERIORISKMARKER combinations occurred at an approximate rate of approximately one in a thousand potential combinations. In contrast, two hundred unique bivariate ARTERIORISKMARKER combinations met a model accuracy hurdle of an AUC of 0.65 in the same data set. Each of these is disclosed in FIG. 13, including 69 two ARTERIORISKMARKER, combinations which met an AUC hurdle of 0.70. Combinations of two ARTERIORISKMARKERS making this higher hurdle occurred again in less than one in twenty of the potential combinations. All of these two ARTERIORISKMARKER combinations with an AUC of 0.70 or better contained either Age or POMC as one of the two included ARTERIORISKMARKERS.

After panel size was increased above bivariate ARTERIORISKMARKERS combination panels, additional other biomarkers also became participants in the higher performing trivariate combinations of three ARTERIORISKMARKERS. Many of these combinations yielded acceptable LDA model performance, equal to or above an AUC of 0.60, both with and without the inclusion of either Age or POMC within the panel. In fact, certain combinations of three or more ARTERIORISKMARKERS were found to exhibit superior performance of an AUC of 0.70 or better, and are listed in FIG. 14, which presents 2,573 unique three ARTERIORISKMARKER combinations. These include many without the inclusion of either Age or POMC. The total three ARTERIORISKMARKER combinations at this level of performance occurred in just over seven percent of the total group of 35,990 unique combinations. Furthermore, included in the 2,573 are 198 three ARTERIORISKMARKER combinations which made an AUC of 0.75 or better. This represents less than one in one hundred of the total possible unique combinations of three or more ARTERIORISKMARKERS.

At combinations comprising four ARTERIORISKMARKERS, the total unique combinations represent 521,855 unique panels. Achieving an AUC of at least 0.75 were 8,153, a less than one in fifty success rate; each of these four ARTERIORISKMARKER combinations are enumerated in FIG. 15. A very high level of diagnostic accuracy, representing an AUC of 0.8 was finally achieved in 29 of the panels listed therein. This represents less than one per ten thousand of the total possible unique combinations of four or more ARTERIORISKMARKERS.

Notably, the preceding analysis of summarized in FIGS. 12 through 15 also demonstrated that no single biomarker was required to practice the invention at an acceptable level of diagnostic accuracy, although several individually identified biomarkers are parts of the most preferred embodiments as disclosed below. It is a feature of the invention that diagnostic or prognostic information lost due to removing one ARTERIORISKMARKER can often be replaced through substitution with one or more other ARTERIORISKMARKERS, and generically by increasing the panel size, subject to the need to increase the study size in order for studies examining very large models encompassing many ARTERIORISKMARKERS to remain statistically significant. It is also a feature of the invention that overall performance and accuracy can often be improved by adding additional biomarkers (e.g., ARTERIORISKMARKERS, traditional laboratory risk factors, and clinical parameters) as additional inputs to a formula or model, as demonstrated above in the relative performance of univariate, bivariate, and trivariate models, and below in the performance of larger models:

The ultimate determinant and gold standard of true risk of arteriovascular events is actual conversions within a sufficiently large study population and observed over the length of time claimed, as was done in the Examples contained herein. However, this is problematic, as it is necessarily a retrospective point of view for the individual patient. As a result, subjects suffering from or at risk of developing arteriovascular disease or an arteriovascular event are commonly diagnosed or identified by methods known in the art, generally using either traditional laboratory risk factors or other non-analyte clinical parameters, and future risk is estimated based on historical experience and registry studies. Such methods include, but are not limited to, measurement of systolic and diastolic blood pressure, in vitro determination of total cholesterol, LDL, HDL, and glucose levels from blood samples, stress tests, ankle-brachial indices (ABI) which is the ratio of systolic blood pressure in the ankle arteries to the systolic blood pressure in the brachial arteries, measurement of human serum C-reactive protein (hsCRP), subfractions of LDL, electrocardiogram (ECG), imaging modalities such as computed tomography (CT), optical coherence tomography (OCT), intravascular ultrasonography (IVUS), carotid B-mode ultrasound, high-resolution IVUS, elastography (palpography), angioscopy, electron beam computed tomography (EBCT), magnetic resonance imaging (MRI) such as contrast-enhanced MRI with superparamagnetic iron oxide and gadolinium fluorine compounds, positron emission tomography (PET) such as fluorodeoxyglucose PET, single photon emission computed tomography (SPECT), immunoscintigraphy, and invasive angiography.

For example, subjects considered at lower risk for developing an arteriovascular disease or experiencing an arteriovascular event include, but are not limited to, the following favorable traditional risk factor traits: serum cholesterol less than 200 mg/dl, systolic blood pressure less than or equal to 120 mm Hg, diastolic blood pressure less than or equal to 80 mm Hg, non-current smoker, no history of diagnosed diabetes, normal insulin sensitivity and secretion, no previously diagnosed CAD, PAD, CVD or hypertension, and no baseline electrocardiogram (ECG) abnormalities. A subject's risk may be assessed by assessing either such single characteristics or by assessing an individual's "index score" constructed mathematically of such single measurement characteristics with reference to predicted risk from a longitudinal study series, as in the Framingham index and NCEP ATP III guidelines. However, even subjects who are asymptomatic and/or subject who do not exhibit any of the aforementioned risk factors, or with low predicted risk, for arteriovascular disease may be at risk for an arteriovascular event. Therefore, the ARTERIORISKMARKERS and methods of use disclosed herein provide for identification and diagnosis of arteriovascular disease or risk of arteriovascular events in such asymptomatic subjects, and to further and more accurately risk stratify both higher and lower risk subjects beyond their predicted risk as assessed by the presence or absence of arteriovascular disease symptoms, traditional risk factors, indices, and guidelines.

Subjects considered at high risk may exhibit baseline ECG abnormalities. Normal heart rate observable by ECG is usually between 60 and 100 beats per minute and the rhythm appears regular. P waves, QRS complexes, T waves appear normal. ST segments are not elevated above or depressed below the baseline of the ECG tracing. The P wave is a record of the movement of electrical activity through the upper heart chambers (atria). The QRS complex is a record of the movement of electrical impulses through the lower heart chambers (ventricles). The ST segment usually appears as a straight, level line between the QRS complex and the T wave. Elevated or lowered ST segments may mean the heart muscle is damaged or not receiving enough blood. The T wave corresponds to the period when the lower heart chambers are relaxing electrically and preparing for their next muscle contraction. However, normal-appearing ECG can occur even in the presence of heart disease.

Abnormalities observed by ECG include heart rhythm. There are many different kinds of irregular heartbeats (arrhythmias). A heart rate less than 60 beats per minutes is called a "bradycardia". A heart rate greater than 100 beats per minutes is called a "tachycardia". Examples of tachycardias may include a fast, irregular heart rhythm that originates in the ventricle (ventricular fibrillation) or a fast, regular heart rhythm that begins in the atrium (atrial flutter). Abnormal conduction of the electrical impulse in the heart can also be seen in other types of arrhythmias.

If the coronary arteries supplying blood to the heart muscle are blocked, the muscle may receive less oxygen and may begin to die (ischemia or heart attack), This damage to the heart muscle may show up on the electrocardiogram. Early ECG signs of poor blood flow to the heart may include lowered (depressed) ST segments, Early ECG signs of heart attack often include raised (elevated) ST segments. Later, as the heart attack persists, Q waves on the ECG may appear and become deeper.

Certain changes in the ECG may suggest thickening of the muscle walls of one or more heart chambers. Conditions that may cause hypertrophy of one or more heart chambers include high blood pressure, coronary artery disease, heart failure, cardiomyopathy, or heart valve disease. Elevated ST segments on the ECG may indicate an inflammation of the heart muscle (myocarditis) or the sac that surrounds the heart (pericarditis). Proper contraction of the heart depends upon normal levels of electrolytes in the blood, such as calcium and potassium. Too much or too little of these electrolytes results in certain rhythm abnormalities, such as abnormal changes in the P wave, QRS complex, or T wave that can be seen on an electrocardiogram. Certain medications for the heart and other conditions can result in ECG changes.

Subjects at increased risk for developing an arteriovascular disease, and for experiencing arteriorvascular events, can include, without limitation, BMI over 25 (BMI between 25-29 are considered "overweight", while BMI of 30 or above is considered "obese"), waist circumference of 40 inches or larger in men or 35 inches or larger in women; current smoking of at least 5 cigarettes per day on average, systolic blood pressure of greater than or equal to 140 mm Hg, diastolic blood pressure of greater than or equal to 90 mm Hg, fasting hyperglycemia, e.g., glucose levels of greater than or equal to 126 mg/dl (wherein subjects who exhibit these glucose levels are considered to be diabetic), and impaired fasting glucose (glucose greater than or equal to 100 mg/dl but below 126 mg/dl).

As noted above, risk prediction for arteriovascular disease or an arteriovascular event can also encompass risk prediction algorithms and computed indices that assess and estimate a subject's absolute risk for developing arteriovascular disease or an arteriovascular event with reference to a historical cohort. Risk assessment using such predictive mathematical algorithms and computed indices has increasingly been incorporated into guidelines for diagnostic testing and treatment, and encompass indices obtained from and validated with, inter alia, stratified samples from a representative population.

As previously mentioned, despite the numerous studies and algorithms that have been used to assess the risk of arteriovascular disease, the evidence-based, multiple risk factor assessment approach is only moderately accurate for the prediction of short- and long-term risk of manifesting an arteriovascular event, particularly sudden death, in asymptomatic or otherwise healthy subjects. Such risk prediction algorithms can be advantageously used with the ARTERIORISKMARKERS of the present invention to distinguish between subjects in a population of interest to determine the risk stratification of developing arteriovascular disease or an arteriovascular event. The ARTERIORISKMARKERS and methods of use disclosed herein provide tools that can be used in combination with such risk prediction algorithms to assess, identify, or diagnose subjects who are asymptomatic and do not exhibit the traditional risk factors.

The data derived from risk factors, risk prediction algorithms, and from the methods of the present invention can be combined and compared by known statistical techniques in order to compare the relative performance of the invention to the other techniques.

Furthermore, the application of such techniques to panels of multiple ARTERIORISKMARKERS is encompassed by or within the ambit of the present invention, as is the use of such combinations and formulae to create single numerical "risk indices" or "risk scores" encompassing information from multiple ARTERIORISKMARKER inputs.

Risk Markers of the Invention (ARTERIORISKMARKERS)

The biomarkers and methods of the present invention allow one of skill in the art to identify, diagnose, or otherwise assess those subjects who do not exhibit any symptoms of arteriovascular disease or an arteriovascular event, but who nonetheless may be at risk for developing arteriovascular disease or an arteriovascular event, or experiencing symptoms characteristic of arteriovascular disease or an arteriovascular event.

One thousand and twenty-three analyte-based biomarkers have been identified as being found to have altered or modified presence or concentration levels in subjects who have arteriovascular disease, or who exhibit symptoms characteristic of arteriovascular disease or an arteriovascular event.

Table 2 comprises the one thousand and twenty-three analyte-based ARTERIORISKMARKERS of the present invention, where the ARTERIORISKMARKER can be assigned to a single gene or gene product, and specifically excluding. One skilled in the art will recognize that the ARTERIORISKMARKERS presented herein encompasses all forms and variants, including but not limited to, polymorphisms, isoforms, mutants, derivatives, precursors including nucleic acids and pro-proteins, cleavage products, receptors (including soluble and transmembrane receptors), ligands, protein-ligand complexes, and post-translationally modified variants (such as cross-linking or glycosylation), fragments, and degradation products, as well as any multiunit nucleic acid, protein, and glycoprotein structures comprised of any of the ARTERIORISKMARKERS as constituent sub-units of the fully assembled structure.

TABLE 2

ARTERIORISKMARKERS

| ARTERIORISKMARKER | Official Name | Common Name | Gene Symbol |
|---|---|---|---|
| 1 | alpha-2-macroglobulin | alpha2-macroglobulin (alpha2-M) - alpha 2M, alpha 2-macroglobulin | A2M |
| 2 | ATP-binding cassette, sub-family A (ABC1), member 1 | ABCA1 - ABC-1, ABC1, CERP, HDLDT1, TGD, ATP binding cassette transporter 1; ATP-binding cassette 1; ATP-binding cassette transporter-1; ATP-binding cassette, sub-family A member 1; cholesterol efflux regulatory protein; high density lipoprotein deficiency, Tangier type, 1; membrane-bound | ABCA1 |
| 3 | ATP-binding cassette, sub-family B (MDR/TAP), member 1 | Multi Drug Resistance 1 - ABC20, CD243, CLCS, GP170, MDR1, P-gp, PGY1, ATP-binding cassette sub-family B member 1; P glycoprotein 1; P-glycoprotein 1; colchicin sensitivity; doxorubicin resistance; multidrug resistance 1 | ABCB1 |

TABLE 2-continued

ARTERIORISKMARKERS

| ARTERIORISKMARKER | Official Name | Common Name | Gene Symbol |
|---|---|---|---|
| 4 | acetyl-Coenzyme A carboxylase beta | acetyl-Coenzyme A carboxylase beta - ACC2, ACCB, HACC275, acetyl-CoA carboxylase 2 | ACACB |
| 5 | acyl-Coenzyme A dehydrogenase, C-4 to C-12 straight chain | medium-chain acyl-coenzyme A dehydrogenase | ACADM |
| 6 | angiotensin I converting enzyme (peptidyl-dipeptidase A) 1 | angiotensin-converting enzyme (ACE) - ACE1, CD143, DCP, DCP1, CD143 antigen; angiotensin I converting enzyme; angiotensin converting enzyme, somatic isoform; carboxycathepsin; dipeptidyl carboxypeptidase 1; kininase II; peptidase P; peptidyl-dipeptidase A; testicular ECA | ACE |
| 7 | angiotensin I converting enzyme (peptidyl-dipeptidase A) 1 | deletion/deletion (D/D) genotype of the angiotensin converting enzyme (ACE) is PROTECTIVE against VTE (venous thromboembolism)/insertion/deletion (I/D) angiotensin converting enzyme (ACE) gene polymorphism - ACE1, CD143, DCP, DCP1, CD143 antigen; angiotensin I converting enzyme; angiotensin converting enzyme, somatic isoform; carboxycathepsin; dipeptidyl carboxypeptidase 1; kininase II; peptidase P; peptidyl-dipeptidase A; testicular ECA | ACE |
| 8 | acyl-CoA synthetase medium-chain family member 2 | fatty acid-CoA ligase-like enzyme polypeptide - HXMA, HYST1046, xenobiotic/medium-chain fatty acid: CoA ligase | ACSM2 |
| 9 | actin, alpha 1, skeletal muscle | skeletal α-actin - ACTA, ASMA, CFTD, CFTD1, CFTDM, MPFD, NEM1, NEM2, NEM3, alpha 1 actin; alpha skeletal muscle actin | ACTA1 |
| 10 | actin, alpha, cardiac muscle | cardial α-actin - CMD1R, cardiac muscle alpha actin; smooth muscle actin | ACTC |
| 11 | actin, gamma 2, smooth muscle, enteric | smooth muscle α actin - ACT, ACTA3, ACTE, ACTL3, ACTSG, actin, gamma 2; actin-like protein; alpha-actin 3; smooth muscle gamma actin | ACTG2 |
| 12 | actinin, alpha 1 | alpha(1)-actinin - alpha-actinin 1 | ACTN1 |
| 13 | adducin 1 (alpha) | alpha-adducin | ADD1 |
| 14 | adiponectin, C1Q and collagen domain containing | Adiponectin - ACDC, ACRP30, APM-1, APM1, GBP28, adiponectin, adipocyte, C1Q and collagen domain containing; adipocyte, C1Q and collagen domain-containing; adiponectin; adipose most abundant gene transcript 1; gelatin-binding protein 28 | ADIPOQ |
| 15 | adiponectin receptor 1 | G Protein Coupled Receptor AdipoR1 - ACDCR1, CGI-45, PAQR1, TESBP1A | ADIPOR1 |
| 16 | adiponectin receptor 2 | G Protein Coupled Receptor AdipoR2 - ACDCR2, PAQR2 | ADIPOR2 |
| 17 | adrenomedullin receptor | Adrenomedullin Receptor - 7TMR, AMR, gamrh, hrhAMR, G-protein coupled receptor | ADMR |
| 18 | adenosine A1 receptor | G-protein-coupled receptor adenosine A1- RDC7 | ADORA1 |
| 19 | adenosine A2b receptor | G-protein-coupled receptor adenosine A2B - ADORA2 | ADORA2B |
| 20 | adenosine A3 receptor | G-protein-coupled receptor adenosine A3 - A3AR, AD026, AD026 protein (AD026) | ADORA3 |
| 21 | adrenergic, alpha-1A-, receptor | Alpha-1A Adrenergic Receptor, ADRA1A - ADRA1C, ADRA1L1, ALPHA1AAR, G protein coupled receptor; adrenergic, alpha -1A-, receptor; adrenergic, alpha-1C-, receptor; alpha-1A-adrenergic receptor | ADRA1A |
| 22 | adrenergic, alpha-1B-, receptor | beta2-adrenergic receptor - ADRA1, ALPHA1BAR, alpha-1B-adrenergic receptor | ADRA1B |
| 23 | adrenergic, alpha-1D-, receptor | adrenergic alpha 1D receptor - ADRA1, ADRA1A, ADRA1R, ALPHA1, DAR, adrenergic, alpha -1D-, receptor; adrenergic, alpha-1A-, receptor; alpha-1D-adrenergic receptor | ADRA1D |
| 24 | adrenergic, alpha-2A-, receptor | G protein-coupled alpha 2A-adrenoceptor (ADRA2A) - ADRA2, ADRA2R, ADRAR, ALPHA2AAR, ZNF32, alpha-2A-adrenergic receptor; alpha-2AAR subtype C10; alpha2A adrenergic receptor | ADRA2A |
| 25 | adrenergic, alpha-2B-, receptor | ADRA2L1, ADRA2RL1, ADRARL1, ALPHA2BAR, G-protein coupled receptor; adrenergic receptor alpha 2B; alpha-2-adrenergic receptor-like 1; alpha-2B-adrenergic receptor | ADRA2B |

TABLE 2-continued

ARTERIORISKMARKERS

| ARTERIORISKMARKER | Official Name | Common Name | Gene Symbol |
|---|---|---|---|
| 26 | adrenergic, beta-2-, receptor, surface | G Protein- Coupled Beta-2 Adrenoceptor - ADRB2R, ADRBR, B2AR, BAR, BETA2AR, beta-2 adrenergic receptor; beta-2 adrenoceptor; catecholamine receptor | ADRB2 |
| 27 | adrenergic, beta-2-, receptor, surface | beta2-adrenergic receptor - ADRB2R, ADRBR, B2AR, BAR, BETA2AR, beta-2 adrenergic receptor; beta-2 adrenoceptor; catecholamine receptor | ADRB2 |
| 28 | adrenergic, beta-3-, receptor | beta-3-adrenergic receptor - BETA3AR, Beta-3 Adrenergic Receptor | ADRB3 |
| 29 | adrenergic, beta, receptor kinase 1 | G Protein- Dependent Receptor Kinase 2 (GRK2) - BARK1, BETA-ARK1, GRK2, beta adrenergic receptor kinase 1 | ADRBK1 |
| 30 | alpha-fetoprotein | serum alpha-fetoprotein - FETA, HPAFP, alpha-1-fetoprotein; alpha-fetoglobulin | AFP |
| 31 | advanced glycosylation end product specific receptor | RAGE - advanced glycosylation end product-specific receptor RAGE3; advanced glycosylation end product-specific receptor variant sRAGE1; advanced glycosylation end product-specific receptor variant sRAGE2; receptor for advanced glycosylation end-products; soluble receptor | AGER |
| 32 | 1-acylglycerol-3-phosphate O-acyltransferase 7 (lysophosphatidic acid acyltransferase, eta) | acylglycerol acyltransferase-like protein MGAT-X2 - AYTL3, LPAAT-eta, PLSC domain containing protein; acyltransferase like 3 | AGPAT7 |
| 33 | angiotensinogen (serpin peptidase inhibitor, clade A, member 8) | AGT M235T variant of angiotensinogen (AGT) gene & see patent info - ANHU, SERPINA8, angiotensin I; angiotensin II precursor; angiotensinogen; angiotensinogen (serine (or cysteine) peptidase inhibitor, clade A, member 8); angiotensinogen (serine (or cysteine) proteinase inhibitor, clade A (alpha-1 antiproteinase, antitrypsin), member 8); pre-angiotensinogen | AGT |
| 34 | angiotensin II receptor, type 1 | G protein-Coupled Receptor AGTR1A - AG2S, AGTR1A, AGTR1B, AT1, AT1B, AT2R1, AT2R1A, AT2R1B, HAT1R, angiotensin receptor 1; angiotensin receptor 1B; type-1B angiotensin II receptor | AGTR1 |
| 35 | angiotensin II receptor, type 2 | G protein-coupled Receptor AGTR2 - AT2, ATGR2, MRX88, angiotensin receptor 2 | AGTR2 |
| 36 | angiotensin II receptor-like 1 | G Protein- Counled Apelin Receptor - APJ, angiotensin receptor-like 1 | AGTRL1 |
| 37 | aryl hydrocarbon receptor | aryl hydrocarbon receptor - AH-receptor; aromatic hydrocarbon receptor | AHR |
| 38 | alpha-2-HS-glycoprotein | alpha-2-HS-glycoprotein, A2HS, AHS, FETUA, HSGA, Alpha-2HS-glycoprotein; fetuin-A | AHSG |
| 39 | A kinase (PRKA) anchor protein 1 | kinase (PRKA) anchor protein 1 - AKAP, AKAP121, AKAP149, AKAP84, D-AKAP1, PRKA1, SAKAP84, A-kinase anchor protein 1; A-kinase anchor protein, 149 kD; dual-specificity A-kinase anchoring protein 1; protein kinase A anchoring protein 1; protein kinase A1; spermatid A-kinase anchor protein 84 | AKAP1 |
| 40 | A kinase (PRKA) anchor protein 10 | A kinase (PRKA) anchor protein 10 - D-AKAP2, PRKA10, A-kinase anchor protein 10; dual-specificity A-kinase anchoring protein 2; mitochondrial A kinase PPKA anchor protein 10; protein kinase A anchoring protein 10 | AKAP10 |
| 41 | A kinase (PRKA) anchor protein 13 | A kinase (PRKA) anchor protein 13 - AKAP-Lbc, BRX, HA-3, Ht31, LBC, PROTO-LB, PROTO-LBC, c-lbc, A-kinase anchor protein 13; A-kinase anchoring protein; breast cancer nuclear receptor-binding auxiliary protein; guanine nucleotide exchange factor Lbc; lymphoid blast crisis oncogene | AKAP13 |
| 42 | aldo-keto reductase family 1, member A1 (aldehyde reductase) | aldehyde reductase: ALR; ALDR1 | AKR1A1 |
| 43 | aldo-keto reductase family 1, member B10 (aldose reductase) | aldose reductase and aldehyde reductase - AKR1B11, AKR1B12, ALDRLn, ARL-1, ARL1, HIS, HSI, aldo-keto reductase family 1, member B10; aldo-keto reductase family 1, | AKR1B10 |

TABLE 2-continued

ARTERIORISKMARKERS

| ARTERIORISKMARKER | Official Name | Common Name | Gene Symbol |
|---|---|---|---|
| | | member B11 (aldose reductase-like); aldose reductase-like 1; aldose reductase-like peptide; aldose reductase-related protein; small intestine reductase | |
| 44 | v-akt murine thymoma viral oncogene homolog 1 | Ser/Thr kinase Akt - PKB, PRKBA, RAC, RAC-ALPHA, RAC-alpha serine/threonine-protein kinase; murine thymoma viral (v-akt) oncogene homolog-1; protein kinase B; rac protein kinase alpha | AKT1 |
| 45 | v-akt murine thymoma viral oncogene homolog 3 (protein kinase B, gamma) | Ser/Thr kinase Akt - PKBG, PRKBG, RAC-PK-gamma, RAC-gamma, STK-2, RAC-gamma serine/threonine protein kinase; protein kinase B gamma; serine threonine protein kinase, Akt-3; v-akt murine thymoma viral oncogene homolog 3 | AKT3 |
| 46 | albumin | Ischemia-modified albumin (IMA) - cell growth inhibiting protein 42; growth-inhibiting protein 20; serum albumin | ALB |
| 47 | aldehyde dehydrogenase 2 family (mitochondrial) | Aldehyde dehydrogenase - ALDH-E2, ALDHI, ALDM, ALDH class 2; acetaldehyde dehydrogenase 2; liver mitochondrial ALDH; mitochondrial aldehyde dehydrogenase 2; nucleus-encoded mitochondrial aldehyde dehydrogenase 2 | ALDH2 |
| 48 | aldolase C, fructose-bisphosphate | Aldolase C - aldolase 3; brain-type aldolase; fructoaldolase C; fructose-1,6-biphosphate triosephosphate lyase; fructose-bisphosphate aldolase C | ALDOC |
| 49 | alpha-1-microglobulin/bikunin precursor | alpha-1-microglobulin - HCP, ITI, ITIL, UTI, Alpha-1-microglobulin/bikunin precursor (inter-alpha-trypsin inhibitor, light chain; protein HC); Alpha-1-microglobulin/bikunin precursor; inter-alpha-trypsin; alpha-1-microglobulin/bikunin; growth-inhibiting protein 19 | AMBP |
| 50 | adenosine monophosphate deaminase 1 (isoform M) | adenosine monophosphate deaminase I (isoform M) - MAD, MADA, Adenosine monophosphate deaminase-1 (muscle) | AMPD1 |
| 51 | angiogenin, ribonuclease, RNase A family, 5 | angiogenin - RNASE4, RNASE5 | ANG |
| 52 | angiopoietin 2 | angiopoietin 2, AGPT2, ANG2, Tie2-ligand; angiopoietin-2; angiopoietin-2B; angiopoietin-2a | ANGPT2 |
| 53 | alanyl (membrane) aminopeptidase (aminopeptidase N, aminopeptidase M, microsomal aminopeptidase, CD13, p150) | Aminopeptidase N - CD13, LAP1, PEPN, gp150, aminopeptidase M; aminopeptidase N; membrane alanine aminopeptidase; microsomal aminopeptidase | ANPEP |
| 54 | annexin A1 | annexins - ANX1, LPC1, annexin I; annexin I (lipocortin I); lipocortin I | ANXA1 |
| 55 | annexin A2 | annexins - ANX2, ANX2L4, CAL1H, LIP2, LPC2, LPC2D, P36, PAP-IV, annexin II; calpactin I heavy polypeptide; chromobindin 8; lipocortin II; placental anticoagulant protein IV | ANXA2 |
| 56 | annexin A3 | annexins - ANX3, Annexin III (lipocortin III); annexin III (lipocortin III, 1,2-cyclic-inositol-phosphate phosphodiesterase, placental anticoagulant protein III, calcimedin 35-alpha); calcimedin 35-alpha | ANXA3 |
| 57 | annexin A4 | annexins - ANX4, PIG28, annexin IV; annexin IV (placental anticoagulant protein II); placental anticoagulant protein II; proliferation-inducing gene 28; proliferation-inducing protein 28 | ANXA4 |
| 58 | annexin A5 | circulating annexin V+ apoptotic microparticles in peripheral blood (Entered annexin V0 into Entrez), ANX5, ENX2, PP4, anchorin CII; annexin 5; endonexin II; lipocortin V; placental anticoagulant protein I | ANXA5 |
| 59 | apolipoprotein A-I | apolipoproteins A-1 and B, amyloidosis; apolipoprotein A-I, preproprotein; apolipoprotein A1; preproapolipoprotein | APOA1 |
| 60 | apolipoprotein A-I | apoA-I, amyloidosis; apolipoprotein A-I, preproprotein; apolipoprotein A1; preproapolipoprotein | APOA1 |
| 61 | apolipoprotein A-II | Apolipoprotein A-II | APOA2 |
| 62 | apolipoprotein A-IV | APOA4 - | APOA4 |
| 63 | APOA5 and Name: apolipoprotein A-V | APOA5 - APO-V, APOAV, RAP3, apolipoprotein A5; apolipoprotein AV; regeneration-associated protein 3 | APOA5 |

TABLE 2-continued

ARTERIORISKMARKERS

| ARTERIORISKMARKER | Official Name | Common Name | Gene Symbol |
|---|---|---|---|
| 64 | apolipoprotein B (including Ag(x) antigen) | apolipoproteins A-1 and B - Apolipoprotein B, FLDB, apoB-100; apoB-48; apolipoprotein B; apolipoprotein B48 | APOB |
| 65 | apolipoprotein B (including Ag(x) antigen) | APOB - FLDB, apoB-100; apoB-48; apolipoprotein B; apolipoprotein B48 | APOB |
| 66 | apolipoprotein C-I | apolipoprotein C-I | APOC1 |
| 67 | apolipoprotein C-II | APOC2 - | APOC2 |
| 68 | apolipoprotein C-III | APOC3 - APOCIII | APOC3 |
| 69 | apolipoprotein D | apolipoprotein D - | APOD |
| 70 | apolipoprotein E | Apolipoprotein E - AD2, apoprotein, Alzheimer disease 2 (APOE*E4-associated, late onset); apolipoprotein E precursor; apolipoprotein E3 | APOE |
| 71 | apolipoprotein H (beta-2-glycoprotein I) | beta2GPI - B2G1, BG, apolipoprotein H; beta-2-glycoprotein I | APOH |
| 72 | apolipoprotein L, 1 | apolipoprotein L1 - apolipoprotein L-I | APOL1 |
| 73 | apolipoprotein M | apolipoprotein M - G3a, HSPC336, NG20, NG20-like protein; alternative name: G3a, NG20 | APOM |
| 74 | v-raf murine sarcoma 3611 viral oncogene homolog | Raf protein - A-RAF, ARAF1, PKS2, RAFA1, Oncogene ARAF1; Ras-binding protein DA-Raf; v-raf murine sarcoma 3611 viral oncogene homolog 1 | ARAF |
| 75 | Rho GTPase activating protein 1 | Rho GTPase activating protein 1 - CDC42GAP, RHOGAP, RHOGAP1, p50rhoGAP, CDC42 GTPase-activating protein | ARHGAP1 |
| 76 | type 1 tumor necrosis factor receptor shedding aminopeptidase regulator | puromycin-insensitive leucyl-specific aminopeptidase -A-LAP, ALAP, APPILS, ARTS1, ERAAP, ERAP1, PILSAP, adipocyte-derived leucine aminopeptidase; aminopeptidase PILS | ARTS-1 |
| 77 | N-acylsphingosine amidohydrolase (acid ceramidase) 1 | Acid ceramidase: AC; PHP; ASAH; PHP32 | ASAH1 |
| 78 | N-acylsphingosine amidohydrolase (non-lysosomal ceramidase) 2 | acid ceramidase - HNAC1, N-acylsphingosine amidohydrolase (non-lysosomal ceramidase) 2B; N-acylsphingosine amidohydrolase 2; acid ceramidase; mitochondrial ceramidase; neutral ceramidase; neutral/alkaline ceramidase; non-lysosomal ceramidase | ASAH2 |
| 79 | aspartate beta-hydroxylase | asparagine hydroxylase - BAH, CASQ2BP1, HAAH, JCTN, junctin, aspartyl/asparaginyl-beta-hydroxylase; humbug; junctate; junctin isoform 1; peptide-aspartate beta-dioxygenase | ASPH |
| 80 | ATPase, Na+/K+ transporting, alpha 1 polypeptide | cation transport ATPase-like - Na+, K+ ATPase alpha subunit; Na+/K+ -ATPase alpha 1 subunit; Na+/K+ ATPase 1; Na, K-ATPase, alpha-A catalytic polypeptide; Na, K-ATPase alpha-1 subunit; Na, K-ATPase catalytic subunit alpha-A protein; Na/K-ATPase alpha subunit fragment (aa 1-149); sodium pump 1; sodium-potassium-ATPase, alpha 1 polypeptide | ATP1A1 |
| 81 | ATPase, Na+/K+ transporting, alpha 2 (+) polypeptide | ATPase, Na+1K+ transporting, alpha 2 (+) - FHM2, MHP2, Na+/K+ -ATPase alpha 2 subunit proprotein; Na+/K+ ATPase 2; Na+/K+ ATPase, alpha-A(+) catalytic polypeptide; Na+/K+ ATPase, alpha-B polypeptide; migraine, hemiplegic 2; sodium pump 2; sodium-potassium ATPase; sodium/potassium-transporting ATPase alpha-2 chain | ATP1A2 |
| 82 | ATPase, Na+/K+ transporting, alpha 4 polypeptide | cation transport ATPase - ATP1A1, ATP1AL2, ATPase, Na+/K+ transporting, alpha polypeptide-like 2; Na+/K+-ATPase alpha 4 subunit; Na+/K+ ATPase 4; Na+/K+ ATPase, alpha-D polypeptide; Na, K-ATPase subunit alpha-C; sodium pump 4; sodium/potassium-transporting ATPase alpha-4 chain | ATP1A4 |
| 83 | ATPase, Ca++ transporting, cardiac muscle, fast twitch 1 | ATPase, Ca++ transporting, cardiac muscle, fast twitch 1 - 12 - ATP2A, SERCA1, ATPase, Ca++ transporting, fast twitch 1; SR Ca(2+)-ATPase 1; calcium pump 1; calcium-transporting ATPase sarcoplasmic reticulum type, fast twitch skeletal muscle isoform; endoplasmic reticulum class 1/2 Ca(2+) ATPase; sarcoplasmic/endoplasmic reticulum calcium ATPase 1 | ATP2A1 |

TABLE 2-continued

ARTERIORISKMARKERS

| ARTERIORISKMARKER | Official Name | Common Name | Gene Symbol |
|---|---|---|---|
| 924 | ATPase, Ca++ transporting, cardiac muscle, slow twitch 2 | cation transport ATPase - ATP2B, DAR, DD, SERCA2, ATPase, Ca++ dependent, slow-twitch, cardiac muscle-2; SR Ca(2+)-ATPase 2; calcium pump 2; calcium-transporting ATPase sarcoplasmic reticulum type, slow twitch skeletal muscle isoform; endoplasmic reticulum class 1/2 Ca(2+) ATPase; sarcoplasmic/endoplasmic reticulum calcium ATPase 2 | ATP2A2 |
| 925 | ATPase, Ca++ transporting, ubiquitous | SERCA3, ATPase, Ca(2+)-transporting, ubiquitous; SR Ca(2+)-ATPase 3; adenosine triphosphatase, calcium; calcium pump 3; calcium-translocating P-type ATPase; sarco/endoplasmic reticulum Ca2+ -ATPase; sarco/endoplasmic reticulum Ca2+ ATPase isoform 3f; sarcoplasmic/endoplasmic reticulum calcium ATPase 3 | ATP2A3 |
| 926 | | Thrombin-Antithrombin III | autoantibody |
| 927 | | anti-PF4/heparin antibodies (for recurrent thrombotic events after acute coronary syndromes) | autoantibody |
| 928 | | anticardiolipin, anti-CL | autoantibody |
| 84 | | Endothelial cell reactive antibody (ECRA)/anti-endothelial cell antibodies (AECA) | autoantibody |
| 85 | | plasmin-alpha 2-antiplasmin complex | autoantibody |
| 86 | arginine vasopressin (neurophysin II, antidiuretic hormone, diabetes insipidus, neurohypophyseal) | copeptin - ADH, ARVP, AVP-NPII, AVRP, VP, arginine vasopressin-neurophysin II; vasopressin-neurophysin II-copeptin, vasopressin | AVP |
| 87 | arginine vasopressin receptor 1A | arginine vasopressin receptor 1 - SCCL vasopressin subtype 1a receptor; V1-vascular vasopressin receptor AVPR1A; V1a vasopressin receptor; antidiuretic hormone receptor 1A; vascular/hepatic-type arginine vasopressin receptor | AVPR1A |
| 929 | arginine vasopressin receptor 1B | arginine vasopressin receptor 3 - AVPR3, antidiuretic hormone receptor 1B; arginine vasopressin receptor 3; pituitary vasopressin receptor 3; vasopressin V1B receptor | AVPR1B |
| 88 | arginine vasopressin receptor 2 (nephrogenic diabetes insipidus) | arginine vasopressin receptor 2 - ADHR, DI1, DIR, DIR3, NDI, V2R, arginine vasopressin receptor 2 | AVPR2 |
| 89 | | *Chlamydia Pneumoniae* (Cp) infection | Bacteria |
| 90 | HLA-B associated transcript 3 | BAT3 - G3, HLA-B associated transcript-3; large proline-rich protein BAT3; scythe, A-B associated transcript 3 A cluster of genes | BAT3 |
| 91 | HLA-B associated transcript 4 | BAT4 - G5, HLA-B associated transcript-4 A-B associated transcript 4 A | BAT4 |
| 92 | HLA-B associated transcript 5 | BAT5 - NG26, HLA-B associated transcript-5, A-B associated transcript 5 A | BAT5 |
| 93 | BCL2-associated X protein | Bax - Bax zeta, apoptosis regulator BAX | BAX |
| 94 | basal cell adhesion molecule (Lutheran blood group) | AU, CD239, LU, MSK19, Auberger b antigen; B-CAM cell surface glycoprotein; B-cell adhesion molecule; F8/G253 antigen; Lutheran blood group (Auberger b antigen included); antigen identified by monoclonal antibody F8; basal cell adhesion molecule; basal cell adhesion molecule (Lu and Au blood groups); glycoprotein 95 kDa | BCAM |
| 95 | branched chain aminotransferase 1, cytosolic | branched chain aminotransferase 1, cytosolic: BCT1, ECA39, MECA39 | BCAT1 |
| 96 | B-cell CLL/lymphoma 2 | BCL-2-Bcl-2, B-cell lymphoma protein 2 | BCL2 |
| 97 | 3-hydroxybutyrate dehydrogenase, type 1 | BDH, MGC2723, MGC4347, MGC9788; (R)-3-hydroxybutyrate dehydrogenase; 3-hydroxybutyrate dehydrogenase; 3-hydroxybutyrate dehydrogenase (heart, mitochondrial); D-beta-hydroxybutyrate dehydrogenase, mitochondrial | BDH1 |
| 98 | Burkitt lymphoma receptor 1, GTP binding protein (chemokine (C-X-C motif) receptor 5) | CXC chemokine receptor 5 - CD185, CXCR5, MDR15, Burkitt lymphoma receptor 1; Burkitt lymphoma receptor 1, GTP-binding protein; Burkitt lymphoma receptor 1, isoform 1; C-X-C chemokine receptor type 5; monocyte-derived receptor 15 | BLR1 |

TABLE 2-continued

ARTERIORISKMARKERS

| ARTERIORISKMARKER | Official Name | Common Name | Gene Symbol |
|---|---|---|---|
| 99 | BMP2 inducible kinase | BMP-2 inducible kinase - BIKE, BMP-2 inducible kinase | BMP2K |
| 100 | v-raf murine sarcoma viral oncogene homolog B1 | Raf protein - B-raf 1, BRAF1, RAFB1, 94 kDa B-raf protein; Murine sarcoma viral (v-raf) oncogene homolog B1 | BRAF |
| 101 | bromodomain containing 3 | bromodomain containing 3 I - ORFX, RING3L, RING3-like gene; bromodomain containing protein 3; bromodomain-containing 3 | BRD3 |
| 102 | BUB1 budding uninhibited by benzimidazoles 1 homolog (yeast) | Bub1 - BUB1A, BUB1L, hBUB1, BUB1 budding uninhibited by benzimidazoles 1 homolog; budding uninhibited by benzimidazoles 1 (yeast homolog); mitotic spindle checkpoint kinase; putative serine/threonine-protein kinase | BUB1 |
| 103 | complement component 3 | complement C3 - acylation-stimulating protein cleavage product; complement component C3, ASP; CPAMD1 | C3 |
| 104 | complement component 3a receptor 1 | G protein coupled receptor C3AR1 (complement component 3a receptor 1) - AZ3B, C3AR, HNFAG09, complement component 3 receptor 1 | C3AR1 |
| 105 | complement component 4A (Rodgers blood group) | complement C4 - C4A anaphylatoxin; Rodgers form of C4; acidic C4; c4 propeptide; complement component 4A; complement component C4B | C4A |
| 106 | complement component 4B (Childo blood group) | C4A, C4A13, C4A91, C4B1, C4B12, C4B2, C4B3, C4B5, C4F, CH, CO4, CPAMD3, C4 complement C4d region; Chido form of C4; basic C4; complement C4B; complement component 4B; complement component 4B, centromeric; complement component 4B, telomeric; complement component C4B | C4B |
| 107 | complement component 5a receptor 1 | COMPLEMENT COMPONENT 5a RECEPTOR - C5A, C5AR, C5R1, CD88, C5a anaphylatoxin receptor; C5a receptor; complement component 5 receptor 1 (C5a ligand); complement component-5 receptor-2 (C5a ligand) | C5AR1 |
| 108 | calcitonin receptor | calcitonin receptor - CRT, CTR, CTR1 | CALCR |
| 109 | calcitonin receptor-like | calcitonin receptor-like receptor - CGRPR, CRLR | CALCRL |
| 110 | calcium/calmodulin-dependent protein kinase (CaM kinase) II beta? | BL-CAM: CaM kinase II beta subunit; CaM-kinase II beta chain; CaMK-II beta subunit; calcium/calmodulin-dependent protein kinase IIB; calcium/calmodulin-dependent protein kinase type II beta chain; proline rich calmodulin-dependent protein kinase | CAMK2B |
| 111 | caspase 3, apoptosis-related cysteine peptidase | caspase-3: PARP cleavage protease; SREBP cleavage activity 1; Yama; apopain; caspase 3; caspase 3, apoptosis-related cysteine protease; cysteine protease CPP32; procaspase3 | CASP3 |
| 112 | caspase 8, apoptosis-related cysteine peptidase | caspase 8 - CAP4, FLICE, MACH, MCH5, FADD-homologous ICE/CED-3-like protease; MACH-alpha-1/2/3 protein; MACH-beta-1/2/3/4 protein; Mch5 isoform alpha; caspase 8; caspase 8, apoptosis-related cysteine protease; cysteine protease; procaspase-8; procaspase-8L | CASP8 |
| 116 | caspase 9, apoptosis-related cysteine peptidase | caspase 9 - APAF-3, APAF3, CASPASE-9c, ICE-LAP6, MCH6, ICE-like apoptotic protease 6; apoptotic protease MCH-6; apoptotic protease activating factor 3; caspase 9; caspase 9, apoptosis-related cysteine protease; caspase-9c protein | CASP9 |
| 113 | cholecystokinin B receptor | cholecystokinin receptor B - CCK-B, GASR - CCK2 receptor; cholecystokinin-B receptor/gastrin; gastrin receptor; gastrin\cholecystokinin brain receptor | CCKBR |
| 114 | chemokine (C-C motif) ligand 1 | I-309; P500; SCYa1; SISe; TCA3; T lymphocyte-secreted protein I-309; inflammatory cytokine I-309; small inducible cytokine A1; small inducible cytokine A1 (I-309, homologous to mouse Tca-3) | CCL1 |

TABLE 2-continued

ARTERIORISKMARKERS

| ARTERIORISKMARKER | Official Name | Common Name | Gene Symbol |
|---|---|---|---|
| 115 | chemokine (C-C motif) ligand 11 | eosinophil chemotactic protein; eotaxin; small inducible cytokine A11; small inducible cytokine subfamily A (Cys-Cys), member 11; small inducible cytokine subfamily A (Cys-Cys), member 11 (eotaxin) | CCL11 |
| 117 | chemokine (C-C motif) ligand 12 | Scya12 | CCL12 |
| 120 | chemokine (C-C motif) ligand 19 | CC chemokine ligand 19; CK beta-11; EBI1-ligand chemokine; OTTHUMP00000000531; beta chemokine exodus-3; exodus-3; macrophage inflammatory protein 3-beta; small inducible cytokine A19; small inducible cytokine subfamily A (Cys-Cys), member 19 | CCL19 |
| 118 | chemokine (C-C motif) ligand 2 | Monocyte chemoattractant protein-1 (MCP-1) - GDCF-2, GDCF-2 HC11, HC11, HSMCR30, MCAF, MCP-1, MCP1, SCYA2, SMC-CF, monocyte chemoattractant protein-1; monocyte chemotactic and activating factor; monocyte chemotactic protein 1, homologous to mouse Sig-je; monocyte secretory protein JE; small inducible cytokine A2; small inducible cytokine A2 (monocyte chemotactic protein 1, homologous to mouse Sig-je); small inducible cytokine subfamily A (Cys-Cys), member 2 | CCL2 |
| 119 | chemokine (C-C motif) ligand 21 | Efficient Chemoattractant for Lymphocytes; OTTHUMP00000000526; OTTHUMP00000000527; beta chemokine exodus-2; exodus-2; secondary lymphoid tissue chemokine; small inducible cytokine A21; small inducible cytokine subfamily A (Cys-Cys), member 21 | CCL21 |
| 121 | chemokine (C-C motif)ligand 3 | GOS19-1; LD78ALPHA; MIP-1-alpha; MIP1A; SCYA3; LD78 alpha beta; small inducible cytokine A3; small inducible cytokine A3 (homologous to mouse Mip-1A) | CCL3 |
| 122 | chemokine (C-C motif) ligand 4 | ACT2; AT744.1; G-26; LAG1; MGC104418; MIP-1-beta; MGC126025; MIP1B; MGC126026; SCYA2; SCYA4; CC chemokine ligand 4; chemokine C-C motif ligand 4; lymphocyte-activation gene 1; secreted protein G-26; small inducible cytokine A4 (homologous to mouse Mip-1B) | CCL4 |
| 123 | chemokine (C-C motif) ligand 5 | SIS-delta; T-cell specific RANTES protein; T-cell specific protein p288; beta-chemokine RANTES; regulated upon activation, normally T-expressed, and presumably secreted; small inducible cytokine A5; small inducible cytokine A5 (RANTES); small inducible cytokine subfamily A (Cys-Cys), member 5 | CCL5 |
| 124 | chemokine (c-C motif) ligand 7 | FIC, MARC; MCP-3; MCP3; MGC138463; MGC138465; NC28; SCYA6; SCYA7; monocyte chemoattractant protein 3; small inducible cytokine A7; small inducible cytokine A7 (monocyte chemotactic protein 3) | CCL7 |
| 125 | chemokine (C-C motif) ligand 7 | chemokine (C-C motif) ligand 7, FIC, MARC, MCP-3, MCP3, MGC138463, MGC138465, NC28, SCYA6, SCYA7, monocyte chemoattractant protein 3; monocyte chemotactic protein 3; small inducible cytokine A7; small inducible cytokine A7 (monocyte chemotactic protein 3) | CCL7 |
| 126 | chemokine (C-C motif) ligand 8 | chemokine (C-C motif) ligand 8, HC14, MCP-2, MCP2, SCYA10, SCYA8, monocyte chemoattractant protein 2; monocyte chemotactic protein 2; small inducible cytokine A8; small inducible cytokine subfamily A (Cys-Cys), member 8; small inducible cytokine subfamily A (Cys-Cys), member 8 (monocyte chemotactic protein 2) | CCL8 |
| 127 | chemokine (C-C motif) ligand 9 | CCL10, Scya10, Scya9 | CCL9 |
| 128 | cyclin A2 | cyclin A - CCN1, CCNA, cyclin A | CCNA2 |
| 129 | cyclin B1 | CCNB1 - G2/mitotic-specific cyclin B1 | CCNB1 |
| 130 | cyclin D1 | cyclin D - BCL1, PRAD1, U21B31, B-cell CLL/lymphoma 1; G1/S-specific cyclin D1; cyclin D1 (PRAD1: parathyroid adenomatosis 1); parathyroid adenomatosis 1 | CCND1 |

TABLE 2-continued

ARTERIORISKMARKERS

| ARTERIORISKMARKER | Official Name | Common Name | Gene Symbol |
|---|---|---|---|
| 131 | cyclin E1 | CycE: cyclin Es; cyclin Et | CCNE1 |
| 132 | cyclin H | CycH: CDK-activating kinase; MO15-associated protein; cyclin-dependent kinase-activating kinase | CCNH |
| 133 | chemokine (C-C motif) receptor 1 | CC chemokine receptor 1 (CCR1) - CD191, CKR-1, CMKBR1, HM145, MIP1aR, SCYAR1, RANTES receptor | CCR1 |
| 134 | chemokine (C-C motif) receptor 10 | chemokine receptor 10 - GPR2, CC chemokine receptor 10; G protein-coupled receptor 2 | CCR10 |
| 135 | chemokine (C-C motif) receptor 2 | C-C Chemokine Receptor 2 - CC-CKR-2, CCR2A, CCR2B, CD192, CKR2, CKR2A, CKR2B, CMKBR2, MCP-1-R, MCP-1 receptor; chemokine (C-C) receptor 2; monocyte chemoattractant protein 1 receptor; monocyte chemotactic protein 1 receptor | CCR2 |
| 136 | chemokine (C-C motif) receptor 3 | CC-CKR-3, CD193, CKR3, CMKBR3, CC chemokine receptor 3; b-chemokine receptor; eosinophil CC chemokine receptor 3; eosinophil eotaxin receptor | CCR3 |
| 137 | chemokine (C-C motif) receptor 4 | C-C Chemokine Receptor 4 - CC-CKR-4, CKR4, CMKBR4, ChemR13, HGCN: 14099, K5-5, chemokine (C-C) receptor 4 | CCR4 |
| 138 | chemokine (C-C motif) receptor 5 | CC-CKR-5, CCCKR5, CD195, CKR-5, CKR5, CMKBR5, C-C chemokine receptor 5; C-C chemokine receptor type 5; CC chemokine receptor 5; CCR5 chemokine receptor; chemokine (C-C) receptor 5; chemokine receptor CCR5; chemr13 | CCR5 |
| 139 | chemokine (C-C motif) receptor 6 | C-C chemokine receptor type 6 - BN-1, CD196, CKR-L3, CKR6, CKRL3, CMKBR6, DCR2, DRY-6, GPR-CY4, GPR29, GPRCY4, STRL22, G protein-coupled receptor 29; chemokine (C-C) receptor 6; chemokine receptor-like 3; seven-transmembrane receptor, lymphocyte, 22 | CCR6 |
| 140 | chemokine (C-C motif) receptor 7 | C-C chemokine receptor type 7 - BLR2, CD197, CDw197, CMKBR7, EBI1, C-C chemokine receptor type 7; CC chemokine receptor 7; EBV-induced G protein-coupled receptor 1; Epstein-Barr virus induced G-protein coupled receptor; Epstein-Barr virus induced gene 1; MIP-3 beta receptor; chemokine (C-C) receptor 7; lymphocyte-specific G protein-coupled peptide receptor | CCR7 |
| 141 | chemokine (C-C motif) receptor 8 | Chemokine Receptor 8 - CDw198, CKR-L1, CKRL1, CMKBR8, CMKBRL2, CY6, GPR-CY6, TER1, CC chemokine receptor 8; CC-chemokine receptor chemr1; chemokine (C-C) receptor 8; chemokine (C-C) receptor-like 2 | CCR8 |
| 142 | chemokine (C-C motif) receptor 9 | Chemokine Receptor 9 - CDw199, GPR-9-6, GPR28, G protein-coupled receptor 28 | CCR9 |
| 143 | chemokine (C-C motif) receptor-like 1 | chemokine receptor 11 - CC-CKR-11, CCBP2, CCR10, CCR11, CCX-CKR, CKR-11, PPR1, VSHK1, C-C chemokine receptor type 11; chemocentryx chemokine receptor; chemokine, cc motif, receptor-like protein 1; orphan seven-transmembrane receptor, chemokine related | CCRL1 |
| 144 | chemokine (C-C motif) receptor-like 2 | chemokine (C-C motif) receptor-like 2: CKRX, CRAM-A, CRAM-B, HCR | CCRL2 |
| 145 | CD14 molecule | CD14 antigen - monocyte receptor | CD14 |
| 146 | CD14 molecule | CD14 (C-260T polymorphism) entered "CD14", CD14 antigen | CD14 |
| 147 | CD163 molecule | CD163 - M130, MM130 - CD163 antigen; macrophage-associated antigen, macrophage-specific antigen | CD163 |
| 148 | CD40 molecule, TNF receptor superfamily member 5 | CD40 molecule, TNF receptor superfamily member 5, Bp50, CDW40, MGC9013, TNFRSF5, p50, B cell surface antigen CD40; B cell-associated molecule; CD40 antigen; CD40 antigen (TNF receptor superfamily member 5); CD40 type II isoform; CD40L receptor; nerve growth factor receptor-related B-lymphocyte activation molecule; tumor necrosis factor receptor superfamily, member 5 | CD40 |

TABLE 2-continued

ARTERIORISKMARKERS

| ARTERIORISKMARKER | Official Name | Common Name | Gene Symbol |
|---|---|---|---|
| 149 | CD40 ligand (TNF superfamily, member 5, hyper-IgM syndrome) | CD40 Ligand (CD40L) (also called soluble CD40L vs. platelet-bound CD40L), CD154, CD40L, HIGM1, IGM, IMD3, T-BAM, TNFSF5, TRAP, gp39, hCD40L, CD40 antigen ligand; CD40 ligand; T-B cell-activating molecule; TNF-related activation protein; tumor necrosis factor (ligand) superfamily member 5; tumor necrosis factor (ligand) superfamily, member 5 (hyper-IgM syndrome); tumor necrosis factor ligand superfamily member 5 | CD40LG |
| 150 | CD44 molecule (Indian blood group) | CD44, CDW44 - ECMR-III, IN, LHR, MC56, MDU2, MDU3, MIC4, MUTCH-I, Pgp1, CD44 antigen; CD44 antigen (Indian blood group); CD44 antigen (homing function and Indian blood group system); CD44 epithelial domain (CD44E); CDW44 antigen; GP90 lymphocyte homing/adhesion receptor; Hermes antigen; antigen gp90 homing receptor; cell adhesion molecule (CD44); cell surface glycoprotein CD44; extracellular matrix receptor-III; heparan sulfate proteoglycan; hyaluronate receptor; phagocytic glycoprotein I | CD44 |
| 151 | CD55 molecule, decay accelerating factor for complement (Cromer blood group) | complement 32: CD55 antigen, decay accelerating factor for complement (Cromer blood group); Cromer blood group; decay accelerating factor for complement; decay accelerating factor for complement (CD55, Cromer blood group system); decay accelerating factor for complement (CD55, Cromer blood group); decay-accelerating factor 3 | CD55 |
| 152 | CD63 molecule | lysosome-associated membrane protein (CD63) - (entered just "CD63" here) LAMP-3, ME491, MLA1, OMA81H, TSPAN30, CD63 antigen; CD63 antigen (melanoma 1 antigen); granulophysin; lysosome-associated membrane glycoprotein 3; melanoma 1 antigen; melanoma-associated antigen ME491; melanoma-associated antigen MLA1; ocular melanoma-associated antigen; tetraspanin-30 | CD63 |
| 153 | cell division cycle 2, G1 to S and G2 to M | CDK1: cell cycle controller CDC2; cell division control protein 2 homolog; cell division cycle 2 protein; cyclin-dependent kinase 1; p34 protein kinase | CDC2 |
| 154 | CDC42 binding protein kinase beta (DMPK-like) | CDC42 binding protein kinase beta (DMPK-like) - MRCKB, CDC42-binding protein kinase beta; CDC42-binding protein kinase beta (DMPK-like); DMPK-like; MRCK beta | CDC42BPB |
| 155 | CDC42 effector protein (Rho GTPase binding) 2 | CDC42 effector protein (Rho GTPase binding) 2 - BORG1, CEP2, CRIB-containing BOGR1 protein; Cdc42 effector protein 2 | CDC42EP2 |
| 930 | CDC42 effector protein (Rho GTPase binding) 3 | CDC42 effector protein (Rho GTPase binding) 3 - BORG2, CEP3, UB1, CRIB-containing BORG2 protein; Cdc42 effector protein 3; MSE55-related protein | CDC42EP3 |
| 931 | CDC6 cell division cycle 6 homolog (S. cerevisiae) | Cdc6: CDC18 (cell division cycle 18, S. pombe, homolog)-like; CDC6 (cell division cycle 6, S. cerevisiae) homolog; CDC6 homolog; CDC6-related protein | CDC6 |
| 932 | cadherin 1, type 1, E-cadherin (epithelial) | Arc-1, CD324, CDHE, ECAD, LCAM, UVO, cadherin 1, E-cadherin (epithelial); cadherin 1, type 1; calcium-dependent adhesion protein, epithelial; cell-CAM 120/80; uvomorulin | CDH1 |
| 933 | cyclin-dependent kinase 4 | CDK4: cell division kinase 4; melanoma cutaneous malignant, 3 | CDK4 |
| 934 | cyclin-dependent kinase 5 | cyclin-dependent kinase 5, PSSALRE, protein kinase CDK5 splicing | CDK5 |
| 935 | cyclin-dependent kinase 6 | CDK6: cell division protein kinase 6 | CDK6 |
| 936 | centromere protein C 1 | centromere protein C 1 - CENPC, centromere autoantigen C1 | CENPC1 |
| 937 | cholesteryl ester transfer protein, plasma | cholesterol ester transfer protein - lipid transfer protein | CETP |
| 156 | CHK1 checkpoint homolog (S. pombe) | Chk1: CHK1 (checkpoint, S. pombe) homolog; CHK1 checkpoint homolog; Checkpoint, S. pombe, homolog of, 1 | CHEK1 |

TABLE 2-continued

ARTERIORISKMARKERS

| ARTERIORISKMARKER | Official Name | Common Name | Gene Symbol |
|---|---|---|---|
| 157 | CHK2 checkpoint homolog (*S. pombe*) | Chk2: CHK2 (checkpoint, *S. pombe*) homolog; checkpoint-like protein CHK2; protein kinase CHK2; serine/threonine-protein kinase CHK2 | CHEK2 |
| 158 | chromogranin A (parathyroid secretory protein 1) | chromogranin-A, CGA, chromogranin A precursor; parathyroid secretory protein 1 | CHGA |
| 159 | chitinase 1 (chitotriosidase) | chitotriosidase - chitotriosidase; plasma methylumbelliferyl tetra-N-acetylchitotetraoside hydrolase | CHIT1 |
| 160 | choline kinase alpha | choline kinase - CHK, CKI | CHKA |
| 161 | choline kinase beta | choline kinase (CHK) - CHETK, CHKL, choline kinase-like, choline/ethanolamine kinase | CHKB |
| 162 | cholinergic receptor, muscarinic 1 | Muscarinic Acetylcholine Receptor M1 - HM1, M1, muscarinic acetylcholine receptor M1, ACM1 | CHRM1 |
| 163 | cholinergic receptor, muscarinic 2 | Muscarinic Acetylcholine Receptor M2 - HM2, 7TM receptor; cholinergic receptor, muscarinic 2, isoform a; muscarinic M2 receptor; muscarinic acetylcholine receptor M2 | CHRM2 |
| 164 | cholinergic receptor, muscarinic 3 | muscarinic acetyl choline receptor 3 - HM3, m3 muscarinic receptor; muscarinic acetylcholine receptor M3 | CHRM3 |
| 165 | cholinergic receptor, muscarinic 4 | ACETYLCHOLINE RECEPTOR, MUSCARINIC 4 - HM4, muscarinic acetylcholine receptor M4 | CHRM4 |
| 166 | cholinergic receptor, muscarinic 5 | muscarinic acetyl choline receptor 5 - HM5, muscarinic acetylcholine receptor M5 | CHRM5 |
| 167 | citron (rho-interacting, serine/threonine kinase 21) | CIT polypeptide - CRIK, STK21, citron; rho-interacting, serine/threonine kinase 21 | CIT |
| 168 | creatine kinase, brain | CK, CK-MB, B-CK, CKBB, brain creatine kinase; creatine kinase B-chain; creatine kinase-B | CKB |
| 169 | creatine kinase, muscle | CK, CK-MB, CKMM, M-CK, creatine kinase M chain; creatine kinase-M; muscle creatine kinase | CKM |
| 170 | creatine kinase, mitochondrial 1A | CK, CK-MB, CKMT1, UMTCK, acidic-type mitochondrial creatine kinase; creatine kinase, mitochondrial 1 (ubiquitous) | CKMT1A |
| 171 | creatine kinase, mitochondrial 1B | CK, CK-MB, CKMT, CKMT1, UMTCK, acidic-type mitochondrial creatine kinase; creatine kinase, mitochondrial 1 (ubiquitous); ubiquitous mitochondrial creatine kinase precursor variant | CKMT1B |
| 172 | creatine kinase, mitochondrial 2 (sarcomeric) | CK, CK-MB, SMTCK, basic-type mitochondrial creatine kinase; sarcomeric mitochondrial creatine kinase | CKMT2 |
| 173 | clusterin | clusterin, AAG4, APOJ, CLI, KUB1, MGC24903, SGP-2, SGP2, SP-40, TRPM-2, TRPM2, aging-associated protein 4; apolipoprotein J; clusterin (complement lysis inhibitor, SP-40,40, sulfated glycoprotein 2, testosterone-repressed prostate message 2, apolipoprotein J); complement lysis inhibitor; complement-associated protein SP-40; sulfated glycoprotein 2; testosterone-repressed prostate message 2 | CLU |
| 174 | chymase 1, mast cell | chymase 1 - CYH, MCT1, chymase 1 preproprotein transcript E; chymase 1 preproprotein transcript I; chymase, heart; chymase, mast cell; mast cell protease I | CMA1 |
| 175 | chemokine-like receptor 1 | chemokine-like receptor 1 - ChemR23, DEZ, orphan G-protein coupled receptor, Dez | CMKLR1 |
| 176 | chemokine orphan receptor 1 | G-protein-coupled receptor RDC1 - GPR159, RDC1, G protein-coupled receptor | CMKOR1 |
| 177 | CKLF-like MARVEL transmembrane domain containing 7 | chemokine-like factor 7: chemokine-like factor super family 7; chemokine-like factor super family member 7 variant 2; chemokine-like factor superfamily 7 | CMTM7 |
| 178 | collagen, type XVIII, alpha 1 | collagen type XVIII-alpha(1): alpha 1 type XVIII collagen; antiangiogenic agent; endostatin; multi-functional protein MFP | COL18A1 |
| 179 | collagen, type I, alpha 1 | collagen α-1: Collagen I, alpha-1 polypeptide; Collagen alpha 1 chain; alpha 1 type I collagen; collagen alpha 1 chain type I; collagen of skin, tendon and bone, alpha-1 chain; osteogenesis imperfecta type IV; pro-alpha-1 collagen type 1; type I collagen alpha 1 chain; type I collagen pro alpha 1(I) chain propeptide; type II procollagen gene fragment | COL1A1 |

TABLE 2-continued

ARTERIORISKMARKERS

| ARTERIORISKMARKER | Official Name | Common Name | Gene Symbol |
|---|---|---|---|
| 180 | collagen, type I, alpha 2 | collagen α-2: Collagen I, alpha-2 polypeptide; Collagen of skin, tendon and bone, alpha-2 chain; alpha 2 type I collagen; alpha 2(I)-collagen; alpha-2 collagen type I; osteogenesis imperfecta type IV; type I procollagen | COL1A2 |
| 181 | collagen III propeptide (PIIIP) | collagen, type III, alpha 1 (Ehlers-Danlos syndrome) type IV, autosomal dominant | COL3A1 |
| 182 | collagen, type V, alpha 2 | collagen type V: AB collagen; Collagen V, alpha-2 polypeptide; alpha 2 type V collagen; collagen, fetal membrane, A polypeptide; type V preprocollagen alpha 2 chain | COL5A2 |
| 183 | ceruloplasmin (ferroxidase) | ceruloplasmin - CP-2, Ceruloplasmin; ferroxidase | CP |
| 184 | carboxypeptidase A3 (mast cell) | carboxypeptidase A3 (CPA3) - mast cell carboxypeptidase A3 | CPA3 |
| 185 | carboxypeptidase B2 (plasma, carboxypeptidase U) | thrombin activatable fibrinolysis inhibitor (TAFI) - CPU, PCPB, TAFI, carboxypeptidase B-like protein; carboxypeptidase U; plasma carboxypeptidase B2; thrombin-activable fibrinolysis inhibitor; thrombin-activatable fibrinolysis inhibitor | CPB2 |
| 186 | carboxypeptidase B2 (plasma, carboxypeptidase U) | carboxypeptidase B2 (plasma, carboxypeptidase U) - CPU, PCPB, TAFI, (carboxypeptidase B2 (plasma)); carboxypeptidase B-like protein; carboxypeptidase U; plasma carboxypeptidase B2; thrombin-activable fibrinolysis inhibitor; thrombin-activatable fibrinolysis inhibitor | CPB2 |
| 187 | carboxypeptidase B2 (plasma, carboxypeptidase U) | carboxypeptidase B2 (plasma, carboxypeptidase U) - CPU, PCPB, TAFI, (carboxypeptidase B2 (plasma)); carboxypeptidase B-like protein; carboxypeptidase U; plasma carboxypeptidase B2; thrombin-activable fibrinolysis inhibitor; thrombin-activatable fibrinolysis inhibitor | CPB2 |
| 188 | carboxypeptidase N, polypeptide 1, 50 kD | CPN - CPN, SCPN, carboxypeptidase N polypeptide 1 50 kD | CPN1 |
| 189 | corticotropin releasing hormone receptor 2 | corticotropin releasing hormone receptor 2 - CRFR2 | CRHR2 |
| 190 | carnitine O-octanoyltransferase | carnitine O-octanoyltransferase - COT | CROT |
| 191 | C-reactive protein, pentraxin-related | C-Reactive Protein, CRP, PTX1 | CRP |
| 192 | C-reactive protein, pentraxin-related | CRP gene +1444C > T variant - C-Reactive Protein, CRP, PTX1 | CRP |
| 193 | colony stimulating factor 1 (macrophage) | colony stimulating factor 1; macrophage colony stimulating factor | CSF1 |
| 194 | colony stimulating factor 2 (granulocyte-macrophage) | Granulocyte-macrophage colony stimulating factor - GMCSF, colony stimulating factor 2; granulocyte-macrophage colony stimulating factor; molgramostin; sargramostim | CSF2 |
| 195 | colony stimulating factor 3 (granulocyte) | colony stimulating factor 3; filgrastim; granulocyte colony stimulating factor; lenograstim; pluripoietin | CSF3 |
| 196 | casein kinase 1, delta | casein kinase 1, delta, isoform 1 - HCKID | CSNK1D |
| 197 | chondroitin sulfate proteoglycan 2 (versican) | versican - VERSICAN | CSPG2 |
| 198 | cardiotrophin 1 | cardiotrophin-1 - CT-1, CT1, cardiophin 1 | CTF1 |
| 199 | connective tissue growth factor | Connective tissue growth factor - CCN2, IGFBP8, NOV2, hypertrophic chondrocyte-specific protein 24; insulin-like growth factor-binding protein 8 | CTGF |
| 200 | cathepsin B | cathepsin B - prochathepsin B, APPS; CPSB, APP secretase; amyloid precursor protein secretase; cathepsin B1; cysteine protease; preprocathepsin B | CTSB |
| 201 | chemokine (C-X-C motif) ligand 1 (melanoma growth stimulating activity, alpha) | GRO1, GROa, MGSA, MGSA alpha, MGSA-a, NAP-3, SCYB1: GRO1 oncogene (melanoma growth stimulating activity, alpha); GRO1 oncogene (melanoma growth-stimulating activity); chemokine (C-X-C motif) ligand 1; melanoma growth stimulatory activity alpha | CXCL1 |
| 202 | chemokine (C-X-C motif) ligand 10 | chemokine (C-X-C motif) ligand 10, C7, IFI10, INP10, IP-10, SCYB10, crg-2, gIP-10, mob-1, gamma IP10; interferon-inducible cytokine IP-10; protein 10 from interferon (gamma)-induced cell line; small inducible cytokine B10; small inducible cytokine subfamily B (Cys-X-Cys), member 10 | CXCL10 |

TABLE 2-continued

ARTERIORISKMARKERS

| ARTERIORISKMARKER | Official Name | Common Name | Gene Symbol |
|---|---|---|---|
| 204 | chemokine (C-X-C motif) ligand 2 | CINC-2a, GRO2, GROb, MGSA beta, MGSA-b, MIP-2a, MIP2, MIP2A, SCYB2; GRO2 oncogene; melanoma growth stimulatory activity beta | CXCL2 |
| 203 | chemokine (C-X-C motif) ligand 3 | CD182; CD183; CKR-L2; CMKAR3; GPR9; IP10; IP10-R; Mig-R; MigR; G protein-coupled receptor 9; IP 10 receptor; Mig receptor; chemokine (C-X-C) receptor 3; | CXCR3 |
| 205 | chemokine (C-X-C motif) receptor 4 | CXC chemokine receptor 4 - CD184, FB22, HM89, HSY3RR, LAP3, LCR1, LESTR, NPY3R, NPYR, NPYRL, NPYY3R, WHIM, C-X-C chemokine receptor type 4; CD184 antigen; chemokine (C-X-C motif), receptor 4 (fusin); chemokine receptor 4; fusin; leukocyte-derived seven-transmembrane-domain receptor; lipopolysaccharide-associated protein 3; neuropeptide Y receptor Y3; seven transmembrane helix receptor; seven-transmembrane-segment receptor, spleen; stromal cell-derived factor 1 receptor | CXCR4 |
| 206 | chemokine (C-X-C motif) receptor 6 | CXC Chemokine Receptor 6 - BONZO, CD186, STRL33, TYMSTR, G protein-coupled receptor; G protein-coupled receptor TYMSTR | CXCR6 |
| 207 | cytochrome c, somatic | cytochrome c - CYC, HCS, cytochrome c | CYCS |
| 208 | cytochrome P450, family 11, subfamily B, polypeptide 1 | cytochrome P450 CYP11-B1: cytochrome P450, subfamily XIB (steroid 11-beta-hydroxylase), polypeptide 1; cytochrome p450 X1B1; steroid 11-beta-hydroxylase; steroid 11-beta-monooxygenase | CYP11B1 |
| 209 | cytochrome P450, family 11, subfamily B, polypeptide 2 | aldosterone synthase: aldosterone synthase; cytochrome P450, subfamily XIB (steroid 11-beta-hydroxylase), polypeptide 2; cytochrome P450, subfamily XIB polypeptide 2; steroid 11-beta-monooxygenase; steroid 11-beta/18-hydroxylase; steroid 18-hydroxylase; steroid 18-hydroxylase, aldosterone synthase, P450C18, P450aldo | CYP11B2 |
| 210 | cytochrome P450, family 2, subfamily C, polypeptide 9 | minor allele of CYP2C9*2 - CPC9, CYP2C, CYP2C10, P450 MP-4, P450 PB-1, P450IIC9, cytochrome P-450 S-mephenytoin 4-hydroxylase; cytochrome P450, subfamily IIC (mephenytoin 4-hydroxylase), polypeptide 10; cytochrome P450, subfamily IIC (mephenytoin 4-hydroxylase), polypeptide 9; cytochrome p4502C9; flavoprotein-linked monooxygenase; mephenytoin 4-hydroxylase; microsomal monooxygenase; xenobiotic monooxygenase | CYP2C9 |
| 211 | cysteinyl leukotriene receptor 1 | Cysteinyl Leukotriene Receptor 1 - CYSLT1, CYSLT1R, CYSLTR, HG55, HMTMF81, LTD4 receptor; cysteinyl leukotriene D4 receptor; cysteinyl leukotriene receptor 1 splice variant V | CYSLTR1 |
| 212 | cysteinyl leukotriene receptor 2 | Cysteinyl Leukotriene Receptor 2 - CYSLT2, CYSLT2R, GPCR, HG57, HPN321, KPG_011, hGPCR21, G protein-coupled receptor; G-protein coupled receptor protein; cysteinyl leukotriene CysLT2 receptor | CYSLTR2 |
| 213 | doublecortin and CaM kinase-like 1 | DCAMKL1-like serine/threonine kinase - doublecortin and CaM kinase-like 1, DCLK, doublecortin-like kinase | DCAMKL1 |
| 214 | desmin | desmin - CMD11, CSM1, CSM2, intermediate filament protein | DES |
| 215 | deafness, autosomal dominant 5 | deafness, autosomal dominant 5 I - ICERE-1, deafness, autosomal dominant 5 protein; nonsyndromic hearing impairment protein | DFNA5 |
| 216 | diacetylglycerol o-acyltransferase 2-like 4 | acylglycerol acyltransferase-like proteins, DC4, DC4L | DGAT2L4 |
| 217 | dehydrogenase/reductase(SDR family) member 3 | RDH17, Rsdr1, SDR1, retSDR1; short-chain dehydrogenase/reductase 1 | DHRS3 |
| 218 | dehydrogenase/reductase (SDR family) member 4 | short chain dehydrogenase/reductase - DHRS4L2, SCAD-SRL, SDR-SRL, humNRDR, NADP(H)-dependent retinol dehydrogenase/reductase B1 isoform; NADP(H)-dependent retinol dehydrogenase/reductase B2 isoform; NADP(H)-dependent retinol | DHRS4 |

TABLE 2-continued

ARTERIORISKMARKERS

| ARTERIORISKMARKER | Official Name | Common Name | Gene Symbol |
|---|---|---|---|
| | | dehydrogenase/reductase short isoform; NADP-dependent retinol dehydrogenase; NADPH-dependent retinol dehydrogenase/reductase; peroxisomal short-chain alcohol dehydrogenase | |
| 219 | DnaJ (Hsp40) homolog, subfamily A, member 1 | pDJA1 - DJ-2, DjA1, HDJ2, HSDJ, HSJ2, HSPF4, hDJ-2, heat shock protein, DNAJ-like 2 | DNAJA1 |
| 220 | dolichyl-phosphate (UDP-N-acetylglucosamine) N-acetylglucosaminephosphotransferase 1 (GlcNAc-1-P transferase) | dolichyl-phosphate N-acetylglucosaminephosphotransferase 1 | DPAGT1 |
| 221 | dipeptidase 1 (renal) | dipeptidase 1 (DPEP1) - MBD1, MDP, RDP | DPEP1 |
| 222 | dipeptidyl-peptidase 3 | dipeptidyl-peptidase 3 - DPPIII, dipeptidyl aminopeptidase III; dipeptidyl arylamidase III; dipeptidyl peptidase III; dipeptidylpeptidase 3; dipeptidylpeptidase III | DPP3 |
| 223 | dipeptidyl-peptidase 4 (CD26, adenosine deaminase complexing protein 2) | dipeptidylpeptidase IV - ADABP, ADCP2, CD26, DPPIV, TP103, T-cell activation antigen CD26; adenosine deaminase complexing protein 2; dipeptidylpeptidase IV; dipeptidylpeptidase IV (CD26, adenosine deaminase complexing protein 2) | DPP4 |
| 224 | dipeptidyl-peptidase 7 | dipeptidylpeptidase 7 - DPP2, DPPII, QPP - carboxytripeptidase; dipeptidyl aminopeptidase II; dipeptidyl arylamidase II; dipeptidyl peptidase 7; dipeptidyl-peptidase II precursor; dipeptidylpeptidase 7 | DPP7 |
| 225 | dipeptidyl-peptidase 9 | dipeptidyl-peptidase 9 - DPRP2, dipeptidyl peptidase IV-related protein-2; dipeptidylpeptidase 9 | DPP9 |
| 226 | dopamine receptor D1 | dopamine receptor D1 - DADR, DRD1A | DRD1 |
| 227 | dopamine receptor D3 | dopamine receptor D3 - D3DR | DRD3 |
| 228 | dopamine receptor D4 | dopamine receptor D4 - dopamine receptor D4, D4DR: D(2C) dopamine receptor; see also Acc#: L12398; seven transmembrane helix receptor | DRD4 |
| 229 | dopamine receptor D5 | dopamine receptor D5 - DBDR, DRD1B, DRD1L2, D1beta dopamine receptor; dopamine receptor D1B | DRD5 |
| 230 | endothelial differentiation, lysophosphatidic acid G-protein-coupled receptor, 2 | endothelial differentiation, lysophosphatidic acid G-protein-coupled receptor 2 - Gpcr26, LPA1, LPAR1, Mrec1.3, edg-2, rec.1.3, vzg-1, ventricular zone gene 1 | EDG2 |
| 231 | endothelial differentiation, sphingolipid G-protein-coupled receptor, 3 | endothelial differentiation sphingolipid G-protein-coupled receptor 3 - EDG-3, LPB3, S1P3, S1PR3, G protein-coupled receptor, endothelial differentiation gene-3; S1P receptor EDG3; sphingosine 1-phosphate receptor 3 | EDG3 |
| 232 | endothelial differentiation, sphingolipid G-protein-coupled receptor, 5 | endothelial differentiation sphingolipid G-protein-coupled receptor 5 polypeptide - AGR16, EDG-5, Gpcr13, H218, LPB2, S1P2, S1PR2, S1P receptor EDG5; sphingosine 1-phosphate receptor 2 | EDG5 |
| 233 | endothelial differentiation, lysophosphatidic acid G-protein-coupled receptor, 6 | LPC1; S1P4; S1PR4; SLP4; sphingosine 1-phosphate receptor 4; phingosine 1-phosphate receptor Edg-6; endothelial differentiation; G protein coupled receptor 6; G protein-coupled receptor 6 | EDG6 |
| 234 | endothelial differentiation, lysophosphatidic acid G-protein-coupled receptor, 7 | endothelial differentiation lysophosphatic acid G-protein-coupled receptor 7 - Edg-7, GPCR, HOFNH30, LP-A3, LPA3, LPAR3, LPA receptor EDG7; calcium-mobilizing lysophosphatidic acid receptor LP-A3; endothelial cell differentiation gene 7 | EDG7 |
| 235 | endothelin 1 | endothelin-1-ET1 | EDN1 |
| 236 | endothelin 1 | endothelin-1-ET1 | EDN1 |
| 237 | endothelin 2 | EDN2: ET2 | EDN2 |
| 238 | endothelin 3 | endothelin III: ET3, ET3, truncated endothelin 3 | EDN3 |
| 239 | endothelin receptor type A | endothelin receptor type A - ETA, ETRA, G protein-coupled receptor | EDNRA |
| 240 | endothelin receptor type B | G protein-coupled receptor ETB - ABCDS, ETB, ETRB, HSCR, HSCR2, Hirschsprung disease 2 | EDNRB |
| 967 | epidermal growth factor (beta-urogastrone) | epidermal growth factor (beta-urogastrone), URG, urogastrone | EGF |
| 968 | elastase 2, neutrophil | Elastase - HLE, HNE, NE, PMN-E, bone marrow serine protease; leukocyte elastase; medullasin; polymorphonuclear elastase | ELA2 |

TABLE 2-continued

ARTERIORISKMARKERS

| ARTERIORISKMARKER | Official Name | Common Name | Gene Symbol |
|---|---|---|---|
| 241 | elastin (supravalvular aortic stenosis, Williams-Beuren syndrome) | elastin: Williams syndrome region; elastin; tropoelastin | ELN |
| 242 | endoglin (Osler-Rendu-Weber syndrome 1) | Endoglin - CD105, END, HHT1, ORW, ORW1, Endoglin; endoglin | ENG |
| 969 | enolase 2 (gamma, neuronal) | enolase, gamma, neurone-specific - 2-phospho-D-glycerate hydrolyase; enolase 2; neural enolase; neuron specific gamma enolase; neurone-specific enolase | ENO2 |
| 243 | enolase 3 (beta, muscle) | β-enolase: 2-phospho-D-glycerate hydrolyase; ENO3, muscle enolase 3 beta; beta enolase; enolase 3; enolase-3, beta, muscle; muscle specific enolase; skeletal muscle enolase | ENO3 |
| 244 | ectonucleotide pyrophosphatase/phosphodiesterase 7 | Sphingomyelinase - ALK-SMase, alkaline sphingomyelinase | ENPP7 |
| 245 | ectonucleoside triphosphate diphosphohydrolase 1 | CD39, ATPDase, CD39, NTPDase-1, CD39 antigen; ecto-ATP diphosphohydrolase 1; ecto-apyrase; lymphoid cell activation antigen | ENTPD1 |
| 246 | erythropoietin | erythropoietin (EPO) - epoetin | EPO |
| 247 | esterase A4 | esterase - Esterase-A4 | ESA4 |
| 248 | esterase B3 | esterase - Esterase-B3 | ESB3 |
| 249 | esterase D/formylglutathione hydrolase | esterase - Esterase D; S-formylglutathione hydrolase; esterase 10 | ESD |
| 250 | ethanolamine kinase 1 | ethanolamine kinase 1 (EKI1) - EKI, EKI1 | ETNK1 |
| 251 | coagulation factor X | Prothrombin time (PT) (Entered Prothrombin into Entrez), FX, FXA, Stuart factor; Stuart-Prower factor; factor Xa; prothrombinase | F10 |
| 252 | coagulation factor XI (plasma thromboplastin antecedent) | Factor XI, activated partial thromboplasmin time (APTT), (entered thromboplastin and Factor XI into Entrez), FXI, platelet coagulation factor XI | F11 |
| 253 | F11 receptor | junction adhesion molecules-1, 2, and 3 - CD321, JAM, JAM-1, JAM-A, JAM1, JAMA, JCAM, KAT, PAM-1, junctional adhesion molecule 1; junctional adhesion molecule A; platelet F11 receptor; platelet adhesion molecule | F11R |
| 254 | coagulation factor XII (Hageman factor) | Coagulation factor XII - Hageman factor; coagulation factor XII | F12 |
| 255 | coagulation factor XIII, A1 polypeptide | Coagulation Factor XIII - Coagulation factor XIII A chain; Coagulation factor XIII, A polypeptide; TGase; (coagulation factor XIII, A1 polypeptide); coagulation factor XIII A1 subunit; factor XIIIa, coagulation factor XIII A1 subunit | F13A1 |
| 256 | coagulation factor XIII, A1 polypeptide | FXIII gene L34 polymorphism - Coagulation factor XIII A chain; Coagulation factor XIII, A polypeptide; TGase; (coagulation factor XIII, A1 polypeptide); coagulation factor XIII A1 subunit; factor XIIIa | F13A1 |
| 257 | coagulation factor XIII, B polypeptide | Coagulation Factor XIII - TGase; coagulation factor XIII B subunit | F13B |
| 258 | coagulation factor II (thrombin) | Prothrombin time (PT) (Entered Prothrombin into Entrez), PT, coagulation factor II; prothrombin; prothrombin B-chain; serine protease | F2 |
| 259 | coagulation factor II (thrombin) | prothrombin G20210A mutation - PT, coagulation factor II; prothrombin; prothrombin B-chain; serine protease | F2 |
| 260 | coagulation factor II (thrombin) receptor | protease activated receptor 1 - CF2R, HTR, PAR1, TR, coagulation factor II receptor; protease-activated receptor 1; thrombin receptor | F2R |
| 261 | coagulation factor II (thrombin) receptor | protease-activated receptor 1 (a GPCR) - NK2R, NKNAR, SKR, TAC2R, NK-2 receptor; Tachykinin receptor 2 (substance K receptor; neurokinin 2 receptor); neurokinin 2 receptor; neurokinin-2 receptor; seven transmembrane helix receptor; tachykinin 2 receptor (substance K receptor, neurokinin 2 receptor) | F2R |
| 262 | coagulation factor II (thrombin) receptor-like 1 | G Protein Coupled Proteinase Activated Receptor 2 - GPR11, PAR2, G protein-coupled receptor-11; protease-activated receptor 2 | F2RL1 |
| 263 | coagulation factor II (thrombin) receptor-like 2 | G-protein coupled proteinase activated receptor 3 - PAR3, Coagulation factor II receptor-like 2 (protease-actovated receptor 3); coagulation factor II receptor-like 2; protease-activated receptor 3; thrombin receptor-like 2 | F2RL2 |
| 264 | coagulation factor II (thrombin) receptor-like 3 | G Protein Coupled Proteinase Activated Receptor 4 - PAR4, protease-activated receptor-4 | F2RL3 |

TABLE 2-continued

ARTERIORISKMARKERS

| ARTERIORISKMARKER | Official Name | Common Name | Gene Symbol |
|---|---|---|---|
| 265 | coagulation factor III (thromboplastin, tissue factor) | activated partial thromboplasmin time (APTT), (entered thromboplastin into Entrez) CD142, TF, TFA, coagulation factor III; tissue factor | F3 |
| 266 | coagulation factor V (proaccelerin, labile factor) | Factor V gene - mutation at nucleotide position 1691 - FVL, PCCF, factor V, activated protein c cofactor; coagulation factor V; coagulation factor V jinjiang A2 domain; factor V Leiden; labile factor | F5 |
| 267 | coagulation factor V (proaccelerin, labile factor) | Factor V, FVL, PCCF, factor V, activated protein c cofactor; coagulation factor V; coagulation factor V jinjiang A2 domain; factor V Leiden; labile factor | F5 |
| 268 | coagulation factor VII (serum prothrombin conversion accelerator) | FVII coagulation protein; coagulation factor VII; cogulation factor VII; eptacog alfa | F7 |
| 269 | coagulation factor VII (serum prothrombin conversion accelerator) | factor VII - FVII coagulation protein; coagulation factor VII; cogulation factor VII; eptacog alfa | F7 |
| 270 | coagulation factor VIII, procoagulant component (hemophilia A) | Factor VIII, AHF, F8 protein, F8B, F8C, FVIII, HEMA, coagulation factor VIII; coagulation factor VIII, isoform b; coagulation factor VIIIc; factor VIII F8B; procoagulant component, isoform b | F8 |
| 271 | coagulation factor IX | Coagulation Factor IX - Christmas factor; Coagulation factor IX (plasma thromboplastic component); Factor 9; Factor IX; coagulant factor IX; coagulation factor IX; truncated coagulation factor IX | F9 |
| 272 | fatty acid binding protein 2, intestinal | intestinal fatty acid binding protein - FABPI, I-FABP, Fatty acid-binding protein, intestinal; intestinal fatty acid binding protein 2 | FABP2 |
| 273 | fatty acid binding protein 3, muscle and heart (mammary-derived growth inhibitor) | fatty acid-binding protein, heart-type (H FABP) - Fatty acid-binding protein 3, muscle; fatty acid binding protein 11; fatty acid binding protein 3; mammary-derived growth inhibitor | FABP3 |
| 274 | fibroblast activation protein, alpha | fibroblast activation protein - DPPIV, FAPA, SEPRASE, fibroblast activation protein, alpha subunit; integral membrane serine protease | FAP |
| 275 | Fas (TNF receptor superfamily, member 6) | soluble Fas/APO-1 (sFas), ALPS1A, APO-1, APT1, Apo-1 Fas, CD95, FAS1, FASTM, TNFRSF6, APO-1 cell surface antigen; CD95 antigen; Fas antigen; apoptosis antigen 1; tumor necrosis factor receptor superfamily, member 6 | FAS |
| 276 | Fas ligand (TNF superfamily, member 6) | Fas ligand (sFasL), APT1LG1, CD178, CD95L, FASL, TNFSF6, CD95 ligand; apoptosis (APO-1) antigen ligand 1; fas ligand; tumor necrosis factor (ligand) superfamily, member 6 | FASLG |
| 277 | Fc fragment of IgG, low affinity IIa, receptor (CD32) | FcgammaRIIa - CD32, CD32A, CDw32, FCG2, FCGR2, FCGR2A1, FcGR, IGFR2, Fc fragment of IgG, low affinity IIa, receptor for (CD32) | FCGR2A |
| 278 | Fc fragment of IgG, low affinity IIa, receptor (CD32) | FcgammaRIIa - CD32, CD32A, CDw32, FCG2, FCGR2, FCGR2A1, FcGR, IGFR2, Fc fragment of IgG, low affinity IIa, receptor for (CD32) | FCGR2A |
| 279 | Fc fragment of IgG, low affinity IIIa, receptor (CD16a) | FcgammaRIIA-R/H131, the FcgammaRIIIB-Na1/Na2, and the FcgammaRIIIA-F/V158 polymorphisms (entered FcgammaRIIIA), CD16, CD16a, FCG3, FCGR3, IGFR3, Fc fragment of IgG, low affinity III, receptor for (CD16); Fc fragment of IgG, low affinity IIIa, receptor for (CD16); Fc gamma receptor III-A; Fc-gamma receptor IIIb (CD16); FcgammaRIIIA | FCGR3A |
| 280 | Fc fragment of IgG, low affinity IIIb, receptor (CD16b) | FcgammaRIIA-R/H131, the FcgammaRIIIB-Na1/Na2, and the FcgammaRIIIA-F/V158 polymorphisms (entered FcgammaRIIIB), CD16, CD16b, FCG3, FCGR3, Fc fragment of IgG, low affinity IIIb, receptor for (CD16); Fc-gamma receptor; Fc-gamma receptor IIIB; Fc-gamma receptor IIIb (CD 16); low affinity immunoglobulin gamma Fc region receptor III-B | FCGR3B |
| 281 | ficolin (collagen/fibrinogen domain containing lectin) 2 (hucolin) | Fibrinogen, EBP-37, FCNL, P35, ficolin-2, L-ficolin; collagen/fibrinogen domain-containing protein 2; ficolin (collagen/fibrinogen domain-containing lectin) 2; ficolin (collagen/fibrinogen domain-containing lectin) 2 (hucolin); ficolin 2; ficolin B; hucolin; serum lectin p35 | FCN2 |

TABLE 2-continued

ARTERIORISKMARKERS

| ARTERIORISKMARKER | Official Name | Common Name | Gene Symbol |
|---|---|---|---|
| 282 | ficolin (collagen/fibrinogen domain containing) 3 (Hakata antigen) | Fibrinogen, FCNH, HAKA1, H-ficolin; Hakata antigen; collagen/fibrinogen domain-containing lectin 3 p35; collagen/fibrinogen domain-containing protein 3; ficolin (collagen/fibrinogen domain-containing) 3 (Hakata antigen); ficolin 3; ficolin-3 | FCN3 |
| 283 | free fatty acid receptor 1 | G protein-coupled receptor 40 - FFA1R, GPR40, G protein-coupled receptor 40 | FFAR1 |
| 284 | free fatty acid receptor 3 | G protein coupled receptor 41 - FFA3R, GPR41, G protein-coupled receptor 41 | FFAR3 |
| 285 | fibrinogen alpha chain | Fibrin, Fib2, fibrinogen, A alpha polypeptide; fibrinogen, alpha chain, isoform alpha preproprotein; fibrinogen, alpha polypeptide | FGA |
| 286 | fibrinogen beta chain | Fibrin, B beta polypeptide; fibrinogen, beta chain; fibrinogen, beta chain, preproprotein, fibrinopeptide B beta 1-42, fibrinopeptide B beta 15-42 | FGB |
| 287 | fibroblast growth factor 1 (acidic) | fibroblast growth factor 1 (acidic): endothelial cell growth factor, alpha; endothelial cell growth factor, beta; heparin-binding growth factor 1 precursor | FGF1 |
| 288 | fibroblast growth factor 2 (basic) | Fibrin, BFGF, FGFB, HBGH-2, basic fibroblast growth factor; basic fibroblast growth factor bFGF; fibroblast growth factor 2; heparin-binding growth factor 2 precusor; prostatropin | FGF2 |
| 289 | fibrinogen gamma chain | Fibrin, fibrinogen, gamma chain; fibrinogen, gamma polypeptide | FGG |
| 290 | fibroblast growth factor (acidic) intracellular binding protein | acidic fibroblast growth factor - FGFIBP, FIBP-1, FGF intracellular binding protein | FIBP |
| 291 | FK506 binding protein 1A, 12 kDa | FK506 binding protein 1A - FKBP-12, FKBP1, FKBP12, FKBP12C, PKC12, PKCI2, PPIASE, FK506 binding protein 1A (12 kD); FK506-binding protein 1; FK506-binding protein 12; FK506-binding protein 1A; FK506-binding protein 1A (12 kD); FK506-binding protein, T-cell, 12-kD; immunophilin FKBP12; peptidyl-prolyl cis-trans isomerase; protein kinase C inhibitor 2; rotamase | FKBP1A |
| 292 | formyl peptide receptor-like 1 | N-Formyl Peptide Receptor Like 1 - ALXR, FMLP-R-II, FMLPX, FPR2A, FPRH1, FPRH2, HM63, LXA4R, lipoxin A4 receptor (formyl peptide receptor related) | FPRL1 |
| 293 | formyl peptide receptor-like 2 | formyl peptide receptor-like 2 polypeptide - FML2_HUMAN, FMLPY, FPRH1, FPRH2, RMLP-R-I, FMLP-related receptor II | FPRL2 |
| 294 | fibronectin type III and SPRY domain containing 1 | Fibronectin, GLFND, MIR1, fibronectin type 3 and SPRY (spla, ryanodine) domain containing (with coiled-coil motif) 1; fibronectin type 3 and SPRY domain containing 1; fibronectin type 3 and SPRY domain-containing protein | FSD1 |
| 295 | follistatin | follistatin - FS | FST |
| 296 | ferritin | FTH; PLIF; FTHL6; PIG15; apoferritin; placenta immunoregulatory factor; proliferation-inducing protein 15 | FTH1 |
| 297 | ferritin, light polypeptide | ferritin - L apoferritin; ferritin L subunit; ferritin L-chain; ferritin light chain; ferritin light polypeptide-like 3 | FTL |
| 298 | ferritin mitochondrial | ferritin - ferritin H subunit; ferritin heavy chain-like; mitochondrial ferritin | FTMT |
| 299 | FYN oncogene related to SRC, FGR, YES | FYN oncogene related to SRC - proto-oncogene tyrosine-protein kinase FYN - SLK, SYN, OKT3-induced calcium influx regulator; c-syn protooncogene; protein-tyrosine kinase fyn; proto-oncogene tyrosine-protein kinase fyn; src-like kinase; src/yes-related novel gene; tyrosine kinase p59fyn(T) | FYN |
| 300 | FYN oncogene related to SRC, FGR, YES | proto-oncogene tyrosine-protein kinase FYN - SLK, SYN, OKT3-induced calcium influx regulator; c-syn protooncogene; protein-tyrosine kinase fyn; proto-oncogene tyrosine-protein kinase fyn; src-like kinase; src/yes-related novel gene; tyrosine kinase p59fyn(T) | FYN |
| 301 | growth arrest and DNA-damage-inducible, alpha | Gadd45 - DDIT1, GADD45, DNA damage-inducible transcript 1; DNA damage-inducible transcript-1; DNA-damage-inducible transcript 1 | GADD45A |

TABLE 2-continued

ARTERIORISKMARKERS

| ARTERIORISKMARKER | Official Name | Common Name | Gene Symbol |
|---|---|---|---|
| 302 | galanin | GALN; GLNN; galanin-related peptide | GAL |
| 303 | glucagon receptor | glucagon receptor -GGR, | GCGR |
| 304 | growth differentiation factor 15 | NSAID (nonsteroidal anti-inflammatory drug)-activated protein 1; PTGF-beta; prostate differentiator factor | GDF15 |
| 305 | glial fibrillary acidic protein | glial fibrillary acidic protein - intermediate filament protein | GFAP |
| 306 | gamma-glutamyltransferase 1 | GGT; GTG; CD224; glutamyl transpeptidase; gamma-glutamyl transpeptidase | GGT1 |
| 307 | gamma-glutamyltransferase 1 | gamma-glutamyltransferase (GGT) - CD224, GGT, GTG, gamma-glutamyl transpeptidase; glutamyl transpeptidase | GGT1 |
| 308 | gamma-glutamyltransferase 2 | gamma-glutamyltransferase (GGT) - GGT | GGT2 |
| 309 | growth hormone 1 | growth hormone - GH, GH-N, GHN, hGH-N, pituitary growth hormone | GH1 |
| 310 | growth hormone receptor | growth hormone receptor - GHBP, growth hormone binding protein; growth hormone receptor variant; serum binding protein; somatotropin receptor | GHR |
| 311 | ghrelin/obestatin preprohormone | ghrelin - MTLRP, ghrelin, obestatin, ghrelin; ghrelin precursor; ghrelin, growth hormone secretagogue receptor ligand; motilin-related peptide | GHRL |
| 312 | growth hormone secretagogue receptor | Growth Hormone Secretagogue Receptor - ghrelin receptor | GHSR |
| 313 | gap junction protein, alpha 1, 43 kDa (connexin 43) | connexin 43: connexin 43; gap junction protein, alpha-like; oculodentodigital dysplasia (syndactyly type III) | GJA1 |
| 314 | glucagon-like peptide 1 receptor | glucagon-like peptide 1 receptor - | GLP1R |
| 315 | glucagon-like peptide 2 receptor | glucagon-like peptide 2 receptor - | GLP2R |
| 316 | guanine nucleotide binding protein (G protein), alpha inhibiting activity polypeptide 2 | G-protein, α-subunit of inhibitory (GI-α) - GIP, GNAI2B, GTP-binding regulatory protein Gi alpha-2 chain | GNAI2 |
| 317 | guanine nucleotide binding protein (G protein), beta polypeptide 3 | G-protein beta-3 subunit - G protein, beta-3 subunit; GTP-binding regulatory protein beta-3 chain; guanine nucleotide-binding protein G(I)/G(S)/G(T) beta subunit 3; guanine nucleotide-binding protein, beta-3 subunit; hypertension associated protein; transducin beta chain 3 | GNB3 |
| 318 | glutamic-oxaloacetic transaminase 2, mitochondrial | aspartate aminotransferase, mitochondrial - aspartate aminotransferase 2 | GOT2 |
| 319 | glycoprotein 1b (platelet), alpha polypeptide | GPIb receptor - BSS, CD42B, CD42b-alpha, GP1B, platelet glycoprotein 1b alpha polypeptide; platelet membrane glycoprotein 1b-alpha subunit | GP1BA |
| 320 | glycerol phosphatase, beta- | GPB - | GPB |
| 321 | glycosylphosphatidylinositol specific phospholipase D1 | glycosyl phosphatidyl inositol-specific phospholipase D - GPIPLD, GPIPLDM, PIGPLD, PIGPLD1, GPI-specific phospholipase D; glycoprotein phospholipase D; glycosylphosphatIdylinositol-specific phospholipase D; glycosylphosphatidylinositol specific phospholipase D1, isoform 2; phospholipase D, phosphatidylinositol-glycan-specific | GPLD1 |
| 322 | G protein-coupled receptor 1 | G protein-coupled receptor 1 | GPR1 |
| 323 | G protein-coupled receptor 103 | G protein-Coupled Receptor 103 - AQ27, SP9155, QRFP receptor | GPR103 |
| 324 | G protein-coupled receptor 107 | Lung Seven Transmembrane Receptor 1 - LUSTR1, lung seven transmembrane receptor 1 | GPR107 |
| 325 | G protein-coupled receptor 109A | hm74-like g protein coupled receptor - HM74a, HM74b, PUMAG, Puma-g, G protein-coupled receptor HM74a | GPR109A |
| 326 | G protein-coupled receptor 109B | G-Protein Coupled Receptor 74 - HM74, PUMAG, Puma-g, GTP-binding protein; putative chemokine receptor | GPR109B |
| 327 | G protein-coupled receptor 12 | G protein-coupled receptor 12 - GPCR21 | GPR12 |
| 328 | G protein-coupled receptor 132 | G2A-RECEPTOR - G2A, G protein-coupled receptor G2A; G2 accumulation protein | GPR132 |
| 329 | G protein-coupled receptor 15 | G Protein-Coupled Receptor 15 - | GPR15 |
| 330 | G protein-coupled receptor 151 | galanin receptor-like GPCR - GALRL, GPCR, PGR7, galanin receptor-like; putative G-protein coupled receptor | GPR151 |
| 331 | G protein-coupled receptor 17 | G Protein-Coupled Receptor 17 - | GPR17 |

TABLE 2-continued

ARTERIORISKMARKERS

| ARTERIORISKMARKER | Official Name | Common Name | Gene Symbol |
|---|---|---|---|
| 332 | G protein-coupled receptor 171 | G Protein-Coupled Receptor H963 - H963, platelet activating receptor homolog | GPR171 |
| 333 | G protein-coupled receptor 173 | seven transmembrane G protein coupled receptor - SREB3, G-protein coupled receptor 173; super conserved receptor expressed in brain 3 | GPR173 |
| 334 | G protein-coupled receptor 18 | G Protein Coupled Receptor 18 - | GPR18 |
| 335 | G protein-coupled receptor 19 | G-protein coupled receptor 19 - | GPR19 |
| 336 | G protein-coupled receptor 20 | G protein-coupled receptor 20 - | GPR20 |
| 337 | G protein-coupled receptor 21 | G protein-coupled orphan receptor 21 - | GPR21 |
| 338 | G protein-coupled receptor 22 | G protein Coupled Receptor 22 - tcag7.108 | GPR22 |
| 339 | G protein-coupled receptor 23 | G protein-Coupled P2Y Purinoreceptor 9 - LPAR4, P2RY9, P2Y5-LIKE, P2Y9 | GPR23 |
| 340 | G protein-coupled receptor 25 | G Protein-Coupled receptor 25 | GPR25 |
| 341 | G protein-coupled receptor 26 | G-protein coupled receptor 26 - | GPR26 |
| 342 | G protein-coupled receptor 27 | G-protein coupled receptor 27 - SREB1, super conserved receptor expressed in brain 1, GPR27 | GPR27 |
| 343 | G protein-coupled receptor 3 | G protein coupled receptor 3 polypeptide - ACCA, adenylate cyclase constitutive activator | GPR3 |
| 344 | G protein-coupled receptor 30 | G-protein coupled receptor 30 - CMKRL2, DRY12, FEG-1, GPCR-Br, LERGU, LERGU2, LyGPR, chemokine receptor-like 2; flow-induced endothelial G-protein coupled receptor; leucine rich protein in GPR30 3'UTR | GPR30 |
| 345 | G protein-coupled receptor 31 | G protein-coupled receptor 31 - (G protein-coupled receptor 31) | GPR31 |
| 346 | G protein-coupled receptor 32 | G-Protein Coupled Receptor 32 - | GPR32 |
| 347 | G protein-coupled receptor 34 | G protein-coupled receptor 34 - | GPR34 |
| 348 | G protein-coupled receptor 35 | G protein-coupled receptor 35 - | GPR35 |
| 349 | G protein-coupled receptor 35 | G-Protein Coupled Receptor R35 - | GPR35 |
| 350 | G protein-coupled receptor 37 (endothelin receptor type B-like) | endothelin receptor type B-like protein 1 - EDNRBL, PAELR, hET(B)R-LP, G protein-coupled receptor 37; Parkin-associated endothelin receptor-like receptor; endothelin receptor type B-like | GPR37 |
| 351 | G protein-coupled receptor 37 (endothelin receptor type B-like) | G-protein-coupled receptor 37 - EDNRBL, PAELR, hET(B)R-LP, G protein-coupled receptor 37; Parkin-associated endothelin receptor-like receptor; endothelin receptor type B-like, BG37 | GPR37 |
| 352 | G protein-coupled receptor 39 | G-protein-coupled-receptor 39 - | GPR39 |
| 353 | G protein-coupled receptor 4 | G Protein Coupled Receptor 4 | GPR4 |
| 354 | G protein-coupled receptor 42 | G protein-coupled receptor 42 - FFAR1L, GPR41L | GPR42 |
| 355 | G protein-coupled receptor 44 | G-protein coupled receptor 58 - CD294, CRTH2, chemoattractant receptor-homologous molecule expressed on TH2 cells | GPR44 |
| 356 | G protein-coupled receptor 45G protein-coupled receptor 45 | G-Protein Coupled Receptor 45 - PSP24, PSP24(ALPHA), PSP24A, high-affinity lysophosphatidic acid receptor | GPR45 |
| 357 | G protein-coupled receptor 50 | G-protein coupled receptor 50 - H9 | GPR50 |
| 358 | G protein-coupled receptor 52 | G-protein coupled receptor 52 - | GPR52 |
| 359 | G protein-coupled receptor 6 | G-protein coupled receptor 6 polypeptide - | GPR6 |
| 360 | G protein-coupled receptor 64 | G Protein-coupled Receptor 64 - HE6, TM7LN2, G protein-coupled receptor, epididymis-specific (seven transmembrane family) | GPR64 |
| 361 | G protein-coupled receptor 65 | G-Protein Coupled Receptor 65 - TDAG8, hTDAG8, T-cell death-associated gene 8 | GPR65 |
| 362 | G protein-coupled receptor 68 | ovarian cancer G-protein coupled receptor 1 - OGR1, ovarian cancer G protein-coupled receptor, 1 | GPR68 |
| 363 | G protein-coupled receptor 75 | G protein-coupled receptor 75 - GPR-chr2 | GPR75 |
| 364 | G protein-coupled receptor 77 | G protein-coupled receptor 77 - C5L2, GPF77, G protein-coupled receptor C5L2 | GPR77 |
| 365 | G protein-coupled receptor 82 | G protein-coupled receptor 82 | GPR82 |
| 366 | G protein-coupled receptor 83 | G-Protein Coupled Receptors 72 - GIR, GPR72, G protein-coupled receptor 72; G-protein coupled receptor 72; glucocorticoid induced recept | GPR83 |
| 367 | G protein-coupled receptor 84 | G protein-coupled receptor 84 - EX33, GPCR4, inflammation-related G protein-coupled receptor EX33 | GPR84 |
| 368 | G protein-coupled receptor 85 | G protein-coupled receptor 85 - SREB, SREB2, seven transmembrane helix receptor; super conserved receptor expressed in brain 2 | GPR85 |

TABLE 2-continued

ARTERIORISKMARKERS

| ARTERIORISKMARKER | Official Name | Common Name | Gene Symbol |
|---|---|---|---|
| 369 | G protein-coupled receptor 87 | G protein-Coupled Receptor 87 - FKSG78, GPR95, KPG_002, G protein-coupled receptor 95 | GPR87 |
| 370 | G protein-coupled receptor 88 | G protein-coupled receptor 88 - STRG, G-protein coupled receptor 88 | GPR88 |
| 371 | G protein-coupled receptor 92 | G-protein coupled receptor 92 - GPR93, KPG_010, G-protein coupled receptor; internal gene name of KIRIN laboratory: H95; putative G protein-coupled receptor 92 | GPR92 |
| 372 | G protein-coupled receptor, family C, group 5, member B | G Protein-Coupled Receptor, Family C, Group 5, Member B-RAIG-2, RAIG2, G protein-coupled receptor, family C, group 1, member B; retinoic acid responsive gene protein | GPRC5B |
| 373 | G protein-coupled receptor, family C, group 5, member C | G Protein-Coupled Receptor Family C Group 5 Member C - RAIG-3, RAIG3, G protein-coupled receptor family C, group 5, member C; orphan G-protein coupled receptor; retinoic acid responsive gene protein | GPRC5C |
| 374 | G protein-coupled receptor kinase 1 | G protein-dependent receptor kinase 1 (GRK1) - GPRK1, RHOK, RK, rhodopsin kinase | GRK1 |
| 375 | G protein-coupled receptor kinase 4 | G protein-coupled receptor 4 kinase - GPRK2L, GPRK4, GRK4a, IT11, G protein-coupled receptor kinase 2-like (*Drosophila*); G-protein coupled receptor kinase 4 | GRK4 |
| 376 | G protein-coupled receptor kinase 5 | G protein-coupled receptor 5 kinase - GPRK5 | GRK5 |
| 377 | G protein-coupled receptor kinase 6 | G protein-coupled receptor 6 kinase - GPRK6 | GRK6 |
| 378 | G protein-coupled receptor kinase 7 | G protein coupled receptor kinase 7 - | GRK7 |
| 379 | glutamate receptor, metabotropic 1 | metabotropic glutamate receptor 5 - GPRC1A, GRM1A, MGLUR1, MGLUR1A, mGlu1 | GRM1 |
| 380 | glutamate receptor, metabotropic 2 | metabotropic glutamate receptor 2 - GLUR2, GPRC1B, MGLUR2, mGlu2, glutamate receptor homolog | GRM2 |
| 381 | glutamate receptor, metabotropic 4 | metabotropic glutamate receptor 4 - GPRC1D, MGLUR4, mGlu4 | GRM4 |
| 382 | glutamate receptor, metabotropic 5 | metabotropic glutamate receptor 3 - GPRC1E, MGLUR5, MGLUR5A, MGLUR5B, mGlu5 | GRM5 |
| 383 | glutamate receptor, metabotropic 7 | metabotropic glutamate receptor 7 - GLUR7, GPRC1G, MGLUR7, mGlu7 | GRM7 |
| 384 | glutamate receptor, metabotropic 8 | metabotropic glutamate receptor 8 - GLUR8, GPRC1H, MGLUR8, mGlu8 | GRM8 |
| 385 | glycogen synthase kinase 3 alpha | glycogen synthase kinase 3 alpha - | GSK3A |
| 386 | glycogen synthase kinase 3 beta | glycogen synthase kinase 3 beta - | GSK3B |
| 387 | glutathione S-transferase M1 | Glutathione S transferase M1/GST mu-1 (GSTM1), GST1, GSTM1-1, GSTM1a-1a, GSTM1b-1b, GTH4, GTM1, H-B, MU, MU-1, GST class-mu 1; HB subunit 4; S-(hydroxyalkyl)glutathione lyase; glutathione S-alkyltransferase; glutathione S-aralkyltransferase; glutathione S-aryltransferase; glutathione S-transferase, Mu-1 | GSTM1 |
| 388 | glutathione S-transferase M2 (muscle) | GST4, GSTM, GSTM2-2, GTHMUS, GST class-mu 2; GST, muscle; S-(hydroxyalkyl)glutathione lyase M2; glutathione S-alkyltransferase M2; glutathione S-aralkyltransferase M2; glutathione S-aryltransferase M2; glutathione S-transferase 4; glutathione S-transferase M1; glutathione S-transferase M2; glutathione S-transferase Mu 2 | GSTM2 |
| 389 | glutathione S-transferase theta 1 | Glutathione S transferase T1/GST theta-1 (GSTT1) | GSTT1 |
| 390 | guanylate cyclase 1, soluble, alpha 2 | GC-SA2, GUC1A2 | GUCY1A2 |
| 391 | guanylate cyclase 1, soluble, alpha 3 | guanylate cyclase, α1-subunit of the soluble - GC-SA3, GUC1A3, GUCA3, GUCSA3, GC-S-alpha-1; soluble guanylate cyclase large subunit | GUCY1A3 |
| 392 | guanylate cyclase 1, soluble, beta 3 | guanylatcyclase, β1-subunit of the soluble - GC-S-beta-1, GC-SB3, GUC1B3, GUCB3, GUCSB3 | GUCY1B3 |
| 393 | factor VII activating protein; hepatocyte growth factor activator-like protein; hyuronan-binding protein 2; hyaluronic acid binding protein 2; plasma hyaluronan binding protein | hyaluronan binding protein 2 | HABP2 |
| 394 | hyaluronan synthase 2 | hyaluronan synthase 2 (HAS-2) - | HAS2 |
| 395 | hemoglobin, alpha 1 | circulating CD31+ apoptotic microparticles in peripheral blood, (Entered CD31 into Entrez), CD31, alpha 1 globin; alpha one globin; alpha-1 | HBA1 |

TABLE 2-continued

ARTERIORISKMARKERS

| ARTERIORISKMARKER | Official Name | Common Name | Gene Symbol |
|---|---|---|---|
| | | globin; alpha-1-globin; alpha-2 globin; alpha-2-globin; hemoglobin alpha 1 globin chain; hemoglobin alpha 2; hemoglobin alpha-1 chain; hemoglobin alpha-2 | |
| 396 | hemoglobin, alpha 1 | hemoglobin, alpha 1, CD31, MGC126895, MGC126897, alpha 1 globin; alpha one globin; alpha-1 globin; alpha-1-globin; alpha-2 globin; alpha-2-globin; hemoglobin alpha 1 globin chain; hemoglobin alpha 2; hemoglobin alpha-1 chain; hemoglobin alpha-2 | HBA1 |
| 397 | hypocretin (orexin) receptor 2 | G Protein- Coupled Receptor OX1R - OX2R - hypocretin receptor-2; orexin receptor 2; orexin receptor-2 | HCRTR2 |
| 398 | hexosaminidase A (alpha polypeptide) | hexosaminidase A - TSD, N-acetyl-beta-glucosaminidase; beta-N-acetylhexosaminidase; hexosaminidase A | HEXA |
| 399 | hexosaminidase B (beta polypeptide) | hexosaminidase B - ENC-1AS, N-acetyl-beta-glucosaminidase; hexosaminidase B | HEXB |
| 400 | hepatocyte growth factor (hepapoietin A; scatter factor) | Hepatocyte growth factor (HGF) - F-TCF, HGFB, HPTA, SF, fibroblast-derived tumor cytotoxic factor; hepatocyte growth factor; hepatopoietin A; lung fibroblast-derived mitogen; scatter factor | HGF |
| 401 | hypoxia-inducible factor 1, alpha subunit (basic helix-loop-helix transcription factor) | HIF - HIF-1alpha, HIF1-ALPHA, MOP1, PASD8, ARNT interacting protein; hypoxia-inducible factor 1, ATPase Ca++ binding protein: ARNT interacting protein; hypoxia-inducible factor 1, alpha subunit; member of PAS superfamily 1 | HIF1A |
| 402 | hepatocyte nuclear factor 4, alpha | Hepatocyte nuclear factor 4, alpha - HNF4, HNF4a7, HNF4a8, HNF4a9, MODY, MODY1, NR2A1, NR2A21, TCF, TCF14 Other Designations: HNF4-alpha; hepatic nuclear factor 4 alpha; hepatocyte nuclear factor 4 alpha; transcription factor-14 | HNF4A |
| 403 | hepatocyte nuclear factor 4, alpha | hepatocyte nuclear factor 4 - HNF4, HNF4a7, HNF4a8, HNF4a9, MODY, MODY1, NR2A1, NR2A21, TCF, TCF14, HNF4-alpha; hepatic nuclear factor 4 alpha; hepatocyte nuclear factor 4 alpha; transcription factor-14 | HNF4A |
| 404 | haptoglobin | haptoglobin - hp2-alpha | HP |
| 405 | hepsin (transmembrane protease, serine 1) | protease hepsin - TMPRSS1 | HPN |
| 406 | hemopexin | haemopexin - hemopexin | HPX |
| 407 | hydroxysteroid (11-beta) dehydrogenase 2 | 11betaHSD2: AME; AME1; HSD2; HSD11K | HSD11B2 |
| 408 | heat shock 70 kDa protein 1A | dnaK-type molecular chaperone HSP70-1; heat shock 70 kD protein 1A; heat shock 70 kDa protein 1B; heat shock-induced protein | HSPA1A |
| 409 | heat shock 70 kDa protein 8 | Heat shock protein 70, HSC54, HSC70, HSC71, HSP71, HSP73, HSPA10, LAP1, NIP71, LPS-associated protein 1; N-myristoyltransferase inhibitor protein 71; constitutive heat shock protein 70; heat shock 70 kD protein 8; heat shock 70 kd protein 10; heat shock cognate protein 54; heat shock cognate protein, 71-kDa; lipopolysaccharide-associated protein 1; uncharacterized bone marrow protein BM034 | HSPA8 |
| 410 | heat shock 70 kDa protein 9 (mortalin) | CSA, GRP75, HSPA9B, MGC4500, MOT, MOT2, MTHSP75, PBP74, mot-2; 75 kDa glucose regulated protein; heat shock 70 kD protein 9; heat shock 70 kD protein 9B (mortalin-2); heat shock 70 kDa protein 9B; heat shock 70 kDa protein 9B (mortalin-2); mortalin, perinuclear; p66-mortalin; peptide-binding protein 74; stress-70 protein, mitochondrial | HSPA9 |
| 411 | heat shock 70 kDa protein 9B (mortalin-2) | heat shock 70 kDa protein 9B-CSA, GRP75, HSPA9, MOT, MOT2, MTHSP75, PBP74, mot-2, 75 kDa glucose regulated protein; heat shock 70 kD protein 9; heat shock 70 kD protein 9B (mortalin-2); heat shock 70 kDa protein 9B; mortalin, perinuclear; p66-mortalin; peptide-binding protein 74; stress-70 protein, mitochondrial | HSPA9B |
| 412 | 5-hydroxytryptamine (serotonin) receptor 1F | 5-hydroxytryptamine receptor 1F - 5-HT1F, HTR1EL, MR7, 5-hydroxytryptamine receptor 1F; GENE RECEPTEUR 5HT6 HUMAIN | HTR1F |

TABLE 2-continued

ARTERIORISKMARKERS

| ARTERIORISKMARKER | Official Name | Common Name | Gene Symbol |
|---|---|---|---|
| 413 | 5-hydroxytryptamine (serotonin) receptor 2A | 5-hydroxytryptamine 2A polypeptide, 5HT2a polypeptide - 5-HT2A, HTR2, 5-HT2 receptor | HTR2A |
| 414 | 5-hydroxytryptamine (serotonin) receptor 2B | 5-hydroxytryptamine (serotonin) receptor 2B - 5-HT(2B), 5-HT2B | HTR2B |
| 415 | 5-hydroxytryptamine (serotonin) receptor 2C | 5-hydroxytryptamine receptor 2C polypeptide - 5-HT2C, HTR1C | HTR2C |
| 416 | 5-hydroxytryptamine (serotonin) receptor 3A | 5-Hydroxytryptamine Receptor 3A - 5-HT-3, 5-HT3A, 5-HT3R, 5HT3R, HTR3, 5-hydroxytryptamine (serotonin) receptor-3; 5HT3 serotonin receptor; Serotonin-gated ion channel receptor; serotonin receptor; truncated receptor, containing only 3 transmembrane domains | HTR3A |
| 417 | 5-hydroxytryptamine (serotonin) receptor 3B | 5-hydroxytryptamine receptor 3B - 5-HT3B, 5-hydroxytryptamine (serotonin) receptor 3B precursor; 5-hydroxytryptamine 3 receptor B subunit; serotonin-gated ion channel subunit | HTR3B |
| 418 | 5-hydroxytryptamine (serotonin) receptor 3, family member C | 5-Hydroxytryptamine Receptor 3C - 5-hydroxytryptamine receptor 3 subunit C, 5HT3c | HTR3C |
| 419 | 5-hydroxytryptamine (serotonin) receptor 4 | 5-hydroxytryptamine receptor 4 - 5-HT4, 5-HT4R, 5-hydroxytryptamine4 receptor; cardiac 5-HT4 receptor; serotonin 5-HT4 receptor | HTR4 |
| 420 | 5-hydroxytryptamine (serotonin) receptor 5A | SEROTONIN 5-HT5A RECEPTOR - 5-HT5A, 5-hydroxytryptamine receptor 5A | HTR5A |
| 421 | 5-hydroxytryptamine (serotonin) receptor 6 | G-Protein Coupled Receptor 5-HT6 - 5-HT6 | HTR6 |
| 422 | 5-hydroxytryptamine (serotonin) receptor 7 (adenylate cyclase-coupled) | 5-hydroxytryptamine receptor 7 - 5-HT7, 5-hydroxytryptamine receptor 7; serotonin 5-HT-7 receptor | HTR7 |
| 423 | intercellular adhesion molecule 1 (CD54), human rhinovirus receptor | soluble intercellular adhesion molecule-1, BB2, CD54, P3.58, 60 bp after segment 1; cell surface glycoprotein; cell surface glycoprotein P3.58; intercellular adhesion molecule 1 | ICAM1 |
| 424 | intercellular adhesion molecule 3 | ICAM 3 - CD50, CDW50, ICAM-R, intercellular adhesion molecule-3 | ICAM3 |
| 425 | carboxy-terminal-telopeptide of type I collagen (ICTP) | collagen I degradation byproduct (ICTP), carboxy-terminal-telopeptide of type I collagen (ICTP) | ICTP |
| 426 | interferon, gamma | IFNG: IFG; IFI | IFNG |
| 966 | | Cryoglobulines (CG) | Ig |
| 427 | insulin-like growth factor 1 (somatomedin C) | IGF-1: somatomedin C. insulin-like growth factor-1 | IGF1 |
| 428 | insulin-like growth factor 1 receptor | insulin like growth factor 1 receptor - CD221, IGFIR, JTK13, clone 1900 unknown protein | IGF1R |
| 429 | insulin-like growth factor binding protein 1 | insulin-like growth factor binding protein-1 (IGFBP-1) - AFBP, IBP1, IGF-BP25, PP12, hIGFBP-1, IGF-binding protein 1; alpha-pregnancy-associated endometrial globulin; amniotic fluid binding protein; binding protein-25; binding protein-26; binding protein-28; growth hormone independent-binding protein; placental protein 12 | IGFBP1 |
| 430 | insulin-like growth factor binding protein 3 | insulin-like growth factor binding protein 3: IGF-binding protein 3 - BP-53, IBP3, IGF-binding protein 3; acid stable subunit of the 140 K IGF complex; binding protein 29; binding protein 53; growth hormone-dependent binding protein | IGFBP3 |
| 431 | interleukin 10 | IL-10, CSIF, IL-10, IL10A, TGIF, cytokine synthesis inhibitory factor | IL10 |
| 432 | interleukin 12B (natural killer cellstimulatory factor 2, cytotoxic lymphocyte maturation factor 2, p40) | CLMF, CLMF2, IL-12B, NKSF, NKSF2; IL12, subunit p40; cytotoxic lymphocyte maturation factor 2, p40; interleukin 12, p40; interleukin 12B; interleukin-12 beta chain; natural killer cell stimulatory factor, 40 kD subunit; natural killer cell stimulatory factor-2 | IL12B |
| 433 | interleukin 13 | interleukin 13, ALRH, BHR1, IL-13, MGC116786, MGC116788, MGC116789, P600 | IL13 |
| 434 | interleukin 17D | IL17D: interleukin 27 | IL17D |
| 435 | interleukin 17 receptor D | SEF, IL-17RD, IL17RLM, SEF, similar expression to FGF protein | IL17RD |
| 436 | interleukin 18 (interferon-gamma-inducing factor) | IL-18-IGIF, IL-18, IL-1g, IL1F4, IL-1 gamma; interferon-gamma-inducing factor; interleukin 18; interleukin-1 gamma; interleukin-18 | IL18 |
| 437 | interleukin 1, beta | interleukin-1 beta (IL-1 beta) - IL-1, IL1-BETA, IL1F2, catabolin; preinterleukin 1 beta; pro-interleukin-1-beta | IL1B |

TABLE 2-continued

ARTERIORISKMARKERS

| ARTERIORISKMARKER | Official Name | Common Name | Gene Symbol |
|---|---|---|---|
| 438 | interleukin 1, beta | IL-1B(+3954)T (associated with higher CRP levels) - IL-1, IL1-BETA, IL1F2, catabolin; preinterleukin 1 beta; pro-interleukin-1-beta | IL1B |
| 439 | interleukin 1 family, member 5 (delta) | Interleukin 1 - FIL1, FIL1(DELTA), FIL1D, IL1HY1, IL1L1, IL1RP3, IL-1 related protein 3; IL-1F5 (IL-1HY1, FIL1-delta, IL-1RP3, IL-IL1, IL-1-delta); IL-1ra homolog; IL1F5 (Canonical product IL-1F5a); family of interleukin 1-delta; interleukin 1 family, member 5; interleukin 1, delta; interleukin-1 HY1; interleukin-1 receptor antagonist homolog 1; interleukin-1-like protein 1 | IL1F5 |
| 440 | interleukin 1 receptor, type 1 | IL1RA-CD121A, IL-1R-alpha, IL1R, IL1RA, P80, IL-1 receptor (fibroblast type): antigen CD121a; interleukin 1 receptor alpha, type I; interleukin receptor 1 | IL1R1 |
| 441 | interleukin 1 receptor-like 1 | interleukin-1 receptor family member, ST2 - DER4, FIT-1, ST2, ST2L, ST2V, T1, homolog of mouse growth stimulation-expressed gene; interleukin 1 receptor-related protein | IL1RL1 |
| 442 | interleukin 1 receptor antagonist | interleukin-1 receptor antagonist (IL-1Ra) - ICIL-1RA, IL-1ra3, IL1F3, IL1RA, IRAP, IL1RN (IL1F3); intracellular IL-1 receptor antagonist type II; intracellular interleukin-1 receptor antagonist (icIL-1ra); type II interleukin-1 receptor antagonist | IL1RN |
| 443 | interleukin 1 receptor antagonist | IL-1RN(VNTR)*2 (associated with lower CRP levels) - ICIL-1RA, IL-1ra3, IL1F3, IL1RA, IRAP, IL1RN (IL1F3); intracellular IL-1 receptor antagonist type II; intracellular interleukin-1 receptor antagonist (icIL-1ra); type II interleukin-1 receptor antagonist | IL1RN |
| 444 | interleukin 2 | interleukin-2 (IL-2) - IL-2, TCGF, lymphokine, T cell growth factor; aldesleukin; interleukin-2; involved in regulation of T-cell clonal expansion | IL2 |
| 445 | interleukin 2 receptor, alpha | IL-2R - CD25, IL2R, TCGFR, Interleukin-2 receptor, interleukin 2 receptor, alpha chain | IL2RA |
| 446 | interleukin 2 receptor, beta | IL-2R - CD122, P70-75, CD122 antigen; high affinity IL-2 receptor beta subunit; interleukin 2 receptor beta | IL2RB |
| 447 | interleukin 3 (colony-stimulating factor, multiple) | IL-3, MCGF, MGC79398, MGC79399, MULTI-CSF; P-cell stimulating factor; hematopoietic growth factor; interleukin 3; mast-cell growth factor; multilineage-colony-stimulating factor | IL3 |
| 448 | interkeukin 4 | BSF1, IL-4, MGC79402 B_cell stimulatory factor 1; lymphocyte stimulatory factor 1 | IL4 |
| 449 | interleukin 5 (colony-stimulating factor, eosinophil) | EDF, IL-5, TRF; B cell differentiation factor I; T-cell replacing factor; eosinophil differentiation factor; interleukin 5; interleukin-5 | IL5 |
| 450 | interleukin 6 (interferon, beta 2) | Interleukin-6 (IL-6), BSF2, HGF, HSF, IFNB2, IL-6 | IL6 |
| 451 | interleukin 6 receptor | interleukin-6 receptor, soluble (sIL-6R) - CD126, IL-6R-1, IL-6R-alpha, IL6RA, CD126 antigen; interleukin 6 receptor alpha subunit | IL6R |
| 452 | interleukin 6 signal transducer (gp130, oncostatin M receptor) | gp130, soluble (sgp130) - CD130, CDw130, GP130, GP130-RAPS, IL6R-beta, CD130 antigen; IL6ST nirs variant 3; gp130 of the rheumatoid arthritis antigenic peptide-bearing soluble form; gp130 transducer chain; interleukin 6 signal transducer; interleukin receptor beta chain; membrane glycoprotein gp130; oncostatin M receptor | IL6ST |
| 453 | interleukin 7 | IL-7, IL7 nirs variant 1; IL7 nirs variant 2; IL7 nirs variant 4 | IL7 |
| 454 | interleukin 8 | Interleukin-8 (IL-8), 3-10C, AMCF-I, CXCL8, GCP-1, GCP1, IL-8, K60, LECT, LUCT, LYNAP, MDNCF, MONAP, NAF, NAP-1, NAP1, SCYB8, TSG-1, b-ENAP, CXC chemokine ligand 8; LUCT/interleukin-8; T cell chemotactic factor; beta-thromboglobulin-like protein; chemokine (C-X-C motif) ligand 8; emoctakin; granulocyte chemotactic protein 1; lymphocyte-derived neutrophil-activating factor; monocyte derived neutrophil-activating protein; monocyte-derived neutrophil chemotactic factor; neutrophil-activating factor; neutrophil- | IL8 |

TABLE 2-continued

ARTERIORISKMARKERS

| ARTERIORISKMARKER | Official Name | Common Name | Gene Symbol |
|---|---|---|---|
| 455 | interleukin 8 receptor, alpha | activating peptide 1; neutrophil-activating protein 1; protein 3-10C; small inducible cytokine subfamily B, member 8 C-C; C-C CKR-1; CD128; CD181; CDw128a; CKR-1; CMKAR1; CXCR1; IL8R1; IL8RBA, IL-8 receptor; IL-8 receptor type 1; chemokine (C-X-C motif) receptor 1; chemokine (C-X-C) receptor 1; high affinity interleukin-8 receptor A; interleukin-8 receptor alpha; interleukin-8 receptor type 1; interleukin-8 receptor type A | IL8RA |
| 456 | interleukin 8 receptor, beta | CXC chemokine receptor 2 - CD182, CDw128b, CMKAR2, CXCR2, IL8R2, IL8RA - CXCR2 gene for IL8 receptor type B; GRO/MGSA receptor; chemokine (C-X-C motif) receptor 2; chemokine (CXC) receptor 2; high affinity interleukin-8 receptor B; interleukin 8 receptor B; interleukin 8 receptor beta; interleukin 8 receptor type 2; interleukin-8 receptor type B | IL8RB |
| 457 | integrin-linked kinase | integrin-linked kinase 1 - P59 | ILK |
| 458 | integrin-linked kinase-2 | integrin-linked kinase 2 | ILK-2 |
| 459 | inhibin, beta A (activin A, activin AB alpha polypeptide) | activin A - EDF, FRP, Inhibin, beta-1; inhibin beta A | INHBA |
| 460 | insulin | insulin, proinsulin | INS |
| 461 | insulin-like 4 (placenta) | insulin-like 4 gene - EPIL, PLACENTIN, early placenta insulin-like peptide (EPIL); insulin-like 4 | INSL4 |
| 462 | CD220, HHF5 | insulin receptor | INSR |
| 463 | IQ motif containing GTPase activating protein 1 | IQ motif containing GTPase activating protein 1 - HUMORFA01, SAR1, p195, RasGAP-like with IQ motifs | IQGAP1 |
| 464 | IQ motif containing GTPase activating protein 2 | IQ motif containing GTPase activating protein 2 | IQGAP2 |
| 465 | integrin, alpha 2b (platelet glycoprotein IIb of IIb/IIIa complex, antigen CD41) | glycoprotein-IIb - CD41, CD41B, GP2B, GPIIb, GTA, HPA3, integrin alpha 2b; integrin, alpha 2b (platelet glycoprotein IIb of IIb/IIIa complex, antigen CD41B); platelet fibrinogen receptor, alpha subunit; platelet-specific antigen BAK, GP IIb/IIIa | ITGA2B |
| 466 | integrin, alpha L (antigen CD11A (p180), lymphocyte function-associated antigen 1; alpha polypeptide) | integrin alpha-L - CD11A, LFA-1, LFA1A, LFA-1 alpha; antigen CD11A (p180), lymphocyte function-associated antigen 1, alpha polypeptide; integrin alpha L; integrin gene promoter; lymphocyte function-associated antigen 1 | ITGAL |
| 467 | integrin, beta 2 (complement component 3 receptor 3 and 4 subunit) | Mac-1 (CD11b/CD18) leukocyte adhesion molecule - CD18, LAD, LCAMB, LFA-1, MAC-1, MF17, MF17, cell surface adhesion glycoprotein (LFA-1/CR3/P150,959 beta subunit precursor); complement receptor C3 beta-subunit; integrin beta 2; integrin beta chain, beta 2; integrin, beta 2; integrin, beta 2 (antigen CD18 (p95), lymphocyte function-associated antigen 1; macrophage antigen 1 (mac-1) beta subunit); leukocyte cell adhesion molecule CD18; leukocyte-associated antigens CD18/11A, CD18/11B, CD18/11C | ITGB2 |
| 468 | integrin, beta 3 (platelet glycoprotein IIIa, antigen CD61) | glycoprotein IIb/IIIa - CD61, GP3A, GPIIIa, integrin beta chain, beta 3; platelet glycoprotein IIIa precursor | ITGB3 |
| 469 | integrin, beta 3 (platelet glycoprotein IIIa, antigen CD61) | platelet glycoprotein IIIa Leu33Pro allele/ Pl(A1/A2) polymorphism of GPIIIa/Pl(A2) (Leu33Pro) polymorphism of beta(3) integrins/ polymorphism responsible for the Pl(A2) alloantigen on the beta(3)-component - CD61, GP3A, GPIIIa, integrin beta chain, b | ITGB3 |
| 470 | junctional adhesion molecule 2 | junction adhesion molecules-1, 2, and 3 - C21orf43, CD322, JAM-B, JAMB, PRO245, VE-JAM, VEJAM, JAM-IT/VE-JAM; junctional adhesion molecule B; vascular endothelial junction-associated molecule | JAM2 |
| 471 | junctional adhesion molecule 3 | junction adhesion molecules-1, 2, and 3 - JAM-C, JAMC, junctional adhesion molecule C | JAM3 |
| 472 | potassium voltage-gated channel, shaker-related subfamily, member 2 | voltage-gated-K+ channel (KV1.2) - HBK5, HK4, HUKIV, KV1.2, MK2, NGK1, RBK2, potassium channel; voltage-gated potassium channel protein Kv1.2 | KCNA2 |

TABLE 2-continued

ARTERIORISKMARKERS

| ARTERIORISKMARKER | Official Name | Common Name | Gene Symbol |
|---|---|---|---|
| 473 | potassium voltage-gated channel, shaker-related subfamily, member 5 | voltage-gated-K+ channel (KV1.5) - HCK1, HK2, HPCN1, KV1.5, PCN1, cardiac potassium channel; insulinoma and islet potassium channel; potassium channel 1; potassium channel protein; voltage-gated potassium channel; voltage-gated potassium channel protein Kv1.5 | KCNA5 |
| 474 | potassium voltage-gated channel, shaker-related subfamily, beta member 1 | voltage-gated-K+ channel β subunit: potassium channel beta 3 chain; potassium channel beta3 subunit; potassium channel shaker chain beta 1a; potassium voltage-gated channel beta subunit; voltage-gated potassium channel beta-1 subunit | KCNAB1 |
| 475 | potassium voltage-gated channel, Isk-related family, member 2 | LQT5, LQT6, MIRP1, cardiac voltage-gated potassium channel accessory subunit 2; minK-related peptide-1; minimum potassium ion channel-related peptide 1; potassium channel subunit, MiRP1; potassium voltage-gated channel subfamily E member 2; voltage-gated K+ channel subunit MIRP1 | KCNE2 |
| 476 | potassium voltage-gated channel, subfamily H (eag-related), member 2 | ERG1, HERG, HERG1, Kv11.1, LQT2, cause of Long QT Syndrome Type 2; ether-a-go-go-related potassium channel protein; human eag-related gene; potassium channel HERG; potassium channel HERG1; potassium voltage-gated channel, subfamily H, member 2; voltage-gated potassium channel; voltage-gated potassium channel, subfamily H, member 2 | KCNH2 |
| 477 | potassium inwardly-rectifying channel, subfamily J, member 2 | KCNJ2 - HHBIRK1, HHIRK1, IRK1, KIR2.1, LQT7, cardiac inward rectifier potassium channel; inward rectifier K+ channel KIR2.1; inward rectifier potassium channel 2; potassium inwardly-rectifying channel J2 | KCNJ2 |
| 478 | potassium inwardly-rectifying channel, subfamily J, member 3 | Protein- Coupled Inwardly Rectifying Potassium Channel - GIRK1, KIR3.1, G protein-activated inward rectifier potassium channel 1; inward rectifier K+ channel KIR3.1; potassium inwardly-rectifying channel J3 | KCNJ3 |
| 479 | potassium inwardly-rectifying channel, subfamily J, member 6 | protein-coupled-inwardly-rectifying- potassium-channel-GIRK2 - BIR1, GIRK2, KATP2, KCNJ7, KIR3.2, hiGIRK2, G protein-activated inward rectifier potassium channel 2; inward rectifier potassium channel KIR3.2; potassium inwardly-rectifying channel J6 | KCNJ6 |
| 480 | potassium inwardly-rectifying channel, subfamily J, member 9 | RP11-536C5.1, GIRK3, KIR3.3; G protein-activated inward rectifier potassium channel 3; G protein-coupled inward rectifier potassium channel; inwardly rectifier K+ channel KIR3.3; potassium inwardly-rectifying channel subfamily J9 | KCNJ9 |
| 481 | potassium channel, subfamily K, member 1 | potassium channel subfamily K, member 1 - DPK, HOHO, TWIK-1, TWIK1, potassium channel, subfamily K, member 1 (TWIK-1); potassium inwardly-rectifying channel, subfamily K, member 1 | KCNK1 |
| 482 | Potassium Channel Subfamily K. Member 10 | K2p10.1, TREK-2, TREK2; 2P domain potassium channel TREK2; TWIK related K+ channel 2; outward rectifying potassium channel protein TREK-2; potassium channel TREK-2 | KCNK10 |
| 483 | potassium channel, subfamily K, member 2 | potassium channel subfamily K, member 2 - TPKC1, TREK, TREK-1, TREK1, hTREK-1c, hTREK-1e, TWIK-related potassium channel 1; potassium channel, subfamily K, member 2 (TREK-1); potassium inwardly-rectifying channel, subfamily K, member 2; tandem-pore-domain potassium channel TREK-1 splice variant e; two-pore potassium channel 1 | KCNK2 |
| 484 | potassium channel, subfamily K, member 3 | potassium channel subfamily K, member 3 - OAT1, TASK, TASK-1, TBAK1, Kcnk3 channel; TWIK-related acid-sensitive K+ channel; acid-sensitive potassium channel protein TASK; cardiac potassium channel; potassium channel, subfamily K, member 3 (TASK); potassium channel, subfamily K, member 3 (TASK-1); potassium inwardly-rectifying channel, subfamily K, member 3; two P domain potassium channel | KCNK3 |

TABLE 2-continued

ARTERIORISKMARKERS

| ARTERIORISKMARKER | Official Name | Common Name | Gene Symbol |
|---|---|---|---|
| 485 | potassium channel, subfamily K, member 4 | potassium channel subfamily K, member 4 - TRAAK, TRAAK1, TRAAK; TWIK-related arachidonic acid-stimulated potassium channel protein; two pore K+ channel KT4.1 | KCNK4 |
| 486 | potassium channel, subfamily K, member 5 | potassium channel subfamily K, member 5 - TASK-2, TASK2, TWIK-related acid-sensitive K+ channel 2; acid-sensitive potassium channel protein TASK-2; potassium channel, subfamily K, member 1 (TASK-2); potassium channel, subfamily K, member 5 (TASK-2) | KCNK5 |
| 487 | potassium channel, subfamily K, member 6 | potassium channel subfamily K, member 6 - KCNK8, TOSS, TWIK-2, TWIK2, TWIK-originated sodium similarity sequence; inward rectifying potassium channel protein TWIK-2; potassium channel, subfamily K, member 6 (TWIK-2) | KCNK6 |
| 488 | potassium channel, subfamily K, member 7 | Potassium Channel Subfamily K Member 7 - TWIK3, potassium channel, subfamily K, member 7, isoform B; two pore domain K+ channel | KCNK7 |
| 489 | potassium channel, subfamily K, member 9 | Potassium Channels Subfamily K Member 9 - KT3.2, TASK-3, TASK3, TWIK-related acid-sensitive K+ channel 3; acid-sensitive potassium channel protein TASK-3; potassium channel TASK3; potassium channel, subfamily K, member 9 (TASK-3) | KCNK9 |
| 490 | potassium voltage-gated channel, KQT-like subfamily, member 1 | KCNQ1-ATFB1, KCNA8, KCNA9, KVLQT1, Kv1.9, Kv7.1, LQT, LQT1, RWS, WRS, kidney and cardiac voltage dependend K+ channel; long (electrocardiographic) QT syndrome, Ward-Romano syndrome 1; slow delayed rectifier channel subunit | KCNQ1 |
| 491 | Kell blood group, metalloendopeptidase | X-pro dipeptidase like peptidase - ECE3; CD238, PEPD-like | KEL |
| 492 | mixed lineage kinase 4 | MLK4 alpha, MLK4 beta - MLK4 | KIAA1804 |
| 493 | G protein-coupled receptor 54 | G-protein coupled receptor 54 - | KISS1R |
| 494 | kallikrein 1, renal/pancreas/salivary | kallikrein 1 - KLKR, Klk6, hK1, glandular kallikrein 1; kallikrein 1; kallikrein serine protease 1; tissue kallikrein | KLK1 |
| 495 | kallikrein 10 | kallikrein 10 - NES1, PRSSL1, breast normal epithelial cell associated serine protease; normal epithelial cell-specific 1; protease, serine-like, 1 | KLK10 |
| 496 | kallikrein 11 | kallikrein 11 - PRSS20, TLSP, hippostasin; protease, serine, 20 trypsin-like; protease, serine, trypsin-like | KLK11 |
| 497 | kallikrein 12 | kallikrein 12 - KLK-L5, kallikrein-like protein 5 | KLK12 |
| 498 | kallikrein 15 | kallikrein 15 - ACO, HSRNASPH, ACO protease; kallikrein-like serine protease; prostinogen | KLK15 |
| 499 | kallikrein 2, prostatic | kallikrein 2 - KLK2A2, hK2, glandular kallikrein 2 | KLK2 |
| 500 | kallikrein 5 | kallikrein 5 - KLK-L2, KLKL2, SCTE, kallikrein-like protein 2; stratum corneum tryptic enzyme | KLK5 |
| 501 | kallikrein 6 (neurosin, zyme) | kallikrein 6 - Bssp, Klk7, NEUROSIN, PRSS18, PRSS9, SP59, ZYME, hK6, kallikrein 6; protease M; protease, serine, 18; protease, serine, 9 | KLK6 |
| 502 | kallikrein 7 (chymotryptic, stratum corneum) | kallikrein 7 - PRSS6, SCCE, kallikrein 7 splice variant 3; protease, serine, 6; stratum corneum chymotryptic enzyme | KLK7 |
| 503 | kallikrein 8 (neuropsin/ovasin) | kallikrein 8 - HNP, NP, NRPN, PRSS19, TADG14, kallikrein 8; neuropsin; neuropsin type 1; neuropsin type 2; ovasin; protease, serine, 19; tumor-associated differentially expressed gene 14 | KLK8 |
| 504 | kallikrein 9 | kallikrein 9 - KLK-L3, KLK8, KLKL3, kallikrein 8; kallikrein 9 splice variant 2; kallikrein-like protein 3 | KLK9 |
| 505 | kallikrein B, plasma (Fletcher factor) 1 | kallikrein 3 - KLK3 - Kallikrein, plasma; kallikrein 3, plasma; kallikrein B plasma; kininogenin; plasma kallikrein B1 | KLKB1 |
| 506 | kininogen 1 | high molecular weight kininogen - BDK, KNG, kininogen, alpha-2-thiol proteinase inhibitor, bradykinin | KNG1 |
| 507 | lymphocyte-activation gene 3 | Lymphocyte-activation protein 3 - CD223, lymphocyte-activation protein 3 | LAG3 |

TABLE 2-continued

ARTERIORISKMARKERS

| ARTERIORISKMARKER | Official Name | Common Name | Gene Symbol |
|---|---|---|---|
| 508 | laminin, alpha 3 | laminin alpha - E170, LAMNA, LOCS, lama3a, BM600 150 kD subunit; epiligrin 170 kda subunit; epiligrin alpha 3 subunit; kalinin 165 kD subunit; laminin alpha 3 subunit; laminin, alpha 3 (nicein (150 kD), kalinin (165 kD), BM600 (150 kD), epilegrin); laminin-5 alpha 3 chain; nicein 150 kD subunit | LAMA3 |
| 509 | laminin, beta 3 | laminin - LAMNB1, BM600-125 kDa; kalinin-140 kDa; laminin subunit beta 3; laminin, beta 3 (nicein (125 kD), kalinin (140 kD), BM600 (125 kD)); nicein-125 kDa | LAMB3 |
| 510 | laminin, gamma 2 | laminin-gamma(2) - B2T, BM600, EBR2, EBR2A, LAMB2T, LAMNB2, BM600-100 kDa; kalinin (105 kD); kalinin-105 kDa; laminin, gamma 2 (nicein (100 kD), kalinin (105 kD), BM600 (100 kD), Herlitz junctional epidermolysis bullosa)); nicein (100 kDa); nicein-100 kDa | LAMC2 |
| 511 | lysosome-associated membrane protein | CD107a, LAMPA, LGP120 | LAMP1 |
| 512 | lecithin-cholesterol acyltransferase | LCAT - | LCAT |
| 513 | lipocalin 2 (oncogene 24p3) | neutrophil proteinase-associated lipocalin (NGAL) - NGAL | LCN2 |
| 514 | lymphocyte cytosolic protein 2 (SH2 domain containing leukocyte protein of 76 kDa) | lymphocyte cytosolic protein 2 - SLP-76, SLP76, 76 kDa tyrosine phosphoprotein; SH2 domain-containing leukocyte protein of 76 kD; lymphocyte cytosolic protein 2; lymphocyte cytosolic protein 2 (SH2 domain-containing leukocyte protein of 76 kD) | LCP2 |
| 515 | low density lipoprotein receptor (familial hypercholesterolemia) | LDLR - FH, FHC, LDL receptor; LDLR precursor; low density lipoprotein receptor | LDLR |
| 516 | left-right determination factor 2 | endometrial bleeding-associated factor: endometrial bleeding associated factor; endometrial bleeding associated factor (left-right determination, factor A; transforming growth factor beta superfamily); transforming growth factor, beta-4 (endometrial bleeding-associated factor; LEFTY A) | LEFTY2 |
| 517 | leptin (obesity homolog, mouse) | leptin - OB, OBS, leptin; leptin (murine obesity homolog); obesity; obesity (murine homolog, leptin) | LEP |
| 518 | leptin receptor | leptin receptor, soluble - CD295, OBR, OB receptor | LEPR |
| 519 | legumain | putative cysteine protease 1 - AEP, LGMN1, PRSC1, asparaginyl endopeptidase; cysteine protease 1; protease, cysteine, 1 (legumain) | LGMN |
| 520 | leucine-rich repeat-containing G protein-coupled receptor 5 | G Protein-Coupled Receptor 49 - FEX, GPR49, GPR67, GRP49, HG38, G protein-coupled receptor 49; G protein-coupled receptor 67; orphan G protein-coupled receptor HG38 | LGR5 |
| 521 | leucine-rich repeat-containing G protein-coupled receptor 6 | leucine-rich repeat-containing GPCR 6 - GPCR, gonadotropin receptor | LGR6 |
| 522 | leucine-rich repeat-containing G protein-coupled receptor 7 | Leucine- Rich Repeat-Containing G-Protein Coupled Receptor 7 - LGR7.1, LGR7.10, LGR7.2, RXFP1, relaxin family peptide receptor 1 | LGR7 |
| 523 | leucine-rich repeat-containing G protein-coupled receptor 8 | G-protein coupled receptor 105 - GPR106, GREAT, LGR8.1, RXFP2, G protein coupled receptor affecting testicular descent | LGR8 |
| 524 | LIM domain kinase 1 | LIM domain kinase 1 - LIMK, LIM motif-containing protein kinase | LIMK1 |
| 525 | lipase A, lysosomal acid, cholesterol esterase (Wolman disease) | lipase A, lysosomal acid, cholesterol esterase (Wolman disease) - CESD, LAL; cholesterol ester hydrolase; lipase A; lysosomal acid lipase; sterol esterase | LIPA |
| 526 | lipase, hepatic | LIPC - HL, HTGL, LIPH, lipase C | LIPC |
| 527 | lipase, hepatic | LIPC - HL, HTGL, LIPH, lipase C | LIPC |
| 528 | lipoprotein, Lp(a) | lipoprotein (a) [Lp(a)], AK38, APOA, LP, Apolipoprotein Lp(a); antiangiogenic AK38 protein; apolipoprotein(a) | LPA |
| 529 | latrophilin 1 | secretin-type GPCR - CIRL1, CL1, LEC2, calcium-independent alpha-latrotoxin receptor 1; lectomedin-2 | LPHN1 |
| 530 | latrophilin 2 | secretin-type GPCR - CIRL2, CL2, LEC1, LPHH1, calcium-independent alpha-latrotoxin receptor 2; latrophilin 1; latrophilin homolog 1; latrophilin homolog 2 (cow); lectomedin-1 | LPHN2 |

TABLE 2-continued

ARTERIORISKMARKERS

| ARTERIORISKMARKER | Official Name | Common Name | Gene Symbol |
|---|---|---|---|
| 531 | latrophilin 3 | secretin-type GPCR - CIRL3, LEC3, calcium-independent alpha-latrotoxin receptor 3; latrophilin homolog 3 (cow); lectomedin 3 | LPHN3 |
| 532 | lipoprotein lipase | LPL - LIPD | LPL |
| 533 | low density lipoprotein-related protein 1 (alpha-2-macroglobulin receptor) | lipoprotein receptor-related protein 1 (soluble (sLRP1) (alpha-2-macroglobulin receptor) - A2MR, APOER, APR, CD91; LRP, TGFBR5, alpha-2-macroglobulin receptor; low density lipoprotein-related protein 1; type V tgf-beta receptor | LRP1 |
| 534 | lymphotoxin alpha (TNF superfamily, member 1) | lymphotoxin alpha (TNF superfamily, member 1) - LT, TNFB, TNFSF1, lymphotoxin alpha; tumor necrosis factor beta | LTA |
| 535 | leukotriene B4 receptor | G-protein-coupled receptor LTB4 - BLT1, BLTR, CMKRL1, GPR16, LTB4R1, LTBR1, P2RY7, P2Y7, G protein-coupled receptor 16; chemokine receptor-like 1; purinergic receptor P2Y, G-protein coupled, 7 | LTB4R |
| 536 | mitogen-activated protein kinase kinase 2 | mitogen-activated protein kinase kinase 5 - MAPKK2, MEK2, MKK2, PRKMK2, ERK activator kinase 2; MAP kinase kinase 2; MAPK/ERK kinase 2; dual specificity mitogen-activated protein kinase kinase 2; mitogen-activated protein kinase kinase 2, p45, MAP2K5 polypeptide | MAP2K2 |
| 537 | mitogen-activated protein kinase kinase 3 | MKK3 - MAPKK3, MEK3, MKK3, PRKMK3, MAP kinase kinase 3; MAPK/ERK kinase 3; dual specificity mitogen activated protein kinase kinase 3 | MAP2K3 |
| 538 | mitogen-activated protein kinase kinase kinase 1 | mitogen activated protein kinase MAP3KX - MAPKKK1, MEKK, MEKK1, MAP/ERK kinase kinase 1; MAPK/ERK kinase kinase 1; MEK kinase 1 | MAP3K1 |
| 539 | mitogen-activated protein kinase kinase kinase 10 | mitogen-activated protein kinase kinase kinase 10 - MLK2, MST, MKN28 derived nonreceptor_type serine/threonine kinase; MKN28 kinase; mixed lineage kinase 2 | MAP3K10 |
| 540 | mitogen-activated protein kinase kinase kinase 11 | mitogen-activated protein kinase kinase kinase-11 - MLK-3, MLK3, PTK1, SPRK, SH3 domain-containing proline-rich kinase; mixed lineage kinase 3; protein-tyrosine kinase PTK1 | MAP3K11 |
| 541 | mitogen-activated protein kinase kinase kinase 13 | mitogen-activated protein kinase kinase kinase 13 - LZK, leucine zipper-bearing kinase | MAP3K13 |
| 542 | mitogen-activated protein kinase kinase kinase 2 | mitogen activated protein kinase MAP3KX - MEKK2, MEKK2B, MAP/ERK kinase kinase 2; MAPK/ERK kinase kinase 2; MEK kinase 2 | MAP3K2 |
| 543 | mitogen-activated protein kinase kinase kinase 3 | mitogen activated protein kinase MAP3KX - MAPKKK3, MEKK3, MAP/ERK kinase kinase 3; MAPK/ERK kinase kinase 3 | MAP3K3 |
| 544 | mitogen-activated protein kinase kinase kinase 5 | Mitogen Activated Protein Kinase Kinase Kinase 5 - ASK1, MAPKKK5, MEKK5, MAP/ERK kinase kinase 5; MAPK/ERK kinase kinase 5; apoptosis signal regulating kinase | MAP3K5 |
| 545 | mitogen-activated protein kinase kinase kinase 9 | mitogen-activated protein kinase kinase kinase 3 - MLK1, PRKE1, mixed lineage kinase 1 (tyr and ser/thr specificity) | MAP3K9 |
| 546 | mitogen-activated protein kinase 1 | p38 mitogen-activated protein kinase (MAPK)-ERK, ERK2, ERT1, MAPK2, P42MAPK, PRKM1, PRKM2, p38, p40, p41, p41mapk, extracellular signal-regulated kinase 2; mitogen-activated protein kinase 2; protein tyrosine kinase ERK2 | MAPK1 |
| 547 | mitogen-activated protein kinase 11 | p38 mitogen-activated protein kinase (MAPK) - P38B, P38BETA2, PRKM11, SAPK2, SAPK2B, p38-2, p38Beta, mitogen-activated protein kinase p38 beta; mitogen-activated protein kinase p38-2; stress-activated protein kinase-2; stress-activated protein kinase-2b | MAPK11 |
| 548 | mitogen-activated protein kinase 14 | p38 mitogen-activated protein kinase (MAPK) - CSBP1, CSBP2, CSPB1, EXIP, Mxi2, PRKM14, PRKM15, RK, SAPK2A, p38, p38ALPHA, Csaids binding protein; MAP kinase Mxi2; MAX-interacting protein 2; | MAPK14 |

TABLE 2-continued

ARTERIORISKMARKERS

| ARTERIORISKMARKER | Official Name | Common Name | Gene Symbol |
|---|---|---|---|
| | | cytokine suppressive anti-inflammatory drug binding protein; p38 MAP kinase; p38 mitogen activated protein kinase; p38alpha Exip; stress-activated protein kinase 2A | |
| 549 | microtubule-associated protein tau | tau protein-DDPAC, FTDP-17, MAPTL, MSTD, MTBT1, MTBT2, PPND, TAU, G protein beta1/gamma2 subunit-interacting factor 1; microtubule-associated protein tau, isoform 4; tau protein | MAPT |
| 550 | megakaryocyte-associated tyrosine kinase | megakaryocyte-associated tyrosine protein kinase - CHK, CTK, HHYLTK, HYL, HYLTK, Lsk, Csk-homologous kinase; Csk-type protein tyrosine kinase; HYL tyrosine kinase; hematopoietic consensus tyrosine-lacking kinase; hydroxyaryl-protein kinase; leukocyte carboxyl-terminal src kinase related gene; protein kinase HYL; tyrosine kinase MATK; tyrosine-protein kinase CTK; tyrosylprotein kinase | MATK |
| 551 | myoglobin | Myoglobin, PVALB | MB |
| 552 | myelin basic protein | myelin basic protein (MBP) | MBP |
| 553 | membrane-bound transcription factor peptidase, site 1 | subtilase-like serine protease - PCSK8, S1P, SKI-1, membrane-bound transcription factor protease, site 1; membrane-bound transcription factor site-1 protease; site-1 protease; subtilisin/kexin isozyme-1 | MBTPS1 |
| 554 | melanocortin 1 receptor (alpha melanocyte stimulating hormone receptor) | melanocortin 1 receptor - MSH-R, melanocortin 1 receptor; melanocyte stimulating hormone receptor; melanotropin receptor | MC1R |
| 555 | melanocortin 2 receptor (adrenocorticotropic hormone) | melanocortin-2 - ACTHR, ACTH receptor; MC2 receptor; adrenocorticotropic hormone receptor; corticotropin receptor; melanocortin 2 receptor | MC2R |
| 556 | melanocortin 3 receptor | G protein coupled receptor MC3 - MC3 | MC3R |
| 557 | melanocortin 4 receptor | G protein coupled receptor MC4 - | MC4R |
| 558 | melanocortin 5 receptor | G protein coupled receptor MC5 | MC5R |
| 559 | melanin-concentrating hormone receptor 1 | G Protein-Coupled Receptor 24 - GPR24, MCH1R, SLC1, G protein-coupled receptor 24; G-protein coupled receptor 24 isoform 1, GPCR24 | MCHR1 |
| 560 | Mdm2, transformed 3T3 cell double minute 2, p53 binding protein (mouse | MDM2 - hdm2, mouse double minute 2 homolog; mouse double minute 2, human homolog of; p53-binding protein; p53-binding protein MDM2; ubiquitin-protein ligase E3 Mdm2 | MDM2 |
| 561 | c-mer proto-oncogene tyrosine kinase | receptor tyrosine kinase MerTK - MER, c-mer, MER receptor tyrosine kinase; STK kinase | MERTK |
| 562 | methionyl aminopeptidase 1 | METHIONINE AMINOPEPTIDASE 1 (MetAP1) - | METAP1 |
| 563 | methionyl aminopeptidase 2 | methionine aminopeptidase 2 polypeptide - MNPEP, p67 | METAP2 |
| 564 | MLCK protein | MGC126319, MGC126320, MLCK2; cardiac-MyBP-C associated Ca/CaM kinase; myosin light chain kinase | MLCK |
| 565 | motilin receptor | G-protein-coupled receptor 38 - GPR38, MTLR1, G protein-coupled receptor 38 | MLNR |
| 566 | membrane metallo-endopeptidase (neutral endopeptidase, enkephalinase, CALLA, CD10) | neutral endopeptidase 24.11 (NEP) - CALLA, CD10, NEP, membrane metallo-endopeptidase; neprilysin | MME |
| 567 | matrix metallopeptidase 1 (interstitial collagenase) | matrix metalloproteinase-1 - CLG, CLGN, fibroblast collagenase; interstitial collagenase; matrix metalloprotease 1; matrix metalloproteinase 1; matrix metalloproteinase 1 (interstitial collagenase) | MMP1 |
| 568 | matrix metallopeptidase 11 (stromelysin 3) | SL-3, ST3, STMY3, matrix metalloproteinase 11; matrix metalloproteinase 11 (stromelysin 3); stromelysin 3; stromelysin III | MMP11 |
| 569 | matrix metallopeptidase 12 (macrophage elastase) | Matrix Metalloproteinases (MMP), HME, MME, macrophage elastase; macrophage metalloelastase; matrix metalloproteinase 12; matrix metalloproteinase 12 (macrophage elastase) | MMP12 |
| 570 | matrix metallopeptidase 14 (membrane-inserted) | Matrix Metalloproteinases (MMP), MMP-X1, MT1-MMP, MTMMP1, matrix metalloproteinase 14; matrix metalloproteinase 14 (membrane-inserted); membrane type 1 | MMP14 |

TABLE 2-continued

ARTERIORISKMARKERS

| ARTERIORISKMARKER | Official Name | Common Name | Gene Symbol |
|---|---|---|---|
| | | metalloprotease; membrane-type matrix metalloproteinase 1; membrane-type-1 matrix metalloproteinase | |
| 571 | matrix metallopeptidase 2 (gelatinase A, 72 kDa gelatinase, 72 kDa type IV collagenase) | Matrix Metalloproteinases (MMP), MMP-2, CLG4, CLG4A, MMP-II, MONA, TBE-1, 72 kD type IV collagenase; collagenase type IV-A; matrix metalloproteinase 2; matrix metalloproteinase 2 (gelatinase A, 72 kD gelatinase, 72 kD type IV collagenase); matrix metalloproteinase 2 (gelatinase A, 72 kDa gelatinase, 72 kDa type IV collagenase); matrix metalloproteinase-II; neutrophil gelatinase | MMP2 |
| 572 | matrix metallopeptidase 3 (stromelysin 1, progelatinase) | Matrix Metalloproteinases (MMP), SL-1, STMY, STMY1, STR1, matrix metalloproteinase 3; matrix metalloproteinase 3 (stromelysin 1, progelatinase); proteoglycanase; stromelysin 1; transin-1 | MMP3 |
| 573 | matrix metallopeptidase 9 (gelatinase B, 92 kDa gelatinase, 92 kDa type IV collagenase) | Matrix Metalloproteinases (MMP), MMP-9, CLG4B, GELB, 92 kD type IV collagenase; gelatinase B; macrophage gelatinase; matrix metalloproteinase 9; matrix metalloproteinase 9 (gelatinase B, 92 kD gelatinase, 92 kD type IV collagenase); matrix metalloproteinase 9 (gelatinase B, 92 kDa gelatinase, 92 kDa type IV collagenase); type V collagenase | MMP9 |
| 574 | marapsin 2 | marapsin - marapsin 2 | MPN2 |
| 575 | myeloperoxidase | Myeloperoxidase - myeloperoxidase | MPO |
| 576 | MAS-related GPR, member D | MAS-RELATED GENE - MRGD, TGR7, mas-related G protein-coupled MRGD | MRGPRD |
| 577 | MAS-related GPR, member E | Mas related G-protein coupled receptor E - GPR167, MRGE, G protein-coupled receptor 167; mas-related G protein-coupled MRGE | MRGPRE |
| 578 | MAS-related GPR, member F | human rta-like g protein-coupled receptor - mas related gene F, GPR140, GPR168, RTA, mrgF, G protein-coupled receptor 168; G protein-coupled receptor MrgF; seven transmembrane helix receptor | MRGPRF |
| 579 | MAS-related GPR, member X1 | Mas-related gene X1 - sensory neuron-specific G protein-coupled receptor 4, GPCR, MRGX1, SNSR4, G protein-coupled receptor MRGX1; G protein-coupled receptor SNSR3 | MRGPRX1 |
| 580 | MAS-related GPR, member X3 | Mas-related G-protein coupled receptor 3 - sensory neuron-specific G protein-coupled receptor 1, GPCR, MRGX3, SNSR1, G protein-coupled receptor MRGX3; G protein-coupled receptor SNSR1; G protein-coupled receptor SNSR2 | MRGPRX3 |
| 581 | 5,10-methylenetetrahydrofolate reductase (NADPH) | methylenetetrahydrofolate reductase - methylenetetrahydrofolate reductase intermediate form, red blood cell 5-methyltetrahydrofolate (RBC 5-MTHFR) - (MTHFR A1298C) mutation | MTHFR |
| 582 | melatonin receptor 1A | melatonin receptor type 1A - MEL-1A-R, melatonin receptor type 1A | MTNR1A |
| 583 | melatonin receptor 1B | melatonin receptor type 1B - MEL-1B-R, melatonin receptor MEL1B; melatonin receptor type 1B | MTNR1B |
| 584 | microsomal triglyceride transfer protein | microsomal triglyceride transfer protein - ABL, MTP, microsomal triglyceride transfer protein (large polypeptide, 88 kD); microsomal triglyceride transfer protein (large polypeptide, 88 kDa); microsomal triglyceride transfer protein large subunit | MTTP |
| 585 | mucin 16, cell surface associated | CA-125, CA125, CA125 ovarian cancer antigen; mucin 16 | MUC16 |
| 586 | myeloid differentiation primary response gene (88) | myeloid differentiation primary response gene | MYD88 |
| 587 | myosin, heavy polypeptide 11, smooth muscle | smooth muscle heavy chain - AAT4, FAA4, SMHC, SMMHC, smooth muscle myosin heavy chain 11 | MYH11 |
| 588 | myosin, heavy polypeptide 6, cardiac muscle, alpha (cardiomyopathy, hypertrophic 1) | myosin heavy chain, cardiac - ASD3, MYHC, MYHCA, alpha-MHC, alpha myosin heavy chain; alpha-myosin heavy chain; myosin heavy chain 6; myosin heavy chain, cardiac muscle alpha isoform | MYH6 |

TABLE 2-continued

ARTERIORISKMARKERS

| ARTERIORISKMARKER | Official Name | Common Name | Gene Symbol |
|---|---|---|---|
| 589 | myosin, heavy polypeptide 7, cardiac muscle, beta | myosin heavy chain, cardiac - CMD1S, CMH1, MPD1, MYHCB, beta-myosin heavy chain; myopathy, distal 1; myosin heavy chain (AA 1-96); rhabdomyosarcoma antigen MU-RMS-40.7A | MYH7 |
| 590 | myosin, heavy polypeptide 7B, cardiac muscle, beta | myosin heavy chain, cardiac - MYH14, U937-associated antigen; antigen MLAA-21; myosin heavy chain-like | MYH7B |
| 591 | myosin, light polypeptide 1, alkali; skeletal, fast | myosin light chain I, cardiac - MLC1F, MLC3F, A1 catalytic; A2 catalytic; fast skeletal myosin alkali light chain 1 | MYL1 |
| 592 | myosin, light polypeptide 2, regulatory, cardiac, slow | myosin light chain II, cardiac - CMH10, MLC2, myosin light chain 2 | MYL2 |
| 593 | myocardin | myocardin - MYCD | MYOCD |
| 594 | folate hydrolase (prostate-specific membrane antigen) 1 | N-acetylated alpha-linked acidic dipeptidase 2 - FGCP, FOLH, GCP2, GCPII, NAALAD1, NAALAdase, PSM, PSMA, mGCP, N-acetylated alpha-linked acidic dipeptidase 1; folate hydrolase 1; folylpoly-gamma-glutamate carboxypeptidase; glutamate carboxylase II; glutamate carboxypeptidase II; membrane glutamate carboxypeptidase; prostate-specific membrane antigen; pteroylpoly-gamma-glutamate carboxypeptidase | NAALAD2 |
| 595 | N-acetylated alpha-linked acidic dipeptidase-like 1 | N-acetylated alpha-linked acidic dipeptidase-like 1 - I100, NAALADASEL, 100 kDa ileum brush border membrane protein; N-acetylated alpha-linked acidic dipeptidase-like; ileal dipeptidylpeptidase | NAALADL1 |
| 596 | NGFI-A binding protein 1 (EGR1 binding protein 1) | NGFI-A-binding protein - EGR1 binding protein 1; NGFI-A binding protein 1; NGFI-A-binding protein 1 | NAB1 |
| 597 | NGFI-A binding protein 2 (EGR1 binding protein 2) | MADER, EGR1 binding protein 2; NGFI-A binding protein 2; NGFIA-binding protein-2; melanoma-associated delayed early response protein | NAB2 |
| 598 | napsin A aspartic peptidase | napsin 1 - KAP, Kdap, NAP1, NAPA, SNAPA, napsin A; pronapsin A | NAPSA |
| 599 | neural cell adhesion molecule 1 | VCAM-1 - neural cell adhesion molecule 1, CD56, MSK39, NCAM, antigen recognized by monoclonal antibody 5.1H11; neural cell adhesion molecule, NCAM | NCAM1 |
| 600 | NADH dehydrogenase (ubiquinone) 1 alpha subcomplex, 2, 8 kDa | CD14 (C-260T polymorphism) entered "CD14", B8, CD14, NADH dehydrogenase (ubiquinone) 1 alpha subcomplex, 2 (8 kD, B8) | NDUFA2 |
| 601 | NIMA (never in mitosis gene a)-related kinase 1 | serine/threonine protein kinase NEK1 - NY-REN-55, protein-serine/threonine kinase gene; serine/threonine-protein kinase Nek1 | NEK1 |
| 602 | NIMA (never in mitosis gene a)-related kinase 3 | never in mitosis gene A-related kinase 3 polypeptide - HSPK36, NIMA-related kinase 3; glycogen synthase A kinase; hydroxyalkyl-protein kinase; phosphorylase B kinase kinase; serine/threonine-protein kinase NEK3 | NEK3 |
| 603 | NIMA (never in mitosis gene a)- related kinase 8 | NEK-like serine/threonine kinase - JCK, NEK12A, NIMA-family kinase NEK8; NIMA-related kinase 12a; NIMA-related kinase 8; serine/thrionine-protein kinase NEK8 | NEK8 |
| 604 | nerve growth factor, beta polypeptide | B-type neurotrophic growth factor (BNGF) - beta-nerve growth factor; nerve growth factor, beta subunit | NGFB |
| 605 | neuromedin B receptor | Neuromedin B Receptor - | NMBR |
| 606 | neuromedin U receptor 1 | Neuromedin U 1 receptor - (FM-3), FM-3, GPC-R, GPR66, NMU1R, G protein-coupled receptor 66 | NMUR1 |
| 607 | neuromedin U receptor 2 | neuromedin U2 receptor - FM4, NMU2R | NMUR2 |
| 608 | nitric oxide synthase 2A (inducible, hepatocytes) | inducible nitric oxide synthase - HEP-NOS, INOS, NOS, NOS2, NOS, type II; nitric oxide synthase 2A; nitric oxide synthase, macrophage | NOS2A |
| 609 | nitric oxide synthase 3 (endothelial cell) | 393 ecNOS allele/missense Glu298Asp variant of endothelial nitric oxide synthase gene/T(−786)--> C mutation in the 5'-flanking region of the endothelial nitric oxide synthase gene - ECNOS, NOS III, eNOS, endothelial nitric oxidase synthase; endothelia | NOS3 |

TABLE 2-continued

ARTERIORISKMARKERS

| ARTERIORISKMARKER | Official Name | Common Name | Gene Symbol |
|---|---|---|---|
| 610 | NADPH oxidase 1 | NAD(P)H oxidase - GP91-2, MOX1, NOH-1, NOH1, NADPH oxidase homolog-1; mitogenic oxidase (pyridine nucleotide-dependent superoxide-generating) | NOX1 |
| 611 | NADPH oxidase 3 | NAD(P)H oxidase - GP91-3 - NADPH oxidase catalytic subunit-like 3 | NOX3 |
| 612 | NAD(P)H oxidase - NADPH oxidase 4 | NAD(P)H oxidase - KOX, KOX-1, RENOX | NOX4 |
| 613 | NADPH oxidase, EF-hand calcium binding domain 5 | NAD(P)H oxidase - NOX5A, NOX5B, NADPH oxidase, EF hand calcium-binding domain 5 | NOX5 |
| 614 | neuropeptides B/W receptor 1 | G protein-coupled receptor 7 - GPR7, G protein-coupled receptor 7; neuropeptides B/W receptor type 1; opioid-somatostatin-like receptor 7 | NPBWR1 |
| 615 | neuropeptides B/W receptor 2 | G-protein coupled receptor 8 - GPR8, G protein-coupled receptor 8; opioid-somatostatin-like receptor 8 | NPBWR2 |
| 616 | aminopeptidase-like 1 | aminopeptidase-like 1 - | NPEPL1 |
| 617 | aminopeptidase puromycin sensitive | puromycin sensitive aminopeptidase - MP100, PSA, metalloproteinase MP100; puromycin-sensitive aminopeptidase | NPEPPS |
| 618 | neuropeptide FF receptor 1 | neuropeptide FF receptor 1 - GPR147, NPFF1, NPFF1R1, OT7T022, G protein-coupled receptor 147 | NPFFR1 |
| 619 | neuropeptide FF receptor 2 | neuropeptide FF receptor 2 - GPR74, NPFF2, NPGPR, G protein-coupled receptor 74; neuropeptide FF 2; neuropeptide G protein-coupled receptor | NPFFR2 |
| 620 | natriuretic peptide precursor A | atrial naturetic peptide (ANP) - ANF, ANP, CDD-ANF, PND, atrial natriuretic peptide; pronatriodilatin, natriuretic peptide, atrial, N-terminal (N-ANP), natriuretic peptide, atrial, propeptide (31-67) | NPPA |
| 621 | natriuretic peptide precursor B | B-type Natriuretic Peptide (BNP), BNP, brain type natriuretic peptide, natriuretic protein, natriuretic peptide, brain, N-terminal (NT-BNP), natriuretic peptide, brain, pro-form (proBNP) | NPPB |
| 622 | natriuretic peptide precursor C | natriuretic peptide, atrial C-terminal (C-ANP) - CNP, C-type natriuretic precursor | NPPC |
| 623 | natriuretic peptide receptor A/guanylate cyclase A (atrionatriuretic peptide receptor A) | natriuretic peptide receptor A - ANPRA, ANPa, GUC2A, GUCY2A, NPRA Other Designations: natriuretic peptide A type receptor | NPR1 |
| 624 | neuropeptide Y receptor Y1 | G Protein-Coupled Receptor NPY1 - NPYR, modulator of neuropeptide Y receptor | NPY1R |
| 625 | neuropeptide Y receptor Y2 | G Protein-Coupled Receptor NPY2 - | NPY2R |
| 626 | nuclear receptor subfamily 0, group B, member 2 | Nuclear Receptor Subfamily O. Group B.' Member 2 (NR0B2) - SHP, SHP1, orphan nuclear receptor SHP; short heterodimer partner; small heterodimer partner | NR0B2 |
| 627 | nuclear receptor subfamily 1, group D, member 1 | Human Nuclear Receptor NR1D1 - EAR1, THRA1, THRAL, ear-1, hRev, Rev-erb-alpha; thyroid hormone receptor, alpha-like | NR1D1 |
| 628 | nuclear receptor subfamily 1, group H, member 2 | Liver X Receptor Beta - LXR-b, LXRB, NER, NER-I, RIP15, UNR, LX receptor beta; liver X receptor beta; nuclear orphan receptor LXR-beta; oxysterols receptor LXR-beta; steroid hormone-nuclear receptor NER; ubiquitously-expressed nuclear receptor | NR1H2 |
| 629 | nuclear receptor subfamily 1, group H, member 3 | LXR-alpha - LXR-a, LXRA, RLD-1, liver X receptor, alpha | NR1H3 |
| 630 | nuclear receptor subfamily 1, group H, member 4 | nuclear receptor subfamily 1, group H, member 4 - BAR, FXR, HRR-1, HRR1, RIP14, farnesoid X receptor | NR1H4 |
| 631 | nuclear receptor subfamily 2, group E, member 1 | nuclear receptor subfamily 2, group E member 1 - TLL, TLX, XTLL, tailless (Drosophila) homolog; tailless homolog (Drosophila) | NR2E1 |
| 632 | nuclear receptor subfamily 3, group C, member 2 | NR3C2, MCR, MLR, MR, mineralocorticoid receptor (aldosterone receptor) | NR3C2 |
| 633 | nuclear receptor subfamily 4, group A, member 1 | Nuclear Receptor NR4A1 - GFRP1, HMR, N10, NAK-1, NGFIB, NP10, NUR77, TR3, TR3 orphan receptor; early response protein NAK1; growth factor-inducible nuclear protein N10; hormone receptor; orphan nuclear receptor HMR; steroid receptor TR3 | NR4A1 |
| 634 | nuclear receptor subfamily 4, group A, member 2 | Nuclear Receptor NR4A2 - HZF-3, NOT, NURR1, RNR1, TINUR, NGFI-B/nur77 beta-type transcription factor homolog; T-cell nuclear | NR4A2 |

TABLE 2-continued

ARTERIORISKMARKERS

| ARTERIORISKMARKER | Official Name | Common Name | Gene Symbol |
|---|---|---|---|
| | | receptor NOT; intermediate-early receptor protein; nur related protein-1 (mouse), human homolog of; orphan nuclear receptor NURR1; transcriptionally inducible nuclear receptor related 1 | |
| 635 | nuclear receptor subfamily 4, group A, member 3 | Nuclear Receptor NR4A3 - CHN, CSMF, MINOR, NOR1, TEC, chondrosarcoma, extraskeletal myxoid, fused to EWS; mitogen induced nuclear orphan receptor; neuron derived orphan receptor; translocated in extraskeletal chondrosarcoma | NR4A3 |
| 636 | nuclear receptor subfamily 5, group A, member 1 | nuclear receptor subfamily 5, group A, member 1 - AD4BP, ELP, FTZ1, FTZF1, SF-1, SF1, fushi tarazu factor (*Drosophila*) homolog 1; nuclear receptor AdBP4; steroidogenic factor 1 | NR5A1 |
| 637 | neutral sphingomyelinase 3 | Sphingomyelinase | NSMASE3 |
| 638 | neurotrophic tyrosine kinase, receptor, type 1 | neurotrophin receptor - MTC, TRK, TRK1, TRKA, p140-TrkA, Oncogene TRK; high affinity nerve growth factor receptor; tyrosine kinase receptor; tyrosine kinase receptor A | NTRK1 |
| 639 | neurotrophic tyrosine kinase, receptor, type 2 | neurotrophin receptor - GP145-TrkB, TRKB, BDNF/NT-3 growth factors receptor; tyrosine kinase receptor B | NTRK2 |
| 640 | neurotrophic tyrosine kinase, receptor, type 3 | neurotrophin receptor - TRKC, gp145(trkC), NT-3 growth factor receptor; neurotrophin 3 receptor; tyrosine kinase receptor C | NTRK3 |
| 641 | neurotensin receptor 1 (high affinity) | Neurotensin Receptor 1 - NTR, neurotensin receptor 1 | NTSR1 |
| 642 | ornithine decarboxylase 1 | ornithindecarboxylase | ODC1 |
| 643 | oxidised low density lipoprotein (lectin-like) receptor 1 | lectin-like oxidized low-density lipoprotein receptor (LOX-1), CLEC8A, LOX1, SCARE1, lectin-type oxidized LDL receptor 1; scavenger receptor class E, member 1 | OLR1 |
| 644 | opioid receptor, delta 1 | G-protein coupled opioid receptor delta 1 - OPRD | OPRD1 |
| 645 | opioid receptor, kappa 1 | G protein-coupled opioid receptor kappa 1 - KOR, OPRK, Opiate receptor, kappa-1; kappa opioid receptor | OPRK1 |
| 646 | orosomucoid 1 | orosomucoid (alpha(1)-acid glycoprotein), AGP-A, AGP1, ORM, Orosomucoid-1 (alpha-1-acid glycoprotein-1); alpha-1-acid glycoprotein 1 | ORM1 |
| 647 | orosomucoid 2 | α1-acid glycoprotein: alpha-1-acid glycoprotein, type 2 | ORM2 |
| 648 | oncostatin M | oncostatin M - | OSM |
| 649 | oxoeicosanoid (OXE) receptor 1 | G Protein Coupled Receptor TG1019 - GPCR, GPR170, TG1019, 5-oxo-ETE acid G-protein-coupled receptor 1; G-protein coupled receptor TG1019 | OXER1 |
| 650 | oxytocin receptor | Oxytocin Receptor - OT-R | OXTR |
| 651 | purinergic receptor P2Y, G-protein coupled, 1 | Purinoceptor 2 Type Y - P2Y1, ATP receptor; P2 purinoceptor subtype Y1; P2Y purinoceptor 1; platelet ADP receptor; purinergic receptor P2Y1 | P2RY1 |
| 652 | purinergic receptor P2Y, G-protein coupled, 10 | G Protein Coupled Receptor P2Y10 - P2Y10, G-protein coupled purinergic receptor P2Y10; P2Y purinoceptor 10; P2Y-like receptor | P2RY10 |
| 653 | purinergic receptor P2Y, G-protein coupled, 11 | G Protein-Coupled Receptor P2Y11 - P2Y11, P2Y purinoceptor 11; P2Y11 receptor; purinergic receptor P2Y11 | P2RY11 |
| 654 | purinergic receptor P2Y, G-protein coupled, 12 | G Protein-Coupled Receptor P2Y12 - ADPG-R, HORK3, P2T(AC), P2Y(AC), P2Y(ADP), P2Y(cyc), P2Y12, SP1999, ADP-glucose receptor; G-protein coupled receptor SP1999; Gi-coupled ADP receptor HORK3; P2Y purinoceptor 12; platelet ADP receptor; purinergic receptor P2RY12; purinergic receptor P2Y, G-protein coupled 12; purinergic receptor P2Y12; putative G-protein coupled receptor | P2RY12 |
| 655 | purinergic receptor P2Y, G-protein coupled, 13 | G Protein-Coupled Receptor 86-FKSG77, GPCR1, GPR86, GPR94, P2Y13, SP174, G protein-coupled receptor 86 | P2RY13 |

TABLE 2-continued

ARTERIORISKMARKERS

| ARTERIORISKMARKER | Official Name | Common Name | Gene Symbol |
|---|---|---|---|
| 656 | purinergic receptor P2Y, G-protein coupled, 2 | Purinoceptor 2 Type Y (P2Y2) - HP2U, P2RU1, P2U, P2U1, P2UR, P2Y2, P2Y2R, ATP receptor; P2U nucleotide receptor; P2U purinoceptor 1; P2Y purinoceptor 2; purinergic receptor P2Y2; purinoceptor P2Y2 | P2RY2 |
| 657 | pyrimidinergic receptor P2Y, G-protein coupled, 4 | Purinoceptor 4 Type Y (P2Y4) - NRU, P2P, P2Y4, UNR, C381P2Y purinoceptor 4; pyrimidinergic receptor P2Y4; uridine nucleotide receptor | P2RY4 |
| 658 | purinergic receptor P2Y, G-protein coupled, 5 | Purinoceptor 5 Type Y (P2Y5) - P2Y5, G-protein coupled purinergic receptor P2Y5; P2Y purinoceptor 5; RB intron encoded G-protein coupled receptor; purinergic receptor 5 | P2RY5 |
| 659 | pyrimidinergic receptor P2Y, G-protein coupled, 6 | G protein-Coupled P2Y Purinoreceptor 6 - P2Y6, G-coupled nucleotide receptor; P2 purinoceptor; P2Y purinoceptor 6; P2Y6 receptor; pyrimidinergic receptor P2Y6 | P2RY6 |
| 660 | procollagen-proline, 2-oxoglutarate 4-dioxygenase (proline 4-hydroxylase), alpha polypeptide II | prolyl 4-hydroxylase alpha-2 subunit - 4-PH alpha 2, prolyl 4-hydroxylase, alpha II subunit | P4HA2 |
| 661 | platelet-activating factor acetylhydrolase, isoform Ib, alpha subunit 45 kDa | Platelet-activating factor acetylhydrolase (PAF-AH), LIS1, LIS2, MDCR, PAFAH, Platelet-activating factor acetylhydrolase, isoform 1B, alpha subunit; lissencephaly 1 protein; platelet-activating factor acetylhydrolase, alpha subunit (45 kD) | PAFAH1B1 |
| 662 | platelet-activating factor acetylhydrolase 2, 40 kDa | Platelet-activating factor acetylhydrolase (PAF-AH), HSD-PLA2, platelet-activating factor acetylhydrolase 2; platelet-activating factor acetylhydrolase 2 (40 kD) | PAFAH2 |
| 663 | p21/Cdc42/Rac1-activated kinase 1 (STE20 homolog, yeast) | P21/CDC42/RAC1-activated kinase 1 - PAKalpha, p21-activated kinase 1; p21/Cdc42/Rac1-activated kinase 1 (yeast Ste20-related) | PAK1 |
| 664 | p21 (CDKN1A)-activated kinase 2 | P21/CDC42/RAC1-activated kinase 1 - PAK65, PAKgamma, S6/H4 kinase; p21-activated kinase 2 | PAK2 |
| 665 | p21 (CDKN1A)-activated kinase 3 | CDKN1A, MRX30, MRX47, OPHN3, PAK3beta, bPAK, hPAK3, oligophrenin-3; p21-activated kinase 3; p21-activated kinase-3 | PAK3 |
| 666 | pregnancy-associated plasma protein A, pappalysin 1 | Pregnancy-associated plasma protein a - ASBABP2, DIPLA1, IGFBP-4ase, PAPA, PAPP-A, PAPPA1, aspecific BCL2 ARE-binding protein 2; differentially placenta 1 expressed protein; insulin-like growth factor-dependent IGF binding protein-4 protease; pregnacy-associated plasma protein A; pregnancy-associated plasma protein A | PAPPA |
| 667 | progestin and adipoQ receptor family member V | steroid progestin receptor gamma - MPRG - membrane progestin receptor gamma | PAQR5 |
| 668 | progestin and adipoQ receptor family member VII | steroid progestin receptor alpha - MPRA, mSR, membrane progestin receptor alpha | PAQR7 |
| 669 | progestin and adipoQ receptor family member VIII | steroid progestin receptor beta - C6orf33, LMPB1, MPRB, lysosomal membrane protein in brain-1; membrane progestin receptor beta | PAQR8 |
| 670 | poly (ADP-ribose) polymerase family, member 1 | poly(ADP-ribose) polymerase - ADPRT, ADPRT1, PARP, PARP-1, PPOL, pADPRT-1, ADP-ribosyltransferase (NAD+; poly (ADP-ribose) polymerase); ADP-ribosyltransferase NAD(+); poly(ADP-ribose) polymerase; poly(ADP-ribose) synthetase; poly(ADP-ribosyl)transferase | PARP1 |
| 671 | poly (ADP-ribose) polymerase family, member 2 | poly(ADP-ribose) polymerase - ADPRT2, ADPRTL2, ADPRTL3, PARP-2, pADPRT-2, ADP-ribosyltransferase (NAD+; poly(ADP-ribose) polymerase)-like 2; poly (ADP-ribosyl) transferase-like 2; poly(ADP-ribose) synthetase | PARP2 |
| 672 | poly (ADP-ribose) polymerase family, member 3 | poly(ADP-ribose) polymerase - ADPRT3, ADPRTL2, ADPRTL3, IRT1, hPARP-3, pADPRT-3, ADP-ribosyltransferase (NAD+; poly (ADP-ribose) polymerase)-like 2; ADP-ribosyltransferase (NAD+; poly (ADP-ribose) polymerase)-like 3; NAD+ ADP-ribosyltransferase 3; poly(ADP-ribose) polymerase 3; poly(ADP-ribose) synthetase-3 | PARP3 |

TABLE 2-continued

ARTERIORISKMARKERS

| ARTERIORISKMARKER | Official Name | Common Name | Gene Symbol |
|---|---|---|---|
| 673 | poly (ADP-ribose) polymerase family, member 4 | poly(ADP-ribose) polymerase - ADPRTL1, PARPL, PH5P, VAULT3, VPARP, p193, ADP-ribosyltransferase (NAD+; poly (ADP-ribose) polymerase)-like 1; H5 proline-rich; I-alpha-I-related; PARP-related; poly(ADP-ribose) synthetase; poly(ADP-ribosyl)transferase-like 1; vault protein, 193-kDa | PARP4 |
| 674 | proliferating cell nuclear antigen | PCNA - DNA polymerase delta auxiliary protein; cyclin | PCNA |
| 675 | proprotein convertase subtilisin/kexin type 9 | PCSK9 gene or in the NARC-1 - FH3, HCHOLA3, NARC-1, NARC1, hypercholesterolemia, autosomal dominant 3; neural apoptosis regulated convertase 1 | PCSK9 |
| 676 | phosphodiesterase 10A | phosphodiesterase 10A - HSPDE10A, (phosphodiesterase 10A); phosphodiesterase 10A1 (PDE10A1) | PDE10A |
| 677 | phosphodiesterase 11A | phosphodiesterase 11A1 - PDE11A1, cyclic nucleotide phosphodiesterase 11A1; phosphodiesterase 11A1; phosphodiesterase 11A3 | PDE11A |
| 678 | phosphodiesterase 1A, calmodulin-dependent | phosphodiesterase 1A - HCAM1, HSPDE1A, 3',5' cyclic nucleotide phosphodiesterase; calcium/calmodulin-stimulated cyclic nucleotide phosphodiesterase; calmodulin-dependent phosphodiesterase; phosphodiesterase-1A | PDE1A |
| 679 | phosphodiesterase 1B, calmodulin-dependent | phosphodiesterase 1B - PDE1B1, PDES1B, Phosphodiesterase-1B; calcium/calmodulin-stimulated cyclic nucleotide phosphodiesterase; calmodulin-stimulated phosphodiesterase PDE1B1; phosphodiesterase 1B; phosphodiesterase 1B, calmodulin-dependent; presumed 63 kDa form of the type 1 cyclic nucleotide phosphodiesterase family known as PDE1B | PDE1B |
| 680 | phosphodiesterase 1C, calmodulin-dependent 70 kDa | phosphodiesterase 1C - Hcam3, Human 3',5' cyclic nucleotide phosphodiesterase (HSPDE1C1A); phosphodiesterase 1C, calmodulin-dependent (70 kD) | PDE1C |
| 681 | phosphodiesterase 3A, cGMP-inhibited | phosphodiesterase 3A - CGI-PDE, cGMP-inhibited 3',5'-cyclic phosphodiesterase A; cyclic GMP inhibited phosphodiesterase A | PDE3A |
| 682 | phosphodiesterase 3B, cGMP-inhibited | phosphodiesterase 3 B - cGIPDE1, cyclic nucleotide phosphodiesterase | PDE3B |
| 683 | phosphodiesterase 4A, cAMP-specific (phosphodiesterase E2 dunce homolog, Drosophila) | phosphodiesterase 4A - DPDE2, PDE4, Phosphodiesterase-4A, cAMP-specific (dunce (Drosophila)-homolog; cAMP-specific phosphodiesterase; cyclic AMP phosphodiesterase PDE4A11; cyclic AMP-specific phosphodiesterase HSPDE4A10; phosphodiesterase 4A, cAMP-specific (dunce (Drosophila)-homolog phosphodiesterase E2); phosphodiesterase isozyme 4 | PDE4A |
| 684 | phosphodiesterase 4B, cAMP-specific (phosphodiesterase E4 dunce homolog, Drosophila) | phosphodiesterase 4B - DPDE4, PDEIVB, cAMP-specific 3',5'-cyclic phosphodiesterase 4B; dunce-like phosphodiesterase E4; phosphodiesterase 4B, cAMP-specific; phosphodiesterase 4B, cAMP-specific (dunce (Drosophila)-homolog phosphodiesterase E4) | PDE4B |
| 685 | phosphodiesterase 4C, cAMP-specific (phosphodiesterase E1 dunce homolog, Drosophila) | phosphodiesterase 4C - DPDE1, ISOFORM OF CAMP-DEPENDENT 3',5'-CYCLIC PHOSPHODIESTERASE 4C; PDE4C [amino acids 597-712]; PDE4C-delta54, cAMP-specific (dunce (Drosophila)-homolog; dunce (Drosophila)-homolog phosphodiesterase E1; phosphodiesterase 4C, cAMP-specific (dunce (Drosophila)-homolog phosphodiesterase E1) | PDE4C |
| 686 | phosphodiesterase 4D, cAMP-specific (phosphodiesterase E3 dunce homolog, Drosophila) | phosphodiesterase 4D - DPDE3, HSPDE4D, PDE4DN2, STRK1, cAMP-specific phosphodiesterase 4D; cAMP-specific phosphodiesterase PDE4D6; dunce-like phosphodiesterase E3; phosphodiesterase 4D, cAMP-specific (dunce (Drosophila)-homolog phosphodiesterase E3) | PDE4D |

TABLE 2-continued

ARTERIORISKMARKERS

| ARTERIORISKMARKER | Official Name | Common Name | Gene Symbol |
|---|---|---|---|
| 687 | phosphodiesterase 6B, cGMP-specific, rod, beta (congenital stationary night blindness 3, autosomal dominant) | PHOSPHODIESTERASE 6B - CSNB3, PDEB, phosphodiesterase 6B, cGMP-specific, rod, beta | PDE6B |
| 688 | phosphodiesterase 6C, cGMP-specific, cone, alpha prime | phosphodiesterase PDE6C - PDEA2 | PDE6C |
| 689 | phosphodiesterase 7A | phosphodiesterase 7a1 - HCP1, PDE7, phosphodiesterase isozyme 7 | PDE7A |
| 690 | phosphodiesterase 7B | phosphodiesterase 7b - high-affinity cAMP-specific 3',5'-cyclic phosphodiesterase; rolipram-insensitive phosphodiesterase type 7 | PDE7B |
| 691 | phosphodiesterase 8A | phosphodiesterase 8A - HsT19550, cAMP-specific cyclic nucleotide phosphodiesterase 8A; high-affinity cAMP-specific and IBMX-insensitive 3',5'-cyclic phosphodiesterase 8A | PDE8A |
| 692 | phosphodiesterase 8B | phosphodiesterase 8B - 3',5' cyclic nucleotide phosphodiesterase 8B | PDE8B |
| 693 | phosphodiesterase 9A | PHOSPHODIESTERASE 9A1 - HSPDE9A2, CGMP-specific 3',5'-cyclic phosphodiesterase type 9; phosphodiesterase PDE9A21 | PDE9A |
| 694 | platelet-derived growth factor alpha polypeptide | platelet derived growth factor (PDGF-alpha): PDGF A-chain; platelet-derived growth factor alpha; platelet-derived growth factor alpha chain | PDGFA |
| 695 | platelet-derived growth factor beta polypeptide (simian sarcoma viral (v-sis) oncogene homolog | Platelet-derived growth factor beta polypeptide - PDGF2, SIS, SSV, c-sis, HUMANES PDGF-B GEN AUS PGEM2-PDGF-B, PDGF, B chain; PDGF-B VORLAEUFERSEQUENZ; Platelet-derived growth factor, beta polypeptide (oncogene SIS); becaplermin; oncogene SIS; platelet-derived growth factor 2; platelet-derived growth factor beta; platelet-derived growth factor, B chain; v-sis platelet-derived growth factor beta polypeptide (simian sarcoma viral oncogene homolog) | PDGFB |
| 696 | platelet-derived growth factor beta polypeptide (simian sarcoma viral (v-sis) oncogene homolog) | Platelet-derived growth factor beta polypeptide - PDGF2, SIS, SSV, c-sis, HUMANES PDGF-B GEN AUS PGEM2-PDGF-B, PDGF, B chain; PDGF-B VORLAEUFERSEQUENZ; Platelet-derived growth factor, beta polypeptide (oncogene SIS); becaplermin; oncogene SIS; platelet-derived growth factor 2; platelet-derived growth factor beta; platelet-derived growth factor, B chain; v-sis platelet-derived growth factor beta polypeptide (simian sarcoma viral oncogene homolog) | PDGFB |
| 697 | platelet-derived growth factor beta polypeptide (simian sarcoma viral (v-sis) oncogene homolog) | platelet-derived growth factor beta polypeptide (simian sarcoma viral (v-sis) oncogene homolog), FLJ12858, PDGF2, SIS, SSV, c-sis, HUMANES PDGF-B GEN AUS PGEM2-PDGF-B, FLANKIERT VON 5'-ECORI UND 3'-HINDIII RESTRIKTIONSSCHNITTSTELLEN; PDGF, B chain; PDGF-B VORLAEUFERSEQUENZ; Platelet-derived growth factor, beta polypeptide (oncogene SIS); becaplermin; oncogene SIS; platelet-derived growth factor 2; platelet-derived growth factor beta; platelet-derived growth factor, B chain; v-sis platelet-derived growth factor beta polypeptide (simian sarcoma viral oncogene homolog) | PDGFB |
| 698 | platelet-derived growth factor receptor, alpha polypeptide | platelet derived growth factor PDGF-alpha receptor | PDGFRA |
| 699 | platelet-derived growth factor receptor, beta polypeptide | platelet derived growth factor PDGF-beta receptor - CD140B, JTK12, PDGF-R-beta, PDGFR, PDGFR1 beta platelet-derived growth factor receptor; platelet-derived growth factor receptor beta | PDGFRB |
| 700 | pyruvate dehydrogenase kinase, isozyme 1 | pyruvate dehydrogenase kinase 1 (PDK1) - mitochondrial pyruvate dehydrogenase kinase isoenzyme 1; pyruvate dehydrogenase kinase, isoenzyme 1 | PDK1 |
| 701 | pyruvate dehydrogenase kinase, isozyme 2 | pyruvate dehydrogenase kinase 2 (PDK2) - pyruvate dehydrogenase kinase, isoenzyme 2 | PDK2 |
| 702 | pyruvate dehydrogenase kinase, isozyme 3 | pyruvate dehydrogenase kinase 3 (PDK3) - pyruvate dehydrogenase kinase, isoenzyme 3 | PDK3 |

TABLE 2-continued

ARTERIORISKMARKERS

| ARTERIORISKMARKER | Official Name | Common Name | Gene Symbol |
|---|---|---|---|
| 703 | pyruvate dehydrogenase kinase, isozyme 4 + A4 | pyruvate dehydrogenase kinase 1 (PDK1) - pyruvate dehydrogenase kinase 4; pyruvate dehydrogenase kinase, isoenzyme 4 | PDK4 |
| 704 | platelet/endothelial cell adhesion molecule (CD31 antigen) | circulating CD31+ apoptotic microparticles in peripheral blood, (Entered CD31 into Entrez), CD31, PECAM-1, CD31/EndoCAM; PECAM-1, CD31/EndoCAM; adhesion molecule | PECAM1 |
| 705 | proenkephalin | proenkephalin (no "other" names listed than official name) | PENK |
| 706 | peptidase D | X-pro dipeptidase - PROLIDASE, Xaa-Pro dipeptidase; proline dipeptidase | PEPD |
| 707 | platelet factor 4 (chemokine (C-X-C motif) ligand 4) | platelet factor 4 (PF4) - CXCL4, SCYB4 | PF4 |
| 708 | phosphoglycerate mutase family member 4 | phosphoglycerate mutase (PGM) B-type - PGAM-B, PGAM3, phosphoglycerate mutase family 3; phosphoglycerate mutase family 4; phosphoglycerate mutase processed protein | PGAM4 |
| 709 | plasma glutamate carboxypeptidase | plasma glutamate carboxypeptidase - aminopeptidase | PGCP |
| 710 | placental growth factor, vascular endothelial growth factor-related protein | placental growth factor - PLGF, PlGF-2 | PGF |
| 711 | serum placental growth factor | Placenta growth factor [Precursor], PlGF, PLGF | PGF |
| 712 | phosphate regulating endopeptidase homolog, X-linked (hypophosphatemia, vitamin D resistant rickets) | phosphate regulating endopeptidase homolog - HPDR, HPDR1, HYP, HYP1, PEX, XLH, X-linked phosphate regulating endopeptidase homolog; phosphate regulating gene with homologies to endopeptidases on the X chromosome; phosphate regulating gene with homologies to endopeptidases on the X chromosome (hypophosphatemia, vitamin D resistant rickets) | PHEX |
| 713 | phospholipase A2, group VII (platelet-activating factor acetylhydrolase, plasma) | lipoprotein-associated phospholipase A2 (Lp-PLA2) (associated with coronary endothelial dysfunction). LDL-PLA2, PAFAH, phospholipase A2, group VII; platelet-activating factor acetylhydrolase | PLA2G7 |
| 714 | plasminogen activator, tissue | tissue Plasminogen Activator (tPA), T-PA, TPA, alteplase; plasminogen activator, tissue type; reteplase; t-plasminogen activator; tissue plasminogen activator (t-PA) | PLAT |
| 715 | phospholipase C, beta 1 (phosphoinositide-specific) | Phosphoinositide-specific-phospholipase-B1: 1-phosphatidyl-D-myo-inositol-4,5-bisphosphate; 1-phosphatidylinositol-4,5-bisphosphate phosphodiesterase beta 1; PLC-beta-1; inositoltrisphosphohydrolas | PLCB1 |
| 716 | phospholipase C-like 1 | phospholipase C-like protein - PLC-L, PLCE, PLCL, PLDL1, phospholipase C, epsilon | PLCL1 |
| 717 | phospholipase C-like 2 | phospholipase C-like protein - KIAA1092, PLCE2, phospholipase C, epsilon 2 | PLCL2 |
| 718 | plasminogen | plasminogen - covering first half of fourth kringle | PLG |
| 719 | phospholamban | phospholamban - CMD1P, PLB, cardiac phospholamban | PLN |
| 720 | proopiomelanocortin (adrenocorticotropin/beta-lipotropin/alpha-melanocyte stimulating hormone/beta-melanocyte stimulating hormone/beta-endorphin) | proopiomelanocortin - beta-LPH; beta-MSH; alpha-MSH; gamma-LPH; gamma-MSH; corticotropin; beta-endorphin; met-enkephalin; lipotropin beta; lipotropin gamma; melanotropin beta; N-terminal peptide; melanotropin alpha; melanotropin gamma; pro-ACTH-endorphin; adrenocorticotropin; pro-opiomelanocortin; corticotropin-lipotrophin; adrenocorticotropic hormone; alpha-melanocyte-stimulating hormone; corticotropin-like intermediary peptide | POMC |
| 721 | paraoxonase 1 ESA, PON, Paraoxonase | paraoxonase-ESA, PON, Paraoxonase | PON1 |
| 722 | paraoxonase 2 | paraoxonase-A-esterase 2; aromatic esterase 2; serum aryldialkylphosphatase 2; serum paraoxonase/arylesterase 2 | PON2 |
| 723 | paraoxonase 3 | paraoxonase - paraoxanase-3; serum paraoxonase/lactonase 3 | PON3 |
| 724 | phosphatidic acid phosphatase type 2A | LLP1a, LPP1, PAP-2a, PAP2, PAP2a2, PAP2alpha2, PAPalpha1, lipid phosphate phosphohydrolase 1; lipid phosphate phosphohydrolase 1a; phosphatidic acid phosphatase 2a; phosphatidic acid | PPAP2A |

TABLE 2-continued

ARTERIORISKMARKERS

| ARTERIORISKMARKER | Official Name | Common Name | Gene Symbol |
|---|---|---|---|
| 725 | phosphatidic acid phosphatase type 2C | phosphohydrolase type 2a; type 2 phosphatidic acid phosphohydrolase; type-2 phosphatidic acid phosphatase alpha<br>phosphatidic acid phosphatase type 2C-like - LPP2, PAP-2c, PAP2-g, lipid phosphate phosphohydrolase 2; phosphatidic acid phosphohydrolase type 2c; type-2 phosphatidic acid phosphatase-gamma | PPAP2C |
| 726 | peroxisome proliferative activated receptor, alpha | Peroxisome proliferator-activated receptor (PPAR), NR1C1, PPAR, hPPAR, PPAR alpha | PPARA |
| 727 | peroxisome proliferative activated receptor, delta | Peroxisome proliferator-activated receptor (PPAR), FAAR, NR1C2, NUC1, NUCI, NUCII, PPAR-beta, PPARB, nuclear hormone receptor 1, PPAR Delta | PPARD |
| 728 | peroxisome proliferative activated receptor, gamma | Peroxisome proliferator-activated receptor (PPAR), HUMPPARG, NR1C3, PPARG1, PPARG2, PPAR gamma; peroxisome proliferative activated receptor gamma; peroxisome proliferator activated-receptor gamma; peroxisome proliferator-activated receptor gamma 1; ppar gamma2 | PPARG |
| 729 | pro-platelet basic protein (chemokine (C-X-C motif) ligand 7) | beta-thromboglobulin (BTG) - B-TG1, Beta-TG, CTAP3, CTAPIII, CXCL7, LA-PF4, LDGF, MDGF, NAP-2, NAP-2-L1, PBP, SCYB7, TC1, TC2, TGB, TGB1, THBGB, THBGB1 - CXC chemokine ligand 7; beta-thromboglobulin; connective tissue-activating peptide III; low-affinity platelet factor IV; neutrophil-activating peptide-2; pro-platelet basic protein; pro-platelet basic protein (includes platelet basic protein, beta-thromboglobulin, connective tissue-activating peptide III, neutrophil-activating peptide-2); small inducible cytokine B7; small inducible cytokine subfamily B, member 7; thrombocidin 1; thrombocidin 2; thromboglobulin, beta-1 | PPBP |
| 730 | pro-platelet basic protein-like 1 (includes platelet basic protein, beta-thromboglobulin, connective tissue-activating peptide III, neutrophil-activating peptide-2-like 1) | beta-thromboglobulin (betaTG) - TGB2, Thromboglobulin, beta-2; beta-thromboglobulin; connective tissue-activating peptide I; platelet basic protein | PPBPL1 |
| 731 | protective protein for beta-galactosidase (galactosialidosis) | Protective protein for beta-galactosidase - CTSA, GLB2, GSL, NGBE, PPCA, Protective protein for beta-galactosidase (cathepsin A); beta-galactosidase 2; beta-galactosidase protective protein; protective protein for beta-galactosidase | PPGB |
| 732 | protein phosphatase 1, regulatory (inhibitor) subunit 15A | Growth arrest and DNA damage protein 34 (GADD34), GADD34, growth arrest and DNA-damage-inducible 34; protein phosphatase 1, regulatory subunit 15A | PPP1R15A |
| 733 | protein phosphatase 3 (formerly 2B), regulatory subunit B, 19 kDa, alpha isoform (calcineurin B, type I) | calcineurin - CALNB1, CNB, CNB1, calcineurin B; protein phosphatase 3 (formerly 2B), regulatory subunit B (19 kD), alpha isoform (calcineurin B, type I); protein phosphatase 3, regulatory subunit B, alpha isoform 1 | PPP3R1 |
| 734 | protein phosphatase 3 (formerly 2B), regulatory subunit B, 19 kDa, beta isoform (calcineurin B, type II) | calcineurin - PPP3RL, CBLP-like; calcineurin B, type II; calcineurin B-like protein; protein phosphatase 3 (formerly 2B), regulatory subunit B (19 kD), beta isoform (calcineurin B, type II); protein phosphatase 3 regulatory subunit B, beta isoform | PPP3R2 |
| 735 | pancreatic polypeptide receptor 1 | G Protein- Coupled Receptor NPY4 - NPY4-R, NPY4R, PP1, Y4 | PPYR1 |
| 736 | proteoglycan 4 | glycosaminoglycans - CACP, HAPO, JCAP, MSF, SZP, Jacobs camptodactyly-arthropathy-pericarditis syndrome gene; articular superficial zone protein; (MSF: megakaryocyte stimulating factor); camptodactyly, arthropathy, coxa vara, pericarditis syndrome gene; lubricin; megakaryocyte stimulating factor; proteoglycan 4, (megakaryocyte stimulating factor, articular superficial zone protein, camptodactyly, arthropathy, coxa vara, pericarditis syndrome) | PRG4 |
| 737 | protein kinase C, gamma | protein kinase C gamma - PKC-gamma, PKCC, PKCG, SCA14, spinocerebellar ataxia 14 | PRKCG |

TABLE 2-continued

ARTERIORISKMARKERS

| ARTERIORISKMARKER | Official Name | Common Name | Gene Symbol |
|---|---|---|---|
| 738 | protein kinase, DNA-activated, catalytic polypeptide | DNA-PK: DNAPK, DNPK1, HYRC, HYRC1, XRCC7, p350 | PRKDC |
| 739 | protein kinase, cGMP-dependent, type I | Protein Kinase, cGMP-Dependent - CGKI, FLJ36117, PGK, PRKG1B, PRKGR1B, cGKI-BETA, cGKI-alpha, Protein kinase, cGMP-dependent, regulatory, type I; protein kinase, cGMP-dependent, regulatory, type I, beta | PRKG1 |
| 740 | prolactin releasing hormone receptor | G-protein coupled receptor 10 - GPR10, GR3, PrRPR, G protein-coupled receptor 10; prolactin releasing peptide receptor; prolactin-releasing hormone receptor | PRLHR |
| 741 | protein C (inactivator of coagulation factors Va and VIIIa) | Protein C - PROC1, protein C | PROC |
| 742 | protein C receptor, endothelial (EPCR) | protein C receptor (endothelial) - CCCA, CCD41, CD201, EPCR, APC receptor; CD201 antigen; activated protein C receptor; cell cycle, centrosome-associated protein; centrocyclin; endothelial protein C receptor | PROCR |
| 743 | prokineticin receptor 1 | G protein coupled receptor 73a - GPR73, GPR73a, PKR1, ZAQ, G protein-coupled receptor 73; G protein-coupled receptor ZAQ | PROKR1 |
| 744 | protein S (alpha) | Protein S - PROS, PS 26, PS21, PS22, PS23, PS24, PS25, PSA, Protein S, protein Sa, preproprotein S; propiece of latent protein S; truncated CDS due to variation | PROS1 |
| 745 | protein Z, vitamin K-dependent plasma glycoprotein | PZ | PROZ |
| 746 | proline rich Gla (G-carboxyglutamic acid) 3 (transmembrane) | gamma carboxyglutamic acid (gla) - TMG3, transmembrane gamma-carboxyglutamic acid protein 3 | PRRG3 |
| 747 | proline rich Gla (G-carboxyglutamic acid) 4 (transmembrane) | gamma carboxyglutamic acid (gla) - TMG4, transmembrane gamma-carboxyglutamic acid protein 4 | PRRG4 |
| 748 | protease, serine, 1 (trypsin 1) | eosinophil serine protease 1 (PRSS1) - TRP1, TRY1, TRY4, TRYP1, cationic trypsinogen; digestive zymogen; nonfunctional trypsin 1; protease serine 1; protease, serine, 1; serine protease 1; trypsin 1; trypsin I; trypsinogen 1; trypsinogen A | PRSS1 |
| 749 | protease, serine, 8 (prostasin) | serine protease 8 - CAP1, PROSTASIN, channel-activating protease 1; prostasin | PRSS8 |
| 750 | growth-inhibiting protein 26 | prostate-specific membrane antigen-like - GCP3, GCP III; N-acetylated-alpha-linked-acidic dipeptidase; glutamate carboxypeptidase III; hypothetical protein LOC219595; prostate-specific membrane antigen-like | PSMAL |
| 751 | prostaglandin E receptor 1 (subtype EP1), 42 kDa | G protein coupled receptor prostaglandin E2 EP1 - EP1PGE receptor, EP1 subtype; prostaglandin E receptor 1, subtype EP1; prostanoid EP1 receptor | PTGER1 |
| 752 | prostaglandin E receptor 2 (subtype EP2), 53 kDa | G-Protein Coupled Receptor Prostaglandin E2 EP2 - EP2 Prostaglandin E receptor 2, EP2 subtype, 53 kD | PTGER2 |
| 753 | prostaglandin E receptor 3 (subtype EP3) | G protein Coupled Receptor Prostaglandin E2 EP3 1 - EP3, EP3-I, EP3-II, EP3-III, EP3-IV, EP3e, PGE receptor, EP3 subtype; alternative splicing; prostaglandin E receptor 3, subtype EP3; prostaglandin E2 receptor; prostaglandin receptor (PGE-2); prostanoid EP3 receptor | PTGER3 |
| 754 | prostaglandin E receptor 4 (subtype EP4) | G Protein Coupled Receptor Prostaglandin E2 EP4 - EP4, EP4R, PGE receptor, EP4 subtype; prostaglandin E receptor 4, subtype EP4; prostaglandin E2 receptor | PTGER4 |
| 755 | prostaglandin F receptor (FP) | G-Protein Coupled Receptor Prostaglandin F2-alpha - FP, PGF receptor; PGF2 alpha receptor; prostaglandin F receptor; prostaglandin F2 alpha receptor; prostaglandin receptor (2-alpha); prostanoid FP receptor | PTGFR |
| 756 | prostaglandin I2 (prostacyclin) receptor (IP) | prostaglandin I2 receptor - IP, PRIPR, PGI receptor; prostacyclin receptor; prostanoid IP receptor | PTGIR |
| 757 | prostaglandin I2 (prostacyclin) synthase | prostacyclin synthetase (PGI-II synthetase) | PTGIS |
| 758 | prostaglandin-endoperoxide synthase 1 (prostaglandin G/H synthase and cyclooxygenase) | Pro17Leu variant of PTGS1 - COX1, COX3, PCOX1, PGG/HS, PGHS-1, PGHS1, PHS1, PTGHS, prostaglandin G/H synthase and | PTGS1 |

TABLE 2-continued

ARTERIORISKMARKERS

| ARTERIORISKMARKER | Official Name | Common Name | Gene Symbol |
|---|---|---|---|
| | | cyclooxygenase; prostaglandin-endoperoxide synthase 1 | |
| 759 | prostaglandin-endoperoxide synthase 2 (prostaglandin G/H synthase and cyclooxygenase) | Cyclo-oxygenase-2 (COX-2) - COX-2, COX2, PGG/HS, PGHS-2, PHS-2, hCox-2, cyclooxygenase 2b; prostaglandin G/H synthase and cyclooxygenase; prostaglandin-endoperoxide synthase 2 | PTGS2 |
| 760 | parathyroid hormone-like hormone | parathyroid hormone related protein: PTH-related protein; humoral hypercalcemia of malignancy; osteostatin; parathyroid hormone-like protein; parathyroid hormone-like related protein; parathyroid hormone-related protein; parathyroid-like protein | PTHLH |
| 761 | parathyroid hormone-like hormone | parathormone-like protein (PTH/parathyroidhormone related protein) - HHM, PLP, PTHR, PTHRP, PTH-related protein; humoral hypercalcemia of malignancy; osteostatin; parathyroid hormone-like protein; parathyroid hormone-like related protein; parathyroid hormone-related protein; parathyroid-like protein | PTHLH |
| 762 | parathyroid hormone receptor 1 | parathyroid hormone receptor 1 - PTHR, PTH receptor; PTH/PTHr receptor; PTH/PTHrP receptor; PTH/PTHrP type I receptor; parathyroid hormone/parathyroid hormone-related peptide receptor; parathyroid hormone/parathyroid hormone-related protein receptor; seven transmembrane helix receptor | PTHR1 |
| 763 | pituitary tumor-transforming 1 | PTTG: ESP1-associated protein 1; pituitary tumor-transforming protein 1; tumor-transforming protein 1 | PTTG1 |
| 764 | phosphorylase, glycogen; brain | glycogen phosphorylase BB - brain glycogen phosphorylase; glycogen phosphorylase B (cardiac? - Anderson reference?) | PYGB |
| 765 | v-raf-1 murine leukemia viral oncogene homolog 1 | Raf protein-CRAF, Raf-1, c-Raf, Oncogene RAF1; raf proto-oncogene serine/threonine protein kinase | RAF1 |
| 766 | retinoic acid receptor, alpha | retinoic acid receptor alpha - NR1B1, RAR, Retinoic acid receptor, alpha polypeptide; nucleophosmin-retinoic acid receptor alpha fusion protein NPM-RAR long form; nucleophosmin-retinoic acid receptor alpha fusion protein NPM-RAR short form | RARA |
| 767 | retinoic acid receptor, beta | Nuclear Receptor Subfamily 1, Group B. Member 2 (NR1B2) - HAP, NR1B2, RRB2, HBV-activated protein; RAR-epsilon; hepatitis B virus activated protein; retinoic acid receptor beta 2; retinoic acid receptor beta 4; retinoic acid receptor beta 5; retinoic acid receptor, beta polypeptide | RARB |
| 768 | retinoblastoma-like 1 (p107) | p107 - CP107, PRB1, 107 kDa retinoblastoma-associated protein; cellular protein 107; retinoblastoma-like protein 1 | RBL1 |
| 769 | renin | REN: angiotensin-forming enzyme precursor; angiotensinogenase precursor; renin precursor, renal | REN |
| 770 | resistin | resistin - ADSF, FIZZ3, RETN1, RSTN, XCP1, C/EBP-epsilon regulated myeloid-specific secreted cysteine-rich protein precursor 1; found in inflammatory zone 3 | RETN |
| 771 | regulator of G-protein signalling 2, 24 kDa | RGS2 - G0S8, G0 to G1 switch regulatory 8, 24 kD; cell growth-inhibiting protein 31 | RGS2 |
| 772 | rhomboid, veinlet-like 1 (Drosophila) | rhomboid-related protein - RHBDL, RRP, Rhomboid, drosophila, homolog of; rhomboid (veinlet, Drosophila)-like; rhomboid, veinlet-like 1 | RHBDL1 |
| 773 | rhomboid, veinlet-like 2 (Drosophila) | rhomboid-related protein - RRP2, rhomboid (veinlet, Drosophila)-like 2; rhomboid-related protein 2 | RHBDL2 |
| 774 | arginyl aminopeptidase (aminopeptidase B) | Arginyl Amino-peptidase RNPEP - aminopeptidase B | RNPEP |
| 775 | arginyl aminopeptidase (aminopeptidase B)-like 1 | arginyl aminopeptidase B-like 1 - argininyl aminopeptidase-like 1 | RNPEPL1 |
| 776 | Rho-associated, coiled-coil containing protein kinase 1 | Rho-associated protein kinase 1 - P160ROCK, p160-ROCK | ROCK1 |

TABLE 2-continued

ARTERIORISKMARKERS

| ARTERIORISKMARKER | Official Name | Common Name | Gene Symbol |
|---|---|---|---|
| 777 | Rho-associated, coiled-coil containing protein kinase 2 | Rho-associated protein kinase 1 - | ROCK2 |
| 778 | relaxin family peptide receptor 3 | somatostatin- and angiogenin-like peptide receptor - GPCR135, RLN3R1, SALPR, G-protein coupled receptor SALPR; relaxin 3 receptor 1; somatostatin and angiotensin-like peptide receptor | RXFP3 |
| 779 | retinoid X receptor, alpha | Retinoid X Receptor Alpha - NR2B1 | RXRA |
| 780 | retinoid X receptor, gamma | Retinoid X Receptor Gamma - NR2B3, RXRC, retinoic acid receptor RXR-gamma | RXRG |
| 781 | RYK receptor-like tyrosine kinase | Ryk - JTK5, JTK5A, RYK1, JTK5A protein tyrosine kinase; hydroxyaryl-protein kinase | RYK |
| 782 | ryanodine receptor 2 (cardiac) | calcium-release channel (ryanodin receptor II) | RYR2 |
| 783 | S100 calcium binding protein, beta (neural) | S-100b (astroglial protein, candidate marker for cerebral tissue damage) (entered S-100b into Entrez) - NEF, S100, S-100 calcium-binding protein, beta chain; S100 beta; S100 calcium-binding protein, beta; S100 calcium-binding protein, beta (neural) | S100B |
| 784 | serum amyloid A1 cluster | Serum Amyloid A (SAA), SAA, SAA4, serum amyloid A cluster | SAA@ |
| 785 | serum amyloid A1 | Serum Amyloid A (SAA), PIG4, SAA, TP53I4, tumor protein p53 inducible protein 4 | SAA1 |
| 786 | serum amyloid A2 | Serum Amyloid A (SAA) (no "other names listed other than official name) | SAA2 |
| 787 | serum amyloid A4, constitutive | Serum Amyloid A (SAA), C-SAA, CSAA | SAA4 |
| 788 | stearoyl-CoA desaturase (delta-9-desaturase) | Stearoyl CoA desaturase - FADS5, PRO0998, SCD1, acyl-CoA desaturase; delta-9-desaturase; fatty acid desaturase; predicted protein of HQ0998; stearoyl-CoA desaturase | SCD |
| 789 | secretoglobin, family 1A, member 1 (uteroglobin) | uteroglobin - CC10, CC16, CCSP, UGB, Uteroglobin (Clara-cell specific 10-kD protein); uteroglobin | SCGB1A1 |
| 790 | sodium channel, voltage-gated, type V, alpha (long QT syndrome 3) | CDCD2, CMD1E, CMPD2, HB1, HB2, HH1, IVF, LQT3, Nav1.5, SSS1, cardiac sodium channel alpha subunit; cardiomyopathy, dilated 1E (autosomal dominant); sodium channel, voltage-gated, type V, alpha polypeptide (long (electrocardiographic) QT syndrome 3); voltage-gated sodium channel type V alpha | SCN5A |
| 791 | sterol carrier protein 2 | sterol carrier protein 2, DKFZp686C12188, DKFZp686D11188, NLTP, NSL-TP, SCPX, nonspecific lipid-transfer protein; sterol carrier protein X | SCP2 |
| 792 | serine carboxypeptidase 1 | retinoid-inducible serine carboxypeptidase - HSCP1, RISC, serine carboxypeptidase 1 precursor protein | SCPEP1 |
| 793 | selectin E (endothelial adhesion molecule 1) | E-selectin, CD62E, ELAM, ELAM1, ESEL, LECAM2, leukocyte endothelial cell adhesion molecule 2; selectin E, endothelial adhesion molecule 1 | SELE |
| 794 | selectin L (lymphocyte adhesion molecule 1) | L-Selectin - CD62L, LAM-1, LAM1, LECAM1, LNHR, LSEL, LYAM1, Leu-8, Lyam-1, PLNHR, TQ1, hLHRc, Leu-8 antigen; Leu-8 antigen short form; leukocyte adhesion molecule-1 (LAM-1); lymph node homing receptor; lymphocyte adhesion molecule 1; selectin L | SELL |
| 795 | selectin P (granule membrane protein 140 kDa, antigen CD62) | CD62, CD62P, GMP140, GRMP, PADGEM, PSEL, antigen CD62; granulocyte membrane protein; selectin P; selectin P (granule membrane protein 140 kD, antigen CD62) | SELP |
| 796 | selectin P ligand | CLA, CD162, PSGL-1, PSGL1, cutaneous lymphocyte-associated antigen | SELPLG |
| 797 | serpin peptidase inhibitor, clade A (alpha-1 antiproteinase, antitrypsin), member 1 | alpha(1)-antitrypsin-A1A, A1AT, AAT, PI, PI1, alpha-1-antitrypsin MBrescia variant; protease inhibitor 1 (anti-elastase), alpha-1-antitrypsin; serine (or cysteine) proteinase inhibitor, clade A (alpha-1 antiproteinase, antitrypsin), member 1 | SERPINA1 |
| 798 | serpin peptidase inhibitor, clade A (alpha-1 antiproteinase, antitrypsin), member 2 | alpha(1)-antitrypsin - ARGS, ATR, PIL, psiATR, Protease inhibitor 1-like; protease inhibitor 1 (alpha-1-antitrypsin)-like; serine (or cysteine) proteinase inhibitor, clade A (alpha-1 antiproteinase, antitrypsin), member 2 | SERPINA2 |

TABLE 2-continued

ARTERIORISKMARKERS

| ARTERIORISKMARKER | Official Name | Common Name | Gene Symbol |
|---|---|---|---|
| 799 | serpin peptidase inhibitor, clade A (alpha-1 antiproteinase, antitrypsin), member 3 | Alpha (1)-antichymotrypsin - alpha-1-antichymotrypsin; antichymotrypsin; growth-inhibiting protein 24; growth-inhibiting protein 25; serine (or cysteine) proteinase inhibitor, clade A, member 3; serpin peptidase inhibitor, clade A, member 3 | SERPINA3 |
| 800 | serpin peptidase inhibitor, clade A (alpha-1 antiproteinase, antitrypsin), member 5 | protein C inhibitor (PCI) - PAI3, PCI, PLANH3, PROCI, Protein C inhibitor (plasminogen activator inhibitor-3); protein C inhibitor; protein C inhibitor (plasminogen activator inhibitor III); serine (or cysteine) proteinase inhibitor, clade A (alpha-1 antiproteinase, antitrypsin), member 5 | SERPINA5 |
| 801 | serpin peptidase inhibitor, clade A (alpha-1 antiproteinase, antitrypsin), member 7 | alpha(1)-antitrypsin - RP1-82J11.2, TBG, alpha-1 antiproteinase, antitrypsin; serine (or cysteine) proteinase inhibitor, clade A (alpha-1 antiproteinase, antitrypsin), member 7; serine (or cysteine) proteinase inhibitor, clade A, member 7; thyroxin-binding globulin; thyroxine-binding globulin | SERPINA7 |
| 802 | serpin peptidase inhibitor, clade C (antithrombin), member 1 | Anti-thrombin III (ATIII), AT3, ATIII, antithrombin; antithrombin (aa 375-432); antithrombin III; coding sequence signal peptide antithrombin part 1; serine (or cysteine) proteinase inhibitor, clade C (antithrombin), member 1; signal peptide antithrombin part 1 | SERPINC1 |
| 803 | serpin peptidase inhibitor, clade D (heparin cofactor), member 1 | HCII - HC2, HCF2, HCII, HLS2, LS2, heparin cofactor II; leuserpin 2; serine (or cysteine) proteinase inhibitor, clade D (heparin cofactor), member 1 | SERPIND1 |
| 804 | serpin peptidase inhibitor, clade E (nexin, plasminogen activator inhibitor type 1), member 1 | plasminogen activator inhibitor-1 - PAI, PAI-1, PAI1, PLANH1, plasminogen activator inhibitor, type I; plasminogen activator inhibitor-1; serine (or cysteine) proteinase inhibitor, clade E (nexin, plasminogen activator inhibitor type 1), member 1 | SERPINE1 |
| 805 | serpin peptidase inhibitor, clade E (nexin, plasminogen activator inhibitor type 1), member 1 | Plasminogen activator inhibitor I - PAI, PAI-1, PAI1, PLANH1, plasminogen activator inhibitor, type I; plasminogen activator inhibitor-1; serine (or cysteine) proteinase inhibitor, clade E (nexin, plasminogen activator inhibitor type 1), member 1 | SERPINE1 |
| 806 | serpin peptidase inhibitor, clade F | Alpha 2 antiplasmin - alpha-2-antiplasmin; alpha-2-plasmin inhibitor; serine (or cysteine) proteinase inhibitor, clade F (alpha-2 antiplasmin, pigment epithelium derived factor), member 2 | SERPINF2 |
| 807 | serpin peptidase inhibitor, clade G (C1 inhibitor), member 1 | complement C1 inactivator - complement component 1 inhibitor; plasma protease C1 inhibitor; serine (or cysteine) proteinase inhibitor, clade G (C1 inhibitor), member 1, (angioedema, hereditary); serine/cysteine proteinase inhibitor clade G member 1 splice variant 3 | SERPING1 |
| 808 | sarcoglycan, delta (35 kDa dystrophin-associated glycoprotein) | sarcoglycan - 35DAG, CMD1L, DAGD, SG-delta, SGCDP, SGD, 35 kD dystrophin-associated glycoprotein; delta-sarcoglycan; dystrophin associated glycoprotein, delta sarcoglycan; placental delta sarcoglycan; sarcoglycan, delta (35 kD dystrophin-associated glycoprotein) | SGCD |
| 809 | serum/glucocorticoid regulated kinase | Serum/Glucocorticoid Regulated Kinase 1 - SGK1, serine/threonine protein kinase SGK; serum and glucocorticoid regulated kinase | SGK |
| 810 | serum/glucocorticoid regulated kinase family, member 3 | serum/glucocorticoid regulated kinase-like - CISK, SGK2, SGKL, cytokine-independent survival kinase; serum/glucocorticoid regulated kinase 3; serum/glucocorticoid regulated kinase-like | SGK3 |
| 811 | sphingosine-1-phosphate lyase 1 | sphingosine phosphate lyase - SPL | SGPL1 |
| 812 | sphingosine-1-phosphate phosphatase 1 | FLJ39004, SPP2; sphingosine 1-phosphate phosphohydrolase 2 | SGPP2 |
| 813 | sex hormone-binding globulin | sex hormone-binding globulin (SHBG) - ABP, Sex hormone-binding globulin (androgen binding protein) | SHBG |
| 814 | S-phase kinase-associated protein 2 (p45) | Skp2: CDK2/cyclin A-associated protein p45; S-phase kinase-associated protein 2 | SKP2 |

TABLE 2-continued

ARTERIORISKMARKERS

| ARTERIORISKMARKER | Official Name | Common Name | Gene Symbol |
|---|---|---|---|
| 815 | solute carrier family 22 (organic cation transporter), member 1 | Organic Cation Transporter SLC22A1 - HOCT1, OCT1, oct1_cds, organic cation transporter 1; solute carrier family 22 member 1 | SLC22A1 |
| 816 | solute carrier family 22 (organic anion/cation transporter), member 10 | organic cation transporter SLC22A10 - OAT5, hOAT5, organic anion transporter 5, UST3-LIKE2 | SLC22A10 |
| 817 | solute carrier family 22 (organic anion/cation transporter), member 11 | Organic Cation Transporter SLC22A11 - OAT4, hOAT4, organic anion transporter 4; solute carrier family 22 member 11 | SLC22A11 |
| 818 | solute carrier family 22 (organic anion/cation transporter), member 12 | Organic Cation Transporter SLC22A12 - OAT4L, RST, URAT1, organic anion transporter 4-like; solute carrier family 22 member 12; urate anion exchanger 1; urate transporter 1 | SLC22A12 |
| 819 | solute carrier family 22 (organic cation transporter), member 13 | organic cationic transporter-like 3 - OCTL1, OCTL3, ORCTL3, organic cation transporter like 3; organic cationic transporter-like 3 | SLC22A13 |
| 820 | solute carrier family 22 (organic cation transporter), member 14 | Organic Cationic Transporter-Like 4 - OCTL2, OCTL4, ORCTL4, organic cation transporter like 4; organic cationic transporter-like 4 | SLC22A14 |
| 821 | solute carrier family 22 (organic cation transporter), member 15 | ORGANIC CATION TRANSPORTER FLIPT1 - FLIPT1, fly-like putative organic ion transporter 1; trans-like protein | SLC22A15 |
| 822 | solute carrier family 22 (organic cation transporter), member 16 | Putative Organic Ion Transporter OKB1 - CT2, FLIPT2, OCT6, OKB1; carnitine transporter 2; fly-like putative organic ion transporter 2; organic cation transporter 6; solute carrier family 22, member 16 | SLC22A16 |
| 823 | solute carrier family 22 (organic cation transporter), member 17 | Potent Brain Type Organic Ion Transporter - BOCT, BOIT, hBOIT, potent brain type organic ion transporter | SLC22A17 |
| 824 | solute carrier family 22 (organic cation transporter), member 18 | Organic Cation Transporter SLC22A1L - BWR1A, BWSCR1A, HET, IMPT1, ITM, ORCTL2, SLC22A1L, TSSC5, p45-BWR1A, Beckwith-Wiedemann syndrome chromosome region 1, candidate A; efflux transporter-like protein; imprinted multi-membrane spanning polyspecific transporter-related protein; organic cation transporter-like 2; p45 Beckwith-Wiedemann region 1A; solute carrier family 22 (organic cation transporter), member 1-like; tumor suppressing subtransferable candidate 5; tumor-suppressing STF cDNA 5 | SLC22A18 |
| 825 | solute carrier family 22 (organic cation transporter), member 2 | Organic Cation Transporter SLC22A2 - OCT2, organic cation transporter (OCT2); organic cation transporter 2; solute carrier family 22 member 2 | SLC22A2 |
| 826 | solute carrier family 22 (extraneuronal monoamine transporter), member 3 | Organic Cation Transporter SLC22A3 - EMT, EMTH, OCT3, EMT organic cation transporter 3; extraneuronal monoamine transporter; organic cation transporter 3; solute carrier family 22 member 3 | SLC22A3 |
| 827 | solute carrier family 22 (organic cation transporter), member 4 | Organic Cation Transporter SLC22A4 - OCTN1, integral membrane transport protein; organic cation transporter 4; solute carrier family 22 member 4 | SLC22A4 |
| 828 | solute carrier family 22 (organic cation transporter), member 5 | Organic Cation Transporter SLC22A5 - CDSP, OCTN2, high-affinity sodium dependent carnitine cotransporter; organic cation transporter 5; organic cation/carnitine transporter 2; solute carrier family 22 member 5 | SLC22A5 |
| 829 | solute carrier family 22 (organic anion transporter), member 6 | Organic Cation Transporter SLC22A6 - HOAT1, OAT1, PAHT, ROAT1, para-aminohippurate transporter; renal organic anion transporter 1; solute carrier family 22 member 6 | SLC22A6 |
| 833 | solute carrier family 22 (organic anion transporter), member 7 | Organic anion Transporter SLC22A7 - NLT, OAT2, liver-specific transporter; organic anion transporter 2; solute carrier family 22 member 7 | SLC22A7 |
| 830 | solute carrier family 22 (organic anion transporter), member 8 | organic anion transporter SLC22A8 - OAT3, organic anion transporter 3; solute carrier family 22 member 8 | SLC22A8 |
| 831 | solute carrier family 22 (organic anion/cation transporter), member 9 | organic anion transporting (OAT)-like protein UST3-LIKE1 - HOAT4, OAT4, UST3H, ust3, organic anion transporter 4 | SLC22A9 |
| 832 | solute carrier family 22 (organic anion/cation transporter), member 9 | Organic Cation Transporter SLC22A9 - HOAT4, OAT4, UST3H, ust3, organic anion transporter 4 | SLC22A9 |

TABLE 2-continued

ARTERIORISKMARKERS

| ARTERIORISKMARKER | Official Name | Common Name | Gene Symbol |
|---|---|---|---|
| 834 | solute carrier family 27 (fatty acid transporter), member 2 | fatty acid CoA ligase-like AMP-binding enzyme - ACSVL1, FACVL1, FATP2, HsT17226, VLACS, VLCS, hFACVL1, very long-chain fatty-acid-coenzyme A ligase 1; very-long-chain acyl-CoA synthetase | SLC27A2 |
| 835 | solute carrier family 31 (copper transporters) member 1 | COPT1; CTR1; MGC75487; hCTR1; copper transporter homolog 1; copper transporter 1 | SLC31A1 |
| 836 | solute carrier family 6 (neurotransmitter transporter, GABA), member 11 | neurotransmitter transporters - GAT-3, GAT3 | SLC6A11 |
| 837 | solute carrier family 6 (neurotransmitter transporter, serotonin), member 4 | neurotransmitter transporters - 5-HTT, 5HTT, HTT, OCD1, SERT, hSERT, 5-hydroxytryptamine transporter; 5HT transporter; Na+/Cl− dependent serotonin transporter; serotonin transporter; sodium-dependent serotonin transporter; solute carrier family 6 member 4 | SLC6A4 |
| 838 | solute carrier family 9 (sodium/hydrogen exchanger), member 1 (antiporter, Na+/H+, amiloride sensitive) | sodium proton exchanger (NHE-I) - APNH, NHE1, Na+/H+ antiporter, amiloride-sensitive; Na—Li countertransporter; sodium/hydrogen exchanger 1; solute carrier family 9 (sodium/hydrogen exchanger), isoform 1 (antiporter, Na+/H+, amiloride sensitive); solute carrier family 9, isoform A1 | SLC9A1 |
| 839 | sphingomyelin phosphodiesterase 1, acid lysosomal (acid sphingomyelinase) | ASM, NPD, acid sphingomyelinase; sphingomyelin phosphodiesterase 1, acid lysosomal | SMPD1 |
| 840 | smoothelin | smoothelin | SMTN |
| 841 | superoxide dismutase 1, soluble (amyotrophic lateral sclerosis 1 (adult)) | superoxide-dismutase: Cu/Zn superoxide dismutase; Cu/Zn superoxide dismutase; SOD, soluble; indophenoloxidase A | SOD1 |
| 842 | secreted phosphoprotein 1 (osteopontin, bone sialoprotein I, early T-lymphocyte activation 1) | osteopontin: secreted phosphoprotein 1; secreted phosphoprotein-1 (osteopontin, bone sialoprotein) | SPP1 |
| 843 | somatostatin receptor 1 | somatostatin receptor 1 - SRIF-2, G-protein coupled receptor; somatostatin receptor isoform 1 | SSTR1 |
| 844 | somatostatin receptor 2 | somatostatin receptor subtype 2 | SSTR2 |
| 845 | somatostatin receptor 3 | somatostatin receptor 3 - | SSTR3 |
| 846 | somatostatin receptor 4 | somatostatin receptor 4 - G-protein coupled receptor | SSTR4 |
| 847 | somatostatin receptor 5 | somatostatin receptor 5 - somatostatin receptor subtype 5 | SSTR5 |
| 848 | succinate receptor 1 | G protein-coupled receptor 91 - GPR91, G protein-coupled receptor 91; P2Y purinoceptor 1 | SUCNR1 |
| 849 | trace amine associated receptor 1 | trace amine receptor 1 - TA1, TAR1, TRAR1, trace amine receptor 1 | TAAR1 |
| 850 | trace amine associated receptor 2 | G-protein coupled receptor 58 - GPR58, G protein-coupled receptor 58 | TAAR2 |
| 851 | trace amine associated receptor 3 | G-protein coupled receptor 57 - G protein-coupled receptor 57, GPR57, GPR58, TAAR3 | TAAR3 |
| 852 | trace amine associated receptor 5 | putative neurotransmitter receptor - PNR, putative neurotransmitter receptor | TAAR5 |
| 853 | trace amine associated receptor 6 | G protein-coupled receptor polypeptide (TA4 receptor) - TA4, TRAR4, trace amine receptor 4 | TAAR6 |
| 854 | trace amine associated receptor 8 | TA5 receptor - GPR102, TA5, TAR5, TRAR5, G protein-coupled receptor 102; trace amine receptor 5 | TAAR8 |
| 855 | tachykinin receptor 1 | Tachykinin Receptor 1 - NK1R, NKIR, SPR, TAC1R, NK-1 receptor; Tachykinin receptor 1 (substance P receptor; neurokinin-1 receptor); neurokinin 1 receptor; tachykinin 1 receptor (substance P receptor, neurokinin 1 receptor) | TACR1 |
| 856 | tachykinin receptor 2 | Tachykinin Receptor 2 - NK2R, NKNAR, SKR, TAC2R, NK-2 receptor; Tachykinin receptor 2 (substance K receptor; neurokinin 2 receptor); neurokinin 2 receptor; neurokinin-2 receptor; seven transmembrane helix receptor; tachykinin 2 receptor (substance K receptor, neurokinin 2 receptor) | TACR2 |
| 857 | tachykinin receptor 3 | Tachykinin Receptor 3 - NK3R, TAC3RL, NK-3 receptor; neurokinin B receptor | TACR3 |
| 858 | TBC1 domain family, member 2 | TBC1 domain family member 2 - PARIS-I, PARIS1, TBC1D2A, prostate antigen recognized and identified by SEREX (serological identification of anitgens by recombinant expression cloning) | TBC1D2 |

TABLE 2-continued

ARTERIORISKMARKERS

| ARTERIORISKMARKER | Official Name | Common Name | Gene Symbol |
|---|---|---|---|
| 859 | thromboxane A2 receptor | thromboxane A2 - TXA2-R, PROSTANOID TP RECEPTOR | TBXA2R |
| 860 | transcription factor 2, hepatic; LF-B3; variant hepatic nuclear factor | hepatocyte nuclear factor 2 - FJHN, HNF1B, HNF1beta, HNF2, LFB3, MODY5, VHNF1, transcription factor 2 | TCF2 |
| 861 | transcription factor CP2 | SEF - CP2, LBP-1C, LSF, SEF, TFCP2C, SAA3 enhancer factor; Transcription factor CP2, alpha globin | TFCP2 |
| 862 | tissue factor pathway inhibitor (lipoprotein-associated coagulation inhibitor) | Tissue factor pathway inhibitor (TFPI) - EPI, LACI | TFPI |
| 863 | transforming growth factor, beta 1 (Camurati-Engelmann disease) | TGF-beta: TGF-beta 1 protein; diaphyseal dysplasia 1, progressive; transforming growth factor beta 1; transforming growth factor, beta 1; transforming growth factor-beta 1, CED, DPD1, TGFB | TGFB1 |
| 864 | transforming growth factor, beta 2 | TGF beta 2 - TGF-beta2 | TGFB2 |
| 865 | transforming growth factor, beta receptor III (betaglycan, 300 kDa) | TGF-3: TGF-beta3 | TGFB3 |
| 866 | thrombomodulin | soluble thrombomodulin - CD141, THRM, TM, CD141 antigen; fetomodulin | THBD |
| 867 | thrombospondin 1 | thrombospondin - THBS, TSP, TSP1, thrombospondin-1p180 | THBS1 |
| 868 | thrombospondin 2 | thrombospondin 2 - TSP2 | THBS2 |
| 869 | thyroid hormone receptor, alpha (erythroblastic leukemia viral (v-erb-a) oncogene homolog, avian) | thyroid hormone receptor alpha - AR7, EAR-7.1, EAR-7.2, EAR7, ERB-T-1, ERBA, ERBA-ALPHA, ERBA1, NR1A1, THRA1, THRA2, THRA3, TR-ALPHA-1, c-ERBA-1, c-ERBA-ALPHA-2, EAR-7.1/EAR-7.2; ERBA-related 7; avian erythroblastic leukemia viral (v-erb-a) oncogene homolog; thyroid hormone receptor, alpha; thyroid hormone receptor, alpha (avian erythroblastic leukemia viral (v-erb-a) oncogene homolog); thyroid hormone receptor, alpha 1; thyroid hormone receptor, alpha-2; thyroid hormone receptor, alpha-3; triiodothyronine receptor | THRA |
| 870 | thyroid hormone receptor, beta (erythroblastic leukemia viral (v-erb-a) oncogene homolog 2, avian) | thyroid hormone receptor-beta - ERBA-BETA, ERBA2, GRTH, NR1A2, THR1, THRB1, THRB2, avian erythroblastic leukemia viral (v-erb-a) oncogene homolog 2; generalized resistance to thyroid hormone; oncogene ERBA2; thyroid hormone receptor beta 1; thyroid hormone receptor, beta; thyroid hormone receptor, beta (avian erythroblastic leukemia viral (v-erb-a) oncogene homolog 2) | THRB |
| 871 | TIMP metallopeptidase inhibitor 1 | Tissue inhibitors of metalloproteinase (TIMPs) - CLGI, EPA, EPO, HCI, TIMP, erythroid potentiating activity; fibroblast collagenase inhibitor; tissue inhibitor of metalloproteinase 1; tissue inhibitor of metalloproteinase 1 (erythroid potentiating activity, collagenase inhibitor) | TIMP1 |
| 872 | TIMP metallopeptidase inhibitor 2 | Tissue inhibitors of metalloproteinase (TIMPs) - CSC-21K, tissue inhibitor of metalloproteinase 2; tissue inhibitor of metalloproteinase 2 precursor; tissue inhibitor of metalloproteinases 2 | TIMP2 |
| 873 | TIMP metallopeptidase inhibitor 3 (Sorsby fundus dystrophy, pseudoinflammatory) | Tissue inhibitors of metalloproteinase (TIMPs) - HSMRK222, K222, K222TA2, SFD, MIG-5 protein; tissue inhibitor of metalloproteinase 3; tissue inhibitor of metalloproteinase 3 (Sorsby fundus dystrophy, pseudoinflammatory) | TIMP3 |
| 874 | TIMP metallopeptidase inhibitor 4 | Tissue inhibitors of metalloproteinase (TIMPs) - tissue inhibitor of metalloproteinase 4 | TIMP4 |
| 875 | TLR4 and Name: toll-like receptor 4 | TLR4 299Gly allele associated with DECREASED CAD risk - CD284, TOLL, hToll, homolog of *Drosophila* toll | TLR4 |
| 876 | transmembrane protease, serine 13 | mosaic serine protease - MSP, MSPL, mosaic serine protease; transmembrane protease, serine 11 | TMPRSS13 |
| 877 | transmembrane protease, serine 2 | transmembrane serine protease 2 - PRSS10, epitheliasin | TMPRSS2 |
| 878 | transmembrane protease, serine 3 | transmembrane serine protease 3 - DFNB10, DFNB8, ECHOS1, TADG12, serine protease TADG12 | TMPRSS3 |

TABLE 2-continued

ARTERIORISKMARKERS

| ARTERIORISKMARKER | Official Name | Common Name | Gene Symbol |
|---|---|---|---|
| 879 | transmembrane protease, serine 4 | transmembrane serine protease 4 - MT-SP2, TMPRSS3, membrane-type serine protease 2; transmembrane serine protease 3 | TMPRSS4 |
| 880 | transmembrane protease, serine 5 (spinesin) | transmembrane serine protease 5 - SPINESIN, transmembrane protease, serine 5 | TMPRSS5 |
| 881 | thymosin, beta 4, X-linked | Thymosine beta 4 - FX, PTMB4, TB4X, TMSB4, prothymosin beta-4; thymosin beta-4; thymosin, beta 4; thymosin, beta 4, X chromosome | TMSB4X |
| 882 | thymosin, beta 4, Y-linked | Thymosine beta 4 - TB4Y, thymosin beta-4, Y isoform; thymosin, beta 4, Y chromosome | TMSB4Y |
| 883 | tumor necrosis factor (TNF superfamily, member 2) | TNF-alpha (tumour necrosis factor-alpha) - DIF, TNF-alpha, TNFA, TNFSF2, APC1 protein; TNF superfamily, member 2; TNF, macrophage-derived; TNF, monocyte-derived; cachectin; tumor necrosis factor alpha | TNF |
| 884 | tumor necrosis factor (TNF superfamily, member 2) | tumor necrosis factor receptor 2 - DIF, TNF-alpha, TNFA, TNFSF2, APC1 protein; TNF superfamily, member 2; TNF, macrophage-derived; TNF, monocyte-derived; cachectin; tumor necrosis factor alpha | TNF |
| 885 | tumor necrosis factor receptor superfamily, member 10b | soluble necrosis factor receptor - CD262, DR5, KILLER, KILLER/DR5, TRAIL-R2, TRAILR2, TRICK2, TRICK2A, TRICK2B, TRICKB, ZTNFR9, Fas-like protein precursor; TNF-related apoptosis-inducing ligand receptor 2; TRAIL receptor 2; apoptosis inducing protein TRICK2A/2B; apoptosis inducing receptor TRAIL-R2; cytotoxic TRAIL receptor-2; death domain containing receptor for TRAIL/Apo-2L; death receptor 5; p53-regulated DNA damage-inducible cell death receptor(killer); tumor necrosis factor receptor-like protein ZTNFR9 | TNFRSF10B |
| 886 | tumor necrosis factor receptor superfamily, member 10c, decoy without an intracellular domain | soluble necrosis factor receptor - CD263, DCR1, LIT, TRAILR3, TRID, TNF related TRAIL receptor; TNF related apoptosis-inducing ligand receptor 3; TRAIL receptor 3; antagonist decoy receptor for TRAIL/Apo-2L; decoy receptor 1; decoy without an intracellular domain; lymphocyte inhibitor of TRAIL; tumor necrosis factor receptor superfamily, member 10c | TNFRSF10C |
| 887 | tumor necrosis factor receptor superfamily, member 10d, decoy with truncated death domain | soluble necrosis factor receptor - CD264, DCR2, TRAILR4, TRUNDD, TNF receptor-related receptor for TRAIL; TRAIL receptor 4; TRAIL receptor with a truncated death domain; decoy receptor 2; decoy with truncated death domain; tumor necrosis factor receptor superfamily, member 10d | TNFRSF10D |
| 888 | tumor necrosis factor receptor superfamily, member 11a, NFKB activator | CD265, EOF, FEO, ODFR, OFE, PDB2, RANK, TRANCER, osteoclast differentiation factor receptor; receptor activator of nuclear factor-kappa B; tumor necrosis factor receptor superfamily, member 11a; tumor necrosis factor receptor superfamily, member 11a, activator of NFKB | TNFRSF11A |
| 923 | tumor necrosis factor receptor superfamily, member 11b (osteoprotegerin) | OPG (osteoprotegerin), OCIF, OPG, TR1, osteoclastogenesis inhibitory factor; osteoprotegerin | TNFRSF11B |
| 889 | tumor necrosis factor receptor superfamily, member 14 (herpesvirus entry mediator) | soluble necrosis factor receptor - ATAR, HVEA, HVEM, LIGHTR, TR2, CD40-like protein precursor; herpesvirus entry mediator; herpesvirus entry mediator A; tumor necrosis factor receptor superfamily, member 14; tumor necrosis factor receptor-like gene2 | TNFRSF14 |
| 890 | tumor necrosis factor receptor superfamily, member 1A | tumor necrosis factor receptor 1 gene R92Q polymorphism - CD120a, FPF, TBP1, TNF-R, TNF-R-I, TNF-R55, TNFAR, TNFR1, TNFR55, TNFR60, p55, p55-R, p60, tumor necrosis factor binding protein 1; tumor necrosis factor receptor 1; tumor necrosis factor receptor type 1; tumor necrosis factor-alpha receptor | TNFRSF1A |

TABLE 2-continued

ARTERIORISKMARKERS

| ARTERIORISKMARKER | Official Name | Common Name | Gene Symbol |
|---|---|---|---|
| 891 | tumor necrosis factor receptor superfamily, member 1B | soluble necrosis factor receptor - CD120b, TBPII, TNF-R-II, TNF-R75, TNFBR, TNFR2, TNFR80, p75, p75TNFR, p75 TNF receptor; tumor necrosis factor beta receptor; tumor necrosis factor binding protein 2; tumor necrosis factor receptor 2 | TNFRSF1B |
| 892 | tumor necrosis factor receptor superfamily, member 25 | soluble necrosis factor receptor - APO-3, DDR3, DR3, LARD, TNFRSF12, TR3, TRAMP, WSL-1, WSL-LR, apoptosis inducing receptor; apoptosis-mediating receptor; death domain receptor 3; death domain receptor 3 soluble form; death receptor beta; lymphocyte associated receptor of death; translocating chain-association membrane protein; tumor necrosis factor receptor superfamily, member 12; tumor necrosis factor receptor superfamily, member 12 (translocating chain-association membrane protein) | TNFRSF25 |
| 893 | tumor necrosis factor superfamily, member 8 | CD30, DIS166E, KI-1, CD30 antigen; CD30L receptor; Ki-1 antigen; cytokine receptor CD30; lymphocyte activation antigen CD30 | TNFRSF8 |
| 894 | tumor necrosis factor (ligand) superfamily, member 10 | TNF-related apoptosis-inducing ligand (APO-2L) (TRAIL), APO2L, Apo-2L, CD253, TL2, TRAIL, Apo-2 ligand; TNF-related apoptosis inducing ligand TRAIL | TNFSF10 |
| 895 | tumor necrosis factor (ligand) superfamily, member 11 | CD254, ODF, OPGL, RANKL, TRANCE, hRANKL2, sOdfTNF-related; activation-induced cytokine; osteoclast differentiation factor; osteoprotegerin ligand; receptor activator of nuclear factor kappa B ligand; tumor necrosis factor ligand superfamily, member 11 | TNFSF11 |
| 896 | troponin C type 1 (slow) | TNC, TNNC; Troponin-C1, slow; cardiac troponin C; troponin C, slow; troponin C1, slow | TNNC1 |
| 897 | troponin I type 3 (cardiac) | cardiac Troponin I, CMH7, TNNC1, cTnI, familial hypertrophic cardiomyopathy 7; troponin I, cardiac | TNNI3 |
| 898 | TNNI3 interacting kinase | cardiac-related ankyrin-repeat protein kinase - CARK, TNNI3 interacting kinase variant; cardiac ankyrin repeat kinase | TNNI3K |
| 899 | troponin T type 1 (skeletal, slow) | ANM, MGC104241; troponin T1, skeletal, slow; troponin-T1, skeletal, | TNNT1 |
| 900 | troponin T type 2 (cardiac) | cardiac Troponin T, CMD1D, CMH2, TnTC, cTnT, troponin T type 2, cardiac; troponin T, cardiac muscle; troponin T2, cardiac | TNNT2 |
| 901 | tropomyosin 1 (alpha) | tropomyosin, α-skeletal - HTM-alpha, TMSA, TPM1-alpha, TPM1-kappa, alpha tropomyosin; sarcomeric tropomyosin kappa; tropomyosin 1 alpha chain | TPM1 |
| 902 | tropomyosin 3 | tropomysin 3 - NEM1, TRK | TPM3 |
| 903 | tripeptidyl peptidase I | TpP - CLN2, GIG1, LINCL, TPP I, TPP-I, ceroid-lipofuscinosis, neuronal 2, late infantile (Jansky-Bielschowsky disease); growth-inhibiting protein 1; tripeptidyl-peptidase I | TPP1 |
| 904 | tripeptidyl peptidase II | Tripeptidyl Peptidase 2 - TRIPEPTIDYL PEPTIDASE II | TPP2 |
| 905 | tryptase alpha/beta 1 | mast cell Tryptase, TPS1, TPS2, TPSB1, alpha II, lung tryptase; mast cell protease II; mast cell tryptase; pituitary tryptase; skin tryptase; tryptase 1; tryptase II; tryptase beta 1; tryptase, alpha; tryptase-I; tryptase-III | TPSAB1 |
| 906 | tryptase beta 2 | mast cell Tryptase, TPS2, TPSB1, tryptaseC, beta; beta II; beta III; lung tryptase; mast cell protease I; mast cell tryptase; pituitary tryptase; skin tryptase; tryptase II; tryptase III; tryptaseB | TPSB2 |
| 907 | tryptase delta 1 | mast cell Tryptase, MCP7L1, MMCP-7L, hmMCP-3-like tryptase III; hmMCP-7-like; mMCP-7-like delta II tryptase; mMCP-7-like-1; mMCP-7-like-2; mast cell protease 7-like; mast cell tryptase | TPSD1 |
| 908 | tryptase gamma 1 | mast cell Tryptase, PRSS31, TMT, trpA, gamma I; gamma II; lung tryptase; mast cell protease II; mast cell tryptase; pituitary tryptase; skin tryptase; transmembrane tryptase | TPSG1 |

TABLE 2-continued

ARTERIORISKMARKERS

| ARTERIORISKMARKER | Official Name | Common Name | Gene Symbol |
|---|---|---|---|
| 909 | thyrotropin-releasing hormone degrading enzyme | thyrotropin-releasing hormone degrading ectoenzyme - PAP-II, PGPEP2, TRH-DE, pyroglutamyl-peptidase II; thyrotropin-releasing hormone degrading ectoenzyme | TRHDE |
| 910 | transient receptor potential cation channel, subfamily V, member 1 | vanilloid receptor 1 - VR1, capsaicin receptor; transient receptor potential vanilloid 1a; transient receptor potential vanilloid 1b; vanilloid receptor subtype 1, capsaicin receptor; transient receptor potential vanilloid subfamily 1 (TRPV1) | TRPV1 |
| 911 | thymidylate synthetase | thymidylate synthase - HsT422, TMS, TS, Tsase, Thymidylate synthase | TYMS |
| 912 | UDP glycosyltransferase 8 (UDP-galactose ceramide galactosyltransferase) | ceramide glucosyl transferase - CGT | UGT8 |
| 913 | urotensin 2 receptor | G-protein coupled receptor 14 - GPR14, UTR, UTR2, G protein-coupled receptor 14 | UTS2R |
| 914 | vascular cell adhesion molecule 1 | (soluble) vascular cell adhesion molecule-1, CD106, INCAM-100, CD106 antigen, VCAM-1 | VCAM1 |
| 915 | vinculin | vinculin - MVCL | VCL |
| 916 | vitamin D (1,25- dihydroxyvitamin D3) receptor | vitamin D receptor 1 - NR1I1 - vitamin D (1,25-dihydroxyvitamin D3) receptor | VDR |
| 917 | vascular endothelial growth factor | VEGF - VEGFA, VPF, vascular endothelial growth factor A; vascular permeability factor | VEGF |
| 918 | vascular endothelial growth factor A | MGC70609, VEGF, VEGF-A, VPF; vascular permeability factor, VEGF(A)21 | VEGFA |
| 919 | vasoactive intestinal peptide receptor 1 | vasoactive intestinal peptide receptor 1 - HVR1, II, PACAP-R-2, RCD1, RDC1, VIPR, VIRG, VPAC1, PACAP type II receptor; VIP receptor, type I; pituitary adenylate cyclase activating polypeptide receptor, type II | VIPR1 |
| 920 | vasoactive intestinal peptide receptor 2 | Vasoactive Intestinal Peptide Receptor 2 - VPAC2 | VIPR2 |
| 921 | vitronectin | fibrin monomer, complement S-protein; epibolin; serum spreading factor; somatomedin B; vitronectin (serum spreading factor, somatomedin B, complement S-protein) | VTN |
| 922 | von Willebrand factor A domain containing 2 | von Willebrand Factor propeptide (vWFAgII) - AMACO, CCSP-2, A-domain containing protein similar to matrilin and collagen; colon cancer diagnostic marker; colon cancer secreted protein-2 | VWA2 |
| 938 | von Willebrand factor | von Willebrand factor, F8VWF, VWD, coagulation factor VIII VWF | VWF |
| 939 | chemokine (C motif) receptor 1 | G protein-coupled receptor 5 - CCXCR1, GPR5, G protein-coupled receptor 5; XC chemokine receptor 1; chemokine (C motif) XC receptor 1; lymphotactin receptor | XCR1 |
| 940 | X-prolyl aminopeptidase (aminopeptidase P) 1, soluble | x-prolyl aminopeptidase (aminopeptidase P) 1 - SAMP, XPNPEP, XPNPEPL, XPNPEPL1, X-prolyl aminopeptidase (aminopeptidase P) 1, soluble (SAMP, XPNPEP, XPNPEPL); X-prolyl aminopeptidase (aminopeptidase P)-like | XPNPEP1 |
| 941 | X-prolyl aminopeptidase (aminopeptidase P) 2, membrane-bound | X-prolyl aminopeptidase 2 - X-prolyl aminopeptidase 2 (aminopeptidase P); X-prolyl aminopeptidase 2, membrane-bound; aminoacylproline aminopeptidase; aminopeptidase P | XPNPEP2 |
| 942 | sterile alpha motif and leucine zipper containing kinase AZK | sterile-alpha motif and leucine zipper containing kinase - AZK, MLK7, MLT, MLTK, MRK, mlklak, MLK-like mitogen-activated protein triple kinase; MLK-related kinase; cervical cancer suppressor gene 4 protein; leucine zipper- and sterile alpha motif-containing kinase; mitogen-activated protein kinase kinase kinase MLT; mixed lineage kinase 7; mixed lineage kinase with a leucine zipper and a sterile alpha motif; mixed lineage kinase-related kinase; mixed lineage kinase-related kinase MRK-beta | ZAK |
| 943 | leukocyte-platelet aggregates (LPA) - measured by whole blood flow cytometry | leukocyte-platelet aggregates (LPA) - measured by whole blood flow cytometry | zCells |
| 944 | Mobilization of CD34/CXCR4+, CD34/CD117+, c-met+ stem cells | Mobilization of CD34/CXCR4+, CD34/CD117+, c-met+ stem cells | zCells |
| 945 | CD14+CD16+ monocytes | CD14+CD16+ monocytes | zCells |
| 946 | circulating endothelial cells | circulating endothelial cells | zCells |
| 947 | HLADR+ CD3+ and CD69+CD4+ cells | HLADR+ CD3+ and CD69+CD4+ cells | zCells |
| 948 | Circulating hHSP60-specific CD4 + CD28null cells | Circulating hHSP60-specific CD4 + CD28null cells | zCells |

TABLE 2-continued

ARTERIORISKMARKERS

| ARTERIORISKMARKER | Official Name | Common Name | Gene Symbol |
|---|---|---|---|
| 949 | erythrocyte aggregability | erythrocyte aggregability | zCells |
| 950 | Cytomegalovirus infection | CMV infection | zCMV |
| 951 | D-Dimer | D-Dimer, Fragment D-dimer, Fibrin degradation fragment, Fibrin Degradation Products (FDP) | zD-Dimer |
| 952 | 4-hydroxynonenal (HNE) | 4-hydroxynonenal (HNE) | zHNE |
| 953 | malondialdehyde-modified low density lipoprotein (MDA-LDL) | malondialdehyde-modified low density lipoprotein (MDA-LDL) | zMDA-LDL |
| 954 | thromboxane A2 | Thromboxane (TX) A(2), a cyclooxygenase-derived mediator | zMetabolite |
| 955 | thromboxane B2 | 11-Dehydro-thromboxane B2, a stable thromboxane metabolite, is a full agonistof chemoattractant receptor-homologous molecule expressed on TH2 cells (CRTH2)in human eosinophils andbasophils | zMetabolite |
| 956 | uric acid | uric acid | zMetabolite |
| 957 | Unbound free fatty acids (FFA(u)) | Unbound free fatty acids (FFA(u)) | zMetabolite |
| 958 | neopterin | neopterin | zMetabolite |
| 959 | glucose | altered glycemia | zMetabolite |
| 960 | malondialdehyde (MDA) | malondialdehyde (MDA) | zMetabolite |
| 961 | calcium | coronary calcium - (coronary for CEP) & (ionized calcium for OFP) | zMetabolite |
| 962 | lactic acid | lactic acid | zMetabolite |
| 963 | prostacyclin | PGI2-present in urine | zMetabolite |
| 964 | Total Sialic Acid (TSA) | Total Sialic Acid (TSA) | zMetabolite |
| 965 | citric acid | citric acid | zMetabolite |
| 970 | citrulline | citrulline | zMetabolite |
| 971 | uridine | uridine | zMetabolite |
| 972 | hyaluronan | hyaluronan | zMetabolite |
| 973 | alanine | alanine | zMetabolite |
| 974 | argininosuccinate | argininosuccinate | zMetabolite |
| 975 | Gamma-aminobutyric acid (GABA) | Gamma-aminobutyric acid (GABA) | zMetabolite |
| 976 | aconitic acid | aconitic acid | zMetabolite |
| 977 | hydroxyhippuric acid | hydroxyhippuric acid | zMetabolite |
| 978 | hypoxanthine | hypoxanthine | zMetabolite |
| 979 | inosine | inosine | zMetabolite |
| 980 | oxaloacetate | oxaloacetate | zMetabolite |
| 981 | phenylalanine | phenylalanine | zMetabolite |
| 982 | serine | serine | zMetabolite |
| 983 | tryptophan | tryptophan | zMetabolite |
| 984 | lysophosphatidic acid | lysophosphatidic acid | zMetabolite |
| 985 | 8-isoprostane-prostaglandin F 2 (Iso-P) | 8-isoprostane-prostaglandin F 2 (Iso-P) | zMetabolite |
| 986 | Remnant-like lipoprotein particles cholesterol; RLP-C | Remnant-like lipoprotein particles cholesterol; RLP-C | zMetabolite |
| 987 | 6-ketoprostaglandin F1a | 6-ketoprostaglandin F1a, the stable metabolite of prostacyclin (PGI2) | zMetabolite |
| 988 | chlorine soluble mucoprotein | chlorine soluble mucoprotein | zMetabolite |
| 989 | neutrophil protease-4 (NP4) | neutrophil protease-4 (NP4) | zMetabolite |
| 990 | protenin | protenin | zMetabolite |
| 991 | Intraplatelet Tetrahydrobiopterin (BH[4]) | Intraplatelet BH(4) | zMetabolite |
| 992 | hydroxybutyrate dehydrogenase (HBDH) | hydroxybutyrate dehydrogenase (HBDH) | zMetabolite |
| 993 | Med2 | Subunit of the RNA polymerase II mediator complex; associates with core polymerase subunits to form the RNA polymerase II holoenzyme; essential for transcriptional regulation | zMetabolite |
| 994 | 2,3-dinor-6-keto Prostaglandin F1α | 2,3-dinor-6-keto PGF1α | zMetabolite |
| 995 | 8,12-iso-iPF2α | 8,12-iso-iPF2α | zMetabolite |
| 996 | acylglycerol acyltransferase-like proteins DC4 | acylglycerol acyltransferase-like proteins DC4 | zMetabolite |
| 997 | ATPase Ca++ binding protein | ATPase Ca++ binding protein | zMetabolite |
| 998 | calcium-dependent alpha-latrotoxin receptor | calcium-dependent alpha-latrotoxin receptor | zMetabolite |
| 999 | cardiovascular disorder plasma polypeptide | cardiovascular disorder plasma polypeptide | zMetabolite |
| 1000 | G-protein-coupled receptor H7TBA62 | G-protein-coupled receptor H7TBA62, Polynucleotide encoding G-protein coupled receptor (H7TBA62) | zMetabolite |
| 1001 | hematopoietin receptor-like protein | hematopoietin receptor-like protein | zMetabolite |
| 1002 | HM74-like G protein coupled receptor | HM74-like G protein coupled receptor | zMetabolite |
| 1003 | IGS70 | IGS70 | zMetabolite |
| 1004 | neuropeptide Y G protein-coupled receptor | neuropeptide Y G protein-coupled receptor | zMetabolite |
| 1005 | organic anion transporter ust3 like 3 | organic anion transporter ust3 like 3 | zMetabolite |
| 1006 | phosphate channel interacting protein | phosphate channel interacting protein | zMetabolite |
| 1007 | phosphodiesterase 9a3 | phosphodiesterase 9a3 | zMetabolite |
| 1008 | phosphodiesterase 9a4 | phosphodiesterase 9a4 | zMetabolite |
| 1009 | plasma 13-HODE | plasma 13-HODE | zMetabolite |
| 1010 | secretin-like G protein-coupled receptor | secretin-like G protein-coupled receptor | zMetabolite |

TABLE 2-continued

ARTERIORISKMARKERS

| ARTERIORISKMARKER | Official Name | Common Name | Gene Symbol |
|---|---|---|---|
| 1011 | iPF2α-III | iPF2α-III | zMetabolite |
| 1012 | LFA-2 | LFA-2, human lymphocyte membrane protein | zMetabolite |
| 1013 | phosphoglyceric acid mutase-MB | phosphoglyceric acid mutase-MB | zMetabolite |
| 1014 | renin-angiotensin system | renin-angiotensin system | zMetabolite |
| 1015 | sphingosine | sphingosine | zMetabolite |
| 1016 | mitochondrial DNA | mitochondrial DNA | zmtDNA |
| 1017 | C terminal propeptide of Type I procollagen (PICP) | C terminal propeptide of Type I procollagen (PICP) - CICP, collagen I synthesis byproduct (PICP) | zPICP |
| 1018 | collagen III synthesis byproduct (PIIINP) | collagen III synthesis byproduct (PIIINP) | zPIIINP |
| 1019 | amino-terminal propeptide of type I procollagen (PINP) | Amino-terminal propeptide of type I procollagen (PINP), collagen I synthesis byproduct (PINP) | zPINP |
| 1020 | collagen I synthesis byproduct (PIP) | collagen I synthesis byproduct (PIP) | zPIP |
| 1021 | Homocysteine (total) | Homocysteine (total) | ztHcy |
| 1022 | a vascular endothelial cell specific and LIM domain containing molecule | a vascular endothelial cell specific and LIM domain containing molecule | zVELP2 |
| 1023 | white blood cell count | white blood cell count | zWBC Count |

In addition to the above listed analyte-based ARTERIORISKMARKERS, all of the previously described Clinical Parameters and Traditional Laboratory Risk Factors are also considered ATERIORISKMARKERS.

Additional ARTERIORISKMARKERS are those described in co-pending applications, U.S. patent application Ser. No. 11/546,874 and U.S. patent application Ser. No. 11/788,260, the disclosures of which are herein incorporated in their entirety.

One skilled in the art will note that the above listed ARTERIORISKMARKERS come from a diverse set of physiological and biological pathways, including many which are not commonly accepted to be related to arteriovascular disease. These groupings of different ARTERIORISKMARKERS, even within those high significance segments, may presage differing signals of the stage or rate of the progression of the disease. Such distinct groupings of ARTERIORISKMARKERS may allow a more biologically detailed and clinically useful signal from the ARTERIORISKMARKERS as well as opportunities for pattern recognition within the ARTERIORISKMARKER algorithms combining the multiple ARTERIORISKMARKER signals.

The present invention concerns, in one aspect, a subset of ARTERIORISKMARKERS; other ARTERIORISKMARKERS and even biomarkers which are not listed in the above Table 2, but related to these physiological and biological pathways, may prove to be useful given the signal and information provided from these studies. To the extent that other biomarker pathway participants (i.e., other biomarker participants in common pathways with those biomarkers contained within the list of ARTERIORISKMARKERS in the above Table 2) are also relevant pathway participants in arteriovascular disease or an arteriovascular event, they may be functional equivalents to the biomarkers thus far disclosed in Table 2. These other pathway participants are also considered ARTERIORISKMARKERS in the context of the present invention, provided they additionally share certain defined characteristics of a good biomarker, which would include both involvement in the herein disclosed biological processes and also analytically important characteristics such as the bioavailability of said biomarkers at a useful signal to noise ratio, and in a useful and accessible sample matrix such as blood serum, Such requirements typically limit the diagnostic usefulness of many members of a biological pathway, and frequently occurs only in pathway members that constitute secretory substances, those accessible on the plasma membranes of cells, as well as those that are released into the serum upon cell death, due to apoptosis or for other reasons such as endothelial remodeling or other cell turnover or cell necrotic processes, whether or not they are related to the disease progression of arteriovascular disease or an arteriovascular event. However, the remaining and future biomarkers that meet this high standard for ARTERIORISKMARKERS are likely to be quite valuable.

Furthermore, other unlisted biomarkers will be very highly correlated with the biomarkers listed as ARTERIORISKMARKERS in Table 1 (for the purpose of this application, any two variables will be considered to be "very highly correlated" when they have a Coefficient of Determination ($R^2$) of 0.5 or greater). The present invention encompasses such functional and statistical equivalents to the aforementioned ARTERIORISKMARKERS. Furthermore, the statistical utility of such additional ARTERIORISKMARKERS is substantially dependent on the cross-correlation between multiple biomarkers and any new biomarkers will often be required to operate within a panel in order to elaborate the meaning of the underlying biology.

One or more, preferably two or more of the listed ARTERIORISKMARKERS can be detected in the practice of the present invention. For example, two (2), three (3), four (4), five (5), ten (10), fifteen (15), twenty (20), forty (40), fifty (50), seventy-five (75), one hundred (100), one hundred and twenty five (125), one hundred and fifty (150), one hundred and seventy-five (175), two hundred (200), two hundred and ten (210), two hundred and twenty (220), two hundred and thirty (230), two hundred and forty (240), two hundred and fifty (250), two hundred and sixty (260) or more, four hundred (400) or more, six hundred (600) or more, eight hundred (800) or more, and 1000 (1000) or more ARTERIORISKMARKERS can be detected.

In some aspects, all 1023 ARTERIORISKMARKERS listed herein can be detected. Preferred ranges from which the number of ARTERIORISKMARKERS can be detected include ranges bounded by any minimum selected from between one and 1,023, particularly two, five, ten, twenty, fifty, seventy-five, one hundred, one hundred and twenty five, one hundred and fifty, one hundred and seventy-five, two hundred, two hundred and ten, two hundred and twenty, two hundred and thirty, two hundred and forty, two hundred and fifty, five hundred, seven hundred, and 1000 paired with any maximum up to the total known ARTERIORISK-MARKERS, particularly five, ten, twenty, fifty, and seventy-five. Particularly preferred ranges include two to five (2-5), two to ten (2-10), two to fifty (2-50), two to seventy-five (2-75), two to one hundred (2-100), five to ten (5-10), five to twenty (5-20), five to fifty (5-50), five to seventy-five (5-75), five to one hundred (5-100), ten to twenty (10-20), ten to fifty (10-50), ten to seventy-five (10-75), ten to one hundred (10-100), twenty to fifty (20-50), twenty to seventy-five (20-75), twenty to one hundred (20-100), fifty to seventy-five (50-75), fifty to one hundred (50-100), one hundred to one hundred and twenty-five (100-125), one hundred and twenty-five to one hundred and fifty (125-150), one hundred and fifty to one hundred and seventy five (150-175), one hundred and seventy-five to two hundred (175-200), two hundred to two hundred and ten (200-210), two hundred and ten to two hundred and twenty (210-220), two hundred and twenty to two hundred and thirty (220-230), two hundred and thirty to two hundred and forty (230-240), two hundred and forty to two hundred and fifty (240-250), two hundred and fifty to two hundred and sixty (250-260), two hundred and sixty to more than three hundred (260-300), three hundred and fifty to more than five hundred (350-500), five hundred and fifty to more than seven hundred (550-700), seven hundred and fifty to one thousand (750-1000), and one thousand and fifty to more than one thousand and twenty (1050-1020).

Construction of ARTERIORISKMARKER Panels

Groupings of ARTERIORISKMARKERS can be included in "panels." A "panel" within the context of the present invention means a group of biomarkers (whether they are ARTERIORISKMARKERS, clinical parameters, or traditional laboratory risk factors) that includes more than one ARTERIORISKMARKER. A panel can also comprise additional biomarkers, e.g., clinical parameters, traditional laboratory risk factors, known to be present or associated with arteriovascular disease, in combination with a selected group of the ARTERIORISKMARKERS listed in Table 2.

As noted above, many of the individual ARTERIORISK-MARKERS, clinical parameters, and traditional laboratory risk factors listed, when used alone and not as a member of a multi-biomarker panel of ARTERIORISKMARKERS, have little or no clinical use in reliably distinguishing individual normal subjects, subjects at risk for having an arteriovascular event, and subjects having arteriovascular disease from each other in a selected general population, and thus cannot reliably be used alone in classifying any subject between those three states. Even where there are statistically significant differences in their mean measurements in each of these populations, as commonly occurs in studies which are sufficiently powered, such biomarkers may remain limited in their applicability to an individual subject, and contribute little to diagnostic or prognostic predictions for that subject. A common measure of statistical significance is the p-value, which indicates the probability that an observation has arisen by chance alone; preferably, such p-values are 0.05 or less, representing a 5% or less chance that the observation of interest arose by chance. Such p-values depend significantly on the power of the study performed. As discussed above, in the study populations of the below Examples, none of the individual ARTERIORISKMARK-ERS demonstrated a very high degree of diagnostic accuracy when used by itself for the diagnosis of arteriovascular disease or an arteriovascular event, even though many showed statistically significant differences between the study populations (as seen in FIG. 4 and FIG. 5 in the Examples). However, when each ARTERIORISKMARKER is taken individually to assess the individual subjects of the population, such ARTERIORISKMARKERS are of limited use in the intended risk indications for the invention (as is shown in FIG. 14).

Figure 6:
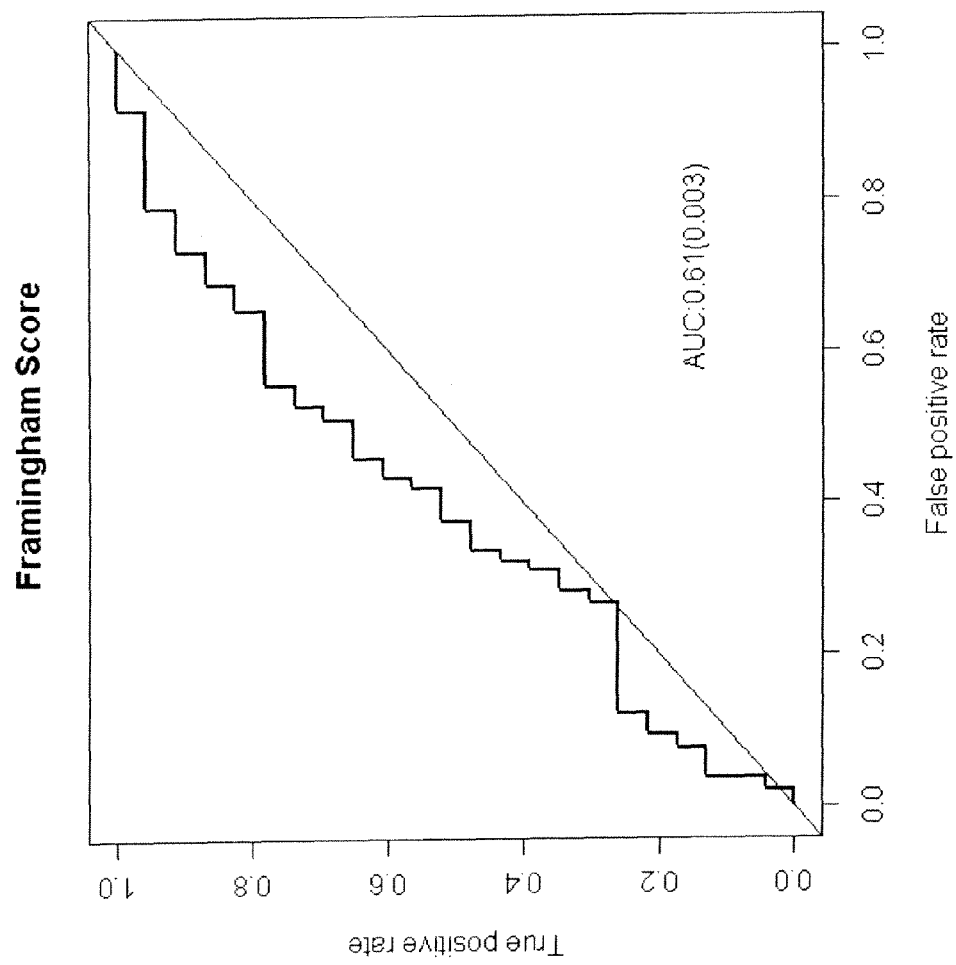
FIG. 6 is a chart depicting the Receiver Operator Characteristic (ROC) curve of a global risk assessment index according to the Framingham model for risk of future cardiovascular events, as measured and calculated for the Example 1 populations (sensitivity and specificity of the Framingham model to cardiovascular events excluding stroke patients from the analysis) and with the Area Under the Curve (AUC) statistic of 0.61 calculated and shown in the legend.

Combinations of multiple clinical parameters used singly alone or together in formulas is another approach, but also generally has difficulty in reliably achieving a high degree of diagnostic accuracy for individual subjects when tested across multiple study populations except when the blood-borne biomarkers are included (by way of example, FIG. 6 demonstrates this in the Examples). Even when individual traditional laboratory risk factors that are blood-borne biomarkers are added to clinical parameters, as with HDLC within the Framingham Risk Score of Wilson (1998), it is difficult to reliably achieve a high degree of diagnostic accuracy for individual subjects when tested across multiple study populations. Used herein, for a formula or biomarker (including ARTERIORISKMARKERS, clinical parameters, and traditional laboratory risk factors) to "reliably achieve" a given level of diagnostic accuracy meant to achieve this metric under cross-validation (such as LOO-CV or 10-Fold CV within the original population) or in more than one population (e.g., demonstrate it beyond the original population in which the formula or biomarker was originally measured and trained). It is recognized that biological variability is such that it is unlikely that any given formula or biomarker will achieve the same level of diagnostic accuracy in every individual population in which it can be measured, and that substantial similarity between such training and validation populations is assumed and, indeed, required.

Despite this individual ARTERIORISKMARKER performance, and the general performance of formulas combining only the traditional clinical parameters and few traditional laboratory risk factors, the present inventors have noted that certain specific combinations of two or more ARTERIOR-ISKMARKERS can also be used as multi-biomarker panels comprising combinations of ARTERIORISKMARKERS that are known to be involved in one or more physiological or biological pathways, and that such information can be combined and made clinically useful through the use of various formulae, including statistical classification algorithms and others, combining and in many cases extending the performance characteristics of the combination beyond that of the individual ARTERIORISKMARKERS. These specific combinations show an acceptable level of diagnostic accuracy, and, when sufficient information from multiple ARTERIORISKMARKERS is combined in a trained formula, often reliably achieve a high level of diagnostic accuracy transportable from one population to another.

The general concept of how two less specific or lower performing ARTERIORISKMARKERS are combined into novel and more useful combinations for the intended indications, is a key aspect of the invention. Multiple biomarkers can often yield better performance than the individual components when proper mathematical and clinical algorithms are used; this is often evident in both sensitivity and specificity, and results in a greater AUC. Secondly, there is often novel unperceived information in the existing biomarkers, as such was necessary in order to achieve through the new formula an improved level of sensitivity or specificity. This hidden information may hold true even for biomarkers which are generally regarded to have suboptimal clinical performance on their own. In fact, the suboptimal performance in terms of high false positive rates on a single biomarker measured alone may very well be an indicator that some important additional information is contained within the biomarker results—information which would not be elucidated absent the combination with a second biomarker and a mathematical formula.

Several statistical and modeling algorithms known in the art can be used to both assist in ARTERIORISKMARKER selection choices and optimize the algorithms combining these choices. Statistical tools such as factor and cross-biomarker correlation/covariance analyses allow more rationale approaches to panel construction. Mathematical clustering and classification tree showing the Euclidean standardized distance between the ARTERIORISKMARK- The inventors have observed that certain ARTERIORISKMARKERS are frequently selected across many different formulas and model types for biomarker selection and model formula construction. One aspect of the present invention relates to selected key biomarkers that are categorized based on the frequency of the presence of the ARTERIORISKMARKERS and in the best fit models of given types taken across multiple population studies.

One such grouping of several classes of ARTERIORISKMARKERS is presented below in Table 3 and again in FIG. 1.

TABLE 3

ARTERIORISKMARKER Categories Preferred in Panel Constructions

| Clinical Parameters | Traditional Laboratory Risk Factors | Core Markers I | Core Markers II | Supplemental Markers I | Supplemental Markers II | Additional Markers I | Additional Markers II |
|---|---|---|---|---|---|---|---|
| Age | CHOL (Cholesterol) | ANG | CCL2 | APOA1 | APOB | ACE | ANGPT2 |
| BMI | (Cholesterol) | CD40 | IGF1 | CDK6 | APOE | ADIPOQ | CCL11 |
| Diabetes | CRP | DPP4 | LEP | EGF | BAX | AGER | CCL13 |
| DBP | FGA | IL6ST | VEGF | FTH1 | C3 | AHSG | CCL7 |
| (DiastolicBP) | Glucose | POMC | | IGFBP1 | CD14 | ICAM1 | CCL8 |
| FamHX | HBA1C (A1c) | VCAM1 | | IL18 | ENG | IGFBP3 | CSF1 |
| (Family History) | HDLC (HDL) | | | IL2RA | HGF | INHBA | CXCL10 |
| Hip | INS (Insulin, | | | IL6R | HP | PLAT | IFNG |
| (Circumference) | SCp) | | | IL8 | | SELP | IL3 |
| HT (Height) | LDL (LDL) | | | SELE | | SHBG | IL5 |
| RACE | LPA | | | TNFRSF1B | | VWF | IL7 |
| (Ethnicity) | TRIG | | | | | APOA2 | MMP9 |
| SBP | (Triglycerides) | | | | | FAS | NGFB |
| (Systolic BP) | VLDL | | | | | FASLG | TNF |
| Sex | | | | | | IL6 | |
| Smoking | | | | | | MMP2 | |
| Waist | | | | | | RETN | |
| (Circumference) | | | | | | TGFB1 | |
| WT (Weight) | | | | | | TNFRSF1A | |

ERS can be advantageously used. While such grouping may or may not give direct insight into the biology and desired informational content targets for ideal arteriovascular event formula, it is the result of a method of factor analysis intended to group collections of ARTERIORISKMARKERS with similar information content (see Examples below for more statistical techniques commonly employed). Pathway informed seeding of such statistical classification techniques also may be employed, as may rational approaches based on the selection of individual ARTERIORISKMARKERS based on their participation across in particular pathways or physiological functions.

Ultimately, formula such as statistical classification algorithms can be directly used to both select ARTERIORISKMARKERS and to generate and train the optimal formula necessary to combine the results from multiple ARTERIORISKMARKERS into a single index. Often, techniques such as forward (from zero potential explanatory parameters) and backwards selection (from all available potential explanatory parameters) are used, and information criteria, such as AIC or BIC, are used to quantify the tradeoff between the performance and diagnostic accuracy of the panel and the number of ARTERIORISKMARKERS used. The position of the individual ARTERIORISKMARKER on a forward or backwards selected panel can be closely related to its provision of incremental information content for the algorithm, so the order of contribution is highly dependent on the other constituent ARTERIORISKMARKERS in the panel.

For the purposes of Table 3, the Examples and Figures, Glucose includes fasting plasma glucose (Glucose), or glucose levels during and after oral glucose tolerance (Gluc120) or other challenge testing. INS includes fasting insulin (Insulin), or insulin levels during and after oral glucose tolerance (Ins120) or other challenge testing. Used generally, it includes its precursor pro-insulin, and cleavage product soluble C-peptide (SCp).

In the context of the present invention, and without limitation of the foregoing, Table 3 above may be used to construct an ARTERIORISKMARKER panel comprising a series of individual ARTERIORISKMARKERS. The table, derived using the above statistical and pathway informed classification techniques, is intended to assist in the construction of preferred embodiments of the invention by choosing individual ARTERIORISKMARKERS from selected categories of multiple ARTERIORISKMARKERS. Preferably, at least two biomarkers from one or more of the above lists of Clinical Parameters, Traditional Laboratory Risk Factors, Core Markers I and II, Supplemental Markers I and II, and Additional Markers I and II are selected, however, the invention also concerns selection of at least two, at least three, at least four, at least five, at least six, at least seven, at least eight, at least nine, at least ten, at least eleven, and at least twelve of these biomarkers, and larger panels up to the entire set of biomarkers listed herein. For example, at least two, at least three, at least four, at least five, at least six, at least seven, at least eight, at least nine, at least ten, at least eleven, or at least twelve biomarkers can be selected from Core Biomarkers I and II, or from Supplemental Biomarkers I and II.

Using the categories presented above and without intending to limit the practice of the invention, several panel selection approaches can be used independently or, when larger panels are desired, in combination in order to achieve improvements in the diagnostic accuracy of a ARTERIORISKMARKER panel over the individual ARTERIORISKMARKERS. A preferred approach involves first choosing one or more ARTERIORISKMARKERS from the columns labeled Core Biomarkers I and II, which represents those ARTERIORISKMARKERS most frequently chosen using the various selection algorithms. While biomarker substitutions are possible with this approach, several biomarker selection formulas, across multiple studies and populations, have demonstrated and confirmed the importance of those ARTERIORISKMARKERS listed in the Core Biomarkers I and II columns shown above for the discrimination of subjects likely to convert to arteriovascular events from those who are not likely to do so. In general, for smaller panels, the higher performing ARTERIORISKMARKER panels generally contain ARTERIORISKMARKERS chosen first from the list in the Core Biomarker I column, with the highest levels of performance when several ARTERIORISKMARKERS are chosen from this category. ARTERIORISKMARKERS in the Core Biomarker II column can also be chosen first, and, in sufficiently large panels may also achieve high degrees of accuracy, but generally are most useful in combination with the ARTERIORISKMARKERS in the Core Biomarker I column shown above.

Panels of ARTERIORISKMARKERS chosen in the above fashion may also be supplemented with one or more ARTERIORISKMARKERS chosen from either or both of the columns labeled Supplemental Markers I and Additional Markers II or from the columns labeled "Traditional Laboratory Risk Factors" and "Clinical Parameters." Of the Traditional Laboratory Risk Factors, preference is given to HDLC and CRP, then FGA, finally Insulin and Glucose. Of the Clinical Parameters, preference is given to Age and measures of blood pressure (SBP and DBP) and of waist or hip circumference. Such Additional Biomarkers can be added to panels constructed from one or more ARTERIORISKMARKERS from the Core Biomarker I and/or Core Biomarker II columns.

Finally, such Supplemental Biomarkers can also be used individually as initial seeds in construction of several panels together with other ARTERIORISKMARKERS. The ARTERIORISKMARKERS identified in the Supplemental Biomarkers I and Supplemental Biomarkers II column are identified as common substitution strategies for Core Biomarkers particularly in larger panels, and panels so constructive often still arrive at acceptable diagnostic accuracy and overall ARTERIORISKMARKER panel performance. In fact, as a group, some substitutions of Core Biomarkers for Supplemental Biomarkers are beneficial for panels over a certain size, and can result in different models and selected sets of ARTERIORISKMARKERS in the panels selected using forward versus stepwise (looking back and testing each previous ARTERIORISKMARKER's individual contribution with each new ARTERIORISKMARKER addition to a panel) selection formula. Multiple biomarker substitutes for individual Core Biomarkers may also be derived from substitution analysis (presenting only a constrained set of biomarkers, without the relevant Core Biomarker, to the selection formula used, and comparing the before and after panels constructed) and replacement analysis (replacing the relevant Core Biomarker with every other potential biomarker parameter, reoptimizing the formula coefficients or weights appropriately, and ranking the best replacements by a performance criteria).

As implied above, in all such panel construction techniques, initial and subsequent Core or Supplemental Biomarkers, or Traditional Laboratory Risk Factors or Clinical Parameters, may also be deliberately selected from a field of many potential ARTERIORISKMARKERS by ARTERIORISKMARKER selection formula, including the actual performance of each derived statistical classifier algorithm itself in a training subject population, in order to maximize the improvement in performance at each incremental addition of a ARTERIORISKMARKER. In this manner, many acceptably performing panels can be constructed using any number of ARTERIORISKMARKERS up to the total set measured in one's individual practice of the invention (as summarized in FIG. 7, and in detail in FIGS. 10, 11,20 and 21 for the relevant Example populations). This technique is also of great use when the number of potential ARTERIORISKMARKERS is constrained for other reasons of practicality or economics, as the order of ARTERIORISKMARKER selection is demonstrated in the Examples to vary upon the total ARTERIORISKMARKERS available to the formula used in selection. It is a feature of the invention that the order and identity of the specific ARTERIORISKMARKERS selected under any given formula may vary based on both the starting list of potential biomarker parameters presented to the formula (the total pool from which biomarkers may be selected to form panels) as well as due to the training population characteristics and level of diversity, as shown in the Examples below.

Examples of specific ARTERIORISKMARKER panel construction derived using the above general techniques are also disclosed herein in the Examples, without limitation of the foregoing, our techniques of biomarker panel construction, or the applicability of alternative ARTERIORISKMARKERS or biomarkers from functionally equivalent classes which are also involved in the same constituent physiological and biological pathways. Of particular note are the panels summarized in FIG. 13 through 15, which include ARTERIORISKMARKERS shown in the above Tables 2 and 3 together with Traditional Laboratory Risk Factors and Clinical Parameters, and describe their AUC performance in fitted formulas within the relevant identified population and biomarker sets.

Figures 1, 2A:
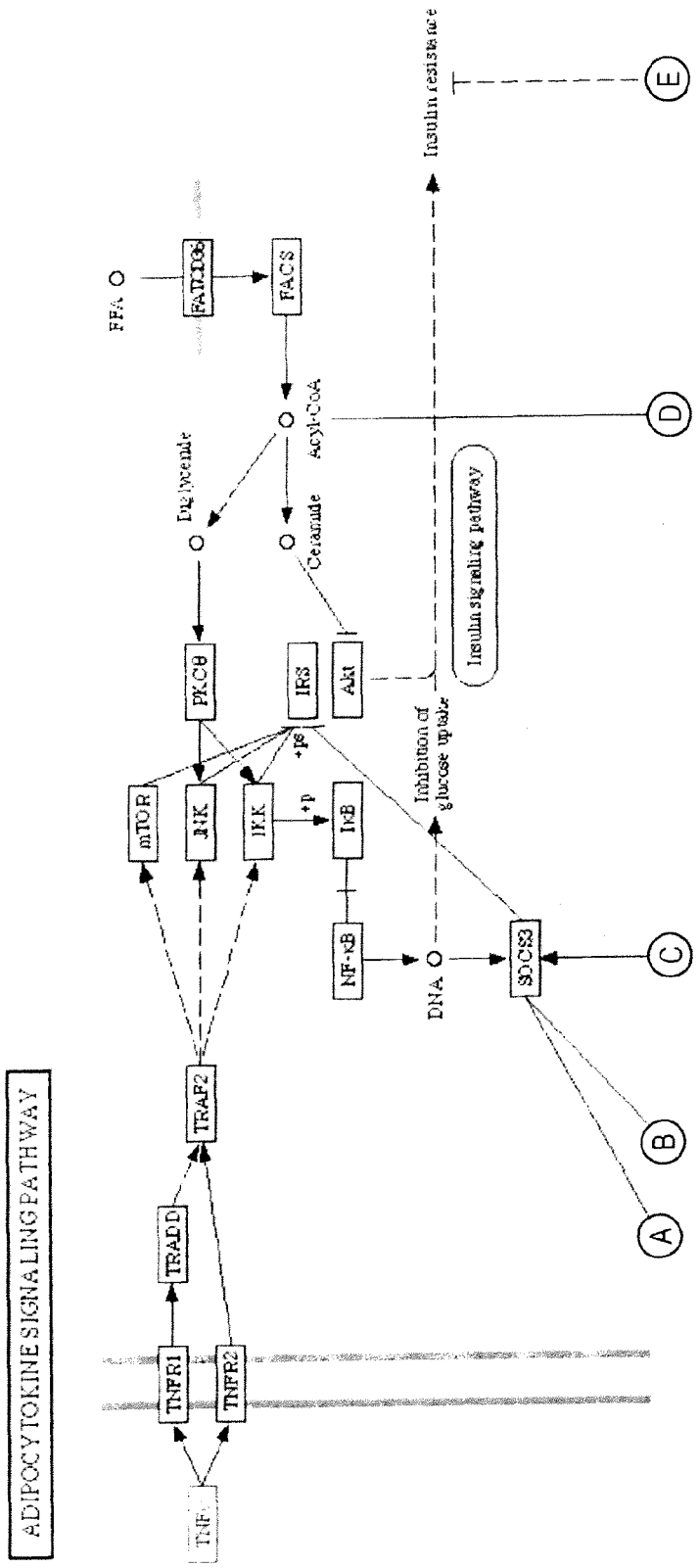
Figures 2, 2A:
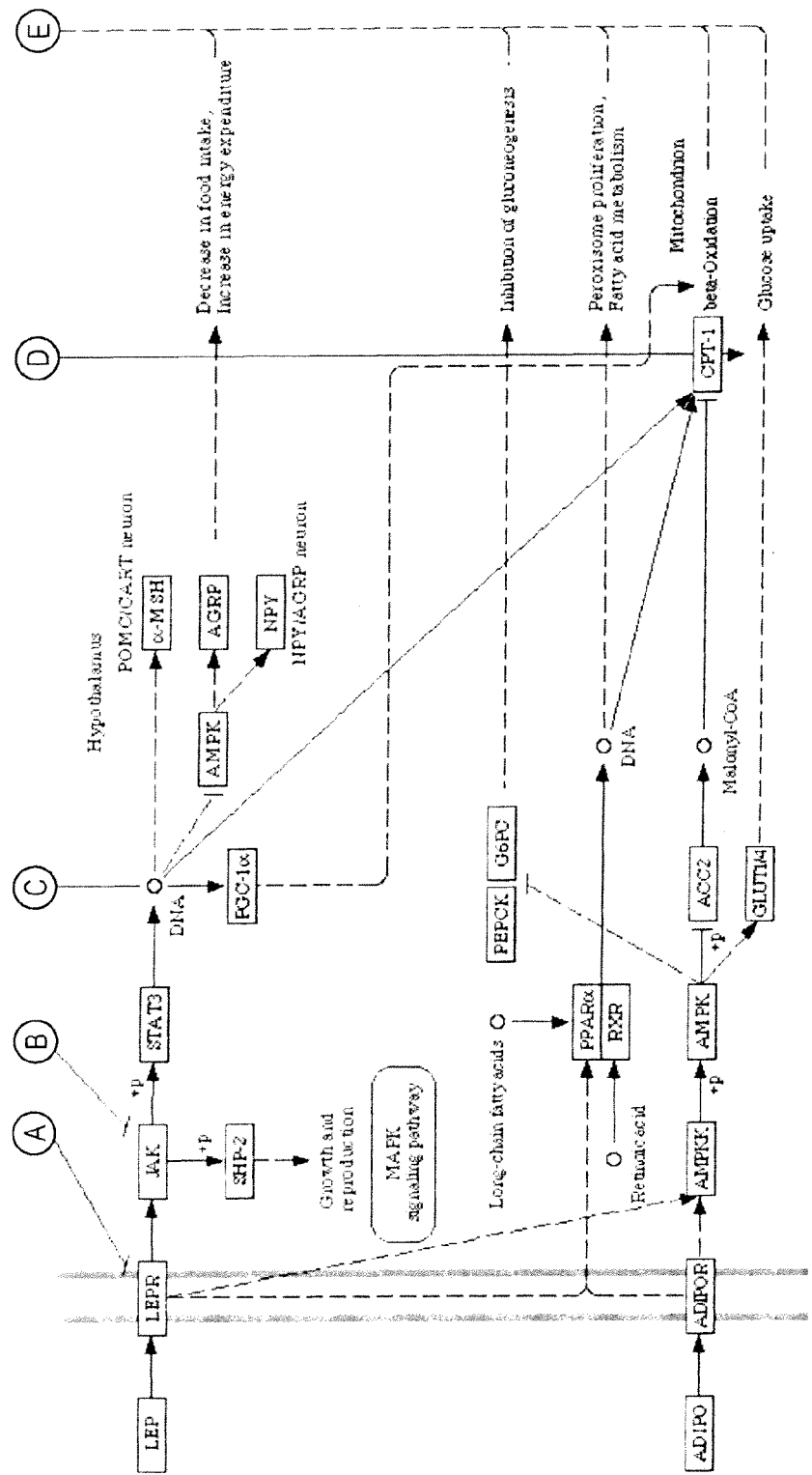
Figure 2B:
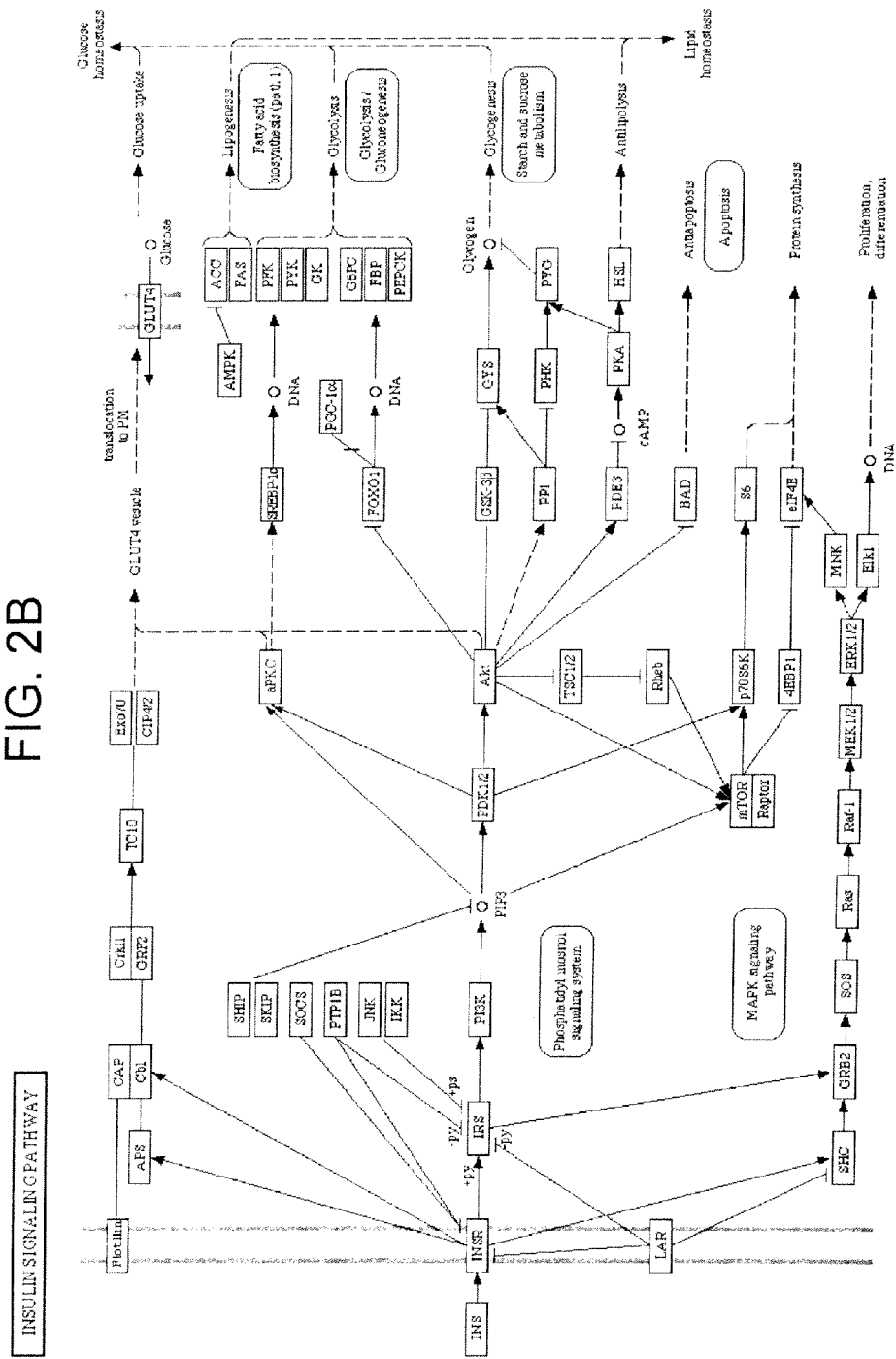
Figures 1, 2C:
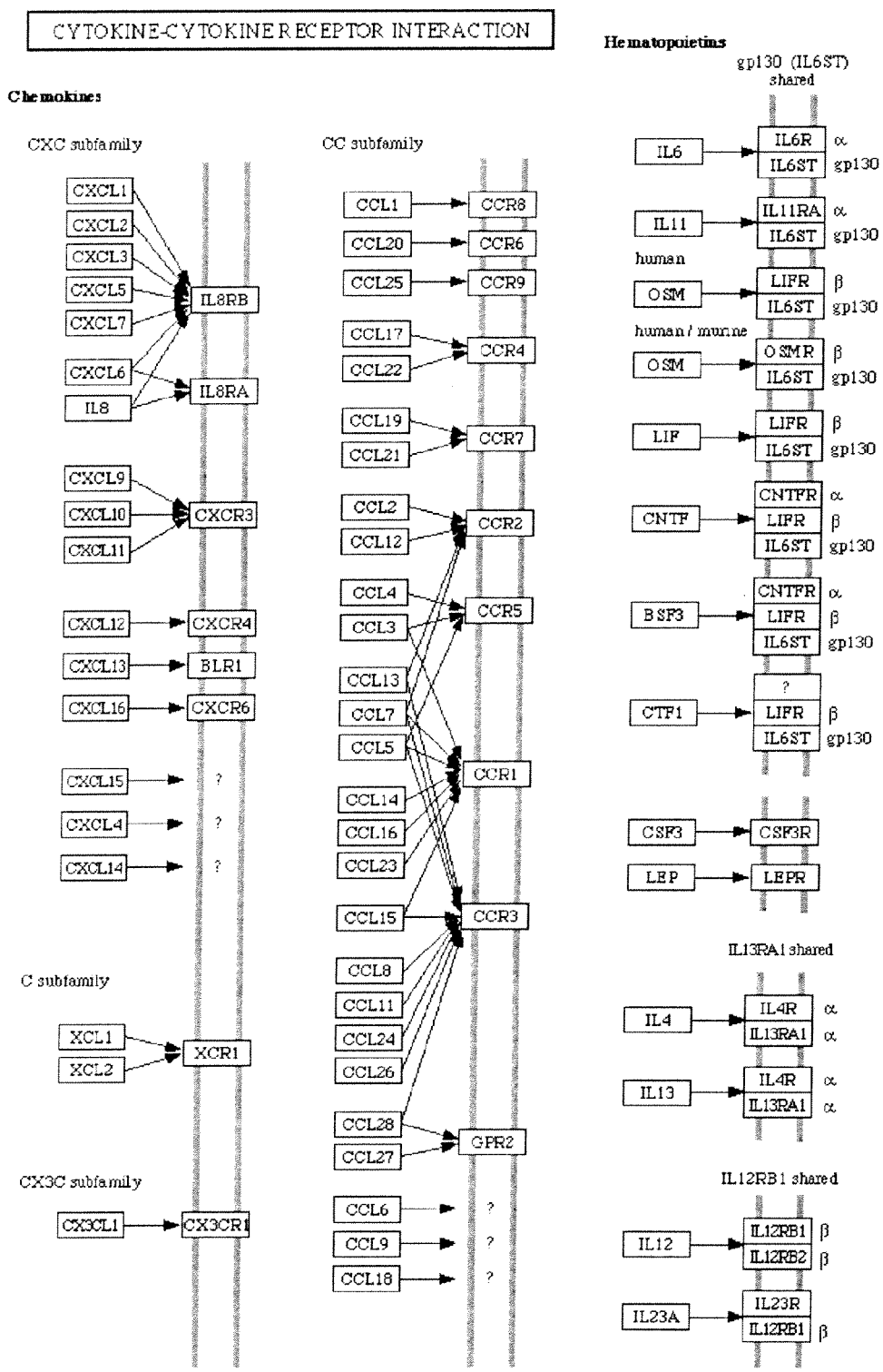
Figures 2, 2C:
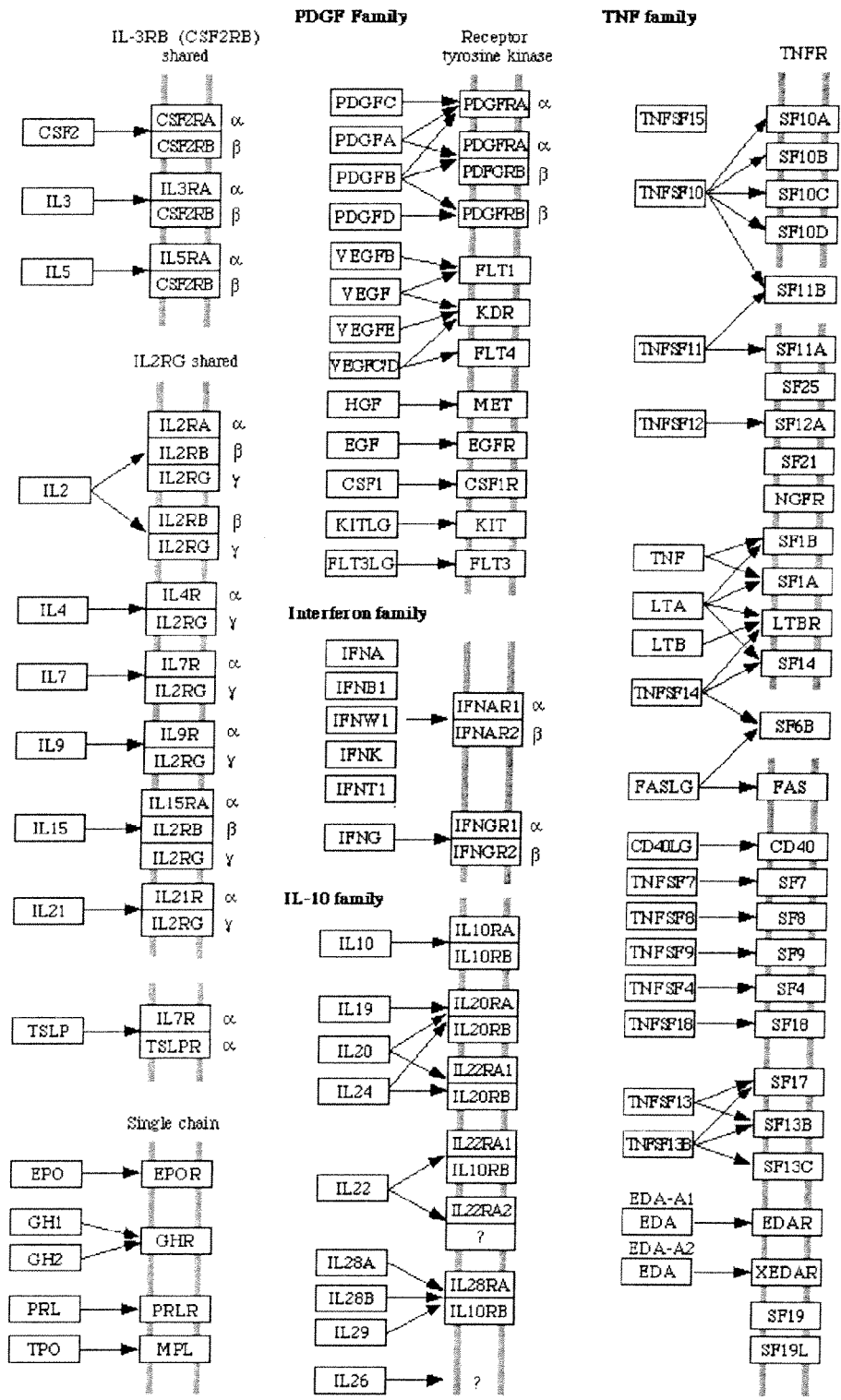
Figure 2C:
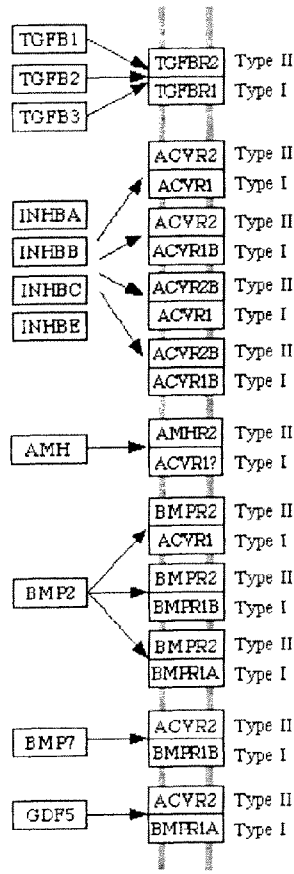
Figure 2:
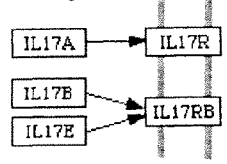
Figures 1, 2D:
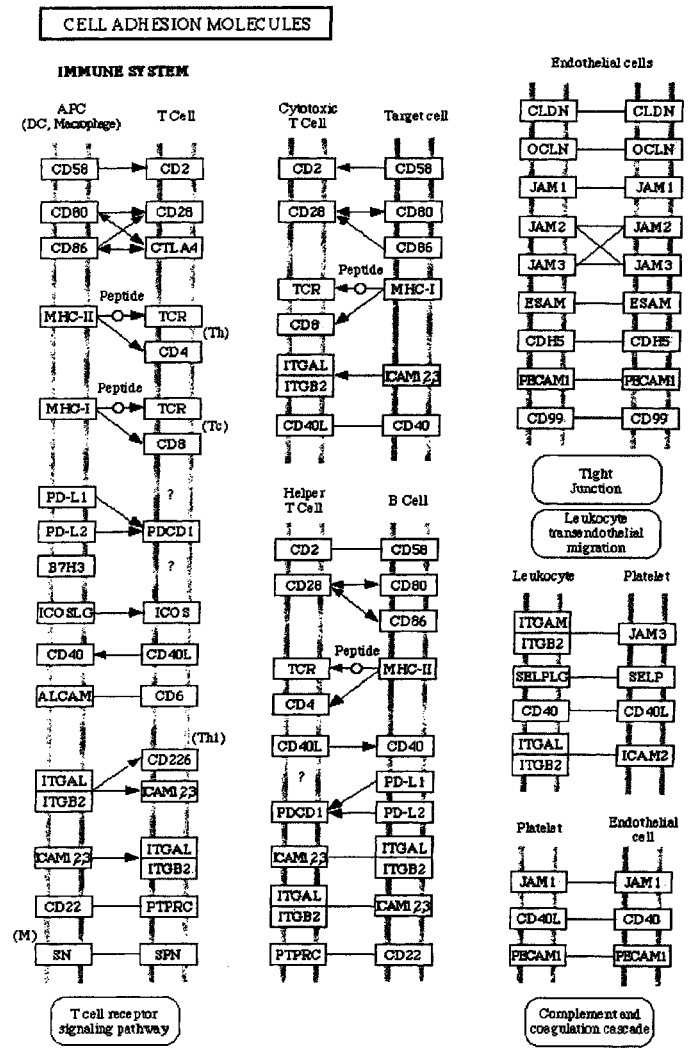
Figures 2, 2D:
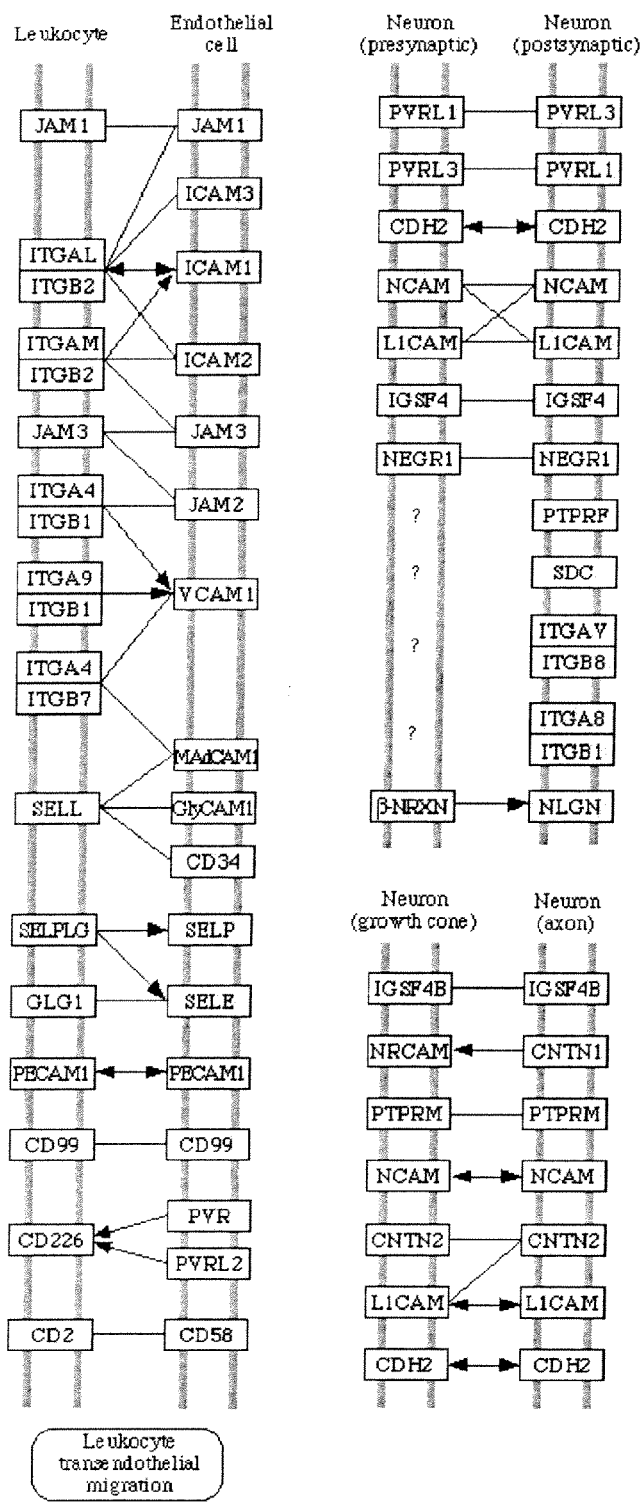
Figures 2, 2D, 3:
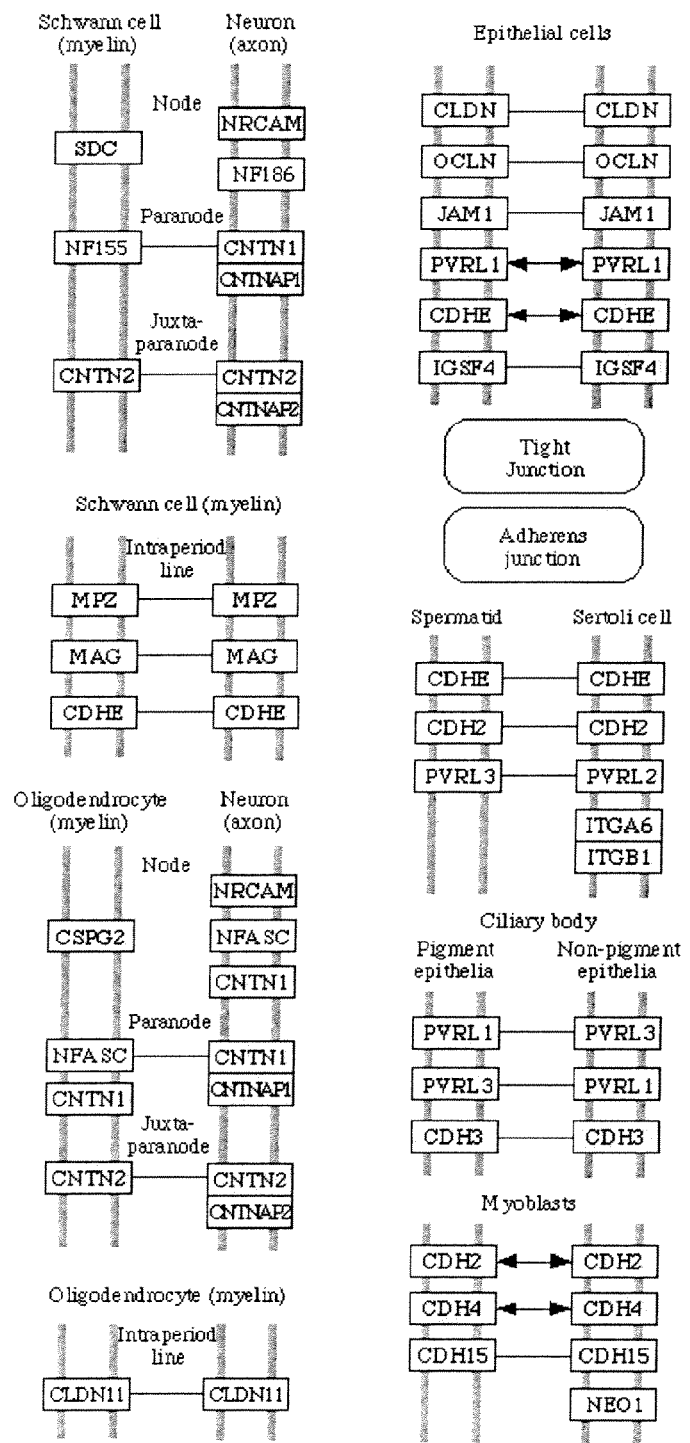
Figures 1, 2E:
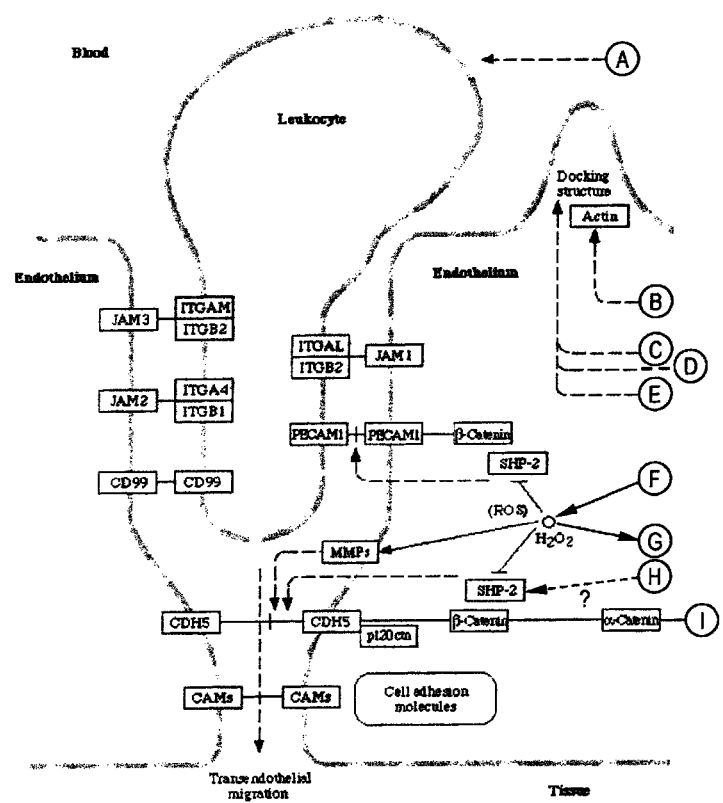
Figures 2, 2E:
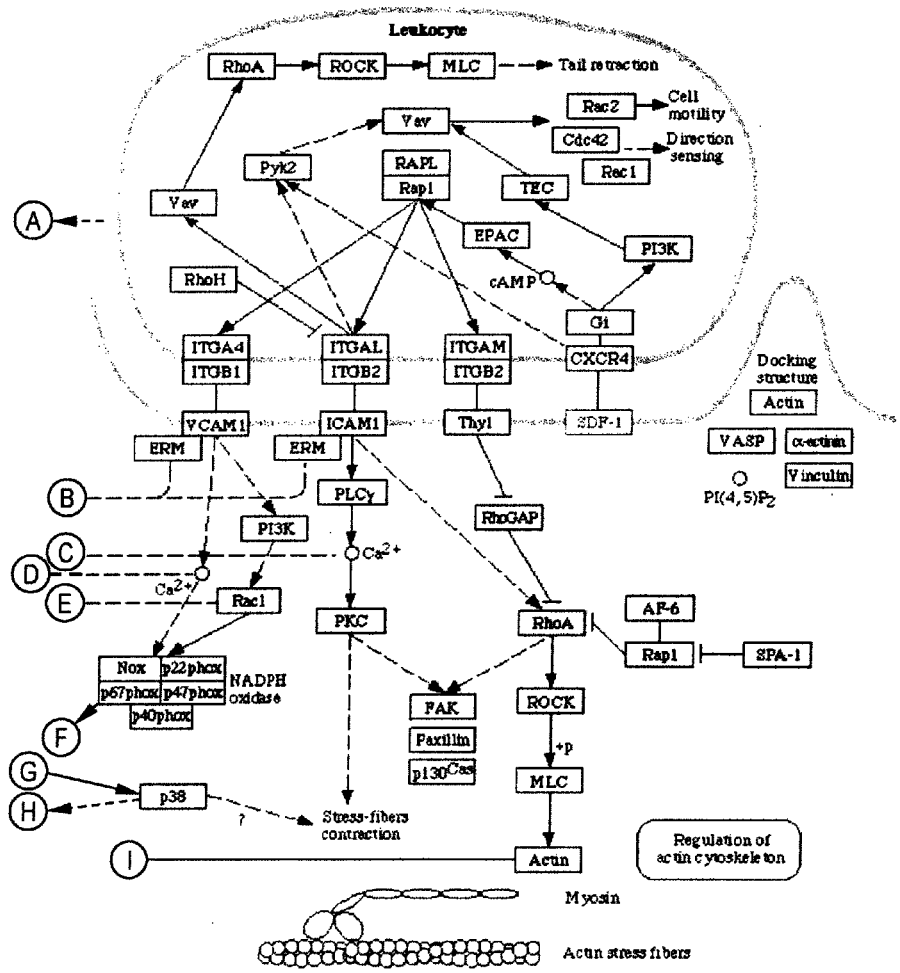
Figures 1, 2F:
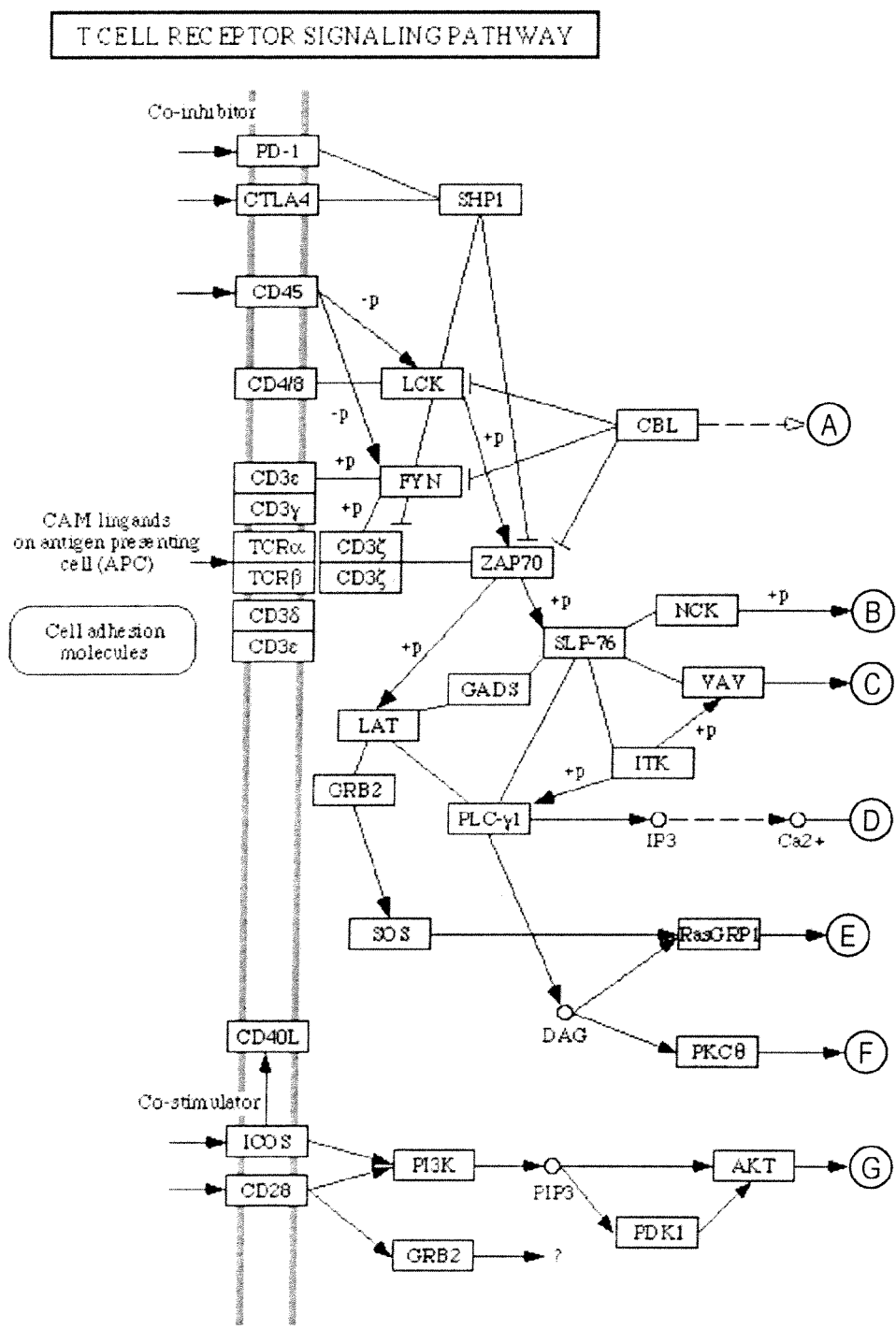
Figures 2, 2F:
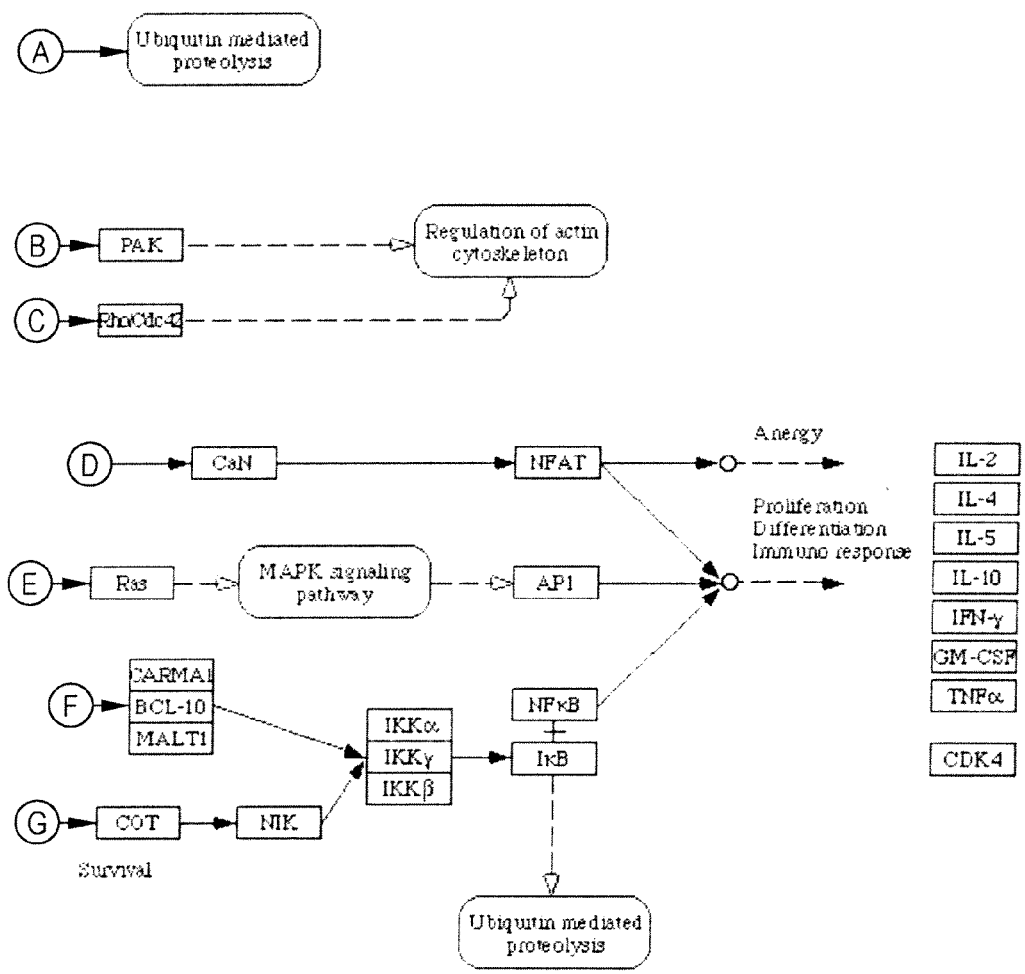
Figures 1, 2G:
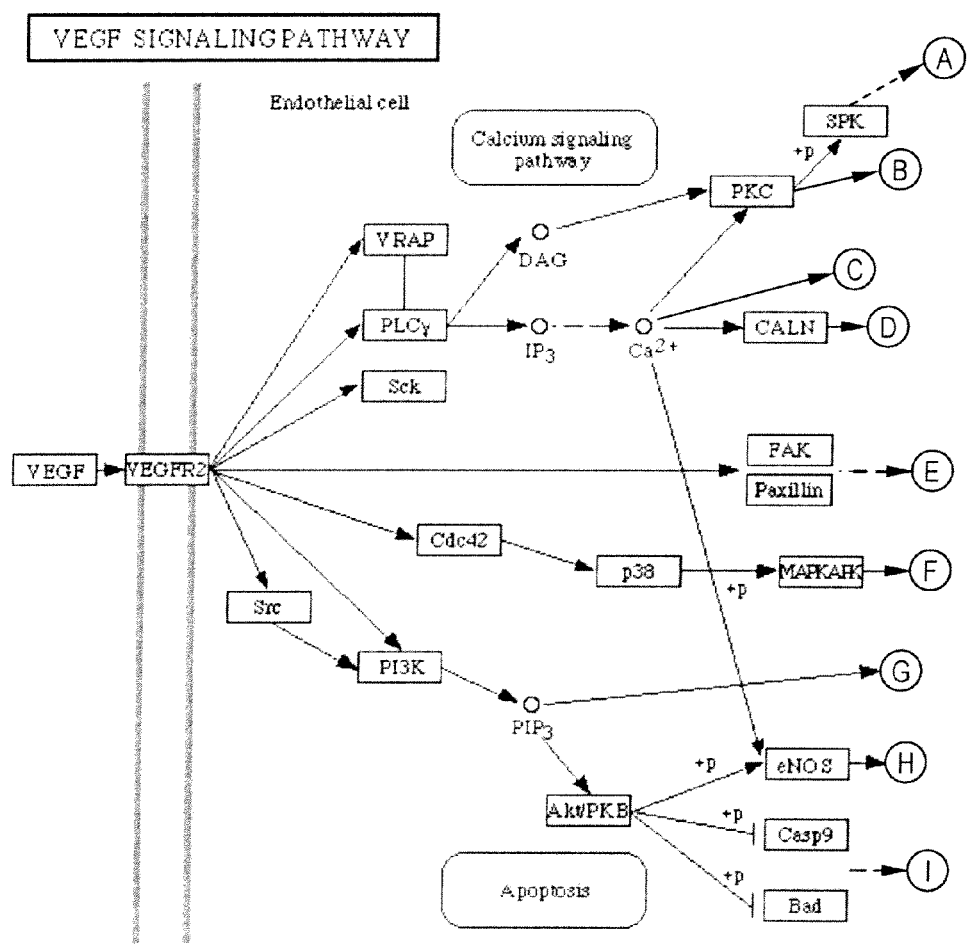
Figures 2, 2G:
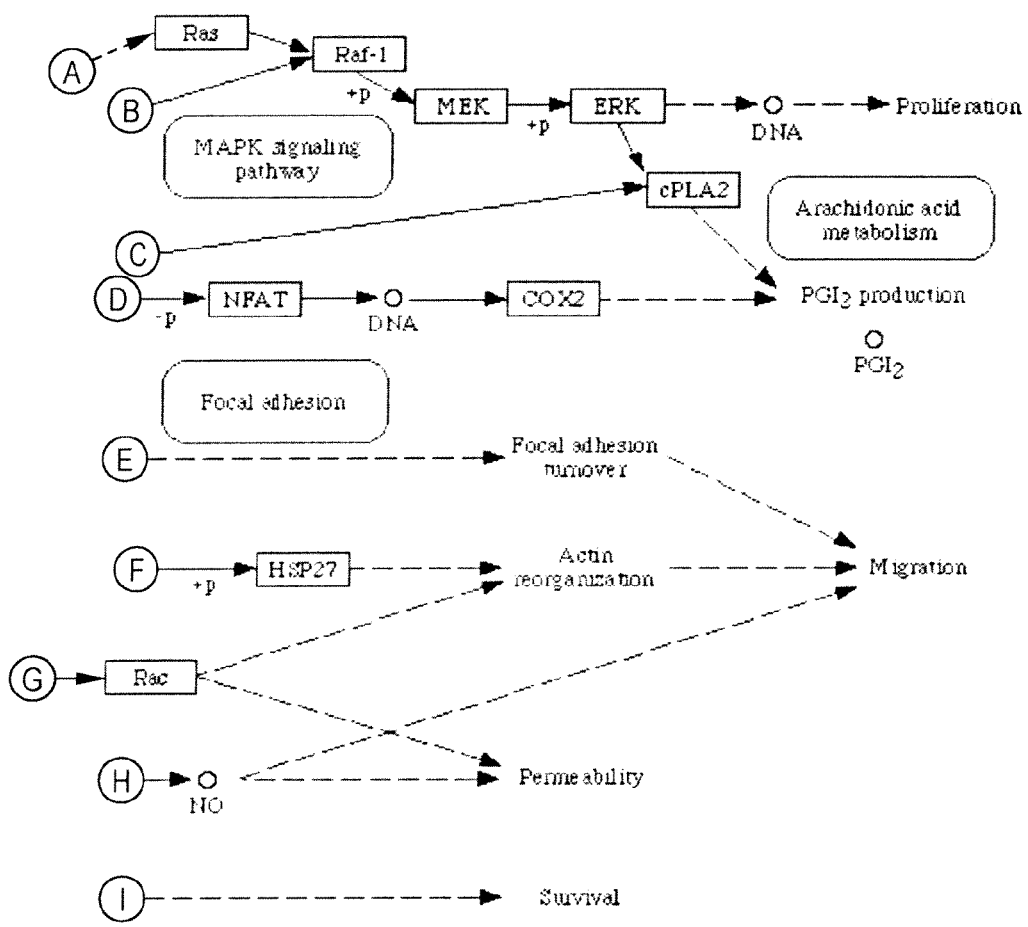
Figures 1, 2H:
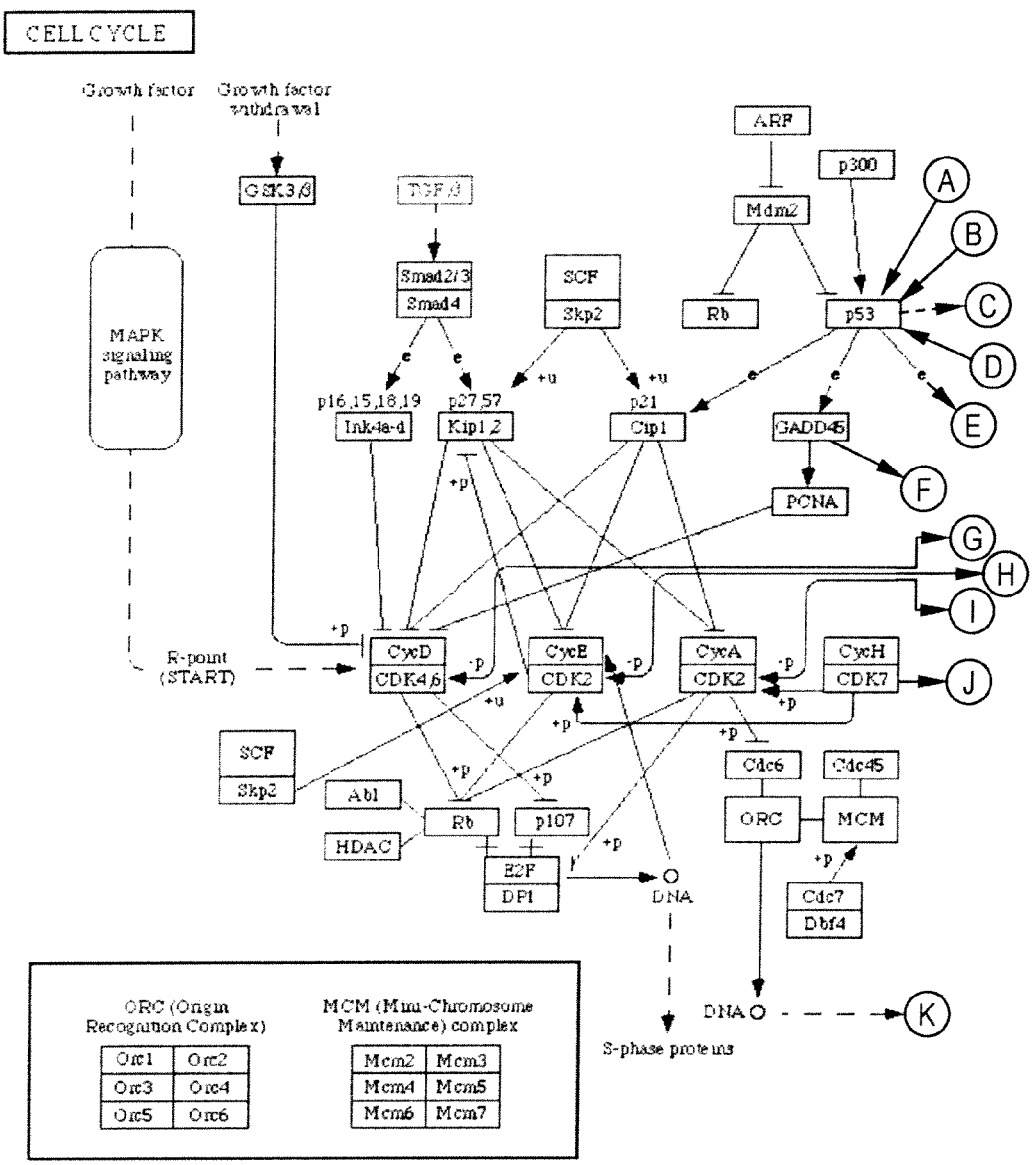
Figures 2, 2H:
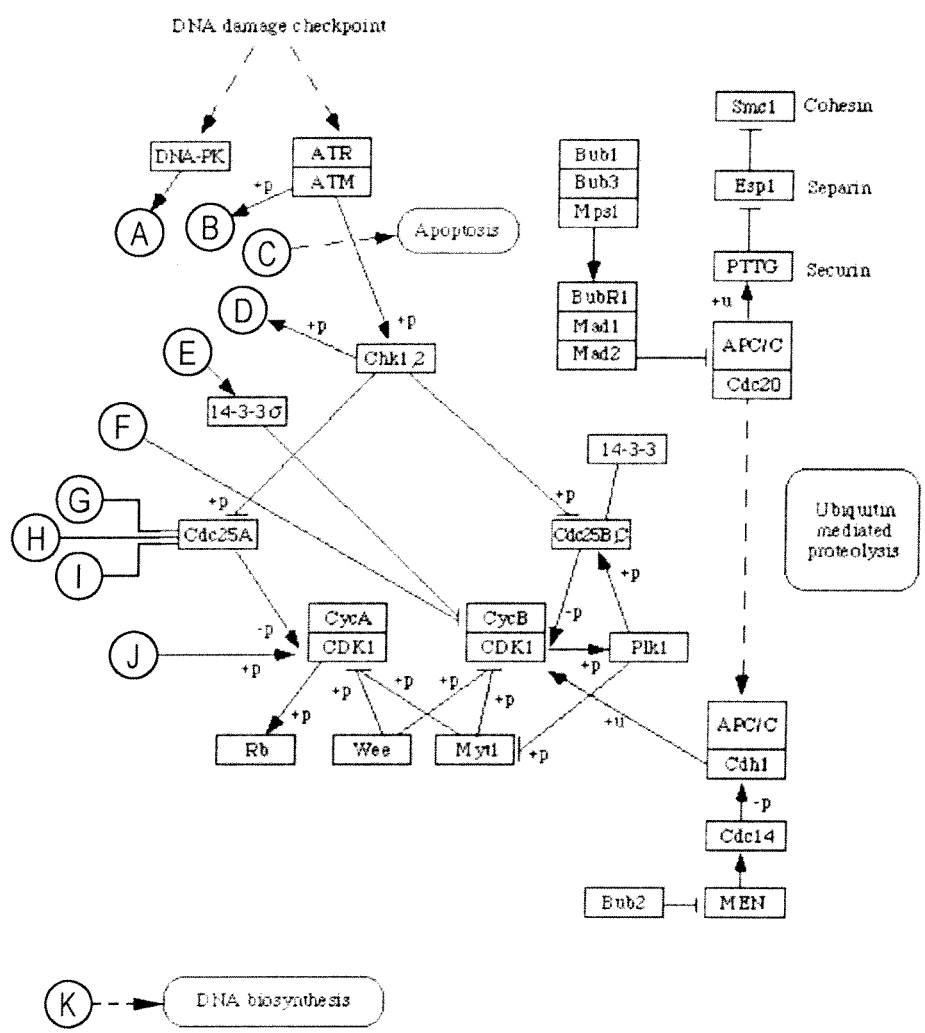
Figures 1, 2I:
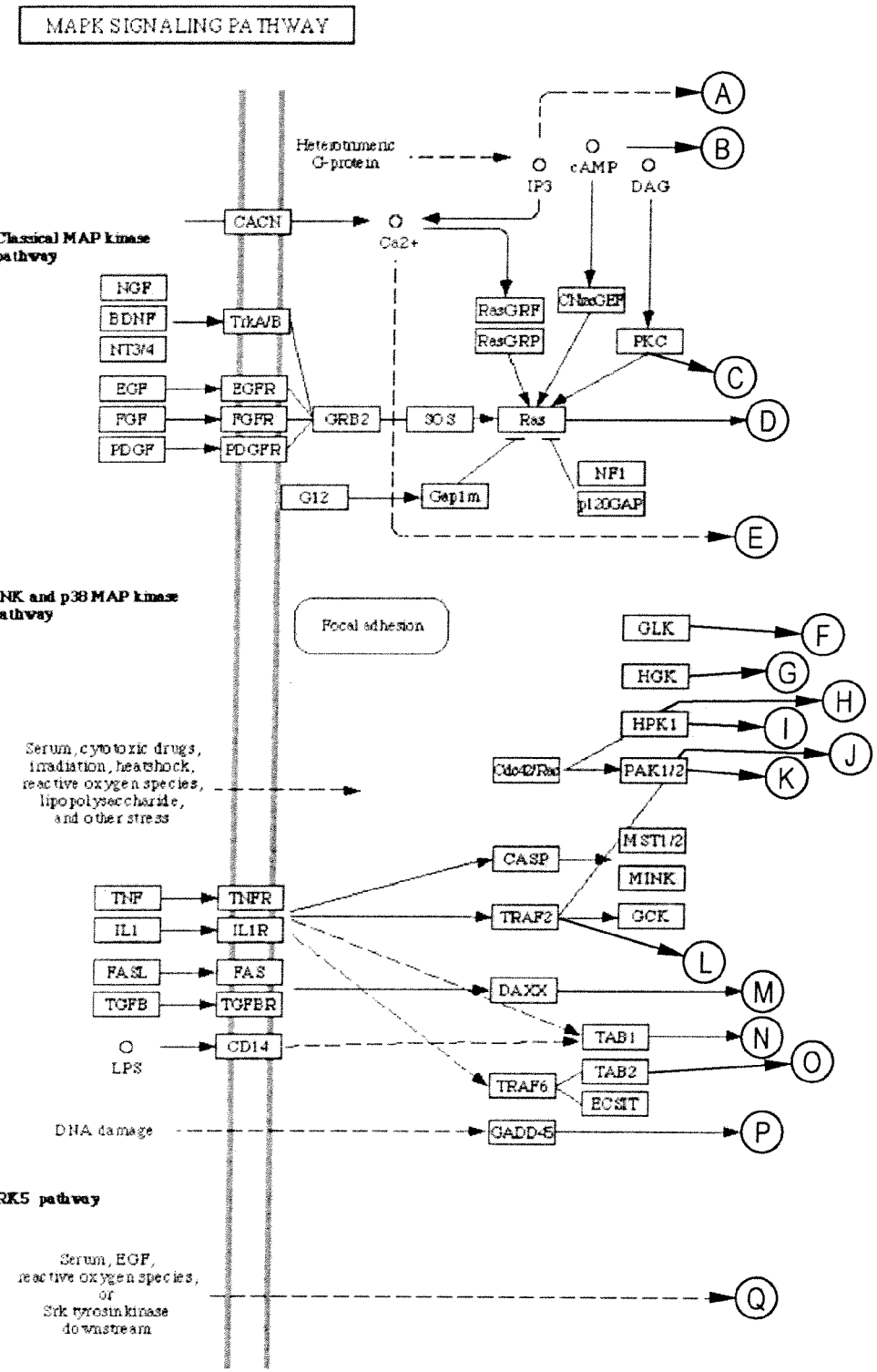
Figures 2, 2I:
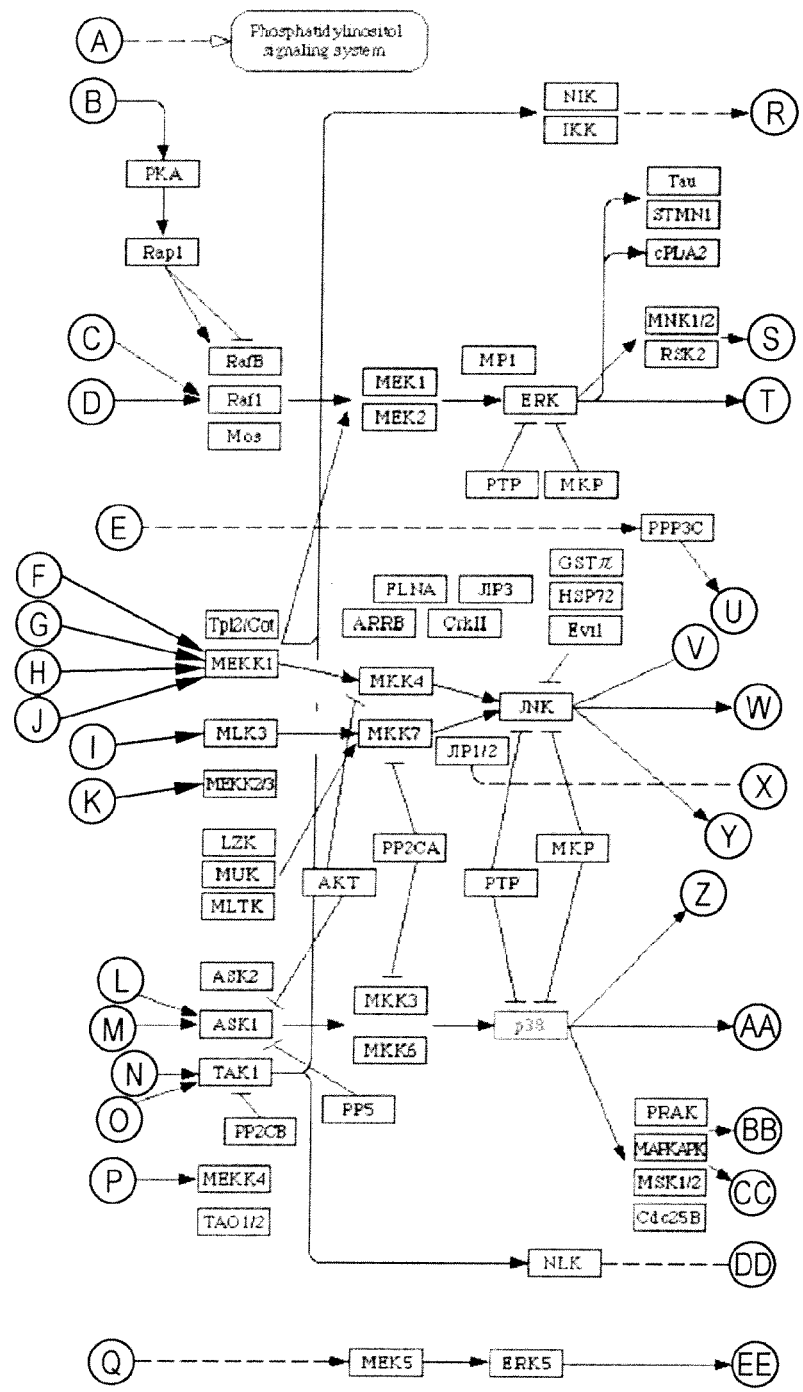
Figures 2, 2I, 3:
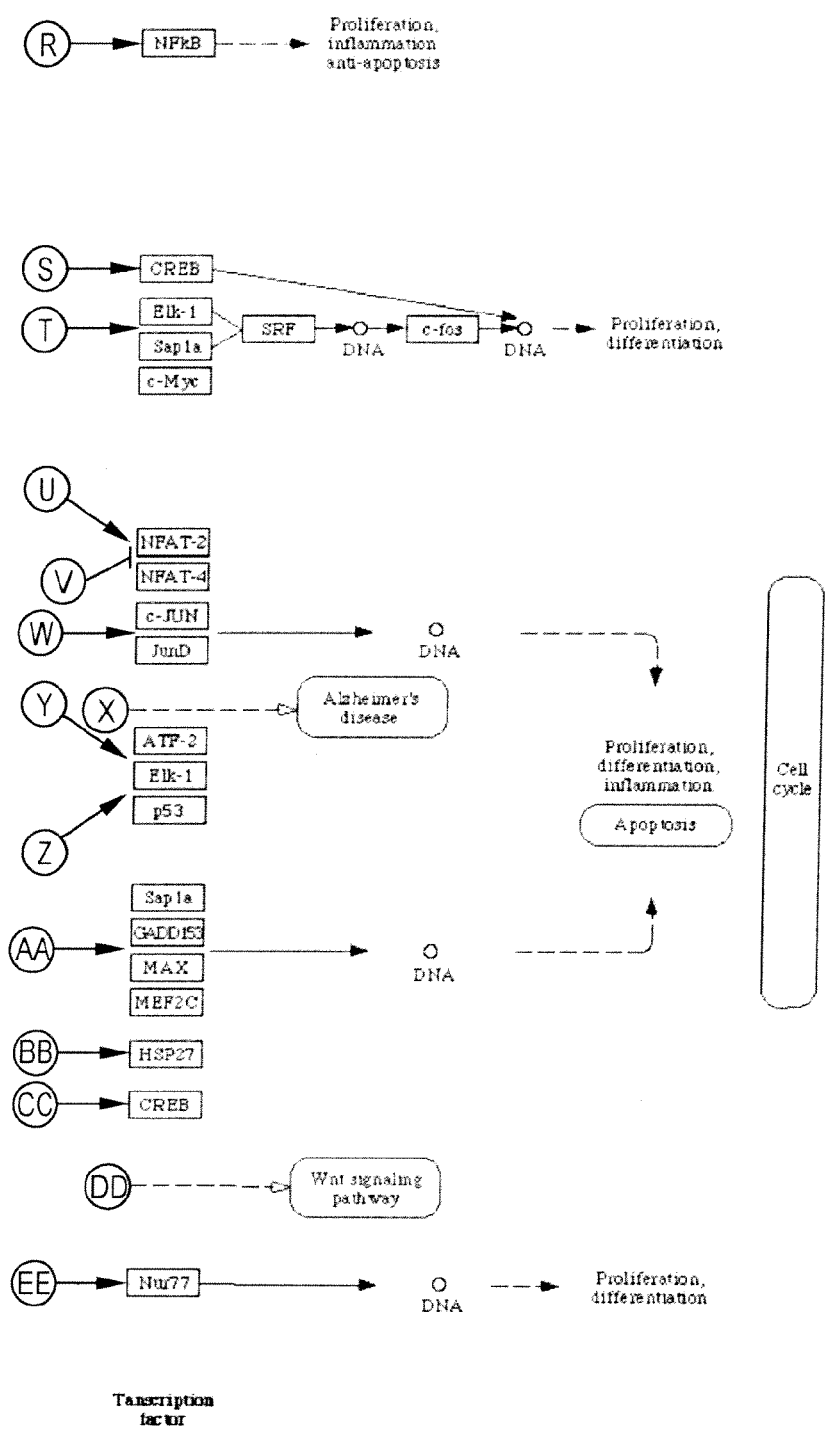
Figures 1, 2J:
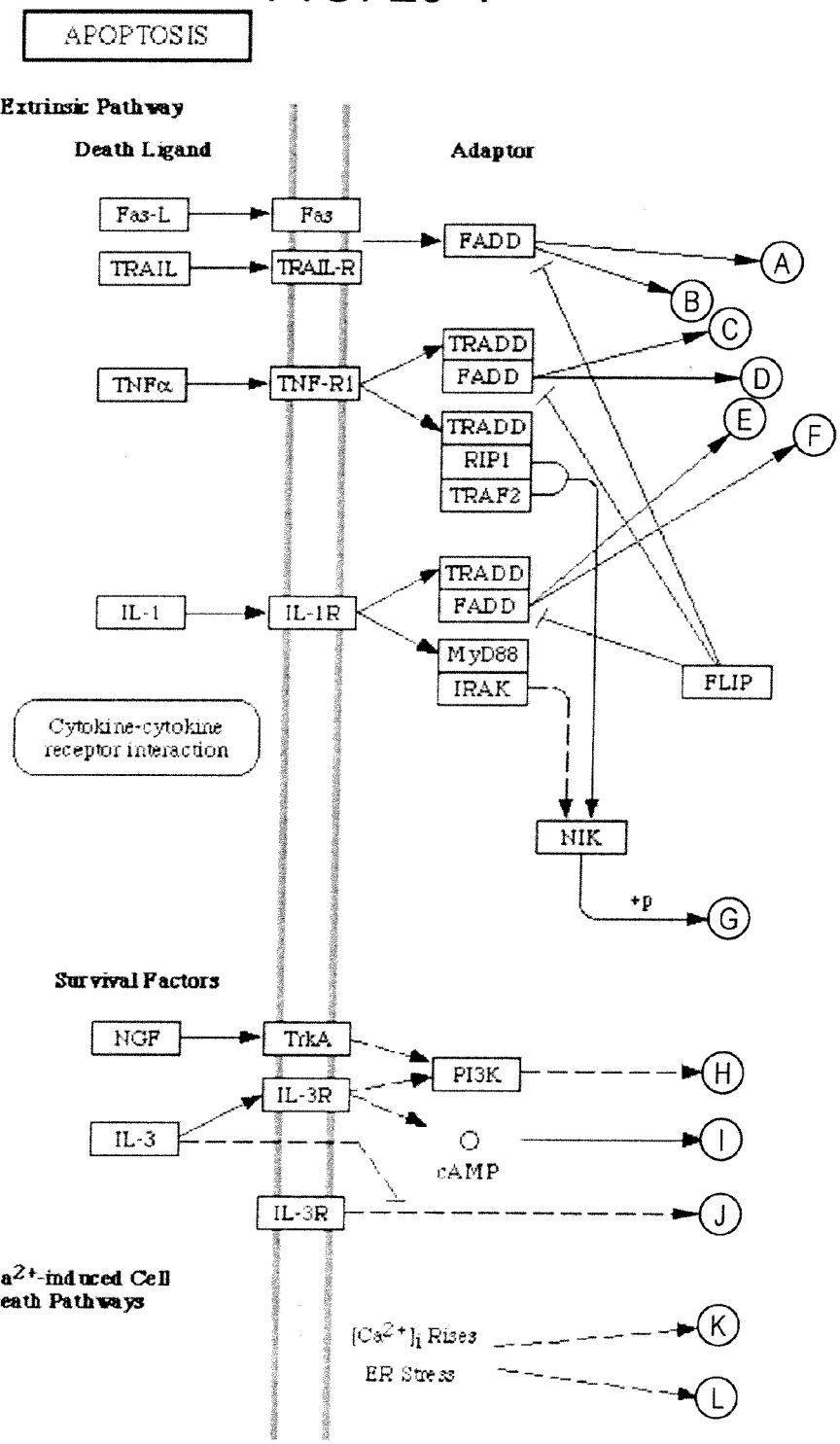
Figures 2, 2J, 3:
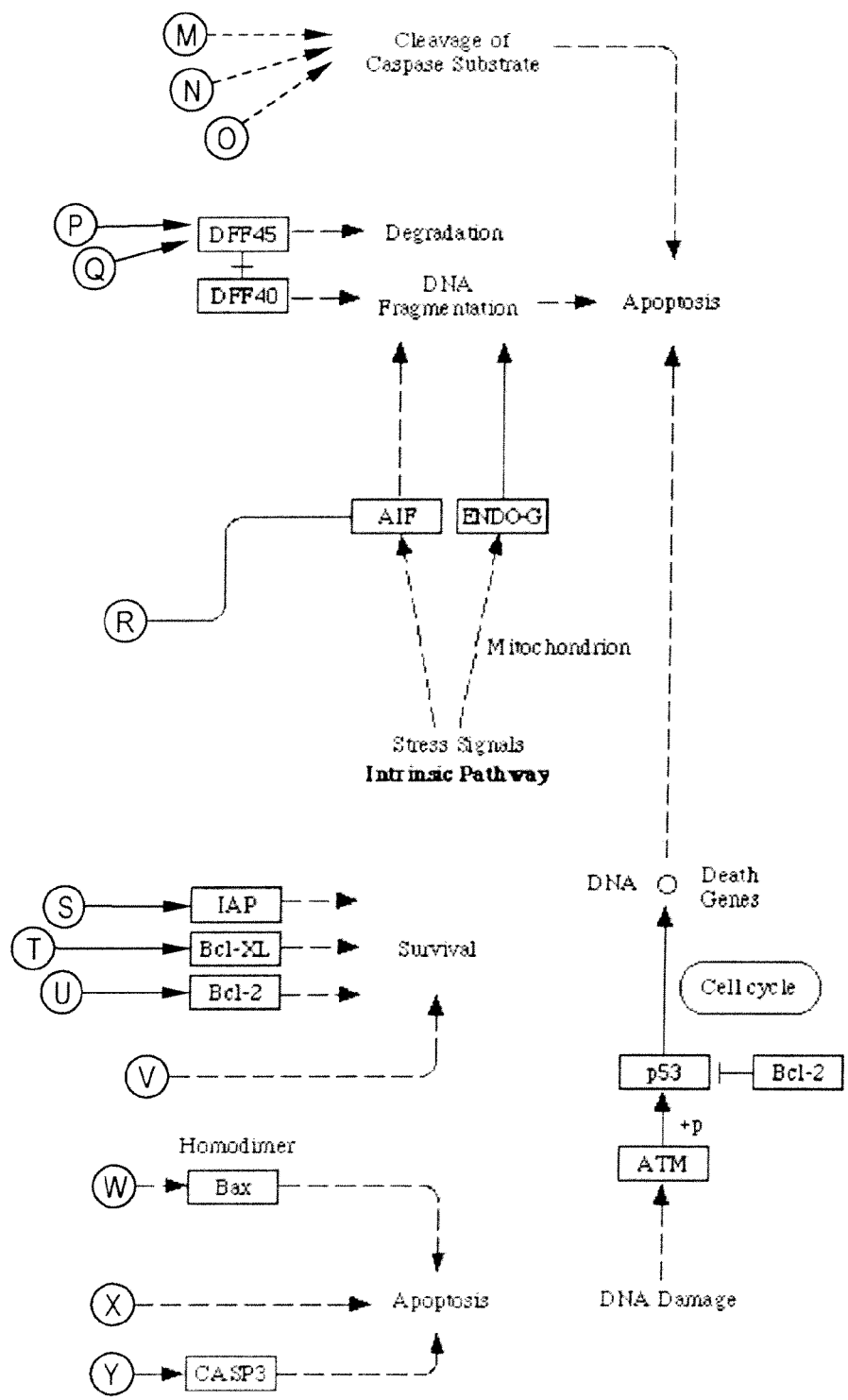
Figures 1, 2K:
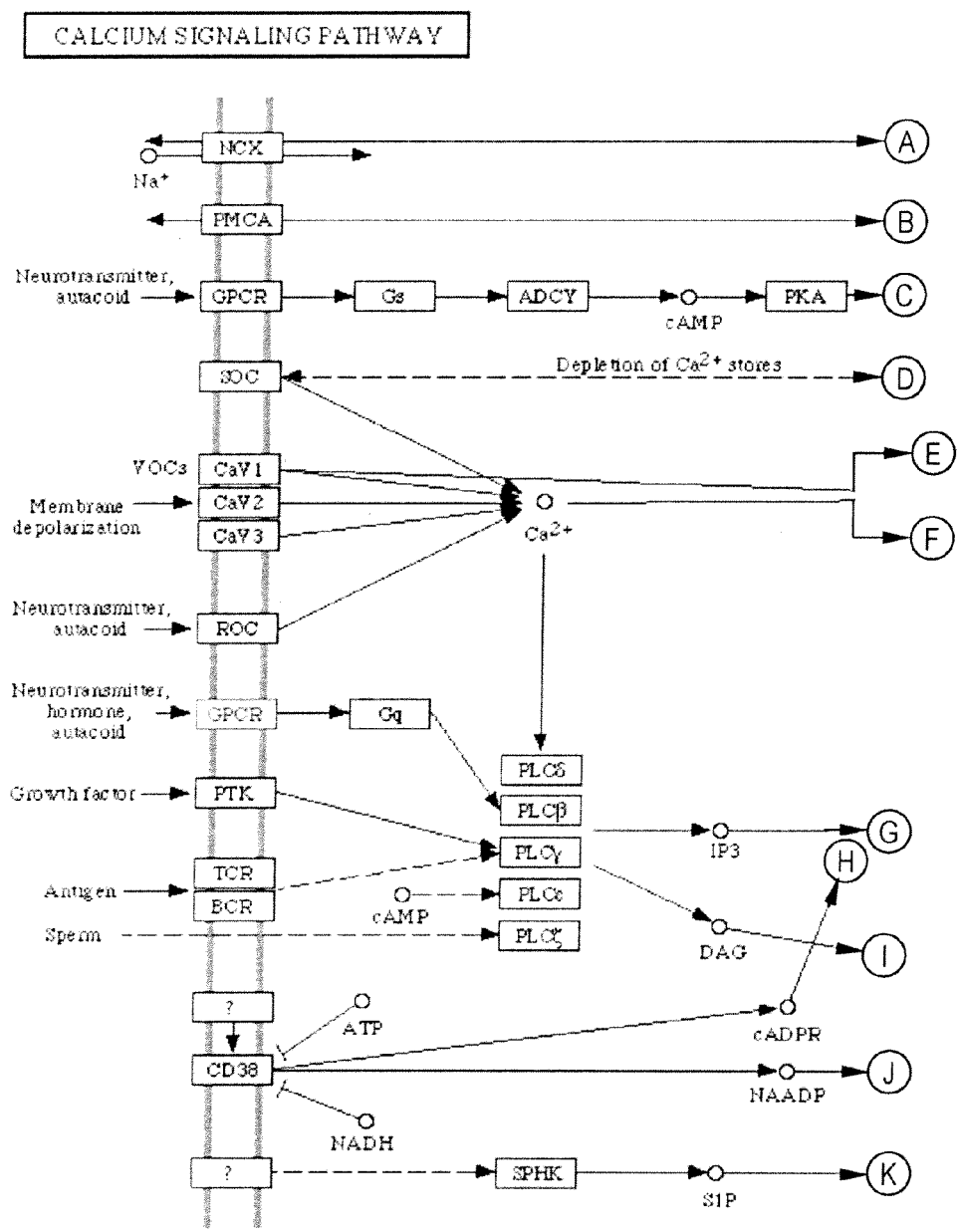
Figures 2, 2K:
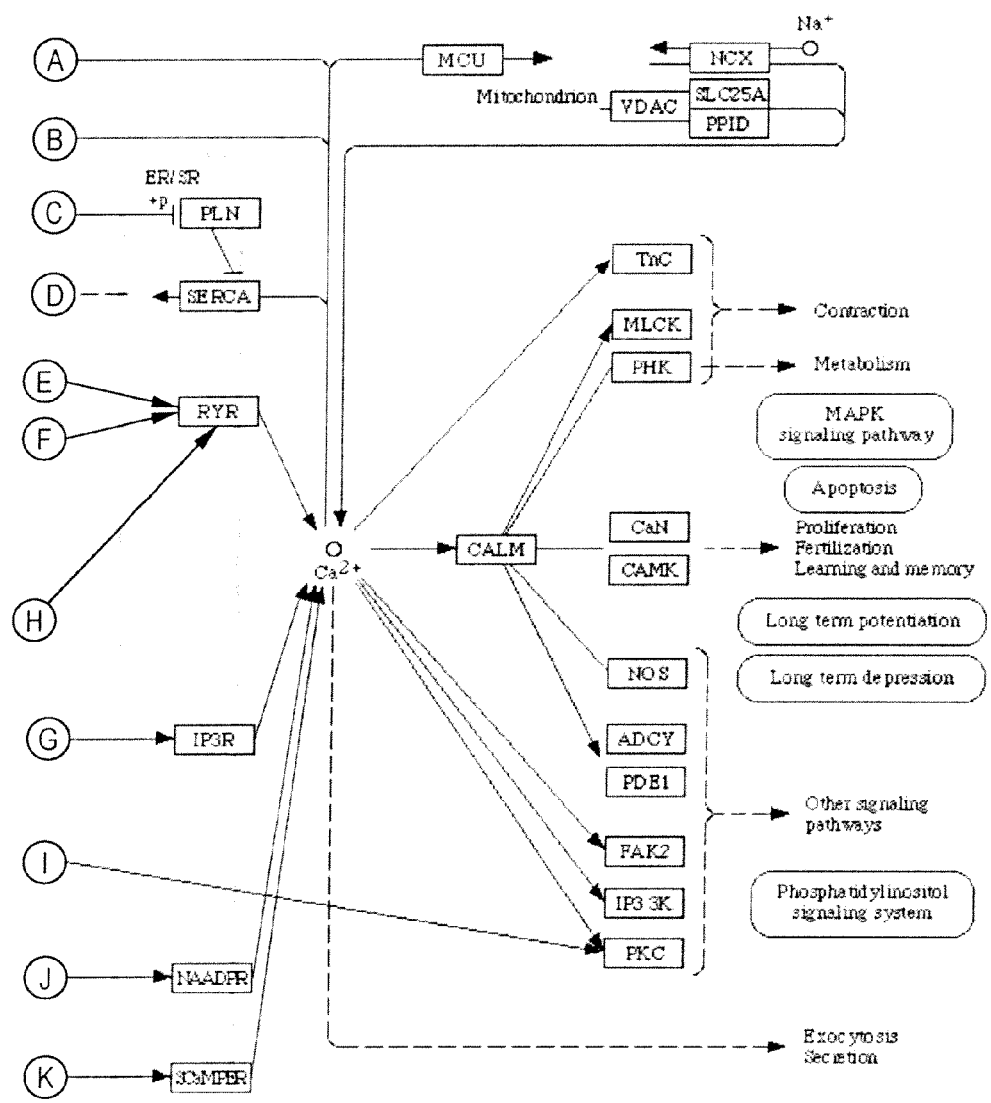
Figures 1, 2L:
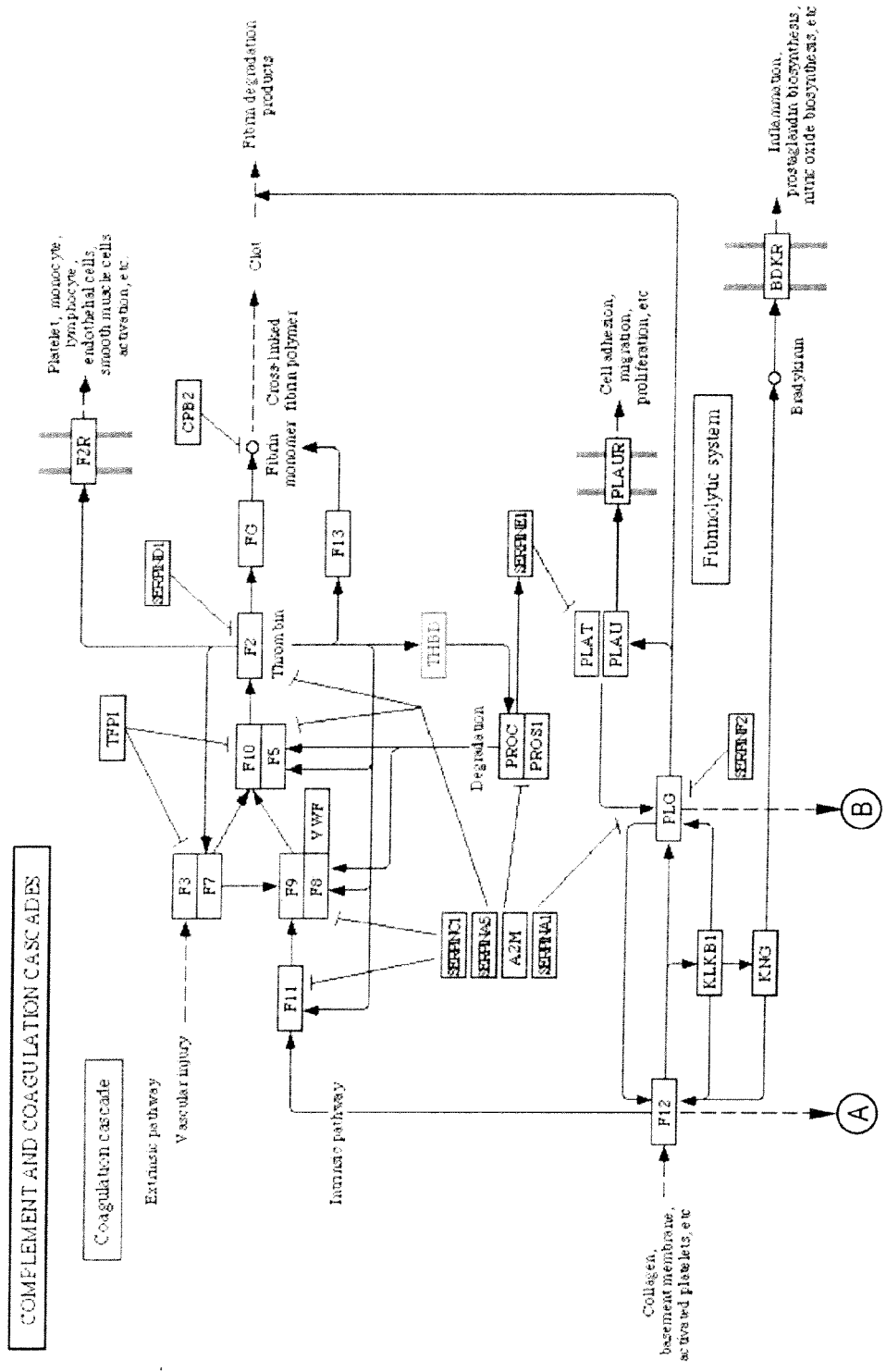
Figures 2, 2L:
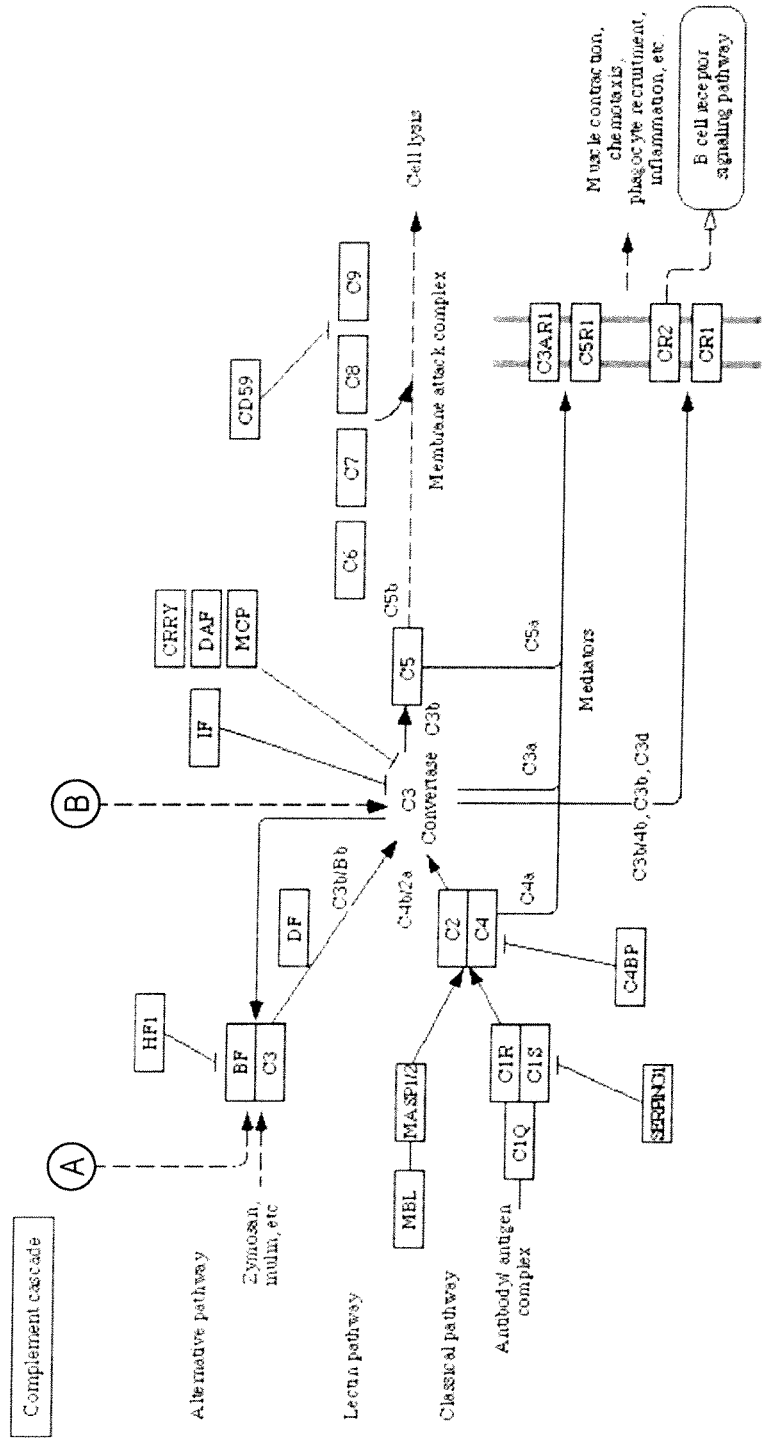
Figures 1, 2M:
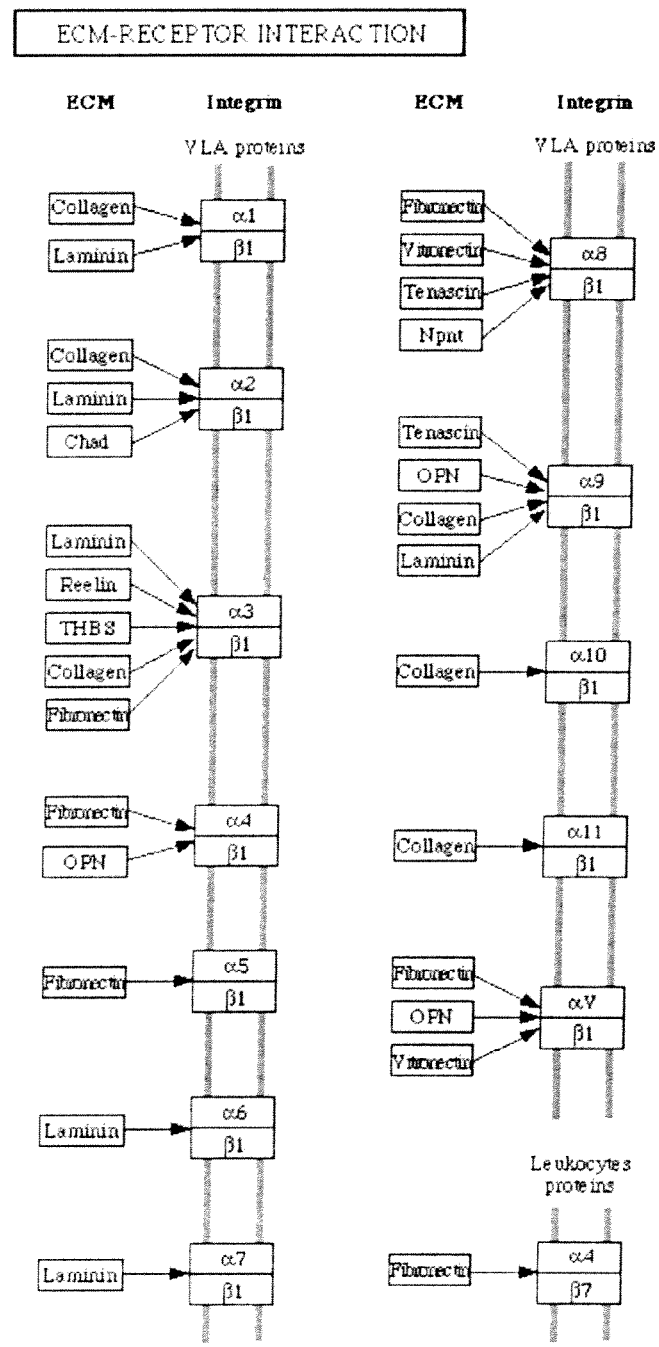
Figures 2, 2M:
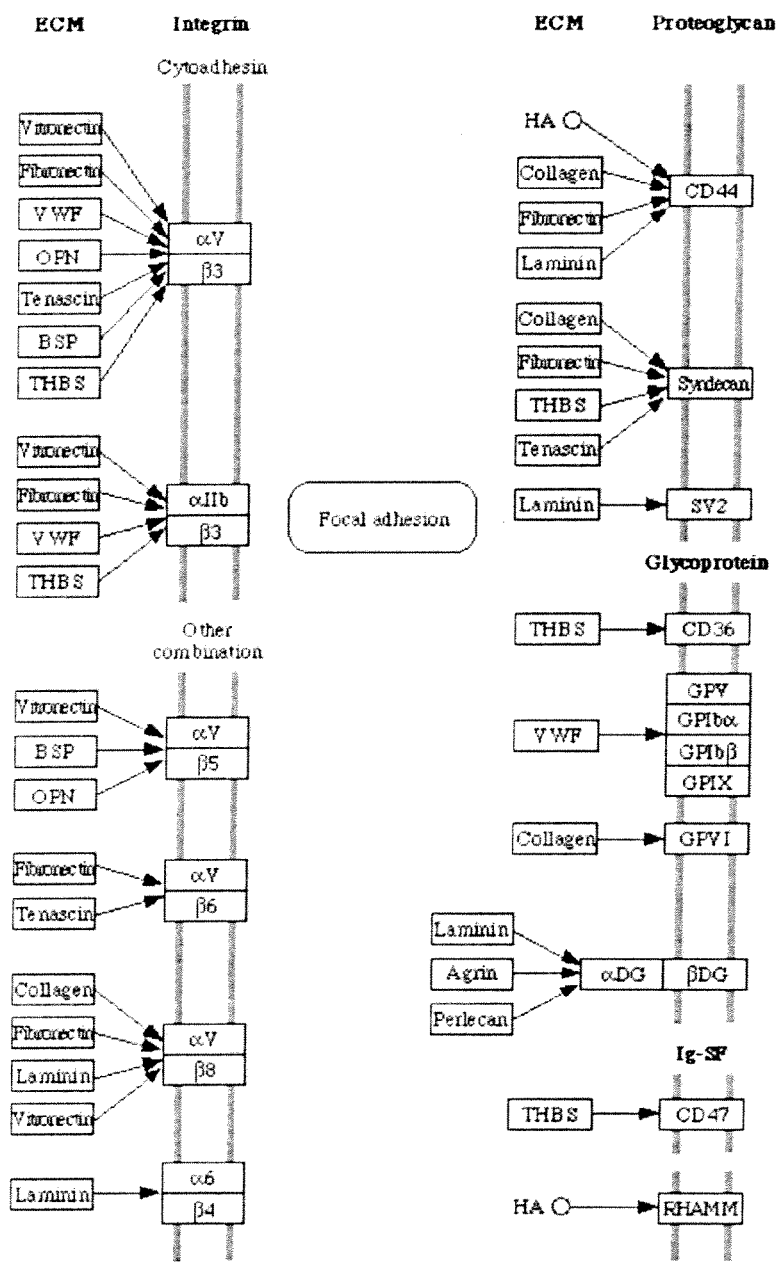
Figures 1, 2N:
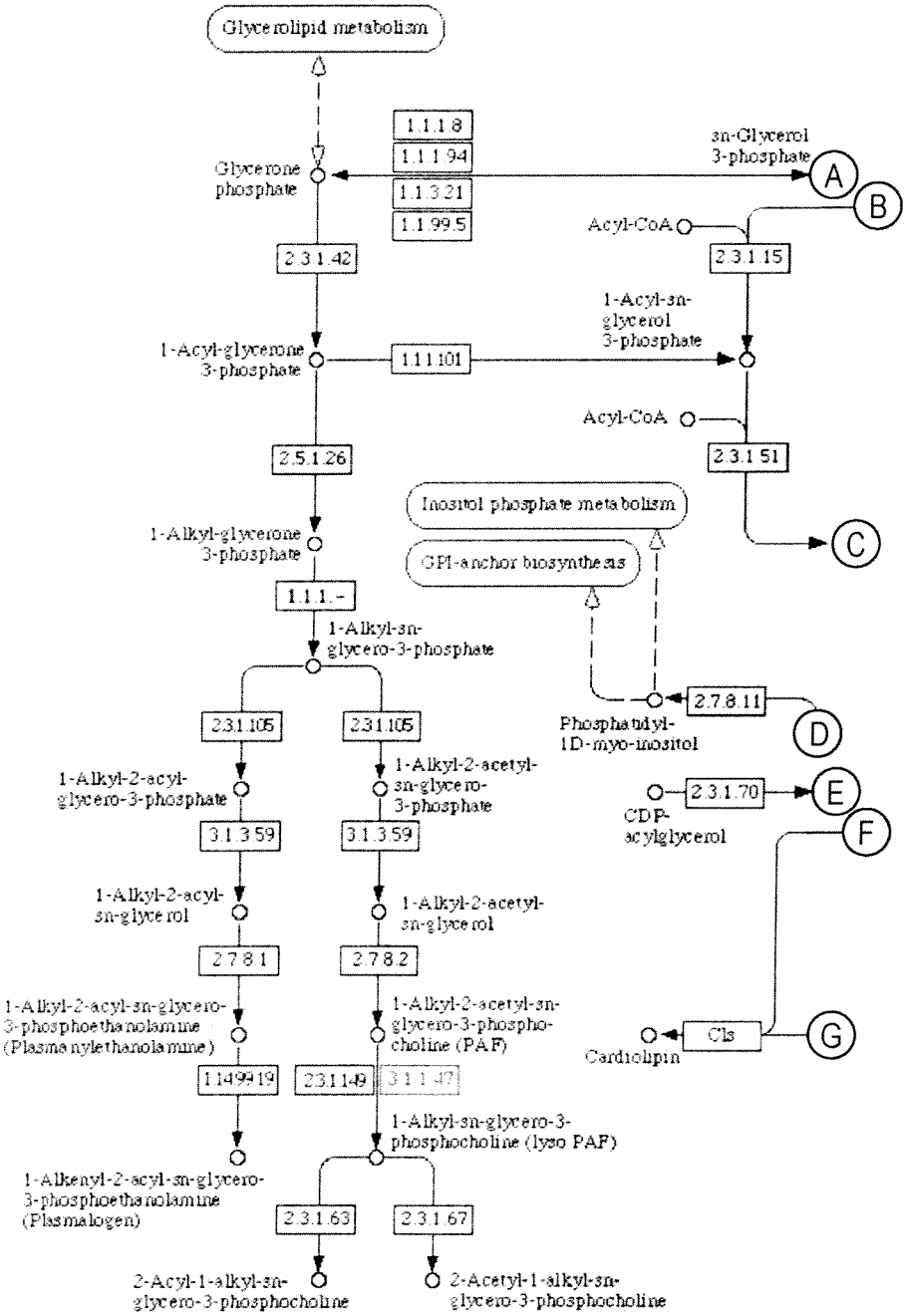
Figures 2, 2N:
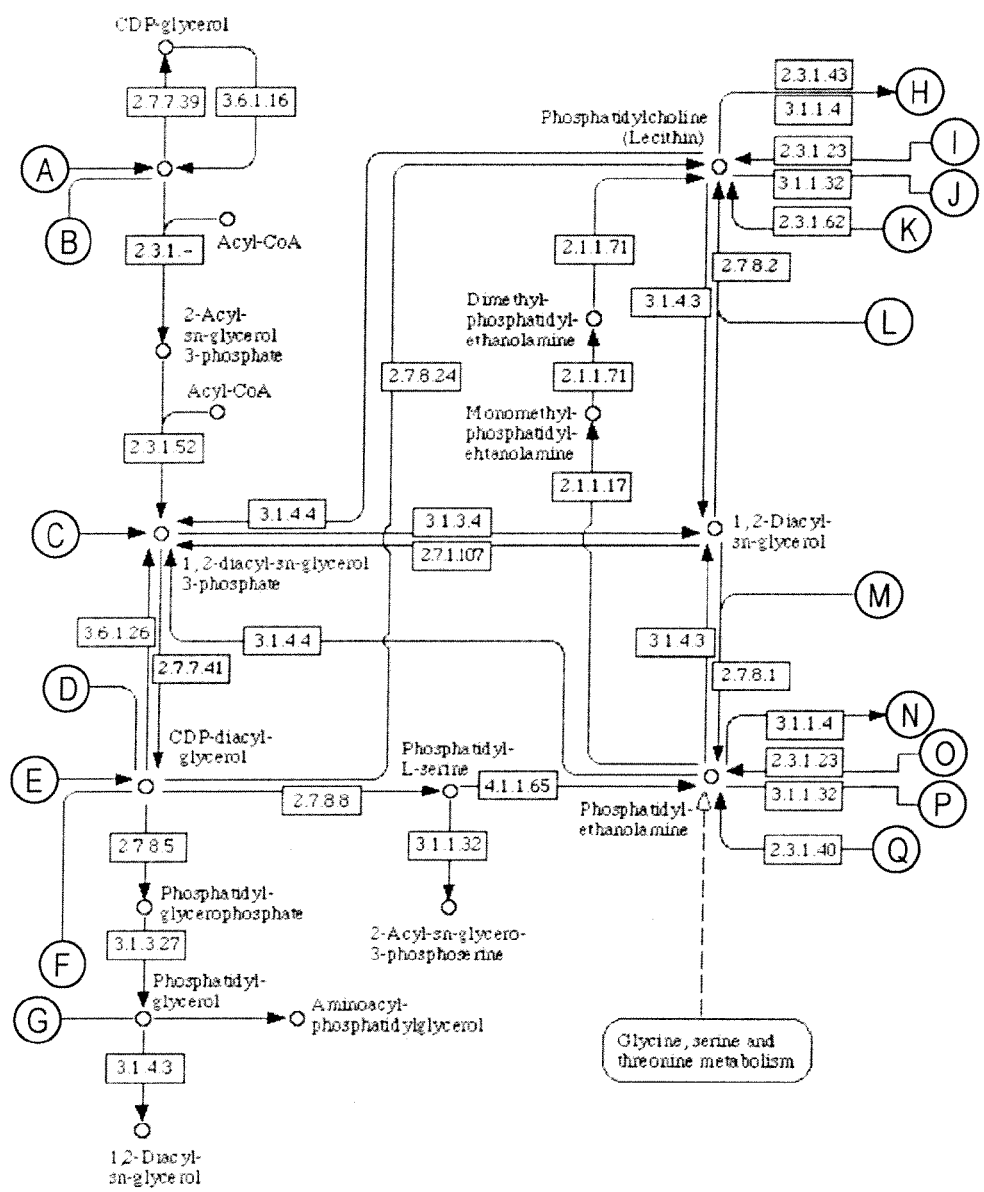
Figures 2, 2N, 3:
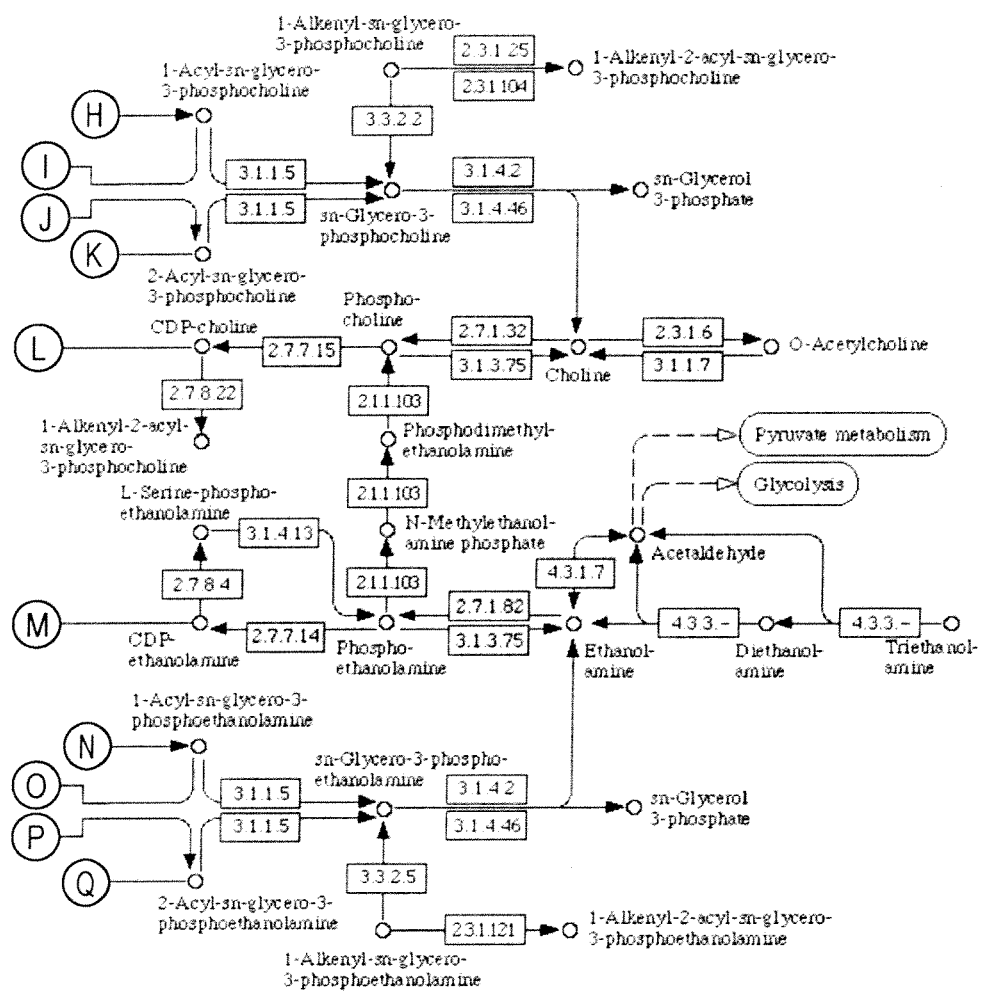
Figures 1, 2O:
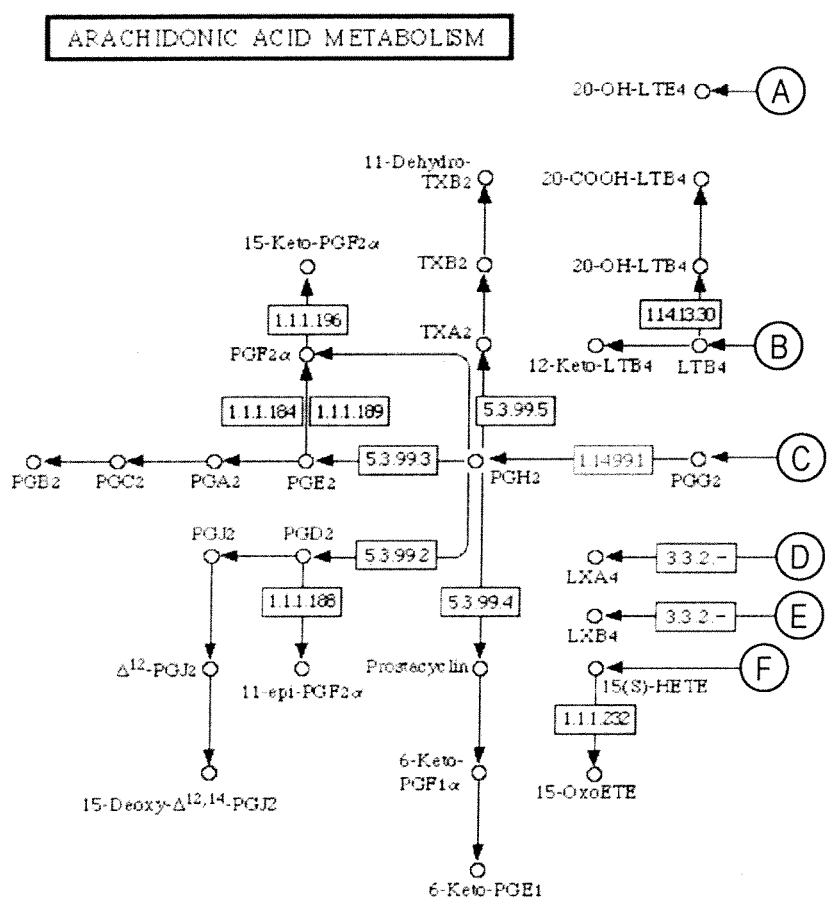
Figures 2, 2O:
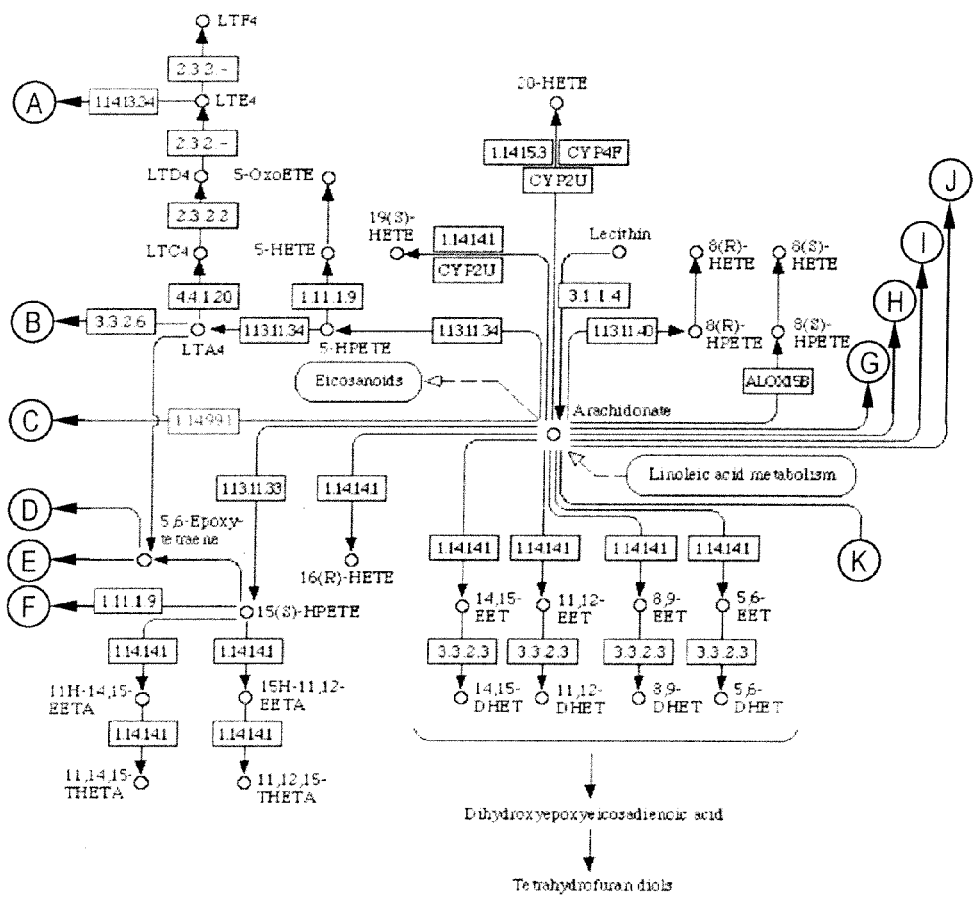
Figures 2, 2O, 3:
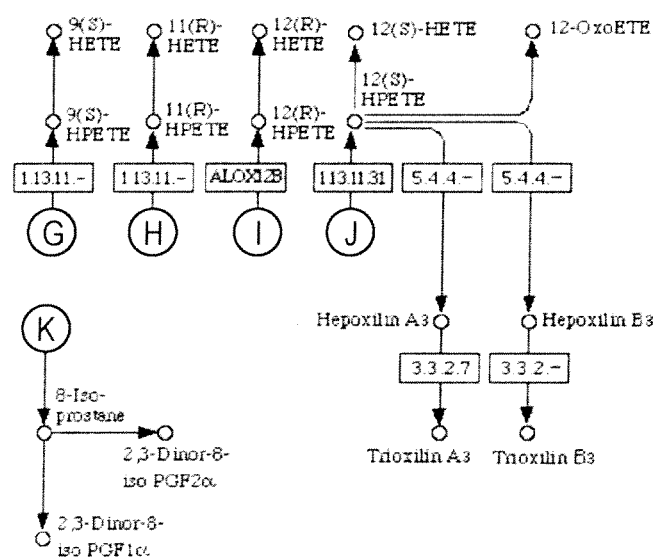
Figures 1, 2P:
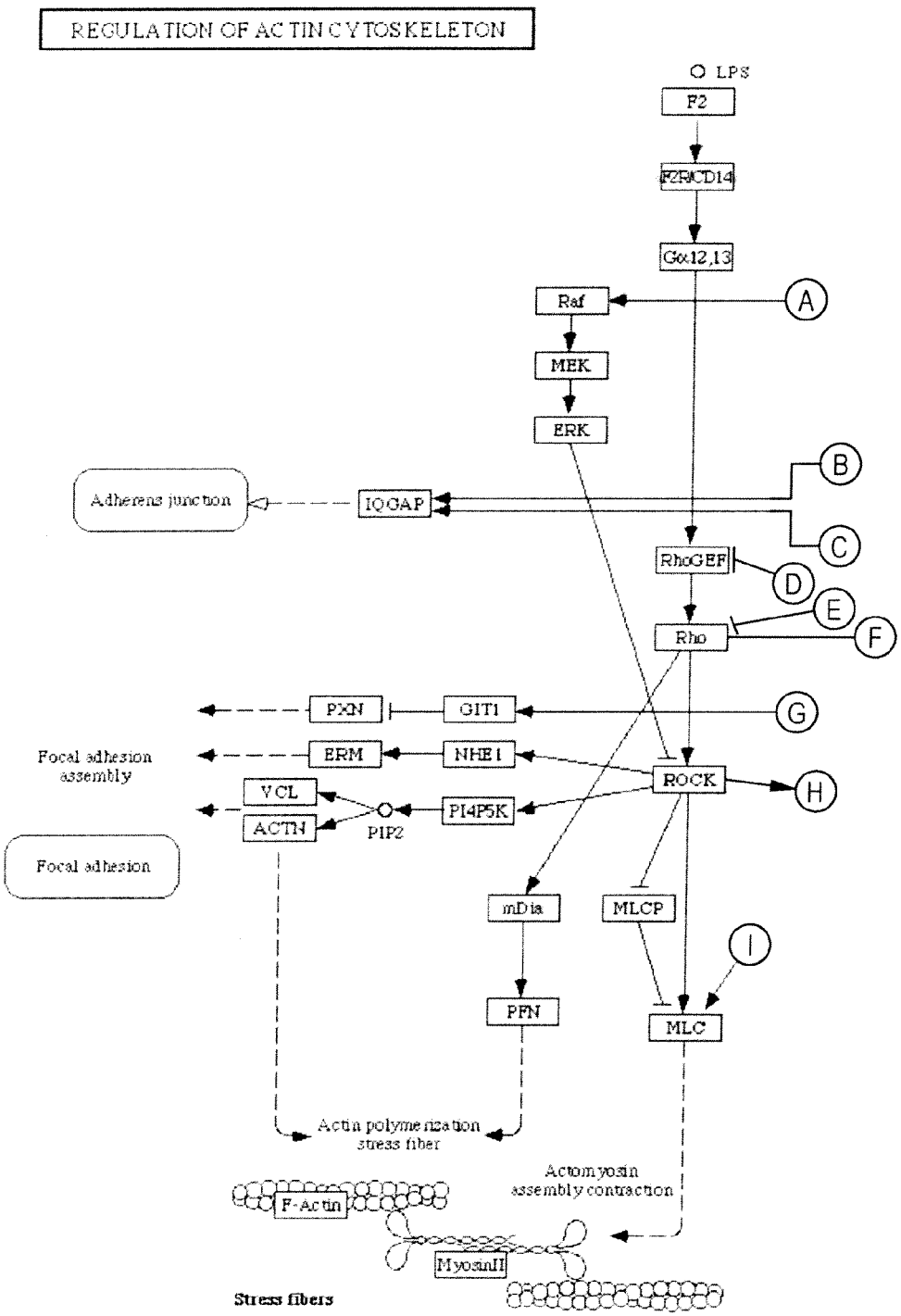
Figures 2, 2P:
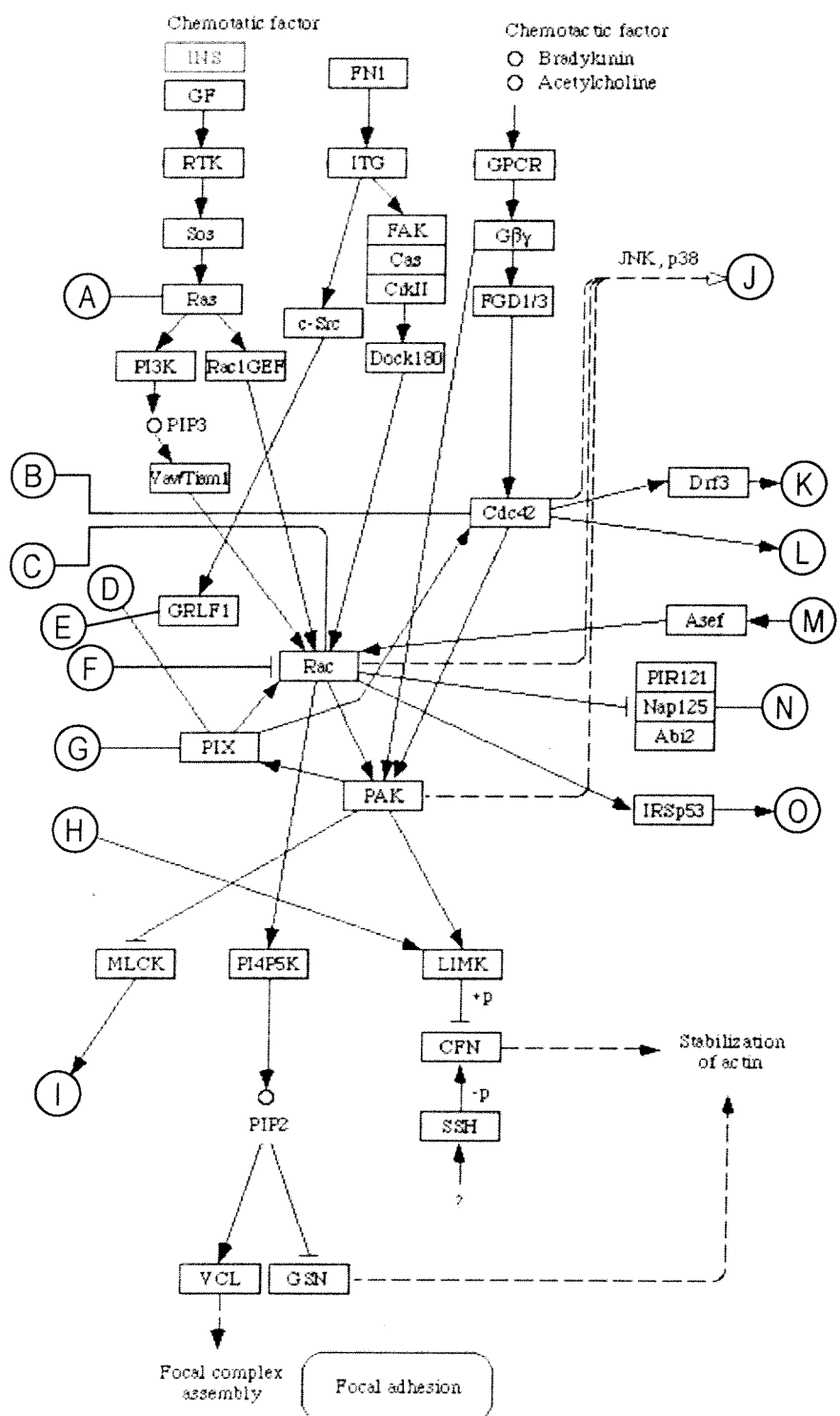
Figures 2, 2P, 3:
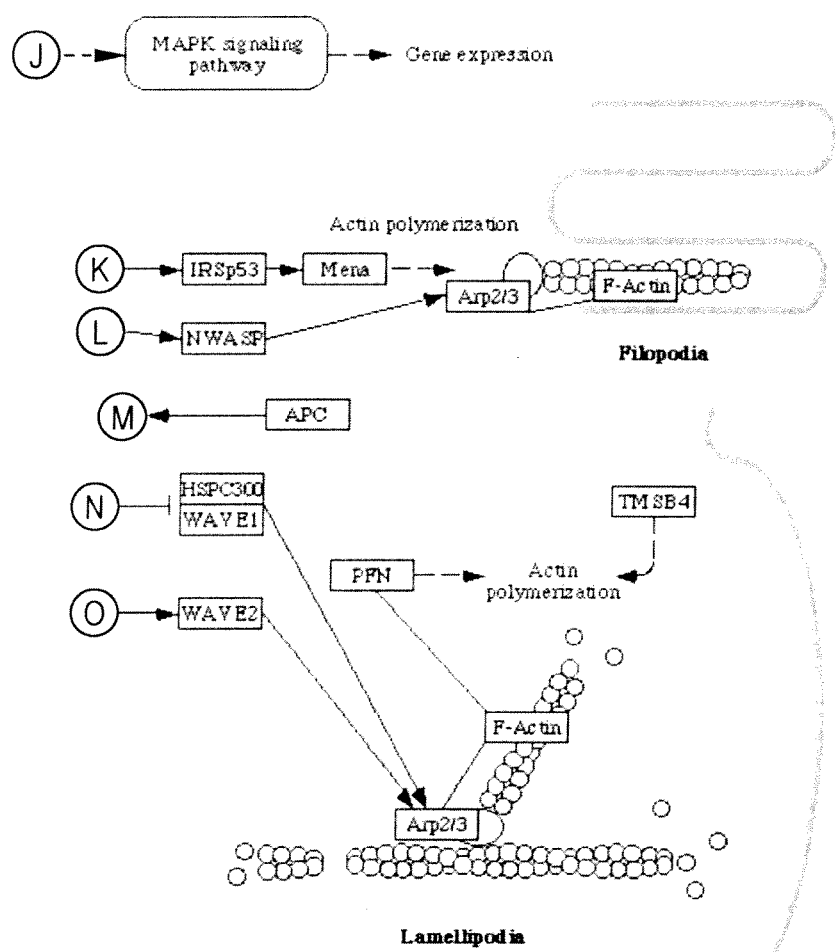

Of further note is FIG. 2, which is a flow chart depicting ARTERIORISKMARKER pathophysiology and progression and biomarker functions, pathways and other categories over the spectrum of arteriovascular disease, including numerical references to the canonical molecular pathways as currently listed within the Kyoto University Encyclopedia of Genes and Genomes (KEGG) web site. Such pathway diagrams listed at the KEGG web site include references to each of the various biomarker participants within the given pathway, relating biomarkers both directly and indirectly associated with arteriovascular disease. These KEGG pathways are furthermore depicted in the following FIGS. 2A through 2P, and referenced below in the marker grouping discussion.

Two or more ARTERIORISKMARKERs of the present invention can also be combined into marker panels comprising combinations of ARTERIORISKMARKERS that are known to be involved in one or more physiological pathways. Examples of ARTERIORISKMARKER Component Categories and a representative number of ARTERIORISKMARKERS implicated in the physiological pathways for such Component Categories are disclosed herein, without limitation of the forgoing techniques of marker panel construction, or of the applicability of alternative ARTERIORISKMARKERS or biomarkers from functionally equivalent classes which are also involved in the same Component Categories and their constituent physiological pathways.

Accordingly, ARTERIORISKMARKERS according to the invention can be classified into panels that comprise biomarkers specific to a particular disease pathway, disease site, disease stage, disease kinetics, and can also comprise markers that can be used to exclude and distinguish arteriovascular diseases from each other ("exclusion markers"). Such panels can comprise two or more ARTERIORISKMARKERS, but can also comprise one ARTERIORISKMARKER, where that one ARTERIORISKMARKER can provide information about several pathways, diseases, disease kinetics, or disease stages.

For example, pathway activity marker panels can comprise one or more ARTERIORISKMARKERS that are indicative of general physiological pathways that are active in the subject and associated with an arteriovascular disease, such as, but not limited to inflammation, platelet aggregation, apoptosis, angiogenesis, lipid metabolism, and vascular calcification. Disease site marker panels can comprise one or more ARTERIORISKMARKERS that are indicative of a particular site of disease, such as sites involved in CAD (coronary arteries), PAD (peripheral arteries), or CVD (cerebrovascular arteries). Such panels can comprise markers of necrosis at high sensitivity, such as, but not limited to ARTERIORISKMARKERS corresponding to creatine kinase MB isozyme (CKMB), troponin I, and troponin T. Another marker panel that is useful in the practice of the present invention is a disease stage marker, wherein one or more ARTERIORISKMARKERS are indicative of the expression kinetics that vary with the absolute stage of progression for the thrombosis prior to the subject exhibiting symptoms of the arteriovascular disease. Such ARTERIORISKMARKERS include, without limitation, thrombus precursor protein (TpP) and d-dimer. The invention also concerns marker panels that comprise one or more ARTERIORISKMARKERS that are indicative of the speed of progression of an arteriovascular disease, wherein the ARTERIORISKMARKERS provide information on the kinetics of expression and how they vary with the speed of disease progression. For example, such ARTERIORISKMARKERS include, without limitation, chemoattractants and cell activation markers having enzymatic effects on disease development progression. An additional marker panel provided by the present invention comprises "exclusion markers", wherein one or more ARTERIORISKMARKERS are indicative of a common disease that do not correspond to or are not involved in arteriovascular disease, or which distinguish among different characteristics and sequelae associated with a particular type of arteriovascular disease.

TABLE 4

Category A - Adipose and Insulin Metabolism

Figure 3:
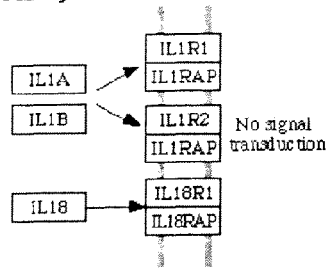

| Pathway | Figure | ARTERIORISKMARKERS |
|---|---|---|
| Adipocytokine Signaling Pathway | KEGG 4920; FIG. 3 | TNF, LEP, ADIPOQ, PPARA, PPARD, PPARG |
| Insulin Signaling Pathway | KEGG 4910; FIG. 4 | INS, INSR, PDE3, GSK3B, PDK1, PDK2 |

TABLE 5

Category B - Inflammation and Leukocyte Infiltration

| Pathway | Figure | ARTERIORISKMARKERS |
|---|---|---|
| Cytokine-Cytokine Receptor Interaction Pathway | KEGG 4060; FIG. 2-C | BLR1, CCL2 (MCP-1), CCL5 (RANTES), CCL9 (MIP-1g), CCL11 (Eotaxin), CCL12 (MCP-5), CCL19 (MIP-3b), CCL21 (TCA4/6CKine), CSF1, CSF2 (GM-CSF), CSF3 (GCSF), CXCL1 (KC), CXCL2 (MIP-2) CXCR4, CXCR6, GDF15 (MIC1), IFNA, IFNG, IL1B, IL2, IL3, IL4, IL5, IL6, IL8, IL10, IL12B, IL17D (IL27), IL18, PPBP, PF4, TNFA, TNFSF11 (RANKL), CRP, SAA |
| Cell Adhesion Molecule Pathway | KEGG 4514; FIG. 2-D | ICAM1, ICAM2, ICAM3, JAM2, JAM3, PECAM1, VCAM1, E-selectin, SELP (P-selectin), SELPLG, vWF, CD40, CD40L, ITGAL, ITGB2, IT |
| Leukocyte Transendothelial Migration Pathway | KEGG 4670; FIG. 2-E | JAM1, MMP1, MMP2, MMP3, MMP9, MMP11, MMP12, MMP14 |
| T Cell Receptor Signaling Pathway | KEGG 4660; FIG. 2-F | CDK4, IFNG, TNFA |

TABLE 6

Category C - Cell Proliferation and Death

| Pathway | Figure | ARTERIORISKMARKERS |
|---|---|---|
| VEGF Signaling Pathway | KEGG 4370; FIG. 2-G | VEGF, PIGF, HGF, FGF |
| Cell Cycle Pathway | KEGG 4110; FIG. 2-H | TGFB1, CCNE1, CCNH, CDK4, CDK6, PCNA, SKP2 |
| MAPK Signaling Pathway | KEGG 4010; FIG. 2-I | MAPK14 (p38), HSPA8, HSP72, FGF, CD14, PDGFA, ACTN1(Actinin), VCL (Vinculin) |
| Apoptosis Pathway | KEGG 4210; FIG. 2-J | TNFA, CASP3, CASP9 |
| Calcium Signaling Pathway | KEGG 4020; FIG. 2-K | CCNB1, F2R, PDGFRB, TnC, MLCK |

TABLE 7

Category D - Oxidative Stress, Cell Matrix and Coagulation

| Pathway | Figure | ARTERIORISKMARKERS |
|---|---|---|
| Complement and Coagulation Cascade Pathway | KEGG 4610; FIG. 2-L | C3, C4, vWF, F2, F3, F5, F7, F9, F10, F12, F13, CpB2, TFPI, PROC (Protein C), SERPIN G1, PLAT (TPA), PLG (Plasminopen), CD55 (DAF) |
| Extracellular Matrix (ECM) - Receptor Interaction Pathway | KEGG 4512; FIG. 2-M | MMP-1, MMP-2, MMP-9, PAPP-A, FSD1 (Fibronectin), LAM3 (Laminin), ITGA, ITGB, VCL (Vinculin) |
| Oxidative Metabolism | KEGG 0564, 0590; FIGS. 2-N and 2-O | MPO, sPLA2, Lp-PLA2, ENO2 (Enolase), PGAM4, Ox-LDL, IMA (Ischemia Modified Albumin) |
| Regulation of Actin Cytoskeleton Pathway | KEGG 4810; FIG. 2-P | ACTN1 (Actinin), CD14, F2RL1 |

TABLE 8

| Category E - Acute and Post-Acute Event Markers | | |
|---|---|---|
| Pathway | Figure | ARTERIORISKMARKERS |
| Cellular Necrosis | — | CKMB, Troponin I, Troponin C, Troponin T, Tropomyosin, Myoglobin, Myosin Light Chain, Total CK, Actin, Myosin, Fibronectin |
| Hemodynamic Stress and Remodelling | — | BNP, proNT-BNP, ANP |

TABLE 9

| Category F - Arteriovasculate Physiological | | |
|---|---|---|
| Pathway | Figure | ARTERIORISKMARKERS |
| Physiological ARTERIORISKMARKERS | — | Blood Pressure, Weight, Body-Mass Index, Resting Heart Rate, Sex, Age, Diabetes, Smoking, Hip or Waist Circumference |

TABLE 10

| Category G - Algorithms and Index Construction | | |
|---|---|---|
| Pathway | Figure | ARTERIORISKMARKERS |
| Statistical and Syntactic (Structural) Classification Algorithms and Index Construction Methods | — | Linear classifiers (Fisher's linear discriminant, Logistic regression, Nave Bayes classifier, Perceptron), k-nearest neighbor, Boosting, Decision Trees, Neural Networks, Bayesian Networks, Support Vector Machines, Hidden Markov Models |

ARTERIORISKMARKERS according to the present invention need not be limited or bound by the categories A-G as disclosed above, but may also be analyzed in total or individually, or in clusters not reflected in categories A-G. Furthermore, the above component marker listings do not purport to be complete; further references to the KEGG pathways contained within FIG. 2 are made above so as to enable the more rapid addition of new biomarkers into the above groupings when they are shown to be functional or statistical equivalents of an existing ARTERORISKMARKER.

Table 11 provides a summary of specific example ARTERIORISKMARKER panels and their inclusion of one or more biomarkers from one or more categories A-G, as indicated below.

TABLE 11

ARTERIORISKMARKER Panels Using One Or More ARTERIORISKMARKERS Each From One Or More Component Categories A-G

| | Categories Used: | | | | | | |
|---|---|---|---|---|---|---|---|
| | 1 | 2 | 3 | 4 | 5 | 6 | 7 |
| Examples of ARTERIO- RISK- | A | AB | ABC | ABCD | ABCDE | ABCDEF | ABCDEFG |
| | B | AC | ABD | ABCE | ABCDF | ABCDEG | |
| | C | AD | ABE | ABCF | ABCDG | ABCDFG | |
| MARKER Panels | D | AE | ABF | ABCG | ABCEF | ABCEFG | |
| | E | AF | ABG | ABDE | ABCEG | ABDEFG | |
| | F | AG | ACD | ABDF | ABCFG | ACDEFG | |
| | G | BC | ACE | ABDG | ABDEF | BCDEFG | |
| | | BD | ACF | ABEF | ABDEG | | |
| | | BE | ACG | ABEG | ABDFG | | |
| | | BF | ADE | ABFG | ABEFG | | |
| | | BG | ADF | ACDE | ACDEF | | |
| | | CD | ADG | ACDF | ACDEG | | |
| | | CE | AEF | ACDG | ACDFG | | |
| | | CF | AEG | ACEF | ACEFG | | |
| | | CG | AFG | ACEG | ADEFG | | |
| | | DE | BCD | ACFG | BCDEF | | |
| | | DF | BCE | ADEF | BCDEG | | |
| | | DG | BCF | ADEG | BCDFG | | |
| | | EF | BCG | ADFG | BCEFG | | |
| | | EG | BDE | AEFG | BDEFG | | |
| | | FG | BDF | BCDE | CDEFG | | |
| | | | BDG | BCDF | | | |
| | | | BEF | BCDG | | | |
| | | | BEG | BCEF | | | |
| | | | BFG | BCEG | | | |
| | | | CDE | BCFG | | | |
| | | | CDF | BDEF | | | |
| | | | CDG | BDEG | | | |
| | | | CEF | BDFG | | | |
| | | | CEG | BEFG | | | |
| | | | CFG | CDEF | | | |
| | | | DEF | CDEG | | | |
| | | | DEG | CDFG | | | |
| | | | DFG | CEFG | | | |
| | | | EFG | DEFG | | | |

As seen in FIG. 2, the manifestations of the ARTERIORISKMARKERS and the categories proceeds with the progression of the disease, allowing several of such categories to serve as a measure of disease status or of the speed of disease progression. Furthermore, constituent ARTERIORISKMARKERS within categories such as the Cellular Necrosis group can also provide specificity as to the focal organ site of the arteriovascular disease, for example, whether CAD, PAD, or CVD, as certain ARTERIORISKMARKERS have particular tissue specificity, as is the case with the cardiac troponins (I and T), which are highly specific for CAD.

Furthermore, given that arteriovascular disease often affects the microvasculature for some time before having sufficient impact on the macrovasculature to cause patient symptoms, these markers may be usable in this "site of disease indicator" role (as part of an overall panel) earlier than in the acute symptomatic phase where they are currently used. A prerequisite to this is that sufficient assay analytical performance is achieved to allow lower limits of detection and quantification of necrotic markers coming from asymptomatic microvasculature ischemic events.

The ARTERIORISKMARKER panels of the present invention can also be used to generate reference values from a population of subjects who exhibit no symptoms (or who are asymptomatic) for an arteriovascular disease, or subjects who exhibit similar risk factors for an arteriovascular disease, such as similar body mass index, similar total cholesterol, similar LDL/HDL levels, similar blood glucose levels, similar systolic and/or diastolic blood pressure, subjects of same or similar age, subjects in the same or similar ethnic group, subjects exhibiting similar symptoms of an arteriovascular disease, or subjects having family histories of atherosclerosis, atherothrombosis, CAD, PAD, or CVD.

Construction of Clinical Algorithms

Any formula may be used to combine ARTERIORISKMARKER results into indices useful in the practice of the invention. As indicated above, and without limitation, such indices may indicate, among the various other indications, the probability, likelihood, absolute or relative risk, time to or rate of conversion from one to another disease states, or make predictions of future biomarkers measurements of arteriovascular disease such as HDLC, LDL, CRP, coronary calcium scoring, used in the diagnosis of frank arteriovascular disease. This may be for a specific time period or horizon, or for remaining lifetime risk, or simply be provided as an index relative to another reference subject population.

Although various preferred formula are described here, several other model and formula types beyond those mentioned herein and in the definitions above are well known to one skilled in the art. The actual model type or formula used may itself be selected from the field of potential models based on the performance and diagnostic accuracy characteristics of its results in a training population. The specifics of the formula itself may commonly be derived from ARTERIORISKMARKER results in the relevant training population. Amongst other uses, such formula may be intended to map the feature space derived from one or more ARTERIORISKMARKER inputs to a set of subject classes (e.g. useful in predicting class membership of subjects as normal, at risk for having an arteriovascular event, having arteriovascular disease), to derive an estimation of a probability function of risk using a Bayesian approach (e.g. the risk of arteriovascular disease or an arteriovascular event), or to estimate the class-conditional probabilities, then use Bayes' rule to produce the class probability function as in the previous case.

Preferred formulas include the broad class of statistical classification algorithms, and in particular the use of discriminant analysis. The goal of discriminant analysis is to predict class membership from a previously identified set of features. In the case of linear discriminant analysis (LDA), the linear combination of features is identified that maximizes the separation among groups by some criteria. Features can be identified for LDA using an eigengene based approach with different thresholds (ELDA) or a stepping algorithm based on a multivariate analysis of variance (MANOVA). Forward, backward, and stepwise algorithms can be performed that minimize the probability of no separation based on the Hotelling-Lawley statistic.

Eigengene-based Linear Discriminant Analysis (ELDA) is a feature selection technique developed by Shen et al. (2006). The formula selects features (e.g. biomarkers) in a multivariate framework using a modified eigen analysis to identify features associated with the most important eigenvectors. "Important" is defined as those eigenvectors that explain the most variance in the differences among samples that are trying to be classified relative to some threshold.

A support vector machine (SVM) is a classification formula that attempts to find a hyperplane that separates two classes. This hyperplane contains support vectors, data points that are exactly the margin distance away from the hyperplane. In the likely event that no separating hyperplane exists in the current dimensions of the data, the dimensionality is expanded greatly by projecting the data into larger dimensions by taking non-linear functions of the original variables (Venables and Ripley, 2002). Although not required, filtering of features for SVM often improves prediction. Features (e.g., biomarkers) can be identified for a support vector machine using a non-parametric Kruskal-Wallis (KW) test to select the best univariate features. A random forest (RF, Breiman, 2001) or recursive partitioning (RPART, Breiman et al., 1984) can also be used separately or in combination to identify biomarker combinations that are most important. Both KW and RF require that a number of features be selected from the total. RPART creates a single classification tree using a subset of available biomarkers.

Other formula may be used in order to pre-process the results of individual ARTERIORISKMARKER measurement into more valuable forms of information, prior to their presentation to the predictive formula. Most notably, normalization of biomarker results, using either common mathematical transformations such as logarithmic or logistic functions, as normal or other distribution positions, in reference to a population's mean values, etc. are all well known to those skilled in the art (as shown in FIGS. 4 and 5, and described in the Examples, such transformation and normalization of individual biomarker concentrations may commonly be performed in the practice of the invention). Of particular interest are a set of normalizations based on Clinical Parameters such as age, gender, race, or sex, where specific formula are used solely on subjects within a class or continuously combining a Clinical Parameter as an input. In other cases, analyte-based biomarkers can be combined into calculated variables (much as BMI is a calculation using Height and Weight) which are subsequently presented to a formula.

In addition to the individual parameter values of one subject potentially being normalized, an overall predictive formula for all subjects, or any known class of subjects, may itself be recalibrated or otherwise adjusted based on adjustment for a population's expected prevalence and mean biomarker parameter values, according to the technique outlined in D'Agostino et al, (2001) JAMA 286:180-187, or other similar normalization and recalibration techniques. Such epidemiological adjustment statistics may be captured, confirmed, improved and updated continuously through a registry of past data presented to the model, which may be machine readable or otherwise, or occasionally through the retrospective query of stored samples or reference to historical studies of such parameters and statistics. Additional examples that may be the subject of formula recalibration or other adjustments include statistics used in studies by Pepe, M. S. et al, 2004 on the limitations of odds ratios; Cook, M R., 2007 relating to ROC curves; and Vasan, R. S., 2006 regarding biomarkers of cardiovascular disease.

Finally, the numeric result of a classifier formula itself may be transformed post-processing by its reference to an actual clinical population and study results and observed endpoints, in order to calibrate to absolute risk and provide confidence intervals for varying numeric results of the classifier or risk formula. An example of this is the presentation of absolute risk, and confidence intervals for that risk, derived using an actual clinical study, chosen with reference to the output of the recurrence score formula in the Oncotype Dx product of Genomic Health, Inc. (Redwood City, Calif.). A further modification is to adjust for smaller sub-populations of the study based on the output of the classifier or risk formula and defined and selected by their Clinical Parameters, such as age or sex.

Modifications for Therapeutic Intervention Panels

An ARTERIORISKMARKER panel can be constructed and formula derived specifically to enhance performance for use also in subjects undergoing therapeutic interventions, or a separate panel and formula may alternatively be used solely in such patient populations. An aspect of the invention is the use of specific known characteristics of ARTERIORISKMARKERS and their changes in such subjects for such panel construction and formula derivation. Such modifications may enhance the performance of various indications noted above in arteriovascular disease prevention, and diagnosis, therapy, monitoring, and prognosis of arteriovascular disease or arteriovascular events.

Several of the ARTERIORISKMARKERS disclosed herein are known to those skilled in the art to vary predictably under therapeutic intervention, whether lifestyle (e.g. diet and exercise), surgical (e.g. coronary artery bypass graft (CABG), percutaneous intervention (PCI), bare metal, bioabsorbable or drug eluting (DES) stem placement, bariatric surgery) or pharmaceutical (e.g., one of the various classes of drugs mentioned herein or known to modify common risk factors or risk of arterio) intervention. For example, a PubMed search using the terms "POMC drug," will return over 21,100 references, many with respect to the changes or non-changes in the levels of proopiomelanocortin (POMC) in subjects treated with various individual disease-modulating agents, for both arteriovascular and other diseases. In particularly there is a documented history with the glucocorticoid drug class, but also such representative class drugs as candesartan, insulin, glyburid have all been studied with POMC.

Similar evidence of variance under therapeutic intervention is widely available for many of the biomarkers listed in Table 3, such as CRP, FGA, INS, LEP, DPP4, amongst others. Relationships have been noted in the literature between serum levels of ANG and heparin and sodium, and between CD40 and dexamethosone together with other corticosteroids, as well as with statins. VCAM1 and LEP have evidence of being affected by both statins and TZDs such as rosiglitazone.

Certain of the biomarkers listed, most particularly the Clinical Parameters and the Traditional Laboratory Risk Factors (including such biomarkers as SBP, DBP, CHOL, HDL, and HBA1c), are furthermore traditionally used as surrogate or primary endpoint markers of efficacy for entire classes of arteriovascular disease-modulating agents, thus most certainly changing in a statistically significant way.

Still others, including genetic biomarkers, such as those polymorphisms known in the PPARG and INSR (and generally all genetic biomarkers absent somatic mutation), are similarly known not to vary in their measurement under particular therapeutic interventions. Such variation may or may not impact the general validity of a given panel, but will often impact the index values reported, and may require different marker selection, the formula to be re-optimized or other changes to the practice of the invention. Alternative model calibrations may also be practiced in order to adjust the normally reported results under a therapeutic intervention, including the use of manual table lookups and adjustment factors.

Such properties of the individual ARTERIORISKMARKERS can thus be anticipated and exploited to select, guide, and monitor therapeutic interventions. For example, specific ARTERIORISKMARKERS may be added to, or subtracted from, the set under consideration in the construction of the ARTERIORISKMARKER PANELS, based on whether they are known to vary, or not to vary, under therapeutic intervention. Alternatively, such ARTERIORISKMARKERS may be individually normalized or formula recalibrated to adjust for such effects according to the above and other means well known to those skilled in the art.

Combination with Clinical Parameters and Traditional Laboratory Risk Factors

Any of the aforementioned Clinical Parameters may be used in the practice of the invention as an ARTERIORISKMARKER input to a formula or as a pre-selection criteria defining a relevant population to be measured using a particular ARTERIORISKMARKER panel and formula. As noted above, Clinical Parameters may also be useful in the biomarker normalization and pre-processing, or in ARTERIORISKMARKER selection, panel construction, formula type selection and derivation, and formula result post-processing. A similar approach can be taken with the Traditional Laboratory Risk Factors, as either an input to a formula or as a pre-selection criteria.

Measurement of ARTERIORISKMARKERS

Biomarkers may be measured in using several techniques designed to achieve more predictable subject and analytical variability. On subject variability, many of the above ARTERIORISKMARKERS are commonly measured in a fasting state, and most commonly in the morning, providing a reduced level of subject variability due to both food consumption and metabolism and diurnal variation. The invention hereby claims all fasting and temporal-based sampling procedures using the ARTERIORISKMARKERS described herein. Pre-processing adjustments of ARTERIORISKMARKER results may also be intended to reduce this effect.

The actual measurement of levels or amounts of the ARTERIORISKMARKERS can be determined at the protein or nucleic acid level using any method known in the art. For example, at the nucleic acid level, Northern and Southern hybridization analysis, as well as ribonuclease protection assays using probes which specifically recognize one or more of these sequences can be used to determine gene expression. Alternatively, amounts of ARTERIORISKMARKERS can be measured using reverse-transcription-based PCR assays (RT-PCR), e.g., using primers specific for the differentially expressed sequence of genes. Amounts of ARTERIORISKMARKERS can also be determined at the protein level, e.g., by measuring the levels of peptides encoded by the gene products described herein, or activities thereof. Such methods are well known in the art and include, e.g., immunoassays based on antibodies to proteins encoded by the genes, aptamers or molecular imprints. Any biological material can be used for the detection/quantification of the protein or its activity. Alternatively, a suitable method can be selected to determine the activity of proteins encoded by the marker genes according to the activity of each protein analyzed.

The ARTERIORISKMARKER proteins, polypeptides, mutations, and polymorphisms thereof can be detected in any suitable manner, but is typically detected by contacting a sample from the subject with an antibody which binds the ARTERIORISKMARKER protein, polypeptide, mutation, or polymorphism and then detecting the presence or absence of a reaction product. The antibody may be monoclonal, polyclonal, chimeric, or a fragment of the foregoing, as discussed in detail above, and the step of detecting the reaction product may be carried out with any suitable immunoassay. The sample from the subject is typically a biological fluid as described above, and may be the same sample of biological fluid used to conduct the method described above.

Immunoassays carried out in accordance with the present invention may be homogeneous assays or heterogeneous assays. In a homogeneous assay the immunological reaction usually involves the specific antibody (e.g., anti ARTERIORISKMARKER protein antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels which may be employed include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are oligonucleotides, immunoblotting, immunofluorescence methods, immunoprecipitation, chemiluminescence methods, electrochemiluminescence (ECL) or enzyme-linked immunoassays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label."

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., $^{35}S$, $^{125}I$, $^{131}I$) enzyme labels (e.g., horseradish peroxidase, alkaline phosphatase), and fluorescent labels (e.g., fluorescein, Alexa, green fluorescent protein, rhodamine) in accordance with known techniques.

Antibodies can also be useful for detecting post-translational modifications of ARTERIORISKMARKER proteins, polypeptides, mutations, and polymorphisms, such as tyrosine phosphorylation, threonine phosphorylation, serine phosphorylation, glycosylation (e.g., O-GlcNAc). Such antibodies specifically detect the phosphorylated amino acids in a protein or proteins of interest, and can be used in immunoblotting, immunofluorescence, and ELISA assays described herein. These antibodies are well-known to those skilled in the art, and commercially available. Post-translational modifications can also be determined using metastable ions in reflector matrix-assisted laser desorption ionization-time of flight mass spectrometry (MALDI-TOF) (Wirth, U. et al. (2002) Proteomics 2(10): 1445-51).

For ARTERIORISKMARKER proteins, polypeptides, mutations, and polymorphisms known to have enzymatic activity, the activities can be determined in vitro using enzyme assays known in the art. Such assays include, without limitation, kinase assays, phosphatase assays, reductase assays, among many others. Modulation of the kinetics of enzyme activities can be determined by measuring the rate constant $K_M$ using known algorithms, such as the Hill plot, Michaelis-Menten equation, linear regression plots such as Lineweaver-Burk analysis, and Scatchard plot.

Using sequence information provided by the database entries for the ARTERIORISKMARKER sequences, expression of the ARTERIORISKMARKER sequences can be detected (if present) and measured using techniques well known to one of ordinary skill in the art. For example, sequences within the sequence database entries corresponding to ARTERIORISKMARKER sequences, or within the sequences disclosed herein, can be used to construct probes for detecting ARTERIORISKMARKER RNA sequences in, e.g., Northern blot hybridization analyses or methods which specifically, and, preferably, quantitatively amplify specific nucleic acid sequences. As another example, the sequences can be used to construct primers for specifically amplifying the ARTERIORISKMARKER sequences in, e.g., amplification-based detection methods such as reverse-transcription based polymerase chain reaction (RT-PCR). When alterations in gene expression are associated with gene amplification, deletion, polymorphisms, and mutations, sequence comparisons in test and reference populations can be made by comparing relative amounts of the examined DNA sequences in the test and reference cell populations.

Expression of the genes disclosed herein can be measured at the RNA level using any method known in the art. For example, Northern hybridization analysis using probes which specifically recognize one or more of these sequences can be used to determine gene expression. Alternatively, expression can be measured using reverse-transcription-based PCR assays (RT-PCR), e.g., using primers specific for the differentially expressed sequences. RNA can also be quantified using, for example, other target amplification methods (e.g., TMA, SDA, NASBA), or signal amplification methods (e.g., bDNA), and the like.

Alternatively, ARTERIORISKMARKER protein and nucleic acid metabolites can be measured. The term "metabolite" includes any chemical or biochemical product of a metabolic process, such as any compound produced by the processing, cleavage or consumption of a biological molecule (e.g., a protein, nucleic acid, carbohydrate, or lipid). Metabolites can be detected in a variety of ways known to one of skill in the art, including the refractive index spectroscopy (RI), ultra-violet spectroscopy (UV), fluorescence analysis, radiochemical analysis, near-infrared spectroscopy (near-IR), nuclear magnetic resonance spectroscopy (NMR), light scattering analysis (LS), mass spectrometry, pyrolysis mass spectrometry, nephelometry, dispersive Raman spectroscopy, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, NMR and IR detection. (See, WO 04/056456 and WO 04/088309, each of which are hereby incorporated by reference in their entireties) In this regard, other ARTERIORISKMARKER analytes can be measured using the above-mentioned detection methods, or other methods known to the skilled artisan. For example, circulating calcium ions ($Ca^{2+}$) can be detected in a sample using fluorescent dyes such as the Fluo series, Fura-2A, Rhod-2, among others. Other ARTERIORISKMARKER metabolites can be similarly detected using reagents that are specifically designed or tailored to detect such metabolites.

Kits

The invention also includes a ARTERIORISKMARKER-detection reagent, e.g., nucleic acids that specifically identify one or more ARTERIORISKMARKER nucleic acids by having homologous nucleic acid sequences, such as oligonucleotide sequences, complementary to a portion of the ARTERIORISKMARKER nucleic acids or antibodies to proteins encoded by the ARTERIORISKMARKER nucleic acids packaged together in the form of a kit. The oligonucleotides can be fragments of the ARTERIORISKMARKER genes. For example the oligonucleotides can be 200, 150, 100, 50, 25, 10 or less nucleotides in length. The kit may contain in separate containers a nucleic acid or antibody (either already bound to a solid matrix or packaged separately with reagents for binding them to the matrix), control formulations (positive and/or negative), and/or a detectable label such as fluorescein, green fluorescent protein, rhodamine, cyanine dyes, Alexa dyes, luciferase, radiolabels, among others. Instructions (e.g., written, tape, VCR, CD-ROM, etc.) for carrying out the assay may be included in the kit. The assay may for example be in the form of a Northern hybridization or a sandwich ELISA as known in the art.

For example, ARTERIORISKMARKER detection reagents can be immobilized on a solid matrix such as a porous strip to form at least one ARTERIORISKMARKER detection site. The measurement or detection region of the porous strip may include a plurality of sites containing a nucleic acid. A test strip may also contain sites for negative and/or positive controls. Alternatively, control sites can be located on a separate strip from the test strip. Optionally, the different detection sites may contain different amounts of immobilized nucleic acids, e.g., a higher amount in the first detection site and lesser amounts in subsequent sites. Upon the addition of test sample, the number of sites displaying a detectable signal provides a quantitative indication of the amount of ARTERIORISKMARKERS present in the sample. The detection sites may be configured in any suitably detectable shape and are typically in the shape of a bar or dot spanning the width of a test strip.

Alternatively, the kit contains a nucleic acid substrate array comprising one or more nucleic acid sequences. The nucleic acids on the array specifically identify one or more nucleic acid sequences represented by ARTERIORISKMARKERS 1-1023. In various embodiments, the expression of 2, 3, 4, 5, 6, 7, 8, 9, 10, 15, 20, 25, 40, 50, 100, 125, 150, 175, 200, 300, 400, 500, 600, 700, 800, 900, 1000 or more of the sequences represented by ARTERIORISKMARKERS 1-1023 can be identified by virtue of binding to the array. The substrate array can be on, e.g., a solid substrate, e.g., a "chip" as described in U.S. Pat. No. 5,744,305. Alternatively, the substrate array can be a solution array, e.g., xMAP (Luminex, Austin, Tex.), Cyvera (Illumina, San Diego, Calif.), CellCard (Vitra Bioscience, Mountain View, Calif.) and Quantum Dots' Mosaic (Invitrogen, Carlsbad, Calif.).

Suitable sources for antibodies for the detection of ARTERIORISKMARKERS includecommercially available sources such as, for example, Abazyme, Abnova, Affinity Biologicals, AntibodyShop, Biogenesis, Biosense Laboratories, Calbiochem, Cell Sciences, Chemicon International, Chemokine, Clontech, Cytolab, DAKO, Diagnostic BioSystems, eBioscience, Endocrine Technologies, Enzo Biochem, Eurogentec, Fusion Antibodies, Genesis Biotech, GloboZymes, Haematologic Technologies, Immunodetect, Immunodiagnostik, Immunometrics, Immunostar, Immunovision, Biogenex, Invitrogen, Jackson ImmunoResearch Laboratory, KMI Diagnostics, Koma Biotech, LabFrontier Life Science Institute, Lee Laboratories, Lifescreen, Maine Biotechnology Services, Mediclone, MicroPharm Ltd., ModiQuest, Molecular Innovations, Molecular Probes, Neoclone, Neuromics, New England Biolabs, Novocastra, Novus Biologicals, Oncogene Research Products, Orbigen, Oxford Biotechnology, Panvera, PerkinElmer Life Sciences, Pharmingen, Phoenix Pharmaceuticals, Pierce Chemical Company, Polymun Scientific, Polysiences, Inc., Promega Corporation, Proteogenix, Protos Immunoresearch, QED Biosciences, Inc., R&D Systems, Repligen, Research Diagnostics, Roboscreen, Santa Cruz Biotechnology, Seikagaku America, Serological Corporation, Serotec, SigmaAldrich, StemCell Technologies, Synaptic Systems GmbH, Technopharm, Terra Nova Biotechnology, TiterMax, Trillium Diagnostics, Upstate Biotechnology, US Biological, Vector Laboratories, Wako Pure Chemical Industries, and Zeptometrix. However, the skilled artisan can routinely make antibodies, nucleic acid probes, e.g., oligonucleotides, aptamers, siRNAs, antisense oligonucleotides, against any of the ARTERIORISKMARKERS in Table 2.

EXAMPLES

Materials and Methods

Source Reagents: A large and diverse array of vendors that were used to source immunoreagents as a starting point for assay development, such as, but not limited to, Abazyme, Abnova, Affinity Biologicals, AntibodyShop, Biogenesis, Biosense Laboratories, Calbiochem, Cell Sciences, Chemicon International, Chemokine, Clontech, Cytolab, DAKO, Diagnostic BioSystems, eBioscience, Endocrine Technologies, Enzo Biochem, Eurogentec, Fusion Antibodies, Genesis Biotech, GloboZymes, Haematologic Technologies, Immunodetect, Immunodiagnostik, Immunometrics, Immunostar, Immunovision, Biogenex, Invitrogen, Jackson ImmunoResearch Laboratory, KMI Diagnostics, Koma Biotech, LabFrontier Life Science Institute, Lee Laboratories, Lifescreen, Maine Biotechnology Services, Mediclone, MicroPharm Ltd., ModiQuest, Molecular Innovations, Molecular Probes, Neoclone, Neuromics, New England Biolabs, Novocastra, Novus Biologicals, Oncogene Research Products, Orbigen, Oxford Biotechnology, Panvera, PerkinElmer Life Sciences, Pharmingen, Phoenix Pharmaceuticals, Pierce Chemical Company, Polymun Scientific, Polysiences, Inc., Promega Corporation, Proteogenix, Protos Immunoresearch, QED Biosciences, Inc., R&D Systems, Repligen, Research Diagnostics, Roboscreen, Santa Cruz Biotechnology, Seikagaku America, Serological Corporation, Serotec, SigmaAldrich, StemCell Technologies, Synaptic Systems GmbH, Technopharm, Terra Nova Biotechnology, TiterMax, Trillium Diagnostics, Upstate Biotechnology, US Biological, Vector Laboratories, Wako Pure Chemical Industries, and Zeptometrix. A search for capture antibodies, detection antibodies, and analytes was performed to configure a working sandwich immunoassay. The reagents were ordered and received into inventory.

Immunoassays were developed in three steps: Prototyping, Validation, and Kit Release. Prototyping was conducted using standard ELISA formats when the two antibodies used in the assay were from different host species. Using standard conditions, anti-host secondary antibodies conjugated with horse radish peroxidase were evaluated in a standard curve. If a good standard curve was detected, the assay proceeded to the next step. Assays that had the same host antibodies went directly to the next step (e.g., mouse monoclonal sandwich assays).

Validation of working assays was performed using the Zeptosense detection platform from Singulex, Inc. (St. Louis, Mo.). The detection antibody was first conjugated to the fluorescent dye Alexa 647. The conjugations used standard NHS ester chemistry, for example, according to the manufacturer. Once the antibody was labeled, the assay was tested in a sandwich assay format using standard conditions. Each assay well was solubilized in a denaturing buffer, and the material was read on the Zeptosense platform.

Once a working Zeptosense standard curve was demonstrated, assays were typically applied to 24-96 serum samples to determine the normal distribution of the target analyte across clinical samples. The amount of serum required to measure the biomarker within the linear dynamic range of the assay was determined, and the assay proceeded to kit release. For the initial validated assays, 0.004 microliters were used per well on average.

Each component of the kit including manufacturer, catalog numbers, lot numbers, stock and working concentrations, standard curve, and serum requirements were compiled into a standard operating procedures for each biomarker assay. This kit was then released for use to test clinical samples.

Example 1

Example 1 presents the practice of the invention in a longitudinal case-control study design. The starting sample was a large population based longitudinal study following approximately 6,300 patients over a minimum of five years to date. In the initial smaller subset study and analysis presented here, patients were first selected based on no prior history of acute arteriovascular events at baseline study entry, and risk enriched to an estimated applicable clinical population most likely to be tested by an ATERIORISK-MARKER combination panel by applying an "entry" baseline requirement of age greater than or equal to 39 years old and body mass index of greater than or equal to 25.

This population was then filtered to remove those who subsequently experienced an arteriovascular event during the study, such events including a broad definition of myocardial infarction, unstable angina, revascularization (such as thrombolysis, PCI or CABG), or ischemic stroke (hemorrhagic strokes were removed). A randomized sampling of 33 of these subjects who ultimately converted to arteriovascular events during the course of the study (Converters) were initially selected as a Case arm for marker discovery and initial algorithm training.

A general prevalence based randomized sample control arm of 724 of the total subjects was selected from the remaining age and BMI enriched population which did not experience a subsequent acute arteriovascular event during the study duration was also selected (Controls).

Example 1 herein focuses on a subset Case group of 26 subjects of the 33, excluding those 7 subjects who experienced strokes (and without any other arteriovascular events) during the duration of the study, resulting in a subset comprising solely those who experienced myocardial infarction (14 subjects), angina requiring hospitalization (11 patients), any revascularization procedure (17 patients), or any combination of these arteriovascular events. None of these 26 patients also experienced strokes during this period.

Example 2 focuses on the entire group of 33 Converters, including the 7 stroke patients. Summary descriptive subject statistics and risk factor distributions are presented in Table 11 below and in FIG. 3.

TABLE 11

Study Design for Example 1 (26 Cases) and Example 2 (33 Cases)

| | | Excluding Stroke | | | Including Stroke | |
| --- | --- | --- | --- | --- | --- | --- |
| | | Cases (n = 26) | Controls (n = 724) | | Cases (n = 33) | Controls (n = 724) |
| Age | Mean | 54 | 49 | Age | Mean | 53 | 49 |
| | (sd) | (4.7) | (6.4) | | (sd) | (5) | (6.4) |
| Sex | Male | 21 | 441 | Sex | Male | 28 | 441 |
| | Female | 5 | 283 | | Female | 5 | 283 |
| Family Hist. | No | 24 | 656 | Family Hist. | No | 30 | 656 |
| (Cardiac) | Yes | 2 | 68 | (Cardiac) | Yes | 3 | 68 |
| Hyperlipidemia | No | 8 | 212 | Hyperlipidemia | No | 11 | 212 |
| | Yes | 18 | 512 | | Yes | 22 | 512 |
| Diabetes | No | 23 | 635 | Diabetes | No | 29 | 635 |
| | Yes | 3 | 89 | | Yes | 4 | 89 |
| Smoking | No | 18 | 517 | Smoking | No | 22 | 517 |
| | Yes | 8 | 207 | | Yes | 11 | 207 |
| Dyslipidemia | No | 5 | 151 | Dyslipidemia | No | 6 | 151 |
| | Yes | 21 | 573 | | Yes | 27 | 573 |
| Hypertension | No | 12 | 336 | Hypertension | No | 12 | 338 |
| | Yes | 14 | 386 | | Yes | 21 | 386 |
| High HDL | No | 23 | 546 | High HDL | No | 29 | 548 |
| | Yes | 3 | 176 | | Yes | 4 | 176 |

TABLE 11-continued

Study Design for Example 1 (26 Cases) and Example 2 (33 Cases)

| | Excluding Stroke | | | Including Stroke | | |
|---|---|---|---|---|---|---|
| | | Cases (n = 26) | Controls (n = 724) | | Cases (n = 33) | Controls (n = 724) |
| Risk Factor Score* | −1 | 0 | 12 | Risk Factor Score* −1 | 0 | 12 |
| | 0 | 2 | 90 | 0 | 2 | 90 |
| | 1 | 3 | 134 | 1 | 3 | 134 |
| | 2 | 5 | 167 | 2 | 7 | 167 |
| | 3 | 5 | 178 | 3 | 6 | 178 |
| | 4 | 8 | 103 | 4 | 11 | 103 |
| | 5 | 3 | 36 | 5 | 4 | 36 |
| | 6 | 0 | 4 | 6 | 0 | 4 |

*Definition of Risk Factor Score
One point for each risk factor as below:
LDL > 160
HDL < 40 (IF HDL >= 60 then Score is −1)
CHOL > 200
BP: SBP >= 140 OR DP >= 90
AGE >= 45 (MEN) or AGE >= 55 (WOMEN)
Baseline Diabetes: Present Baseline (at study entry) samples were tested according to the above methods and results recorded for a representative grouping of 61 ARTERIORISKMARKERS, with biomarkers selected primarily on the basis of the strength of published literature supporting an association with ateriovascular and cardiometabolic disease.

Data Analysis

Prior to statistical methods being applied, each ARTERIORISKMARKER assay plate was reviewed for pass/fail criteria. Parameters taken into consideration included number of samples within range of the standard curve, serum control within the range of the standard curve, CVs of samples and dynamic range of assay.

A model based on the continuous input model of the Framingham Risk Score of Wilson (1998), comprising eight ATERIORISKMARKER inputs (Age, CHOL, HDLC, SBP, DBP, Smoking, Diabetes, and Sex), was calculated in order to have a baseline to measure improvement from the incorporation of differing ARTERIORISKMARKERS into the potential formulas. FIG. 6 is a chart depicting the Receiver Operator Characteristic (ROC) curve of a global risk assessment index according to the Framingham model for risk of future cardiovascular events, as measured and calculated for the Example 1 populations (sensitivity and specificity of the Framingham model to cardiovascular events excluding stroke patients from the analysis) and with the Area Under the Curve (AUC) statistic of 0.61 calculated and shown in the legend. Additionally, various best fit models for the populations of Example 1 were also constructing using all of the Clinical Parameters and Traditional Laboratory Risk Factors of the invention (which include all of the aforementioned Framingham variables), this is presented, together with full models encompassing all of the blood-bourne ATERIORISKMARKERS and the total tested set of ATERIORISKMARKERS in FIG. 16.

Prior to formula analysis, ATERIORISKMARKER parameters were transformed, according to the methodologies shown for each ATERIORISKMARKER in FIG. 4, and missing results were imputed. If the amount of missing data was greater than 1%, various imputation techniques were employed to evaluate the effect on the results, otherwise the k-nearest neighbor method (library EMV, R Project) was used using correlation as the distance metric and 6 nearest neighbors to estimate the missing values.

Excessive covariation, multicolinearity, between variables were evaluated graphically and by computing pairwise correlation coefficients. When the correlation coefficients exceeded 0.75, a strong lack of independence between biomarkers was indicated, suggesting that they should be evaluated separately. Univariate summary statistics including means, standard deviations, and odds ratios were computed using logistic regression.

FIG. 4 is a is a table summarizing the measured values and variances of certain selected ARTERIORISKMARKERS studied within the Examples given, including their concentration or other measurement units, mathematical normalization transformations (used in model formula and multi-biomarker index construction), transformed mean and standard deviation values, and back-transformed (raw) mean biomarker concentration or other value as measured for both the Total Cases (Converter to Arteriovascular Events, n=33) and Controls (Non-Converter to Cardiovascular Events, n=724) of the Examples, as well as a comparison of the mean values with a statistical p-value given, using a two-tailed t-test for the null hypothesis (the random probability that group means are equal). The given concentrations represent population based means and standard deviations useful in the construction and optimization of assays in the practice of the invention.

FIG. 5 is is a table further dividing the Cases cohort into sub-groupings based on the event type, separating stroke into one cohort, and, for the non-stroke subjects, based on the time elapsed from the baseline entry date to the study (also the sample collection date for the samples tested for ARTERIORISKMARKERS) to the earliest arteriovascular event date. Subsequent examination of subject records also indicated a group of 3 subjects who likely had an arteriovascular event prior to the baseline, these were also separated into a cohort. This table also provides the measured means and variances for each sub-group as otherwise described in FIG. 4 applying the same summary statistics, additionally providing statistical p-values for a one-way Analysis of Variance (ANOVA) and non-parametric Kruskal-Wallis analysis of variance (KW). Several markers show statistically significant differences across the sub-groups, indicating an ability to both distinguish stroke from other arteriovascular events and also to distinguish between early and late converters to arteriovascular events when combined with appropriate models.

Biomarker Selection and Model Building

Figure 7:
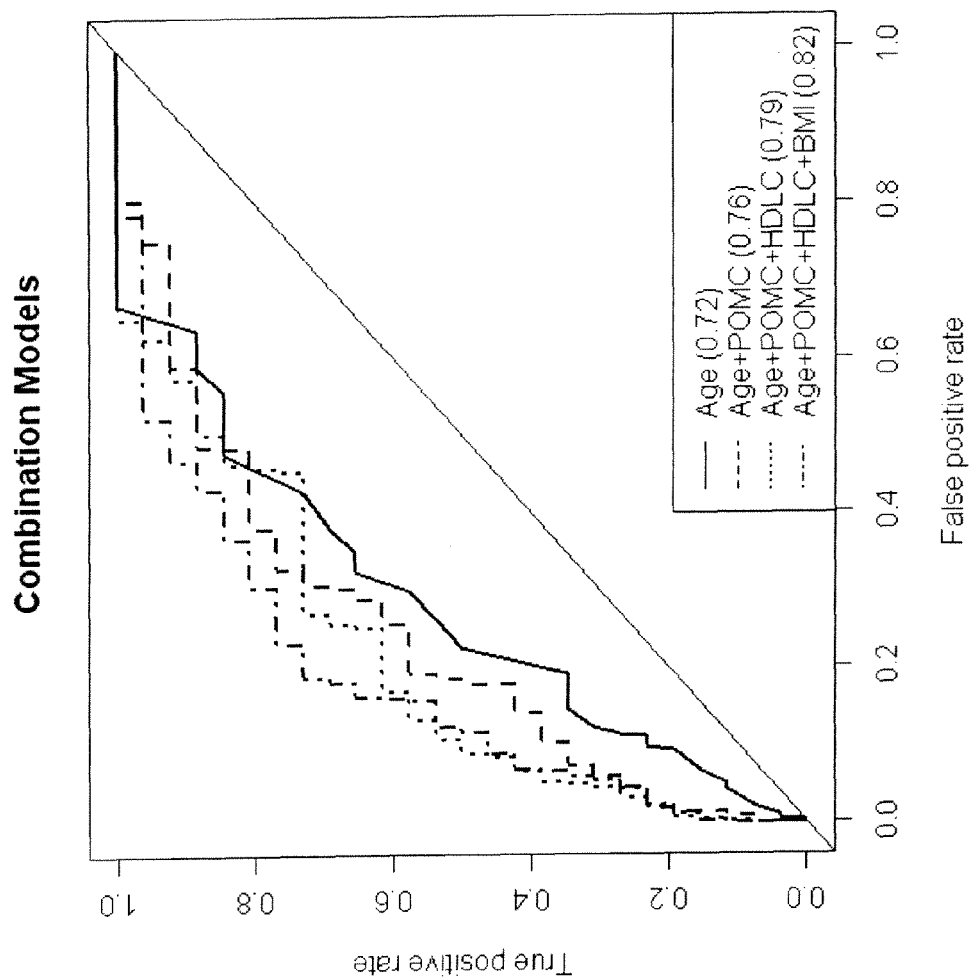
FIG. 7 is a chart depicting the ROC curves of multiple fitted linear discrimant analysis (LDA) models for risk of future arteriovascular events, as measured and calculated for the Example 1 populations, starting with a single ARTERI-ORISKMARKER clinical parameter (Age) ROC curve, then adding an additional ARTERIORISKMARKER (POMC, HDLC, and BMI) and reoptimizing the model at each subsequent ROC curve, with the AUC calculated and shown in the legend for each step. These increasing curve AUCs demonstrate the additional discrimination value imparted by the additional marker, increasing from 0.72 to 0.82.

Characteristics of the populations of Example 1 were considered in various predictive models, model types, and model parameters, and the AUC results of these formula are summarized in FIG. 19. Several stepwise marker addition algorithms were constructed from null and full sets, as well as groupings seeded by initial markers and alternative selection strategies as described herein; an example of a cumulative step analysis and ROC curve result is presented in FIG. 7 for the ARTERIORISKMARKER of POMC, which evidenced strong prognostic value in the populations of the example, particularly when combined with Core Markers, Clinical Parameters and the Traditional Laboratory Risk Factors disclosed in the invention. FIG. 7 is a chart depicting the ROC curves of multiple fitted linear discriminant analysis (LDA) models for risk of future arteriovascular events, as measured and calculated for the Example 1 populations, starting with a single ARTERIORISKMARKER clinical parameter (Age) ROC curve, then adding an additional ARTERIORISKMARKER (POMC, HDLC, and BMI) and reoptimizing the model at each subsequent ROC curve, with the AUC calculated and shown in the legend for each step. These increasing curve AUCs demonstrate the additional discrimination value imparted by the additional marker, increasing from 0.72 to 0.82.

Figure 8:
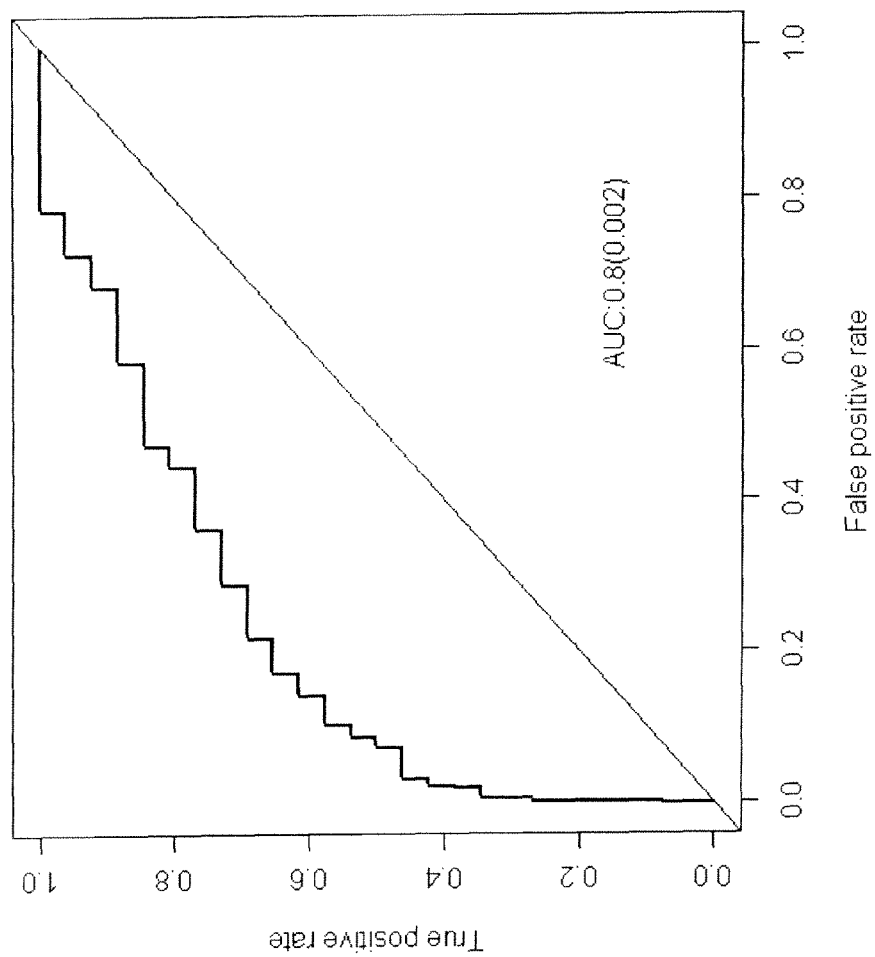
FIG. 8 is a chart depicting the ROC curves of a seven biomarker fitted LDA model for risk of future arteriovascular events, as measured and calculated for the Example 1 populations, with the AUC calculated and shown in the legend. This LDA model was forward selected from a group limited to blood-bourne ARTERIORISKMARKERS as its sole parameters, and included POMC, HDLC, VEGF, LEP, IL6ST, Ins120, and IGF1 as inputs, with a calculated AUC of 0.8.

Multiple model building techniques designed to trade off model size with performance were used. Models utilizing both blood-borne only ATERIORISKMARKERS, as might be most useful in a remote laboratory or site separated from the collection of the Clinical Parameters, and also using all ARTERIORISKMARKERS, were constructed. Two examples are provided in FIG. 8 and FIG. 9. FIG. 8 is a chart depicting the ROC curves of a seven biomarker fitted LDA model for risk of future arteriovascular events, as measured and calculated for the Example 1 populations, with the AUC calculated and shown in the legend. This LDA model was forward selected from a group limited to blood-bourne ARTERIORISKMARKERS as its sole parameters, and included POMC, HDLC, VEGF, LEP, IL6ST, Ins120, and IGF1 as inputs, with a calculated AUC of 0.8.

Figure 9:
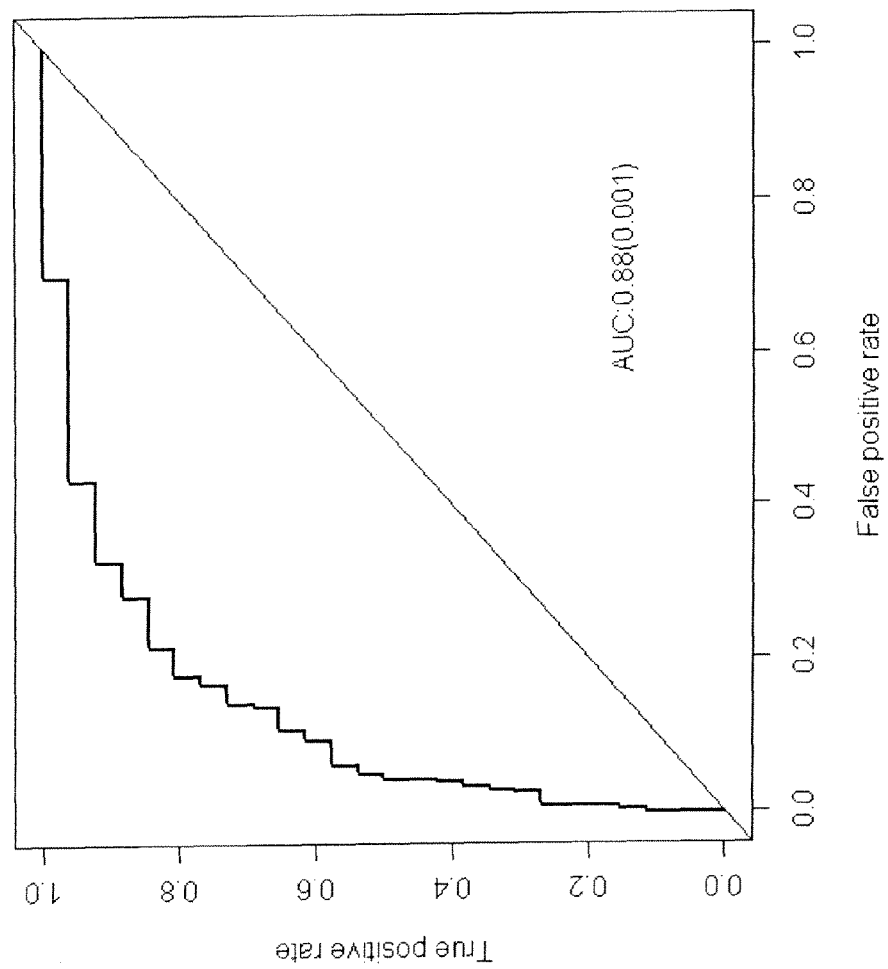
FIG. 9 is a chart depicting the ROC curves of a nine biomarker fitted LDA model for risk of future arteriovascular events, as measured and calculated for the Example 1 populations, with the AUC calculated and shown in the legend. This LDA model was forward selected from the complete group of both the selected blood-bourne analyte and clinical parameter ARTERIORISKMARKERS, and included Age, POMC, HDLC, CCL2, BMI, VEGF, IL18, IL6ST, EGF, with a calculated AUC of 0.88.

FIG. 9 is a chart depicting the ROC curves of a nine biomarker fitted LDA model for risk of future arteriovascular events, as measured and calculated for the Example 1 populations, with the AUC calculated and shown in the legend. This LDA model was forward selected from the complete group of both the selected blood-bourne analyte and clinical parameter ARTERIORISKMARKERS, and included Age, POMC, FIDLC, CCL2, BMI, VEGF, IL18, IL6ST, EGF, with a calculated AUC of 0.88.

Figure 10:
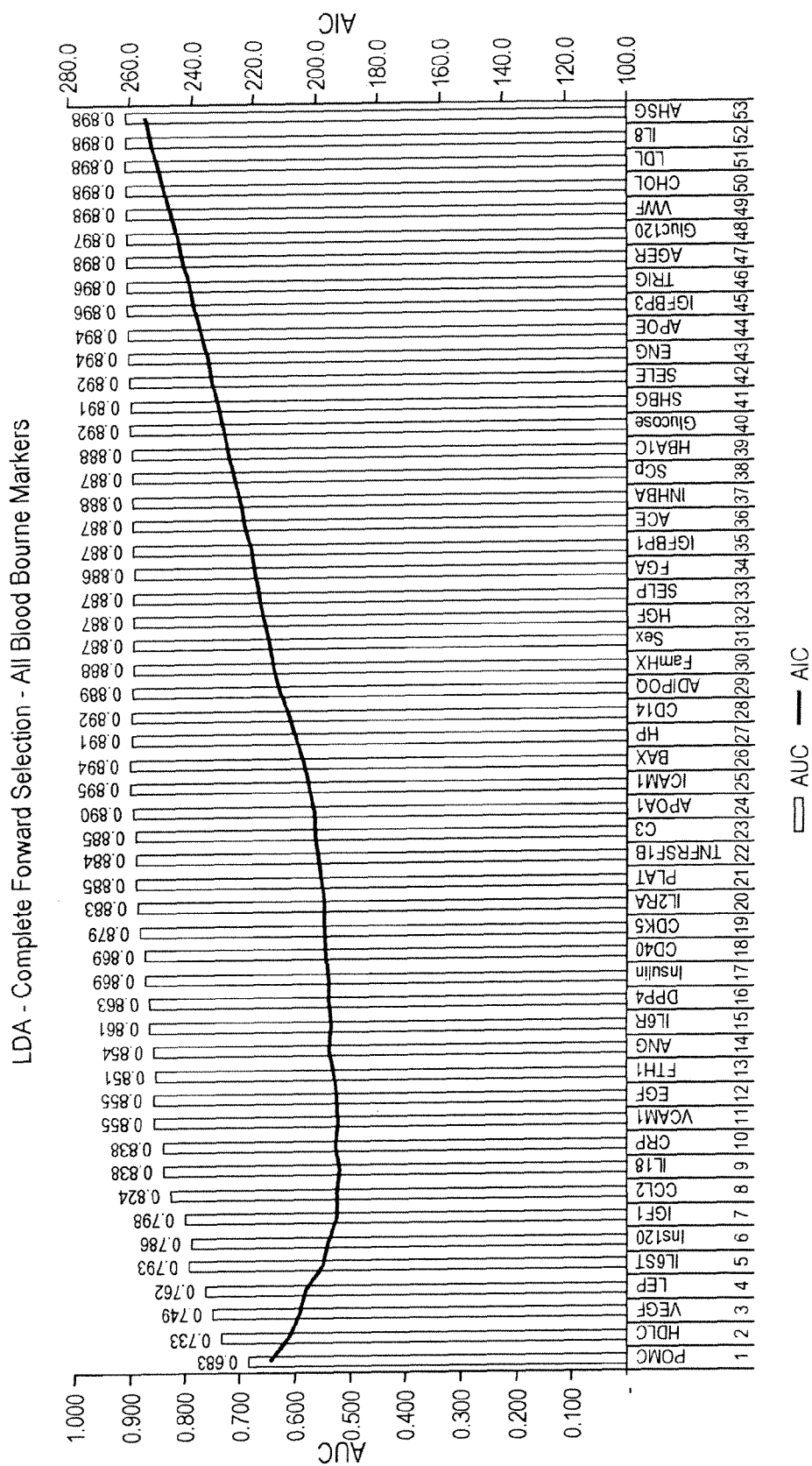
FIG. 10 is a chart depicting the ROC curve calculated AUC statistics for multiple expanding "best forward selected" LDA models, starting from a single ARTERIORISKMARKER and then at each step adding one more incremental forward selected ARTERIORISKMARKER, re-optimizing the LDA model, and graphing the derived AUC statistic using the results from the Example 1 study populations. This continues through 53 selected ARTERIORISKMARKERS selected from a total set of the selected blood-bourne ARTERIORISKMARKERS, Sex and Family History (FamHX). A superimposed line shows the parallel changes in Akaike's Information Criterion (AIC), a measure of the goodness of fit of an estimated statistical model which trades off model complexity (size in total number of ARTERIORISKMARKER inputs) against how well the model fits the data (a lower AIC is relatively better than a higher one).
Figure 11:
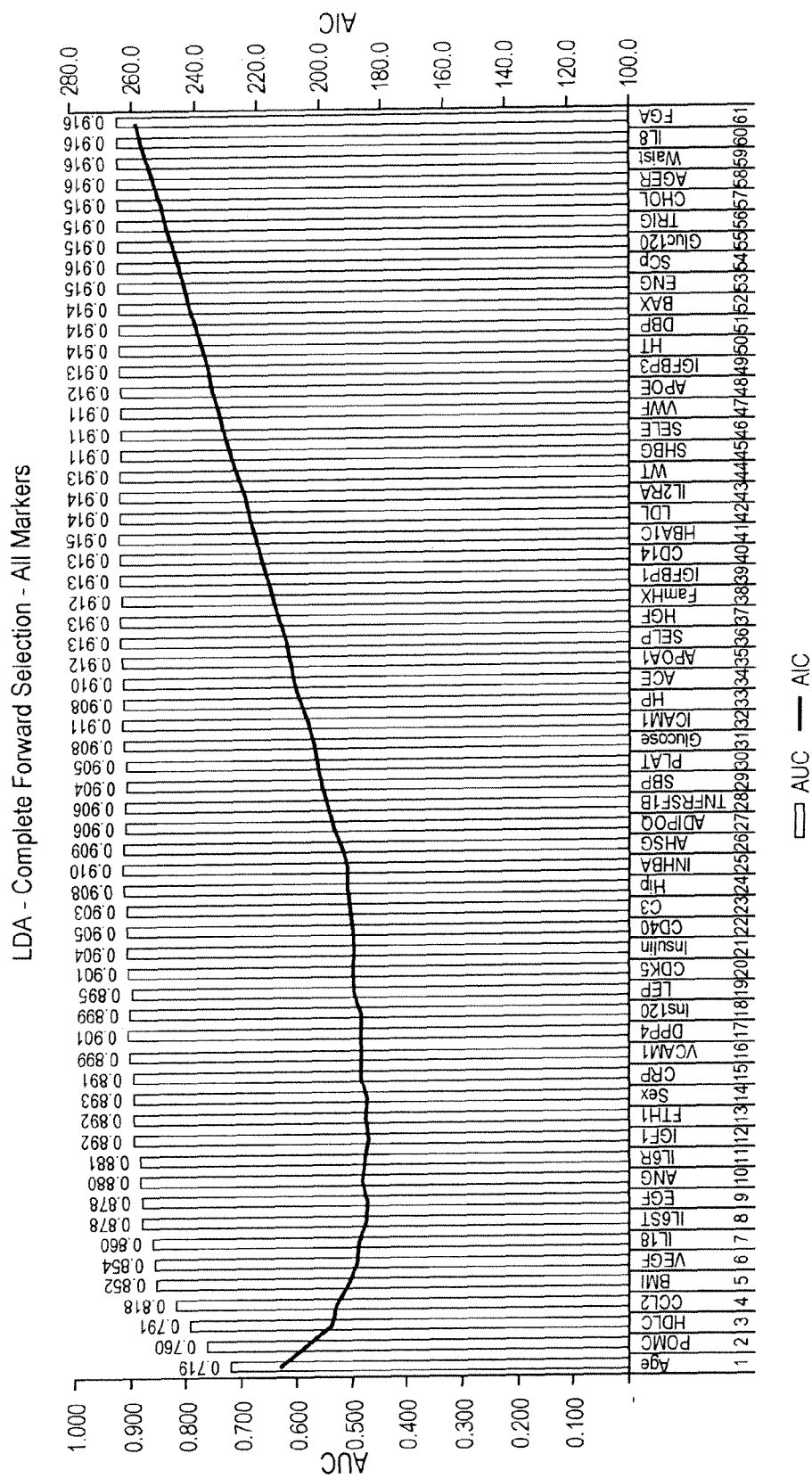
FIG. 11 is a chart depicting the ROC curve calculated AUC statistics for multiple expanding "best forward selected" LDA models, starting from a single ARTERIORISKMARKER and then at each step adding one more incremental forward selected ARTERIORISKMARKER, re-optimizing the LDA model, and graphing the derived AUC statistic using the results from the Example 1 study populations. This continues through 61 ARTERIORISKMARKERS representing the complete group of both the selected blood-bourne analyte and clinical parameter ARTERIORISKMARKERS. The AIC is included as in the previous chart.

Forward selection and complete enumeration techniques were used in order to confirm the ranking, ordering, and apparent categorization of the various ARTERIORISKMARKERS. FIG. 10 and FIG. 11 present two such analyses performed using the results from the Example 1 population. FIG. 10 is a chart depicting the ROC curve calculated AUC statistics for multiple expanding "best forward selected" LDA models, starting from a single ARTERIORISKMARKER and then at each step adding one more incremental forward selected ARTERIORISKMARKER, re-optimizing the LDA model, and graphing the derived AUC statistic. This continues through 53 selected ARTERIORISKMARKERS selected from a total set of the selected blood-bourne ARTERIORISKMARKERS, Sex and Family History (FamHX). A superimposed line shows the parallel changes in Akaike's Information Criterion (AIC), a measure of the goodness of fit of an estimated statistical model which trades off model complexity (size in total number of ARTERIORISKMARKER inputs) against how well the model fits the data (a lower AIC is relatively better than a higher one).

FIG. 11 is also a chart depicting the ROC curve calculated AUC statistics for multiple expanding "best forward selected" LDA models, starting from a single ARTERIORISKMARKER and then at each step adding one more incremental forward selected ARTERIORISKMARKER, re-optimizing the LDA model, and graphing the derived AUC statistic. This continues through 61 ARTERIORISKMARKERS representing the complete group of both the selected blood-bourne analyte and clinical parameter ARTERIORISKMARKERS. The AIC is included as in the previous chart.

Complete enumeration of various model sizes, as measured in numbers of ARTERIORISKMARKERS incorporated, was performed in order to confirm the substitutability of various markers and of the various ARTERIORISKMARKER categories of the invention. FIG. 12 is a table summarizing the complete enumeration of fitted LDA models for all single, two, three, and four ARTERIORISKMARKER combinations possible from a starting set of 61 selected ARTERIORISKMARKERS, including both blood-bourne analytes and clinical parameters. The table indicates first the total possible panel combinations, which expands from 61 for single ARTERIORISKMARKERS to 521,855 for four ARTERIORISKMARKER combinations. It then gives the number of combinations which produce fitted LDA models that achieve an equal or greater AUC than that shown as the hurdle in the leftmost column of the table (all as calculated in the populations of Example 1). For example, in the row indicated 0.75, from all possible two ARTERIORISKMARKER combinations (1,830 combinations), only 2 combinations (0.11% of the total two ARTERIORISKMARKER combinations possible) resulted in a fitted LDA model that equalled or exceeded an AUC of 0.75, while only 198 three ARTERIORISKMARKER combinations (0.55% of 35,990 possible three ARTERIORISKMARKER combinations) resulted in fitted LDA models exceeding the same hurdle, and so on. No single markers reached this hurdle; in fact, in the data set used only Age and POMC equaled or exceeded an AUC of 0.65.

The highest performing subsets of the complete enumerated combinations, as measured in the populations of Example 1, are presented in FIGS. 13 through 15. FIG. 13 is a table listing all 200 individual two marker combinations (10.93% out of a total 1,830 unique combinations possible) achieving an AUC of 0.65 or better according to the analysis summarized previously. FIG. 14 is a table listing all 2,573 individual two marker combinations (7.15% out of a total 1,830 unique combinations possible) achieving an AUC of 0.70 or better according to the analysis summarized previously. FIG. 15 is a table listing all 8,153 individual two marker combinations (1.56% out of a total 521,855 unique combinations possible) achieving an AUC of 0.75 or better according to the analysis summarized previously.

Figure 16:
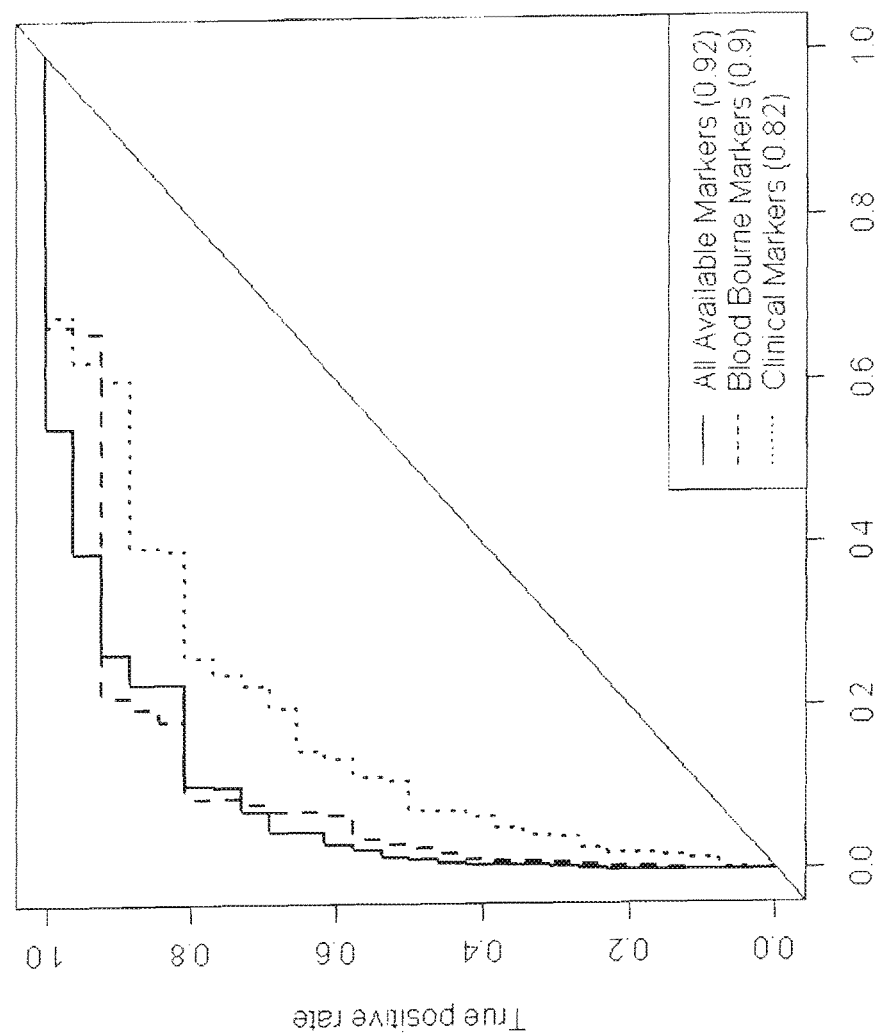
FIG. 16 is a chart depicting the ROC curves of multiple fitted full models, utilizing the best model of any type by achieved ROC curve (chosen from model types including LDA (multiple selection and model size criteria), SVM (Random Forest, Top Kruskal-Wallis), and ELDA (multiple thresholds)) for risk of future arteriovascular events, as measured and calculated for the Example 1 populations. This chart encompasses models selected from three different overlapping subsets of ARTERIORISKMARKERS from a total set of 61 selected ARTERIORISKMARKERS. One subset encompassed all "Clinical Marker" ARTERIORISKMARKERS, including both the non-analyte clinical parameters as well as only the blood-bourne traditional laboratory risk factors most commonly used in current global risk assessment models: CHOL, HDLC, LDL, HBA1C, Glucose, and Insulin; it achieved a maximum AUC of 0.82. Another group included only the "Blood-Bourne Markers" analyte-based ARTERIORISKMARKERS without non-analyte clinical parameters; it achieved an ROC of 0.86. The final set included all 61 selected ARTERIORISKMARKERS; it achieved an AUC of 0.92. This analysis demonstrates selected use of blood-bourne ARTERIORISKMARKERS imparts incremental information even to the full set of standard clinical parameters and traditional laboratory risk factors.

This was continued with analysis of "full" models, consisting of various subsets and the total number of ARTERIORISKMARKERS available to the individual marker selection model. FIG. 16 is a chart depicting the ROC curves of multiple fitted full models, utilizing the best model of any type by achieved ROC curve (chosen from model types including LDA (multiple selection and model size criteria), SVM (Random Forest, Top Kruskal-Wallis), and ELDA (multiple thresholds)) for risk of future arteriovascular events, as measured and calculated for the Example 1 populations. This chart encompasses models selected from three different overlapping subsets of ARTERIORISK-MARKERS from a total set of 61 selected ARTERIORISK-MARKERS. One subset encompassed all "Clinical Marker" ARTERIORISKMARKERS, including both the non-analyte clinical parameters as well as only the blood-bourne traditional laboratory risk factors most commonly used in current global risk assessment models: CHOL, HDLC, LDL, HBA1C, Glucose, and Insulin; it achieved a maximum AUC of 0.82, Another group included only the "Blood-Bourne Markers" analyte-based ARTERIORISKMARKERS without non-analyte clinical parameters; it achieved an ROC of 0.86. The final set included all 61 selected ARTERIORISK-MARKERS; it achieved an AUC of 0.92. This analysis demonstrates selected use of blood-bourne ARTERIORISK-MARKERS imparts incremental information even to the full set of standard clinical parameters and traditional laboratory risk factors.

Figure 17:
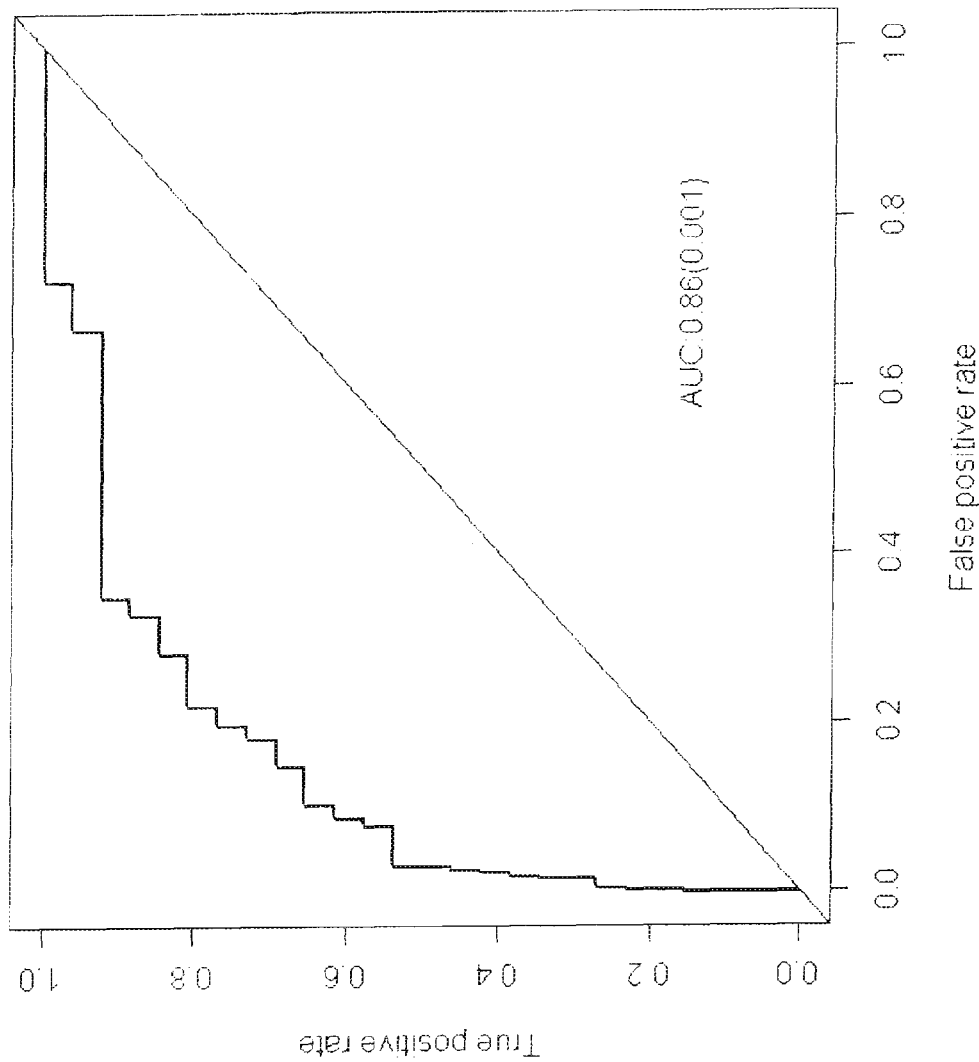
FIG. 17 is a chart depicting the ROC curve of the best blood-bourne ARTERIORISKMARKER model from FIG. 16, selected from only the blood-borne ARTERIORISKMARKERS, including its AUC statistic of 0.86 as shown in the legend.
Figure 18:
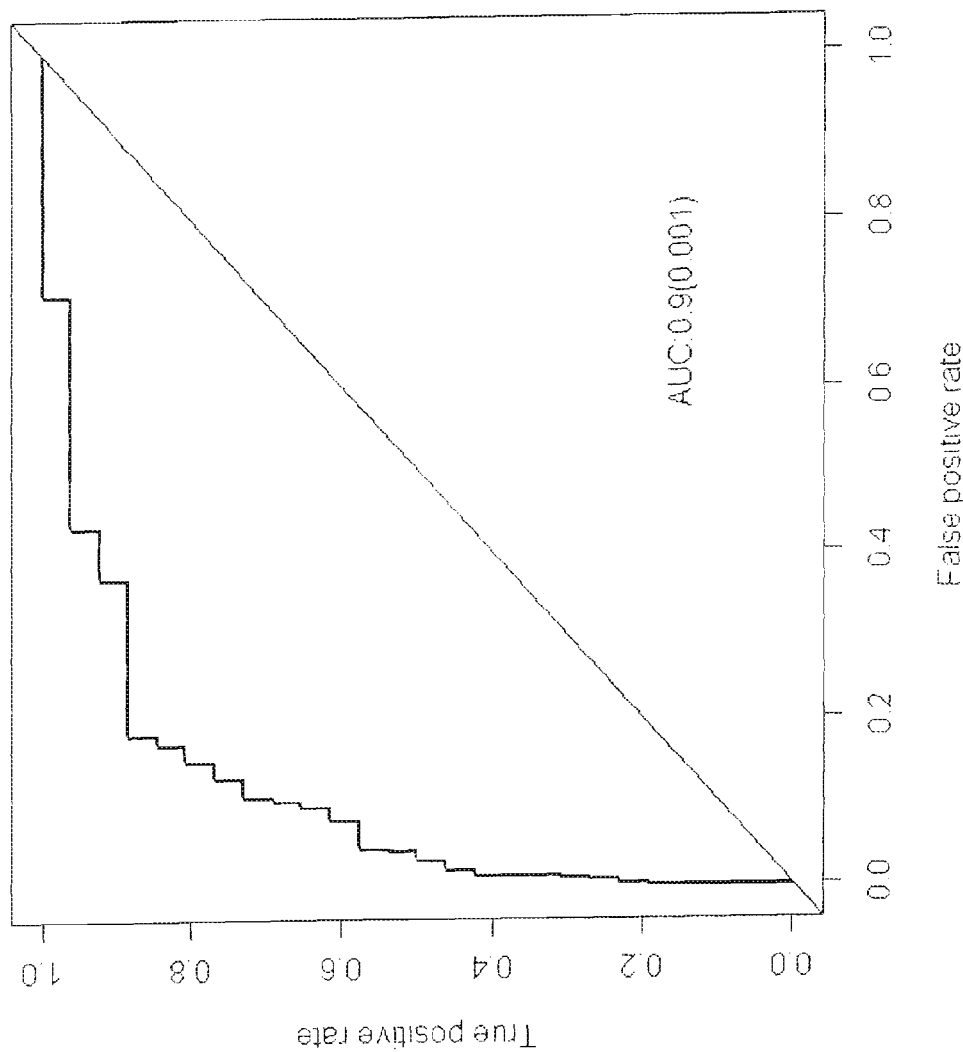
FIG. 18 is a chart depicting the ROC curve of the best total ARTERIORISKMARKER model from FIG. 16, selected from all 61 possible ARTERIORISKMARKERS, including its AUC statistic of 0.90 as shown in the legend.

FIG. 17 is a chart depicting the ROC curve of the best blood-bourne ARTERIORISKMARKER model from FIG. 16, selected from only the blood-borne ARTERIORISK-MARKERS, including its AUC statistic of 0.86 as shown in the legend. FIG. 18 is a chart depicting the ROC curve of the best total ARTERIORISKMARKER model from FIG. 16, selected from all 61 possible ARTERIORISKMARKERS, including its AUC statistic of 0.90 as shown in the legend.

In general, Linear Discriminant Analysis (LDA) models maintained the most predictable performance under cross-validation. As a representative example LDA model, the below coefficients represent the terms of the linear discriminant (LD) of the respective LDA models shown in, given in the form of:

LD=coefficient1*biomarker1+
coefficient2*biomarker2coefficient3*biomarker3+

The terms "biomarker1," "biomarker2," "biomarker3" . . . , represent the transformed values of the respective parameter as presented above in FIG. 4, with concentrations generally being log transformed, LDL being transformed using the square root function, and Age, HBA1C, HT, SCp values being used raw. Transformations were performed to correct the biomarkers for violations of univariate normality.

Table 12 shows the results of an LDA calculation for the LDA model presented as an ROC curve in FIG. 8, using actual transformed values for two subjects, one Case and one Control. Table 13 shows similar results for the LDA model of FIG. 9.

TABLE 12

LDA Calculation Example from LDA Model of FIG. 8

| | Coefficients LD | Transformed Values 108441 (NC) | Transformed Values 109001 (-C) | LDA 108441 (NC) | LDA 109001 (-C) |
|---|---|---|---|---|---|
| POMC | 1.818722 | 0.9469045 | 0.9862581 | 1.722156 | 1.793729 |
| HDLC | 2.756437 | 0.2380461 | 0.1398791 | 0.656159 | 0.385568 |
| VEGF | -1.21085 | -0.9776551 | -0.2535115 | 1.183793 | 0.306964 |
| LEP | 1.268985 | 1.627581 | 1.416401 | 2.065376 | 1.797391 |
| IL6ST | -2.24028 | 2.595694 | 2.238538 | -5.81509 | -5.01496 |
| Ins120 | -1.03408 | 1.968483 | 2.252853 | -2.03556 | -2.32962 |
| IGF1 | 0.759008 | 0.8657718 | 0.8696624 | 0.657127 | 0.66008 |
| | | | LD1 | -1.56604 | -2.40085 |

TABLE 13

LDA Calculation Example from LDA Model of FIG. 9

| | Coefficients LD | Transformed Values 108441 (NC) | Transformed Values 109001 (-C) | LDA 108441 (NC) | LDA 109001 (-C) |
|---|---|---|---|---|---|
| Age | -0.08447 | 59.9 | 54.9 | -5.05953 | -4.6372 |
| POMC | 1.820517 | 0.9469045 | 0.9862581 | 1.723856 | 1.7955 |
| HDLC | 5.071465 | 0.2380461 | 0.1398791 | 1.207242 | 0.709392 |
| CCL2 | -1.00237 | -0.9285024 | -1.1653494 | .930707 | 1.168116 |
| BMI | 5.502393 | 1.4133 | 1.372912 | 7.776532 | 7.554301 |
| VEGF | -1.09844 | -0.9776551 | -0.2535115 | 1.073892 | 0.278466 |
| IL18 | 1.430255 | -0.5086353 | -0.6702777 | -0.72748 | -0.95867 |
| IL6ST | -1.50694 | 2.595694 | 2.238538 | -3.91156 | -3.37335 |
| EGF | 0.757834 | -0.5828459 | -0.3940661 | -0.4417 | -0.29864 |
| | | | LD1 | 2.571956 | 2.237922 |

As known by one skilled in the art, various other LDA operations and analysis techniques can be used to then categorize an individual subject as at risk for a future arteriovascular event, including deriving an optimized direct LDA value "cutoff" using the LDA function output directly as the result, as is commonly done in diagnostics using biomarker ROC curve analysis for new disease markers, or using a normal distance function from the overall Case and Control Mean LDA values and applying the results to the pre-test probability of experiencing an arteriovascular event by using Bayseian methods.

Example 2

Similar analysis was performed for the populations of Example 2, which included stroke in the Case arm, as was summarized in FIG. 3.

FIG. 19 is a table providing information on the inputs used under different ARTERIORISKMARKER model types and selection techniques, with resulting "best" models given model design and constraints, within both of the different case populations of Example 1 (excluding stroke from the Case arm) and Example 2 (including stroke in the Case arm). Of particular note is the consistency of selection of certain markers, which are the Core Markers of the invention, across three or more model types, multiple model constraints, and marker selection techniques.

Differences in marker selection using the same models and marker selection criteria across the different cohorts excluding versus including stroke converters, and amongst the markers when restricted to blood-bourne markers only versus allowed to select all variables, may demonstrate both the substitutability of certain biomarkers, where multiple solutions to the model optimization are likely, and the impact of population and diagnostic indication/intended use on the best fitted models. Several techniques of result normalization, model cross-validation, and model calibration are disclosed herein which may be employed in various scenarios as appropriate. Furthermore, the consistency of AUC results between Example 1 and Example 2 indicates the applicability of various implementations of the invention for both differing arteriovascular event endpoints, which typically are considered to represent the greater difference in pathophysiology than commonly seen in any one of CAD, PAD, or CVD.

Figure 20:
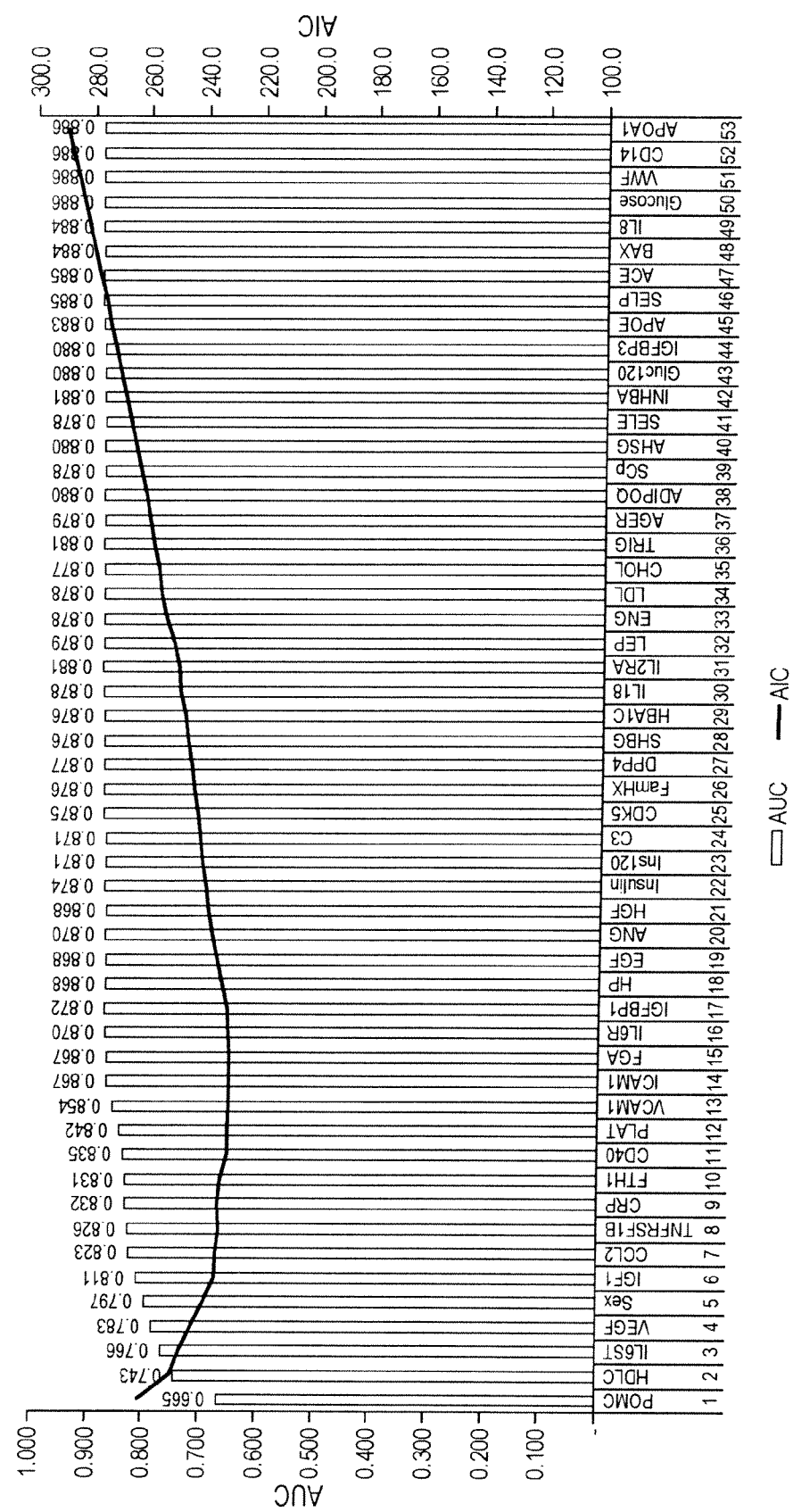
FIG. 20 is a chart depicting the ROC curve calculated AUC statistics for multiple expanding "best forward selected" LDA models, starting from a single ARTERIORISKMARKER and then at each step adding one more incremental forward selected ARTERIORISKMARKER, re-optimizing the LDA model, and graphing the derived AUC statistic using the results from the Example 2 study populations. This continues through 53 selected ARTERIORISKMARKERS selected from a total set of the selected blood-bourne ARTERIORISKMARKERS, Sex and Family History (FamHX). The AIC is included as in the previous charts.
Figure 21:
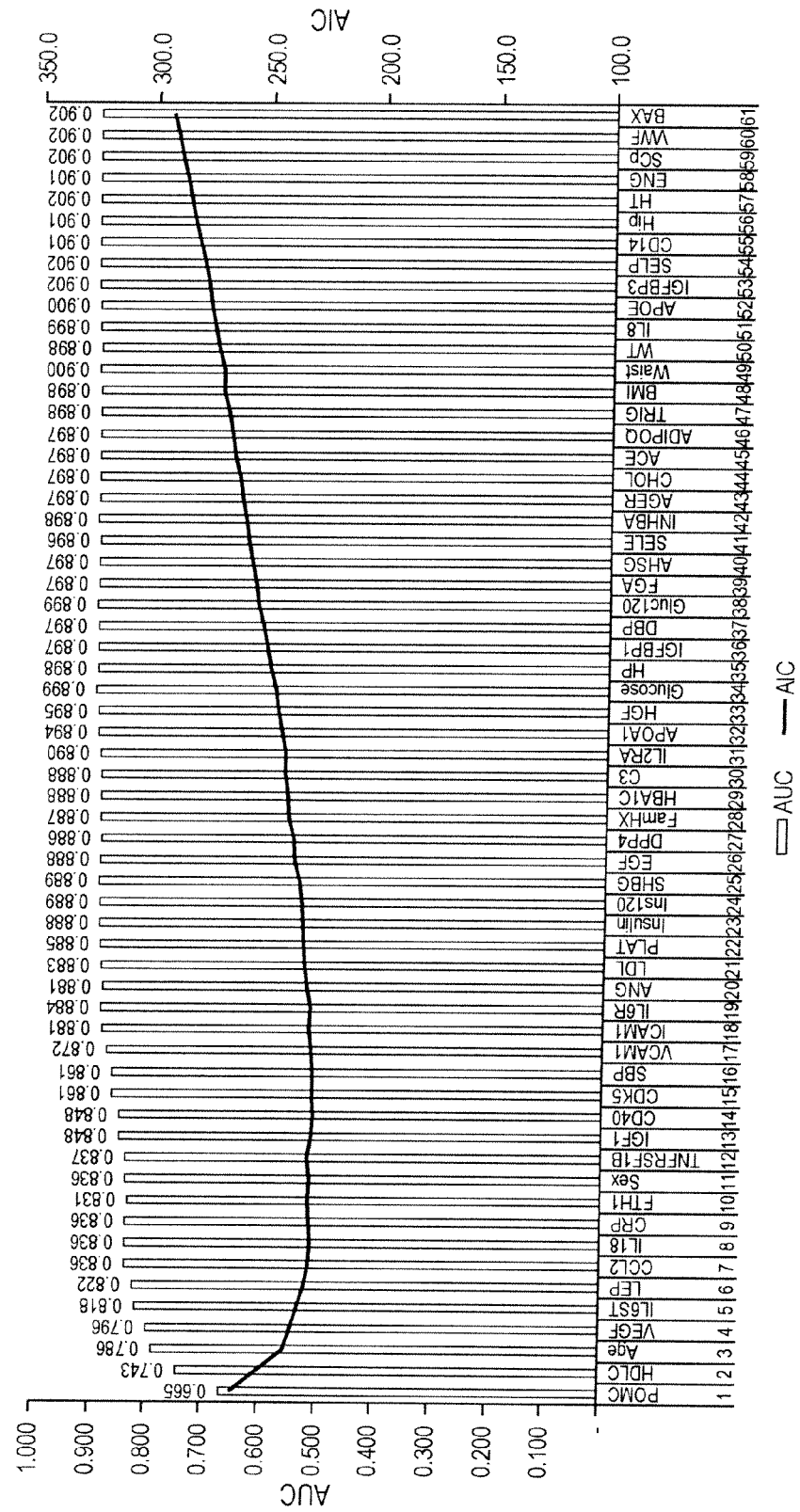
FIG. 21 is a chart depicting the ROC curve calculated AUC statistics for multiple expanding "best forward selected" LDA models, starting from a single ARTERIORISKMARKER and then at each step adding one more incremental forward selected ARTERIORISKMARKER, re-optimizing the LDA model, and graphing the derived AUC statistic using the results from the Example 2 study populations. This continues through 61 ARTERIORISKMARKERS representing the complete group of both the selected blood-bourne analyte and clinical parameter ARTERIORISKMARKERS. The AIC is included as in the previous charts.

Complete forward selection of solely blood-bourne and all 61 ARTERIORISKMARKERS was performed for the populations of Example 2 and are presented in FIGS. 20 and 21. FIG. 20 is a chart depicting the ROC curve calculated AUC statistics for multiple expanding "best forward selected" LDA models, starting from a single ARTERIOR-ISKMARKER and then at each step adding one more incremental forward selected ARTERIORISKMARKER, re-optimizing the LDA model, and graphing the derived AUC statistic. This continues through 53 selected ARTERIORISKMARKERS selected from a total set of the selected blood-bourne ARTERIORISKMARKERS, Sex and Family History (FamHX). The AIC is included as in the previous charts.

FIG. 21 is a chart depicting the ROC curve calculated AUC statistics for multiple expanding "best forward selected" LDA models, starting from a single ARTERIOR-ISKMARKER and then at each step adding one more incremental forward selected ARTERIORISKMARKER, re-optimizing the LDA model, and graphing the derived AUC statistic. This continues through 61 ARTERIORISK-MARKERS representing the complete group of both the selected blood-bourne analyte and clinical parameter ARTERIORISKMARKERS. The AIC is included as in the previous charts.

A comparison of the selection ranking order of the markers shown in Example 2 versus those shown in the comparable analysis of Example 1, presented previously in FIGS. 10 and 11, provides further evidence of the ability to optimize models for individual types of arteriovascular disease.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating an asymptomatic cardiovascular subject or a previously undiagnosed cardiovascular subject determine to be at risk for a future arteriovascular event or disease comprising:
   providing a blood sample isolated from an asymptomatic cardiovascular subject or a previously undiagnosed cardiovascular subject;
   measuring at least four component ARTERIORISK-MARKERS in the blood sample selected from one or more groups consisting of Core Markers I, Core Markers II, Traditional Laboratory Risk Factors, Supplemental Markers I, Supplemental Markers II, Additional Markers I, and Additional Markers II, wherein at least one component ARTERIORISKMARKER is adiponectin;
   calculating an index value from an output of a Support Vector Machine (SVM) model, wherein inputs to the model comprise the measurements, and further wherein the model was developed by fitting data from a longitudinal study of a selected population of individuals and the fitted data comprises levels of the biomarkers and an end point in the selected population of individuals, wherein a calculated area under the curve (AUC) of the model is greater than or equal to 0.70, and wherein the end point is the risk of the cardiovascular event or the cardiovascular event; and
   administering to the subject a therapeutic or prophylactic agent.

2. The method of claim 1, wherein the index value is correlated with the risk of the cardiovascular event or the cardiovascular event.

3. The method of claim 2, wherein the risk evaluation comprises normalizing the component ARTERIORISK-MARKER measurements to reference values.

4. The method of claim 1, further comprising measuring at least two component ARTERIORISKMARKERS within Core Markers I.

5. The method of claim 1, further comprising measuring at least two component ARTERIORISKMARKERS within Core Markers II.

6. The method of claim 1, further comprising measuring at least two component ARTERIORISKMARKERS within Traditional Laboratory Risk Factors.

7. The method of claim 1, further comprising measuring at least two component ARTERIORISKMARKERS within Clinical Parameters.

8. The method of claim 1, further comprising measuring at least two component ARTERIORISKMARKERS within Supplemental Markers I or Supplemental Markers II.

9. The method of claim 1, further comprising measuring at least two component ARTERIORISKMARKERS within Additional Markers I or Additional Markers II.

10. The method of claim 1, wherein the measurement of at least one of the biomarkers of the panel is unaffected by treatment of the subject with one or more therapeutic interventions.

11. The method of claim 1, wherein the measurement of at least one of the biomarkers of the panel is affected by treatment of the subject with one or more therapeutic interventions.

12. The method of claim 1, further comprising measuring or determining one or more clinical parameters chosen from age, body mass index (BMI), diabetes, diastolic blood pressure (DBP), family history (FamHX), hip (circumference), height (HT), ethnicity (RACE), systolic blood pressure (SBP), gender (SEX), smoking, waist (circumference), and weight (WT).

13. The method of claim 1, further comprising one or more additional biomarker chosen from POMC, HDLC, and VEGF.

14. A method for treating an asymptomatic cardiovascular subject or a previously undiagnosed cardiovascular subject comprising:
   administering to the subject a therapeutic or prophylactic agent, wherein the subject has been determined to be at risk of developing arteriovascular disease or a arteriovascular event by a method comprising:
   measuring at least four component ARTERIORISK-MARKERS in the blood sample selected from one or more groups consisting of Core Markers I, Core Markers II, Traditional Laboratory Risk Factors, Supplemental Markers I, Supplemental Markers II, Additional Markers I, and Additional Markers II, wherein at least one component ARTERIORISKMARKER is adiponectin; and
   calculating an index value from an output of a Support Vector Machine (SVM) model, wherein inputs to the model comprise the measurements, and further wherein the model was developed by fitting data from a longitudinal study of a selected population of individuals and the fitted data comprises levels of the biomarkers and an end point in the selected population of individuals, wherein a calculated area under the curve (AUC) of the model is greater than or equal to 0.70, and wherein the end point is the risk of the cardiovascular event or the cardiovascular event.

* * * * *